(12) United States Patent
Shelton, IV et al.

(10) Patent No.: US 11,399,837 B2
(45) Date of Patent: Aug. 2, 2022

(54) MECHANISMS FOR MOTOR CONTROL ADJUSTMENTS OF A MOTORIZED SURGICAL INSTRUMENT

(71) Applicant: Ethicon LLC, Guaynabo, PR (US)

(72) Inventors: Frederick E. Shelton, IV, Hillsboro, OH (US); Shane R. Adams, Lebanon, OH (US)

(73) Assignee: Cilag GmbH International, Zug (CH)

( * ) Notice: Subject to any disclaimer, the term of this patent is extended or adjusted under 35 U.S.C. 154(b) by 146 days.

(21) Appl. No.: 16/458,119

(22) Filed: Jun. 30, 2019

(65) Prior Publication Data
US 2020/0405314 A1    Dec. 31, 2020

Related U.S. Application Data

(60) Provisional application No. 62/868,457, filed on Jun. 28, 2019.

(51) Int. Cl.
*A61B 17/115* (2006.01)
*A61B 90/96* (2016.01)
(Continued)

(52) U.S. Cl.
CPC ........ *A61B 17/1155* (2013.01); *A61B 17/072* (2013.01); *A61B 90/96* (2016.02);
(Continued)

(58) Field of Classification Search
CPC ..... A61B 17/115; A61B 17/072; A61B 90/96; A61B 90/98; A61B 2017/00367;
(Continued)

(56) References Cited

U.S. PATENT DOCUMENTS 66,052 A    6/1867  Smith
662,587 A    11/1900  Blake
(Continued)

FOREIGN PATENT DOCUMENTS

AU    2012200594 A1    2/2012
AU    2012203035 A1    6/2012
(Continued)

OTHER PUBLICATIONS

ASTM procedure D2240-00, "Standard Test Method for Rubber Property-Durometer Hardness," (Published Aug. 2000).
(Continued)

*Primary Examiner* — Anna K Kinsaul
*Assistant Examiner* — Veronica Martin

(57) ABSTRACT

A surgical instrument is disclosed including an end effector, a shaft, and a housing. The end effector includes an RFID tag configured to store end effector information. The shaft includes a first RFID scanner and a second RFID tag configured to store shaft information. The first RFID scanner is configured to detect the first RFID tag in a first attached configuration. The housing includes a second RFID scanner configured to detect the second RFID tag in a second attached configuration, a motor configured to apply a load to the end effector, and a control circuit. The control circuit is configured to receive input from the first RFID scanner indicative of the end effector information, receive input from the second RFID scanner indicative of the shaft information, and adjust at least one parameter of operation of the motor based on the end effector information and the shaft information.

19 Claims, 43 Drawing Sheets

(51) Int. Cl.
  *A61B 90/98* (2016.01)
  *A61B 17/072* (2006.01)
  *A61B 17/00* (2006.01)
(52) U.S. Cl.
  CPC .... *A61B 90/98* (2016.02); *A61B 2017/00367* (2013.01); *A61B 2017/07228* (2013.01); *A61B 2017/07264* (2013.01); *A61B 2017/07271* (2013.01); *A61B 2017/07278* (2013.01)
(58) Field of Classification Search
  CPC ........... A61B 2017/07228; A61B 2017/07264; A61B 2017/07271; A61B 2017/07278; A61B 2090/0811
  See application file for complete search history.

(56) References Cited

U.S. PATENT DOCUMENTS

| | | |
|---|---|---|
| 670,748 A | 3/1901 | Weddeler |
| 719,487 A | 2/1903 | Minor |
| 804,229 A | 11/1905 | Hutchinson |
| 903,739 A | 11/1908 | Lesemann |
| 951,393 A | 3/1910 | Hahn |
| 1,075,556 A | 10/1913 | Fenoughty |
| 1,082,105 A | 12/1913 | Anderson |
| 1,188,721 A | 6/1916 | Bittner |
| 1,306,107 A | 6/1919 | Elliott |
| 1,314,601 A | 9/1919 | McCaskey |
| 1,466,128 A | 8/1923 | Hallenbeck |
| 1,677,337 A | 7/1928 | Grove |
| 1,794,907 A | 3/1931 | Kelly |
| 1,849,427 A | 3/1932 | Hook |
| 1,944,116 A | 1/1934 | Stratman |
| 1,954,048 A | 4/1934 | Jeffrey et al. |
| 2,028,635 A | 1/1936 | Wappler |
| 2,037,727 A | 4/1936 | La Chapelle |
| 2,120,951 A | 6/1938 | Hodgman |
| 2,132,295 A | 10/1938 | Hawkins |
| 2,161,632 A | 6/1939 | Nattenheimer |
| D120,434 S | 5/1940 | Gold |
| 2,211,117 A | 8/1940 | Hess |
| 2,214,870 A | 9/1940 | West |
| 2,224,108 A | 12/1940 | Ridgway |
| 2,224,882 A | 12/1940 | Peck |
| 2,318,379 A | 5/1943 | Davis et al. |
| 2,329,440 A | 9/1943 | La Place |
| 2,377,581 A | 6/1945 | Shaffrey |
| 2,406,389 A | 8/1946 | Royal Lee |
| 2,420,552 A | 5/1947 | Morrill |
| 2,441,096 A | 5/1948 | Happe |
| 2,448,741 A | 9/1948 | Scott et al. |
| 2,450,527 A | 10/1948 | Smith |
| 2,491,872 A | 12/1949 | Neuman |
| 2,507,872 A | 5/1950 | Unsinger |
| 2,526,902 A | 10/1950 | Rublee |
| 2,527,256 A | 10/1950 | Jackson |
| 2,578,686 A | 12/1951 | Fish |
| 2,638,901 A | 5/1953 | Sugarbaker |
| 2,674,149 A | 4/1954 | Benson |
| 2,701,489 A | 2/1955 | Osborn |
| 2,711,461 A | 6/1955 | Happe |
| 2,724,289 A | 11/1955 | Wight |
| 2,742,955 A | 4/1956 | Dominguez |
| 2,804,848 A | 9/1957 | O'Farrell et al. |
| 2,808,482 A | 10/1957 | Zanichkowsky et al. |
| 2,825,178 A | 3/1958 | Hawkins |
| 2,853,074 A | 9/1958 | Olson |
| 2,856,192 A | 10/1958 | Schuster |
| 2,887,004 A | 5/1959 | Stewart |
| 2,957,353 A | 10/1960 | Lewis |
| 2,959,974 A | 11/1960 | Emrick |
| 3,026,744 A | 3/1962 | Rouse William H |
| 3,032,769 A | 5/1962 | Palmer |
| 3,035,256 A | 5/1962 | Egbert |
| 3,060,972 A | 10/1962 | Sheldon |
| 3,075,062 A | 1/1963 | Iaccarino |
| 3,078,465 A | 2/1963 | Bobrov |
| 3,079,606 A | 3/1963 | Bobrov et al. |
| 3,080,564 A | 3/1963 | Strekopitov et al. |
| 3,166,072 A | 1/1965 | Sullivan, Jr. |
| 3,180,236 A | 4/1965 | Beckett |
| 3,196,869 A | 7/1965 | Scholl |
| 3,204,731 A | 9/1965 | Bent et al. |
| 3,266,494 A | 8/1966 | Brownrigg et al. |
| 3,269,630 A | 8/1966 | Fleischer |
| 3,269,631 A | 8/1966 | Takaro |
| 3,275,211 A | 9/1966 | Hirsch et al. |
| 3,315,863 A | 4/1967 | O'Dea |
| 3,317,103 A | 5/1967 | Cullen et al. |
| 3,317,105 A | 5/1967 | Astafjev et al. |
| 3,357,296 A | 12/1967 | Lefever |
| 3,359,978 A | 12/1967 | Smith, Jr. |
| 3,377,893 A | 4/1968 | Shorb |
| 3,480,193 A | 11/1969 | Ralston |
| 3,490,675 A | 1/1970 | Green et al. |
| 3,494,533 A | 2/1970 | Green et al. |
| 3,499,591 A | 3/1970 | Green |
| 3,503,396 A | 3/1970 | Pierie et al. |
| 3,509,629 A | 5/1970 | Kidokoro |
| 3,551,987 A | 1/1971 | Wilkinson |
| 3,568,675 A | 3/1971 | Harvey |
| 3,572,159 A | 3/1971 | Tschanz |
| 3,583,393 A | 6/1971 | Takahashi |
| 3,589,589 A | 6/1971 | Akopov |
| 3,598,943 A | 8/1971 | Barrett |
| 3,604,561 A | 9/1971 | Mallina et al. |
| 3,608,549 A | 9/1971 | Merrill |
| 3,618,842 A | 11/1971 | Bryan |
| 3,635,394 A | 1/1972 | Natelson |
| 3,638,652 A | 2/1972 | Kelley |
| 3,640,317 A | 2/1972 | Panfili |
| 3,643,851 A | 2/1972 | Green et al. |
| 3,650,453 A | 3/1972 | Smith, Jr. |
| 3,661,339 A | 5/1972 | Shimizu |
| 3,661,666 A | 5/1972 | Foster et al. |
| 3,662,939 A | 5/1972 | Bryan |
| 3,685,250 A | 8/1972 | Henry et al. |
| 3,688,966 A | 9/1972 | Perkins et al. |
| 3,695,646 A | 10/1972 | Mommsen |
| 3,709,221 A | 1/1973 | Riely |
| 3,717,294 A | 2/1973 | Green |
| 3,724,237 A | 4/1973 | Wood |
| 3,726,755 A | 4/1973 | Shannon |
| 3,727,904 A | 4/1973 | Gabbey |
| 3,734,207 A | 5/1973 | Fishbein |
| 3,740,994 A | 6/1973 | De Carlo, Jr. |
| 3,744,495 A | 7/1973 | Johnson |
| 3,746,002 A | 7/1973 | Haller |
| 3,747,603 A | 7/1973 | Adler |
| 3,747,692 A | 7/1973 | Davidson |
| 3,751,902 A | 8/1973 | Kingsbury et al. |
| 3,752,161 A | 8/1973 | Bent |
| 3,799,151 A | 3/1974 | Fukaumi et al. |
| 3,808,452 A | 4/1974 | Hutchinson |
| 3,815,476 A | 6/1974 | Green et al. |
| 3,819,100 A | 6/1974 | Noiles et al. |
| 3,821,919 A | 7/1974 | Knohl |
| 3,826,978 A | 7/1974 | Kelly |
| 3,836,171 A | 9/1974 | Hayashi et al. |
| 3,837,555 A | 9/1974 | Green |
| 3,841,474 A | 10/1974 | Maier |
| 3,851,196 A | 11/1974 | Hinds |
| 3,863,639 A | 2/1975 | Kleaveland |
| 3,863,940 A | 2/1975 | Cummings |
| 3,883,624 A | 5/1975 | McKenzie et al. |
| 3,885,491 A | 5/1975 | Curtis |
| 3,887,393 A | 6/1975 | La Rue, Jr. |
| 3,892,228 A | 7/1975 | Mitsui |
| 3,894,174 A | 7/1975 | Cartun |
| 3,902,247 A | 9/1975 | Fleer et al. |
| 3,940,844 A | 3/1976 | Colby et al. |
| 3,944,163 A | 3/1976 | Hayashi et al. |
| 3,950,686 A | 4/1976 | Randall |
| 3,952,747 A | 4/1976 | Kimmell, Jr. |

(56) References Cited

U.S. PATENT DOCUMENTS

| | | |
|---|---|---|
| 3,955,581 A | 5/1976 | Spasiano et al. |
| 3,959,879 A | 6/1976 | Sellers |
| RE28,932 E | 8/1976 | Noiles et al. |
| 3,972,734 A | 8/1976 | King |
| 3,973,179 A | 8/1976 | Weber et al. |
| 3,981,051 A | 9/1976 | Brumlik |
| 3,999,110 A | 12/1976 | Ramstrom et al. |
| 4,025,216 A | 5/1977 | Hives |
| 4,027,746 A | 6/1977 | Kine |
| 4,034,143 A | 7/1977 | Sweet |
| 4,038,987 A | 8/1977 | Komiya |
| 4,054,108 A | 10/1977 | Gill |
| 4,060,089 A | 11/1977 | Noiles |
| 4,066,133 A | 1/1978 | Voss |
| 4,085,337 A | 4/1978 | Moeller |
| 4,100,820 A | 7/1978 | Evett |
| 4,106,446 A | 8/1978 | Yamada et al. |
| 4,106,620 A | 8/1978 | Brimmer et al. |
| 4,108,211 A | 8/1978 | Tanaka |
| 4,111,206 A | 9/1978 | Vishnevsky et al. |
| 4,127,227 A | 11/1978 | Green |
| 4,129,059 A | 12/1978 | Van Eck |
| 4,132,146 A | 1/1979 | Uhlig |
| 4,135,517 A | 1/1979 | Reale |
| 4,149,461 A | 4/1979 | Simeth |
| 4,154,122 A | 5/1979 | Severin |
| 4,160,857 A | 7/1979 | Nardella et al. |
| 4,169,990 A | 10/1979 | Lerdman |
| 4,180,285 A | 12/1979 | Reneau |
| 4,185,701 A | 1/1980 | Boys |
| 4,190,042 A | 2/1980 | Sinnreich |
| 4,198,734 A | 4/1980 | Brumlik |
| 4,198,982 A | 4/1980 | Fortner et al. |
| 4,203,444 A | 5/1980 | Bonnell et al. |
| 4,207,898 A | 6/1980 | Becht |
| 4,213,562 A | 7/1980 | Garrett et al. |
| 4,226,242 A | 10/1980 | Jarvik |
| 4,239,431 A | 12/1980 | Davini |
| 4,241,861 A | 12/1980 | Fleischer |
| 4,244,372 A | 1/1981 | Kapitanov et al. |
| 4,250,436 A | 2/1981 | Weissman |
| 4,261,244 A | 4/1981 | Becht et al. |
| 4,272,002 A | 6/1981 | Moshofsky |
| 4,272,662 A | 6/1981 | Simpson |
| 4,274,304 A | 6/1981 | Curtiss |
| 4,274,398 A | 6/1981 | Scott, Jr. |
| 4,275,813 A | 6/1981 | Noiles |
| 4,278,091 A | 7/1981 | Borzone |
| 4,282,573 A | 8/1981 | Imai et al. |
| 4,289,131 A | 9/1981 | Mueller |
| 4,289,133 A | 9/1981 | Rothfuss |
| 4,290,542 A | 9/1981 | Fedotov et al. |
| D261,356 S | 10/1981 | Robinson |
| 4,293,604 A | 10/1981 | Campbell |
| 4,296,654 A | 10/1981 | Mercer |
| 4,296,881 A | 10/1981 | Lee |
| 4,304,236 A | 12/1981 | Conta et al. |
| 4,305,539 A | 12/1981 | Korolkov et al. |
| 4,312,363 A | 1/1982 | Rothfuss et al. |
| 4,312,685 A | 1/1982 | Riedl |
| 4,317,451 A | 3/1982 | Cerwin et al. |
| 4,319,576 A | 3/1982 | Rothfuss |
| 4,321,002 A | 3/1982 | Froehlich |
| 4,321,746 A | 3/1982 | Grinage |
| 4,328,839 A | 5/1982 | Lyons et al. |
| 4,331,277 A | 5/1982 | Green |
| 4,340,331 A | 7/1982 | Savino |
| 4,347,450 A | 8/1982 | Colligan |
| 4,348,603 A | 9/1982 | Huber |
| 4,349,028 A | 9/1982 | Green |
| 4,350,151 A | 9/1982 | Scott |
| 4,353,371 A | 10/1982 | Cosman |
| 4,357,940 A | 11/1982 | Muller |
| 4,361,057 A | 11/1982 | Kochera |
| 4,366,544 A | 12/1982 | Shima et al. |
| 4,369,013 A | 1/1983 | Abildgaard et al. |
| 4,373,147 A | 2/1983 | Carlson, Jr. |
| 4,376,380 A | 3/1983 | Burgess |
| 4,379,457 A | 4/1983 | Gravener et al. |
| 4,380,312 A | 4/1983 | Landrus |
| 4,382,326 A | 5/1983 | Rabuse |
| 4,383,634 A | 5/1983 | Green |
| 4,389,963 A | 6/1983 | Pearson |
| 4,393,728 A | 7/1983 | Larson et al. |
| 4,394,613 A | 7/1983 | Cole |
| 4,396,139 A | 8/1983 | Hall et al. |
| 4,397,311 A | 8/1983 | Kanshin et al. |
| 4,402,445 A | 9/1983 | Green |
| 4,406,621 A | 9/1983 | Bailey |
| 4,408,692 A | 10/1983 | Sigel et al. |
| 4,409,057 A | 10/1983 | Molenda et al. |
| 4,415,112 A | 11/1983 | Green |
| 4,416,276 A | 11/1983 | Newton et al. |
| 4,417,890 A | 11/1983 | Dennehey et al. |
| 4,421,264 A | 12/1983 | Arter et al. |
| 4,423,456 A | 12/1983 | Zaidenweber |
| 4,425,915 A | 1/1984 | Ivanov |
| 4,428,376 A | 1/1984 | Mericle |
| 4,429,695 A | 2/1984 | Green |
| 4,430,997 A | 2/1984 | DiGiovanni et al. |
| 4,434,796 A | 3/1984 | Karapetian et al. |
| 4,438,659 A | 3/1984 | Desplats |
| 4,442,964 A | 4/1984 | Becht |
| 4,448,194 A | 5/1984 | DiGiovanni et al. |
| 4,451,743 A | 5/1984 | Suzuki et al. |
| 4,452,376 A | 6/1984 | Klieman et al. |
| 4,454,887 A | 6/1984 | Kruger |
| 4,459,519 A | 7/1984 | Erdman |
| 4,461,305 A | 7/1984 | Cibley |
| 4,467,805 A | 8/1984 | Fukuda |
| 4,468,597 A | 8/1984 | Baumard et al. |
| 4,469,481 A | 9/1984 | Kobayashi |
| 4,470,414 A | 9/1984 | Imagawa et al. |
| 4,471,780 A | 9/1984 | Menges et al. |
| 4,471,781 A | 9/1984 | Di Giovanni et al. |
| 4,473,077 A | 9/1984 | Noiles et al. |
| 4,475,679 A | 10/1984 | Fleury, Jr. |
| 4,476,864 A | 10/1984 | Tezel |
| 4,478,220 A | 10/1984 | Di Giovanni et al. |
| 4,480,641 A | 11/1984 | Failla et al. |
| 4,481,458 A | 11/1984 | Lane |
| 4,483,562 A | 11/1984 | Schoolman |
| 4,485,816 A | 12/1984 | Krumme |
| 4,485,817 A | 12/1984 | Swiggett |
| 4,486,928 A | 12/1984 | Tucker et al. |
| 4,488,523 A | 12/1984 | Shichman |
| 4,489,875 A | 12/1984 | Crawford et al. |
| 4,493,983 A | 1/1985 | Taggert |
| 4,494,057 A | 1/1985 | Hotta |
| 4,499,895 A | 2/1985 | Takayama |
| 4,500,024 A | 2/1985 | DiGiovanni et al. |
| D278,081 S | 3/1985 | Green |
| 4,503,842 A | 3/1985 | Takayama |
| 4,505,272 A | 3/1985 | Utyamyshev et al. |
| 4,505,273 A | 3/1985 | Braun et al. |
| 4,505,414 A | 3/1985 | Filipi |
| 4,506,671 A | 3/1985 | Green |
| 4,512,038 A | 4/1985 | Alexander et al. |
| 4,514,477 A | 4/1985 | Kobayashi |
| 4,520,817 A | 6/1985 | Green |
| 4,522,327 A | 6/1985 | Korthoff et al. |
| 4,526,174 A | 7/1985 | Froehlich |
| 4,527,724 A | 7/1985 | Chow et al. |
| 4,530,357 A | 7/1985 | Pawloski et al. |
| 4,530,453 A | 7/1985 | Green |
| 4,531,522 A | 7/1985 | Bedi et al. |
| 4,532,927 A | 8/1985 | Miksza, Jr. |
| 4,540,202 A | 9/1985 | Amphoux et al. |
| 4,548,202 A | 10/1985 | Duncan |
| 4,556,058 A | 12/1985 | Green |
| 4,560,915 A | 12/1985 | Soultanian |
| 4,565,109 A | 1/1986 | Tsay |
| 4,565,189 A | 1/1986 | Mabuchi |
| 4,566,620 A | 1/1986 | Green et al. |

(56) References Cited

U.S. PATENT DOCUMENTS

| | | |
|---|---|---|
| 4,569,346 A | 2/1986 | Poirier |
| 4,569,469 A | 2/1986 | Mongeon et al. |
| 4,571,213 A | 2/1986 | Ishimoto |
| 4,573,468 A | 3/1986 | Conta et al. |
| 4,573,469 A | 3/1986 | Golden et al. |
| 4,573,622 A | 3/1986 | Green et al. |
| 4,576,165 A | 3/1986 | Green et al. |
| 4,576,167 A | 3/1986 | Noiles |
| 4,580,712 A | 4/1986 | Green |
| 4,585,153 A | 4/1986 | Failla et al. |
| 4,586,501 A | 5/1986 | Claracq |
| 4,586,502 A | 5/1986 | Bedi et al. |
| 4,589,416 A | 5/1986 | Green |
| 4,589,582 A | 5/1986 | Bilotti |
| 4,589,870 A | 5/1986 | Citrin et al. |
| 4,591,085 A | 5/1986 | Di Giovanni |
| RE32,214 E | 7/1986 | Schramm |
| 4,597,753 A | 7/1986 | Turley |
| 4,600,037 A | 7/1986 | Hatten |
| 4,604,786 A | 8/1986 | Howie, Jr. |
| 4,605,001 A | 8/1986 | Rothfuss et al. |
| 4,605,004 A | 8/1986 | Di Giovanni et al. |
| 4,606,343 A | 8/1986 | Conta et al. |
| 4,607,636 A | 8/1986 | Kula et al. |
| 4,607,638 A | 8/1986 | Crainich |
| 4,608,980 A | 9/1986 | Aihara |
| 4,608,981 A | 9/1986 | Rothfuss et al. |
| 4,610,250 A | 9/1986 | Green |
| 4,610,383 A | 9/1986 | Rothfuss et al. |
| 4,612,933 A | 9/1986 | Brinkerhoff et al. |
| D286,180 S | 10/1986 | Korthoff |
| D286,442 S | 10/1986 | Korthoff et al. |
| 4,617,893 A | 10/1986 | Donner et al. |
| 4,617,914 A | 10/1986 | Ueda |
| 4,619,262 A | 10/1986 | Taylor |
| 4,619,391 A | 10/1986 | Sharkany et al. |
| 4,624,401 A | 11/1986 | Gassner et al. |
| D287,278 S | 12/1986 | Spreckelmeier |
| 4,628,459 A | 12/1986 | Shinohara et al. |
| 4,628,636 A | 12/1986 | Folger |
| 4,629,107 A | 12/1986 | Fedotov et al. |
| 4,632,290 A | 12/1986 | Green et al. |
| 4,633,861 A | 1/1987 | Chow et al. |
| 4,633,874 A | 1/1987 | Chow et al. |
| 4,634,419 A | 1/1987 | Kreizman et al. |
| 4,635,638 A | 1/1987 | Weintraub et al. |
| 4,641,076 A | 2/1987 | Linden |
| 4,642,618 A | 2/1987 | Johnson et al. |
| 4,642,738 A | 2/1987 | Meller |
| 4,643,173 A | 2/1987 | Bell et al. |
| 4,643,731 A | 2/1987 | Eckenhoff |
| 4,646,722 A | 3/1987 | Silverstein et al. |
| 4,646,745 A | 3/1987 | Noiles |
| 4,651,734 A | 3/1987 | Doss et al. |
| 4,652,820 A | 3/1987 | Maresca |
| 4,654,028 A | 3/1987 | Suma |
| 4,655,222 A | 4/1987 | Florez et al. |
| 4,662,555 A | 5/1987 | Thornton |
| 4,663,874 A | 5/1987 | Sano et al. |
| 4,664,305 A | 5/1987 | Blake, III et al. |
| 4,665,916 A | 5/1987 | Green |
| 4,667,674 A | 5/1987 | Korthoff et al. |
| 4,669,647 A | 6/1987 | Storace |
| 4,671,278 A | 6/1987 | Chin |
| 4,671,280 A | 6/1987 | Dorband et al. |
| 4,671,445 A | 6/1987 | Barker et al. |
| 4,672,964 A | 6/1987 | Dee et al. |
| 4,675,944 A | 6/1987 | Wells |
| 4,676,245 A | 6/1987 | Fukuda |
| 4,679,460 A | 7/1987 | Yoshigai |
| 4,679,719 A | 7/1987 | Kramer |
| 4,684,051 A | 8/1987 | Akopov et al. |
| 4,688,555 A | 8/1987 | Wardle |
| 4,691,703 A | 9/1987 | Auth et al. |
| 4,693,248 A | 9/1987 | Failla |
| 4,698,579 A | 10/1987 | Richter et al. |
| 4,700,703 A | 10/1987 | Resnick et al. |
| 4,705,038 A | 11/1987 | Sjostrom et al. |
| 4,708,141 A | 11/1987 | Inoue et al. |
| 4,709,120 A | 11/1987 | Pearson |
| 4,715,520 A | 12/1987 | Roehr, Jr. et al. |
| 4,719,917 A | 1/1988 | Barrows et al. |
| 4,721,099 A | 1/1988 | Chikama |
| 4,722,340 A | 2/1988 | Takayama et al. |
| 4,724,840 A | 2/1988 | McVay et al. |
| 4,727,308 A | 2/1988 | Huljak et al. |
| 4,728,020 A | 3/1988 | Green et al. |
| 4,728,876 A | 3/1988 | Mongeon et al. |
| 4,729,260 A | 3/1988 | Dudden |
| 4,730,726 A | 3/1988 | Holzwarth |
| 4,741,336 A | 5/1988 | Failla et al. |
| 4,743,214 A | 5/1988 | Tai-Cheng |
| 4,744,363 A | 5/1988 | Hasson |
| 4,747,820 A | 5/1988 | Hornlein et al. |
| 4,750,902 A | 6/1988 | Wuchinich et al. |
| 4,752,024 A | 6/1988 | Green et al. |
| 4,754,909 A | 7/1988 | Barker et al. |
| 4,755,070 A | 7/1988 | Cerutti |
| 4,761,326 A | 8/1988 | Barnes et al. |
| 4,763,669 A | 8/1988 | Jaeger |
| 4,767,044 A | 8/1988 | Green |
| D297,764 S | 9/1988 | Hunt et al. |
| 4,773,420 A | 9/1988 | Green |
| 4,777,780 A | 10/1988 | Holzwarth |
| 4,781,186 A | 11/1988 | Simpson et al. |
| 4,784,137 A | 11/1988 | Kulik et al. |
| 4,787,387 A | 11/1988 | Burbank, III et al. |
| 4,788,485 A | 11/1988 | Kawagishi et al. |
| D298,967 S | 12/1988 | Hunt |
| 4,790,225 A | 12/1988 | Moody et al. |
| 4,790,314 A | 12/1988 | Weaver |
| 4,805,617 A | 2/1989 | Bedi et al. |
| 4,805,823 A | 2/1989 | Rothfuss |
| 4,807,628 A | 2/1989 | Peters et al. |
| 4,809,695 A | 3/1989 | Gwathmey et al. |
| 4,815,460 A | 3/1989 | Porat et al. |
| 4,817,643 A | 4/1989 | Olson |
| 4,817,847 A | 4/1989 | Redtenbacher et al. |
| 4,819,853 A | 4/1989 | Green |
| 4,821,939 A | 4/1989 | Green |
| 4,827,552 A | 5/1989 | Bojar et al. |
| 4,827,911 A | 5/1989 | Broadwin et al. |
| 4,828,542 A | 5/1989 | Hermann |
| 4,828,944 A | 5/1989 | Yabe et al. |
| 4,830,855 A | 5/1989 | Stewart |
| 4,832,158 A | 5/1989 | Farrar et al. |
| 4,833,937 A | 5/1989 | Nagano |
| 4,834,096 A | 5/1989 | Oh et al. |
| 4,834,720 A | 5/1989 | Blinkhorn |
| 4,838,859 A | 6/1989 | Strassmann |
| 4,844,068 A | 7/1989 | Arata et al. |
| 4,848,637 A | 7/1989 | Pruitt |
| 4,856,078 A | 8/1989 | Konopka |
| 4,860,644 A | 8/1989 | Kohl et al. |
| 4,862,891 A | 9/1989 | Smith |
| 4,863,423 A | 9/1989 | Wallace |
| 4,865,030 A | 9/1989 | Polyak |
| 4,868,530 A | 9/1989 | Ahs |
| 4,868,958 A | 9/1989 | Suzuki et al. |
| 4,869,414 A | 9/1989 | Green et al. |
| 4,869,415 A | 9/1989 | Fox |
| 4,873,977 A | 10/1989 | Avant et al. |
| 4,875,486 A | 10/1989 | Rapoport et al. |
| 4,880,015 A | 11/1989 | Nierman |
| 4,890,613 A | 1/1990 | Golden et al. |
| 4,892,244 A | 1/1990 | Fox et al. |
| 4,893,622 A | 1/1990 | Green et al. |
| 4,894,051 A | 1/1990 | Shiber |
| 4,896,584 A | 1/1990 | Stoll et al. |
| 4,896,678 A | 1/1990 | Ogawa |
| 4,900,303 A | 2/1990 | Lemelson |
| 4,903,697 A | 2/1990 | Resnick et al. |
| 4,909,789 A | 3/1990 | Taguchi et al. |
| 4,915,100 A | 4/1990 | Green |

(56) References Cited

U.S. PATENT DOCUMENTS

| | | |
|---|---|---|
| 4,919,679 A | 4/1990 | Averill et al. |
| 4,921,479 A | 5/1990 | Grayzel |
| 4,925,082 A | 5/1990 | Kim |
| 4,928,699 A | 5/1990 | Sasai |
| 4,930,503 A | 6/1990 | Pruitt |
| 4,930,674 A | 6/1990 | Barak |
| 4,931,047 A | 6/1990 | Broadwin et al. |
| 4,931,737 A | 6/1990 | Hishiki |
| 4,932,960 A | 6/1990 | Green et al. |
| 4,933,800 A | 6/1990 | Yang |
| 4,933,843 A | 6/1990 | Scheller et al. |
| D309,350 S | 7/1990 | Sutherland et al. |
| 4,938,408 A | 7/1990 | Bedi et al. |
| 4,941,623 A | 7/1990 | Pruitt |
| 4,943,182 A | 7/1990 | Hoblingre |
| 4,944,443 A | 7/1990 | Oddsen et al. |
| 4,946,067 A | 8/1990 | Kelsall |
| 4,948,327 A | 8/1990 | Crupi, Jr. |
| 4,949,707 A | 8/1990 | Levahn et al. |
| 4,951,860 A | 8/1990 | Peters et al. |
| 4,951,861 A | 8/1990 | Schulze et al. |
| 4,954,960 A | 9/1990 | Lo et al. |
| 4,955,959 A | 9/1990 | Tompkins et al. |
| 4,957,212 A | 9/1990 | Duck et al. |
| 4,962,681 A | 10/1990 | Yang |
| 4,962,877 A | 10/1990 | Hervas |
| 4,964,559 A | 10/1990 | Deniega et al. |
| 4,964,863 A | 10/1990 | Kanshin et al. |
| 4,965,709 A | 10/1990 | Ngo |
| 4,970,656 A | 11/1990 | Lo et al. |
| 4,973,274 A | 11/1990 | Hirukawa |
| 4,973,302 A | 11/1990 | Armour et al. |
| 4,976,173 A | 12/1990 | Yang |
| 4,978,049 A | 12/1990 | Green |
| 4,978,333 A | 12/1990 | Broadwin et al. |
| 4,979,952 A | 12/1990 | Kubota et al. |
| 4,984,564 A | 1/1991 | Yuen |
| 4,986,808 A | 1/1991 | Broadwin et al. |
| 4,987,049 A | 1/1991 | Komamura et al. |
| 4,988,334 A | 1/1991 | Hornlein et al. |
| 4,995,877 A | 2/1991 | Ams et al. |
| 4,995,959 A | 2/1991 | Metzner |
| 4,996,975 A | 3/1991 | Nakamura |
| 5,001,649 A | 3/1991 | Lo et al. |
| 5,002,543 A | 3/1991 | Bradshaw et al. |
| 5,002,553 A | 3/1991 | Shiber |
| 5,005,754 A | 4/1991 | Van Overloop |
| 5,009,222 A | 4/1991 | Her |
| 5,009,661 A | 4/1991 | Michelson |
| 5,012,411 A | 4/1991 | Policastro et al. |
| 5,014,898 A | 5/1991 | Heidrich |
| 5,014,899 A | 5/1991 | Presty et al. |
| 5,015,227 A | 5/1991 | Broadwin et al. |
| 5,018,515 A | 5/1991 | Gilman |
| 5,018,657 A | 5/1991 | Pedlick et al. |
| 5,024,652 A | 6/1991 | Dumenek et al. |
| 5,024,671 A | 6/1991 | Tu et al. |
| 5,025,559 A | 6/1991 | McCullough |
| 5,027,834 A | 7/1991 | Pruitt |
| 5,030,226 A | 7/1991 | Green et al. |
| 5,031,814 A | 7/1991 | Tompkins et al. |
| 5,033,552 A | 7/1991 | Hu |
| 5,035,040 A | 7/1991 | Kerrigan et al. |
| 5,037,018 A | 8/1991 | Matsuda et al. |
| 5,038,109 A | 8/1991 | Goble et al. |
| 5,038,247 A | 8/1991 | Kelley et al. |
| 5,040,715 A | 8/1991 | Green et al. |
| 5,042,707 A | 8/1991 | Taheri |
| 5,056,953 A | 10/1991 | Marot et al. |
| 5,060,658 A | 10/1991 | Dejter, Jr. et al. |
| 5,061,269 A | 10/1991 | Muller |
| 5,062,491 A | 11/1991 | Takeshima et al. |
| 5,062,563 A | 11/1991 | Green et al. |
| 5,065,929 A | 11/1991 | Schulze et al. |
| 5,071,052 A | 12/1991 | Rodak et al. |
| 5,071,430 A | 12/1991 | de Salis et al. |
| 5,074,454 A | 12/1991 | Peters |
| 5,077,506 A | 12/1991 | Krause |
| 5,079,006 A | 1/1992 | Urquhart |
| 5,080,556 A | 1/1992 | Carreno |
| 5,083,695 A | 1/1992 | Foslien et al. |
| 5,084,057 A | 1/1992 | Green et al. |
| 5,088,979 A | 2/1992 | Filipi et al. |
| 5,088,997 A | 2/1992 | Delahuerga et al. |
| 5,089,606 A | 2/1992 | Cole et al. |
| 5,094,247 A | 3/1992 | Hernandez et al. |
| 5,098,004 A | 3/1992 | Kerrigan |
| 5,098,360 A | 3/1992 | Hirota |
| 5,100,042 A | 3/1992 | Gravener et al. |
| 5,100,420 A | 3/1992 | Green et al. |
| 5,100,422 A | 3/1992 | Berguer et al. |
| 5,104,025 A | 4/1992 | Main et al. |
| 5,104,397 A | 4/1992 | Vasconcelos et al. |
| 5,104,400 A | 4/1992 | Berguer et al. |
| 5,106,008 A | 4/1992 | Tompkins et al. |
| 5,108,368 A | 4/1992 | Hammerslag et al. |
| 5,109,722 A | 5/1992 | Hufnagle et al. |
| 5,111,987 A | 5/1992 | Moeinzadeh et al. |
| 5,116,349 A | 5/1992 | Aranyi |
| D327,323 S | 6/1992 | Hunt |
| 5,119,009 A | 6/1992 | McCaleb et al. |
| 5,122,156 A | 6/1992 | Granger et al. |
| 5,124,990 A | 6/1992 | Williamson |
| 5,129,570 A | 7/1992 | Schulze et al. |
| 5,137,198 A | 8/1992 | Nobis et al. |
| 5,139,513 A | 8/1992 | Segato |
| 5,141,144 A | 8/1992 | Foslien et al. |
| 5,142,932 A | 9/1992 | Moya et al. |
| 5,151,102 A | 9/1992 | Kamiyama et al. |
| 5,155,941 A | 10/1992 | Takahashi et al. |
| 5,156,315 A | 10/1992 | Green et al. |
| 5,156,609 A | 10/1992 | Nakao et al. |
| 5,156,614 A | 10/1992 | Green et al. |
| 5,158,222 A | 10/1992 | Green et al. |
| 5,158,567 A | 10/1992 | Green |
| D330,699 S | 11/1992 | Gill |
| 5,163,598 A | 11/1992 | Peters et al. |
| 5,164,652 A | 11/1992 | Johnson et al. |
| 5,168,605 A | 12/1992 | Bartlett |
| 5,170,925 A | 12/1992 | Madden et al. |
| 5,171,247 A | 12/1992 | Hughett et al. |
| 5,171,249 A | 12/1992 | Stefanchik et al. |
| 5,171,253 A | 12/1992 | Klieman |
| 5,173,053 A | 12/1992 | Swanson et al. |
| 5,173,133 A | 12/1992 | Morin et al. |
| 5,176,677 A | 1/1993 | Wuchinich |
| 5,176,688 A | 1/1993 | Narayan et al. |
| 5,181,514 A | 1/1993 | Solomon et al. |
| 5,187,422 A | 2/1993 | Izenbaard et al. |
| 5,188,102 A | 2/1993 | Idemoto et al. |
| 5,188,111 A | 2/1993 | Yates et al. |
| 5,190,517 A | 3/1993 | Zieve et al. |
| 5,190,544 A | 3/1993 | Chapman et al. |
| 5,190,560 A | 3/1993 | Woods et al. |
| 5,190,657 A | 3/1993 | Heagle et al. |
| 5,192,288 A | 3/1993 | Thompson et al. |
| 5,193,731 A | 3/1993 | Aranyi |
| 5,195,505 A | 3/1993 | Josefsen |
| 5,195,968 A | 3/1993 | Lundquist et al. |
| 5,197,648 A | 3/1993 | Gingold |
| 5,197,649 A | 3/1993 | Bessler et al. |
| 5,197,966 A | 3/1993 | Sommerkamp |
| 5,197,970 A | 3/1993 | Green et al. |
| 5,200,280 A | 4/1993 | Karasa |
| 5,201,750 A | 4/1993 | Hocherl et al. |
| 5,205,459 A | 4/1993 | Brinkerhoff et al. |
| 5,207,672 A | 5/1993 | Roth et al. |
| 5,207,697 A | 5/1993 | Carusillo et al. |
| 5,209,747 A | 5/1993 | Knoepfler |
| 5,209,756 A | 5/1993 | Seedhom et al. |
| 5,211,649 A | 5/1993 | Kohler et al. |
| 5,211,655 A | 5/1993 | Hasson |
| 5,217,457 A | 6/1993 | Delahuerga et al. |
| 5,217,478 A | 6/1993 | Rexroth |

(56) References Cited

U.S. PATENT DOCUMENTS

| | | |
|---|---|---|
| 5,219,111 A | 6/1993 | Bilotti et al. |
| 5,220,269 A | 6/1993 | Chen et al. |
| 5,221,036 A | 6/1993 | Takase |
| 5,221,281 A | 6/1993 | Klicek |
| 5,222,945 A | 6/1993 | Basnight |
| 5,222,963 A | 6/1993 | Brinkerhoff et al. |
| 5,222,975 A | 6/1993 | Crainich |
| 5,222,976 A | 6/1993 | Yoon |
| 5,223,675 A | 6/1993 | Taft |
| D338,729 S | 8/1993 | Sprecklemeier et al. |
| 5,234,447 A | 8/1993 | Kaster et al. |
| 5,236,269 A | 8/1993 | Handy |
| 5,236,424 A | 8/1993 | Imran |
| 5,236,440 A | 8/1993 | Hlavacek |
| 5,239,981 A | 8/1993 | Anapliotis |
| 5,240,163 A | 8/1993 | Stein et al. |
| 5,242,456 A | 9/1993 | Nash et al. |
| 5,242,457 A | 9/1993 | Akopov et al. |
| 5,244,462 A | 9/1993 | Delahuerga et al. |
| 5,246,156 A | 9/1993 | Rothfuss et al. |
| 5,246,443 A | 9/1993 | Mai |
| 5,253,793 A | 10/1993 | Green et al. |
| 5,258,007 A | 11/1993 | Spetzler et al. |
| 5,258,008 A | 11/1993 | Wilk |
| 5,258,009 A | 11/1993 | Conners |
| 5,258,010 A | 11/1993 | Green et al. |
| 5,258,012 A | 11/1993 | Luscombe et al. |
| 5,259,366 A | 11/1993 | Reydel et al. |
| 5,259,835 A | 11/1993 | Clark et al. |
| 5,260,637 A | 11/1993 | Pizzi |
| 5,261,135 A | 11/1993 | Mitchell |
| 5,261,877 A | 11/1993 | Fine et al. |
| 5,261,922 A | 11/1993 | Hood |
| 5,263,629 A | 11/1993 | Trumbull et al. |
| 5,263,937 A | 11/1993 | Shipp |
| 5,263,973 A | 11/1993 | Cook |
| 5,264,218 A | 11/1993 | Rogozinski |
| 5,268,622 A | 12/1993 | Philipp |
| 5,269,794 A | 12/1993 | Rexroth |
| 5,271,543 A | 12/1993 | Grant et al. |
| 5,271,544 A | 12/1993 | Fox et al. |
| RE34,519 E | 1/1994 | Fox et al. |
| 5,275,322 A | 1/1994 | Brinkerhoff et al. |
| 5,275,323 A | 1/1994 | Schulze et al. |
| 5,275,608 A | 1/1994 | Forman et al. |
| 5,279,416 A | 1/1994 | Malec et al. |
| 5,281,216 A | 1/1994 | Klicek |
| 5,281,400 A | 1/1994 | Berry, Jr. |
| 5,282,806 A | 2/1994 | Haber et al. |
| 5,282,826 A | 2/1994 | Quadri |
| 5,282,829 A | 2/1994 | Hermes |
| 5,284,128 A | 2/1994 | Hart |
| 5,285,381 A | 2/1994 | Iskarous et al. |
| 5,285,945 A | 2/1994 | Brinkerhoff et al. |
| 5,286,253 A | 2/1994 | Fucci |
| 5,289,963 A | 3/1994 | McGarry et al. |
| 5,290,271 A | 3/1994 | Jernberg |
| 5,290,310 A | 3/1994 | Makower et al. |
| 5,291,133 A | 3/1994 | Gokhale et al. |
| 5,292,053 A | 3/1994 | Bilotti et al. |
| 5,293,024 A | 3/1994 | Sugahara et al. |
| 5,297,714 A | 3/1994 | Kramer |
| 5,302,148 A | 4/1994 | Heinz |
| 5,303,606 A | 4/1994 | Kokinda |
| 5,304,204 A | 4/1994 | Bregen |
| D347,474 S | 5/1994 | Olson |
| 5,307,976 A | 5/1994 | Olson et al. |
| 5,308,353 A | 5/1994 | Beurrier |
| 5,308,358 A | 5/1994 | Bond et al. |
| 5,308,576 A | 5/1994 | Green et al. |
| 5,309,387 A | 5/1994 | Mori et al. |
| 5,309,927 A | 5/1994 | Welch |
| 5,312,023 A | 5/1994 | Green et al. |
| 5,312,024 A | 5/1994 | Grant et al. |
| 5,312,329 A | 5/1994 | Beaty et al. |
| 5,313,935 A | 5/1994 | Kortenbach et al. |
| 5,313,967 A | 5/1994 | Lieber et al. |
| 5,314,424 A | 5/1994 | Nicholas |
| 5,314,445 A | 5/1994 | Heidmueller nee Degwitz et al. |
| 5,314,466 A | 5/1994 | Stern et al. |
| 5,318,221 A | 6/1994 | Green et al. |
| 5,320,627 A | 6/1994 | Sorensen et al. |
| D348,930 S | 7/1994 | Olson |
| 5,326,013 A | 7/1994 | Green et al. |
| 5,329,923 A | 7/1994 | Lundquist |
| 5,330,486 A | 7/1994 | Wilk |
| 5,330,487 A | 7/1994 | Thornton et al. |
| 5,330,502 A | 7/1994 | Hassler et al. |
| 5,331,971 A | 7/1994 | Bales et al. |
| 5,332,142 A | 7/1994 | Robinson et al. |
| 5,333,422 A | 8/1994 | Warren et al. |
| 5,333,772 A | 8/1994 | Rothfuss et al. |
| 5,333,773 A | 8/1994 | Main et al. |
| 5,334,183 A | 8/1994 | Wuchinich |
| 5,336,130 A | 8/1994 | Ray |
| 5,336,229 A | 8/1994 | Noda |
| 5,336,232 A | 8/1994 | Green et al. |
| 5,338,317 A | 8/1994 | Hasson et al. |
| 5,339,799 A | 8/1994 | Kami et al. |
| 5,341,724 A | 8/1994 | Vatel |
| 5,341,807 A | 8/1994 | Nardella |
| 5,341,810 A | 8/1994 | Dardel |
| 5,342,380 A | 8/1994 | Hood |
| 5,342,381 A | 8/1994 | Tidemand |
| 5,342,385 A | 8/1994 | Norelli et al. |
| 5,342,395 A | 8/1994 | Jarrett et al. |
| 5,342,396 A | 8/1994 | Cook |
| 5,343,382 A | 8/1994 | Hale et al. |
| 5,343,391 A | 8/1994 | Mushabac |
| 5,344,059 A | 9/1994 | Green et al. |
| 5,344,060 A | 9/1994 | Gravener et al. |
| 5,344,454 A | 9/1994 | Clarke et al. |
| 5,346,504 A | 9/1994 | Ortiz et al. |
| 5,348,259 A | 9/1994 | Blanco et al. |
| 5,350,104 A | 9/1994 | Main et al. |
| 5,350,355 A | 9/1994 | Sklar |
| 5,350,388 A | 9/1994 | Epstein |
| 5,350,391 A | 9/1994 | Iacovelli |
| 5,350,400 A | 9/1994 | Esposito et al. |
| 5,352,229 A | 10/1994 | Goble et al. |
| 5,352,235 A | 10/1994 | Koros et al. |
| 5,352,238 A | 10/1994 | Green et al. |
| 5,353,798 A | 10/1994 | Sieben |
| 5,354,250 A | 10/1994 | Christensen |
| 5,354,303 A | 10/1994 | Spaeth et al. |
| 5,356,006 A | 10/1994 | Alpern et al. |
| 5,356,064 A | 10/1994 | Green et al. |
| 5,358,506 A | 10/1994 | Green et al. |
| 5,358,510 A | 10/1994 | Luscombe et al. |
| 5,359,231 A | 10/1994 | Flowers et al. |
| D352,780 S | 11/1994 | Glaeser et al. |
| 5,359,993 A | 11/1994 | Slater et al. |
| 5,360,305 A | 11/1994 | Kerrigan |
| 5,360,428 A | 11/1994 | Hutchinson, Jr. |
| 5,361,902 A | 11/1994 | Abidin et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,366,134 A | 11/1994 | Green et al. |
| 5,366,479 A | 11/1994 | McGarry et al. |
| 5,368,015 A | 11/1994 | Wilk |
| 5,368,592 A | 11/1994 | Stern et al. |
| 5,369,565 A | 11/1994 | Chen et al. |
| 5,370,645 A | 12/1994 | Klicek et al. |
| 5,372,124 A | 12/1994 | Takayama et al. |
| 5,372,596 A | 12/1994 | Klicek et al. |
| 5,372,602 A | 12/1994 | Burke |
| 5,374,277 A | 12/1994 | Hassler |
| 5,375,588 A | 12/1994 | Yoon |
| 5,376,095 A | 12/1994 | Ortiz |
| 5,379,933 A | 1/1995 | Green et al. |
| 5,381,649 A | 1/1995 | Webb |
| 5,381,782 A | 1/1995 | DeLaRama et al. |

(56) References Cited

U.S. PATENT DOCUMENTS

| | | |
|---|---|---|
| 5,381,943 A | 1/1995 | Allen et al. |
| 5,382,247 A | 1/1995 | Cimino et al. |
| 5,383,460 A | 1/1995 | Jang et al. |
| 5,383,874 A | 1/1995 | Jackson et al. |
| 5,383,880 A | 1/1995 | Hooven |
| 5,383,881 A | 1/1995 | Green et al. |
| 5,383,882 A | 1/1995 | Buess et al. |
| 5,383,888 A | 1/1995 | Zvenyatsky et al. |
| 5,383,895 A | 1/1995 | Holmes et al. |
| 5,388,568 A | 2/1995 | van der Heide |
| 5,389,072 A | 2/1995 | Imran |
| 5,389,098 A | 2/1995 | Tsuruta et al. |
| 5,389,102 A | 2/1995 | Green et al. |
| 5,389,104 A | 2/1995 | Hahnen et al. |
| 5,391,180 A | 2/1995 | Tovey et al. |
| 5,392,979 A | 2/1995 | Green et al. |
| 5,395,030 A | 3/1995 | Kuramoto et al. |
| 5,395,033 A | 3/1995 | Byrne et al. |
| 5,395,034 A | 3/1995 | Allen et al. |
| 5,395,312 A | 3/1995 | Desai |
| 5,395,384 A | 3/1995 | Duthoit et al. |
| 5,397,046 A | 3/1995 | Savage et al. |
| 5,397,324 A | 3/1995 | Carroll et al. |
| 5,400,267 A | 3/1995 | Denen et al. |
| 5,403,276 A | 4/1995 | Schechter et al. |
| 5,403,312 A | 4/1995 | Yates et al. |
| 5,404,106 A | 4/1995 | Matsuda |
| 5,404,870 A | 4/1995 | Brinkerhoff et al. |
| 5,404,960 A | 4/1995 | Wada et al. |
| 5,405,072 A | 4/1995 | Zlock et al. |
| 5,405,073 A | 4/1995 | Porter |
| 5,405,344 A | 4/1995 | Williamson et al. |
| 5,405,360 A | 4/1995 | Tovey |
| 5,407,293 A | 4/1995 | Crainich |
| 5,408,409 A | 4/1995 | Glassman et al. |
| 5,409,498 A | 4/1995 | Braddock et al. |
| 5,409,703 A | 4/1995 | McAnalley et al. |
| D357,981 S | 5/1995 | Green et al. |
| 5,411,481 A | 5/1995 | Allen et al. |
| 5,411,508 A | 5/1995 | Bessler et al. |
| 5,413,107 A | 5/1995 | Oakley et al. |
| 5,413,267 A | 5/1995 | Solyntjes et al. |
| 5,413,268 A | 5/1995 | Green et al. |
| 5,413,272 A | 5/1995 | Green et al. |
| 5,413,573 A | 5/1995 | Koivukangas |
| 5,415,334 A | 5/1995 | Williamson et al. |
| 5,415,335 A | 5/1995 | Knodell, Jr. |
| 5,417,203 A | 5/1995 | Tovey et al. |
| 5,417,361 A | 5/1995 | Williamson, IV |
| 5,419,766 A | 5/1995 | Chang et al. |
| 5,421,829 A | 6/1995 | Olichney et al. |
| 5,422,567 A | 6/1995 | Matsunaga |
| 5,423,471 A | 6/1995 | Mastri et al. |
| 5,423,809 A | 6/1995 | Klicek |
| 5,423,835 A | 6/1995 | Green et al. |
| 5,425,355 A | 6/1995 | Kulick |
| 5,425,745 A | 6/1995 | Green et al. |
| 5,427,298 A | 6/1995 | Tegtmeier |
| 5,431,322 A | 7/1995 | Green et al. |
| 5,431,323 A | 7/1995 | Smith et al. |
| 5,431,645 A | 7/1995 | Smith et al. |
| 5,431,654 A | 7/1995 | Nic |
| 5,431,668 A | 7/1995 | Burbank, III et al. |
| 5,433,721 A | 7/1995 | Hooven et al. |
| 5,437,681 A | 8/1995 | Meade et al. |
| 5,438,302 A | 8/1995 | Goble |
| 5,438,997 A | 8/1995 | Sieben et al. |
| 5,439,155 A | 8/1995 | Viola |
| 5,439,156 A | 8/1995 | Grant et al. |
| 5,439,479 A | 8/1995 | Shichman et al. |
| 5,441,191 A | 8/1995 | Linden |
| 5,441,193 A | 8/1995 | Gravener |
| 5,441,483 A | 8/1995 | Avitall |
| 5,441,494 A | 8/1995 | Ortiz |
| 5,441,499 A | 8/1995 | Fritzsch |
| 5,443,197 A | 8/1995 | Malis et al. |
| 5,443,198 A | 8/1995 | Viola et al. |
| 5,443,463 A | 8/1995 | Stern et al. |
| 5,444,113 A | 8/1995 | Sinclair et al. |
| 5,445,155 A | 8/1995 | Sieben |
| 5,445,304 A | 8/1995 | Plyley et al. |
| 5,445,604 A | 8/1995 | Lang |
| 5,445,644 A | 8/1995 | Pietrafitta et al. |
| 5,446,646 A | 8/1995 | Miyazaki |
| 5,447,265 A | 9/1995 | Vidal et al. |
| 5,447,417 A | 9/1995 | Kuhl et al. |
| 5,447,513 A | 9/1995 | Davison et al. |
| 5,449,355 A | 9/1995 | Rhum et al. |
| 5,449,365 A | 9/1995 | Green et al. |
| 5,449,370 A | 9/1995 | Vaitekunas |
| 5,452,836 A | 9/1995 | Huitema et al. |
| 5,452,837 A | 9/1995 | Williamson, IV et al. |
| 5,454,378 A | 10/1995 | Palmer et al. |
| 5,454,822 A | 10/1995 | Schob et al. |
| 5,454,827 A | 10/1995 | Aust et al. |
| 5,456,401 A | 10/1995 | Green et al. |
| 5,456,917 A | 10/1995 | Wise et al. |
| 5,458,279 A | 10/1995 | Plyley |
| 5,458,579 A | 10/1995 | Chodorow et al. |
| 5,462,215 A | 10/1995 | Viola et al. |
| 5,464,013 A | 11/1995 | Lemelson |
| 5,464,144 A | 11/1995 | Guy et al. |
| 5,464,300 A | 11/1995 | Crainich |
| 5,465,819 A | 11/1995 | Weilant et al. |
| 5,465,894 A | 11/1995 | Clark et al. |
| 5,465,895 A | 11/1995 | Knodel et al. |
| 5,465,896 A | 11/1995 | Allen et al. |
| 5,466,020 A | 11/1995 | Page et al. |
| 5,467,911 A | 11/1995 | Tsuruta et al. |
| 5,468,253 A | 11/1995 | Bezwada et al. |
| 5,470,006 A | 11/1995 | Rodak |
| 5,470,007 A | 11/1995 | Plyley et al. |
| 5,470,008 A | 11/1995 | Rodak |
| 5,470,009 A | 11/1995 | Rodak |
| 5,470,010 A | 11/1995 | Rothfuss et al. |
| 5,471,129 A | 11/1995 | Mann |
| 5,472,132 A | 12/1995 | Savage et al. |
| 5,472,442 A | 12/1995 | Klicek |
| 5,473,204 A | 12/1995 | Temple |
| 5,474,057 A | 12/1995 | Makower et al. |
| 5,474,223 A | 12/1995 | Viola et al. |
| 5,474,566 A | 12/1995 | Alesi et al. |
| 5,474,570 A | 12/1995 | Kockerling et al. |
| 5,474,738 A | 12/1995 | Nichols et al. |
| 5,476,206 A | 12/1995 | Green et al. |
| 5,476,479 A | 12/1995 | Green et al. |
| 5,476,481 A | 12/1995 | Schondorf |
| 5,478,003 A | 12/1995 | Green et al. |
| 5,478,354 A | 12/1995 | Tovey et al. |
| 5,480,089 A | 1/1996 | Blewett |
| 5,480,409 A | 1/1996 | Riza |
| 5,482,197 A | 1/1996 | Green et al. |
| 5,483,952 A | 1/1996 | Aranyi |
| 5,484,095 A | 1/1996 | Green et al. |
| 5,484,398 A | 1/1996 | Stoddard |
| 5,484,451 A | 1/1996 | Akopov et al. |
| 5,485,947 A | 1/1996 | Olson et al. |
| 5,485,952 A | 1/1996 | Fontayne |
| 5,487,377 A | 1/1996 | Smith et al. |
| 5,487,499 A | 1/1996 | Sorrentino et al. |
| 5,487,500 A | 1/1996 | Knodel et al. |
| 5,489,058 A | 2/1996 | Plyley et al. |
| 5,489,256 A | 2/1996 | Adair |
| 5,489,290 A | 2/1996 | Furnish |
| 5,490,819 A | 2/1996 | Nicholas et al. |
| 5,492,671 A | 2/1996 | Krafft |
| 5,496,312 A | 3/1996 | Klicek |
| 5,496,317 A | 3/1996 | Goble et al. |
| 5,497,933 A | 3/1996 | DeFonzo et al. |
| 5,498,164 A | 3/1996 | Ward et al. |
| 5,498,838 A | 3/1996 | Furman |
| 5,501,654 A | 3/1996 | Failla et al. |
| 5,503,320 A | 4/1996 | Webster et al. |
| 5,503,635 A | 4/1996 | Sauer et al. |

(56) References Cited

U.S. PATENT DOCUMENTS

| | | |
|---|---|---|
| 5,503,638 A | 4/1996 | Cooper et al. |
| 5,505,363 A | 4/1996 | Green et al. |
| 5,507,425 A | 4/1996 | Ziglioli |
| 5,507,426 A | 4/1996 | Young et al. |
| 5,507,773 A | 4/1996 | Huitema et al. |
| 5,509,596 A | 4/1996 | Green et al. |
| 5,509,916 A | 4/1996 | Taylor |
| 5,509,918 A | 4/1996 | Romano |
| 5,511,564 A | 4/1996 | Wilk |
| 5,514,129 A | 5/1996 | Smith |
| 5,514,149 A | 5/1996 | Green et al. |
| 5,514,157 A | 5/1996 | Nicholas et al. |
| 5,518,163 A | 5/1996 | Hooven |
| 5,518,164 A | 5/1996 | Hooven |
| 5,520,609 A | 5/1996 | Moll et al. |
| 5,520,634 A | 5/1996 | Fox et al. |
| 5,520,678 A | 5/1996 | Heckele et al. |
| 5,520,700 A | 5/1996 | Beyar et al. |
| 5,522,817 A | 6/1996 | Sander et al. |
| 5,522,831 A | 6/1996 | Sleister et al. |
| 5,527,264 A | 6/1996 | Moll et al. |
| 5,527,320 A | 6/1996 | Carruthers et al. |
| 5,529,235 A | 6/1996 | Boiarski et al. |
| D372,086 S | 7/1996 | Grasso et al. |
| 5,531,305 A | 7/1996 | Roberts et al. |
| 5,531,744 A | 7/1996 | Nardella et al. |
| 5,531,856 A | 7/1996 | Moll et al. |
| 5,533,521 A | 7/1996 | Granger |
| 5,533,581 A | 7/1996 | Barth et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,540,705 A | 7/1996 | Meade et al. |
| 5,541,376 A | 7/1996 | Ladtkow et al. |
| 5,541,489 A | 7/1996 | Dunstan |
| 5,542,594 A | 8/1996 | McKean et al. |
| 5,542,945 A | 8/1996 | Fritzsch |
| 5,542,949 A | 8/1996 | Yoon |
| 5,543,119 A | 8/1996 | Sutter et al. |
| 5,543,695 A | 8/1996 | Culp et al. |
| 5,544,802 A | 8/1996 | Crainich |
| 5,547,117 A | 8/1996 | Hamblin et al. |
| 5,549,583 A | 8/1996 | Sanford et al. |
| 5,549,621 A | 8/1996 | Bessler et al. |
| 5,549,627 A | 8/1996 | Kieturakis |
| 5,549,628 A | 8/1996 | Cooper et al. |
| 5,549,637 A | 8/1996 | Crainich |
| 5,551,622 A | 9/1996 | Yoon |
| 5,553,624 A | 9/1996 | Francese et al. |
| 5,553,675 A | 9/1996 | Pitzen et al. |
| 5,553,765 A | 9/1996 | Knodel et al. |
| 5,554,148 A | 9/1996 | Aebischer et al. |
| 5,554,169 A | 9/1996 | Green et al. |
| 5,556,020 A | 9/1996 | Hou |
| 5,556,416 A | 9/1996 | Clark et al. |
| 5,558,533 A | 9/1996 | Hashizawa et al. |
| 5,558,665 A | 9/1996 | Kieturakis |
| 5,558,671 A | 9/1996 | Yates |
| 5,560,530 A | 10/1996 | Bolanos et al. |
| 5,560,532 A | 10/1996 | DeFonzo et al. |
| 5,561,881 A | 10/1996 | Klinger et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,690 A | 10/1996 | Green et al. |
| 5,562,701 A | 10/1996 | Huitema et al. |
| 5,562,702 A | 10/1996 | Huitema et al. |
| 5,563,481 A | 10/1996 | Krause |
| 5,564,615 A | 10/1996 | Bishop et al. |
| 5,569,161 A | 10/1996 | Ebling et al. |
| 5,569,270 A | 10/1996 | Weng |
| 5,569,284 A | 10/1996 | Young et al. |
| 5,571,090 A | 11/1996 | Sherts |
| 5,571,100 A | 11/1996 | Goble et al. |
| 5,571,116 A | 11/1996 | Bolanos et al. |
| 5,571,285 A | 11/1996 | Chow et al. |
| 5,571,488 A | 11/1996 | Beerstecher et al. |
| 5,573,169 A | 11/1996 | Green et al. |
| 5,573,543 A | 11/1996 | Akopov et al. |
| 5,574,431 A | 11/1996 | McKeown et al. |
| 5,575,054 A | 11/1996 | Klinzing et al. |
| 5,575,789 A | 11/1996 | Bell et al. |
| 5,575,799 A | 11/1996 | Bolanos et al. |
| 5,575,803 A | 11/1996 | Cooper et al. |
| 5,575,805 A | 11/1996 | Li |
| 5,577,654 A | 11/1996 | Bishop |
| 5,578,052 A | 11/1996 | Koros et al. |
| 5,579,978 A | 12/1996 | Green et al. |
| 5,580,067 A | 12/1996 | Hamblin et al. |
| 5,582,611 A | 12/1996 | Tsuruta et al. |
| 5,582,617 A | 12/1996 | Klieman et al. |
| 5,582,907 A | 12/1996 | Pall |
| 5,583,114 A | 12/1996 | Barrows et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,591,170 A | 1/1997 | Spievack et al. |
| 5,591,187 A | 1/1997 | Dekel |
| 5,597,107 A | 1/1997 | Knodel et al. |
| 5,599,151 A | 2/1997 | Daum et al. |
| 5,599,279 A | 2/1997 | Slotman et al. |
| 5,599,344 A | 2/1997 | Paterson |
| 5,599,350 A | 2/1997 | Schulze et al. |
| 5,599,852 A | 2/1997 | Scopelianos et al. |
| 5,601,224 A | 2/1997 | Bishop et al. |
| 5,601,573 A | 2/1997 | Fogelberg et al. |
| 5,601,604 A | 2/1997 | Vincent |
| 5,602,449 A | 2/1997 | Krause et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,607,433 A | 3/1997 | Polla et al. |
| 5,607,436 A | 3/1997 | Pratt et al. |
| 5,607,450 A | 3/1997 | Zvenyatsky et al. |
| 5,607,474 A | 3/1997 | Athanasiou et al. |
| 5,609,285 A | 3/1997 | Grant et al. |
| 5,609,601 A | 3/1997 | Kolesa et al. |
| 5,611,709 A | 3/1997 | McAnulty |
| 5,613,499 A | 3/1997 | Palmer et al. |
| 5,613,937 A | 3/1997 | Garrison et al. |
| 5,613,966 A | 3/1997 | Makower et al. |
| 5,614,887 A | 3/1997 | Buchbinder |
| 5,615,820 A | 4/1997 | Viola |
| 5,618,294 A | 4/1997 | Aust et al. |
| 5,618,303 A | 4/1997 | Marlow et al. |
| 5,618,307 A | 4/1997 | Donlon et al. |
| 5,619,992 A | 4/1997 | Guthrie et al. |
| 5,620,289 A | 4/1997 | Curry |
| 5,620,326 A | 4/1997 | Younker |
| 5,620,452 A | 4/1997 | Yoon |
| 5,624,398 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,626,979 A | 5/1997 | Mitsui et al. |
| 5,628,446 A | 5/1997 | Geiste et al. |
| 5,628,743 A | 5/1997 | Cimino |
| 5,628,745 A | 5/1997 | Bek |
| 5,630,539 A | 5/1997 | Plyley et al. |
| 5,630,540 A | 5/1997 | Blewett |
| 5,630,541 A | 5/1997 | Williamson, IV et al. |
| 5,630,782 A | 5/1997 | Adair |
| 5,631,973 A | 5/1997 | Green |
| 5,632,432 A | 5/1997 | Schulze et al. |
| 5,632,433 A | 5/1997 | Grant et al. |
| 5,633,374 A | 5/1997 | Humphrey et al. |
| 5,634,584 A | 6/1997 | Okorocha et al. |
| 5,636,779 A | 6/1997 | Palmer |

(56) References Cited

U.S. PATENT DOCUMENTS

| | | |
|---|---|---|
| 5,636,780 A | 6/1997 | Green et al. |
| 5,637,110 A | 6/1997 | Pennybacker et al. |
| 5,638,582 A | 6/1997 | Klatt et al. |
| 5,639,008 A | 6/1997 | Gallagher et al. |
| D381,077 S | 7/1997 | Hunt |
| 5,643,291 A | 7/1997 | Pier et al. |
| 5,643,293 A | 7/1997 | Kogasaka et al. |
| 5,643,294 A | 7/1997 | Tovey et al. |
| 5,643,319 A | 7/1997 | Green et al. |
| 5,645,209 A | 7/1997 | Green et al. |
| 5,647,526 A | 7/1997 | Green et al. |
| 5,647,869 A | 7/1997 | Goble et al. |
| 5,649,937 A | 7/1997 | Bito et al. |
| 5,649,956 A | 7/1997 | Jensen et al. |
| 5,651,491 A | 7/1997 | Heaton et al. |
| 5,651,762 A | 7/1997 | Bridges |
| 5,651,821 A | 7/1997 | Uchida |
| 5,653,373 A | 8/1997 | Green et al. |
| 5,653,374 A | 8/1997 | Young et al. |
| 5,653,677 A | 8/1997 | Okada et al. |
| 5,653,721 A | 8/1997 | Knodel et al. |
| 5,653,748 A | 8/1997 | Strecker |
| 5,655,698 A | 8/1997 | Yoon |
| 5,656,917 A | 8/1997 | Theobald |
| 5,657,417 A | 8/1997 | Di Troia |
| 5,657,429 A | 8/1997 | Wang et al. |
| 5,657,921 A | 8/1997 | Young et al. |
| 5,658,238 A | 8/1997 | Suzuki et al. |
| 5,658,281 A | 8/1997 | Heard |
| 5,658,298 A | 8/1997 | Vincent et al. |
| 5,658,300 A | 8/1997 | Bito et al. |
| 5,658,307 A | 8/1997 | Exconde |
| 5,662,258 A | 9/1997 | Knodel et al. |
| 5,662,260 A | 9/1997 | Yoon |
| 5,662,662 A | 9/1997 | Bishop et al. |
| 5,662,667 A | 9/1997 | Knodel |
| 5,664,404 A | 9/1997 | Ivanov et al. |
| 5,665,085 A | 9/1997 | Nardella |
| 5,667,517 A | 9/1997 | Hooven |
| 5,667,526 A | 9/1997 | Levin |
| 5,667,527 A | 9/1997 | Cook |
| 5,667,864 A | 9/1997 | Landoll |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,669,918 A | 9/1997 | Balazs et al. |
| 5,672,945 A | 9/1997 | Krause |
| 5,673,840 A | 10/1997 | Schulze et al. |
| 5,673,841 A | 10/1997 | Schulze et al. |
| 5,673,842 A | 10/1997 | Bittner et al. |
| 5,674,184 A | 10/1997 | Hassler, Jr. |
| 5,674,286 A | 10/1997 | D'Alessio et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,681,341 A | 10/1997 | Lunsford et al. |
| 5,683,349 A | 11/1997 | Makower et al. |
| 5,685,474 A | 11/1997 | Seeber |
| 5,686,090 A | 11/1997 | Schilder et al. |
| 5,688,270 A | 11/1997 | Yates et al. |
| 5,690,269 A | 11/1997 | Bolanos et al. |
| 5,690,675 A | 11/1997 | Sawyer et al. |
| 5,692,668 A | 12/1997 | Schulze et al. |
| 5,693,020 A | 12/1997 | Rauh |
| 5,693,042 A | 12/1997 | Boiarski et al. |
| 5,693,051 A | 12/1997 | Schulze et al. |
| 5,693,494 A | 12/1997 | Becker |
| 5,695,502 A | 12/1997 | Pier et al. |
| 5,695,504 A | 12/1997 | Gifford, III et al. |
| 5,695,524 A | 12/1997 | Kelley et al. |
| 5,697,542 A | 12/1997 | Knodel et al. |
| 5,697,543 A | 12/1997 | Burdorff |
| 5,697,909 A | 12/1997 | Eggers et al. |
| 5,697,943 A | 12/1997 | Sauer et al. |
| 5,700,270 A | 12/1997 | Peyser et al. |
| 5,700,276 A | 12/1997 | Benecke |
| 5,702,387 A | 12/1997 | Arts et al. |
| 5,702,408 A | 12/1997 | Wales et al. |
| 5,702,409 A | 12/1997 | Rayburn et al. |
| 5,704,087 A | 1/1998 | Strub |
| 5,704,534 A | 1/1998 | Huitema et al. |
| 5,706,997 A | 1/1998 | Green et al. |
| 5,706,998 A | 1/1998 | Plyley et al. |
| 5,707,392 A | 1/1998 | Kortenbach |
| 5,709,334 A | 1/1998 | Sorrentino et al. |
| 5,709,335 A | 1/1998 | Heck |
| 5,709,680 A | 1/1998 | Yates et al. |
| 5,709,706 A | 1/1998 | Kienzle et al. |
| 5,711,472 A | 1/1998 | Bryan |
| 5,711,960 A | 1/1998 | Shikinami |
| 5,712,460 A | 1/1998 | Carr et al. |
| 5,713,128 A | 2/1998 | Schrenk et al. |
| 5,713,505 A | 2/1998 | Huitema |
| 5,713,895 A | 2/1998 | Lontine et al. |
| 5,713,896 A | 2/1998 | Nardella |
| 5,713,920 A | 2/1998 | Bezwada et al. |
| 5,715,604 A | 2/1998 | Lanzoni |
| 5,715,836 A | 2/1998 | Kliegis et al. |
| 5,715,987 A | 2/1998 | Kelley et al. |
| 5,715,988 A | 2/1998 | Palmer |
| 5,716,352 A | 2/1998 | Viola et al. |
| 5,716,366 A | 2/1998 | Yates |
| 5,718,359 A | 2/1998 | Palmer et al. |
| 5,718,360 A | 2/1998 | Green et al. |
| 5,718,548 A | 2/1998 | Cotellessa |
| 5,718,714 A | 2/1998 | Livneh |
| 5,720,744 A | 2/1998 | Eggleston et al. |
| D393,067 S | 3/1998 | Geary et al. |
| 5,724,025 A | 3/1998 | Tavori |
| 5,725,536 A | 3/1998 | Oberlin et al. |
| 5,725,554 A | 3/1998 | Simon et al. |
| 5,728,110 A | 3/1998 | Vidal et al. |
| 5,728,113 A | 3/1998 | Sherts |
| 5,728,121 A | 3/1998 | Bimbo et al. |
| 5,730,758 A | 3/1998 | Allgeyer |
| 5,732,712 A | 3/1998 | Adair |
| 5,732,821 A | 3/1998 | Stone et al. |
| 5,732,871 A | 3/1998 | Clark et al. |
| 5,732,872 A | 3/1998 | Bolduc et al. |
| 5,733,308 A | 3/1998 | Daugherty et al. |
| 5,735,445 A | 4/1998 | Vidal et al. |
| 5,735,848 A | 4/1998 | Yates et al. |
| 5,735,874 A | 4/1998 | Measamer et al. |
| 5,736,271 A | 4/1998 | Cisar et al. |
| 5,738,474 A | 4/1998 | Blewett |
| 5,738,629 A | 4/1998 | Moll et al. |
| 5,738,648 A | 4/1998 | Lands et al. |
| 5,741,271 A | 4/1998 | Nakao et al. |
| 5,743,456 A | 4/1998 | Jones et al. |
| 5,747,953 A | 5/1998 | Philipp |
| 5,749,889 A | 5/1998 | Bacich et al. |
| 5,749,893 A | 5/1998 | Vidal et al. |
| 5,749,896 A | 5/1998 | Cook |
| 5,749,968 A | 5/1998 | Melanson et al. |
| 5,752,644 A | 5/1998 | Bolanos et al. |
| 5,752,965 A | 5/1998 | Francis et al. |
| 5,752,970 A | 5/1998 | Yoon |
| 5,752,973 A | 5/1998 | Kieturakis |
| 5,755,717 A | 5/1998 | Yates et al. |
| 5,755,726 A | 5/1998 | Pratt et al. |
| 5,758,814 A | 6/1998 | Gallagher et al. |
| 5,762,255 A | 6/1998 | Chrisman et al. |
| 5,762,256 A | 6/1998 | Mastri et al. |
| 5,762,458 A | 6/1998 | Wang et al. |
| 5,765,565 A | 6/1998 | Adair |
| 5,766,186 A | 6/1998 | Faraz et al. |
| 5,766,188 A | 6/1998 | Igaki |
| 5,766,205 A | 6/1998 | Zvenyatsky et al. |
| 5,769,303 A | 6/1998 | Knodel et al. |
| 5,769,640 A | 6/1998 | Jacobus et al. |
| 5,769,748 A | 6/1998 | Eyerly et al. |
| 5,769,791 A | 6/1998 | Benaron et al. |
| 5,769,892 A | 6/1998 | Kingwell |

(56) References Cited

U.S. PATENT DOCUMENTS

| | | |
|---|---|---|
| 5,772,099 A | 6/1998 | Gravener |
| 5,772,379 A | 6/1998 | Evensen |
| 5,772,578 A | 6/1998 | Heimberger et al. |
| 5,772,659 A | 6/1998 | Becker et al. |
| 5,773,991 A | 6/1998 | Chen |
| 5,776,130 A | 7/1998 | Buysse et al. |
| 5,778,939 A | 7/1998 | Hok-Yin |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,748 A | 7/1998 | Palmer et al. |
| 5,782,749 A | 7/1998 | Riza |
| 5,782,859 A | 7/1998 | Nicholas et al. |
| 5,784,934 A | 7/1998 | Izumisawa |
| 5,785,232 A | 7/1998 | Vidal et al. |
| 5,785,647 A | 7/1998 | Tompkins et al. |
| 5,787,897 A | 8/1998 | Kieturakis |
| 5,791,231 A | 8/1998 | Cohn et al. |
| 5,792,135 A | 8/1998 | Madhani et al. |
| 5,792,162 A | 8/1998 | Jolly et al. |
| 5,792,165 A | 8/1998 | Klieman et al. |
| 5,792,573 A | 8/1998 | Pitzen et al. |
| 5,794,834 A | 8/1998 | Hamblin et al. |
| 5,796,188 A | 8/1998 | Bays |
| 5,797,536 A | 8/1998 | Smith et al. |
| 5,797,537 A | 8/1998 | Oberlin et al. |
| 5,797,538 A | 8/1998 | Heaton et al. |
| 5,797,637 A | 8/1998 | Ervin |
| 5,797,900 A | 8/1998 | Madhani et al. |
| 5,797,906 A | 8/1998 | Rhum et al. |
| 5,797,927 A | 8/1998 | Yoon |
| 5,797,941 A | 8/1998 | Schulze et al. |
| 5,797,959 A | 8/1998 | Castro et al. |
| 5,799,857 A | 9/1998 | Robertson et al. |
| 5,800,379 A | 9/1998 | Edwards |
| 5,800,423 A | 9/1998 | Jensen |
| 5,804,726 A | 9/1998 | Geib et al. |
| 5,804,936 A | 9/1998 | Brodsky et al. |
| 5,806,676 A | 9/1998 | Wasgien |
| 5,807,241 A | 9/1998 | Heimberger |
| 5,807,376 A | 9/1998 | Viola et al. |
| 5,807,378 A | 9/1998 | Jensen et al. |
| 5,807,393 A | 9/1998 | Williamson, IV et al. |
| 5,809,441 A | 9/1998 | McKee |
| 5,810,721 A | 9/1998 | Mueller et al. |
| 5,810,811 A | 9/1998 | Yates et al. |
| 5,810,846 A | 9/1998 | Virnich et al. |
| 5,810,855 A | 9/1998 | Rayburn et al. |
| 5,812,188 A | 9/1998 | Adair |
| 5,813,813 A | 9/1998 | Daum et al. |
| 5,814,055 A | 9/1998 | Knodel et al. |
| 5,814,057 A | 9/1998 | Oi et al. |
| 5,816,471 A | 10/1998 | Plyley et al. |
| 5,817,084 A | 10/1998 | Jensen |
| 5,817,091 A | 10/1998 | Nardella et al. |
| 5,817,093 A | 10/1998 | Williamson, IV et al. |
| 5,817,109 A | 10/1998 | McGarry et al. |
| 5,817,119 A | 10/1998 | Klieman et al. |
| 5,820,009 A | 10/1998 | Melling et al. |
| 5,823,066 A | 10/1998 | Huitema et al. |
| 5,824,333 A | 10/1998 | Scopelianos et al. |
| 5,826,776 A | 10/1998 | Schulze et al. |
| 5,827,271 A | 10/1998 | Buysse et al. |
| 5,827,298 A | 10/1998 | Hart et al. |
| 5,827,323 A | 10/1998 | Klieman et al. |
| 5,829,662 A | 11/1998 | Allen et al. |
| 5,830,598 A | 11/1998 | Patterson |
| 5,833,690 A | 11/1998 | Yates et al. |
| 5,833,695 A | 11/1998 | Yoon |
| 5,833,696 A | 11/1998 | Whitfield et al. |
| 5,836,503 A | 11/1998 | Ehrenfels et al. |
| 5,836,960 A | 11/1998 | Kolesa et al. |
| 5,839,369 A | 11/1998 | Chatterjee et al. |
| 5,839,639 A | 11/1998 | Sauer et al. |
| 5,841,284 A | 11/1998 | Takahashi |
| 5,843,021 A | 12/1998 | Edwards et al. |
| 5,843,096 A | 12/1998 | Igaki et al. |
| 5,843,097 A | 12/1998 | Mayenberger et al. |
| 5,843,122 A | 12/1998 | Riza |
| 5,843,132 A | 12/1998 | Ilvento |
| 5,843,169 A | 12/1998 | Taheri |
| 5,846,254 A | 12/1998 | Schulze et al. |
| 5,847,566 A | 12/1998 | Marritt et al. |
| 5,849,011 A | 12/1998 | Jones et al. |
| 5,849,020 A | 12/1998 | Long et al. |
| 5,849,023 A | 12/1998 | Mericle |
| 5,851,179 A | 12/1998 | Ritson et al. |
| 5,851,212 A | 12/1998 | Zirps et al. |
| 5,853,366 A | 12/1998 | Dowlatshahi |
| 5,855,311 A | 1/1999 | Hamblin et al. |
| 5,855,583 A | 1/1999 | Wang et al. |
| 5,860,581 A | 1/1999 | Robertson et al. |
| 5,860,975 A | 1/1999 | Goble et al. |
| 5,865,361 A | 2/1999 | Milliman et al. |
| 5,865,638 A | 2/1999 | Trafton |
| 5,868,361 A | 2/1999 | Rinderer |
| 5,868,664 A | 2/1999 | Speier et al. |
| 5,868,760 A | 2/1999 | McGuckin, Jr. |
| 5,868,790 A | 2/1999 | Vincent et al. |
| 5,871,135 A | 2/1999 | Williamson, IV et al. |
| 5,873,885 A | 2/1999 | Weidenbenner |
| 5,876,401 A | 3/1999 | Schulze et al. |
| 5,878,193 A | 3/1999 | Wang et al. |
| 5,878,607 A | 3/1999 | Nunes et al. |
| 5,878,937 A | 3/1999 | Green et al. |
| 5,878,938 A | 3/1999 | Bittner et al. |
| 5,881,777 A | 3/1999 | Bassi et al. |
| 5,881,943 A | 3/1999 | Heck et al. |
| 5,891,094 A | 4/1999 | Masterson et al. |
| 5,891,160 A | 4/1999 | Williamson, IV et al. |
| 5,891,558 A | 4/1999 | Bell et al. |
| 5,893,506 A | 4/1999 | Powell |
| 5,893,835 A | 4/1999 | Witt et al. |
| 5,893,878 A | 4/1999 | Pierce |
| 5,894,979 A | 4/1999 | Powell |
| 5,897,552 A | 4/1999 | Edwards et al. |
| 5,897,562 A | 4/1999 | Bolanos et al. |
| 5,899,824 A | 5/1999 | Kurtz et al. |
| 5,899,914 A | 5/1999 | Zirps et al. |
| 5,901,895 A | 5/1999 | Heaton et al. |
| 5,902,312 A | 5/1999 | Frater et al. |
| 5,903,117 A | 5/1999 | Gregory |
| 5,904,647 A | 5/1999 | Ouchi |
| 5,904,693 A | 5/1999 | Dicesare et al. |
| 5,904,702 A | 5/1999 | Ek et al. |
| 5,906,577 A | 5/1999 | Beane et al. |
| 5,906,625 A | 5/1999 | Bito et al. |
| 5,907,211 A | 5/1999 | Hall et al. |
| 5,907,664 A | 5/1999 | Wang et al. |
| 5,908,402 A | 6/1999 | Blythe |
| 5,908,427 A | 6/1999 | McKean et al. |
| 5,909,062 A | 6/1999 | Krietzman |
| 5,911,353 A | 6/1999 | Bolanos et al. |
| 5,915,616 A | 6/1999 | Viola et al. |
| 5,916,225 A | 6/1999 | Kugel |
| 5,918,791 A | 7/1999 | Sorrentino et al. |
| 5,919,198 A | 7/1999 | Graves, Jr. et al. |
| 5,921,956 A | 7/1999 | Grinberg et al. |
| 5,924,864 A | 7/1999 | Loge et al. |
| 5,928,137 A | 7/1999 | Green |
| 5,928,256 A | 7/1999 | Riza |
| 5,931,847 A | 8/1999 | Bittner et al. |
| 5,931,853 A | 8/1999 | McEwen et al. |
| 5,937,951 A | 8/1999 | Izuchukwu et al. |
| 5,938,667 A | 8/1999 | Peyser et al. |
| 5,941,442 A | 8/1999 | Geiste et al. |
| 5,941,890 A | 8/1999 | Voegele et al. |
| 5,944,172 A | 8/1999 | Hannula |
| 5,944,715 A | 8/1999 | Goble et al. |
| 5,946,978 A | 9/1999 | Yamashita |
| 5,947,984 A | 9/1999 | Whipple |
| 5,947,996 A | 9/1999 | Logeman |

(56) References Cited

U.S. PATENT DOCUMENTS

| | | |
|---|---|---|
| 5,948,030 A | 9/1999 | Miller et al. |
| 5,948,429 A | 9/1999 | Bell et al. |
| 5,951,301 A | 9/1999 | Younker |
| 5,951,516 A | 9/1999 | Bunyan |
| 5,951,552 A | 9/1999 | Long et al. |
| 5,951,574 A | 9/1999 | Stefanchik et al. |
| 5,951,575 A | 9/1999 | Bolduc et al. |
| 5,951,581 A | 9/1999 | Saadat et al. |
| 5,954,259 A | 9/1999 | Viola et al. |
| 5,957,831 A | 9/1999 | Adair |
| 5,964,394 A | 10/1999 | Robertson |
| 5,964,774 A | 10/1999 | McKean et al. |
| 5,966,126 A | 10/1999 | Szabo |
| 5,971,916 A | 10/1999 | Koren |
| 5,973,221 A | 10/1999 | Collyer et al. |
| D416,089 S | 11/1999 | Barton et al. |
| 5,976,122 A | 11/1999 | Madhani et al. |
| 5,977,746 A | 11/1999 | Hershberger et al. |
| 5,980,248 A | 11/1999 | Kusakabe et al. |
| 5,984,949 A | 11/1999 | Levin |
| 5,988,479 A | 11/1999 | Palmer |
| 5,990,379 A | 11/1999 | Gregory |
| 5,993,466 A | 11/1999 | Yoon |
| 5,997,528 A | 12/1999 | Bisch et al. |
| 5,997,552 A | 12/1999 | Person et al. |
| 6,001,108 A | 12/1999 | Wang et al. |
| 6,003,517 A | 12/1999 | Sheffield et al. |
| 6,004,319 A | 12/1999 | Goble et al. |
| 6,004,335 A | 12/1999 | Vaitekunas et al. |
| 6,007,521 A | 12/1999 | Bidwell et al. |
| 6,010,054 A | 1/2000 | Johnson et al. |
| 6,010,513 A | 1/2000 | Tormala et al. |
| 6,010,520 A | 1/2000 | Pattison |
| 6,012,494 A | 1/2000 | Balazs |
| 6,013,076 A | 1/2000 | Goble et al. |
| 6,013,991 A | 1/2000 | Philipp |
| 6,015,406 A | 1/2000 | Goble et al. |
| 6,015,417 A | 1/2000 | Reynolds, Jr. |
| 6,017,322 A | 1/2000 | Snoke et al. |
| 6,017,354 A | 1/2000 | Culp et al. |
| 6,017,356 A | 1/2000 | Frederick et al. |
| 6,018,227 A | 1/2000 | Kumar et al. |
| 6,019,745 A | 2/2000 | Gray |
| 6,019,780 A | 2/2000 | Lombardo et al. |
| 6,022,352 A | 2/2000 | Vandewalle |
| 6,023,641 A | 2/2000 | Thompson |
| 6,024,708 A | 2/2000 | Bales et al. |
| 6,024,741 A | 2/2000 | Williamson, IV et al. |
| 6,024,748 A | 2/2000 | Manzo et al. |
| 6,024,750 A | 2/2000 | Mastri et al. |
| 6,024,764 A | 2/2000 | Schroeppel |
| 6,027,501 A | 2/2000 | Goble et al. |
| 6,030,384 A | 2/2000 | Nezhat |
| 6,032,849 A | 3/2000 | Mastri et al. |
| 6,033,105 A | 3/2000 | Barker et al. |
| 6,033,378 A | 3/2000 | Lundquist et al. |
| 6,033,399 A | 3/2000 | Gines |
| 6,033,427 A | 3/2000 | Lee |
| 6,036,641 A | 3/2000 | Taylor et al. |
| 6,036,667 A | 3/2000 | Manna et al. |
| 6,037,724 A | 3/2000 | Buss et al. |
| 6,037,927 A | 3/2000 | Rosenberg |
| 6,039,126 A | 3/2000 | Hsieh |
| 6,039,733 A | 3/2000 | Buysse et al. |
| 6,039,734 A | 3/2000 | Goble |
| 6,042,601 A | 3/2000 | Smith |
| 6,042,607 A | 3/2000 | Williamson, IV et al. |
| 6,043,626 A | 3/2000 | Snyder et al. |
| 6,045,560 A | 4/2000 | McKean et al. |
| 6,047,861 A | 4/2000 | Vidal et al. |
| 6,049,145 A | 4/2000 | Austin et al. |
| 6,050,172 A | 4/2000 | Corves et al. |
| 6,050,472 A | 4/2000 | Shibata |
| 6,050,989 A | 4/2000 | Fox et al. |
| 6,050,990 A | 4/2000 | Tankovich et al. |
| 6,050,996 A | 4/2000 | Schmaltz et al. |
| 6,053,390 A | 4/2000 | Green et al. |
| 6,053,899 A | 4/2000 | Slanda et al. |
| 6,053,922 A | 4/2000 | Krause et al. |
| 6,054,142 A | 4/2000 | Li et al. |
| 6,055,062 A | 4/2000 | Dina et al. |
| RE36,720 E | 5/2000 | Green et al. |
| 6,056,735 A | 5/2000 | Okada et al. |
| 6,056,746 A | 5/2000 | Goble et al. |
| 6,059,806 A | 5/2000 | Hoegerle |
| 6,062,360 A | 5/2000 | Shields |
| 6,063,020 A | 5/2000 | Jones et al. |
| 6,063,025 A | 5/2000 | Bridges et al. |
| 6,063,050 A | 5/2000 | Manna et al. |
| 6,063,095 A | 5/2000 | Wang et al. |
| 6,063,097 A | 5/2000 | Oi et al. |
| 6,063,098 A | 5/2000 | Houser et al. |
| 6,065,679 A | 5/2000 | Levie et al. |
| 6,065,919 A | 5/2000 | Peck |
| 6,066,132 A | 5/2000 | Chen et al. |
| 6,066,151 A | 5/2000 | Miyawaki et al. |
| 6,068,627 A | 5/2000 | Orszulak et al. |
| 6,071,233 A | 6/2000 | Ishikawa et al. |
| 6,072,299 A | 6/2000 | Kurle et al. |
| 6,074,386 A | 6/2000 | Goble et al. |
| 6,074,401 A | 6/2000 | Gardiner et al. |
| 6,075,441 A | 6/2000 | Maloney |
| 6,077,280 A | 6/2000 | Fossum |
| 6,077,286 A | 6/2000 | Cuschieri et al. |
| 6,077,290 A | 6/2000 | Marini |
| 6,079,606 A | 6/2000 | Milliman et al. |
| 6,080,181 A | 6/2000 | Jensen et al. |
| 6,082,577 A | 7/2000 | Coates et al. |
| 6,083,191 A | 7/2000 | Rose |
| 6,083,223 A | 7/2000 | Baker |
| 6,083,234 A | 7/2000 | Nicholas et al. |
| 6,083,242 A | 7/2000 | Cook |
| 6,086,544 A | 7/2000 | Hibner et al. |
| 6,086,600 A | 7/2000 | Kortenbach |
| 6,090,106 A | 7/2000 | Goble et al. |
| 6,090,123 A | 7/2000 | Culp et al. |
| 6,093,186 A | 7/2000 | Goble |
| 6,094,021 A | 7/2000 | Noro et al. |
| D429,252 S | 8/2000 | Haitani et al. |
| 6,099,537 A | 8/2000 | Sugai et al. |
| 6,099,551 A | 8/2000 | Gabbay |
| 6,102,271 A | 8/2000 | Longo et al. |
| 6,102,926 A | 8/2000 | Tartaglia et al. |
| 6,104,162 A | 8/2000 | Sainsbury et al. |
| 6,104,304 A | 8/2000 | Clark et al. |
| 6,106,511 A | 8/2000 | Jensen |
| 6,109,500 A | 8/2000 | Alli et al. |
| 6,110,187 A | 8/2000 | Donlon |
| 6,113,618 A | 9/2000 | Nic |
| 6,117,148 A | 9/2000 | Ravo et al. |
| 6,117,158 A | 9/2000 | Measamer et al. |
| 6,119,913 A | 9/2000 | Adams et al. |
| 6,120,433 A | 9/2000 | Mizuno et al. |
| 6,120,462 A | 9/2000 | Hibner et al. |
| 6,123,241 A | 9/2000 | Walter et al. |
| 6,123,701 A | 9/2000 | Nezhat |
| H1904 H | 10/2000 | Yates et al. |
| RE36,923 E | 10/2000 | Hiroi et al. |
| 6,126,058 A | 10/2000 | Adams et al. |
| 6,126,359 A | 10/2000 | Dittrich et al. |
| 6,126,670 A | 10/2000 | Walker et al. |
| 6,131,789 A | 10/2000 | Schulze et al. |
| 6,131,790 A | 10/2000 | Piraka |
| 6,132,368 A | 10/2000 | Cooper |
| 6,134,962 A | 10/2000 | Sugitani |
| 6,139,546 A | 10/2000 | Koenig et al. |
| 6,142,149 A | 11/2000 | Steen |
| 6,142,933 A | 11/2000 | Longo et al. |
| 6,147,135 A | 11/2000 | Yuan et al. |
| 6,149,660 A | 11/2000 | Laufer et al. |
| 6,151,323 A | 11/2000 | O'Connell et al. |
| 6,152,935 A | 11/2000 | Kammerer et al. |
| 6,155,473 A | 12/2000 | Tompkins et al. |
| 6,156,056 A | 12/2000 | Kearns et al. |

(56) References Cited

U.S. PATENT DOCUMENTS

| | | |
|---|---|---|
| 6,157,169 A | 12/2000 | Lee |
| 6,159,146 A | 12/2000 | El Gazayerli |
| 6,159,200 A | 12/2000 | Verdura et al. |
| 6,159,224 A | 12/2000 | Yoon |
| 6,162,208 A | 12/2000 | Hipps |
| 6,162,220 A | 12/2000 | Nezhat |
| 6,162,537 A | 12/2000 | Martin et al. |
| 6,165,175 A | 12/2000 | Wampler et al. |
| 6,165,184 A | 12/2000 | Verdura et al. |
| 6,165,188 A | 12/2000 | Saadat et al. |
| 6,167,185 A | 12/2000 | Smiley et al. |
| 6,168,605 B1 | 1/2001 | Measamer et al. |
| 6,171,305 B1 | 1/2001 | Sherman |
| 6,171,316 B1 | 1/2001 | Kovac et al. |
| 6,171,330 B1 | 1/2001 | Benchetrit |
| 6,173,074 B1 | 1/2001 | Russo |
| 6,174,308 B1 | 1/2001 | Goble et al. |
| 6,174,309 B1 | 1/2001 | Wrublewski et al. |
| 6,174,318 B1 | 1/2001 | Bates et al. |
| 6,175,290 B1 | 1/2001 | Forsythe et al. |
| 6,179,195 B1 | 1/2001 | Adams et al. |
| 6,179,776 B1 | 1/2001 | Adams et al. |
| 6,181,105 B1 | 1/2001 | Cutolo et al. |
| 6,182,673 B1 | 2/2001 | Kindermann et al. |
| 6,185,356 B1 | 2/2001 | Parker et al. |
| 6,186,142 B1 | 2/2001 | Schmidt et al. |
| 6,186,957 B1 | 2/2001 | Milam |
| 6,187,003 B1 | 2/2001 | Buysse et al. |
| 6,190,386 B1 | 2/2001 | Rydell |
| 6,193,129 B1 | 2/2001 | Bittner et al. |
| 6,197,042 B1 | 3/2001 | Ginn et al. |
| 6,200,311 B1 | 3/2001 | Danek et al. |
| 6,200,330 B1 | 3/2001 | Benderev et al. |
| 6,202,914 B1 | 3/2001 | Geiste et al. |
| 6,206,894 B1 | 3/2001 | Thompson et al. |
| 6,206,897 B1 | 3/2001 | Jamiolkowski et al. |
| 6,206,903 B1 | 3/2001 | Ramans |
| 6,206,904 B1 | 3/2001 | Ouchi |
| 6,209,414 B1 | 4/2001 | Uneme |
| 6,210,403 B1 | 4/2001 | Klicek |
| 6,211,626 B1 | 4/2001 | Lys et al. |
| 6,213,999 B1 | 4/2001 | Platt, Jr. et al. |
| 6,214,028 B1 | 4/2001 | Yoon et al. |
| 6,220,368 B1 | 4/2001 | Ark et al. |
| 6,221,007 B1 | 4/2001 | Green |
| 6,221,023 B1 | 4/2001 | Matsuba et al. |
| 6,223,100 B1 | 4/2001 | Green |
| 6,223,835 B1 | 5/2001 | Habedank et al. |
| 6,224,617 B1 | 5/2001 | Saadat et al. |
| 6,228,080 B1 | 5/2001 | Gines |
| 6,228,081 B1 | 5/2001 | Goble |
| 6,228,083 B1 | 5/2001 | Lands et al. |
| 6,228,084 B1 | 5/2001 | Kirwan, Jr. |
| 6,228,089 B1 | 5/2001 | Wahrburg |
| 6,228,098 B1 | 5/2001 | Kayan et al. |
| 6,231,565 B1 | 5/2001 | Tovey et al. |
| 6,234,178 B1 | 5/2001 | Goble et al. |
| 6,237,604 B1 | 5/2001 | Burnside et al. |
| 6,238,384 B1 | 5/2001 | Peer |
| 6,241,139 B1 | 6/2001 | Milliman et al. |
| 6,241,140 B1 | 6/2001 | Adams et al. |
| 6,241,723 B1 | 6/2001 | Heim et al. |
| 6,245,084 B1 | 6/2001 | Mark et al. |
| 6,248,116 B1 | 6/2001 | Chevillon et al. |
| 6,248,117 B1 | 6/2001 | Blatter |
| 6,249,076 B1 | 6/2001 | Madden et al. |
| 6,249,105 B1 | 6/2001 | Andrews et al. |
| 6,250,532 B1 | 6/2001 | Green et al. |
| 6,251,485 B1 | 6/2001 | Harris et al. |
| D445,745 S | 7/2001 | Norman |
| 6,254,534 B1 | 7/2001 | Butler et al. |
| 6,254,619 B1 | 7/2001 | Garabet et al. |
| 6,254,642 B1 | 7/2001 | Taylor |
| 6,258,107 B1 | 7/2001 | Balazs et al. |
| 6,261,246 B1 | 7/2001 | Pantages et al. |
| 6,261,286 B1 | 7/2001 | Goble et al. |
| 6,261,679 B1 | 7/2001 | Chen et al. |
| 6,264,086 B1 | 7/2001 | McGuckin, Jr. |
| 6,264,087 B1 | 7/2001 | Whitman |
| 6,264,617 B1 | 7/2001 | Bales et al. |
| 6,269,997 B1 | 8/2001 | Balazs et al. |
| 6,270,508 B1 | 8/2001 | Klieman et al. |
| 6,270,916 B1 | 8/2001 | Sink et al. |
| 6,273,252 B1 | 8/2001 | Mitchell |
| 6,273,876 B1 | 8/2001 | Klima et al. |
| 6,273,897 B1 | 8/2001 | Dalessandro et al. |
| 6,277,114 B1 | 8/2001 | Bullivant et al. |
| 6,280,407 B1 | 8/2001 | Manna et al. |
| 6,283,981 B1 | 9/2001 | Beaupre |
| 6,293,927 B1 | 9/2001 | McGuckin, Jr. |
| 6,293,942 B1 | 9/2001 | Goble et al. |
| 6,296,640 B1 | 10/2001 | Wampler et al. |
| 6,302,311 B1 | 10/2001 | Adams et al. |
| 6,302,743 B1 | 10/2001 | Chiu et al. |
| 6,305,891 B1 | 10/2001 | Burlingame |
| 6,306,134 B1 | 10/2001 | Goble et al. |
| 6,306,149 B1 | 10/2001 | Meade |
| 6,306,424 B1 | 10/2001 | Vyakarnam et al. |
| 6,309,397 B1 | 10/2001 | Julian et al. |
| 6,309,400 B2 | 10/2001 | Beaupre |
| 6,309,403 B1 | 10/2001 | Minor et al. |
| 6,312,435 B1 | 11/2001 | Wallace et al. |
| 6,315,184 B1 | 11/2001 | Whitman |
| 6,317,616 B1 | 11/2001 | Glossop |
| 6,319,510 B1 | 11/2001 | Yates |
| 6,320,123 B1 | 11/2001 | Reimers |
| 6,322,494 B1 | 11/2001 | Bullivant et al. |
| 6,324,339 B1 | 11/2001 | Hudson et al. |
| 6,325,799 B1 | 12/2001 | Goble |
| 6,325,805 B1 | 12/2001 | Ogilvie et al. |
| 6,325,810 B1 | 12/2001 | Hamilton et al. |
| 6,328,498 B1 | 12/2001 | Mersch |
| 6,330,965 B1 | 12/2001 | Milliman et al. |
| 6,331,181 B1 | 12/2001 | Tierney et al. |
| 6,331,761 B1 | 12/2001 | Kumar et al. |
| 6,333,029 B1 | 12/2001 | Vyakarnam et al. |
| 6,334,860 B1 | 1/2002 | Dorn |
| 6,334,861 B1 | 1/2002 | Chandler et al. |
| 6,336,926 B1 | 1/2002 | Goble |
| 6,338,737 B1 | 1/2002 | Toledano |
| 6,343,731 B1 | 2/2002 | Adams et al. |
| 6,346,077 B1 | 2/2002 | Taylor et al. |
| 6,348,061 B1 | 2/2002 | Whitman |
| 6,349,868 B1 | 2/2002 | Mattingly et al. |
| D454,951 S | 3/2002 | Bon |
| 6,352,503 B1 | 3/2002 | Matsui et al. |
| 6,352,532 B1 | 3/2002 | Kramer et al. |
| 6,355,699 B1 | 3/2002 | Vyakarnam et al. |
| 6,356,072 B1 | 3/2002 | Chass |
| 6,358,224 B1 | 3/2002 | Tims et al. |
| 6,358,263 B2 | 3/2002 | Mark et al. |
| 6,358,459 B1 | 3/2002 | Ziegler et al. |
| 6,361,542 B1 | 3/2002 | Dimitriu et al. |
| 6,364,828 B1 | 4/2002 | Yeung et al. |
| 6,364,877 B1 | 4/2002 | Goble et al. |
| 6,364,888 B1 | 4/2002 | Niemeyer et al. |
| 6,366,441 B1 | 4/2002 | Ozawa et al. |
| 6,370,981 B2 | 4/2002 | Watarai |
| 6,371,114 B1 | 4/2002 | Schmidt et al. |
| 6,373,152 B1 | 4/2002 | Wang et al. |
| 6,377,011 B1 | 4/2002 | Ben-Ur |
| 6,383,201 B1 | 5/2002 | Dong |
| 6,387,092 B1 | 5/2002 | Burnside et al. |
| 6,387,113 B1 | 5/2002 | Hawkins et al. |
| 6,387,114 B2 | 5/2002 | Adams |
| 6,391,038 B2 | 5/2002 | Vargas et al. |
| 6,392,854 B1 | 5/2002 | O'Gorman |
| 6,394,998 B1 | 5/2002 | Wallace et al. |
| 6,398,779 B1 | 6/2002 | Buysse et al. |
| 6,398,781 B1 | 6/2002 | Goble et al. |
| 6,398,797 B2 | 6/2002 | Bombard et al. |
| 6,402,766 B2 | 6/2002 | Bowman et al. |
| 6,402,780 B2 | 6/2002 | Williamson, IV et al. |
| 6,406,440 B1 | 6/2002 | Stefanchik |

(56) References Cited

U.S. PATENT DOCUMENTS

| | | |
|---|---|---|
| 6,406,472 B1 | 6/2002 | Jensen |
| 6,409,724 B1 | 6/2002 | Penny et al. |
| H2037 H | 7/2002 | Yates et al. |
| 6,412,639 B1 | 7/2002 | Hickey |
| 6,413,274 B1 | 7/2002 | Pedros |
| 6,415,542 B1 | 7/2002 | Bates et al. |
| 6,416,486 B1 | 7/2002 | Wampler |
| 6,416,509 B1 | 7/2002 | Goble et al. |
| 6,419,695 B1 | 7/2002 | Gabbay |
| 6,423,079 B1 | 7/2002 | Blake, III |
| 6,424,885 B1 | 7/2002 | Niemeyer et al. |
| RE37,814 E | 8/2002 | Allgeyer |
| 6,428,070 B1 | 8/2002 | Takanashi et al. |
| 6,428,487 B1 | 8/2002 | Burdorff et al. |
| 6,429,611 B1 | 8/2002 | Li |
| 6,430,298 B1 | 8/2002 | Kettl et al. |
| 6,432,065 B1 | 8/2002 | Burdorff et al. |
| 6,436,097 B1 | 8/2002 | Nardella |
| 6,436,107 B1 | 8/2002 | Wang et al. |
| 6,436,110 B2 | 8/2002 | Bowman et al. |
| 6,436,115 B1 | 8/2002 | Beaupre |
| 6,436,122 B1 | 8/2002 | Frank et al. |
| 6,439,439 B1 | 8/2002 | Rickard et al. |
| 6,439,446 B1 | 8/2002 | Perry et al. |
| 6,440,146 B2 | 8/2002 | Nicholas et al. |
| 6,441,577 B2 | 8/2002 | Blumenkranz et al. |
| D462,758 S | 9/2002 | Epstein et al. |
| 6,443,973 B1 | 9/2002 | Whitman |
| 6,445,530 B1 | 9/2002 | Baker |
| 6,447,518 B1 | 9/2002 | Krause et al. |
| 6,447,523 B1 | 9/2002 | Middleman et al. |
| 6,447,799 B1 | 9/2002 | Ullman |
| 6,447,864 B2 | 9/2002 | Johnson et al. |
| 6,450,391 B1 | 9/2002 | Kayan et al. |
| 6,450,989 B2 | 9/2002 | Dubrul et al. |
| 6,454,781 B1 | 9/2002 | Witt et al. |
| 6,457,338 B1 | 10/2002 | Frenken |
| 6,457,625 B1 | 10/2002 | Tormala et al. |
| 6,458,077 B1 | 10/2002 | Boebel et al. |
| 6,458,142 B1 | 10/2002 | Faller et al. |
| 6,458,147 B1 | 10/2002 | Cruise et al. |
| 6,460,627 B1 | 10/2002 | Below et al. |
| 6,468,275 B1 | 10/2002 | Wampler et al. |
| 6,468,286 B2 | 10/2002 | Mastri et al. |
| 6,471,106 B1 | 10/2002 | Reining |
| 6,471,659 B2 | 10/2002 | Eggers et al. |
| 6,478,210 B2 | 11/2002 | Adams et al. |
| 6,482,063 B1 | 11/2002 | Frigard |
| 6,482,200 B2 | 11/2002 | Shippert |
| 6,482,217 B1 | 11/2002 | Pintor et al. |
| 6,485,490 B2 | 11/2002 | Wampler et al. |
| 6,485,503 B2 | 11/2002 | Jacobs et al. |
| 6,485,667 B1 | 11/2002 | Tan |
| 6,486,286 B1 | 11/2002 | McGall et al. |
| 6,488,196 B1 | 12/2002 | Fenton, Jr. |
| 6,488,197 B1 | 12/2002 | Whitman |
| 6,488,659 B1 | 12/2002 | Rosenman |
| 6,491,201 B1 | 12/2002 | Whitman |
| 6,491,690 B1 | 12/2002 | Goble et al. |
| 6,491,701 B2 | 12/2002 | Tierney et al. |
| 6,491,702 B2 | 12/2002 | Heilbrun et al. |
| 6,492,785 B1 | 12/2002 | Kasten et al. |
| 6,494,882 B1 | 12/2002 | Lebouitz et al. |
| 6,494,885 B1 | 12/2002 | Dhindsa |
| 6,494,888 B1 | 12/2002 | Laufer et al. |
| 6,494,896 B1 | 12/2002 | D'Alessio et al. |
| 6,498,480 B1 | 12/2002 | Manara |
| 6,500,176 B1 | 12/2002 | Truckai et al. |
| 6,500,189 B1 | 12/2002 | Lang et al. |
| 6,500,194 B2 | 12/2002 | Benderev et al. |
| D468,749 S | 1/2003 | Friedman |
| 6,503,139 B2 | 1/2003 | Coral |
| 6,503,257 B2 | 1/2003 | Grant et al. |
| 6,503,259 B2 | 1/2003 | Huxel et al. |
| 6,505,768 B2 | 1/2003 | Whitman |
| 6,506,197 B1 | 1/2003 | Rollero et al. |
| 6,506,399 B2 | 1/2003 | Donovan |
| 6,510,854 B2 | 1/2003 | Goble |
| 6,511,468 B1 | 1/2003 | Cragg et al. |
| 6,512,360 B1 | 1/2003 | Goto et al. |
| 6,514,252 B2 | 2/2003 | Nezhat et al. |
| 6,516,073 B1 | 2/2003 | Schulz et al. |
| 6,517,528 B1 | 2/2003 | Pantages et al. |
| 6,517,535 B2 | 2/2003 | Edwards |
| 6,517,565 B1 | 2/2003 | Whitman et al. |
| 6,517,566 B1 | 2/2003 | Hovland et al. |
| 6,520,971 B1 | 2/2003 | Perry et al. |
| 6,520,972 B2 | 2/2003 | Peters |
| 6,522,101 B2 | 2/2003 | Malackowski |
| 6,524,180 B1 | 2/2003 | Simms et al. |
| 6,525,499 B2 | 2/2003 | Naganuma |
| D471,206 S | 3/2003 | Buzzard et al. |
| 6,527,782 B2 | 3/2003 | Hogg et al. |
| 6,527,785 B2 | 3/2003 | Sancoff et al. |
| 6,530,942 B2 | 3/2003 | Fogarty et al. |
| 6,532,958 B1 | 3/2003 | Buan et al. |
| 6,533,157 B1 | 3/2003 | Whitman |
| 6,533,723 B1 | 3/2003 | Lockery et al. |
| 6,533,784 B2 | 3/2003 | Truckai et al. |
| 6,535,764 B2 | 3/2003 | Imran et al. |
| 6,539,297 B2 | 3/2003 | Weiberle et al. |
| D473,239 S | 4/2003 | Cockerill |
| 6,539,816 B2 | 4/2003 | Kogiso et al. |
| 6,540,737 B2 | 4/2003 | Bacher et al. |
| 6,543,456 B1 | 4/2003 | Freeman |
| 6,545,384 B1 | 4/2003 | Pelrine et al. |
| 6,547,786 B1 | 4/2003 | Goble |
| 6,550,546 B2 | 4/2003 | Thurler et al. |
| 6,551,333 B2 | 4/2003 | Kuhns et al. |
| 6,554,844 B2 | 4/2003 | Lee et al. |
| 6,554,861 B2 | 4/2003 | Knox et al. |
| 6,555,770 B2 | 4/2003 | Kawase |
| 6,558,378 B2 | 5/2003 | Sherman et al. |
| 6,558,379 B1 | 5/2003 | Batchelor et al. |
| 6,558,429 B2 | 5/2003 | Taylor |
| 6,561,187 B2 | 5/2003 | Schmidt et al. |
| 6,565,560 B1 | 5/2003 | Goble et al. |
| 6,566,619 B2 | 5/2003 | Gillman et al. |
| 6,569,085 B2 | 5/2003 | Kortenbach et al. |
| 6,569,171 B2 | 5/2003 | DeGuillebon et al. |
| 6,572,629 B2 | 6/2003 | Kalloo et al. |
| 6,578,751 B2 | 6/2003 | Hartwick |
| 6,582,364 B2 | 6/2003 | Butler et al. |
| 6,582,427 B1 | 6/2003 | Goble et al. |
| 6,582,441 B1 | 6/2003 | He et al. |
| 6,583,533 B2 | 6/2003 | Pelrine et al. |
| 6,585,144 B2 | 7/2003 | Adams et al. |
| 6,585,664 B2 | 7/2003 | Burdorff et al. |
| 6,586,898 B2 | 7/2003 | King et al. |
| 6,587,750 B2 | 7/2003 | Gerbi et al. |
| 6,588,277 B2 | 7/2003 | Giordano et al. |
| 6,588,643 B2 | 7/2003 | Bolduc et al. |
| 6,588,931 B2 | 7/2003 | Betzner et al. |
| 6,589,118 B1 | 7/2003 | Soma et al. |
| 6,589,164 B1 | 7/2003 | Flaherty |
| 6,592,538 B1 | 7/2003 | Hotchkiss et al. |
| 6,592,572 B1 | 7/2003 | Suzuta |
| 6,592,597 B2 | 7/2003 | Grant et al. |
| 6,594,552 B1 | 7/2003 | Nowlin et al. |
| 6,595,914 B2 | 7/2003 | Kato |
| 6,596,296 B1 | 7/2003 | Nelson et al. |
| 6,596,304 B1 | 7/2003 | Bayon et al. |
| 6,596,432 B2 | 7/2003 | Kawakami et al. |
| 6,599,295 B1 | 7/2003 | Tornier et al. |
| 6,599,323 B2 | 7/2003 | Melican et al. |
| D478,665 S | 8/2003 | Isaacs et al. |
| D478,986 S | 8/2003 | Johnston et al. |
| 6,601,749 B2 | 8/2003 | Sullivan et al. |
| 6,602,252 B2 | 8/2003 | Mollenauer |
| 6,602,262 B2 | 8/2003 | Griego et al. |
| 6,603,050 B2 | 8/2003 | Heaton |
| 6,605,078 B2 | 8/2003 | Adams |
| 6,605,669 B2 | 8/2003 | Awokola et al. |
| 6,605,911 B1 | 8/2003 | Klesing |

(56) References Cited

U.S. PATENT DOCUMENTS

| | | |
|---|---|---|
| 6,607,475 B2 | 8/2003 | Doyle et al. |
| 6,611,793 B1 | 8/2003 | Burnside et al. |
| 6,613,069 B2 | 9/2003 | Boyd et al. |
| 6,616,686 B2 | 9/2003 | Coleman et al. |
| 6,619,529 B2 | 9/2003 | Green et al. |
| 6,620,111 B2 | 9/2003 | Stephens et al. |
| 6,620,161 B2 | 9/2003 | Schulze et al. |
| 6,620,166 B1 | 9/2003 | Wenstrom, Jr. et al. |
| 6,625,517 B1 | 9/2003 | Bogdanov et al. |
| 6,626,834 B2 | 9/2003 | Dunne et al. |
| 6,626,938 B1 | 9/2003 | Butaric et al. |
| H2086 H | 10/2003 | Amsler |
| 6,629,630 B2 | 10/2003 | Adams |
| 6,629,974 B2 | 10/2003 | Penny et al. |
| 6,629,988 B2 | 10/2003 | Weadock |
| 6,635,838 B1 | 10/2003 | Kornelson |
| 6,636,412 B2 | 10/2003 | Smith |
| 6,638,108 B2 | 10/2003 | Tachi |
| 6,638,285 B2 | 10/2003 | Gabbay |
| 6,638,297 B1 | 10/2003 | Huitema |
| RE38,335 E | 11/2003 | Aust et al. |
| 6,641,528 B2 | 11/2003 | Torii |
| 6,644,532 B2 | 11/2003 | Green et al. |
| 6,645,201 B1 | 11/2003 | Utley et al. |
| 6,646,307 B1 | 11/2003 | Yu et al. |
| 6,648,816 B2 | 11/2003 | Irion et al. |
| 6,648,901 B2 | 11/2003 | Fleischman et al. |
| 6,652,595 B1 | 11/2003 | Nicolo |
| D484,243 S | 12/2003 | Ryan et al. |
| D484,595 S | 12/2003 | Ryan et al. |
| D484,596 S | 12/2003 | Ryan et al. |
| 6,656,177 B2 | 12/2003 | Truckai et al. |
| 6,656,193 B2 | 12/2003 | Grant et al. |
| 6,659,940 B2 | 12/2003 | Adler |
| 6,660,008 B1 | 12/2003 | Foerster et al. |
| 6,663,623 B1 | 12/2003 | Oyama et al. |
| 6,663,641 B1 | 12/2003 | Kovac et al. |
| 6,666,854 B1 | 12/2003 | Lange |
| 6,666,860 B1 | 12/2003 | Takahashi |
| 6,666,875 B1 | 12/2003 | Sakurai et al. |
| 6,667,825 B2 | 12/2003 | Lu et al. |
| 6,669,073 B2 | 12/2003 | Milliman et al. |
| 6,670,806 B2 | 12/2003 | Wendt et al. |
| 6,671,185 B2 | 12/2003 | Duval |
| D484,977 S | 1/2004 | Ryan et al. |
| 6,676,660 B2 | 1/2004 | Wampler et al. |
| 6,677,687 B2 | 1/2004 | Ho et al. |
| 6,679,269 B2 | 1/2004 | Swanson |
| 6,679,410 B2 | 1/2004 | Wursch et al. |
| 6,681,978 B2 | 1/2004 | Geiste et al. |
| 6,681,979 B2 | 1/2004 | Whitman |
| 6,682,527 B2 | 1/2004 | Strul |
| 6,682,528 B2 | 1/2004 | Frazier et al. |
| 6,682,544 B2 | 1/2004 | Mastri et al. |
| 6,685,698 B2 | 2/2004 | Morley et al. |
| 6,685,727 B2 | 2/2004 | Fisher et al. |
| 6,689,153 B1 | 2/2004 | Skiba |
| 6,692,507 B2 | 2/2004 | Pugsley et al. |
| 6,692,692 B2 | 2/2004 | Stetzel |
| 6,695,198 B2 | 2/2004 | Adams et al. |
| 6,695,199 B2 | 2/2004 | Whitman |
| 6,695,774 B2 | 2/2004 | Hale et al. |
| 6,695,849 B2 | 2/2004 | Michelson |
| 6,696,814 B2 | 2/2004 | Henderson et al. |
| 6,697,048 B2 | 2/2004 | Rosenberg et al. |
| 6,698,643 B2 | 3/2004 | Whitman |
| 6,699,177 B1 | 3/2004 | Wang et al. |
| 6,699,214 B2 | 3/2004 | Gellman |
| 6,699,235 B2 | 3/2004 | Wallace et al. |
| 6,704,210 B1 | 3/2004 | Myers |
| 6,705,503 B1 | 3/2004 | Pedicini et al. |
| 6,709,445 B2 | 3/2004 | Boebel et al. |
| 6,712,773 B1 | 3/2004 | Viola |
| 6,716,215 B1 | 4/2004 | David et al. |
| 6,716,223 B2 | 4/2004 | Leopold et al. |
| 6,716,232 B1 | 4/2004 | Vidal et al. |
| 6,716,233 B1 | 4/2004 | Whitman |
| 6,720,734 B2 | 4/2004 | Norris |
| 6,722,550 B1 | 4/2004 | Ricordi et al. |
| 6,722,552 B2 | 4/2004 | Fenton, Jr. |
| 6,723,087 B2 | 4/2004 | O'Neill et al. |
| 6,723,091 B2 | 4/2004 | Goble et al. |
| 6,723,106 B1 | 4/2004 | Charles et al. |
| 6,723,109 B2 | 4/2004 | Solingen |
| 6,726,651 B1 | 4/2004 | Robinson et al. |
| 6,726,697 B2 | 4/2004 | Nicholas et al. |
| 6,726,705 B2 | 4/2004 | Peterson et al. |
| 6,726,706 B2 | 4/2004 | Dominguez |
| 6,729,119 B2 | 5/2004 | Schnipke et al. |
| 6,731,976 B2 | 5/2004 | Penn et al. |
| 6,736,810 B2 | 5/2004 | Hoey et al. |
| 6,736,825 B2 | 5/2004 | Blatter et al. |
| 6,736,854 B2 | 5/2004 | Vadurro et al. |
| 6,740,030 B2 | 5/2004 | Martone et al. |
| 6,743,230 B2 | 6/2004 | Lutze et al. |
| 6,744,385 B2 | 6/2004 | Kazuya et al. |
| 6,747,121 B2 | 6/2004 | Gogolewski |
| 6,747,300 B2 | 6/2004 | Nadd et al. |
| 6,749,560 B1 | 6/2004 | Konstorum et al. |
| 6,749,600 B1 | 6/2004 | Levy |
| 6,752,768 B2 | 6/2004 | Burdorff et al. |
| 6,752,816 B2 | 6/2004 | Culp et al. |
| 6,754,959 B1 | 6/2004 | Guiette, III et al. |
| 6,755,195 B1 | 6/2004 | Lemke et al. |
| 6,755,338 B2 | 6/2004 | Hahnen et al. |
| 6,755,825 B2 | 6/2004 | Shoenman et al. |
| 6,755,843 B2 | 6/2004 | Chung et al. |
| 6,756,705 B2 | 6/2004 | Pulford, Jr. |
| 6,758,846 B2 | 7/2004 | Goble et al. |
| 6,761,685 B2 | 7/2004 | Adams et al. |
| 6,762,339 B1 | 7/2004 | Klun et al. |
| 6,763,307 B2 | 7/2004 | Berg et al. |
| 6,764,445 B2 | 7/2004 | Ramans et al. |
| 6,766,957 B2 | 7/2004 | Matsuura et al. |
| 6,767,352 B2 | 7/2004 | Field et al. |
| 6,767,356 B2 | 7/2004 | Kanner et al. |
| 6,769,590 B2 | 8/2004 | Vresh et al. |
| 6,769,594 B2 | 8/2004 | Orban, III |
| 6,770,027 B2 | 8/2004 | Banik et al. |
| 6,770,070 B1 | 8/2004 | Balbierz |
| 6,770,072 B1 | 8/2004 | Truckai et al. |
| 6,770,078 B2 | 8/2004 | Bonutti |
| 6,773,409 B2 | 8/2004 | Truckai et al. |
| 6,773,437 B2 | 8/2004 | Ogilvie et al. |
| 6,773,438 B1 | 8/2004 | Knodel et al. |
| 6,775,575 B2 | 8/2004 | Bommannan et al. |
| 6,777,838 B2 | 8/2004 | Miekka et al. |
| 6,778,846 B1 | 8/2004 | Martinez et al. |
| 6,780,151 B2 | 8/2004 | Grabover et al. |
| 6,780,180 B1 | 8/2004 | Goble et al. |
| 6,783,524 B2 | 8/2004 | Anderson et al. |
| 6,784,775 B2 | 8/2004 | Mandell et al. |
| 6,786,382 B1 | 9/2004 | Hoffman |
| 6,786,864 B2 | 9/2004 | Matsuura et al. |
| 6,786,896 B1 | 9/2004 | Madhani et al. |
| 6,788,018 B1 | 9/2004 | Blumenkranz |
| 6,790,173 B2 | 9/2004 | Saadat et al. |
| 6,793,652 B1 | 9/2004 | Whitman et al. |
| 6,793,661 B2 | 9/2004 | Hamilton et al. |
| 6,793,663 B2 | 9/2004 | Kneifel et al. |
| 6,793,669 B2 | 9/2004 | Nakamura et al. |
| 6,796,921 B1 | 9/2004 | Buck et al. |
| 6,799,669 B2 | 10/2004 | Fukumura et al. |
| 6,801,009 B2 | 10/2004 | Makaran et al. |
| 6,802,822 B1 | 10/2004 | Dodge |
| 6,802,843 B2 | 10/2004 | Truckai et al. |
| 6,802,844 B2 | 10/2004 | Ferree |
| 6,805,273 B2 | 10/2004 | Bilotti et al. |
| 6,806,808 B1 | 10/2004 | Watters et al. |
| 6,806,867 B1 | 10/2004 | Arruda et al. |
| 6,808,525 B2 | 10/2004 | Latterell et al. |
| 6,810,359 B2 | 10/2004 | Sakaguchi |
| 6,814,154 B2 | 11/2004 | Chou |
| 6,814,741 B2 | 11/2004 | Bowman et al. |

(56) References Cited

U.S. PATENT DOCUMENTS

| | | |
|---|---|---|
| 6,817,508 B1 | 11/2004 | Racenet et al. |
| 6,817,509 B2 | 11/2004 | Geiste et al. |
| 6,817,974 B2 | 11/2004 | Cooper et al. |
| 6,818,018 B1 | 11/2004 | Sawhney |
| 6,820,791 B2 | 11/2004 | Adams |
| 6,821,273 B2 | 11/2004 | Mollenauer |
| 6,821,282 B2 | 11/2004 | Perry et al. |
| 6,821,284 B2 | 11/2004 | Sturtz et al. |
| 6,827,246 B2 | 12/2004 | Sullivan et al. |
| 6,827,712 B2 | 12/2004 | Tovey et al. |
| 6,827,725 B2 | 12/2004 | Batchelor et al. |
| 6,828,902 B2 | 12/2004 | Casden |
| 6,830,174 B2 | 12/2004 | Hillstead et al. |
| 6,831,629 B2 | 12/2004 | Nishino et al. |
| 6,832,998 B2 | 12/2004 | Goble |
| 6,834,001 B2 | 12/2004 | Myono |
| 6,835,173 B2 | 12/2004 | Couvillon, Jr. |
| 6,835,199 B2 | 12/2004 | McGuckin, Jr. et al. |
| 6,835,336 B2 | 12/2004 | Watt |
| 6,836,611 B2 | 12/2004 | Popovic et al. |
| 6,837,846 B2 | 1/2005 | Jaffe et al. |
| 6,837,883 B2 | 1/2005 | Moll et al. |
| 6,838,493 B2 | 1/2005 | Williams et al. |
| 6,840,423 B2 | 1/2005 | Adams et al. |
| 6,840,938 B1 | 1/2005 | Morley et al. |
| 6,841,967 B2 | 1/2005 | Kim et al. |
| 6,843,403 B2 | 1/2005 | Whitman |
| 6,843,789 B2 | 1/2005 | Goble |
| 6,843,793 B2 | 1/2005 | Brock et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,847,190 B2 | 1/2005 | Schaefer et al. |
| 6,849,071 B2 | 2/2005 | Whitman et al. |
| 6,850,817 B1 | 2/2005 | Green |
| 6,852,122 B2 | 2/2005 | Rush |
| 6,852,330 B2 | 2/2005 | Bowman et al. |
| 6,853,879 B2 | 2/2005 | Sunaoshi |
| 6,858,005 B2 | 2/2005 | Ohline et al. |
| 6,859,882 B2 | 2/2005 | Fung |
| RE38,708 E | 3/2005 | Bolanos et al. |
| D502,994 S | 3/2005 | Blake, III |
| 6,861,142 B1 | 3/2005 | Wilkie et al. |
| 6,861,954 B2 | 3/2005 | Levin |
| 6,863,668 B2 | 3/2005 | Gillespie et al. |
| 6,863,694 B1 | 3/2005 | Boyce et al. |
| 6,863,924 B2 | 3/2005 | Ranganathan et al. |
| 6,866,178 B2 | 3/2005 | Adams et al. |
| 6,866,668 B2 | 3/2005 | Giannetti et al. |
| 6,866,671 B2 | 3/2005 | Tierney et al. |
| 6,867,248 B1 | 3/2005 | Martin et al. |
| 6,869,430 B2 | 3/2005 | Balbierz et al. |
| 6,869,435 B2 | 3/2005 | Blake, III |
| 6,872,214 B2 | 3/2005 | Sonnenschein et al. |
| 6,874,669 B2 | 4/2005 | Adams et al. |
| 6,876,850 B2 | 4/2005 | Maeshima et al. |
| 6,877,647 B2 | 4/2005 | Green et al. |
| 6,878,106 B1 | 4/2005 | Herrmann |
| 6,882,127 B2 | 4/2005 | Konigbauer |
| 6,883,199 B1 | 4/2005 | Lundell et al. |
| 6,884,392 B2 | 4/2005 | Malkin et al. |
| 6,884,428 B2 | 4/2005 | Binette et al. |
| 6,886,730 B2 | 5/2005 | Fujisawa et al. |
| 6,887,244 B1 | 5/2005 | Walker et al. |
| 6,887,710 B2 | 5/2005 | Call et al. |
| 6,889,116 B2 | 5/2005 | Jinno |
| 6,893,435 B2 | 5/2005 | Goble |
| 6,894,140 B2 | 5/2005 | Roby |
| 6,895,176 B2 | 5/2005 | Archer et al. |
| 6,899,538 B2 | 5/2005 | Matoba |
| 6,899,593 B1 | 5/2005 | Moeller et al. |
| 6,899,705 B2 | 5/2005 | Niemeyer |
| 6,899,915 B2 | 5/2005 | Yelick et al. |
| 6,905,057 B2 | 6/2005 | Swayze et al. |
| 6,905,497 B2 | 6/2005 | Truckai et al. |
| 6,905,498 B2 | 6/2005 | Hooven |
| 6,908,472 B2 | 6/2005 | Wiener et al. |
| 6,911,033 B2 | 6/2005 | de Guillebon et al. |
| 6,911,916 B1 | 6/2005 | Wang et al. |
| 6,913,579 B2 | 7/2005 | Truckai et al. |
| 6,913,608 B2 | 7/2005 | Liddicoat et al. |
| 6,913,613 B2 | 7/2005 | Schwarz et al. |
| 6,921,397 B2 | 7/2005 | Corcoran et al. |
| 6,921,412 B1 | 7/2005 | Black et al. |
| 6,923,093 B2 | 8/2005 | Ullah |
| 6,923,803 B2 | 8/2005 | Goble |
| 6,923,819 B2 | 8/2005 | Meade et al. |
| 6,925,849 B2 | 8/2005 | Jairam |
| 6,926,716 B2 | 8/2005 | Baker et al. |
| 6,928,902 B1 | 8/2005 | Eyssallenne |
| 6,929,641 B2 | 8/2005 | Goble et al. |
| 6,929,644 B2 | 8/2005 | Truckai et al. |
| 6,931,830 B2 | 8/2005 | Liao |
| 6,932,218 B2 | 8/2005 | Kosann et al. |
| 6,932,810 B2 | 8/2005 | Ryan |
| 6,936,042 B2 | 8/2005 | Wallace et al. |
| 6,936,948 B2 | 8/2005 | Bell et al. |
| D509,297 S | 9/2005 | Wells |
| D509,589 S | 9/2005 | Wells |
| 6,938,706 B2 | 9/2005 | Ng |
| 6,939,358 B2 | 9/2005 | Palacios et al. |
| 6,942,662 B2 | 9/2005 | Goble et al. |
| 6,942,674 B2 | 9/2005 | Belef et al. |
| 6,945,444 B2 | 9/2005 | Gresham et al. |
| 6,945,981 B2 | 9/2005 | Donofrio et al. |
| 6,949,196 B2 | 9/2005 | Schmitz et al. |
| 6,951,562 B2 | 10/2005 | Zwirnmann |
| 6,953,138 B1 | 10/2005 | Dworak et al. |
| 6,953,139 B2 | 10/2005 | Milliman et al. |
| 6,953,461 B2 | 10/2005 | McClurken et al. |
| 6,957,758 B2 | 10/2005 | Aranyi |
| 6,958,035 B2 | 10/2005 | Friedman et al. |
| D511,525 S | 11/2005 | Hernandez et al. |
| 6,959,851 B2 | 11/2005 | Heinrich |
| 6,959,852 B2 | 11/2005 | Shelton, IV et al. |
| 6,960,107 B1 | 11/2005 | Schaub et al. |
| 6,960,163 B2 | 11/2005 | Ewers et al. |
| 6,960,220 B2 | 11/2005 | Marino et al. |
| 6,962,587 B2 | 11/2005 | Johnson et al. |
| 6,963,792 B1 | 11/2005 | Green |
| 6,964,363 B2 | 11/2005 | Wales et al. |
| 6,966,907 B2 | 11/2005 | Goble |
| 6,966,909 B2 | 11/2005 | Marshall et al. |
| 6,968,908 B2 | 11/2005 | Tokunaga et al. |
| 6,969,385 B2 | 11/2005 | Moreyra |
| 6,969,395 B2 | 11/2005 | Eskuri |
| 6,971,988 B2 | 12/2005 | Orban, III |
| 6,972,199 B2 | 12/2005 | Lebouitz et al. |
| 6,974,435 B2 | 12/2005 | Daw et al. |
| 6,974,462 B2 | 12/2005 | Sater |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,941 B2 | 1/2006 | Whitman et al. |
| 6,981,978 B2 | 1/2006 | Gannoe |
| 6,984,203 B2 | 1/2006 | Tartaglia et al. |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,989,034 B2 | 1/2006 | Hammer et al. |
| 6,990,731 B2 | 1/2006 | Haytayan |
| 6,990,796 B2 | 1/2006 | Schnipke et al. |
| 6,991,146 B2 | 1/2006 | Sinisi et al. |
| 6,993,200 B2 | 1/2006 | Tastl et al. |
| 6,993,413 B2 | 1/2006 | Sunaoshi |
| 6,994,708 B2 | 2/2006 | Manzo |
| 6,995,729 B2 | 2/2006 | Govari et al. |
| 6,996,433 B2 | 2/2006 | Burbank et al. |
| 6,997,931 B2 | 2/2006 | Sauer et al. |
| 6,997,935 B2 | 2/2006 | Anderson et al. |
| 6,998,736 B2 | 2/2006 | Lee et al. |
| 6,998,816 B2 | 2/2006 | Wieck et al. |
| 6,999,821 B2 | 2/2006 | Jenney et al. |

(56) References Cited

U.S. PATENT DOCUMENTS

| | | |
|---|---|---|
| 7,000,818 B2 | 2/2006 | Shelton, IV et al. |
| 7,000,819 B2 | 2/2006 | Swayze et al. |
| 7,000,911 B2 | 2/2006 | McCormick et al. |
| 7,001,380 B2 | 2/2006 | Goble |
| 7,001,408 B2 | 2/2006 | Knodel et al. |
| 7,004,174 B2 | 2/2006 | Eggers et al. |
| 7,007,176 B2 | 2/2006 | Goodfellow et al. |
| 7,008,433 B2 | 3/2006 | Voellmicke et al. |
| 7,008,435 B2 | 3/2006 | Cummins |
| 7,009,039 B2 | 3/2006 | Yayon et al. |
| 7,011,213 B2 | 3/2006 | Clark et al. |
| 7,011,657 B2 | 3/2006 | Truckai et al. |
| 7,014,640 B2 | 3/2006 | Kemppainen et al. |
| 7,018,357 B2 | 3/2006 | Emmons |
| 7,018,390 B2 | 3/2006 | Turovskiy et al. |
| 7,021,399 B2 | 4/2006 | Driessen |
| 7,021,669 B1 | 4/2006 | Lindermeir et al. |
| 7,022,131 B1 | 4/2006 | Derowe et al. |
| 7,023,159 B2 | 4/2006 | Gorti et al. |
| 7,025,064 B2 | 4/2006 | Wang et al. |
| 7,025,732 B2 | 4/2006 | Thompson et al. |
| 7,025,743 B2 | 4/2006 | Mann et al. |
| 7,025,774 B2 | 4/2006 | Freeman et al. |
| 7,025,775 B2 | 4/2006 | Gadberry et al. |
| 7,028,570 B2 | 4/2006 | Ohta et al. |
| 7,029,435 B2 | 4/2006 | Nakao |
| 7,029,439 B2 | 4/2006 | Roberts et al. |
| 7,030,904 B2 | 4/2006 | Adair et al. |
| 7,032,798 B2 | 4/2006 | Whitman et al. |
| 7,032,799 B2 | 4/2006 | Viola et al. |
| 7,033,356 B2 | 4/2006 | Latterell et al. |
| 7,033,378 B2 | 4/2006 | Smith et al. |
| 7,035,716 B2 | 4/2006 | Harris et al. |
| 7,035,762 B2 | 4/2006 | Menard et al. |
| 7,036,680 B1 | 5/2006 | Flannery |
| 7,037,314 B2 | 5/2006 | Armstrong |
| 7,037,344 B2 | 5/2006 | Kagan et al. |
| 7,038,421 B2 | 5/2006 | Trifilo |
| 7,041,088 B2 | 5/2006 | Nawrocki et al. |
| 7,041,102 B2 | 5/2006 | Truckai et al. |
| 7,041,868 B2 | 5/2006 | Greene et al. |
| 7,043,852 B2 | 5/2006 | Hayashida et al. |
| 7,044,350 B2 | 5/2006 | Kameyama et al. |
| 7,044,352 B2 | 5/2006 | Shelton, IV et al. |
| 7,044,353 B2 | 5/2006 | Mastri et al. |
| 7,046,082 B2 | 5/2006 | Komiya et al. |
| 7,048,165 B2 | 5/2006 | Haramiishi |
| 7,048,687 B1 | 5/2006 | Reuss et al. |
| 7,048,716 B1 | 5/2006 | Kucharczyk et al. |
| 7,048,745 B2 | 5/2006 | Tierney et al. |
| 7,052,454 B2 | 5/2006 | Taylor |
| 7,052,494 B2 | 5/2006 | Goble et al. |
| 7,052,499 B2 | 5/2006 | Steger et al. |
| 7,055,730 B2 | 6/2006 | Ehrenfels et al. |
| 7,055,731 B2 | 6/2006 | Shelton, IV et al. |
| 7,056,123 B2 | 6/2006 | Gregorio et al. |
| 7,056,284 B2 | 6/2006 | Martone et al. |
| 7,056,330 B2 | 6/2006 | Gayton |
| 7,059,331 B2 | 6/2006 | Adams et al. |
| 7,059,508 B2 | 6/2006 | Shelton, IV et al. |
| 7,063,671 B2 | 6/2006 | Couvillon, Jr. |
| 7,063,712 B2 | 6/2006 | Vargas et al. |
| 7,064,509 B1 | 6/2006 | Fu et al. |
| 7,066,879 B2 | 6/2006 | Fowler et al. |
| 7,066,944 B2 | 6/2006 | Laufer et al. |
| 7,067,038 B2 | 6/2006 | Trokhan et al. |
| 7,070,083 B2 | 7/2006 | Jankowski |
| 7,070,559 B2 | 7/2006 | Adams et al. |
| 7,070,597 B2 | 7/2006 | Truckai et al. |
| 7,071,287 B2 | 7/2006 | Rhine et al. |
| 7,075,770 B1 | 7/2006 | Smith |
| 7,077,856 B2 | 7/2006 | Whitman |
| 7,080,769 B2 | 7/2006 | Vresh et al. |
| 7,081,114 B2 | 7/2006 | Rashidi |
| 7,081,318 B2 | 7/2006 | Lee et al. |
| 7,083,073 B2 | 8/2006 | Yoshie et al. |
| 7,083,075 B2 | 8/2006 | Swayze et al. |
| 7,083,571 B2 | 8/2006 | Wang et al. |
| 7,083,615 B2 | 8/2006 | Peterson et al. |
| 7,083,619 B2 | 8/2006 | Truckai et al. |
| 7,083,620 B2 | 8/2006 | Jahns et al. |
| 7,083,626 B2 | 8/2006 | Hart et al. |
| 7,086,267 B2 | 8/2006 | Dworak et al. |
| 7,087,049 B2 | 8/2006 | Nowlin et al. |
| 7,087,054 B2 | 8/2006 | Truckai et al. |
| 7,087,071 B2 | 8/2006 | Nicholas et al. |
| 7,090,637 B2 | 8/2006 | Danitz et al. |
| 7,090,673 B2 | 8/2006 | Dycus et al. |
| 7,090,683 B2 | 8/2006 | Brock et al. |
| 7,090,684 B2 | 8/2006 | McGuckin, Jr. et al. |
| 7,091,191 B2 | 8/2006 | Laredo et al. |
| 7,091,412 B2 | 8/2006 | Wang et al. |
| 7,093,492 B2 | 8/2006 | Treiber et al. |
| 7,094,202 B2 | 8/2006 | Nobis et al. |
| 7,094,247 B2 | 8/2006 | Monassevitch et al. |
| 7,094,916 B2 | 8/2006 | Deluca et al. |
| 7,096,972 B2 | 8/2006 | Orozco, Jr. |
| 7,097,089 B2 | 8/2006 | Marczyk |
| 7,097,644 B2 | 8/2006 | Long |
| 7,097,650 B2 | 8/2006 | Weller et al. |
| 7,098,794 B2 | 8/2006 | Lindsay et al. |
| 7,100,949 B2 | 9/2006 | Williams et al. |
| 7,101,187 B1 | 9/2006 | Deconinck et al. |
| 7,101,371 B2 | 9/2006 | Dycus et al. |
| 7,101,394 B2 | 9/2006 | Hamm et al. |
| 7,104,741 B2 | 9/2006 | Krohn |
| 7,108,695 B2 | 9/2006 | Witt et al. |
| 7,108,701 B2 | 9/2006 | Evens et al. |
| 7,108,709 B2 | 9/2006 | Cummins |
| 7,111,768 B2 | 9/2006 | Cummins et al. |
| 7,111,769 B2 | 9/2006 | Wales et al. |
| 7,112,214 B2 | 9/2006 | Peterson et al. |
| RE39,358 E | 10/2006 | Goble |
| D530,339 S | 10/2006 | Hernandez et al. |
| 7,114,642 B2 | 10/2006 | Whitman |
| 7,116,100 B1 | 10/2006 | Mock et al. |
| 7,118,020 B2 | 10/2006 | Lee et al. |
| 7,118,528 B1 | 10/2006 | Piskun |
| 7,118,563 B2 | 10/2006 | Weckwerth et al. |
| 7,118,582 B1 | 10/2006 | Wang et al. |
| 7,119,534 B2 | 10/2006 | Butzmann |
| 7,121,446 B2 | 10/2006 | Arad et al. |
| 7,121,773 B2 | 10/2006 | Mikiya et al. |
| 7,122,028 B2 | 10/2006 | Looper et al. |
| 7,125,403 B2 | 10/2006 | Julian et al. |
| 7,125,409 B2 | 10/2006 | Truckai et al. |
| 7,126,303 B2 | 10/2006 | Farritor et al. |
| 7,126,879 B2 | 10/2006 | Snyder |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,131,445 B2 | 11/2006 | Amoah |
| 7,133,601 B2 | 11/2006 | Phillips et al. |
| 7,134,364 B2 | 11/2006 | Kageler et al. |
| 7,134,587 B2 | 11/2006 | Schwemberger et al. |
| 7,135,027 B2 | 11/2006 | Delmotte |
| 7,137,980 B2 | 11/2006 | Buysse et al. |
| 7,137,981 B2 | 11/2006 | Long |
| 7,139,016 B2 | 11/2006 | Squilla et al. |
| 7,140,527 B2 | 11/2006 | Ehrenfels et al. |
| 7,140,528 B2 | 11/2006 | Shelton, IV |
| 7,141,055 B2 | 11/2006 | Abrams et al. |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,146,191 B2 | 12/2006 | Kerner et al. |
| 7,147,138 B2 | 12/2006 | Shelton, IV |
| 7,147,139 B2 | 12/2006 | Schwemberger et al. |
| 7,147,140 B2 | 12/2006 | Wukusick et al. |
| 7,147,637 B2 | 12/2006 | Goble |
| 7,147,648 B2 | 12/2006 | Lin |
| 7,147,650 B2 | 12/2006 | Lee |
| 7,150,748 B2 | 12/2006 | Ebbutt et al. |

(56) References Cited

U.S. PATENT DOCUMENTS

| | | |
|---|---|---|
| 7,153,300 B2 | 12/2006 | Goble |
| 7,153,314 B2 | 12/2006 | Laufer et al. |
| 7,155,316 B2 | 12/2006 | Sutherland et al. |
| 7,156,863 B2 | 1/2007 | Sonnenschein et al. |
| 7,159,750 B2 | 1/2007 | Racenet et al. |
| 7,160,296 B2 | 1/2007 | Pearson et al. |
| 7,160,299 B2 | 1/2007 | Baily |
| 7,160,311 B2 | 1/2007 | Blatter et al. |
| 7,161,036 B2 | 1/2007 | Oikawa et al. |
| 7,161,580 B2 | 1/2007 | Bailey et al. |
| 7,162,758 B2 | 1/2007 | Skinner |
| 7,163,563 B2 | 1/2007 | Schwartz et al. |
| 7,166,117 B2 | 1/2007 | Hellenkamp |
| 7,166,133 B2 | 1/2007 | Evans et al. |
| 7,168,604 B2 | 1/2007 | Milliman et al. |
| 7,170,910 B2 | 1/2007 | Chen et al. |
| 7,171,279 B2 | 1/2007 | Buckingham et al. |
| 7,172,104 B2 | 2/2007 | Scirica et al. |
| 7,172,593 B2 | 2/2007 | Trieu et al. |
| 7,172,615 B2 | 2/2007 | Morriss et al. |
| 7,174,202 B2 | 2/2007 | Bladen et al. |
| 7,174,636 B2 | 2/2007 | Lowe |
| 7,177,533 B2 | 2/2007 | McFarlin et al. |
| 7,179,223 B2 | 2/2007 | Motoki et al. |
| 7,179,267 B2 | 2/2007 | Nolan et al. |
| 7,182,239 B1 | 2/2007 | Myers |
| 7,182,763 B2 | 2/2007 | Nardella |
| 7,183,737 B2 | 2/2007 | Kitagawa |
| 7,187,960 B2 | 3/2007 | Abreu |
| 7,188,758 B2 | 3/2007 | Viola et al. |
| 7,189,207 B2 | 3/2007 | Viola |
| 7,190,147 B2 | 3/2007 | Gileff et al. |
| 7,193,199 B2 | 3/2007 | Jang |
| 7,195,627 B2 | 3/2007 | Amoah et al. |
| 7,196,911 B2 | 3/2007 | Takano et al. |
| D541,418 S | 4/2007 | Schechter et al. |
| 7,197,965 B1 | 4/2007 | Anderson |
| 7,199,537 B2 | 4/2007 | Okamura et al. |
| 7,199,545 B2 | 4/2007 | Oleynikov et al. |
| 7,202,576 B1 | 4/2007 | Dechene et al. |
| 7,202,653 B2 | 4/2007 | Pai |
| 7,204,404 B2 | 4/2007 | Nguyen et al. |
| 7,204,835 B2 | 4/2007 | Latterell et al. |
| 7,205,959 B2 | 4/2007 | Henriksson |
| 7,206,626 B2 | 4/2007 | Quaid, III |
| 7,207,233 B2 | 4/2007 | Wadge |
| 7,207,471 B2 | 4/2007 | Heinrich et al. |
| 7,207,472 B2 | 4/2007 | Wukusick et al. |
| 7,207,556 B2 | 4/2007 | Saitoh et al. |
| 7,208,005 B2 | 4/2007 | Frecker et al. |
| 7,210,609 B2 | 5/2007 | Leiboff et al. |
| 7,211,081 B2 | 5/2007 | Goble |
| 7,211,084 B2 | 5/2007 | Goble et al. |
| 7,211,092 B2 | 5/2007 | Hughett |
| 7,211,979 B2 | 5/2007 | Khatib et al. |
| 7,213,736 B2 | 5/2007 | Wales et al. |
| 7,214,224 B2 | 5/2007 | Goble |
| 7,215,517 B2 | 5/2007 | Takamatsu |
| 7,217,285 B2 | 5/2007 | Vargas et al. |
| 7,220,260 B2 | 5/2007 | Fleming et al. |
| 7,220,272 B2 | 5/2007 | Weadock |
| 7,225,959 B2 | 6/2007 | Patton et al. |
| 7,225,963 B2 | 6/2007 | Scirica |
| 7,225,964 B2 | 6/2007 | Mastri et al. |
| 7,226,450 B2 | 6/2007 | Athanasiou et al. |
| 7,226,467 B2 | 6/2007 | Lucatero et al. |
| 7,228,505 B2 | 6/2007 | Shimazu et al. |
| 7,229,408 B2 | 6/2007 | Douglas et al. |
| 7,234,624 B2 | 6/2007 | Gresham et al. |
| 7,235,072 B2 | 6/2007 | Sartor et al. |
| 7,235,089 B1 | 6/2007 | McGuckin, Jr. |
| 7,235,302 B2 | 6/2007 | Jing et al. |
| 7,237,708 B1 | 7/2007 | Guy et al. |
| 7,238,195 B2 | 7/2007 | Viola |
| 7,238,901 B2 | 7/2007 | Kim et al. |
| 7,239,657 B1 | 7/2007 | Gunnarsson |
| 7,241,288 B2 | 7/2007 | Braun |
| 7,241,289 B2 | 7/2007 | Braun |
| 7,246,734 B2 | 7/2007 | Shelton, IV |
| 7,247,161 B2 | 7/2007 | Johnston et al. |
| 7,249,267 B2 | 7/2007 | Chapuis |
| 7,252,641 B2 | 8/2007 | Thompson et al. |
| 7,252,660 B2 | 8/2007 | Kunz |
| 7,255,012 B2 | 8/2007 | Hedtke |
| 7,255,696 B2 | 8/2007 | Goble et al. |
| 7,256,695 B2 | 8/2007 | Hamel et al. |
| 7,258,262 B2 | 8/2007 | Mastri et al. |
| 7,258,546 B2 | 8/2007 | Beier et al. |
| 7,260,431 B2 | 8/2007 | Libbus et al. |
| 7,265,374 B2 | 9/2007 | Lee et al. |
| 7,267,677 B2 | 9/2007 | Johnson et al. |
| 7,267,679 B2 | 9/2007 | McGuckin, Jr. et al. |
| 7,272,002 B2 | 9/2007 | Drapeau |
| 7,273,483 B2 | 9/2007 | Wiener et al. |
| D552,623 S | 10/2007 | Vong et al. |
| 7,275,674 B2 | 10/2007 | Racenet et al. |
| 7,276,044 B2 | 10/2007 | Ferry et al. |
| 7,276,068 B2 | 10/2007 | Johnson et al. |
| 7,278,562 B2 | 10/2007 | Mastri et al. |
| 7,278,563 B1 | 10/2007 | Green |
| 7,278,949 B2 | 10/2007 | Bader |
| 7,278,994 B2 | 10/2007 | Goble |
| 7,282,048 B2 | 10/2007 | Goble et al. |
| 7,283,096 B2 | 10/2007 | Geisheimer et al. |
| 7,286,850 B2 | 10/2007 | Frielink et al. |
| 7,287,682 B1 | 10/2007 | Ezzat et al. |
| 7,289,139 B2 | 10/2007 | Amling et al. |
| 7,293,685 B2 | 11/2007 | Ehrenfels et al. |
| 7,295,893 B2 | 11/2007 | Sunaoshi |
| 7,295,907 B2 | 11/2007 | Lu et al. |
| 7,296,722 B2 | 11/2007 | Ivanko |
| 7,296,724 B2 | 11/2007 | Green et al. |
| 7,297,149 B2 | 11/2007 | Vitali et al. |
| 7,300,373 B2 | 11/2007 | Jinno et al. |
| 7,300,431 B2 | 11/2007 | Dubrovsky |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,303,502 B2 | 12/2007 | Thompson |
| 7,303,556 B2 | 12/2007 | Metzger |
| 7,306,597 B2 | 12/2007 | Manzo |
| 7,308,998 B2 | 12/2007 | Mastri et al. |
| 7,311,238 B2 | 12/2007 | Liu |
| 7,313,430 B2 | 12/2007 | Urquhart et al. |
| 7,314,473 B2 | 1/2008 | Jinno et al. |
| 7,320,704 B2 | 1/2008 | Lashinski et al. |
| 7,322,859 B2 | 1/2008 | Evans |
| 7,322,975 B2 | 1/2008 | Goble et al. |
| 7,322,994 B2 | 1/2008 | Nicholas et al. |
| 7,324,572 B2 | 1/2008 | Chang |
| 7,326,203 B2 | 2/2008 | Papineau et al. |
| 7,326,213 B2 | 2/2008 | Benderev et al. |
| 7,328,828 B2 | 2/2008 | Ortiz et al. |
| 7,328,829 B2 | 2/2008 | Arad et al. |
| 7,330,004 B2 | 2/2008 | DeJonge et al. |
| 7,331,340 B2 | 2/2008 | Barney |
| 7,331,343 B2 | 2/2008 | Schmidt et al. |
| 7,331,403 B2 | 2/2008 | Berry et al. |
| 7,331,406 B2 | 2/2008 | Wottreng, Jr. et al. |
| 7,331,969 B1 | 2/2008 | Inganas et al. |
| 7,334,717 B2 | 2/2008 | Rethy et al. |
| 7,334,718 B2 | 2/2008 | McAlister et al. |
| 7,335,199 B2 | 2/2008 | Goble et al. |
| 7,335,401 B2 | 2/2008 | Finke et al. |
| 7,336,045 B2 | 2/2008 | Clermonts |
| 7,336,048 B2 | 2/2008 | Lohr |
| 7,336,183 B2 | 2/2008 | Reddy et al. |
| 7,336,184 B2 | 2/2008 | Smith et al. |
| 7,337,774 B2 | 3/2008 | Webb |
| 7,338,505 B2 | 3/2008 | Belson |
| 7,338,513 B2 | 3/2008 | Lee et al. |
| 7,341,554 B2 | 3/2008 | Sekine et al. |
| 7,341,555 B2 | 3/2008 | Ootawara et al. |

(56) References Cited

U.S. PATENT DOCUMENTS

| | | |
|---|---|---|
| 7,341,591 B2 | 3/2008 | Grinberg |
| 7,343,920 B2 | 3/2008 | Toby et al. |
| 7,344,532 B2 | 3/2008 | Goble et al. |
| 7,344,533 B2 | 3/2008 | Pearson et al. |
| 7,346,344 B2 | 3/2008 | Fontaine |
| 7,346,406 B2 | 3/2008 | Brotto et al. |
| 7,348,763 B1 | 3/2008 | Reinhart et al. |
| 7,348,875 B2 | 3/2008 | Hughes et al. |
| RE40,237 E | 4/2008 | Bilotti et al. |
| 7,351,258 B2 | 4/2008 | Ricotta et al. |
| 7,354,398 B2 | 4/2008 | Kanazawa |
| 7,354,447 B2 | 4/2008 | Shelton, IV et al. |
| 7,354,502 B2 | 4/2008 | Polat et al. |
| 7,357,287 B2 | 4/2008 | Shelton, IV et al. |
| 7,357,806 B2 | 4/2008 | Rivera et al. |
| 7,361,168 B2 | 4/2008 | Makower et al. |
| 7,361,195 B2 | 4/2008 | Schwartz et al. |
| 7,362,062 B2 | 4/2008 | Schneider et al. |
| 7,364,060 B2 | 4/2008 | Milliman |
| 7,364,061 B2 | 4/2008 | Swayze et al. |
| 7,367,485 B2 | 5/2008 | Shelton, IV et al. |
| 7,367,973 B2 | 5/2008 | Manzo et al. |
| 7,368,124 B2 | 5/2008 | Chun et al. |
| 7,371,210 B2 | 5/2008 | Brock et al. |
| 7,371,403 B2 | 5/2008 | McCarthy et al. |
| 7,375,493 B2 | 5/2008 | Calhoon et al. |
| 7,377,918 B2 | 5/2008 | Amoah |
| 7,377,928 B2 | 5/2008 | Zubik et al. |
| 7,378,817 B2 | 5/2008 | Calhoon et al. |
| RE40,388 E | 6/2008 | Gines |
| D570,868 S | 6/2008 | Hosokawa et al. |
| 7,380,695 B2 | 6/2008 | Doll et al. |
| 7,380,696 B2 | 6/2008 | Shelton, IV et al. |
| 7,384,403 B2 | 6/2008 | Sherman |
| 7,384,417 B2 | 6/2008 | Cucin |
| 7,386,365 B2 | 6/2008 | Nixon |
| 7,386,730 B2 | 6/2008 | Uchikubo |
| 7,388,217 B2 | 6/2008 | Buschbeck et al. |
| 7,388,484 B2 | 6/2008 | Hsu |
| 7,391,173 B2 | 6/2008 | Schena |
| 7,394,190 B2 | 7/2008 | Huang |
| 7,396,356 B2 | 7/2008 | Mollenauer |
| 7,397,364 B2 | 7/2008 | Govari |
| 7,398,707 B2 | 7/2008 | Morley et al. |
| 7,398,907 B2 | 7/2008 | Racenet et al. |
| 7,398,908 B2 | 7/2008 | Holsten et al. |
| 7,400,107 B2 | 7/2008 | Schneider et al. |
| 7,400,752 B2 | 7/2008 | Zacharias |
| 7,401,000 B2 | 7/2008 | Nakamura |
| 7,401,721 B2 | 7/2008 | Holsten et al. |
| 7,404,449 B2 | 7/2008 | Bermingham et al. |
| 7,404,508 B2 | 7/2008 | Smith et al. |
| 7,404,509 B2 | 7/2008 | Ortiz et al. |
| 7,404,822 B2 | 7/2008 | Viart et al. |
| D575,793 S | 8/2008 | Ording |
| 7,407,074 B2 | 8/2008 | Ortiz et al. |
| 7,407,075 B2 | 8/2008 | Holsten et al. |
| 7,407,076 B2 | 8/2008 | Racenet et al. |
| 7,407,077 B2 | 8/2008 | Ortiz et al. |
| 7,407,078 B2 | 8/2008 | Shelton, IV et al. |
| 7,408,310 B2 | 8/2008 | Hong et al. |
| 7,410,085 B2 | 8/2008 | Wolf et al. |
| 7,410,086 B2 | 8/2008 | Ortiz et al. |
| 7,410,483 B2 | 8/2008 | Danitz et al. |
| 7,413,563 B2 | 8/2008 | Corcoran et al. |
| 7,416,101 B2 | 8/2008 | Shelton, IV et al. |
| 7,418,078 B2 | 8/2008 | Blanz et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,419,321 B2 | 9/2008 | Tereschouk |
| 7,419,495 B2 | 9/2008 | Menn et al. |
| 7,422,136 B1 | 9/2008 | Marczyk |
| 7,422,138 B2 | 9/2008 | Bilotti et al. |
| 7,422,139 B2 | 9/2008 | Shelton, IV et al. |
| 7,424,965 B2 | 9/2008 | Racenet et al. |
| 7,427,607 B2 | 9/2008 | Suzuki |
| D578,644 S | 10/2008 | Shumer et al. |
| 7,430,772 B2 | 10/2008 | Van Es |
| 7,431,188 B1 | 10/2008 | Marczyk |
| 7,431,189 B2 | 10/2008 | Shelton, IV et al. |
| 7,431,230 B2 | 10/2008 | McPherson et al. |
| 7,431,694 B2 | 10/2008 | Stefanchik et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,435,249 B2 | 10/2008 | Buysse et al. |
| 7,438,209 B1 | 10/2008 | Hess et al. |
| 7,438,718 B2 | 10/2008 | Milliman et al. |
| 7,439,354 B2 | 10/2008 | Lenges et al. |
| 7,441,684 B2 | 10/2008 | Shelton, IV et al. |
| 7,441,685 B1 | 10/2008 | Boudreaux |
| 7,442,201 B2 | 10/2008 | Pugsley et al. |
| 7,443,547 B2 | 10/2008 | Moreno et al. |
| 7,446,131 B1 | 11/2008 | Liu et al. |
| 7,448,525 B2 | 11/2008 | Shelton, IV et al. |
| 7,450,010 B1 | 11/2008 | Gravelle et al. |
| 7,450,991 B2 | 11/2008 | Smith et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,455,682 B2 | 11/2008 | Viola |
| 7,455,687 B2 | 11/2008 | Saunders et al. |
| D582,934 S | 12/2008 | Byeon |
| 7,461,767 B2 | 12/2008 | Viola et al. |
| 7,462,187 B2 | 12/2008 | Johnston et al. |
| 7,464,845 B2 | 12/2008 | Chou |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,467,849 B2 | 12/2008 | Silverbrook et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,221 B2 | 1/2009 | Ewers et al. |
| 7,473,253 B2 | 1/2009 | Dycus et al. |
| 7,473,263 B2 | 1/2009 | Johnston et al. |
| 7,476,237 B2 | 1/2009 | Taniguchi et al. |
| 7,479,147 B2 | 1/2009 | Honeycutt et al. |
| 7,479,608 B2 | 1/2009 | Smith |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,485,124 B2 | 2/2009 | Kuhns et al. |
| 7,485,133 B2 | 2/2009 | Cannon et al. |
| 7,485,142 B2 | 2/2009 | Milo |
| 7,487,899 B2 | 2/2009 | Shelton, IV et al. |
| 7,489,055 B2 | 2/2009 | Jeong et al. |
| 7,490,749 B2 | 2/2009 | Schall et al. |
| 7,491,232 B2 | 2/2009 | Bolduc et al. |
| 7,492,261 B2 | 2/2009 | Cambre et al. |
| 7,494,039 B2 | 2/2009 | Racenet et al. |
| 7,494,460 B2 | 2/2009 | Haarstad et al. |
| 7,494,499 B2 | 2/2009 | Nagase et al. |
| 7,494,501 B2 | 2/2009 | Ahlberg et al. |
| 7,497,137 B2 | 3/2009 | Tellenbach et al. |
| 7,500,979 B2 | 3/2009 | Hueil et al. |
| 7,501,198 B2 | 3/2009 | Barlev et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,507,202 B2 | 3/2009 | Schoellhorn |
| 7,510,107 B2 | 3/2009 | Timm et al. |
| 7,510,534 B2 | 3/2009 | Burdorff et al. |
| 7,510,566 B2 | 3/2009 | Jacobs et al. |
| 7,513,407 B1 | 4/2009 | Chang |
| 7,513,408 B2 | 4/2009 | Shelton, IV et al. |
| 7,517,356 B2 | 4/2009 | Heinrich |
| 7,524,320 B2 | 4/2009 | Tierney et al. |
| 7,527,632 B2 | 5/2009 | Houghton et al. |
| 7,530,984 B2 | 5/2009 | Sonnenschein et al. |

(56) References Cited

U.S. PATENT DOCUMENTS

| | | |
|---|---|---|
| 7,530,985 B2 | 5/2009 | Takemoto et al. |
| 7,533,906 B2 | 5/2009 | Luettgen et al. |
| 7,534,259 B2 | 5/2009 | Lashinski et al. |
| 7,540,867 B2 | 6/2009 | Jinno et al. |
| 7,540,872 B2 | 6/2009 | Schechter et al. |
| 7,542,807 B2 | 6/2009 | Bertolero et al. |
| 7,543,730 B1 | 6/2009 | Marczyk |
| 7,544,197 B2 | 6/2009 | Kelsch et al. |
| 7,546,939 B2 | 6/2009 | Adams et al. |
| 7,546,940 B2 | 6/2009 | Milliman et al. |
| 7,547,287 B2 | 6/2009 | Boecker et al. |
| 7,547,312 B2 | 6/2009 | Bauman et al. |
| 7,549,563 B2 | 6/2009 | Mather et al. |
| 7,549,564 B2 | 6/2009 | Boudreaux |
| 7,549,998 B2 | 6/2009 | Braun |
| 7,552,854 B2 | 6/2009 | Wixey et al. |
| 7,553,173 B2 | 6/2009 | Kowalick |
| 7,553,275 B2 | 6/2009 | Padget et al. |
| 7,554,343 B2 | 6/2009 | Bromfield |
| 7,556,185 B2 | 7/2009 | Viola |
| 7,556,186 B2 | 7/2009 | Milliman |
| 7,556,647 B2 | 7/2009 | Drews et al. |
| 7,559,449 B2 | 7/2009 | Viola |
| 7,559,450 B2 | 7/2009 | Wales et al. |
| 7,559,452 B2 | 7/2009 | Wales et al. |
| 7,559,937 B2 | 7/2009 | de la Torre et al. |
| 7,561,637 B2 | 7/2009 | Jonsson et al. |
| 7,562,910 B2 | 7/2009 | Kertesz et al. |
| 7,563,269 B2 | 7/2009 | Hashiguchi |
| 7,563,862 B2 | 7/2009 | Sieg et al. |
| 7,565,993 B2 | 7/2009 | Milliman et al. |
| 7,566,300 B2 | 7/2009 | Devierre et al. |
| 7,567,045 B2 | 7/2009 | Fristedt |
| 7,568,603 B2 | 8/2009 | Shelton, IV et al. |
| 7,568,604 B2 | 8/2009 | Ehrenfels et al. |
| 7,568,619 B2 | 8/2009 | Todd et al. |
| 7,572,285 B2 | 8/2009 | Frey et al. |
| 7,575,144 B2 | 8/2009 | Ortiz et al. |
| 7,578,825 B2 | 8/2009 | Huebner |
| D600,712 S | 9/2009 | LaManna et al. |
| 7,583,063 B2 | 9/2009 | Dooley |
| 7,584,880 B2 | 9/2009 | Racenet et al. |
| 7,586,289 B2 | 9/2009 | Andruk et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,591,783 B2 | 9/2009 | Boulais et al. |
| 7,591,818 B2 | 9/2009 | Bertolero et al. |
| 7,593,766 B2 | 9/2009 | Faber et al. |
| 7,595,642 B2 | 9/2009 | Doyle |
| 7,597,229 B2 | 10/2009 | Boudreaux et al. |
| 7,597,230 B2 | 10/2009 | Racenet et al. |
| 7,597,693 B2 | 10/2009 | Garrison |
| 7,597,699 B2 | 10/2009 | Rogers |
| 7,598,972 B2 | 10/2009 | Tomita |
| 7,600,663 B2 | 10/2009 | Green |
| 7,604,118 B2 | 10/2009 | Iio et al. |
| 7,604,150 B2 | 10/2009 | Boudreaux |
| 7,604,151 B2 | 10/2009 | Hess et al. |
| 7,604,668 B2 | 10/2009 | Farnsworth et al. |
| 7,605,826 B2 | 10/2009 | Sauer |
| 7,607,557 B2 | 10/2009 | Shelton, IV et al. |
| 7,608,091 B2 | 10/2009 | Goldfarb et al. |
| D604,325 S | 11/2009 | Ebeling et al. |
| 7,611,038 B2 | 11/2009 | Racenet et al. |
| 7,611,474 B2 | 11/2009 | Hibner et al. |
| 7,615,003 B2 | 11/2009 | Stefanchik et al. |
| 7,615,006 B2 | 11/2009 | Abe |
| 7,615,067 B2 | 11/2009 | Lee et al. |
| 7,617,961 B2 | 11/2009 | Viola |
| 7,618,427 B2 | 11/2009 | Ortiz et al. |
| D605,201 S | 12/2009 | Lorenz et al. |
| D606,992 S | 12/2009 | Liu et al. |
| D607,010 S | 12/2009 | Kocmick |
| 7,624,902 B2 | 12/2009 | Marczyk et al. |
| 7,624,903 B2 | 12/2009 | Green et al. |
| 7,625,370 B2 | 12/2009 | Hart et al. |
| 7,625,388 B2 | 12/2009 | Boukhny et al. |
| 7,625,662 B2 | 12/2009 | Vaisnys et al. |
| 7,630,841 B2 | 12/2009 | Comisky et al. |
| 7,631,793 B2 | 12/2009 | Rethy et al. |
| 7,631,794 B2 | 12/2009 | Rethy et al. |
| 7,635,074 B2 | 12/2009 | Olson et al. |
| 7,635,922 B2 | 12/2009 | Becker |
| 7,637,409 B2 | 12/2009 | Marczyk |
| 7,637,410 B2 | 12/2009 | Marczyk |
| 7,638,958 B2 | 12/2009 | Philipp et al. |
| 7,641,091 B2 | 1/2010 | Olson et al. |
| 7,641,092 B2 | 1/2010 | Kruszynski et al. |
| 7,641,093 B2 | 1/2010 | Doll et al. |
| 7,641,095 B2 | 1/2010 | Viola |
| 7,641,671 B2 | 1/2010 | Crainich |
| 7,644,783 B2 | 1/2010 | Roberts et al. |
| 7,644,848 B2 | 1/2010 | Swayze et al. |
| 7,645,230 B2 | 1/2010 | Mikkaichi et al. |
| 7,648,055 B2 | 1/2010 | Marczyk |
| 7,648,457 B2 | 1/2010 | Stefanchik et al. |
| 7,648,519 B2 | 1/2010 | Lee et al. |
| 7,650,185 B2 | 1/2010 | Maile et al. |
| 7,651,017 B2 | 1/2010 | Ortiz et al. |
| 7,651,498 B2 | 1/2010 | Shifrin et al. |
| 7,654,431 B2 | 2/2010 | Hueil et al. |
| 7,655,003 B2 | 2/2010 | Lorang et al. |
| 7,655,004 B2 | 2/2010 | Long |
| 7,655,288 B2 | 2/2010 | Bauman et al. |
| 7,655,584 B2 | 2/2010 | Biran et al. |
| 7,656,131 B2 | 2/2010 | Embrey et al. |
| 7,658,311 B2 | 2/2010 | Boudreaux |
| 7,658,312 B2 | 2/2010 | Vidal et al. |
| 7,658,705 B2 | 2/2010 | Melvin et al. |
| 7,659,219 B2 | 2/2010 | Biran et al. |
| 7,661,448 B2 | 2/2010 | Kim et al. |
| 7,662,161 B2 | 2/2010 | Briganti et al. |
| 7,665,646 B2 | 2/2010 | Prommersberger |
| 7,665,647 B2 | 2/2010 | Shelton, IV et al. |
| 7,666,195 B2 | 2/2010 | Kelleher et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,253 B2 | 3/2010 | Fisher et al. |
| 7,674,255 B2 | 3/2010 | Braun |
| 7,674,263 B2 | 3/2010 | Ryan |
| 7,674,270 B2 | 3/2010 | Layer |
| 7,678,121 B1 | 3/2010 | Knodel |
| 7,682,307 B2 | 3/2010 | Danitz et al. |
| 7,682,367 B2 | 3/2010 | Shah et al. |
| 7,682,686 B2 | 3/2010 | Curro et al. |
| 7,686,201 B2 | 3/2010 | Csiky |
| 7,686,804 B2 | 3/2010 | Johnson et al. |
| 7,686,826 B2 | 3/2010 | Lee et al. |
| 7,688,028 B2 | 3/2010 | Phillips et al. |
| 7,690,547 B2 | 4/2010 | Racenet et al. |
| 7,691,098 B2 | 4/2010 | Wallace et al. |
| 7,691,103 B2 | 4/2010 | Fernandez et al. |
| 7,691,106 B2 | 4/2010 | Schenberger et al. |
| 7,694,864 B2 | 4/2010 | Okada et al. |
| 7,694,865 B2 | 4/2010 | Scirica |
| 7,695,485 B2 | 4/2010 | Whitman et al. |
| 7,695,493 B2 | 4/2010 | Saadat et al. |
| 7,699,204 B2 | 4/2010 | Viola |
| 7,699,835 B2 | 4/2010 | Lee et al. |
| 7,699,844 B2 | 4/2010 | Utley et al. |
| 7,699,846 B2 | 4/2010 | Ryan |
| 7,699,856 B2 | 4/2010 | Van Wyk et al. |
| 7,699,859 B2 | 4/2010 | Bombard et al. |
| 7,699,860 B2 | 4/2010 | Huitema et al. |
| 7,699,868 B2 | 4/2010 | Frank et al. |
| 7,703,653 B2 | 4/2010 | Shah et al. |
| 7,705,559 B2 | 4/2010 | Powell et al. |

(56) References Cited

U.S. PATENT DOCUMENTS

| | | |
|---|---|---|
| 7,706,853 B2 | 4/2010 | Hacker et al. |
| 7,708,180 B2 | 5/2010 | Murray et al. |
| 7,708,181 B2 | 5/2010 | Cole et al. |
| 7,708,182 B2 | 5/2010 | Viola |
| 7,708,758 B2 | 5/2010 | Lee et al. |
| 7,708,768 B2 | 5/2010 | Danek et al. |
| 7,709,136 B2 | 5/2010 | Touchton et al. |
| 7,712,182 B2 | 5/2010 | Zeiler et al. |
| 7,713,190 B2 | 5/2010 | Brock et al. |
| 7,713,542 B2 | 5/2010 | Xu et al. |
| 7,714,239 B2 | 5/2010 | Smith |
| 7,714,334 B2 | 5/2010 | Lin |
| 7,717,312 B2 | 5/2010 | Beetel |
| 7,717,313 B2 | 5/2010 | Criscuolo et al. |
| 7,717,846 B2 | 5/2010 | Zirps et al. |
| 7,717,873 B2 | 5/2010 | Swick |
| 7,717,915 B2 | 5/2010 | Miyazawa |
| 7,717,926 B2 | 5/2010 | Whitfield et al. |
| 7,718,180 B2 | 5/2010 | Karp |
| 7,718,556 B2 | 5/2010 | Matsuda et al. |
| 7,721,930 B2 | 5/2010 | McKenna et al. |
| 7,721,931 B2 | 5/2010 | Shelton, IV et al. |
| 7,721,932 B2 | 5/2010 | Cole et al. |
| 7,721,933 B2 | 5/2010 | Ehrenfels et al. |
| 7,721,934 B2 | 5/2010 | Shelton, IV et al. |
| 7,721,936 B2 | 5/2010 | Shalton, IV et al. |
| 7,722,527 B2 | 5/2010 | Bouchier et al. |
| 7,722,607 B2 | 5/2010 | Dumbauld et al. |
| 7,722,610 B2 | 5/2010 | Viola et al. |
| 7,725,214 B2 | 5/2010 | Diolaiti |
| 7,726,171 B2 | 6/2010 | Langlotz et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,727,954 B2 | 6/2010 | McKay |
| 7,728,553 B2 | 6/2010 | Carrier et al. |
| 7,729,742 B2 | 6/2010 | Govari |
| 7,731,072 B2 | 6/2010 | Timm et al. |
| 7,731,073 B2 | 6/2010 | Wixey et al. |
| 7,731,724 B2 | 6/2010 | Huitema et al. |
| 7,735,703 B2 | 6/2010 | Morgan et al. |
| 7,735,704 B2 | 6/2010 | Bilotti |
| 7,736,254 B2 | 6/2010 | Schena |
| 7,736,306 B2 | 6/2010 | Brustad et al. |
| 7,736,374 B2 | 6/2010 | Vaughan et al. |
| 7,738,971 B2 | 6/2010 | Swayze et al. |
| 7,740,159 B2 | 6/2010 | Shelton, IV et al. |
| 7,742,036 B2 | 6/2010 | Grant et al. |
| 7,743,960 B2 | 6/2010 | Whitman et al. |
| 7,744,624 B2 | 6/2010 | Bettuchi |
| 7,744,627 B2 | 6/2010 | Orban, III et al. |
| 7,744,628 B2 | 6/2010 | Viola |
| 7,747,146 B2 | 6/2010 | Milano et al. |
| 7,748,587 B2 | 7/2010 | Haramiishi et al. |
| 7,748,632 B2 | 7/2010 | Coleman et al. |
| 7,749,204 B2 | 7/2010 | Dhanaraj et al. |
| 7,749,240 B2 | 7/2010 | Takahashi et al. |
| 7,751,870 B2 | 7/2010 | Whitman |
| 7,753,245 B2 | 7/2010 | Boudreaux et al. |
| 7,753,246 B2 | 7/2010 | Scirica |
| 7,753,904 B2 | 7/2010 | Shelton, IV et al. |
| 7,757,924 B2 | 7/2010 | Gerbi et al. |
| 7,758,594 B2 | 7/2010 | Lamson et al. |
| 7,758,612 B2 | 7/2010 | Shipp |
| 7,758,613 B2 | 7/2010 | Whitman |
| 7,762,462 B2 | 7/2010 | Gelbman |
| 7,762,998 B2 | 7/2010 | Birk et al. |
| D622,286 S | 8/2010 | Umezawa |
| 7,766,207 B2 | 8/2010 | Mather et al. |
| 7,766,209 B2 | 8/2010 | Baxter, III et al. |
| 7,766,210 B2 | 8/2010 | Shelton, IV et al. |
| 7,766,821 B2 | 8/2010 | Brunnen et al. |
| 7,766,894 B2 | 8/2010 | Weitzner et al. |
| 7,770,658 B2 | 8/2010 | Ito et al. |
| 7,770,773 B2 | 8/2010 | Whitman et al. |
| 7,770,774 B2 | 8/2010 | Mastri et al. |
| 7,770,775 B2 | 8/2010 | Shelton, IV et al. |
| 7,770,776 B2 | 8/2010 | Chen et al. |
| 7,771,396 B2 | 8/2010 | Stefanchik et al. |
| 7,772,720 B2 | 8/2010 | McGee et al. |
| 7,772,725 B2 | 8/2010 | Siman-Tov |
| 7,775,972 B2 | 8/2010 | Brock et al. |
| 7,776,037 B2 | 8/2010 | Odom |
| 7,776,060 B2 | 8/2010 | Mooradian et al. |
| 7,776,065 B2 | 8/2010 | Griffiths et al. |
| 7,778,004 B2 | 8/2010 | Nerheim et al. |
| 7,779,614 B1 | 8/2010 | McGonagle et al. |
| 7,779,737 B2 | 8/2010 | Newman, Jr. et al. |
| 7,780,054 B2 | 8/2010 | Wales |
| 7,780,055 B2 | 8/2010 | Scirica et al. |
| 7,780,309 B2 | 8/2010 | McMillan et al. |
| 7,780,651 B2 | 8/2010 | Madhani et al. |
| 7,780,663 B2 | 8/2010 | Yates et al. |
| 7,780,685 B2 | 8/2010 | Hunt et al. |
| 7,782,382 B2 | 8/2010 | Fujimura |
| 7,784,662 B2 | 8/2010 | Wales et al. |
| 7,784,663 B2 | 8/2010 | Shelton, IV |
| 7,787,256 B2 | 8/2010 | Chan et al. |
| 7,789,283 B2 | 9/2010 | Shah |
| 7,789,875 B2 | 9/2010 | Brock et al. |
| 7,789,883 B2 | 9/2010 | Takashino et al. |
| 7,789,889 B2 | 9/2010 | Zubik et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,799,044 B2 | 9/2010 | Johnston et al. |
| 7,799,965 B2 | 9/2010 | Patel et al. |
| 7,803,151 B2 | 9/2010 | Whitman |
| 7,806,871 B2 | 10/2010 | Li et al. |
| 7,806,891 B2 | 10/2010 | Nowlin et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,811,275 B2 | 10/2010 | Birk et al. |
| 7,814,816 B2 | 10/2010 | Alberti et al. |
| 7,815,092 B2 | 10/2010 | Whitman et al. |
| 7,815,565 B2 | 10/2010 | Stefanchik et al. |
| 7,815,662 B2 | 10/2010 | Spivey et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,799 B2 | 10/2010 | Merril et al. |
| 7,819,884 B2 | 10/2010 | Lee et al. |
| 7,819,885 B2 | 10/2010 | Cooper |
| 7,819,886 B2 | 10/2010 | Whitfield et al. |
| 7,819,894 B2 | 10/2010 | Mitsuishi et al. |
| 7,823,592 B2 | 11/2010 | Bettuchi et al. |
| 7,823,760 B2 | 11/2010 | Zemlok et al. |
| 7,824,401 B2 | 11/2010 | Manzo et al. |
| 7,824,422 B2 | 11/2010 | Benchetrit |
| 7,824,426 B2 | 11/2010 | Racenet et al. |
| 7,828,189 B2 | 11/2010 | Holsten et al. |
| 7,828,794 B2 | 11/2010 | Sartor |
| 7,828,808 B2 | 11/2010 | Hinman et al. |
| 7,829,416 B2 | 11/2010 | Kudou et al. |
| 7,831,292 B2 | 11/2010 | Quaid et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,833,234 B2 | 11/2010 | Bailly et al. |
| 7,835,823 B2 | 11/2010 | Sillman et al. |
| 7,836,400 B2 | 11/2010 | May et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,837,425 B2 | 11/2010 | Saeki et al. |
| 7,837,685 B2 | 11/2010 | Weinberg et al. |
| 7,837,687 B2 | 11/2010 | Harp |
| 7,837,694 B2 | 11/2010 | Tethrake et al. |
| 7,838,789 B2 | 11/2010 | Stoffers et al. |
| 7,839,109 B2 | 11/2010 | Carmen, Jr. et al. |

(56) References Cited

U.S. PATENT DOCUMENTS

| | | |
|---|---|---|
| 7,840,253 B2 | 11/2010 | Tremblay et al. |
| 7,841,503 B2 | 11/2010 | Sonnenschein et al. |
| 7,842,025 B2 | 11/2010 | Coleman et al. |
| 7,842,028 B2 | 11/2010 | Lee |
| 7,843,158 B2 | 11/2010 | Prisco |
| 7,845,533 B2 | 12/2010 | Marczyk et al. |
| 7,845,534 B2 | 12/2010 | Viola et al. |
| 7,845,535 B2 | 12/2010 | Scircia |
| 7,845,536 B2 | 12/2010 | Viola et al. |
| 7,845,537 B2 | 12/2010 | Shelton, IV et al. |
| 7,845,538 B2 | 12/2010 | Whitman |
| 7,845,912 B2 | 12/2010 | Sung et al. |
| 7,846,085 B2 | 12/2010 | Silverman et al. |
| 7,846,149 B2 | 12/2010 | Jankowski |
| 7,846,161 B2 | 12/2010 | Dumbauld et al. |
| 7,848,066 B2 | 12/2010 | Yanagishima |
| 7,850,623 B2 | 12/2010 | Griffin et al. |
| 7,850,642 B2 | 12/2010 | Moll et al. |
| 7,850,982 B2 | 12/2010 | Stopek et al. |
| 7,853,813 B2 | 12/2010 | Lee |
| 7,854,735 B2 | 12/2010 | Houser et al. |
| 7,854,736 B2 | 12/2010 | Ryan |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,857,813 B2 | 12/2010 | Schmitz et al. |
| 7,861,906 B2 | 1/2011 | Doll et al. |
| 7,862,502 B2 | 1/2011 | Pool et al. |
| 7,862,546 B2 | 1/2011 | Conlon et al. |
| 7,862,579 B2 | 1/2011 | Ortiz et al. |
| 7,866,525 B2 | 1/2011 | Scirica |
| 7,866,527 B2 | 1/2011 | Hall et al. |
| 7,866,528 B2 | 1/2011 | Olson et al. |
| 7,870,989 B2 | 1/2011 | Viola et al. |
| 7,871,418 B2 | 1/2011 | Thompson et al. |
| 7,871,440 B2 | 1/2011 | Schwartz et al. |
| 7,875,055 B2 | 1/2011 | Cichocki, Jr. |
| 7,879,063 B2 | 2/2011 | Khosravi |
| 7,879,070 B2 | 2/2011 | Ortiz et al. |
| 7,883,461 B2 | 2/2011 | Albrecht et al. |
| 7,883,465 B2 | 2/2011 | Donofrio et al. |
| 7,883,540 B2 | 2/2011 | Niwa et al. |
| 7,886,951 B2 | 2/2011 | Hessler |
| 7,886,952 B2 | 2/2011 | Scirica et al. |
| 7,887,530 B2 | 2/2011 | Zemlok et al. |
| 7,887,535 B2 | 2/2011 | Lands et al. |
| 7,887,536 B2 | 2/2011 | Johnson et al. |
| 7,887,563 B2 | 2/2011 | Cummins |
| 7,887,755 B2 | 2/2011 | Mingerink et al. |
| 7,891,531 B1 | 2/2011 | Ward |
| 7,891,532 B2 | 2/2011 | Mastri et al. |
| 7,892,200 B2 | 2/2011 | Birk et al. |
| 7,892,245 B2 | 2/2011 | Liddicoat et al. |
| 7,893,586 B2 | 2/2011 | West et al. |
| 7,896,214 B2 | 3/2011 | Farascioni |
| 7,896,215 B2 | 3/2011 | Adams et al. |
| 7,896,671 B2 | 3/2011 | Kim et al. |
| 7,896,869 B2 | 3/2011 | DiSilvestro et al. |
| 7,896,877 B2 | 3/2011 | Hall et al. |
| 7,896,895 B2 | 3/2011 | Boudreaux et al. |
| 7,896,897 B2 | 3/2011 | Gresham et al. |
| 7,896,900 B2 | 3/2011 | Frank et al. |
| 7,898,198 B2 | 3/2011 | Murphree |
| 7,900,805 B2 | 3/2011 | Shelton, IV et al. |
| 7,900,806 B2 | 3/2011 | Chen et al. |
| 7,901,381 B2 | 3/2011 | Birk et al. |
| 7,905,380 B2 | 3/2011 | Shelton, IV et al. |
| 7,905,381 B2 | 3/2011 | Baxter, III et al. |
| 7,905,881 B2 | 3/2011 | Masuda et al. |
| 7,905,889 B2 | 3/2011 | Catanese, III et al. |
| 7,905,890 B2 | 3/2011 | Whitfield et al. |
| 7,905,902 B2 | 3/2011 | Huitema et al. |
| 7,909,039 B2 | 3/2011 | Hur |
| 7,909,191 B2 | 3/2011 | Baker et al. |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,521 B2 | 3/2011 | Wang et al. |
| 7,914,543 B2 | 3/2011 | Roth et al. |
| 7,914,551 B2 | 3/2011 | Ortiz et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,918,845 B2 | 4/2011 | Saadat et al. |
| 7,918,848 B2 | 4/2011 | Lau et al. |
| 7,918,861 B2 | 4/2011 | Brock et al. |
| 7,918,867 B2 | 4/2011 | Dana et al. |
| 7,922,061 B2 | 4/2011 | Shelton, IV et al. |
| 7,922,063 B2 | 4/2011 | Zemlok et al. |
| 7,922,743 B2 | 4/2011 | Heinrich et al. |
| 7,923,144 B2 | 4/2011 | Kohn et al. |
| 7,926,691 B2 | 4/2011 | Viola et al. |
| 7,926,692 B2 | 4/2011 | Racenet et al. |
| 7,927,328 B2 | 4/2011 | Orszulak et al. |
| 7,928,281 B2 | 4/2011 | Augustine |
| 7,930,040 B1 | 4/2011 | Kelsch et al. |
| 7,930,065 B2 | 4/2011 | Larkin et al. |
| 7,931,660 B2 | 4/2011 | Aranyi et al. |
| 7,931,695 B2 | 4/2011 | Ringeisen |
| 7,931,877 B2 | 4/2011 | Steffens et al. |
| 7,934,630 B2 | 5/2011 | Shelton, IV et al. |
| 7,934,631 B2 | 5/2011 | Balbierz et al. |
| 7,934,896 B2 | 5/2011 | Schnier |
| 7,935,130 B2 | 5/2011 | Williams |
| 7,935,773 B2 | 5/2011 | Hadba et al. |
| 7,936,142 B2 | 5/2011 | Otsuka et al. |
| 7,938,307 B2 | 5/2011 | Bettuchi |
| 7,939,152 B2 | 5/2011 | Haskin et al. |
| 7,941,865 B2 | 5/2011 | Seman, Jr. et al. |
| 7,942,300 B2 | 5/2011 | Rethy et al. |
| 7,942,303 B2 | 5/2011 | Shah |
| 7,942,890 B2 | 5/2011 | D'Agostino et al. |
| 7,944,175 B2 | 5/2011 | Mori et al. |
| 7,945,792 B2 | 5/2011 | Cherpantier |
| 7,945,798 B2 | 5/2011 | Carlson et al. |
| 7,946,453 B2 | 5/2011 | Voegele et al. |
| 7,947,011 B2 | 5/2011 | Birk et al. |
| 7,948,381 B2 | 5/2011 | Lindsay et al. |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,951,071 B2 | 5/2011 | Whitman et al. |
| 7,951,166 B2 | 5/2011 | Orban, III et al. |
| 7,954,682 B2 | 6/2011 | Giordano et al. |
| 7,954,684 B2 | 6/2011 | Boudreaux |
| 7,954,685 B2 | 6/2011 | Viola |
| 7,954,686 B2 | 6/2011 | Baxter et al. |
| 7,954,687 B2 | 6/2011 | Zemlok et al. |
| 7,954,688 B2 | 6/2011 | Argentine et al. |
| 7,955,253 B2 | 6/2011 | Ewers et al. |
| 7,955,257 B2 | 6/2011 | Frasier et al. |
| 7,955,322 B2 | 6/2011 | Devengenzo et al. |
| 7,955,327 B2 | 6/2011 | Sartor et al. |
| 7,955,380 B2 | 6/2011 | Chu et al. |
| 7,959,050 B2 | 6/2011 | Smith et al. |
| 7,959,051 B2 | 6/2011 | Smith et al. |
| 7,959,052 B2 | 6/2011 | Sonnenschein et al. |
| 7,963,432 B2 | 6/2011 | Knodel et al. |
| 7,963,433 B2 | 6/2011 | Whitman et al. |
| 7,963,913 B2 | 6/2011 | Devengenzo et al. |
| 7,963,963 B2 | 6/2011 | Francischelli et al. |
| 7,963,964 B2 | 6/2011 | Santilli et al. |
| 7,964,206 B2 | 6/2011 | Suokas et al. |
| 7,966,236 B2 | 6/2011 | Noriega et al. |
| 7,966,269 B2 | 6/2011 | Bauer et al. |
| 7,966,799 B2 | 6/2011 | Morgan et al. |
| 7,967,178 B2 | 6/2011 | Scirica et al. |
| 7,967,179 B2 | 6/2011 | Olson et al. |
| 7,967,180 B2 | 6/2011 | Scirica |
| 7,967,181 B2 | 6/2011 | Viola et al. |
| 7,967,791 B2 | 6/2011 | Franer et al. |

(56) References Cited

U.S. PATENT DOCUMENTS

| | | |
|---|---|---|
| 7,967,839 B2 | 6/2011 | Flock et al. |
| 7,972,298 B2 | 7/2011 | Wallace et al. |
| 7,972,315 B2 | 7/2011 | Birk et al. |
| 7,976,213 B2 | 7/2011 | Bertolotti et al. |
| 7,976,508 B2 | 7/2011 | Hoag |
| 7,976,563 B2 | 7/2011 | Summerer |
| 7,979,137 B2 | 7/2011 | Tracey et al. |
| 7,980,443 B2 | 7/2011 | Scheib et al. |
| 7,981,025 B2 | 7/2011 | Pool et al. |
| 7,981,102 B2 | 7/2011 | Patel et al. |
| 7,981,132 B2 | 7/2011 | Dubrul et al. |
| 7,987,405 B2 | 7/2011 | Turner et al. |
| 7,988,015 B2 | 8/2011 | Mason, II et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,988,779 B2 | 8/2011 | Disalvo et al. |
| 7,992,757 B2 | 8/2011 | Wheeler et al. |
| 7,993,360 B2 | 8/2011 | Hacker et al. |
| 7,994,670 B2 | 8/2011 | Ji |
| 7,997,054 B2 | 8/2011 | Bertsch et al. |
| 7,997,468 B2 | 8/2011 | Farascioni |
| 7,997,469 B2 | 8/2011 | Olson et al. |
| 8,002,696 B2 | 8/2011 | Suzuki |
| 8,002,784 B2 | 8/2011 | Jinno et al. |
| 8,002,785 B2 | 8/2011 | Weiss et al. |
| 8,002,795 B2 | 8/2011 | Beetel |
| 8,006,365 B2 | 8/2011 | Levin et al. |
| 8,006,885 B2 | 8/2011 | Marczyk |
| 8,006,889 B2 | 8/2011 | Adams et al. |
| 8,007,370 B2 | 8/2011 | Hirsch et al. |
| 8,007,465 B2 | 8/2011 | Birk et al. |
| 8,007,479 B2 | 8/2011 | Birk et al. |
| 8,007,511 B2 | 8/2011 | Brock et al. |
| 8,007,513 B2 | 8/2011 | Nalagatla et al. |
| 8,008,598 B2 | 8/2011 | Whitman et al. |
| 8,010,180 B2 | 8/2011 | Quaid et al. |
| 8,011,550 B2 | 9/2011 | Aranyi et al. |
| 8,011,551 B2 | 9/2011 | Marczyk et al. |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,016,176 B2 | 9/2011 | Kasvikis et al. |
| 8,016,177 B2 | 9/2011 | Bettuchi et al. |
| 8,016,178 B2 | 9/2011 | Olson et al. |
| 8,016,849 B2 | 9/2011 | Wenchell |
| 8,016,855 B2 | 9/2011 | Whitman et al. |
| 8,016,858 B2 | 9/2011 | Whitman |
| 8,016,881 B2 | 9/2011 | Furst |
| 8,020,742 B2 | 9/2011 | Marczyk |
| 8,020,743 B2 | 9/2011 | Shelton, IV |
| 8,021,375 B2 | 9/2011 | Aldrich et al. |
| 8,025,199 B2 | 9/2011 | Whitman et al. |
| 8,025,896 B2 | 9/2011 | Malaviya et al. |
| 8,028,835 B2 | 10/2011 | Yasuda et al. |
| 8,028,882 B2 | 10/2011 | Viola |
| 8,028,883 B2 | 10/2011 | Stopek |
| 8,028,884 B2 | 10/2011 | Sniffin et al. |
| 8,028,885 B2 | 10/2011 | Smith et al. |
| 8,029,510 B2 | 10/2011 | Hoegerle |
| 8,031,069 B2 | 10/2011 | Cohn et al. |
| 8,033,438 B2 | 10/2011 | Scirica |
| 8,033,439 B2 | 10/2011 | Racenet et al. |
| 8,033,440 B2 | 10/2011 | Wenchell et al. |
| 8,033,442 B2 | 10/2011 | Racenet et al. |
| 8,034,077 B2 | 10/2011 | Smith et al. |
| 8,034,337 B2 | 10/2011 | Simard |
| 8,034,363 B2 | 10/2011 | Li et al. |
| 8,035,487 B2 | 10/2011 | Malackowski |
| 8,037,591 B2 | 10/2011 | Spivey et al. |
| 8,038,044 B2 | 10/2011 | Viola |
| 8,038,045 B2 | 10/2011 | Bettuchi et al. |
| 8,038,046 B2 | 10/2011 | Smith et al. |
| 8,038,686 B2 | 10/2011 | Huitema et al. |
| 8,043,207 B2 | 10/2011 | Adams |
| 8,043,328 B2 | 10/2011 | Hahnen et al. |
| 8,044,536 B2 | 10/2011 | Nguyen et al. |
| 8,044,604 B2 | 10/2011 | Hagino et al. |
| 8,047,236 B2 | 11/2011 | Perry |
| 8,048,503 B2 | 11/2011 | Farnsworth et al. |
| 8,052,636 B2 | 11/2011 | Moll et al. |
| 8,056,787 B2 | 11/2011 | Boudreaux et al. |
| 8,056,788 B2 | 11/2011 | Mastri et al. |
| 8,056,789 B1 | 11/2011 | White et al. |
| 8,057,508 B2 | 11/2011 | Shelton, IV |
| 8,058,771 B2 | 11/2011 | Giordano et al. |
| 8,060,250 B2 | 11/2011 | Reiland et al. |
| 8,061,014 B2 | 11/2011 | Smith et al. |
| 8,061,576 B2 | 11/2011 | Cappola |
| 8,062,236 B2 | 11/2011 | Soltz |
| 8,062,306 B2 | 11/2011 | Nobis et al. |
| 8,062,330 B2 | 11/2011 | Prommersberger et al. |
| 8,063,619 B2 | 11/2011 | Zhu et al. |
| 8,066,158 B2 | 11/2011 | Vogel et al. |
| 8,066,166 B2 | 11/2011 | Demmy et al. |
| 8,066,167 B2 | 11/2011 | Measamer et al. |
| 8,066,168 B2 | 11/2011 | Vidal et al. |
| 8,066,720 B2 | 11/2011 | Knodel et al. |
| D650,074 S | 12/2011 | Hunt et al. |
| D650,789 S | 12/2011 | Arnold |
| 8,070,033 B2 | 12/2011 | Milliman et al. |
| 8,070,034 B1 | 12/2011 | Knodel |
| 8,070,035 B2 | 12/2011 | Holsten et al. |
| 8,070,743 B2 | 12/2011 | Kagan et al. |
| 8,074,858 B2 | 12/2011 | Marczyk |
| 8,074,859 B2 | 12/2011 | Kostrzewski |
| 8,074,861 B2 | 12/2011 | Ehrenfels et al. |
| 8,075,476 B2 | 12/2011 | Vargas |
| 8,075,571 B2 | 12/2011 | Vitali et al. |
| 8,079,950 B2 | 12/2011 | Stern et al. |
| 8,079,989 B2 | 12/2011 | Birk et al. |
| 8,080,004 B2 | 12/2011 | Downey et al. |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,084,001 B2 | 12/2011 | Burns et al. |
| 8,084,969 B2 | 12/2011 | David et al. |
| 8,085,013 B2 | 12/2011 | Wei et al. |
| 8,087,562 B1 | 1/2012 | Manoux et al. |
| 8,087,563 B2 | 1/2012 | Milliman et al. |
| 8,089,509 B2 | 1/2012 | Chatenever et al. |
| 8,091,753 B2 | 1/2012 | Viola |
| 8,091,756 B2 | 1/2012 | Viola |
| 8,092,443 B2 | 1/2012 | Bischoff |
| 8,092,932 B2 | 1/2012 | Phillips et al. |
| 8,093,572 B2 | 1/2012 | Kuduvalli |
| 8,096,458 B2 | 1/2012 | Hessler |
| 8,096,459 B2 | 1/2012 | Ortiz et al. |
| 8,097,017 B2 | 1/2012 | Viola |
| 8,100,310 B2 | 1/2012 | Zemlok |
| 8,100,824 B2 | 1/2012 | Hegeman et al. |
| 8,100,872 B2 | 1/2012 | Patel |
| 8,102,138 B2 | 1/2012 | Sekine et al. |
| 8,102,278 B2 | 1/2012 | Deck et al. |
| 8,105,320 B2 | 1/2012 | Manzo |
| 8,105,350 B2 | 1/2012 | Lee et al. |
| 8,107,925 B2 | 1/2012 | Natsuno et al. |
| 8,108,033 B2 | 1/2012 | Drew et al. |
| 8,108,072 B2 | 1/2012 | Zhao et al. |
| 8,109,426 B2 | 2/2012 | Milliman et al. |
| 8,110,208 B1 | 2/2012 | Hen |
| 8,113,405 B2 | 2/2012 | Milliman |
| 8,113,407 B2 | 2/2012 | Holsten et al. |
| 8,113,408 B2 | 2/2012 | Wenchell et al. |
| 8,113,410 B2 | 2/2012 | Hall et al. |
| 8,114,017 B2 | 2/2012 | Bacher |
| 8,114,100 B2 | 2/2012 | Smith et al. |
| 8,114,345 B2 | 2/2012 | Dlugos, Jr. et al. |
| 8,118,206 B2 | 2/2012 | Zand et al. |
| 8,118,207 B2 | 2/2012 | Racenet et al. |
| 8,120,301 B2 | 2/2012 | Goldberg et al. |
| 8,122,128 B2 | 2/2012 | Burke, II et al. |
| 8,123,103 B2 | 2/2012 | Milliman |
| 8,123,523 B2 | 2/2012 | Carron et al. |

(56) References Cited

U.S. PATENT DOCUMENTS

| | | |
|---|---|---|
| 8,123,766 B2 | 2/2012 | Bauman et al. |
| 8,123,767 B2 | 2/2012 | Bauman et al. |
| 8,125,168 B2 | 2/2012 | Johnson et al. |
| 8,127,975 B2 | 3/2012 | Olson et al. |
| 8,127,976 B2 | 3/2012 | Scirica et al. |
| 8,128,624 B2 | 3/2012 | Couture et al. |
| 8,128,643 B2 | 3/2012 | Aranyi et al. |
| 8,128,645 B2 | 3/2012 | Sonnenschein et al. |
| 8,128,662 B2 | 3/2012 | Altarac et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,133,500 B2 | 3/2012 | Ringeisen et al. |
| 8,134,306 B2 | 3/2012 | Drader et al. |
| 8,136,711 B2 | 3/2012 | Beardsley et al. |
| 8,136,712 B2 | 3/2012 | Zingman |
| 8,136,713 B2 | 3/2012 | Hathaway et al. |
| 8,137,339 B2 | 3/2012 | Jinno et al. |
| 8,140,417 B2 | 3/2012 | Shibata |
| 8,141,762 B2 | 3/2012 | Bedi et al. |
| 8,141,763 B2 | 3/2012 | Milliman |
| 8,142,200 B2 | 3/2012 | Crunkilton et al. |
| 8,142,425 B2 | 3/2012 | Eggers |
| 8,142,461 B2 | 3/2012 | Houser et al. |
| 8,142,515 B2 | 3/2012 | Therin et al. |
| 8,143,520 B2 | 3/2012 | Cutler |
| 8,146,790 B2 | 4/2012 | Milliman |
| 8,147,421 B2 | 4/2012 | Farquhar et al. |
| 8,147,456 B2 | 4/2012 | Fisher et al. |
| 8,147,485 B2 | 4/2012 | Wham et al. |
| 8,152,041 B2 | 4/2012 | Kostrzewski |
| 8,152,756 B2 | 4/2012 | Webster et al. |
| 8,154,239 B2 | 4/2012 | Katsuki et al. |
| 8,157,145 B2 | 4/2012 | Shelton, IV et al. |
| 8,157,148 B2 | 4/2012 | Scirica |
| 8,157,151 B2 | 4/2012 | Ingmanson et al. |
| 8,157,152 B2 | 4/2012 | Holsten et al. |
| 8,157,153 B2 | 4/2012 | Shelton, IV et al. |
| 8,157,793 B2 | 4/2012 | Omori et al. |
| 8,157,834 B2 | 4/2012 | Conlon |
| 8,161,977 B2 | 4/2012 | Shelton, IV et al. |
| 8,162,138 B2 | 4/2012 | Bettenhausen et al. |
| 8,162,197 B2 | 4/2012 | Mastri et al. |
| 8,162,668 B2 | 4/2012 | Toly |
| 8,162,933 B2 | 4/2012 | Francischelli et al. |
| 8,162,965 B2 | 4/2012 | Reschke et al. |
| 8,167,185 B2 | 5/2012 | Shelton, IV et al. |
| 8,167,622 B2 | 5/2012 | Zhou |
| 8,167,895 B2 | 5/2012 | D'Agostino et al. |
| 8,167,898 B1 | 5/2012 | Schaller et al. |
| 8,170,241 B2 | 5/2012 | Roe et al. |
| 8,172,004 B2 | 5/2012 | Ho |
| 8,172,120 B2 | 5/2012 | Boyden et al. |
| 8,172,122 B2 | 5/2012 | Kasvikis et al. |
| 8,172,124 B2 | 5/2012 | Shelton, IV et al. |
| 8,177,776 B2 | 5/2012 | Humayun et al. |
| 8,177,797 B2 | 5/2012 | Shimoji et al. |
| 8,179,705 B2 | 5/2012 | Chapuis |
| 8,180,458 B2 | 5/2012 | Kane et al. |
| 8,181,839 B2 | 5/2012 | Beetel |
| 8,181,840 B2 | 5/2012 | Milliman |
| 8,182,422 B2 | 5/2012 | Bayer et al. |
| 8,182,444 B2 | 5/2012 | Uber, III et al. |
| 8,183,807 B2 | 5/2012 | Tsai et al. |
| 8,186,555 B2 | 5/2012 | Shelton, IV et al. |
| 8,186,556 B2 | 5/2012 | Viola |
| 8,186,558 B2 | 5/2012 | Sapienza |
| 8,186,560 B2 | 5/2012 | Hess et al. |
| 8,190,238 B2 | 5/2012 | Moll et al. |
| 8,191,752 B2 | 6/2012 | Scirica |
| 8,192,350 B2 | 6/2012 | Ortiz et al. |
| 8,192,460 B2 | 6/2012 | Orban, III et al. |
| 8,192,651 B2 | 6/2012 | Young et al. |
| 8,193,129 B2 | 6/2012 | Tagawa et al. |
| 8,196,795 B2 | 6/2012 | Moore et al. |
| 8,196,796 B2 | 6/2012 | Shelton, IV et al. |
| 8,197,501 B2 | 6/2012 | Shadeck et al. |
| 8,197,502 B2 | 6/2012 | Smith et al. |
| 8,197,837 B2 | 6/2012 | Jamiolkowski et al. |
| 8,201,720 B2 | 6/2012 | Hessler |
| 8,201,721 B2 | 6/2012 | Zemlok et al. |
| 8,202,549 B2 | 6/2012 | Stucky et al. |
| 8,205,779 B2 | 6/2012 | Ma et al. |
| 8,205,780 B2 | 6/2012 | Sorrentino et al. |
| 8,205,781 B2 | 6/2012 | Baxter, III et al. |
| 8,207,863 B2 | 6/2012 | Neubauer et al. |
| 8,210,411 B2 | 7/2012 | Yates et al. |
| 8,210,414 B2 | 7/2012 | Bettuchi et al. |
| 8,210,415 B2 | 7/2012 | Ward |
| 8,210,416 B2 | 7/2012 | Milliman et al. |
| 8,210,721 B2 | 7/2012 | Chen et al. |
| 8,211,125 B2 | 7/2012 | Spivey |
| 8,214,019 B2 | 7/2012 | Govari et al. |
| 8,215,531 B2 | 7/2012 | Shelton, IV et al. |
| 8,215,532 B2 | 7/2012 | Marczyk |
| 8,215,533 B2 | 7/2012 | Viola et al. |
| 8,220,468 B2 | 7/2012 | Cooper et al. |
| 8,220,688 B2 | 7/2012 | Laurent et al. |
| 8,220,690 B2 | 7/2012 | Hess et al. |
| 8,221,402 B2 | 7/2012 | Francischelli et al. |
| 8,221,424 B2 | 7/2012 | Cha |
| 8,221,433 B2 | 7/2012 | Lozier et al. |
| 8,225,799 B2 | 7/2012 | Bettuchi |
| 8,225,979 B2 | 7/2012 | Farascioni et al. |
| 8,226,553 B2 | 7/2012 | Shelton, IV et al. |
| 8,226,635 B2 | 7/2012 | Petrie et al. |
| 8,226,675 B2 | 7/2012 | Houser et al. |
| 8,226,715 B2 | 7/2012 | Hwang et al. |
| 8,227,946 B2 | 7/2012 | Kim |
| 8,228,020 B2 | 7/2012 | Shin et al. |
| 8,228,048 B2 | 7/2012 | Spencer |
| 8,229,549 B2 | 7/2012 | Whitman et al. |
| 8,231,040 B2 | 7/2012 | Zemlok et al. |
| 8,231,042 B2 | 7/2012 | Hessler et al. |
| 8,231,043 B2 | 7/2012 | Tarinelli et al. |
| 8,235,272 B2 | 8/2012 | Nicholas et al. |
| 8,235,274 B2 | 8/2012 | Cappola |
| 8,236,010 B2 | 8/2012 | Ortiz et al. |
| 8,236,011 B2 | 8/2012 | Harris et al. |
| 8,236,020 B2 | 8/2012 | Smith et al. |
| 8,237,388 B2 | 8/2012 | Jinno et al. |
| 8,240,537 B2 | 8/2012 | Marczyk |
| 8,241,271 B2 | 8/2012 | Millman et al. |
| 8,241,284 B2 | 8/2012 | Dycus et al. |
| 8,241,308 B2 | 8/2012 | Kortenbach et al. |
| 8,241,322 B2 | 8/2012 | Whitman et al. |
| 8,245,594 B2 | 8/2012 | Rogers et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,245,901 B2 | 8/2012 | Stope |
| 8,246,608 B2 | 8/2012 | Omori et al. |
| 8,246,637 B2 | 8/2012 | Viola et al. |
| 8,252,009 B2 | 8/2012 | Weller et al. |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,257,251 B2 | 9/2012 | Shelton, IV et al. |
| 8,257,356 B2 | 9/2012 | Bleich et al. |
| 8,257,386 B2 | 9/2012 | Lee et al. |
| 8,257,391 B2 | 9/2012 | Orban, III et al. |
| 8,257,634 B2 | 9/2012 | Scirica |
| 8,258,745 B2 | 9/2012 | Smith et al. |
| 8,261,958 B1 | 9/2012 | Knodel |
| 8,262,560 B2 | 9/2012 | Whitman |
| 8,262,655 B2 | 9/2012 | Ghabrial et al. |
| 8,266,232 B2 | 9/2012 | Piper et al. |
| 8,267,300 B2 | 9/2012 | Boudreaux |
| 8,267,849 B2 | 9/2012 | Wazer et al. |
| 8,267,924 B2 | 9/2012 | Zemlok et al. |
| 8,267,946 B2 | 9/2012 | Whitfield et al. |
| 8,267,951 B2 | 9/2012 | Whayne et al. |
| 8,268,344 B2 | 9/2012 | Ma et al. |
| 8,269,121 B2 | 9/2012 | Smith |

(56) References Cited

U.S. PATENT DOCUMENTS

| | | |
|---|---|---|
| 8,272,553 B2 | 9/2012 | Mastri et al. |
| 8,272,554 B2 | 9/2012 | Whitman et al. |
| 8,272,918 B2 | 9/2012 | Lam |
| 8,273,404 B2 | 9/2012 | Dave et al. |
| 8,276,594 B2 | 10/2012 | Shah |
| 8,276,801 B2 | 10/2012 | Zemlok et al. |
| 8,276,802 B2 | 10/2012 | Kostrzewski |
| 8,277,473 B2 | 10/2012 | Sunaoshi et al. |
| 8,281,446 B2 | 10/2012 | Moskovich |
| 8,281,973 B2 | 10/2012 | Wenchell et al. |
| 8,281,974 B2 | 10/2012 | Hessler et al. |
| 8,282,654 B2 | 10/2012 | Ferrari et al. |
| 8,285,367 B2 | 10/2012 | Hyde et al. |
| 8,286,723 B2 | 10/2012 | Puzio et al. |
| 8,286,845 B2 | 10/2012 | Perry et al. |
| 8,286,846 B2 | 10/2012 | Smith et al. |
| 8,286,847 B2 | 10/2012 | Taylor |
| 8,287,487 B2 | 10/2012 | Estes |
| 8,287,522 B2 | 10/2012 | Moses et al. |
| 8,287,561 B2 | 10/2012 | Nunez et al. |
| 8,288,984 B2 | 10/2012 | Yang |
| 8,289,403 B2 | 10/2012 | Dobashi et al. |
| 8,290,883 B2 | 10/2012 | Takeuchi et al. |
| 8,292,147 B2 | 10/2012 | Viola |
| 8,292,148 B2 | 10/2012 | Viola |
| 8,292,150 B2 | 10/2012 | Bryant |
| 8,292,151 B2 | 10/2012 | Viola |
| 8,292,152 B2 | 10/2012 | Milliman et al. |
| 8,292,155 B2 | 10/2012 | Shelton, IV et al. |
| 8,292,157 B2 | 10/2012 | Smith et al. |
| 8,292,158 B2 | 10/2012 | Sapienza |
| 8,292,801 B2 | 10/2012 | Dejima et al. |
| 8,292,888 B2 | 10/2012 | Whitman |
| 8,292,906 B2 | 10/2012 | Taylor et al. |
| 8,294,399 B2 | 10/2012 | Suzuki et al. |
| 8,298,161 B2 | 10/2012 | Vargas |
| 8,298,189 B2 | 10/2012 | Fisher et al. |
| 8,298,233 B2 | 10/2012 | Mueller |
| 8,298,677 B2 | 10/2012 | Wiesner et al. |
| 8,302,323 B2 | 11/2012 | Fortier et al. |
| 8,303,621 B2 | 11/2012 | Miyamoto et al. |
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 | 11/2012 | Bindra et al. |
| 8,308,046 B2 | 11/2012 | Prommersberger |
| 8,308,659 B2 | 11/2012 | Scheibe et al. |
| 8,308,725 B2 | 11/2012 | Bell et al. |
| 8,310,188 B2 | 11/2012 | Nakai |
| 8,313,496 B2 | 11/2012 | Sauer et al. |
| 8,313,499 B2 | 11/2012 | Magnusson et al. |
| 8,313,509 B2 | 11/2012 | Kostrzewski |
| 8,317,070 B2 | 11/2012 | Hueil et al. |
| 8,317,071 B1 | 11/2012 | Knodel |
| 8,317,074 B2 | 11/2012 | Ortiz et al. |
| 8,317,437 B2 | 11/2012 | Merkley et al. |
| 8,317,744 B2 | 11/2012 | Kirschenman |
| 8,317,790 B2 | 11/2012 | Bell et al. |
| 8,319,002 B2 | 11/2012 | Daniels et al. |
| D672,784 S | 12/2012 | Clanton et al. |
| 8,322,455 B2 | 12/2012 | Shelton, IV et al. |
| 8,322,589 B2 | 12/2012 | Boudreaux |
| 8,322,590 B2 | 12/2012 | Patel et al. |
| 8,322,901 B2 | 12/2012 | Michelotti |
| 8,323,271 B2 | 12/2012 | Humayun et al. |
| 8,323,789 B2 | 12/2012 | Rozhin et al. |
| 8,324,585 B2 | 12/2012 | McBroom et al. |
| 8,327,514 B2 | 12/2012 | Kim |
| 8,328,061 B2 | 12/2012 | Kasvikis |
| 8,328,062 B2 | 12/2012 | Viola |
| 8,328,063 B2 | 12/2012 | Milliman et al. |
| 8,328,064 B2 | 12/2012 | Racenet et al. |
| 8,328,065 B2 | 12/2012 | Shah |
| 8,328,802 B2 | 12/2012 | Deville et al. |
| 8,328,823 B2 | 12/2012 | Aranyi et al. |
| 8,333,313 B2 | 12/2012 | Boudreaux et al. |
| 8,333,691 B2 | 12/2012 | Schaaf |
| 8,333,764 B2 | 12/2012 | Francischelli et al. |
| 8,333,779 B2 | 12/2012 | Smith et al. |
| 8,334,468 B2 | 12/2012 | Palmer et al. |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,343,150 B2 | 1/2013 | Artale |
| 8,347,978 B2 | 1/2013 | Forster et al. |
| 8,348,118 B2 | 1/2013 | Segura |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,348,837 B2 | 1/2013 | Wenchell |
| 8,348,959 B2 | 1/2013 | Wolford et al. |
| 8,348,972 B2 | 1/2013 | Soltz et al. |
| 8,349,987 B2 | 1/2013 | Kapiamba et al. |
| 8,352,004 B2 | 1/2013 | Mannheimer et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,356,740 B1 | 1/2013 | Knodel |
| 8,357,144 B2 | 1/2013 | Whitman et al. |
| 8,357,158 B2 | 1/2013 | McKenna et al. |
| 8,357,161 B2 | 1/2013 | Mueller |
| 8,359,174 B2 | 1/2013 | Nakashima et al. |
| 8,360,296 B2 | 1/2013 | Zingman |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,361,501 B2 | 1/2013 | DiTizio et al. |
| D676,866 S | 2/2013 | Chaudhri |
| 8,365,972 B2 | 2/2013 | Aranyi et al. |
| 8,365,973 B1 | 2/2013 | White et al. |
| 8,365,975 B1 | 2/2013 | Manoux et al. |
| 8,365,976 B2 | 2/2013 | Hess et al. |
| 8,366,559 B2 | 2/2013 | Papenfuss et al. |
| 8,366,719 B2 | 2/2013 | Markey et al. |
| 8,366,787 B2 | 2/2013 | Brown et al. |
| 8,368,327 B2 | 2/2013 | Benning et al. |
| 8,369,056 B2 | 2/2013 | Senriuchi et al. |
| 8,371,393 B2 | 2/2013 | Higuchi et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,371,494 B2 | 2/2013 | Racenet et al. |
| 8,372,094 B2 | 2/2013 | Bettuchi et al. |
| 8,374,723 B2 | 2/2013 | Zhao et al. |
| 8,376,865 B2 | 2/2013 | Forster et al. |
| 8,377,029 B2 | 2/2013 | Nagao et al. |
| 8,377,044 B2 | 2/2013 | Coe et al. |
| 8,377,059 B2 | 2/2013 | Deville et al. |
| 8,381,828 B2 | 2/2013 | Whitman et al. |
| 8,382,773 B2 | 2/2013 | Whitfield et al. |
| 8,382,790 B2 | 2/2013 | Uenohara et al. |
| D677,273 S | 3/2013 | Randall et al. |
| 8,387,848 B2 | 3/2013 | Johnson et al. |
| 8,388,633 B2 | 3/2013 | Rousseau et al. |
| 8,389,588 B2 | 3/2013 | Ringeisen et al. |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,832 B2 | 3/2013 | Blickle et al. |
| 8,397,971 B2 | 3/2013 | Yates et al. |
| 8,397,972 B2 | 3/2013 | Kostrzewski |
| 8,397,973 B1 | 3/2013 | Hausen |
| 8,398,633 B2 | 3/2013 | Mueller |
| 8,398,669 B2 | 3/2013 | Kim |
| 8,398,673 B2 | 3/2013 | Hinchliffe et al. |
| 8,398,674 B2 | 3/2013 | Prestel |

(56) References Cited

U.S. PATENT DOCUMENTS

| | | |
|---|---|---|
| 8,400,108 B2 | 3/2013 | Powell et al. |
| 8,400,851 B2 | 3/2013 | Byun |
| 8,403,138 B2 | 3/2013 | Weisshaupt et al. |
| 8,403,195 B2 | 3/2013 | Beardsley et al. |
| 8,403,196 B2 | 3/2013 | Beardsley et al. |
| 8,403,198 B2 | 3/2013 | Sorrentino et al. |
| 8,403,832 B2 | 3/2013 | Cunningham et al. |
| 8,403,926 B2 | 3/2013 | Nobis et al. |
| 8,403,945 B2 | 3/2013 | Whitfield et al. |
| 8,403,946 B2 | 3/2013 | Whitfield et al. |
| 8,403,950 B2 | 3/2013 | Palmer et al. |
| D680,646 S | 4/2013 | Hunt et al. |
| 8,408,439 B2 | 4/2013 | Huang et al. |
| 8,408,442 B2 | 4/2013 | Racenet et al. |
| 8,409,079 B2 | 4/2013 | Okamoto et al. |
| 8,409,174 B2 | 4/2013 | Omori |
| 8,409,175 B2 | 4/2013 | Lee et al. |
| 8,409,211 B2 | 4/2013 | Baroud |
| 8,409,222 B2 | 4/2013 | Whitfield et al. |
| 8,409,223 B2 | 4/2013 | Sorrentino et al. |
| 8,411,500 B2 | 4/2013 | Gapihan et al. |
| 8,413,661 B2 | 4/2013 | Rousseau et al. |
| 8,413,870 B2 | 4/2013 | Pastorelli et al. |
| 8,413,871 B2 | 4/2013 | Racenet et al. |
| 8,413,872 B2 | 4/2013 | Patel |
| 8,414,469 B2 | 4/2013 | Diolaiti |
| 8,414,577 B2 | 4/2013 | Boudreaux et al. |
| 8,414,598 B2 | 4/2013 | Brock et al. |
| 8,418,073 B2 | 4/2013 | Mohr et al. |
| 8,418,906 B2 | 4/2013 | Farascioni et al. |
| 8,418,907 B2 | 4/2013 | Johnson et al. |
| 8,418,908 B1 | 4/2013 | Beardsley |
| 8,418,909 B2 | 4/2013 | Kostrzewski |
| 8,419,635 B2 | 4/2013 | Shelton, IV et al. |
| 8,419,717 B2 | 4/2013 | Diolaiti et al. |
| 8,419,747 B2 | 4/2013 | Hinman et al. |
| 8,419,754 B2 | 4/2013 | Laby et al. |
| 8,419,755 B2 | 4/2013 | Deem et al. |
| 8,423,182 B2 | 4/2013 | Robinson et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,424,741 B2 | 4/2013 | McGuckin, Jr. et al. |
| 8,425,600 B2 | 4/2013 | Maxwell |
| 8,427,430 B2 | 4/2013 | Lee et al. |
| 8,430,292 B2 | 4/2013 | Patel et al. |
| 8,430,892 B2 | 4/2013 | Bindra et al. |
| 8,430,898 B2 | 4/2013 | Wiener et al. |
| 8,435,257 B2 | 5/2013 | Smith et al. |
| 8,439,246 B1 | 5/2013 | Knodel |
| 8,439,830 B2 | 5/2013 | McKinley et al. |
| 8,444,036 B2 | 5/2013 | Shelton, IV |
| 8,444,037 B2 | 5/2013 | Nicholas et al. |
| 8,444,549 B2 | 5/2013 | Viola et al. |
| 8,449,536 B2 | 5/2013 | Selig |
| 8,449,560 B2 | 5/2013 | Roth et al. |
| 8,453,904 B2 | 6/2013 | Eskaros et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,912 B2 | 6/2013 | Mastri et al. |
| 8,453,914 B2 | 6/2013 | Laurent et al. |
| 8,454,495 B2 | 6/2013 | Kawano et al. |
| 8,454,551 B2 | 6/2013 | Allen et al. |
| 8,454,628 B2 | 6/2013 | Smith et al. |
| 8,454,640 B2 | 6/2013 | Johnston et al. |
| 8,457,757 B2 | 6/2013 | Cauller et al. |
| 8,459,520 B2 | 6/2013 | Giordano et al. |
| 8,459,521 B2 | 6/2013 | Zemlok et al. |
| 8,459,524 B2 | 6/2013 | Pribanic et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,464,924 B2 | 6/2013 | Gresham et al. |
| 8,464,925 B2 | 6/2013 | Hull et al. |
| 8,465,475 B2 | 6/2013 | Isbell, Jr. |
| 8,465,502 B2 | 6/2013 | Zergiebel |
| 8,465,515 B2 | 6/2013 | Drew et al. |
| 8,469,254 B2 | 6/2013 | Czernik et al. |
| 8,469,946 B2 | 6/2013 | Sugita |
| 8,469,973 B2 | 6/2013 | Meade et al. |
| 8,470,355 B2 | 6/2013 | Skalla et al. |
| D686,240 S | 7/2013 | Lin |
| D686,244 S | 7/2013 | Moriya et al. |
| 8,474,677 B2 | 7/2013 | Woodard, Jr. et al. |
| 8,475,453 B2 | 7/2013 | Marczyk et al. |
| 8,475,454 B1 | 7/2013 | Alshemari |
| 8,475,474 B2 | 7/2013 | Bombard et al. |
| 8,479,968 B2 | 7/2013 | Hodgkinson et al. |
| 8,479,969 B2 | 7/2013 | Shelton, IV |
| 8,480,703 B2 | 7/2013 | Nicholas et al. |
| 8,483,509 B2 | 7/2013 | Matsuzaka |
| 8,485,412 B2 | 7/2013 | Shelton, IV et al. |
| 8,485,413 B2 | 7/2013 | Scheib et al. |
| 8,485,970 B2 | 7/2013 | Widenhouse et al. |
| 8,486,047 B2 | 7/2013 | Stope |
| 8,487,199 B2 | 7/2013 | Palmer et al. |
| 8,487,487 B2 | 7/2013 | Dietz et al. |
| 8,490,851 B2 | 7/2013 | Blier et al. |
| 8,490,852 B2 | 7/2013 | Viola |
| 8,490,853 B2 | 7/2013 | Criscuolo et al. |
| 8,491,581 B2 | 7/2013 | Deville et al. |
| 8,491,603 B2 | 7/2013 | Yeung et al. |
| 8,496,153 B2 | 7/2013 | Demmy et al. |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,498,691 B2 | 7/2013 | Moll et al. |
| 8,499,673 B2 | 8/2013 | Keller |
| 8,499,966 B2 | 8/2013 | Palmer et al. |
| 8,499,992 B2 | 8/2013 | Whitman et al. |
| 8,499,993 B2 | 8/2013 | Shelton, IV et al. |
| 8,499,994 B2 | 8/2013 | D'Arcangelo |
| 8,500,721 B2 | 8/2013 | Jinno |
| 8,500,762 B2 | 8/2013 | Sholev et al. |
| 8,502,091 B2 | 8/2013 | Palmer et al. |
| 8,505,799 B2 | 8/2013 | Viola et al. |
| 8,505,801 B2 | 8/2013 | Ehrenfels et al. |
| 8,506,555 B2 | 8/2013 | Ruiz Morales |
| 8,506,557 B2 | 8/2013 | Zemlok et al. |
| 8,506,580 B2 | 8/2013 | Zergiebel et al. |
| 8,506,581 B2 | 8/2013 | Wingardner, III et al. |
| 8,511,308 B2 | 8/2013 | Hecox et al. |
| 8,512,359 B2 | 8/2013 | Whitman et al. |
| 8,512,402 B2 | 8/2013 | Marczyk et al. |
| 8,517,239 B2 | 8/2013 | Scheib et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,517,938 B2 | 8/2013 | Eisenhardt et al. |
| 8,518,024 B2 | 8/2013 | Williams et al. |
| 8,521,273 B2 | 8/2013 | Kliman |
| 8,523,042 B2 | 9/2013 | Masiakos et al. |
| 8,523,043 B2 | 9/2013 | Ullrich et al. |
| 8,523,787 B2 | 9/2013 | Ludwin et al. |
| 8,523,881 B2 | 9/2013 | Cabiri et al. |
| 8,523,882 B2 | 9/2013 | Huitema et al. |
| 8,523,900 B2 | 9/2013 | Jinno et al. |
| 8,529,588 B2 | 9/2013 | Ahlberg et al. |
| 8,529,599 B2 | 9/2013 | Holsten |
| 8,529,600 B2 | 9/2013 | Woodard, Jr. et al. |
| 8,529,819 B2 | 9/2013 | Ostapoff et al. |
| 8,532,747 B2 | 9/2013 | Nock et al. |
| 8,534,527 B2 | 9/2013 | Brendel et al. |
| 8,534,528 B2 | 9/2013 | Shelton, IV |
| 8,535,304 B2 | 9/2013 | Sklar et al. |
| 8,535,340 B2 | 9/2013 | Allen |
| 8,539,866 B2 | 9/2013 | Nayak et al. |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,540,646 B2 | 9/2013 | Mendez-Coll |

(56) References Cited

U.S. PATENT DOCUMENTS

| | | |
|---|---|---|
| 8,540,733 B2 | 9/2013 | Whitman et al. |
| 8,540,735 B2 | 9/2013 | Mitelberg et al. |
| 8,550,984 B2 | 10/2013 | Takemoto |
| 8,551,076 B2 | 10/2013 | Duval et al. |
| 8,555,660 B2 | 10/2013 | Takenaka et al. |
| 8,556,151 B2 | 10/2013 | Viola |
| 8,556,918 B2 | 10/2013 | Bauman et al. |
| 8,556,935 B1 | 10/2013 | Knodel et al. |
| 8,560,147 B2 | 10/2013 | Taylor et al. |
| 8,561,617 B2 | 10/2013 | Lindh et al. |
| 8,561,870 B2 | 10/2013 | Baxter, III et al. |
| 8,561,871 B2 | 10/2013 | Rajappa et al. |
| 8,561,873 B2 | 10/2013 | Ingmanson et al. |
| 8,562,592 B2 | 10/2013 | Conlon et al. |
| 8,562,598 B2 | 10/2013 | Falkenstein et al. |
| 8,567,656 B2 | 10/2013 | Shelton, IV et al. |
| 8,568,416 B2 | 10/2013 | Schmitz et al. |
| 8,568,425 B2 | 10/2013 | Ross et al. |
| D692,916 S | 11/2013 | Granchi et al. |
| 8,573,459 B2 | 11/2013 | Smith et al. |
| 8,573,461 B2 | 11/2013 | Shelton, IV et al. |
| 8,573,462 B2 | 11/2013 | Smith et al. |
| 8,573,465 B2 | 11/2013 | Shelton, IV |
| 8,574,199 B2 | 11/2013 | von Bulow et al. |
| 8,574,263 B2 | 11/2013 | Mueller |
| 8,575,880 B2 | 11/2013 | Grantz |
| 8,575,895 B2 | 11/2013 | Garrastacho et al. |
| 8,579,176 B2 | 11/2013 | Smith et al. |
| 8,579,178 B2 | 11/2013 | Holsten et al. |
| 8,579,897 B2 | 11/2013 | Vakharia et al. |
| 8,579,937 B2 | 11/2013 | Gresham |
| 8,584,919 B2 | 11/2013 | Hueil et al. |
| 8,584,920 B2 | 11/2013 | Hodgkinson |
| 8,584,921 B2 | 11/2013 | Scirica |
| 8,585,583 B2 | 11/2013 | Sakaguchi et al. |
| 8,585,598 B2 | 11/2013 | Razzaque et al. |
| 8,585,721 B2 | 11/2013 | Kirsch |
| 8,590,760 B2 | 11/2013 | Cummins et al. |
| 8,590,762 B2 | 11/2013 | Hess et al. |
| 8,590,764 B2 | 11/2013 | Hartwick et al. |
| 8,591,400 B2 | 11/2013 | Sugiyama |
| 8,596,515 B2 | 12/2013 | Okoniewski |
| 8,597,745 B2 | 12/2013 | Farnsworth et al. |
| 8,599,450 B2 | 12/2013 | Kubo et al. |
| 8,602,125 B2 | 12/2013 | King |
| 8,602,287 B2 | 12/2013 | Yates et al. |
| 8,602,288 B2 | 12/2013 | Shelton, IV et al. |
| 8,603,077 B2 | 12/2013 | Cooper et al. |
| 8,603,089 B2 | 12/2013 | Viola |
| 8,603,110 B2 | 12/2013 | Maruyama et al. |
| 8,603,135 B2 | 12/2013 | Mueller |
| 8,608,043 B2 | 12/2013 | Scirica |
| 8,608,044 B2 | 12/2013 | Hueil et al. |
| 8,608,045 B2 | 12/2013 | Smith et al. |
| 8,608,046 B2 | 12/2013 | Laurent et al. |
| 8,608,745 B2 | 12/2013 | Guzman et al. |
| 8,613,383 B2 | 12/2013 | Beckman et al. |
| 8,613,384 B2 | 12/2013 | Pastorelli et al. |
| 8,616,427 B2 | 12/2013 | Viola |
| 8,616,431 B2 | 12/2013 | Timm et al. |
| 8,617,155 B2 | 12/2013 | Johnson et al. |
| 8,620,473 B2 | 12/2013 | Diolaiti et al. |
| 8,622,274 B2 | 1/2014 | Yates et al. |
| 8,622,275 B2 | 1/2014 | Baxter, III et al. |
| 8,627,993 B2 | 1/2014 | Smith et al. |
| 8,627,994 B2 | 1/2014 | Zemlok et al. |
| 8,627,995 B2 | 1/2014 | Smith et al. |
| 8,628,467 B2 | 1/2014 | Whitman et al. |
| 8,628,518 B2 | 1/2014 | Blumenkranz et al. |
| 8,628,544 B2 | 1/2014 | Farascioni |
| 8,628,545 B2 | 1/2014 | Cabrera et al. |
| 8,631,987 B2 | 1/2014 | Shelton, IV et al. |
| 8,631,992 B1 | 1/2014 | Hausen et al. |
| 8,631,993 B2 | 1/2014 | Kostrzewski |
| 8,632,462 B2 | 1/2014 | Yoo et al. |
| 8,632,525 B2 | 1/2014 | Kerr et al. |
| 8,632,535 B2 | 1/2014 | Shelton, IV et al. |
| 8,632,539 B2 | 1/2014 | Twomey et al. |
| 8,632,563 B2 | 1/2014 | Nagase et al. |
| 8,636,187 B2 | 1/2014 | Hueil et al. |
| 8,636,190 B2 | 1/2014 | Zemlok et al. |
| 8,636,191 B2 | 1/2014 | Meagher |
| 8,636,193 B2 | 1/2014 | Whitman et al. |
| 8,636,736 B2 | 1/2014 | Yates et al. |
| 8,636,766 B2 | 1/2014 | Milliman et al. |
| 8,639,936 B2 | 1/2014 | Hu et al. |
| 8,640,788 B2 | 2/2014 | Dachs, II et al. |
| 8,646,674 B2 | 2/2014 | Schulte et al. |
| 8,647,258 B2 | 2/2014 | Aranyi et al. |
| 8,652,120 B2 | 2/2014 | Giordano et al. |
| 8,652,151 B2 | 2/2014 | Lehman et al. |
| 8,652,155 B2 | 2/2014 | Houser et al. |
| 8,656,929 B2 | 2/2014 | Miller et al. |
| 8,657,175 B2 | 2/2014 | Sonnenschein et al. |
| 8,657,176 B2 | 2/2014 | Shelton, IV et al. |
| 8,657,177 B2 | 2/2014 | Scirica et al. |
| 8,657,178 B2 | 2/2014 | Hueil et al. |
| 8,657,482 B2 | 2/2014 | Malackowski et al. |
| 8,657,808 B2 | 2/2014 | McPherson et al. |
| 8,657,814 B2 | 2/2014 | Werneth et al. |
| 8,657,821 B2 | 2/2014 | Palermo |
| D701,238 S | 3/2014 | Lai et al. |
| 8,662,370 B2 | 3/2014 | Takei |
| 8,663,106 B2 | 3/2014 | Stivoric et al. |
| 8,663,192 B2 | 3/2014 | Hester et al. |
| 8,663,245 B2 | 3/2014 | Francischelli et al. |
| 8,663,262 B2 | 3/2014 | Smith et al. |
| 8,663,270 B2 | 3/2014 | Donnigan et al. |
| 8,664,792 B2 | 3/2014 | Rebsdorf |
| 8,668,129 B2 | 3/2014 | Olson |
| 8,668,130 B2 | 3/2014 | Hess et al. |
| 8,672,206 B2 | 3/2014 | Aranyi et al. |
| 8,672,207 B2 | 3/2014 | Shelton, IV et al. |
| 8,672,208 B2 | 3/2014 | Hess et al. |
| 8,672,209 B2 | 3/2014 | Crainich |
| 8,672,922 B2 | 3/2014 | Loh et al. |
| 8,672,935 B2 | 3/2014 | Okada et al. |
| 8,672,951 B2 | 3/2014 | Smith et al. |
| 8,673,210 B2 | 3/2014 | Deshays |
| 8,675,820 B2 | 3/2014 | Bale et al. |
| 8,678,263 B2 | 3/2014 | Viola |
| 8,678,994 B2 | 3/2014 | Sonnenschein et al. |
| 8,679,093 B2 | 3/2014 | Farra |
| 8,679,098 B2 | 3/2014 | Hart |
| 8,679,137 B2 | 3/2014 | Bauman et al. |
| 8,679,154 B2 | 3/2014 | Smith et al. |
| 8,679,156 B2 | 3/2014 | Smith et al. |
| 8,679,454 B2 | 3/2014 | Guire et al. |
| 8,684,248 B2 | 4/2014 | Milliman |
| 8,684,249 B2 | 4/2014 | Racenet et al. |
| 8,684,250 B2 | 4/2014 | Bettuchi et al. |
| 8,684,253 B2 | 4/2014 | Giordano et al. |
| 8,684,962 B2 | 4/2014 | Kirschenman et al. |
| 8,685,004 B2 | 4/2014 | Zemlock et al. |
| 8,685,020 B2 | 4/2014 | Weizman et al. |
| 8,690,893 B2 | 4/2014 | Deitch et al. |
| 8,695,866 B2 | 4/2014 | Leimbach et al. |
| 8,696,665 B2 | 4/2014 | Hunt et al. |
| 8,701,958 B2 | 4/2014 | Shelton, IV et al. |
| 8,701,959 B2 | 4/2014 | Shah |
| 8,706,316 B1 | 4/2014 | Hoevenaar |
| 8,708,210 B2 | 4/2014 | Zemlok et al. |
| 8,708,211 B2 | 4/2014 | Zemlok et al. |
| 8,708,212 B2 | 4/2014 | Williams |
| 8,708,213 B2 | 4/2014 | Shelton, IV et al. |
| 8,709,012 B2 | 4/2014 | Muller |
| 8,714,352 B2 | 5/2014 | Farascioni et al. |
| 8,714,429 B2 | 5/2014 | Demmy |
| 8,714,430 B2 | 5/2014 | Natarajan et al. |
| 8,715,256 B2 | 5/2014 | Greener |
| 8,715,302 B2 | 5/2014 | Ibrahim et al. |
| 8,720,766 B2 | 5/2014 | Hess et al. |
| 8,721,630 B2 | 5/2014 | Ortiz et al. |
| 8,721,666 B2 | 5/2014 | Schroeder et al. |

(56) References Cited

U.S. PATENT DOCUMENTS

| | | |
|---|---|---|
| 8,727,197 B2 | 5/2014 | Hess et al. |
| 8,727,199 B2 | 5/2014 | Wenchell |
| 8,727,200 B2 | 5/2014 | Roy |
| 8,727,961 B2 | 5/2014 | Ziv |
| 8,728,099 B2 | 5/2014 | Cohn et al. |
| 8,728,119 B2 | 5/2014 | Cummins |
| 8,733,470 B2 | 5/2014 | Matthias et al. |
| 8,733,611 B2 | 5/2014 | Milliman |
| 8,733,612 B2 | 5/2014 | Ma |
| 8,733,613 B2 | 5/2014 | Huitema et al. |
| 8,733,614 B2 | 5/2014 | Ross et al. |
| 8,734,336 B2 | 5/2014 | Bonadio et al. |
| 8,734,359 B2 | 5/2014 | Ibanez et al. |
| 8,734,478 B2 | 5/2014 | Widenhouse et al. |
| 8,734,831 B2 | 5/2014 | Kim et al. |
| 8,739,033 B2 | 5/2014 | Rosenberg |
| 8,739,417 B2 | 6/2014 | Tokunaga et al. |
| 8,740,034 B2 | 6/2014 | Morgan et al. |
| 8,740,037 B2 | 6/2014 | Shelton, IV et al. |
| 8,740,038 B2 | 6/2014 | Shelton, IV et al. |
| 8,740,987 B2 | 6/2014 | Geremakis et al. |
| 8,746,529 B2 | 6/2014 | Shelton, IV et al. |
| 8,746,530 B2 | 6/2014 | Giordano et al. |
| 8,746,533 B2 | 6/2014 | Whitman et al. |
| 8,746,535 B2 | 6/2014 | Shelton, IV et al. |
| 8,747,238 B2 | 6/2014 | Shelton, IV et al. |
| 8,747,441 B2 | 6/2014 | Konieczynski et al. |
| 8,752,264 B2 | 6/2014 | Ackley et al. |
| 8,752,699 B2 | 6/2014 | Morgan et al. |
| 8,752,747 B2 | 6/2014 | Shelton, IV et al. |
| 8,752,748 B2 | 6/2014 | Whitman et al. |
| 8,752,749 B2 | 6/2014 | Moore et al. |
| 8,753,664 B2 | 6/2014 | Dao et al. |
| 8,757,287 B2 | 6/2014 | Mak |
| 8,757,465 B2 | 6/2014 | Woodard, Jr. et al. |
| 8,758,235 B2 | 6/2014 | Jaworek |
| 8,758,366 B2 | 6/2014 | McLean et al. |
| 8,758,391 B2 | 6/2014 | Swayze et al. |
| 8,758,438 B2 | 6/2014 | Boyce et al. |
| 8,763,875 B2 | 7/2014 | Morgan et al. |
| 8,763,876 B2 | 7/2014 | Kostrzewski |
| 8,763,877 B2 | 7/2014 | Schall et al. |
| 8,763,879 B2 | 7/2014 | Shelton, IV et al. |
| 8,764,732 B2 | 7/2014 | Hartwell |
| 8,765,942 B2 | 7/2014 | Feraud et al. |
| 8,770,458 B2 | 7/2014 | Scirica |
| 8,770,459 B2 | 7/2014 | Racenet et al. |
| 8,770,460 B2 | 7/2014 | Belzer |
| 8,771,169 B2 | 7/2014 | Whitman et al. |
| 8,771,260 B2 | 7/2014 | Conlon et al. |
| 8,777,004 B2 | 7/2014 | Shelton, IV et al. |
| 8,777,082 B2 | 7/2014 | Scirica |
| 8,777,083 B2 | 7/2014 | Racenet et al. |
| 8,777,898 B2 | 7/2014 | Suon et al. |
| 8,783,541 B2 | 7/2014 | Shelton, IV et al. |
| 8,783,542 B2 | 7/2014 | Riestenberg et al. |
| 8,783,543 B2 | 7/2014 | Shelton, IV et al. |
| 8,784,304 B2 | 7/2014 | Mikkaichi et al. |
| 8,784,404 B2 | 7/2014 | Doyle et al. |
| 8,784,415 B2 | 7/2014 | Malackowski et al. |
| 8,789,737 B2 | 7/2014 | Hodgkinson et al. |
| 8,789,739 B2 | 7/2014 | Swensgard |
| 8,789,740 B2 | 7/2014 | Baxter, III et al. |
| 8,789,741 B2 | 7/2014 | Baxter, III et al. |
| 8,790,658 B2 | 7/2014 | Cigarini et al. |
| 8,790,684 B2 | 7/2014 | Dave et al. |
| D711,905 S | 8/2014 | Morrison et al. |
| 8,794,496 B2 | 8/2014 | Scirica |
| 8,794,497 B2 | 8/2014 | Zingman |
| 8,795,159 B2 | 8/2014 | Moriyama |
| 8,795,276 B2 | 8/2014 | Dietz et al. |
| 8,795,308 B2 | 8/2014 | Valin |
| 8,795,324 B2 | 8/2014 | Kawai et al. |
| 8,796,995 B2 | 8/2014 | Cunanan et al. |
| 8,800,681 B2 | 8/2014 | Rousson et al. |
| 8,800,837 B2 | 8/2014 | Zemlok |
| 8,800,838 B2 | 8/2014 | Shelton, IV |
| 8,800,839 B2 | 8/2014 | Beetel |
| 8,800,840 B2 | 8/2014 | Jankowski |
| 8,800,841 B2 | 8/2014 | Ellerhorst et al. |
| 8,801,710 B2 | 8/2014 | Ullrich et al. |
| 8,801,734 B2 | 8/2014 | Shelton, IV et al. |
| 8,801,735 B2 | 8/2014 | Shelton, IV et al. |
| 8,801,752 B2 | 8/2014 | Fortier et al. |
| 8,801,801 B2 | 8/2014 | Datta et al. |
| 8,806,973 B2 | 8/2014 | Ross et al. |
| 8,807,414 B2 | 8/2014 | Ross et al. |
| 8,808,161 B2 | 8/2014 | Gregg et al. |
| 8,808,164 B2 | 8/2014 | Hoffman et al. |
| 8,808,274 B2 | 8/2014 | Hartwell |
| 8,808,294 B2 | 8/2014 | Fox et al. |
| 8,808,308 B2 | 8/2014 | Boukhny et al. |
| 8,808,311 B2 | 8/2014 | Heinrich et al. |
| 8,808,325 B2 | 8/2014 | Hess et al. |
| 8,810,197 B2 | 8/2014 | Juergens |
| 8,811,017 B2 | 8/2014 | Fujii et al. |
| 8,813,866 B2 | 8/2014 | Suzuki |
| 8,814,024 B2 | 8/2014 | Woodard, Jr. et al. |
| 8,814,025 B2 | 8/2014 | Miller et al. |
| 8,814,836 B2 | 8/2014 | Ignon et al. |
| 8,815,594 B2 | 8/2014 | Harris et al. |
| 8,818,523 B2 | 8/2014 | Olson et al. |
| 8,820,603 B2 | 9/2014 | Shelton, IV et al. |
| 8,820,605 B2 | 9/2014 | Shelton, IV |
| 8,820,606 B2 | 9/2014 | Hodgkinson |
| 8,820,607 B2 | 9/2014 | Marczyk |
| 8,820,608 B2 | 9/2014 | Miyamoto |
| 8,821,514 B2 | 9/2014 | Aranyi |
| 8,822,934 B2 | 9/2014 | Sayeh et al. |
| 8,825,164 B2 | 9/2014 | Tweden et al. |
| 8,827,133 B2 | 9/2014 | Shelton, IV et al. |
| 8,827,134 B2 | 9/2014 | Viola et al. |
| 8,827,903 B2 | 9/2014 | Shelton, IV et al. |
| 8,828,046 B2 | 9/2014 | Stefanchik et al. |
| 8,831,779 B2 | 9/2014 | Ortmaier et al. |
| 8,833,219 B2 | 9/2014 | Pierce |
| 8,833,630 B2 | 9/2014 | Milliman |
| 8,833,632 B2 | 9/2014 | Swensgard |
| 8,834,353 B2 | 9/2014 | Dejima et al. |
| 8,834,465 B2 | 9/2014 | Ramstein et al. |
| 8,834,498 B2 | 9/2014 | Byrum et al. |
| 8,834,518 B2 | 9/2014 | Faller et al. |
| 8,840,003 B2 | 9/2014 | Morgan et al. |
| 8,840,603 B2 | 9/2014 | Shelton, IV et al. |
| 8,840,609 B2 | 9/2014 | Stuebe |
| 8,840,876 B2 | 9/2014 | Eemeta et al. |
| 8,844,789 B2 | 9/2014 | Shelton, IV et al. |
| 8,844,790 B2 | 9/2014 | Demmy et al. |
| 8,851,215 B2 | 10/2014 | Goto |
| 8,851,354 B2 | 10/2014 | Swensgard et al. |
| 8,851,355 B2 | 10/2014 | Aranyi et al. |
| 8,852,174 B2 | 10/2014 | Burbank |
| 8,852,185 B2 | 10/2014 | Twomey |
| 8,852,199 B2 | 10/2014 | Deslauriers et al. |
| 8,852,218 B2 | 10/2014 | Hughett, Sr. et al. |
| 8,857,693 B2 | 10/2014 | Schuckmann et al. |
| 8,857,694 B2 | 10/2014 | Shelton, IV et al. |
| 8,858,538 B2 | 10/2014 | Belson et al. |
| 8,858,547 B2 | 10/2014 | Brogna |
| 8,858,571 B2 | 10/2014 | Shelton, IV et al. |
| 8,858,590 B2 | 10/2014 | Shelton, IV et al. |
| 8,864,007 B2 | 10/2014 | Widenhouse et al. |
| 8,864,009 B2 | 10/2014 | Shelton, IV et al. |
| 8,864,010 B2 | 10/2014 | Williams |
| 8,864,750 B2 | 10/2014 | Ross et al. |
| 8,869,912 B2 | 10/2014 | Roßkamp et al. |
| 8,869,913 B2 | 10/2014 | Matthias et al. |
| 8,870,050 B2 | 10/2014 | Hodgkinson |
| 8,870,867 B2 | 10/2014 | Walberg et al. |
| 8,870,912 B2 | 10/2014 | Brisson et al. |
| 8,875,971 B2 | 11/2014 | Hall et al. |
| 8,875,972 B2 | 11/2014 | Weisenburgh, II et al. |
| 8,876,698 B2 | 11/2014 | Sakamoto et al. |
| 8,876,857 B2 | 11/2014 | Burbank |

(56) References Cited

U.S. PATENT DOCUMENTS

| | | | |
|---|---|---|---|
| 8,876,858 B2 | 11/2014 | Braun |
| 8,882,660 B2 | 11/2014 | Phee et al. |
| 8,882,792 B2 | 11/2014 | Dietz et al. |
| 8,884,560 B2 | 11/2014 | Ito |
| 8,887,979 B2 | 11/2014 | Mastri et al. |
| 8,888,688 B2 | 11/2014 | Julian et al. |
| 8,888,695 B2 | 11/2014 | Piskun et al. |
| 8,888,792 B2 | 11/2014 | Harris et al. |
| 8,888,809 B2 | 11/2014 | Davison et al. |
| 8,893,946 B2 | 11/2014 | Boudreaux et al. |
| 8,893,949 B2 | 11/2014 | Shelton, IV et al. |
| 8,894,647 B2 | 11/2014 | Beardsley et al. |
| 8,894,654 B2 | 11/2014 | Anderson |
| 8,899,460 B2 | 12/2014 | Wojcicki |
| 8,899,461 B2 | 12/2014 | Farascioni |
| 8,899,462 B2 | 12/2014 | Kostrzewski et al. |
| 8,899,463 B2 | 12/2014 | Schall et al. |
| 8,899,464 B2 | 12/2014 | Hueil et al. |
| 8,899,465 B2 | 12/2014 | Shelton, IV et al. |
| 8,899,466 B2 | 12/2014 | Baxter, III et al. |
| 8,900,267 B2 | 12/2014 | Woolfson et al. |
| 8,905,287 B2 | 12/2014 | Racenet et al. |
| 8,905,977 B2 | 12/2014 | Shelton et al. |
| 8,910,846 B2 | 12/2014 | Viola |
| 8,910,847 B2 | 12/2014 | Nalagatla et al. |
| 8,911,426 B2 | 12/2014 | Coppeta et al. |
| 8,911,448 B2 | 12/2014 | Stein |
| 8,911,460 B2 | 12/2014 | Neurohr et al. |
| 8,911,471 B2 | 12/2014 | Spivey et al. |
| 8,912,746 B2 | 12/2014 | Reid et al. |
| 8,915,842 B2 | 12/2014 | Weisenburgh, II et al. |
| 8,920,368 B2 | 12/2014 | Sandhu et al. |
| 8,920,433 B2 | 12/2014 | Barrier et al. |
| 8,920,435 B2 | 12/2014 | Smith et al. |
| 8,920,438 B2 | 12/2014 | Aranyi et al. |
| 8,920,443 B2 | 12/2014 | Hiles et al. |
| 8,920,444 B2 | 12/2014 | Hiles et al. |
| 8,922,163 B2 | 12/2014 | Macdonald |
| 8,925,782 B2 | 1/2015 | Shelton, IV |
| 8,925,783 B2 | 1/2015 | Zemlok et al. |
| 8,925,788 B2 | 1/2015 | Hess et al. |
| 8,926,506 B2 | 1/2015 | Widenhouse et al. |
| 8,926,598 B2 | 1/2015 | Mollere et al. |
| 8,931,576 B2 | 1/2015 | Iwata |
| 8,931,679 B2 | 1/2015 | Kostrzewski |
| 8,931,680 B2 | 1/2015 | Milliman |
| 8,931,682 B2 | 1/2015 | Timm et al. |
| 8,931,692 B2 | 1/2015 | Sancak |
| 8,936,614 B2 | 1/2015 | Allen, IV |
| 8,939,343 B2 | 1/2015 | Milliman et al. |
| 8,939,344 B2 | 1/2015 | Olson et al. |
| 8,939,898 B2 | 1/2015 | Omoto |
| 8,944,069 B2 | 2/2015 | Miller et al. |
| 8,945,095 B2 | 2/2015 | Blumenkranz et al. |
| 8,945,098 B2 | 2/2015 | Seibold et al. |
| 8,945,163 B2 | 2/2015 | Voegele et al. |
| 8,955,732 B2 | 2/2015 | Zemlok et al. |
| 8,956,342 B1 | 2/2015 | Russo et al. |
| 8,956,390 B2 | 2/2015 | Shah et al. |
| 8,958,860 B2 | 2/2015 | Banerjee et al. |
| 8,960,519 B2 | 2/2015 | Whitman et al. |
| 8,960,520 B2 | 2/2015 | McCuen |
| 8,960,521 B2 | 2/2015 | Kostrzewski |
| 8,961,191 B2 | 2/2015 | Hanshew |
| 8,961,504 B2 | 2/2015 | Hoarau et al. |
| 8,961,542 B2 | 2/2015 | Whitfield et al. |
| 8,963,714 B2 | 2/2015 | Medhal et al. |
| D725,674 S | 3/2015 | Jung et al. |
| 8,967,443 B2 | 3/2015 | McCuen |
| 8,967,444 B2 | 3/2015 | Beetel |
| 8,967,446 B2 | 3/2015 | Beardsley et al. |
| 8,967,448 B2 | 3/2015 | Carter et al. |
| 8,968,276 B2 | 3/2015 | Zemlok et al. |
| 8,968,308 B2 | 3/2015 | Horner et al. |
| 8,968,312 B2 | 3/2015 | Marczyk et al. |
| 8,968,337 B2 | 3/2015 | Whitfield et al. |
| 8,968,340 B2 | 3/2015 | Chowaniec et al. |
| 8,968,355 B2 | 3/2015 | Malkowski et al. |
| 8,968,358 B2 | 3/2015 | Reschke |
| 8,970,507 B2 | 3/2015 | Holbein et al. |
| 8,973,803 B2 | 3/2015 | Hall et al. |
| 8,973,804 B2 | 3/2015 | Hess et al. |
| 8,973,805 B2 | 3/2015 | Scirica et al. |
| 8,974,440 B2 | 3/2015 | Farritor et al. |
| 8,974,542 B2 | 3/2015 | Fujimoto et al. |
| 8,974,932 B2 | 3/2015 | McGahan et al. |
| 8,978,954 B2 | 3/2015 | Shelton, IV et al. |
| 8,978,955 B2 | 3/2015 | Aronhalt et al. |
| 8,978,956 B2 | 3/2015 | Schall et al. |
| 8,979,843 B2 | 3/2015 | Timm et al. |
| 8,979,890 B2 | 3/2015 | Boudreaux |
| 8,982,195 B2 | 3/2015 | Claus et al. |
| 8,984,711 B2 | 3/2015 | Ota et al. |
| 8,985,240 B2 | 3/2015 | Winnard |
| 8,985,429 B2 | 3/2015 | Balek et al. |
| 8,986,302 B2 | 3/2015 | Aldridge et al. |
| 8,989,903 B2 | 3/2015 | Weir et al. |
| 8,991,676 B2 | 3/2015 | Hess et al. |
| 8,991,677 B2 | 3/2015 | Moore et al. |
| 8,991,678 B2 | 3/2015 | Wellman et al. |
| 8,992,042 B2 | 3/2015 | Eichenholz |
| 8,992,422 B2 | 3/2015 | Spivey et al. |
| 8,992,565 B2 | 3/2015 | Brisson et al. |
| 8,996,165 B2 | 3/2015 | Wang et al. |
| 8,998,058 B2 | 4/2015 | Moore et al. |
| 8,998,059 B2 | 4/2015 | Smith et al. |
| 8,998,060 B2 | 4/2015 | Bruewer et al. |
| 8,998,061 B2 | 4/2015 | Williams et al. |
| 8,998,939 B2 | 4/2015 | Price et al. |
| 9,000,720 B2 | 4/2015 | Stulen et al. |
| 9,002,518 B2 | 4/2015 | Manzo et al. |
| 9,004,339 B1 | 4/2015 | Park |
| 9,004,799 B1 | 4/2015 | Tibbits |
| 9,005,230 B2 | 4/2015 | Yates et al. |
| 9,005,238 B2 | 4/2015 | DeSantis et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,611 B2 | 4/2015 | Ross et al. |
| 9,011,437 B2 | 4/2015 | Woodruff et al. |
| 9,011,439 B2 | 4/2015 | Shalaby et al. |
| 9,011,471 B2 | 4/2015 | Timm et al. |
| 9,014,856 B2 | 4/2015 | Manzo et al. |
| 9,016,539 B2 | 4/2015 | Kostrzewski et al. |
| 9,016,540 B2 | 4/2015 | Whitman et al. |
| 9,016,541 B2 | 4/2015 | Viola et al. |
| 9,016,542 B2 | 4/2015 | Shelton, IV et al. |
| 9,016,545 B2 | 4/2015 | Aranyi et al. |
| 9,017,331 B2 | 4/2015 | Fox |
| 9,017,355 B2 | 4/2015 | Smith et al. |
| 9,017,369 B2 | 4/2015 | Renger et al. |
| 9,017,371 B2 | 4/2015 | Whitman et al. |
| 9,017,849 B2 | 4/2015 | Stulen et al. |
| 9,017,851 B2 | 4/2015 | Felder et al. |
| D729,274 S | 5/2015 | Clement et al. |
| 9,021,684 B2 | 5/2015 | Lenker et al. |
| 9,023,014 B2 | 5/2015 | Chowaniec et al. |
| 9,023,069 B2 | 5/2015 | Kasvikis et al. |
| 9,023,071 B2 | 5/2015 | Miller et al. |
| 9,026,347 B2 | 5/2015 | Gadh et al. |
| 9,027,817 B2 | 5/2015 | Milliman et al. |
| 9,028,468 B2 | 5/2015 | Scarfogliero et al. |
| 9,028,494 B2 | 5/2015 | Shelton, IV et al. |
| 9,028,495 B2 | 5/2015 | Mueller et al. |
| 9,028,510 B2 | 5/2015 | Miyamoto et al. |
| 9,028,511 B2 | 5/2015 | Weller et al. |
| 9,028,519 B2 | 5/2015 | Yates et al. |
| 9,030,166 B2 | 5/2015 | Kano |
| 9,030,169 B2 | 5/2015 | Christensen et al. |
| 9,033,203 B2 | 5/2015 | Woodard, Jr. et al. |
| 9,033,204 B2 | 5/2015 | Shelton, IV et al. |
| 9,034,505 B2 | 5/2015 | Detry et al. |
| 9,038,881 B1 | 5/2015 | Schaller et al. |
| 9,039,690 B2 | 5/2015 | Kersten et al. |

(56) References Cited

U.S. PATENT DOCUMENTS

| | | |
|---|---|---|
| 9,039,694 B2 | 5/2015 | Ross et al. |
| 9,039,720 B2 | 5/2015 | Madan |
| 9,040,062 B2 | 5/2015 | Maeda et al. |
| 9,043,027 B2 | 5/2015 | Durant et al. |
| 9,044,227 B2 | 6/2015 | Shelton, IV et al. |
| 9,044,228 B2 | 6/2015 | Woodard, Jr. et al. |
| 9,044,229 B2 | 6/2015 | Scheib et al. |
| 9,044,230 B2 | 6/2015 | Morgan et al. |
| 9,044,238 B2 | 6/2015 | Orszulak |
| 9,044,241 B2 | 6/2015 | Barner et al. |
| 9,044,261 B2 | 6/2015 | Houser |
| 9,044,281 B2 | 6/2015 | Pool et al. |
| 9,050,083 B2 | 6/2015 | Yates et al. |
| 9,050,084 B2 | 6/2015 | Schmid et al. |
| 9,050,089 B2 | 6/2015 | Orszulak |
| 9,050,100 B2 | 6/2015 | Yates et al. |
| 9,050,120 B2 | 6/2015 | Swarup et al. |
| 9,050,123 B2 | 6/2015 | Krause et al. |
| 9,050,176 B2 | 6/2015 | Datta et al. |
| 9,050,192 B2 | 6/2015 | Mansmann |
| 9,055,941 B2 | 6/2015 | Schmid et al. |
| 9,055,942 B2 | 6/2015 | Balbierz et al. |
| 9,055,943 B2 | 6/2015 | Zemlok et al. |
| 9,055,944 B2 | 6/2015 | Hodgkinson et al. |
| 9,055,961 B2 | 6/2015 | Manzo et al. |
| 9,060,770 B2 | 6/2015 | Shelton, IV et al. |
| 9,060,776 B2 | 6/2015 | Yates et al. |
| 9,060,794 B2 | 6/2015 | Kang et al. |
| 9,060,894 B2 | 6/2015 | Wubbeling |
| 9,061,392 B2 | 6/2015 | Forgues et al. |
| 9,070,068 B2 | 6/2015 | Coveley et al. |
| 9,072,515 B2 | 7/2015 | Hall et al. |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,078,654 B2 | 7/2015 | Whitman et al. |
| 9,084,586 B2 | 7/2015 | Hafner et al. |
| 9,084,601 B2 | 7/2015 | Moore et al. |
| 9,084,602 B2 | 7/2015 | Gleiman |
| 9,086,875 B2 | 7/2015 | Harrat et al. |
| 9,089,326 B2 | 7/2015 | Krumanaker et al. |
| 9,089,330 B2 | 7/2015 | Widenhouse et al. |
| 9,089,338 B2 | 7/2015 | Smith et al. |
| 9,089,352 B2 | 7/2015 | Jeong |
| 9,089,360 B2 | 7/2015 | Messerly et al. |
| 9,091,588 B2 | 7/2015 | Lefler |
| D736,792 S | 8/2015 | Brinda et al. |
| 9,095,339 B2 | 8/2015 | Moore et al. |
| 9,095,346 B2 | 8/2015 | Houser et al. |
| 9,095,362 B2 | 8/2015 | Dachs, II et al. |
| 9,095,367 B2 | 8/2015 | Olson et al. |
| 9,096,033 B2 | 8/2015 | Holop et al. |
| 9,098,153 B2 | 8/2015 | Shen et al. |
| 9,099,863 B2 | 8/2015 | Smith et al. |
| 9,099,877 B2 | 8/2015 | Banos et al. |
| 9,099,922 B2 | 8/2015 | Toosky et al. |
| 9,101,358 B2 | 8/2015 | Kerr et al. |
| 9,101,359 B2 | 8/2015 | Smith et al. |
| 9,101,385 B2 | 8/2015 | Shelton, IV et al. |
| 9,101,475 B2 | 8/2015 | Wei et al. |
| 9,101,621 B2 | 8/2015 | Is |
| 9,107,663 B2 | 8/2015 | Swensgard |
| 9,107,667 B2 | 8/2015 | Hodgkinson |
| 9,107,690 B2 | 8/2015 | Bales, Jr. et al. |
| 9,110,587 B2 | 8/2015 | Kim et al. |
| 9,113,862 B2 | 8/2015 | Morgan et al. |
| 9,113,864 B2 | 8/2015 | Morgan et al. |
| 9,113,865 B2 | 8/2015 | Shelton, IV et al. |
| 9,113,868 B2 | 8/2015 | Felder et al. |
| 9,113,873 B2 | 8/2015 | Marczyk et al. |
| 9,113,874 B2 | 8/2015 | Shelton, IV et al. |
| 9,113,876 B2 | 8/2015 | Zemlok et al. |
| 9,113,879 B2 | 8/2015 | Felder et al. |
| 9,113,880 B2 | 8/2015 | Zemlok et al. |
| 9,113,881 B2 | 8/2015 | Scirica |
| 9,113,883 B2 | 8/2015 | Aronhalt et al. |
| 9,113,884 B2 | 8/2015 | Shelton, IV et al. |
| 9,113,887 B2 | 8/2015 | Behnke, II et al. |
| 9,119,615 B2 | 9/2015 | Felder et al. |
| 9,119,657 B2 | 9/2015 | Shelton, IV et al. |
| 9,119,898 B2 | 9/2015 | Bayon et al. |
| 9,119,957 B2 | 9/2015 | Gantz et al. |
| 9,123,286 B2 | 9/2015 | Park |
| 9,124,097 B2 | 9/2015 | Cruz |
| 9,125,651 B2 | 9/2015 | Mandakolathur Vasudevan et al. |
| 9,125,654 B2 | 9/2015 | Aronhalt et al. |
| 9,125,662 B2 | 9/2015 | Shelton, IV |
| 9,126,317 B2 | 9/2015 | Lawton et al. |
| 9,131,835 B2 | 9/2015 | Widenhouse et al. |
| 9,131,940 B2 | 9/2015 | Huitema et al. |
| 9,131,950 B2 | 9/2015 | Matthew |
| 9,131,957 B2 | 9/2015 | Skarbnik et al. |
| 9,138,225 B2 | 9/2015 | Huang et al. |
| 9,138,226 B2 | 9/2015 | Racenet et al. |
| 9,144,455 B2 | 9/2015 | Kennedy et al. |
| D740,414 S | 10/2015 | Katsura |
| D741,882 S | 10/2015 | Shmilov et al. |
| 9,149,274 B2 | 10/2015 | Spivey et al. |
| 9,149,324 B2 | 10/2015 | Huang et al. |
| 9,149,325 B2 | 10/2015 | Worrell et al. |
| 9,153,994 B2 | 10/2015 | Wood et al. |
| 9,161,753 B2 | 10/2015 | Prior |
| 9,161,769 B2 | 10/2015 | Stoddard et al. |
| 9,161,803 B2 | 10/2015 | Yates et al. |
| 9,161,807 B2 | 10/2015 | Garrison |
| 9,161,855 B2 | 10/2015 | Rousseau et al. |
| 9,164,271 B2 | 10/2015 | Ebata et al. |
| 9,167,960 B2 | 10/2015 | Yamaguchi et al. |
| 9,168,038 B2 | 10/2015 | Shelton, IV et al. |
| 9,168,039 B1 | 10/2015 | Knodel |
| 9,168,042 B2 | 10/2015 | Milliman |
| 9,168,054 B2 | 10/2015 | Turner et al. |
| 9,168,144 B2 | 10/2015 | Rivin et al. |
| 9,171,244 B2 | 10/2015 | Endou et al. |
| 9,179,832 B2 | 11/2015 | Diolaiti |
| 9,179,911 B2 | 11/2015 | Morgan et al. |
| 9,179,912 B2 | 11/2015 | Yates et al. |
| 9,180,223 B2 | 11/2015 | Yu et al. |
| 9,182,244 B2 | 11/2015 | Luke et al. |
| 9,186,046 B2 | 11/2015 | Ramamurthy et al. |
| 9,186,137 B2 | 11/2015 | Farascioni et al. |
| 9,186,140 B2 | 11/2015 | Hiles et al. |
| 9,186,142 B2 | 11/2015 | Fanelli et al. |
| 9,186,143 B2 | 11/2015 | Timm et al. |
| 9,186,148 B2 | 11/2015 | Felder et al. |
| 9,186,221 B2 | 11/2015 | Burbank |
| 9,192,376 B2 | 11/2015 | Almodovar |
| 9,192,380 B2 | 11/2015 | (Tarinelli) Racenet et al. |
| 9,192,384 B2 | 11/2015 | Bettuchi |
| 9,192,430 B2 | 11/2015 | Rachlin et al. |
| 9,192,434 B2 | 11/2015 | Twomey et al. |
| 9,193,045 B2 | 11/2015 | Saur et al. |
| 9,197,079 B2 | 11/2015 | Yip et al. |
| D744,528 S | 12/2015 | Agrawal |
| D746,459 S | 12/2015 | Kaercher et al. |
| 9,198,642 B2 | 12/2015 | Storz |
| 9,198,644 B2 | 12/2015 | Balek et al. |
| 9,198,661 B2 | 12/2015 | Swensgard |
| 9,198,662 B2 | 12/2015 | Barton et al. |
| 9,198,683 B2 | 12/2015 | Friedman et al. |
| 9,204,830 B2 | 12/2015 | Zand et al. |
| 9,204,877 B2 | 12/2015 | Whitman et al. |
| 9,204,878 B2 | 12/2015 | Hall et al. |
| 9,204,879 B2 | 12/2015 | Shelton, IV |
| 9,204,880 B2 | 12/2015 | Baxter, III et al. |
| 9,204,881 B2 | 12/2015 | Penna |
| 9,204,923 B2 | 12/2015 | Manzo et al. |
| 9,204,924 B2 | 12/2015 | Marczyk et al. |
| 9,211,120 B2 | 12/2015 | Scheib et al. |
| 9,211,121 B2 | 12/2015 | Hall et al. |
| 9,211,122 B2 | 12/2015 | Hagerty et al. |
| 9,216,013 B2 | 12/2015 | Scirica et al. |
| 9,216,019 B2 | 12/2015 | Schmid et al. |

(56) References Cited

U.S. PATENT DOCUMENTS

| | | |
|---|---|---|
| 9,216,020 B2 | 12/2015 | Zhang et al. |
| 9,216,030 B2 | 12/2015 | Fan et al. |
| 9,216,062 B2 | 12/2015 | Duque et al. |
| 9,220,500 B2 | 12/2015 | Swayze et al. |
| 9,220,501 B2 | 12/2015 | Baxter, III et al. |
| 9,220,502 B2 | 12/2015 | Zemlok et al. |
| 9,220,504 B2 | 12/2015 | Viola et al. |
| 9,220,508 B2 | 12/2015 | Dannaher |
| 9,220,559 B2 | 12/2015 | Worrell et al. |
| 9,220,570 B2 | 12/2015 | Kim et al. |
| D746,854 S | 1/2016 | Shardlow et al. |
| 9,226,750 B2 | 1/2016 | Weir et al. |
| 9,226,751 B2 | 1/2016 | Shelton, IV et al. |
| 9,226,754 B2 | 1/2016 | D'Agostino et al. |
| 9,226,760 B2 | 1/2016 | Shelton, IV |
| 9,226,761 B2 | 1/2016 | Burbank |
| 9,226,767 B2 | 1/2016 | Stulen et al. |
| 9,226,799 B2 | 1/2016 | Lightcap et al. |
| 9,232,941 B2 | 1/2016 | Mandakolathur Vasudevan et al. |
| 9,232,945 B2 | 1/2016 | Zingman |
| 9,232,979 B2 | 1/2016 | Parihar et al. |
| 9,233,610 B2 | 1/2016 | Kim et al. |
| 9,237,891 B2 | 1/2016 | Shelton, IV |
| 9,237,892 B2 | 1/2016 | Hodgkinson |
| 9,237,895 B2 | 1/2016 | McCarthy et al. |
| 9,237,900 B2 | 1/2016 | Boudreaux et al. |
| 9,237,921 B2 | 1/2016 | Messerly et al. |
| 9,239,064 B2 | 1/2016 | Helbig et al. |
| 9,240,740 B2 | 1/2016 | Zeng et al. |
| 9,241,711 B2 | 1/2016 | Ivanko |
| 9,241,712 B2 | 1/2016 | Zemlok et al. |
| 9,241,714 B2 | 1/2016 | Timm et al. |
| 9,241,716 B2 | 1/2016 | Whitman |
| 9,241,731 B2 | 1/2016 | Boudreaux et al. |
| 9,241,758 B2 | 1/2016 | Franer et al. |
| 9,244,524 B2 | 1/2016 | Inoue et al. |
| D748,668 S | 2/2016 | Kim et al. |
| D749,128 S | 2/2016 | Perez et al. |
| D749,623 S | 2/2016 | Gray et al. |
| D750,122 S | 2/2016 | Shardlow et al. |
| D750,129 S | 2/2016 | Kwon |
| 9,254,131 B2 | 2/2016 | Soltz et al. |
| 9,254,170 B2 | 2/2016 | Parihar et al. |
| 9,259,265 B2 | 2/2016 | Harris et al. |
| 9,259,274 B2 | 2/2016 | Prisco |
| 9,259,275 B2 | 2/2016 | Burbank |
| 9,261,172 B2 | 2/2016 | Solomon et al. |
| 9,265,500 B2 | 2/2016 | Sorrentino et al. |
| 9,265,510 B2 | 2/2016 | Dietzel et al. |
| 9,265,516 B2 | 2/2016 | Casey et al. |
| 9,265,585 B2 | 2/2016 | Wingardner et al. |
| 9,271,718 B2 | 3/2016 | Milad et al. |
| 9,271,727 B2 | 3/2016 | McGuckin, Jr. et al. |
| 9,271,753 B2 | 3/2016 | Butler et al. |
| 9,271,799 B2 | 3/2016 | Shelton, IV et al. |
| 9,272,406 B2 | 3/2016 | Aronhalt et al. |
| 9,274,095 B2 | 3/2016 | Humayun et al. |
| 9,277,919 B2 | 3/2016 | Timmer et al. |
| 9,277,922 B2 | 3/2016 | Carter et al. |
| 9,277,969 B2 | 3/2016 | Brannan et al. |
| 9,282,962 B2 | 3/2016 | Schmid et al. |
| 9,282,963 B2 | 3/2016 | Bryant |
| 9,282,966 B2 | 3/2016 | Shelton, IV et al. |
| 9,282,974 B2 | 3/2016 | Shelton, IV |
| 9,283,028 B2 | 3/2016 | Johnson |
| 9,283,045 B2 | 3/2016 | Rhee et al. |
| 9,283,054 B2 | 3/2016 | Morgan et al. |
| 9,289,206 B2 | 3/2016 | Hess et al. |
| 9,289,207 B2 | 3/2016 | Shelton, IV |
| 9,289,210 B2 | 3/2016 | Baxter, III et al. |
| 9,289,211 B2 | 3/2016 | Williams et al. |
| 9,289,212 B2 | 3/2016 | Shelton, IV et al. |
| 9,289,225 B2 | 3/2016 | Shelton, IV et al. |
| 9,289,256 B2 | 3/2016 | Shelton, IV et al. |
| 9,293,757 B2 | 3/2016 | Toussaint et al. |
| 9,295,464 B2 | 3/2016 | Shelton, IV et al. |
| 9,295,465 B2 | 3/2016 | Farascioni |
| 9,295,466 B2 | 3/2016 | Hodgkinson et al. |
| 9,295,467 B2 | 3/2016 | Scirica |
| 9,295,468 B2 | 3/2016 | Heinrich et al. |
| 9,295,514 B2 | 3/2016 | Shelton, IV et al. |
| 9,295,522 B2 | 3/2016 | Kostrzewski |
| 9,295,565 B2 | 3/2016 | McLean |
| 9,295,784 B2 | 3/2016 | Eggert et al. |
| D753,167 S | 4/2016 | Yu et al. |
| 9,301,691 B2 | 4/2016 | Hufnagel et al. |
| 9,301,752 B2 | 4/2016 | Mandakolathur Vasudevan et al. |
| 9,301,753 B2 | 4/2016 | Aldridge et al. |
| 9,301,755 B2 | 4/2016 | Shelton, IV et al. |
| 9,301,759 B2 | 4/2016 | Spivey et al. |
| 9,301,811 B2 | 4/2016 | Goldberg et al. |
| 9,307,965 B2 | 4/2016 | Ming et al. |
| 9,307,986 B2 * | 4/2016 | Hall ................ A61B 90/98 |
| 9,307,987 B2 | 4/2016 | Swensgard et al. |
| 9,307,988 B2 | 4/2016 | Shelton, IV |
| 9,307,989 B2 | 4/2016 | Shelton, IV et al. |
| 9,307,994 B2 | 4/2016 | Gresham et al. |
| 9,308,009 B2 | 4/2016 | Madan et al. |
| 9,308,011 B2 | 4/2016 | Chao et al. |
| 9,308,646 B2 | 4/2016 | Lim et al. |
| 9,313,915 B2 | 4/2016 | Niu et al. |
| 9,314,246 B2 | 4/2016 | Shelton, IV et al. |
| 9,314,247 B2 | 4/2016 | Shelton, IV et al. |
| 9,314,261 B2 | 4/2016 | Bales, Jr. et al. |
| 9,314,291 B2 | 4/2016 | Schall et al. |
| 9,314,339 B2 | 4/2016 | Mansmann |
| 9,314,908 B2 | 4/2016 | Tanimoto et al. |
| 9,320,518 B2 | 4/2016 | Henderson et al. |
| 9,320,520 B2 | 4/2016 | Shelton, IV et al. |
| 9,320,521 B2 | 4/2016 | Shelton, IV et al. |
| 9,320,523 B2 | 4/2016 | Shelton, IV et al. |
| 9,325,516 B2 | 4/2016 | Pera et al. |
| D755,196 S | 5/2016 | Meyers et al. |
| D756,373 S | 5/2016 | Raskin et al. |
| D756,377 S | 5/2016 | Connolly et al. |
| D757,028 S | 5/2016 | Goldenberg et al. |
| 9,326,767 B2 | 5/2016 | Koch et al. |
| 9,326,768 B2 | 5/2016 | Shelton, IV |
| 9,326,769 B2 | 5/2016 | Shelton, IV et al. |
| 9,326,770 B2 | 5/2016 | Shelton, IV et al. |
| 9,326,771 B2 | 5/2016 | Baxter, III et al. |
| 9,326,788 B2 | 5/2016 | Batross et al. |
| 9,326,812 B2 | 5/2016 | Waaler et al. |
| 9,326,824 B2 | 5/2016 | Inoue et al. |
| 9,327,061 B2 | 5/2016 | Govil et al. |
| 9,331,721 B2 | 5/2016 | Martinez Nuevo et al. |
| 9,332,890 B2 | 5/2016 | Ozawa |
| 9,332,974 B2 | 5/2016 | Henderson et al. |
| 9,332,984 B2 | 5/2016 | Weaner et al. |
| 9,332,987 B2 | 5/2016 | Leimbach et al. |
| 9,333,040 B2 | 5/2016 | Shellenberger et al. |
| 9,333,082 B2 | 5/2016 | Wei et al. |
| 9,337,668 B2 | 5/2016 | Yip |
| 9,339,226 B2 | 5/2016 | van der Walt et al. |
| 9,339,342 B2 | 5/2016 | Prisco et al. |
| 9,345,477 B2 | 5/2016 | Anim et al. |
| 9,345,479 B2 | 5/2016 | (Tarinelli) Racenet et al. |
| 9,345,480 B2 | 5/2016 | Hessler et al. |
| 9,345,481 B2 | 5/2016 | Hall et al. |
| 9,345,503 B2 | 5/2016 | Ishida et al. |
| 9,351,726 B2 | 5/2016 | Leimbach et al. |
| 9,351,727 B2 | 5/2016 | Leimbach et al. |
| 9,351,728 B2 | 5/2016 | Sniffin et al. |
| 9,351,730 B2 | 5/2016 | Schmid et al. |
| 9,351,731 B2 | 5/2016 | Carter et al. |
| 9,351,732 B2 | 5/2016 | Hodgkinson |
| 9,352,071 B2 | 5/2016 | Landgrebe et al. |
| D758,433 S | 6/2016 | Lee et al. |
| D759,063 S | 6/2016 | Chen |
| 9,358,003 B2 | 6/2016 | Hall et al. |
| 9,358,004 B2 | 6/2016 | Sniffin et al. |
| 9,358,005 B2 | 6/2016 | Shelton, IV et al. |
| 9,358,015 B2 | 6/2016 | Sorrentino et al. |
| 9,358,031 B2 | 6/2016 | Manzo |

(56) References Cited

U.S. PATENT DOCUMENTS

| | | |
|---|---|---|
| 9,358,065 B2 | 6/2016 | Ladtkow et al. |
| 9,364,217 B2 | 6/2016 | Kostrzewski et al. |
| 9,364,219 B2 | 6/2016 | Olson et al. |
| 9,364,220 B2 | 6/2016 | Williams |
| 9,364,223 B2 | 6/2016 | Scirica |
| 9,364,226 B2 | 6/2016 | Zemlok et al. |
| 9,364,228 B2 | 6/2016 | Straehnz et al. |
| 9,364,229 B2 | 6/2016 | D'Agostino et al. |
| 9,364,230 B2 | 6/2016 | Shelton, IV et al. |
| 9,364,231 B2 | 6/2016 | Wenchell |
| 9,364,233 B2 | 6/2016 | Alexander, III et al. |
| 9,364,279 B2 | 6/2016 | Houser et al. |
| 9,368,991 B2 | 6/2016 | Qahouq |
| 9,370,341 B2 | 6/2016 | Ceniccola et al. |
| 9,370,358 B2 | 6/2016 | Shelton, IV et al. |
| 9,370,361 B2 | 6/2016 | Viola et al. |
| 9,370,362 B2 | 6/2016 | Petty et al. |
| 9,370,364 B2 | 6/2016 | Smith et al. |
| 9,370,400 B2 | 6/2016 | Parihar |
| 9,375,206 B2 | 6/2016 | Vidal et al. |
| 9,375,218 B2 | 6/2016 | Wheeler et al. |
| 9,375,230 B2 | 6/2016 | Ross et al. |
| 9,375,232 B2 | 6/2016 | Hunt et al. |
| 9,375,255 B2 | 6/2016 | Houser et al. |
| D761,309 S | 7/2016 | Lee et al. |
| 9,381,058 B2 | 7/2016 | Houser et al. |
| 9,383,881 B2 | 7/2016 | Day et al. |
| 9,385,640 B2 | 7/2016 | Sun et al. |
| 9,386,983 B2 | 7/2016 | Swensgard et al. |
| 9,386,984 B2 | 7/2016 | Aronhalt et al. |
| 9,386,985 B2 | 7/2016 | Koch, Jr. et al. |
| 9,386,988 B2 | 7/2016 | Baxter, III et al. |
| 9,387,003 B2 | 7/2016 | Kaercher et al. |
| 9,392,885 B2 | 7/2016 | Vogler et al. |
| 9,393,015 B2 | 7/2016 | Laurent et al. |
| 9,393,017 B2 | 7/2016 | Flanagan et al. |
| 9,393,018 B2 | 7/2016 | Wang et al. |
| 9,393,354 B2 | 7/2016 | Freedman et al. |
| 9,396,369 B1 | 7/2016 | Whitehurst et al. |
| 9,396,669 B2 | 7/2016 | Karkanias et al. |
| 9,398,905 B2 | 7/2016 | Martin |
| 9,398,911 B2 | 7/2016 | Auld |
| D763,277 S | 8/2016 | Ahmed et al. |
| D764,498 S | 8/2016 | Capela et al. |
| 9,402,604 B2 | 8/2016 | Williams et al. |
| 9,402,625 B2 | 8/2016 | Coleman et al. |
| 9,402,626 B2 | 8/2016 | Ortiz et al. |
| 9,402,627 B2 | 8/2016 | Stevenson et al. |
| 9,402,629 B2 | 8/2016 | Ehrenfels et al. |
| 9,402,679 B2 | 8/2016 | Ginnebaugh et al. |
| 9,402,682 B2 | 8/2016 | Worrell et al. |
| 9,402,688 B2 | 8/2016 | Min et al. |
| 9,408,604 B2 | 8/2016 | Shelton, IV et al. |
| 9,408,605 B1 | 8/2016 | Knodel et al. |
| 9,408,606 B2 | 8/2016 | Shelton, IV |
| 9,408,622 B2 | 8/2016 | Stulen et al. |
| 9,411,370 B2 | 8/2016 | Benni et al. |
| 9,413,128 B2 | 8/2016 | Tien et al. |
| 9,414,838 B2 | 8/2016 | Shelton, IV et al. |
| 9,414,849 B2 | 8/2016 | Nagashimada |
| 9,414,880 B2 | 8/2016 | Monson et al. |
| 9,420,967 B2 | 8/2016 | Zand et al. |
| 9,421,003 B2 | 8/2016 | Williams et al. |
| 9,421,014 B2 | 8/2016 | Ingmanson et al. |
| 9,421,030 B2 | 8/2016 | Cole et al. |
| 9,421,060 B2 | 8/2016 | Monson et al. |
| 9,421,062 B2 | 8/2016 | Houser et al. |
| 9,421,682 B2 | 8/2016 | McClaskey et al. |
| 9,427,223 B2 | 8/2016 | Park et al. |
| 9,427,231 B2 | 8/2016 | Racenet et al. |
| 9,429,204 B2 | 8/2016 | Stefan et al. |
| D767,624 S | 9/2016 | Lee et al. |
| 9,433,411 B2 | 9/2016 | Racenet et al. |
| 9,433,414 B2 | 9/2016 | Chen et al. |
| 9,433,419 B2 | 9/2016 | Gonzalez et al. |
| 9,433,420 B2 | 9/2016 | Hodgkinson |
| 9,439,649 B2 | 9/2016 | Shelton, IV et al. |
| 9,439,650 B2 | 9/2016 | McGuckin, Jr. et al. |
| 9,439,651 B2 | 9/2016 | Smith et al. |
| 9,439,668 B2 | 9/2016 | Timm et al. |
| 9,445,808 B2 | 9/2016 | Woodard, Jr. et al. |
| 9,445,813 B2 | 9/2016 | Shelton, IV et al. |
| 9,445,816 B2 | 9/2016 | Swayze et al. |
| 9,445,817 B2 | 9/2016 | Bettuchi |
| 9,446,226 B2 | 9/2016 | Zilberman |
| 9,451,938 B2 | 9/2016 | Res et al. |
| 9,451,958 B2 | 9/2016 | Shelton, IV et al. |
| D768,152 S | 10/2016 | Gutierrez et al. |
| D768,156 S | 10/2016 | Frincke |
| D768,167 S | 10/2016 | Jones et al. |
| D769,315 S | 10/2016 | Scotti |
| D769,930 S | 10/2016 | Agrawal |
| 9,461,340 B2 | 10/2016 | Li et al. |
| 9,463,012 B2 | 10/2016 | Bonutti et al. |
| 9,463,040 B2 | 10/2016 | Jeong et al. |
| 9,463,260 B2 | 10/2016 | Stope |
| 9,468,438 B2 | 10/2016 | Baber et al. |
| 9,468,447 B2 | 10/2016 | Aman et al. |
| 9,470,297 B2 | 10/2016 | Aranyi et al. |
| 9,471,969 B2 | 10/2016 | Zeng et al. |
| 9,474,506 B2 | 10/2016 | Magnin et al. |
| 9,474,513 B2 | 10/2016 | Ishida et al. |
| 9,474,523 B2 | 10/2016 | Meade et al. |
| 9,474,540 B2 | 10/2016 | Stokes et al. |
| 9,475,180 B2 | 10/2016 | Eshleman et al. |
| D770,476 S | 11/2016 | Jitkoff et al. |
| D770,515 S | 11/2016 | Cho et al. |
| D771,116 S | 11/2016 | Dellinger et al. |
| D772,905 S | 11/2016 | Ingenlath |
| 9,480,476 B2 | 11/2016 | Aldridge et al. |
| 9,480,492 B2 | 11/2016 | Aranyi et al. |
| 9,483,095 B2 | 11/2016 | Tran et al. |
| 9,486,186 B2 | 11/2016 | Fiebig et al. |
| 9,486,213 B2 | 11/2016 | Altman et al. |
| 9,486,214 B2 | 11/2016 | Shelton, IV |
| 9,486,215 B2 | 11/2016 | Olson et al. |
| 9,486,302 B2 | 11/2016 | Boey et al. |
| 9,488,197 B2 | 11/2016 | Wi |
| 9,492,146 B2 | 11/2016 | Kostrzewski et al. |
| 9,492,167 B2 | 11/2016 | Shelton, IV et al. |
| 9,492,170 B2 | 11/2016 | Bear et al. |
| 9,492,172 B2 | 11/2016 | Weisshaupt et al. |
| 9,492,189 B2 | 11/2016 | Williams et al. |
| 9,492,192 B2 | 11/2016 | To et al. |
| 9,492,237 B2 | 11/2016 | Kang et al. |
| 9,498,213 B2 | 11/2016 | Marczyk et al. |
| 9,498,219 B2 | 11/2016 | Moore et al. |
| 9,498,231 B2 | 11/2016 | Haider et al. |
| 9,504,455 B2 | 11/2016 | Whitman et al. |
| 9,504,483 B2 | 11/2016 | Houser et al. |
| 9,504,520 B2 | 11/2016 | Worrell et al. |
| 9,504,521 B2 | 11/2016 | Deutmeyer et al. |
| 9,504,528 B2 | 11/2016 | Ivinson et al. |
| 9,507,399 B2 | 11/2016 | Chien |
| D774,547 S | 12/2016 | Capela et al. |
| D775,336 S | 12/2016 | Shelton, IV et al. |
| 9,510,827 B2 | 12/2016 | Kostrzewski |
| 9,510,828 B2 | 12/2016 | Yates et al. |
| 9,510,830 B2 | 12/2016 | Shelton, IV et al. |
| 9,510,846 B2 | 12/2016 | Sholev et al. |
| 9,510,895 B2 | 12/2016 | Houser et al. |
| 9,510,925 B2 | 12/2016 | Hotter et al. |
| 9,517,063 B2 | 12/2016 | Swayze et al. |
| 9,517,065 B2 | 12/2016 | Simms et al. |
| 9,517,068 B2 | 12/2016 | Shelton, IV et al. |
| 9,517,326 B2 | 12/2016 | Hinman et al. |
| 9,521,996 B2 | 12/2016 | Armstrong |
| 9,522,003 B2 | 12/2016 | Weir et al. |
| 9,522,014 B2 | 12/2016 | Nishizawa et al. |
| 9,522,029 B2 | 12/2016 | Yates et al. |
| 9,526,481 B2 | 12/2016 | Storz et al. |
| 9,526,499 B2 | 12/2016 | Kostrzewski et al. |
| 9,526,563 B2 | 12/2016 | Twomey |
| 9,526,564 B2 | 12/2016 | Rusin |

(56) References Cited

U.S. PATENT DOCUMENTS

| | | |
|---|---|---|
| 9,526,921 B2 | 12/2016 | Kimball et al. |
| D776,683 S | 1/2017 | Gobinski et al. |
| D777,773 S | 1/2017 | Shi |
| 9,532,783 B2 | 1/2017 | Swayze et al. |
| 9,539,060 B2 | 1/2017 | Lightcap et al. |
| 9,539,726 B2 | 1/2017 | Simaan et al. |
| 9,545,253 B2 | 1/2017 | Worrell et al. |
| 9,545,258 B2 | 1/2017 | Smith et al. |
| 9,549,732 B2 | 1/2017 | Yates et al. |
| 9,549,733 B2 | 1/2017 | Knodel |
| 9,549,735 B2 | 1/2017 | Shelton, IV et al. |
| 9,549,750 B2 | 1/2017 | Shelton, IV et al. |
| 9,554,794 B2 | 1/2017 | Baber et al. |
| 9,554,796 B2 | 1/2017 | Kostrzewski |
| 9,554,803 B2 | 1/2017 | Smith et al. |
| 9,554,812 B2 | 1/2017 | Inkpen et al. |
| 9,559,624 B2 | 1/2017 | Philipp |
| 9,561,013 B2 | 2/2017 | Tsuchiya |
| 9,561,029 B2 | 2/2017 | Scheib et al. |
| 9,561,030 B2 | 2/2017 | Zhang et al. |
| 9,561,031 B2 | 2/2017 | Heinrich et al. |
| 9,561,032 B2 | 2/2017 | Shelton, IV et al. |
| 9,561,038 B2 | 2/2017 | Shelton, IV et al. |
| 9,561,045 B2 | 2/2017 | Hinman et al. |
| 9,561,072 B2 | 2/2017 | Ko |
| 9,566,061 B2 | 2/2017 | Aronhalt et al. |
| 9,566,062 B2 | 2/2017 | Boudreaux |
| 9,566,065 B2 | 2/2017 | Knodel |
| 9,566,067 B2 | 2/2017 | Milliman et al. |
| 9,572,574 B2 | 2/2017 | Shelton, IV et al. |
| 9,572,576 B2 | 2/2017 | Hodgkinson et al. |
| 9,572,577 B2 | 2/2017 | Lloyd et al. |
| 9,572,592 B2 | 2/2017 | Price et al. |
| 9,574,644 B2 | 2/2017 | Parihar |
| 9,579,088 B2 | 2/2017 | Farritor et al. |
| 9,579,143 B2 | 2/2017 | Ullrich et al. |
| 9,579,158 B2 | 2/2017 | Brianza et al. |
| D780,803 S | 3/2017 | Gill et al. |
| D781,879 S | 3/2017 | Butcher et al. |
| D782,530 S | 3/2017 | Paek et al. |
| 9,585,550 B2 | 3/2017 | Abel et al. |
| 9,585,657 B2 | 3/2017 | Shelton, IV et al. |
| 9,585,658 B2 | 3/2017 | Shelton, IV |
| 9,585,659 B2 | 3/2017 | Viola et al. |
| 9,585,660 B2 | 3/2017 | Laurent et al. |
| 9,585,662 B2 | 3/2017 | Shelton, IV et al. |
| 9,585,663 B2 | 3/2017 | Shelton, IV et al. |
| 9,585,672 B2 | 3/2017 | Bastia |
| 9,590,433 B2 | 3/2017 | Li |
| 9,592,050 B2 | 3/2017 | Schmid et al. |
| 9,592,052 B2 | 3/2017 | Shelton, IV |
| 9,592,053 B2 | 3/2017 | Shelton, IV et al. |
| 9,592,054 B2 | 3/2017 | Schmid et al. |
| 9,597,073 B2 | 3/2017 | Sorrentino et al. |
| 9,597,075 B2 | 3/2017 | Shelton, IV et al. |
| 9,597,078 B2 | 3/2017 | Scirica et al. |
| 9,597,080 B2 | 3/2017 | Milliman et al. |
| 9,597,104 B2 | 3/2017 | Nicholas et al. |
| 9,597,143 B2 | 3/2017 | Madan et al. |
| 9,603,595 B2 | 3/2017 | Shelton, IV et al. |
| 9,603,598 B2 | 3/2017 | Shelton, IV et al. |
| 9,603,599 B2 | 3/2017 | Miller et al. |
| 9,603,991 B2 | 3/2017 | Shelton, IV et al. |
| D783,658 S | 4/2017 | Hurst et al. |
| 9,610,068 B2 | 4/2017 | Kappel et al. |
| 9,610,079 B2 | 4/2017 | Kamei et al. |
| 9,610,080 B2 | 4/2017 | Whitfield et al. |
| 9,610,412 B2 | 4/2017 | Zemlok et al. |
| 9,614,258 B2 | 4/2017 | Takahashi et al. |
| 9,615,826 B2 | 4/2017 | Shelton, IV et al. |
| 9,622,745 B2 | 4/2017 | Ingmanson et al. |
| 9,622,746 B2 | 4/2017 | Simms et al. |
| 9,629,623 B2 | 4/2017 | Lytle, IV et al. |
| 9,629,626 B2 | 4/2017 | Soltz et al. |
| 9,629,627 B2 | 4/2017 | Kostrzewski et al. |
| 9,629,628 B2 | 4/2017 | Aranyi |
| 9,629,629 B2 | 4/2017 | Leimbach et al. |
| 9,629,631 B2 | 4/2017 | Nicholas et al. |
| 9,629,632 B2 | 4/2017 | Linder et al. |
| 9,629,652 B2 | 4/2017 | Mumaw et al. |
| 9,629,814 B2 | 4/2017 | Widenhouse et al. |
| D785,794 S | 5/2017 | Magno, Jr. |
| D786,280 S | 5/2017 | Ma |
| D786,896 S | 5/2017 | Kim et al. |
| D787,547 S | 5/2017 | Basargin et al. |
| D788,123 S | 5/2017 | Shan et al. |
| D788,140 S | 5/2017 | Hemsley et al. |
| 9,636,091 B2 | 5/2017 | Beardsley et al. |
| 9,636,111 B2 | 5/2017 | Wenchell |
| 9,636,112 B2 | 5/2017 | Penna et al. |
| 9,636,113 B2 | 5/2017 | Wenchell |
| 9,636,850 B2 | 5/2017 | Stopek et al. |
| 9,641,122 B2 | 5/2017 | Romanowich et al. |
| 9,642,620 B2 | 5/2017 | Baxter, III et al. |
| 9,642,642 B2 | 5/2017 | Lim |
| 9,649,096 B2 | 5/2017 | Sholev |
| 9,649,110 B2 | 5/2017 | Parihar et al. |
| 9,649,111 B2 | 5/2017 | Shelton, IV et al. |
| 9,649,190 B2 | 5/2017 | Mathies |
| 9,655,613 B2 | 5/2017 | Schaller |
| 9,655,614 B2 | 5/2017 | Swensgard et al. |
| 9,655,615 B2 | 5/2017 | Knodel et al. |
| 9,655,616 B2 | 5/2017 | Aranyi |
| 9,655,624 B2 | 5/2017 | Shelton, IV et al. |
| 9,661,991 B2 | 5/2017 | Glossop |
| 9,662,108 B2 | 5/2017 | Williams |
| 9,662,110 B2 | 5/2017 | Huang et al. |
| 9,662,111 B2 | 5/2017 | Holsten et al. |
| 9,662,116 B2 | 5/2017 | Smith et al. |
| 9,662,131 B2 | 5/2017 | Omori et al. |
| D788,792 S | 6/2017 | Alessandri et al. |
| D789,384 S | 6/2017 | Lin et al. |
| D790,570 S | 6/2017 | Butcher et al. |
| 9,668,728 B2 | 6/2017 | Williams et al. |
| 9,668,729 B2 | 6/2017 | Williams et al. |
| 9,668,732 B2 | 6/2017 | Patel et al. |
| 9,668,733 B2 | 6/2017 | Williams |
| 9,668,734 B2 | 6/2017 | Kostrzewski et al. |
| 9,668,735 B2 | 6/2017 | Beetel |
| 9,675,344 B2 | 6/2017 | Combrowski et al. |
| 9,675,348 B2 | 6/2017 | Smith et al. |
| 9,675,351 B2 | 6/2017 | Hodgkinson et al. |
| 9,675,354 B2 | 6/2017 | Weir et al. |
| 9,675,355 B2 | 6/2017 | Shelton, IV et al. |
| 9,675,368 B2 | 6/2017 | Guo et al. |
| 9,675,372 B2 | 6/2017 | Laurent et al. |
| 9,675,375 B2 | 6/2017 | Houser et al. |
| 9,675,405 B2 | 6/2017 | Trees et al. |
| 9,675,819 B2 | 6/2017 | Dunbar et al. |
| 9,681,870 B2 | 6/2017 | Baxter, III et al. |
| 9,681,873 B2 | 6/2017 | Smith et al. |
| 9,681,884 B2 | 6/2017 | Clem et al. |
| 9,687,230 B2 | 6/2017 | Leimbach et al. |
| 9,687,231 B2 | 6/2017 | Baxter, III et al. |
| 9,687,232 B2 | 6/2017 | Shelton, IV et al. |
| 9,687,233 B2 | 6/2017 | Fernandez et al. |
| 9,687,236 B2 | 6/2017 | Leimbach et al. |
| 9,687,237 B2 | 6/2017 | Schmid et al. |
| 9,687,253 B2 | 6/2017 | Detry et al. |
| 9,689,466 B2 | 6/2017 | Kanai et al. |
| 9,690,362 B2 | 6/2017 | Leimbach et al. |
| 9,693,772 B2 | 7/2017 | Ingmanson et al. |
| 9,693,774 B2 | 7/2017 | Gettinger et al. |
| 9,693,775 B2 | 7/2017 | Agarwal et al. |
| 9,693,777 B2 | 7/2017 | Schellin et al. |
| 9,700,309 B2 | 7/2017 | Jaworek et al. |
| 9,700,310 B2 | 7/2017 | Morgan et al. |
| 9,700,312 B2 | 7/2017 | Kostrzewski et al. |
| 9,700,314 B2 | 7/2017 | Marczyk |
| 9,700,315 B2 | 7/2017 | Chen et al. |
| 9,700,317 B2 | 7/2017 | Aronhalt et al. |
| 9,700,318 B2 | 7/2017 | Scirica et al. |
| 9,700,319 B2 | 7/2017 | Motooka et al. |
| 9,700,320 B2 | 7/2017 | Dinardo et al. |

(56) References Cited

U.S. PATENT DOCUMENTS

| | | |
|---|---|---|
| 9,700,321 B2 | 7/2017 | Shelton, IV et al. |
| 9,700,334 B2 | 7/2017 | Hinman et al. |
| 9,702,823 B2 | 7/2017 | Maher et al. |
| 9,706,674 B2 | 7/2017 | Collins et al. |
| 9,706,981 B2 | 7/2017 | Nicholas et al. |
| 9,706,991 B2 | 7/2017 | Hess et al. |
| 9,706,993 B2 | 7/2017 | Hessler et al. |
| 9,707,003 B2 | 7/2017 | Hoell, Jr. et al. |
| 9,707,005 B2 | 7/2017 | Strobl et al. |
| 9,707,026 B2 | 7/2017 | Malackowski et al. |
| 9,707,033 B2 | 7/2017 | Parihar et al. |
| 9,707,043 B2 | 7/2017 | Bozung |
| 9,707,684 B2 | 7/2017 | Ruiz Morales et al. |
| 9,713,468 B2 | 7/2017 | Harris et al. |
| 9,713,470 B2 | 7/2017 | Scirica et al. |
| 9,713,474 B2 | 7/2017 | Lorenz |
| D795,919 S | 8/2017 | Bischoff et al. |
| 9,717,497 B2 | 8/2017 | Zerkle et al. |
| 9,717,498 B2 | 8/2017 | Aranyi et al. |
| 9,718,190 B2 | 8/2017 | Larkin et al. |
| 9,722,236 B2 | 8/2017 | Sathrum |
| 9,724,091 B2 | 8/2017 | Shelton, IV et al. |
| 9,724,092 B2 | 8/2017 | Baxter, III et al. |
| 9,724,094 B2 | 8/2017 | Baber et al. |
| 9,724,095 B2 | 8/2017 | Gupta et al. |
| 9,724,096 B2 | 8/2017 | Thompson et al. |
| 9,724,098 B2 | 8/2017 | Baxter, III et al. |
| 9,724,118 B2 | 8/2017 | Schulte et al. |
| 9,724,163 B2 | 8/2017 | Orban |
| 9,730,692 B2 | 8/2017 | Shelton, IV et al. |
| 9,730,695 B2 | 8/2017 | Leimbach et al. |
| 9,730,697 B2 | 8/2017 | Morgan et al. |
| 9,730,717 B2 | 8/2017 | Katsuki et al. |
| 9,730,757 B2 | 8/2017 | Brudniok |
| 9,731,410 B2 | 8/2017 | Hirabayashi et al. |
| 9,733,663 B2 | 8/2017 | Leimbach et al. |
| 9,737,297 B2 | 8/2017 | Racenet et al. |
| 9,737,298 B2 | 8/2017 | Isbell, Jr. |
| 9,737,299 B2 | 8/2017 | Yan |
| 9,737,301 B2 | 8/2017 | Baber et al. |
| 9,737,302 B2 | 8/2017 | Shelton, IV et al. |
| 9,737,303 B2 | 8/2017 | Shelton, IV et al. |
| 9,737,365 B2 | 8/2017 | Hegeman et al. |
| 9,743,927 B2 | 8/2017 | Whitman |
| 9,743,928 B2 | 8/2017 | Shelton, IV et al. |
| 9,743,929 B2 | 8/2017 | Leimbach et al. |
| D798,319 S | 9/2017 | Bergstrand et al. |
| 9,750,498 B2 | 9/2017 | Timm et al. |
| 9,750,499 B2 | 9/2017 | Leimbach et al. |
| 9,750,501 B2 | 9/2017 | Shelton, IV et al. |
| 9,750,502 B2 | 9/2017 | Scirica et al. |
| 9,750,503 B2 | 9/2017 | Milliman |
| 9,750,639 B2 | 9/2017 | Barnes et al. |
| 9,757,123 B2 | 9/2017 | Giordano et al. |
| 9,757,124 B2 | 9/2017 | Schellin et al. |
| 9,757,126 B2 | 9/2017 | Cappola |
| 9,757,128 B2 | 9/2017 | Baber et al. |
| 9,757,129 B2 | 9/2017 | Williams |
| 9,757,130 B2 | 9/2017 | Shelton, IV |
| 9,763,662 B2 | 9/2017 | Shelton, IV et al. |
| 9,763,668 B2 | 9/2017 | Whitfield et al. |
| 9,770,245 B2 | 9/2017 | Swayze et al. |
| 9,770,274 B2 | 9/2017 | Pool et al. |
| D798,886 S | 10/2017 | Prophete et al. |
| D800,742 S | 10/2017 | Rhodes |
| D800,744 S | 10/2017 | Jitkoff et al. |
| D800,766 S | 10/2017 | Park et al. |
| D800,904 S | 10/2017 | Leimbach et al. |
| 9,775,608 B2 | 10/2017 | Aronhalt et al. |
| 9,775,609 B2 | 10/2017 | Shelton, IV et al. |
| 9,775,610 B2 | 10/2017 | Nicholas et al. |
| 9,775,611 B2 | 10/2017 | Kostrzewski |
| 9,775,613 B2 | 10/2017 | Shelton, IV et al. |
| 9,775,614 B2 | 10/2017 | Shelton, IV et al. |
| 9,775,618 B2 | 10/2017 | Bettuchi et al. |
| 9,775,635 B2 | 10/2017 | Takei |
| 9,775,678 B2 | 10/2017 | Lohmeier |
| 9,782,169 B2 | 10/2017 | Kimsey et al. |
| 9,782,170 B2 | 10/2017 | Zemlok et al. |
| 9,782,180 B2 | 10/2017 | Smith et al. |
| 9,782,187 B2 | 10/2017 | Zergiebel et al. |
| 9,782,193 B2 | 10/2017 | Thistle |
| 9,782,214 B2 | 10/2017 | Houser et al. |
| 9,788,834 B2 | 10/2017 | Schmid et al. |
| 9,788,835 B2 | 10/2017 | Morgan et al. |
| 9,788,836 B2 | 10/2017 | Overmyer et al. |
| 9,788,847 B2 | 10/2017 | Jinno |
| 9,788,851 B2 | 10/2017 | Dannaher et al. |
| 9,788,902 B2 | 10/2017 | Inoue et al. |
| 9,795,379 B2 | 10/2017 | Leimbach et al. |
| 9,795,380 B2 | 10/2017 | Shelton, IV et al. |
| 9,795,381 B2 | 10/2017 | Shelton, IV |
| 9,795,382 B2 | 10/2017 | Shelton, IV |
| 9,795,383 B2 | 10/2017 | Aldridge et al. |
| 9,795,384 B2 | 10/2017 | Weaner et al. |
| 9,797,486 B2 | 10/2017 | Zergiebel et al. |
| 9,801,626 B2 | 10/2017 | Parihar et al. |
| 9,801,627 B2 | 10/2017 | Harris et al. |
| 9,801,628 B2 | 10/2017 | Harris et al. |
| 9,801,634 B2 | 10/2017 | Shelton, IV et al. |
| 9,802,033 B2 | 10/2017 | Hibner et al. |
| 9,804,618 B2 | 10/2017 | Leimbach et al. |
| D803,234 S | 11/2017 | Day et al. |
| D803,235 S | 11/2017 | Markson et al. |
| D803,850 S | 11/2017 | Chang et al. |
| 9,808,244 B2 | 11/2017 | Leimbach et al. |
| 9,808,246 B2 | 11/2017 | Shelton, IV et al. |
| 9,808,247 B2 | 11/2017 | Shelton, IV et al. |
| 9,808,248 B2 | 11/2017 | Hoffman |
| 9,808,249 B2 | 11/2017 | Shelton, IV |
| 9,814,460 B2 | 11/2017 | Kimsey et al. |
| 9,814,462 B2 | 11/2017 | Woodard, Jr. et al. |
| 9,814,463 B2 | 11/2017 | Williams et al. |
| 9,814,530 B2 | 11/2017 | Weir et al. |
| 9,814,561 B2 | 11/2017 | Forsell |
| 9,815,118 B1 | 11/2017 | Schmitt et al. |
| 9,820,445 B2 | 11/2017 | Simpson et al. |
| 9,820,737 B2 | 11/2017 | Beardsley et al. |
| 9,820,738 B2 | 11/2017 | Lytle, IV et al. |
| 9,820,741 B2 | 11/2017 | Kostrzewski |
| 9,820,768 B2 | 11/2017 | Gee et al. |
| 9,825,455 B2 | 11/2017 | Sandhu et al. |
| 9,826,976 B2 | 11/2017 | Parihar et al. |
| 9,826,977 B2 | 11/2017 | Leimbach et al. |
| 9,826,978 B2 | 11/2017 | Shelton, IV et al. |
| 9,829,698 B2 | 11/2017 | Haraguchi et al. |
| D806,108 S | 12/2017 | Day |
| 9,833,235 B2 | 12/2017 | Penna et al. |
| 9,833,236 B2 | 12/2017 | Shelton, IV et al. |
| 9,833,238 B2 | 12/2017 | Baxter, III et al. |
| 9,833,239 B2 | 12/2017 | Yates et al. |
| 9,833,241 B2 | 12/2017 | Huitema et al. |
| 9,833,242 B2 | 12/2017 | Baxter, III et al. |
| 9,839,420 B2 | 12/2017 | Shelton, IV et al. |
| 9,839,421 B2 | 12/2017 | Zerkle et al. |
| 9,839,422 B2 | 12/2017 | Schellin et al. |
| 9,839,423 B2 | 12/2017 | Vendely et al. |
| 9,839,427 B2 | 12/2017 | Swayze et al. |
| 9,839,428 B2 | 12/2017 | Baxter, III et al. |
| 9,839,429 B2 | 12/2017 | Weisenburgh, II et al. |
| 9,839,480 B2 | 12/2017 | Pribanic et al. |
| 9,839,481 B2 | 12/2017 | Blumenkranz et al. |
| 9,844,368 B2 | 12/2017 | Boudreaux et al. |
| 9,844,369 B2 | 12/2017 | Huitema et al. |
| 9,844,372 B2 | 12/2017 | Shelton, IV et al. |
| 9,844,373 B2 | 12/2017 | Swayze et al. |
| 9,844,374 B2 | 12/2017 | Lytle, IV et al. |
| 9,844,375 B2 | 12/2017 | Overmyer et al. |
| 9,844,376 B2 | 12/2017 | Baxter, III et al. |
| 9,844,379 B2 | 12/2017 | Shelton, IV et al. |
| 9,848,871 B2 | 12/2017 | Harris et al. |
| 9,848,873 B2 | 12/2017 | Shelton, IV |
| 9,848,875 B2 | 12/2017 | Aronhalt et al. |
| 9,848,877 B2 | 12/2017 | Shelton, IV et al. |

(56) References Cited

U.S. PATENT DOCUMENTS

| | | |
|---|---|---|
| 9,850,994 B2 | 12/2017 | Schena |
| D808,989 S | 1/2018 | Ayvazian et al. |
| 9,855,039 B2 | 1/2018 | Racenet et al. |
| 9,855,040 B2 | 1/2018 | Kostrzewski |
| 9,855,662 B2 | 1/2018 | Ruiz Morales et al. |
| 9,861,261 B2 | 1/2018 | Shahinian |
| 9,861,359 B2 | 1/2018 | Shelton, IV et al. |
| 9,861,361 B2 | 1/2018 | Aronhalt et al. |
| 9,861,362 B2 | 1/2018 | Whitman et al. |
| 9,861,366 B2 | 1/2018 | Aranyi |
| 9,861,382 B2 | 1/2018 | Smith et al. |
| 9,861,446 B2 | 1/2018 | Lang |
| 9,867,612 B2 | 1/2018 | Parihar et al. |
| 9,867,613 B2 | 1/2018 | Marczyk et al. |
| 9,867,615 B2 | 1/2018 | Fanelli et al. |
| 9,867,617 B2 | 1/2018 | Ma |
| 9,867,618 B2 | 1/2018 | Hall et al. |
| 9,867,620 B2 | 1/2018 | Fischvogt et al. |
| 9,868,198 B2 | 1/2018 | Nicholas et al. |
| 9,872,682 B2 | 1/2018 | Hess et al. |
| 9,872,683 B2 | 1/2018 | Hopkins et al. |
| 9,872,684 B2 | 1/2018 | Hall et al. |
| 9,872,722 B2 | 1/2018 | Lech |
| 9,877,721 B2 | 1/2018 | Schellin et al. |
| 9,877,722 B2 | 1/2018 | Schellin et al. |
| 9,877,723 B2 | 1/2018 | Hall et al. |
| 9,877,776 B2 | 1/2018 | Boudreaux |
| D810,099 S | 2/2018 | Riedel |
| 9,883,843 B2 | 2/2018 | Garlow |
| 9,883,860 B2 | 2/2018 | Leimbach |
| 9,883,861 B2 | 2/2018 | Shelton, IV et al. |
| 9,884,456 B2 | 2/2018 | Schellin et al. |
| 9,888,914 B2 | 2/2018 | Martin et al. |
| 9,888,919 B2 | 2/2018 | Leimbach et al. |
| 9,888,921 B2 | 2/2018 | Williams et al. |
| 9,888,924 B2 | 2/2018 | Ebersole et al. |
| 9,889,230 B2 | 2/2018 | Bennett et al. |
| 9,895,147 B2 | 2/2018 | Shelton, IV |
| 9,895,148 B2 | 2/2018 | Shelton, IV et al. |
| 9,895,813 B2 | 2/2018 | Blumenkranz et al. |
| 9,901,339 B2 | 2/2018 | Farascioni |
| 9,901,341 B2 | 2/2018 | Kostrzewski |
| 9,901,342 B2 | 2/2018 | Shelton, IV et al. |
| 9,901,344 B2 | 2/2018 | Moore et al. |
| 9,901,345 B2 | 2/2018 | Moore et al. |
| 9,901,346 B2 | 2/2018 | Moore et al. |
| 9,901,406 B2 | 2/2018 | State et al. |
| 9,901,412 B2 | 2/2018 | Lathrop et al. |
| D813,899 S | 3/2018 | Erant et al. |
| 9,907,456 B2 | 3/2018 | Miyoshi |
| 9,907,552 B2 | 3/2018 | Measamer et al. |
| 9,907,553 B2 | 3/2018 | Cole et al. |
| 9,907,600 B2 | 3/2018 | Stulen et al. |
| 9,907,620 B2 | 3/2018 | Shelton, IV et al. |
| 9,913,641 B2 | 3/2018 | Takemoto et al. |
| 9,913,642 B2 | 3/2018 | Leimbach et al. |
| 9,913,644 B2 | 3/2018 | McCuen |
| 9,913,646 B2 | 3/2018 | Shelton, IV |
| 9,913,647 B2 | 3/2018 | Weisenburgh, II et al. |
| 9,913,648 B2 | 3/2018 | Shelton, IV et al. |
| 9,913,694 B2 | 3/2018 | Brisson |
| 9,913,733 B2 | 3/2018 | Piron et al. |
| 9,918,704 B2 | 3/2018 | Shelton, IV et al. |
| 9,918,714 B2 | 3/2018 | Gibbons, Jr. |
| 9,918,715 B2 | 3/2018 | Menn |
| 9,918,716 B2 | 3/2018 | Baxter, III et al. |
| 9,918,717 B2 | 3/2018 | Czernik |
| 9,918,730 B2 | 3/2018 | Trees et al. |
| 9,924,941 B2 | 3/2018 | Burbank |
| 9,924,942 B2 | 3/2018 | Swayze et al. |
| 9,924,943 B2 | 3/2018 | Mohan Pinjala et al. |
| 9,924,944 B2 | 3/2018 | Shelton, IV et al. |
| 9,924,945 B2 | 3/2018 | Zheng et al. |
| 9,924,946 B2 | 3/2018 | Vendely et al. |
| 9,924,947 B2 | 3/2018 | Shelton, IV et al. |
| 9,924,961 B2 | 3/2018 | Shelton, IV et al. |
| 9,931,106 B2 | 4/2018 | Au et al. |
| 9,931,116 B2 | 4/2018 | Racenet et al. |
| 9,931,117 B2 | 4/2018 | Hathaway et al. |
| 9,931,118 B2 | 4/2018 | Shelton, IV et al. |
| 9,931,120 B2 | 4/2018 | Chen et al. |
| 9,936,949 B2 | 4/2018 | Measamer et al. |
| 9,936,950 B2 | 4/2018 | Shelton, IV et al. |
| 9,936,951 B2 | 4/2018 | Hufnagel et al. |
| 9,936,952 B2 | 4/2018 | Demmy |
| 9,936,954 B2 | 4/2018 | Shelton, IV et al. |
| 9,937,626 B2 | 4/2018 | Rockrohr |
| 9,943,309 B2 | 4/2018 | Shelton, IV et al. |
| 9,943,310 B2 | 4/2018 | Harris et al. |
| 9,943,312 B2 | 4/2018 | Posada et al. |
| 9,949,754 B2 | 4/2018 | Newhauser et al. |
| 9,953,193 B2 | 4/2018 | Butler et al. |
| D819,072 S | 5/2018 | Clediere |
| 9,955,954 B2 | 5/2018 | Destoumieux et al. |
| 9,955,965 B2 | 5/2018 | Chen et al. |
| 9,955,966 B2 | 5/2018 | Zergiebel |
| 9,956,677 B2 | 5/2018 | Baskar et al. |
| 9,962,129 B2 | 5/2018 | Jerebko et al. |
| 9,962,157 B2 | 5/2018 | Sapre |
| 9,962,158 B2 | 5/2018 | Hall et al. |
| 9,962,159 B2 | 5/2018 | Heinrich et al. |
| 9,962,161 B2 | 5/2018 | Scheib et al. |
| 9,968,354 B2 | 5/2018 | Shelton, IV et al. |
| 9,968,355 B2 | 5/2018 | Shelton, IV et al. |
| 9,968,356 B2 | 5/2018 | Shelton, IV et al. |
| 9,968,397 B2 | 5/2018 | Taylor et al. |
| 9,974,529 B2 | 5/2018 | Shelton, IV et al. |
| 9,974,538 B2 | 5/2018 | Baxter, III et al. |
| 9,974,539 B2 | 5/2018 | Yates et al. |
| 9,974,541 B2 | 5/2018 | Calderoni |
| 9,974,542 B2 | 5/2018 | Hodgkinson |
| 9,980,713 B2 | 5/2018 | Aronhalt et al. |
| 9,980,724 B2 | 5/2018 | Farascioni et al. |
| 9,980,729 B2 | 5/2018 | Moore et al. |
| 9,980,769 B2 | 5/2018 | Trees et al. |
| D819,680 S | 6/2018 | Nguyen |
| D819,682 S | 6/2018 | Howard et al. |
| D819,684 S | 6/2018 | Dart |
| D820,307 S | 6/2018 | Jian et al. |
| D820,867 S | 6/2018 | Dickens et al. |
| 9,987,000 B2 | 6/2018 | Shelton, IV et al. |
| 9,987,003 B2 | 6/2018 | Timm et al. |
| 9,987,006 B2 | 6/2018 | Morgan et al. |
| 9,987,008 B2 | 6/2018 | Scirica et al. |
| 9,987,095 B2 | 6/2018 | Chowaniec et al. |
| 9,987,097 B2 | 6/2018 | van der Weide et al. |
| 9,987,099 B2 | 6/2018 | Chen et al. |
| 9,993,248 B2 | 6/2018 | Shelton, IV et al. |
| 9,993,258 B2 | 6/2018 | Shelton, IV et al. |
| 9,993,284 B2 | 6/2018 | Boudreaux |
| 9,999,408 B2 | 6/2018 | Boudreaux et al. |
| 9,999,423 B2 | 6/2018 | Schuckmann et al. |
| 9,999,426 B2 | 6/2018 | Moore et al. |
| 9,999,431 B2 | 6/2018 | Shelton, IV et al. |
| 9,999,472 B2 | 6/2018 | Weir et al. |
| 10,004,497 B2 | 6/2018 | Overmyer et al. |
| 10,004,498 B2 | 6/2018 | Morgan et al. |
| 10,004,500 B2 | 6/2018 | Shelton, IV et al. |
| 10,004,501 B2 | 6/2018 | Shelton, IV et al. |
| 10,004,505 B2 | 6/2018 | Moore et al. |
| 10,004,506 B2 | 6/2018 | Shelton, IV et al. |
| D822,206 S | 7/2018 | Shelton, IV et al. |
| 10,010,322 B2 | 7/2018 | Shelton, IV et al. |
| 10,010,324 B2 | 7/2018 | Huitema et al. |
| 10,010,395 B2 | 7/2018 | Puckett et al. |
| 10,013,049 B2 | 7/2018 | Leimbach et al. |
| 10,016,199 B2 | 7/2018 | Baber et al. |
| 10,016,656 B2 | 7/2018 | Devor et al. |
| 10,022,120 B2 | 7/2018 | Martin et al. |
| 10,022,123 B2 | 7/2018 | Williams et al. |
| 10,022,125 B2 | 7/2018 | (Prommersberger) Stopek et al. |
| 10,024,407 B2 | 7/2018 | Aranyi et al. |
| 10,028,742 B2 | 7/2018 | Shelton, IV et al. |
| 10,028,743 B2 | 7/2018 | Shelton, IV et al. |

(56) References Cited

U.S. PATENT DOCUMENTS

| | | |
|---|---|---|
| 10,028,744 B2 | 7/2018 | Shelton, IV et al. |
| 10,028,761 B2 | 7/2018 | Leimbach et al. |
| 10,029,108 B2 | 7/2018 | Powers et al. |
| 10,029,125 B2 | 7/2018 | Shapiro et al. |
| 10,034,344 B2 | 7/2018 | Yoshida |
| 10,034,668 B2 | 7/2018 | Ebner |
| D826,405 S | 8/2018 | Shelton, IV et al. |
| 10,039,440 B2 | 8/2018 | Fenech et al. |
| 10,039,529 B2 | 8/2018 | Kerr et al. |
| 10,039,532 B2 | 8/2018 | Srinivas et al. |
| 10,039,545 B2 | 8/2018 | Sadowski et al. |
| 10,041,822 B2 | 8/2018 | Zemlok |
| 10,045,769 B2 | 8/2018 | Aronhalt et al. |
| 10,045,776 B2 | 8/2018 | Shelton, IV et al. |
| 10,045,778 B2 | 8/2018 | Yates et al. |
| 10,045,779 B2 | 8/2018 | Savage et al. |
| 10,045,781 B2 | 8/2018 | Cropper et al. |
| 10,045,782 B2 | 8/2018 | Murthy Aravalli |
| 10,045,869 B2 | 8/2018 | Forsell |
| 10,052,044 B2 | 8/2018 | Shelton, IV et al. |
| 10,052,099 B2 | 8/2018 | Morgan et al. |
| 10,052,100 B2 | 8/2018 | Morgan et al. |
| 10,052,102 B2 | 8/2018 | Baxter, III et al. |
| 10,052,104 B2 | 8/2018 | Shelton, IV et al. |
| 10,052,164 B2 | 8/2018 | Overmyer |
| 10,058,317 B2 | 8/2018 | Fan et al. |
| 10,058,327 B2 | 8/2018 | Weisenburgh, II et al. |
| 10,058,373 B2 | 8/2018 | Takashino et al. |
| 10,058,395 B2 | 8/2018 | Devengenzo et al. |
| 10,058,963 B2 | 8/2018 | Shelton, IV et al. |
| 10,064,620 B2 | 9/2018 | Gettinger et al. |
| 10,064,621 B2 | 9/2018 | Kerr et al. |
| 10,064,622 B2 | 9/2018 | Murthy Aravalli |
| 10,064,624 B2 | 9/2018 | Shelton, IV et al. |
| 10,064,639 B2 | 9/2018 | Ishida et al. |
| 10,064,649 B2 | 9/2018 | Golebieski et al. |
| 10,064,688 B2 | 9/2018 | Shelton, IV et al. |
| 10,070,861 B2 | 9/2018 | Spivey et al. |
| 10,070,863 B2 | 9/2018 | Swayze et al. |
| 10,071,452 B2 | 9/2018 | Shelton, IV et al. |
| 10,076,325 B2 | 9/2018 | Huang et al. |
| 10,076,326 B2 | 9/2018 | Yates et al. |
| 10,076,340 B2 | 9/2018 | Belagali et al. |
| 10,080,552 B2 | 9/2018 | Nicholas et al. |
| D830,550 S | 10/2018 | Miller et al. |
| D831,209 S | 10/2018 | Huitema et al. |
| D831,676 S | 10/2018 | Park et al. |
| D832,301 S | 10/2018 | Smith |
| 10,085,624 B2 | 10/2018 | Isoda et al. |
| 10,085,643 B2 | 10/2018 | Bandic et al. |
| 10,085,728 B2 | 10/2018 | Jogasaki et al. |
| 10,085,746 B2 | 10/2018 | Fischvogt |
| 10,085,748 B2 | 10/2018 | Morgan et al. |
| 10,085,749 B2 | 10/2018 | Cappola et al. |
| 10,085,750 B2 | 10/2018 | Zergiebel et al. |
| 10,085,751 B2 | 10/2018 | Overmyer et al. |
| 10,085,754 B2 | 10/2018 | Sniffin et al. |
| 10,085,806 B2 | 10/2018 | Hagn et al. |
| 10,092,290 B2 | 10/2018 | Yigit et al. |
| 10,092,292 B2 | 10/2018 | Boudreaux et al. |
| 10,098,635 B2 | 10/2018 | Burbank |
| 10,098,636 B2 | 10/2018 | Shelton, IV et al. |
| 10,098,640 B2 | 10/2018 | Bertolero et al. |
| 10,098,642 B2 | 10/2018 | Baxter, III et al. |
| 10,099,303 B2 | 10/2018 | Yoshida et al. |
| 10,101,861 B2 | 10/2018 | Kiyoto |
| 10,105,126 B2 | 10/2018 | Sauer |
| 10,105,128 B2 | 10/2018 | Cooper et al. |
| 10,105,136 B2 | 10/2018 | Yates et al. |
| 10,105,139 B2 | 10/2018 | Yates et al. |
| 10,105,140 B2 | 10/2018 | Malinouskas et al. |
| 10,105,142 B2 | 10/2018 | Baxter, III et al. |
| 10,105,149 B2 | 10/2018 | Haider et al. |
| 10,106,932 B2 | 10/2018 | Anderson et al. |
| 10,111,657 B2 | 10/2018 | McCuen |
| 10,111,658 B2 | 10/2018 | Chowaniec et al. |
| 10,111,660 B2 | 10/2018 | Hemmann |
| 10,111,665 B2 | 10/2018 | Aranyi et al. |
| 10,111,679 B2 | 10/2018 | Baber et al. |
| 10,111,698 B2 | 10/2018 | Scheib et al. |
| 10,111,702 B2 | 10/2018 | Kostrzewski |
| D833,608 S | 11/2018 | Miller et al. |
| 10,117,649 B2 | 11/2018 | Baxter et al. |
| 10,117,650 B2 | 11/2018 | Nicholas et al. |
| 10,117,652 B2 | 11/2018 | Schmid et al. |
| 10,117,653 B2 | 11/2018 | Leimbach et al. |
| 10,117,654 B2 | 11/2018 | Ingmanson et al. |
| 10,123,798 B2 | 11/2018 | Baxter, III et al. |
| 10,123,845 B2 | 11/2018 | Yeung |
| 10,124,493 B2 | 11/2018 | Rothfuss et al. |
| 10,130,352 B2 | 11/2018 | Widenhouse et al. |
| 10,130,359 B2 | 11/2018 | Hess et al. |
| 10,130,360 B2 | 11/2018 | Olson et al. |
| 10,130,361 B2 | 11/2018 | Yates et al. |
| 10,130,363 B2 | 11/2018 | Huitema et al. |
| 10,130,366 B2 | 11/2018 | Shelton, IV et al. |
| 10,130,367 B2 | 11/2018 | Cappola et al. |
| 10,130,382 B2 | 11/2018 | Gladstone |
| 10,130,738 B2 | 11/2018 | Shelton, IV et al. |
| 10,130,830 B2 | 11/2018 | Miret Carceller et al. |
| 10,133,248 B2 | 11/2018 | Fitzsimmons et al. |
| 10,135,242 B2 | 11/2018 | Baber et al. |
| 10,136,879 B2 | 11/2018 | Ross et al. |
| 10,136,887 B2 | 11/2018 | Shelton, IV et al. |
| 10,136,889 B2 | 11/2018 | Shelton, IV et al. |
| 10,136,890 B2 | 11/2018 | Shelton, IV et al. |
| 10,136,891 B2 | 11/2018 | Shelton, IV et al. |
| D835,659 S | 12/2018 | Anzures et al. |
| D836,124 S | 12/2018 | Fan |
| 10,143,474 B2 | 12/2018 | Bucciaglia et al. |
| 10,149,679 B2 | 12/2018 | Shelton, IV et al. |
| 10,149,680 B2 | 12/2018 | Parihar et al. |
| 10,149,682 B2 | 12/2018 | Shelton, IV et al. |
| 10,149,683 B2 | 12/2018 | Smith et al. |
| 10,149,712 B2 | 12/2018 | Manwaring et al. |
| 10,152,789 B2 | 12/2018 | Carnes et al. |
| 10,154,841 B2 | 12/2018 | Weaner et al. |
| 10,159,481 B2 | 12/2018 | Whitman et al. |
| 10,159,482 B2 | 12/2018 | Swayze et al. |
| 10,159,483 B2 | 12/2018 | Beckman et al. |
| 10,159,506 B2 | 12/2018 | Boudreaux et al. |
| 10,161,816 B2 | 12/2018 | Jackson et al. |
| 10,163,065 B1 | 12/2018 | Koski et al. |
| 10,163,589 B2 | 12/2018 | Zergiebel et al. |
| 10,164,466 B2 | 12/2018 | Calderoni |
| D837,244 S | 1/2019 | Kuo et al. |
| D837,245 S | 1/2019 | Kuo et al. |
| 10,166,023 B2 | 1/2019 | Vendely et al. |
| 10,166,025 B2 | 1/2019 | Leimbach et al. |
| 10,166,026 B2 | 1/2019 | Shelton, IV et al. |
| 10,172,611 B2 | 1/2019 | Shelton, IV et al. |
| 10,172,615 B2 | 1/2019 | Marczyk et al. |
| 10,172,616 B2 | 1/2019 | Murray et al. |
| 10,172,617 B2 | 1/2019 | Shelton, IV et al. |
| 10,172,618 B2 | 1/2019 | Shelton, IV et al. |
| 10,172,619 B2 | 1/2019 | Harris et al. |
| 10,172,620 B2 | 1/2019 | Harris et al. |
| 10,172,636 B2 | 1/2019 | Stulen et al. |
| 10,172,669 B2 | 1/2019 | Felder et al. |
| 10,175,127 B2 | 1/2019 | Collins et al. |
| 10,178,992 B2 | 1/2019 | Wise et al. |
| 10,180,463 B2 | 1/2019 | Beckman et al. |
| 10,182,813 B2 | 1/2019 | Leimbach et al. |
| 10,182,815 B2 | 1/2019 | Williams et al. |
| 10,182,816 B2 | 1/2019 | Shelton, IV et al. |
| 10,182,818 B2 | 1/2019 | Hensel et al. |
| 10,182,819 B2 | 1/2019 | Shelton, IV |
| 10,182,868 B2 | 1/2019 | Meier et al. |
| 10,188,385 B2 | 1/2019 | Kerr et al. |
| 10,188,389 B2 | 1/2019 | Vendely et al. |
| 10,188,393 B2 | 1/2019 | Smith et al. |
| 10,188,394 B2 | 1/2019 | Shelton, IV et al. |
| 10,190,888 B2 | 1/2019 | Hryb et al. |
| D839,900 S | 2/2019 | Gan |

(56) References Cited

U.S. PATENT DOCUMENTS

| | | |
|---|---|---|
| D841,667 S | 2/2019 | Coren |
| 10,194,801 B2 | 2/2019 | Elhawary et al. |
| 10,194,904 B2 | 2/2019 | Viola et al. |
| 10,194,907 B2 | 2/2019 | Marczyk et al. |
| 10,194,908 B2 | 2/2019 | Duque et al. |
| 10,194,910 B2 | 2/2019 | Shelton, IV et al. |
| 10,194,912 B2 | 2/2019 | Scheib et al. |
| 10,194,913 B2 | 2/2019 | Nalagatla et al. |
| 10,194,976 B2 | 2/2019 | Boudreaux |
| 10,194,992 B2 | 2/2019 | Robinson |
| 10,201,348 B2 | 2/2019 | Scheib et al. |
| 10,201,349 B2 | 2/2019 | Leimbach et al. |
| 10,201,363 B2 | 2/2019 | Shelton, IV |
| 10,201,364 B2 | 2/2019 | Leimbach et al. |
| 10,201,365 B2 | 2/2019 | Boudreaux et al. |
| 10,201,381 B2 | 2/2019 | Zergiebel et al. |
| 10,206,605 B2 | 2/2019 | Shelton, IV et al. |
| 10,206,676 B2 | 2/2019 | Shelton, IV |
| 10,206,677 B2 | 2/2019 | Harris et al. |
| 10,206,678 B2 | 2/2019 | Shelton, IV et al. |
| 10,206,748 B2 | 2/2019 | Burbank |
| 10,210,244 B1 | 2/2019 | Branavan et al. |
| 10,211,586 B2 | 2/2019 | Adams et al. |
| 10,213,198 B2 | 2/2019 | Aronhalt et al. |
| 10,213,201 B2 | 2/2019 | Shelton, IV et al. |
| 10,213,202 B2 | 2/2019 | Flanagan et al. |
| 10,213,203 B2 | 2/2019 | Swayze et al. |
| 10,213,204 B2 | 2/2019 | Aranyi et al. |
| 10,213,262 B2 | 2/2019 | Shelton, IV et al. |
| D842,328 S | 3/2019 | Jian et al. |
| 10,219,811 B2 | 3/2019 | Haider et al. |
| 10,219,832 B2 | 3/2019 | Bagwell et al. |
| 10,220,522 B2 | 3/2019 | Rockrohr |
| 10,226,239 B2 | 3/2019 | Nicholas et al. |
| 10,226,249 B2 | 3/2019 | Jaworek et al. |
| 10,226,250 B2 | 3/2019 | Beckman et al. |
| 10,226,251 B2 | 3/2019 | Scheib et al. |
| 10,226,274 B2 | 3/2019 | Worrell et al. |
| 10,231,634 B2 | 3/2019 | Zand et al. |
| 10,231,653 B2 | 3/2019 | Bohm et al. |
| 10,231,734 B2 | 3/2019 | Thompson et al. |
| 10,231,794 B2 | 3/2019 | Shelton, IV et al. |
| 10,238,385 B2 | 3/2019 | Yates et al. |
| 10,238,386 B2 | 3/2019 | Overmyer et al. |
| 10,238,387 B2 | 3/2019 | Yates et al. |
| 10,238,389 B2 | 3/2019 | Yates et al. |
| 10,238,390 B2 | 3/2019 | Harris et al. |
| 10,238,391 B2 | 3/2019 | Leimbach et al. |
| D844,666 S | 4/2019 | Espeleta et al. |
| D844,667 S | 4/2019 | Espeleta et al. |
| D845,342 S | 4/2019 | Espeleta et al. |
| D847,199 S | 4/2019 | Whitmore |
| 10,244,991 B2 | 4/2019 | Shademan et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,032 B2 | 4/2019 | Shelton, IV |
| 10,245,033 B2 | 4/2019 | Overmyer et al. |
| 10,245,034 B2 | 4/2019 | Shelton, IV et al. |
| 10,245,035 B2 | 4/2019 | Swayze et al. |
| 10,245,038 B2 | 4/2019 | Hopkins et al. |
| 10,245,058 B2 | 4/2019 | Omori et al. |
| 10,251,648 B2 | 4/2019 | Harris et al. |
| 10,251,649 B2 | 4/2019 | Schellin et al. |
| 10,251,725 B2 | 4/2019 | Valentine et al. |
| 10,258,322 B2 | 4/2019 | Fanton et al. |
| 10,258,330 B2 | 4/2019 | Shelton, IV et al. |
| 10,258,331 B2 | 4/2019 | Shelton, IV et al. |
| 10,258,332 B2 | 4/2019 | Schmid et al. |
| 10,258,333 B2 | 4/2019 | Shelton, IV et al. |
| 10,258,336 B2 | 4/2019 | Baxter, III et al. |
| 10,258,418 B2 | 4/2019 | Shelton, IV et al. |
| 10,264,797 B2 | 4/2019 | Zhang et al. |
| 10,265,065 B2 | 4/2019 | Shelton, IV et al. |
| 10,265,067 B2 | 4/2019 | Yates et al. |
| 10,265,068 B2 | 4/2019 | Harris et al. |
| 10,265,072 B2 | 4/2019 | Shelton, IV et al. |
| 10,265,073 B2 | 4/2019 | Scheib et al. |
| 10,265,074 B2 | 4/2019 | Shelton, IV et al. |
| 10,265,090 B2 | 4/2019 | Ingmanson et al. |
| 10,271,840 B2 | 4/2019 | Sapre |
| 10,271,844 B2 | 4/2019 | Valentine et al. |
| 10,271,845 B2 | 4/2019 | Shelton, IV |
| 10,271,846 B2 | 4/2019 | Shelton, IV et al. |
| 10,271,847 B2 | 4/2019 | Racenet et al. |
| 10,271,849 B2 | 4/2019 | Vendely et al. |
| 10,271,851 B2 | 4/2019 | Shelton, IV et al. |
| D847,989 S | 5/2019 | Shelton, IV et al. |
| D848,473 S | 5/2019 | Zhu et al. |
| D849,046 S | 5/2019 | Kuo et al. |
| 10,278,696 B2 | 5/2019 | Gurumurthy et al. |
| 10,278,697 B2 | 5/2019 | Shelton, IV et al. |
| 10,278,702 B2 | 5/2019 | Shelton, IV et al. |
| 10,278,703 B2 | 5/2019 | Nativ et al. |
| 10,278,707 B2 | 5/2019 | Thompson et al. |
| 10,278,722 B2 | 5/2019 | Shelton, IV et al. |
| 10,278,780 B2 | 5/2019 | Shelton, IV |
| 10,285,694 B2 | 5/2019 | Viola et al. |
| 10,285,695 B2 | 5/2019 | Jaworek et al. |
| 10,285,699 B2 | 5/2019 | Vendely et al. |
| 10,285,700 B2 | 5/2019 | Scheib |
| 10,285,705 B2 | 5/2019 | Shelton, IV et al. |
| 10,292,701 B2 | 5/2019 | Scheib et al. |
| 10,292,704 B2 | 5/2019 | Harris et al. |
| 10,292,707 B2 | 5/2019 | Shelton, IV et al. |
| 10,293,100 B2 | 5/2019 | Shelton, IV et al. |
| 10,293,553 B2 | 5/2019 | Racenet et al. |
| 10,299,787 B2 | 5/2019 | Shelton, IV |
| 10,299,788 B2 | 5/2019 | Heinrich et al. |
| 10,299,789 B2 | 5/2019 | Marczyk et al. |
| 10,299,790 B2 | 5/2019 | Beardsley |
| 10,299,792 B2 | 5/2019 | Huitema et al. |
| 10,299,817 B2 | 5/2019 | Shelton, IV et al. |
| 10,299,818 B2 | 5/2019 | Riva |
| 10,299,878 B2 | 5/2019 | Shelton, IV et al. |
| 10,303,851 B2 | 5/2019 | Nguyen et al. |
| D850,617 S | 6/2019 | Shelton, IV et al. |
| D851,676 S | 6/2019 | Foss et al. |
| D851,762 S | 6/2019 | Shelton, IV et al. |
| 10,307,159 B2 | 6/2019 | Harris et al. |
| 10,307,160 B2 | 6/2019 | Vendely et al. |
| 10,307,161 B2 | 6/2019 | Jankowski |
| 10,307,163 B2 | 6/2019 | Moore et al. |
| 10,307,170 B2 | 6/2019 | Parfett et al. |
| 10,307,202 B2 | 6/2019 | Smith et al. |
| 10,314,559 B2 | 6/2019 | Razzaque et al. |
| 10,314,577 B2 | 6/2019 | Laurent et al. |
| 10,314,578 B2 | 6/2019 | Leimbach et al. |
| 10,314,580 B2 | 6/2019 | Scheib et al. |
| 10,314,582 B2 | 6/2019 | Shelton, IV et al. |
| 10,314,584 B2 | 6/2019 | Scirica et al. |
| 10,314,587 B2 | 6/2019 | Harris et al. |
| 10,314,588 B2 | 6/2019 | Turner et al. |
| 10,314,589 B2 | 6/2019 | Shelton, IV et al. |
| 10,314,590 B2 | 6/2019 | Shelton, IV et al. |
| 10,315,566 B2 | 6/2019 | Choi et al. |
| 10,321,907 B2 | 6/2019 | Shelton, IV et al. |
| 10,321,909 B2 | 6/2019 | Shelton, IV et al. |
| 10,321,927 B2 | 6/2019 | Hinman |
| 10,327,743 B2 | 6/2019 | St. Goar et al. |
| 10,327,764 B2 | 6/2019 | Harris et al. |
| 10,327,765 B2 | 6/2019 | Timm et al. |
| 10,327,767 B2 | 6/2019 | Shelton, IV et al. |
| 10,327,769 B2 | 6/2019 | Overmyer et al. |
| 10,327,776 B2 | 6/2019 | Harris et al. |
| 10,327,777 B2 | 6/2019 | Harris et al. |
| D854,032 S | 7/2019 | Jones et al. |
| D854,151 S | 7/2019 | Shelton, IV et al. |
| 10,335,144 B2 | 7/2019 | Shelton, IV et al. |
| 10,335,145 B2 | 7/2019 | Harris et al. |
| 10,335,147 B2 | 7/2019 | Rector et al. |
| 10,335,148 B2 | 7/2019 | Shelton, IV et al. |
| 10,335,149 B2 | 7/2019 | Baxter, III et al. |

(56) References Cited

U.S. PATENT DOCUMENTS

| | | |
|---|---|---|
| 10,335,150 B2 | 7/2019 | Shelton, IV |
| 10,335,151 B2 | 7/2019 | Shelton, IV et al. |
| 10,337,148 B2 | 7/2019 | Rouse et al. |
| 10,342,533 B2 | 7/2019 | Shelton, IV et al. |
| 10,342,535 B2 | 7/2019 | Scheib et al. |
| 10,342,541 B2 | 7/2019 | Shelton, IV et al. |
| 10,342,543 B2 | 7/2019 | Shelton, IV et al. |
| 10,342,623 B2 | 7/2019 | Huelman et al. |
| 10,349,937 B2 | 7/2019 | Williams |
| 10,349,939 B2 | 7/2019 | Shelton, IV et al. |
| 10,349,941 B2 | 7/2019 | Marczyk et al. |
| 10,349,963 B2 | 7/2019 | Fiksen et al. |
| 10,350,016 B2 | 7/2019 | Burbank et al. |
| 10,357,246 B2 | 7/2019 | Shelton, IV et al. |
| 10,357,247 B2 | 7/2019 | Shelton, IV et al. |
| 10,357,248 B2 | 7/2019 | Dalessandro et al. |
| 10,357,252 B2 | 7/2019 | Harris et al. |
| 10,363,031 B2 | 7/2019 | Alexander, III et al. |
| 10,363,033 B2 | 7/2019 | Timm et al. |
| 10,363,036 B2 | 7/2019 | Yates et al. |
| 10,363,037 B2 | 7/2019 | Aronhalt et al. |
| D855,634 S | 8/2019 | Kim |
| D856,359 S | 8/2019 | Huang et al. |
| 10,368,838 B2 | 8/2019 | Williams et al. |
| 10,368,861 B2 | 8/2019 | Baxter, III et al. |
| 10,368,863 B2 | 8/2019 | Timm et al. |
| 10,368,864 B2 | 8/2019 | Harris et al. |
| 10,368,865 B2 | 8/2019 | Harris et al. |
| 10,368,867 B2 | 8/2019 | Harris et al. |
| 10,368,892 B2 | 8/2019 | Stulen et al. |
| 10,376,263 B2 | 8/2019 | Morgan et al. |
| 10,383,626 B2 | 8/2019 | Soltz |
| 10,383,628 B2 | 8/2019 | Kang et al. |
| 10,383,629 B2 | 8/2019 | Ross et al. |
| 10,383,630 B2 | 8/2019 | Shelton, IV et al. |
| 10,383,633 B2 | 8/2019 | Shelton, IV et al. |
| 10,383,634 B2 | 8/2019 | Shelton, IV et al. |
| 10,390,823 B2 | 8/2019 | Shelton, IV et al. |
| 10,390,825 B2 | 8/2019 | Shelton, IV et al. |
| 10,390,828 B2 | 8/2019 | Vendely et al. |
| 10,390,829 B2 | 8/2019 | Eckert et al. |
| 10,390,830 B2 | 8/2019 | Schulz |
| 10,390,841 B2 | 8/2019 | Shelton, IV et al. |
| 10,390,897 B2 | 8/2019 | Kostrzewski |
| D860,219 S | 9/2019 | Rasmussen et al. |
| D861,035 S | 9/2019 | Park et al. |
| 10,398,433 B2 | 9/2019 | Boudreaux et al. |
| 10,398,434 B2 | 9/2019 | Shelton, IV et al. |
| 10,398,436 B2 | 9/2019 | Shelton, IV et al. |
| 10,398,460 B2 | 9/2019 | Overmyer |
| 10,404,136 B2 | 9/2019 | Oktavec et al. |
| 10,405,854 B2 | 9/2019 | Schmid et al. |
| 10,405,857 B2 | 9/2019 | Shelton, IV et al. |
| 10,405,859 B2 | 9/2019 | Harris et al. |
| 10,405,863 B2 | 9/2019 | Wise et al. |
| 10,405,914 B2 | 9/2019 | Manwaring et al. |
| 10,405,932 B2 | 9/2019 | Overmyer |
| 10,405,937 B2 | 9/2019 | Black et al. |
| 10,413,155 B2 | 9/2019 | Inoue |
| 10,413,291 B2 | 9/2019 | Worthington et al. |
| 10,413,293 B2 | 9/2019 | Shelton, IV et al. |
| 10,413,294 B2 | 9/2019 | Shelton, IV et al. |
| 10,413,297 B2 | 9/2019 | Harris et al. |
| 10,413,370 B2 | 9/2019 | Yates et al. |
| 10,413,373 B2 | 9/2019 | Yates et al. |
| 10,420,548 B2 | 9/2019 | Whitman et al. |
| 10,420,549 B2 | 9/2019 | Yates et al. |
| 10,420,550 B2 | 9/2019 | Shelton, IV |
| 10,420,551 B2 | 9/2019 | Calderoni |
| 10,420,552 B2 | 9/2019 | Shelton, IV et al. |
| 10,420,553 B2 | 9/2019 | Shelton, IV et al. |
| 10,420,554 B2 | 9/2019 | Collings et al. |
| 10,420,555 B2 | 9/2019 | Shelton, IV et al. |
| 10,420,558 B2 | 9/2019 | Nalagatla et al. |
| 10,420,559 B2 | 9/2019 | Marczyk et al. |
| 10,420,560 B2 | 9/2019 | Shelton, IV et al. |
| 10,420,561 B2 | 9/2019 | Shelton, IV et al. |
| 10,420,577 B2 | 9/2019 | Chowaniec et al. |
| D861,707 S | 10/2019 | Yang |
| D862,518 S | 10/2019 | Niven et al. |
| D863,343 S | 10/2019 | Mazlish et al. |
| D864,388 S | 10/2019 | Barber |
| D865,174 S | 10/2019 | Auld et al. |
| D865,175 S | 10/2019 | Widenhouse et al. |
| 10,426,463 B2 | 10/2019 | Shelton, IV et al. |
| 10,426,466 B2 | 10/2019 | Contini et al. |
| 10,426,467 B2 | 10/2019 | Miller et al. |
| 10,426,468 B2 | 10/2019 | Contini et al. |
| 10,426,469 B2 | 10/2019 | Shelton, IV et al. |
| 10,426,471 B2 | 10/2019 | Shelton, IV et al. |
| 10,426,476 B2 | 10/2019 | Harris et al. |
| 10,426,477 B2 | 10/2019 | Harris et al. |
| 10,426,478 B2 | 10/2019 | Shelton, IV et al. |
| 10,426,481 B2 | 10/2019 | Aronhalt et al. |
| 10,426,555 B2 | 10/2019 | Crowley et al. |
| 10,433,837 B2 | 10/2019 | Worthington et al. |
| 10,433,839 B2 | 10/2019 | Scheib et al. |
| 10,433,840 B2 | 10/2019 | Shelton, IV et al. |
| 10,433,844 B2 | 10/2019 | Shelton, IV et al. |
| 10,433,845 B2 | 10/2019 | Baxter, III et al. |
| 10,433,846 B2 | 10/2019 | Vendely et al. |
| 10,433,849 B2 | 10/2019 | Shelton, IV et al. |
| 10,433,918 B2 | 10/2019 | Shelton, IV et al. |
| 10,441,279 B2 | 10/2019 | Shelton, IV et al. |
| 10,441,280 B2 | 10/2019 | Timm et al. |
| 10,441,281 B2 | 10/2019 | Shelton, IV et al. |
| 10,441,285 B2 | 10/2019 | Shelton, IV et al. |
| 10,441,286 B2 | 10/2019 | Shelton, IV et al. |
| 10,441,345 B2 | 10/2019 | Aldridge et al. |
| 10,441,369 B2 | 10/2019 | Shelton, IV et al. |
| 10,448,948 B2 | 10/2019 | Shelton, IV et al. |
| 10,448,950 B2 | 10/2019 | Shelton, IV et al. |
| 10,448,952 B2 | 10/2019 | Shelton, IV et al. |
| 10,456,122 B2 | 10/2019 | Koltz et al. |
| 10,456,132 B2 | 10/2019 | Gettinger et al. |
| 10,456,133 B2 | 10/2019 | Yates et al. |
| 10,456,137 B2 | 10/2019 | Vendely et al. |
| 10,456,140 B2 | 10/2019 | Shelton, IV et al. |
| D865,796 S | 11/2019 | Xu et al. |
| 10,463,367 B2 | 11/2019 | Kostrzewski et al. |
| 10,463,369 B2 | 11/2019 | Shelton, IV et al. |
| 10,463,370 B2 | 11/2019 | Yates et al. |
| 10,463,371 B2 | 11/2019 | Kostrzewski |
| 10,463,372 B2 | 11/2019 | Shelton, IV et al. |
| 10,463,373 B2 | 11/2019 | Mozdzierz et al. |
| 10,463,382 B2 | 11/2019 | Ingmanson et al. |
| 10,463,383 B2 | 11/2019 | Shelton, IV et al. |
| 10,463,384 B2 | 11/2019 | Shelton, IV et al. |
| 10,470,762 B2 | 11/2019 | Leimbach et al. |
| 10,470,763 B2 | 11/2019 | Yates et al. |
| 10,470,764 B2 | 11/2019 | Baxter, III et al. |
| 10,470,767 B2 | 11/2019 | Gleiman et al. |
| 10,470,768 B2 | 11/2019 | Harris et al. |
| 10,470,769 B2 | 11/2019 | Shelton, IV et al. |
| 10,471,282 B2 | 11/2019 | Kirk et al. |
| 10,471,576 B2 | 11/2019 | Totsu |
| 10,471,607 B2 | 11/2019 | Butt |
| 10,478,181 B2 | 11/2019 | Shelton, IV et al. |
| 10,478,182 B2 | 11/2019 | Taylor |
| 10,478,185 B2 | 11/2019 | Nicholas |
| 10,478,187 B2 | 11/2019 | Shelton, IV et al. |
| 10,478,188 B2 | 11/2019 | Harris et al. |
| 10,478,189 B2 | 11/2019 | Bear et al. |
| 10,478,190 B2 | 11/2019 | Miller et al. |
| 10,478,207 B2 | 11/2019 | Lathrop |
| 10,482,292 B2 | 11/2019 | Clouser et al. |
| 10,485,536 B2 | 11/2019 | Ming et al. |
| 10,485,537 B2 | 11/2019 | Yates et al. |
| 10,485,539 B2 | 11/2019 | Shelton, IV et al. |
| 10,485,541 B2 | 11/2019 | Shelton, IV et al. |
| 10,485,542 B2 | 11/2019 | Shelton, IV et al. |
| 10,485,543 B2 | 11/2019 | Shelton, IV et al. |
| 10,485,546 B2 | 11/2019 | Shelton, IV et al. |
| 10,485,547 B2 | 11/2019 | Shelton, IV et al. |

(56) References Cited

U.S. PATENT DOCUMENTS

| | | |
|---|---|---|
| D869,655 S | 12/2019 | Shelton, IV et al. |
| D870,742 S | 12/2019 | Cornell |
| 10,492,783 B2 | 12/2019 | Shelton, IV et al. |
| 10,492,785 B2 | 12/2019 | Overmyer et al. |
| 10,492,787 B2 | 12/2019 | Smith et al. |
| 10,492,814 B2 | 12/2019 | Snow et al. |
| 10,492,847 B2 | 12/2019 | Godara et al. |
| 10,492,851 B2 | 12/2019 | Hughett, Sr. et al. |
| 10,498,269 B2 | 12/2019 | Zemlok et al. |
| 10,499,890 B2 | 12/2019 | Shelton, IV et al. |
| 10,499,914 B2 | 12/2019 | Huang et al. |
| 10,499,917 B2 | 12/2019 | Scheib et al. |
| 10,499,918 B2 | 12/2019 | Schellin et al. |
| 10,500,000 B2 | 12/2019 | Swayze et al. |
| 10,500,309 B2 | 12/2019 | Shah et al. |
| 10,507,034 B2 | 12/2019 | Timm |
| 10,508,720 B2 | 12/2019 | Nicholas |
| 10,512,461 B2 | 12/2019 | Gupta et al. |
| 10,512,462 B2 | 12/2019 | Felder et al. |
| 10,517,590 B2 | 12/2019 | Giordano et al. |
| 10,517,592 B2 | 12/2019 | Shelton, IV et al. |
| 10,517,594 B2 | 12/2019 | Shelton, IV et al. |
| 10,517,595 B2 | 12/2019 | Hunter et al. |
| 10,517,596 B2 | 12/2019 | Hunter et al. |
| 10,517,599 B2 | 12/2019 | Baxter, III et al. |
| 10,517,682 B2 | 12/2019 | Giordano et al. |
| 10,524,784 B2 | 1/2020 | Kostrzewski |
| 10,524,787 B2 | 1/2020 | Shelton, IV et al. |
| 10,524,788 B2 | 1/2020 | Vendely et al. |
| 10,524,789 B2 | 1/2020 | Swayze et al. |
| 10,524,790 B2 | 1/2020 | Shelton, IV et al. |
| 10,524,795 B2 | 1/2020 | Nalagatla et al. |
| 10,531,874 B2 | 1/2020 | Morgan et al. |
| 10,531,887 B2 | 1/2020 | Shelton, IV et al. |
| 10,537,324 B2 | 1/2020 | Shelton, IV et al. |
| 10,537,325 B2 | 1/2020 | Bakos et al. |
| 10,537,351 B2 | 1/2020 | Shelton, IV et al. |
| 10,542,908 B2 | 1/2020 | Mei et al. |
| 10,542,974 B2 | 1/2020 | Yates et al. |
| 10,542,976 B2 | 1/2020 | Calderon et al. |
| 10,542,978 B2 | 1/2020 | Chowaniec et al. |
| 10,542,979 B2 | 1/2020 | Shelton, IV et al. |
| 10,542,982 B2 | 1/2020 | Beckman et al. |
| 10,542,985 B2 | 1/2020 | Zhan et al. |
| 10,542,988 B2 | 1/2020 | Schellin et al. |
| 10,542,991 B2 | 1/2020 | Shelton, IV et al. |
| 10,548,504 B2 | 2/2020 | Shelton, IV et al. |
| 10,548,593 B2 | 2/2020 | Shelton, IV et al. |
| 10,548,600 B2 | 2/2020 | Shelton, IV et al. |
| 10,548,673 B2 | 2/2020 | Harris et al. |
| 10,561,418 B2 | 2/2020 | Richard et al. |
| 10,561,419 B2 | 2/2020 | Beardsley |
| 10,561,420 B2 | 2/2020 | Harris et al. |
| 10,561,422 B2 | 2/2020 | Schellin et al. |
| 10,561,432 B2 | 2/2020 | Estrella et al. |
| 10,561,474 B2 | 2/2020 | Adams et al. |
| 10,562,160 B2 | 2/2020 | Iwata et al. |
| 10,568,493 B2 | 2/2020 | Blase et al. |
| 10,568,621 B2 | 2/2020 | Shelton, IV et al. |
| 10,568,624 B2 | 2/2020 | Shelton, IV et al. |
| 10,568,625 B2 | 2/2020 | Harris et al. |
| 10,568,626 B2 | 2/2020 | Shelton, IV et al. |
| 10,568,629 B2 | 2/2020 | Shelton, IV et al. |
| 10,568,632 B2 | 2/2020 | Miller et al. |
| 10,568,652 B2 | 2/2020 | Hess et al. |
| 10,569,071 B2 | 2/2020 | Harris et al. |
| D879,808 S | 3/2020 | Harris et al. |
| D879,809 S | 3/2020 | Harris et al. |
| 10,575,868 B2 | 3/2020 | Hall et al. |
| 10,580,320 B2 | 3/2020 | Kamiguchi et al. |
| 10,582,928 B2 | 3/2020 | Hunter et al. |
| 10,588,231 B2 | 3/2020 | Sgroi, Jr. et al. |
| 10,588,623 B2 | 3/2020 | Schmid et al. |
| 10,588,625 B2 | 3/2020 | Weaner et al. |
| 10,588,626 B2 | 3/2020 | Overmyer et al. |
| 10,588,629 B2 | 3/2020 | Malinouskas et al. |
| 10,588,630 B2 | 3/2020 | Shelton, IV et al. |
| 10,588,631 B2 | 3/2020 | Shelton, IV et al. |
| 10,588,632 B2 | 3/2020 | Shelton, IV et al. |
| 10,588,633 B2 | 3/2020 | Shelton, IV et al. |
| 10,595,835 B2 | 3/2020 | Kerr et al. |
| 10,595,862 B2 | 3/2020 | Shelton, IV et al. |
| 10,595,882 B2 | 3/2020 | Parfett et al. |
| 10,595,887 B2 | 3/2020 | Shelton, IV et al. |
| 10,595,929 B2 | 3/2020 | Boudreaux et al. |
| 10,603,036 B2 | 3/2020 | Hunter et al. |
| 10,603,039 B2 | 3/2020 | Vendely et al. |
| 10,603,041 B2 | 3/2020 | Miller et al. |
| 10,603,117 B2 | 3/2020 | Schings et al. |
| 10,603,128 B2 | 3/2020 | Zergiebel et al. |
| 10,610,224 B2 | 4/2020 | Shelton, IV et al. |
| 10,610,236 B2 | 4/2020 | Baril |
| 10,610,313 B2 | 4/2020 | Bailey et al. |
| 10,610,346 B2 | 4/2020 | Schwartz |
| 10,617,411 B2 | 4/2020 | Williams |
| 10,617,412 B2 | 4/2020 | Shelton, IV et al. |
| 10,617,413 B2 | 4/2020 | Shelton, IV et al. |
| 10,617,414 B2 | 4/2020 | Shelton, IV et al. |
| 10,617,416 B2 | 4/2020 | Leimbach et al. |
| 10,617,417 B2 | 4/2020 | Baxter, III et al. |
| 10,617,418 B2 | 4/2020 | Barton et al. |
| 10,617,420 B2 | 4/2020 | Shelton, IV et al. |
| 10,624,616 B2 | 4/2020 | Mukherjee et al. |
| 10,624,630 B2 | 4/2020 | Deville et al. |
| 10,624,633 B2 | 4/2020 | Shelton, IV et al. |
| 10,624,634 B2 | 4/2020 | Shelton, IV et al. |
| 10,624,635 B2 | 4/2020 | Harris et al. |
| 10,624,709 B2 | 4/2020 | Remm |
| 10,624,861 B2 | 4/2020 | Widenhouse et al. |
| 10,625,062 B2 | 4/2020 | Matlock et al. |
| 10,631,857 B2 | 4/2020 | Kostrzewski |
| 10,631,858 B2 | 4/2020 | Burbank |
| 10,631,859 B2 | 4/2020 | Shelton, IV et al. |
| 10,631,860 B2 | 4/2020 | Bakos et al. |
| 10,636,104 B2 | 4/2020 | Mazar et al. |
| 10,639,018 B2 | 5/2020 | Shelton, IV et al. |
| 10,639,034 B2 | 5/2020 | Harris et al. |
| 10,639,035 B2 | 5/2020 | Shelton, IV et al. |
| 10,639,036 B2 | 5/2020 | Yates et al. |
| 10,639,037 B2 | 5/2020 | Shelton, IV et al. |
| 10,639,089 B2 | 5/2020 | Manwaring et al. |
| 10,639,115 B2 | 5/2020 | Shelton, IV et al. |
| 10,645,905 B2 | 5/2020 | Gandola et al. |
| 10,646,220 B2 | 5/2020 | Shelton, IV et al. |
| 10,646,292 B2 | 5/2020 | Solomon et al. |
| 10,653,413 B2 | 5/2020 | Worthington et al. |
| 10,653,417 B2 | 5/2020 | Shelton, IV et al. |
| 10,653,435 B2 | 5/2020 | Shelton, IV et al. |
| 10,660,640 B2 | 5/2020 | Yates et al. |
| 10,667,408 B2 | 5/2020 | Sgroi, Jr. et al. |
| D888,953 S | 6/2020 | Baxter, III et al. |
| 10,667,808 B2 | 6/2020 | Baxter, III et al. |
| 10,667,809 B2 | 6/2020 | Bakos et al. |
| 10,667,810 B2 | 6/2020 | Shelton, IV et al. |
| 10,667,811 B2 | 6/2020 | Harris et al. |
| 10,667,818 B2 | 6/2020 | McLain et al. |
| 10,674,895 B2 | 6/2020 | Yeung et al. |
| 10,675,021 B2 | 6/2020 | Harris et al. |
| 10,675,024 B2 | 6/2020 | Shelton, IV et al. |
| 10,675,025 B2 | 6/2020 | Swayze et al. |
| 10,675,026 B2 | 6/2020 | Harris et al. |
| 10,675,028 B2 | 6/2020 | Shelton, IV et al. |
| 10,675,035 B2 | 6/2020 | Zingman |
| 10,675,102 B2 | 6/2020 | Forgione et al. |
| 10,677,035 B2 | 6/2020 | Balan et al. |
| 10,682,134 B2 | 6/2020 | Shelton, IV et al. |
| 10,682,136 B2 | 6/2020 | Harris et al. |
| 10,682,137 B2 | 6/2020 | Stokes et al. |
| 10,682,138 B2 | 6/2020 | Shelton, IV et al. |
| 10,682,141 B2 | 6/2020 | Moore et al. |
| 10,682,142 B2 | 6/2020 | Shelton, IV et al. |
| 10,687,806 B2 | 6/2020 | Shelton, IV et al. |
| 10,687,809 B2 | 6/2020 | Shelton, IV et al. |
| 10,687,810 B2 | 6/2020 | Shelton, IV et al. |

(56) References Cited

U.S. PATENT DOCUMENTS

| | | |
|---|---|---|
| 10,687,812 B2 | 6/2020 | Shelton, IV et al. |
| 10,687,813 B2 | 6/2020 | Shelton, IV et al. |
| 10,687,817 B2 | 6/2020 | Shelton, IV et al. |
| 10,687,819 B2 | 6/2020 | Stokes et al. |
| 10,687,904 B2 | 6/2020 | Harris et al. |
| 10,695,053 B2 | 6/2020 | Hess et al. |
| 10,695,055 B2 | 6/2020 | Shelton, IV et al. |
| 10,695,057 B2 | 6/2020 | Shelton, IV et al. |
| 10,695,058 B2 | 6/2020 | Lytle, IV et al. |
| 10,695,062 B2 | 6/2020 | Leimbach et al. |
| 10,695,063 B2 | 6/2020 | Morgan et al. |
| 10,695,074 B2 | 6/2020 | Carusillo |
| 10,695,081 B2 | 6/2020 | Shelton, IV et al. |
| 10,695,123 B2 | 6/2020 | Allen, IV |
| 10,695,187 B2 | 6/2020 | Moskowitz et al. |
| D890,784 S | 7/2020 | Shelton, IV et al. |
| 10,702,266 B2 | 7/2020 | Parihar et al. |
| 10,702,267 B2 | 7/2020 | Hess et al. |
| 10,702,270 B2 | 7/2020 | Shelton, IV et al. |
| 10,702,271 B2 | 7/2020 | Aranyi et al. |
| 10,705,660 B2 | 7/2020 | Xiao |
| 10,709,446 B2 | 7/2020 | Harris et al. |
| 10,709,468 B2 | 7/2020 | Shelton, IV et al. |
| 10,709,469 B2 | 7/2020 | Shelton, IV et al. |
| 10,709,496 B2 | 7/2020 | Moua et al. |
| 10,716,563 B2 | 7/2020 | Shelton, IV et al. |
| 10,716,565 B2 | 7/2020 | Shelton, IV et al. |
| 10,716,568 B2 | 7/2020 | Hall et al. |
| 10,716,614 B2 | 7/2020 | Yates et al. |
| 10,717,179 B2 | 7/2020 | Koenig et al. |
| 10,722,232 B2 | 7/2020 | Yates et al. |
| 10,722,233 B2 | 7/2020 | Wellman |
| 10,722,292 B2 | 7/2020 | Arya et al. |
| 10,722,293 B2 | 7/2020 | Arya et al. |
| 10,722,317 B2 | 7/2020 | Ward et al. |
| D893,717 S | 8/2020 | Messerly et al. |
| 10,729,432 B2 | 8/2020 | Shelton, IV et al. |
| 10,729,436 B2 | 8/2020 | Shelton, IV et al. |
| 10,729,443 B2 | 8/2020 | Cabrera et al. |
| 10,729,458 B2 | 8/2020 | Stoddard et al. |
| 10,729,501 B2 | 8/2020 | Leimbach et al. |
| 10,729,509 B2 | 8/2020 | Shelton, IV et al. |
| 10,736,616 B2 | 8/2020 | Scheib et al. |
| 10,736,628 B2 | 8/2020 | Yates et al. |
| 10,736,629 B2 | 8/2020 | Shelton, IV et al. |
| 10,736,630 B2 | 8/2020 | Huang et al. |
| 10,736,633 B2 | 8/2020 | Vendely et al. |
| 10,736,634 B2 | 8/2020 | Shelton, IV et al. |
| 10,736,636 B2 | 8/2020 | Baxter, III et al. |
| 10,736,644 B2 | 8/2020 | Windolf et al. |
| 10,743,849 B2 | 8/2020 | Shelton, IV et al. |
| 10,743,850 B2 | 8/2020 | Hibner et al. |
| 10,743,851 B2 | 8/2020 | Swayze et al. |
| 10,743,868 B2 | 8/2020 | Shelton, IV et al. |
| 10,743,870 B2 | 8/2020 | Hall et al. |
| 10,743,872 B2 | 8/2020 | Leimbach et al. |
| 10,743,873 B2 | 8/2020 | Overmyer et al. |
| 10,743,874 B2 | 8/2020 | Shelton, IV et al. |
| 10,743,875 B2 | 8/2020 | Shelton, IV et al. |
| 10,743,877 B2 | 8/2020 | Shelton, IV et al. |
| 10,743,930 B2 | 8/2020 | Nagtegaal |
| 10,751,048 B2 | 8/2020 | Whitman et al. |
| 10,751,053 B2 | 8/2020 | Harris et al. |
| 10,751,076 B2 | 8/2020 | Laurent et al. |
| 10,751,138 B2 | 8/2020 | Giordano et al. |
| 10,758,229 B2 | 9/2020 | Shelton, IV et al. |
| 10,758,230 B2 | 9/2020 | Shelton, IV et al. |
| 10,758,232 B2 | 9/2020 | Shelton, IV et al. |
| 10,758,233 B2 | 9/2020 | Scheib et al. |
| 10,758,259 B2 | 9/2020 | Demmy et al. |
| 10,765,425 B2 | 9/2020 | Yates et al. |
| 10,765,427 B2 | 9/2020 | Shelton, IV et al. |
| 10,765,429 B2 | 9/2020 | Leimbach et al. |
| 10,765,430 B2 | 9/2020 | Wixey |
| 10,765,432 B2 | 9/2020 | Moore et al. |
| 10,765,442 B2 | 9/2020 | Strobl |
| 10,772,625 B2 | 9/2020 | Shelton, IV et al. |
| 10,772,628 B2 | 9/2020 | Chen et al. |
| 10,772,629 B2 | 9/2020 | Shelton, IV et al. |
| 10,772,630 B2 | 9/2020 | Wixey |
| 10,772,631 B2 | 9/2020 | Zergiebel et al. |
| 10,772,632 B2 | 9/2020 | Kostrzewski |
| 10,772,651 B2 | 9/2020 | Shelton, IV et al. |
| 10,779,818 B2 | 9/2020 | Zemlok et al. |
| 10,779,820 B2 | 9/2020 | Harris et al. |
| 10,779,821 B2 | 9/2020 | Harris et al. |
| 10,779,822 B2 | 9/2020 | Yates et al. |
| 10,779,823 B2 | 9/2020 | Shelton, IV et al. |
| 10,779,824 B2 | 9/2020 | Shelton, IV et al. |
| 10,779,825 B2 | 9/2020 | Shelton, IV et al. |
| 10,779,826 B2 | 9/2020 | Shelton, IV et al. |
| 10,779,903 B2 | 9/2020 | Wise et al. |
| 10,780,539 B2 | 9/2020 | Shelton, IV et al. |
| 10,786,248 B2 | 9/2020 | Rousseau et al. |
| 10,786,253 B2 | 9/2020 | Shelton, IV et al. |
| 10,786,255 B2 | 9/2020 | Hodgkinson et al. |
| 10,792,038 B2 | 10/2020 | Becerra et al. |
| 10,796,471 B2 | 10/2020 | Leimbach et al. |
| 10,799,240 B2 | 10/2020 | Shelton, IV et al. |
| 10,799,306 B2 | 10/2020 | Robinson et al. |
| 10,806,448 B2 | 10/2020 | Shelton, IV et al. |
| 10,806,449 B2 | 10/2020 | Shelton, IV et al. |
| 10,806,450 B2 | 10/2020 | Yates et al. |
| 10,806,451 B2 | 10/2020 | Harris et al. |
| 10,806,453 B2 | 10/2020 | Chen et al. |
| 10,806,479 B2 | 10/2020 | Shelton, IV et al. |
| 10,813,638 B2 | 10/2020 | Shelton, IV et al. |
| 10,813,639 B2 | 10/2020 | Shelton, IV et al. |
| 10,813,640 B2 | 10/2020 | Adams et al. |
| 10,813,641 B2 | 10/2020 | Setser et al. |
| 10,813,683 B2 | 10/2020 | Baxter, III et al. |
| 10,813,705 B2 | 10/2020 | Hares et al. |
| 10,813,710 B2 | 10/2020 | Grubbs |
| 10,820,939 B2 | 11/2020 | Sartor |
| 10,828,028 B2 | 11/2020 | Harris et al. |
| 10,828,030 B2 | 11/2020 | Weir et al. |
| 10,828,032 B2 | 11/2020 | Leimbach et al. |
| 10,828,033 B2 | 11/2020 | Shelton, IV et al. |
| 10,828,089 B2 | 11/2020 | Clark et al. |
| 10,835,245 B2 | 11/2020 | Swayze et al. |
| 10,835,246 B2 | 11/2020 | Shelton, IV et al. |
| 10,835,247 B2 | 11/2020 | Shelton, IV et al. |
| 10,835,249 B2 | 11/2020 | Schellin et al. |
| 10,835,251 B2 | 11/2020 | Shelton, IV et al. |
| 10,835,330 B2 | 11/2020 | Shelton, IV et al. |
| 10,842,357 B2 | 11/2020 | Moskowitz et al. |
| 10,842,473 B2 | 11/2020 | Scheib et al. |
| 10,842,488 B2 | 11/2020 | Swayze et al. |
| 10,842,489 B2 | 11/2020 | Shelton, IV |
| 10,842,490 B2 | 11/2020 | DiNardo et al. |
| 10,842,491 B2 | 11/2020 | Shelton, IV et al. |
| 10,842,492 B2 | 11/2020 | Shelton, IV et al. |
| D904,612 S | 12/2020 | Wynn et al. |
| D906,355 S | 12/2020 | Messerly et al. |
| 10,849,621 B2 | 12/2020 | Whitfield et al. |
| 10,849,623 B2 | 12/2020 | Dunki-Jacobs et al. |
| 10,849,697 B2 | 12/2020 | Yates et al. |
| 10,856,866 B2 | 12/2020 | Shelton, IV et al. |
| 10,856,867 B2 | 12/2020 | Shelton, IV et al. |
| 10,856,868 B2 | 12/2020 | Shelton, IV et al. |
| 10,856,869 B2 | 12/2020 | Shelton, IV et al. |
| 10,856,870 B2 | 12/2020 | Harris et al. |
| 10,863,981 B2 | 12/2020 | Overmyer et al. |
| 10,863,984 B2 | 12/2020 | Shelton, IV et al. |
| 10,863,986 B2 | 12/2020 | Yates et al. |
| 10,869,664 B2 | 12/2020 | Shelton, IV |
| 10,869,665 B2 | 12/2020 | Shelton, IV et al. |
| 10,869,666 B2 | 12/2020 | Shelton, IV et al. |
| 10,869,669 B2 | 12/2020 | Shelton, IV et al. |
| 10,874,290 B2 | 12/2020 | Walen et al. |
| 10,874,391 B2 | 12/2020 | Shelton, IV et al. |
| 10,874,392 B2 | 12/2020 | Scirica et al. |
| 10,874,393 B2 | 12/2020 | Satti, III et al. |
| 10,874,396 B2 | 12/2020 | Moore et al. |

(56) References Cited

U.S. PATENT DOCUMENTS

| | | |
|---|---|---|
| 10,874,399 B2 | 12/2020 | Zhang |
| 10,879,275 B2 | 12/2020 | Li et al. |
| D907,647 S | 1/2021 | Siebel et al. |
| D907,648 S | 1/2021 | Siebel et al. |
| D908,216 S | 1/2021 | Messerly et al. |
| 10,881,395 B2 | 1/2021 | Merchant et al. |
| 10,881,396 B2 | 1/2021 | Shelton, IV et al. |
| 10,881,399 B2 | 1/2021 | Shelton, IV et al. |
| 10,881,401 B2 | 1/2021 | Baber et al. |
| 10,881,446 B2 | 1/2021 | Strobl |
| 10,888,318 B2 | 1/2021 | Parihar et al. |
| 10,888,321 B2 | 1/2021 | Shelton, IV et al. |
| 10,888,322 B2 | 1/2021 | Morgan et al. |
| 10,888,323 B2 | 1/2021 | Chen et al. |
| 10,888,325 B2 | 1/2021 | Harris et al. |
| 10,888,328 B2 | 1/2021 | Shelton, IV et al. |
| 10,888,329 B2 | 1/2021 | Moore et al. |
| 10,888,330 B2 | 1/2021 | Moore et al. |
| 10,888,369 B2 | 1/2021 | Messerly et al. |
| 10,892,899 B2 | 1/2021 | Shelton, IV et al. |
| 10,893,853 B2 | 1/2021 | Shelton, IV et al. |
| 10,893,863 B2 | 1/2021 | Shelton, IV et al. |
| 10,893,864 B2 | 1/2021 | Harris et al. |
| 10,893,867 B2 | 1/2021 | Leimbach et al. |
| 10,898,183 B2 | 1/2021 | Shelton, IV et al. |
| 10,898,184 B2 | 1/2021 | Yates et al. |
| 10,898,185 B2 | 1/2021 | Overmyer et al. |
| 10,898,186 B2 | 1/2021 | Bakos et al. |
| 10,898,190 B2 | 1/2021 | Yates et al. |
| 10,898,193 B2 | 1/2021 | Shelton, IV et al. |
| 10,898,194 B2 | 1/2021 | Moore et al. |
| 10,898,195 B2 | 1/2021 | Moore et al. |
| 10,903,685 B2 | 1/2021 | Yates et al. |
| D910,847 S | 2/2021 | Shelton, IV et al. |
| 10,905,415 B2 | 2/2021 | DiNardo et al. |
| 10,905,418 B2 | 2/2021 | Shelton, IV et al. |
| 10,905,420 B2 | 2/2021 | Jasemian et al. |
| 10,905,422 B2 | 2/2021 | Bakos et al. |
| 10,905,423 B2 | 2/2021 | Baber et al. |
| 10,905,426 B2 | 2/2021 | Moore et al. |
| 10,905,427 B2 | 2/2021 | Moore et al. |
| 10,911,515 B2 | 2/2021 | Blasi et al. |
| 10,912,559 B2 | 2/2021 | Harris et al. |
| 10,912,562 B2 | 2/2021 | Dunki-Jacobs et al. |
| 10,912,575 B2 | 2/2021 | Shelton, IV et al. |
| 10,918,364 B2 | 2/2021 | Applegate et al. |
| 10,918,380 B2 | 2/2021 | Morgan et al. |
| 10,918,385 B2 | 2/2021 | Overmyer et al. |
| 10,918,386 B2 | 2/2021 | Shelton, IV et al. |
| 10,919,156 B2 | 2/2021 | Roberts et al. |
| 10,925,600 B2 | 2/2021 | McCuen |
| 10,925,605 B2 | 2/2021 | Moore et al. |
| D914,878 S | 3/2021 | Shelton, IV et al. |
| 10,932,772 B2 | 3/2021 | Shelton, IV et al. |
| 10,932,774 B2 | 3/2021 | Shelton, IV |
| 10,932,775 B2 | 3/2021 | Shelton, IV et al. |
| 10,932,778 B2 | 3/2021 | Smith et al. |
| 10,932,779 B2 | 3/2021 | Vendely et al. |
| 10,932,804 B2 | 3/2021 | Scheib et al. |
| 10,932,806 B2 | 3/2021 | Shelton, IV et al. |
| 10,932,872 B2 | 3/2021 | Shelton, IV et al. |
| 10,944,728 B2 | 3/2021 | Wiener et al. |
| 10,945,727 B2 | 3/2021 | Shelton, IV et al. |
| 10,945,728 B2 | 3/2021 | Morgan et al. |
| 10,945,729 B2 | 3/2021 | Shelton, IV et al. |
| 10,945,731 B2 | 3/2021 | Baxter, III et al. |
| 10,952,708 B2 | 3/2021 | Scheib et al. |
| 10,952,727 B2 | 3/2021 | Giordano et al. |
| 10,952,728 B2 | 3/2021 | Shelton, IV et al. |
| 10,952,759 B2 | 3/2021 | Messerly et al. |
| 10,952,767 B2 | 3/2021 | Kostrzewski et al. |
| 10,959,722 B2 | 3/2021 | Morgan et al. |
| 10,959,725 B2 | 3/2021 | Kerr et al. |
| 10,959,727 B2 | 3/2021 | Hunter et al. |
| 10,959,731 B2 | 3/2021 | Casasanta, Jr. et al. |
| 10,959,744 B2 | 3/2021 | Shelton, IV et al. |
| D917,500 S | 4/2021 | Siebel et al. |
| 10,966,627 B2 | 4/2021 | Shelton, IV et al. |
| 10,966,717 B2 | 4/2021 | Shah et al. |
| 10,966,718 B2 | 4/2021 | Shelton, IV et al. |
| 10,966,791 B2 | 4/2021 | Harris et al. |
| 10,973,515 B2 | 4/2021 | Harris et al. |
| 10,973,516 B2 | 4/2021 | Shelton, IV et al. |
| 10,973,517 B2 | 4/2021 | Wixey |
| 10,973,519 B2 | 4/2021 | Weir et al. |
| 10,973,520 B2 | 4/2021 | Shelton, IV et al. |
| 10,980,534 B2 | 4/2021 | Yates et al. |
| 10,980,535 B2 | 4/2021 | Yates et al. |
| 10,980,536 B2 | 4/2021 | Weaner et al. |
| 10,980,537 B2 | 4/2021 | Shelton, IV et al. |
| 10,980,538 B2 | 4/2021 | Nalagatla et al. |
| 10,980,539 B2 | 4/2021 | Harris et al. |
| 10,980,560 B2 | 4/2021 | Shelton, IV et al. |
| 10,983,646 B2 | 4/2021 | Yoon et al. |
| 10,987,102 B2 | 4/2021 | Gonzalez et al. |
| 10,987,178 B2 | 4/2021 | Shelton, IV et al. |
| 10,993,713 B2 | 5/2021 | Shelton, IV et al. |
| 10,993,715 B2 | 5/2021 | Shelton, IV et al. |
| 10,993,716 B2 | 5/2021 | Shelton, IV et al. |
| 10,993,717 B2 | 5/2021 | Shelton, IV et al. |
| 11,000,278 B2 | 5/2021 | Shelton, IV et al. |
| 11,007,004 B2 | 5/2021 | Shelton, IV et al. |
| 11,007,022 B2 | 5/2021 | Shelton, IV et al. |
| 11,013,552 B2 | 5/2021 | Widenhouse et al. |
| 11,013,563 B2 | 5/2021 | Shelton, IV et al. |
| 11,020,016 B2 | 6/2021 | Wallace et al. |
| 11,026,687 B2 | 6/2021 | Shelton, IV et al. |
| 11,026,712 B2 | 6/2021 | Shelton, IV et al. |
| 11,026,713 B2 | 6/2021 | Stokes et al. |
| 11,026,751 B2 | 6/2021 | Shelton, IV et al. |
| 11,071,542 B2 | 7/2021 | Chen et al. |
| 11,090,047 B2 | 8/2021 | Shelton, IV et al. |
| 11,123,069 B2 | 9/2021 | Baxter, III et al. |
| 11,202,633 B2 | 12/2021 | Harris et al. |
| 2001/0000531 A1 | 4/2001 | Casscells et al. |
| 2001/0025183 A1 | 9/2001 | Shahidi |
| 2001/0025184 A1 | 9/2001 | Messerly |
| 2001/0034530 A1 | 10/2001 | Malackowski et al. |
| 2002/0014510 A1 | 2/2002 | Richter et al. |
| 2002/0022810 A1 | 2/2002 | Urich |
| 2002/0022836 A1 | 2/2002 | Goble et al. |
| 2002/0022861 A1 | 2/2002 | Jacobs et al. |
| 2002/0023126 A1 | 2/2002 | Flavin |
| 2002/0029032 A1 | 3/2002 | Arkin |
| 2002/0029036 A1 | 3/2002 | Goble et al. |
| 2002/0042620 A1 | 4/2002 | Julian et al. |
| 2002/0087048 A1 | 7/2002 | Brock et al. |
| 2002/0091374 A1 | 7/2002 | Cooper |
| 2002/0095175 A1 | 7/2002 | Brock et al. |
| 2002/0103494 A1 | 8/2002 | Pacey |
| 2002/0111624 A1 | 8/2002 | Witt et al. |
| 2002/0116063 A1 | 8/2002 | Giannetti et al. |
| 2002/0117534 A1 | 8/2002 | Green et al. |
| 2002/0127265 A1 | 9/2002 | Bowman et al. |
| 2002/0128633 A1 | 9/2002 | Brock et al. |
| 2002/0134811 A1 | 9/2002 | Napier et al. |
| 2002/0135474 A1 | 9/2002 | Sylliassen |
| 2002/0138086 A1 | 9/2002 | Sixto et al. |
| 2002/0143340 A1 | 10/2002 | Kaneko |
| 2002/0151770 A1 | 10/2002 | Noll et al. |
| 2002/0158593 A1 | 10/2002 | Henderson et al. |
| 2002/0177848 A1 | 11/2002 | Truckai et al. |
| 2002/0185514 A1 | 12/2002 | Adams et al. |
| 2002/0188170 A1 | 12/2002 | Santamore et al. |
| 2002/0188287 A1 | 12/2002 | Zvuloni et al. |
| 2003/0009193 A1 | 1/2003 | Corsaro |
| 2003/0011245 A1 | 1/2003 | Fiebig |
| 2003/0012805 A1 | 1/2003 | Chen et al. |
| 2003/0040670 A1 | 2/2003 | Govari |
| 2003/0045835 A1 | 3/2003 | Anderson et al. |
| 2003/0047230 A1 | 3/2003 | Kim |
| 2003/0050654 A1 | 3/2003 | Whitman et al. |
| 2003/0066858 A1 | 4/2003 | Holgersson |
| 2003/0078647 A1 | 4/2003 | Vallana et al. |

(56) References Cited

U.S. PATENT DOCUMENTS

| | | |
|---|---|---|
| 2003/0083648 A1 | 5/2003 | Wang et al. |
| 2003/0084983 A1 | 5/2003 | Rangachari et al. |
| 2003/0093103 A1 | 5/2003 | Malackowski et al. |
| 2003/0094356 A1 | 5/2003 | Waldron |
| 2003/0096158 A1 | 5/2003 | Takano et al. |
| 2003/0114851 A1 | 6/2003 | Truckai et al. |
| 2003/0121586 A1 | 7/2003 | Mitra et al. |
| 2003/0139741 A1 | 7/2003 | Goble et al. |
| 2003/0149406 A1 | 8/2003 | Martineau et al. |
| 2003/0153908 A1 | 8/2003 | Goble et al. |
| 2003/0153968 A1 | 8/2003 | Geis et al. |
| 2003/0163029 A1 | 8/2003 | Sonnenschein et al. |
| 2003/0163085 A1 | 8/2003 | Tanner et al. |
| 2003/0164172 A1 | 9/2003 | Chumas et al. |
| 2003/0181900 A1 | 9/2003 | Long |
| 2003/0190584 A1 | 10/2003 | Heasley |
| 2003/0195387 A1 | 10/2003 | Kortenbach et al. |
| 2003/0205029 A1 | 11/2003 | Chapolini et al. |
| 2003/0212005 A1 | 11/2003 | Petito et al. |
| 2003/0216732 A1 | 11/2003 | Truckai et al. |
| 2003/0236505 A1 | 12/2003 | Bonadio et al. |
| 2004/0006335 A1 | 1/2004 | Garrison |
| 2004/0006340 A1 | 1/2004 | Latterell et al. |
| 2004/0007608 A1 | 1/2004 | Ehrenfels et al. |
| 2004/0024457 A1 | 2/2004 | Boyce et al. |
| 2004/0028502 A1 | 2/2004 | Cummins |
| 2004/0030333 A1 | 2/2004 | Goble |
| 2004/0034287 A1 | 2/2004 | Hickle |
| 2004/0034357 A1 | 2/2004 | Beane et al. |
| 2004/0044295 A1 | 3/2004 | Reinert et al. |
| 2004/0044364 A1 | 3/2004 | DeVries et al. |
| 2004/0049121 A1 | 3/2004 | Yaron |
| 2004/0049172 A1 | 3/2004 | Root et al. |
| 2004/0059362 A1 | 3/2004 | Knodel et al. |
| 2004/0068161 A1 | 4/2004 | Couvillon |
| 2004/0068224 A1 | 4/2004 | Couvillon et al. |
| 2004/0068307 A1 | 4/2004 | Goble |
| 2004/0070369 A1 | 4/2004 | Sakakibara |
| 2004/0073222 A1 | 4/2004 | Koseki |
| 2004/0078037 A1 | 4/2004 | Batchelor et al. |
| 2004/0082952 A1 | 4/2004 | Dycus et al. |
| 2004/0085180 A1 | 5/2004 | Juang |
| 2004/0092992 A1 | 5/2004 | Adams et al. |
| 2004/0093020 A1 | 5/2004 | Sinton |
| 2004/0093024 A1 | 5/2004 | Lousararian et al. |
| 2004/0098040 A1 | 5/2004 | Taniguchi et al. |
| 2004/0101822 A1 | 5/2004 | Wiesner et al. |
| 2004/0102783 A1 | 5/2004 | Sutterlin et al. |
| 2004/0108357 A1 | 6/2004 | Milliman et al. |
| 2004/0110439 A1 | 6/2004 | Chaikof et al. |
| 2004/0115022 A1 | 6/2004 | Albertson et al. |
| 2004/0116952 A1 | 6/2004 | Sakurai et al. |
| 2004/0119185 A1 | 6/2004 | Chen |
| 2004/0122419 A1 | 6/2004 | Neuberger |
| 2004/0122423 A1 | 6/2004 | Dycus et al. |
| 2004/0133095 A1 | 7/2004 | Dunki-Jacobs et al. |
| 2004/0133189 A1 | 7/2004 | Sakurai |
| 2004/0143297 A1 | 7/2004 | Ramsey |
| 2004/0147909 A1 | 7/2004 | Johnston et al. |
| 2004/0153100 A1 | 8/2004 | Ahlberg et al. |
| 2004/0158261 A1 | 8/2004 | Vu |
| 2004/0164123 A1 | 8/2004 | Racenet et al. |
| 2004/0166169 A1 | 8/2004 | Malaviya et al. |
| 2004/0167572 A1 | 8/2004 | Roth et al. |
| 2004/0181219 A1 | 9/2004 | Goble et al. |
| 2004/0193189 A1 | 9/2004 | Kortenbach et al. |
| 2004/0197367 A1 | 10/2004 | Rezania et al. |
| 2004/0199181 A1 | 10/2004 | Knodel et al. |
| 2004/0204735 A1 | 10/2004 | Shiroff et al. |
| 2004/0218451 A1 | 11/2004 | Said et al. |
| 2004/0222268 A1 | 11/2004 | Bilotti et al. |
| 2004/0225186 A1 | 11/2004 | Horne et al. |
| 2004/0232201 A1 | 11/2004 | Wenchell et al. |
| 2004/0236352 A1 | 11/2004 | Wang et al. |
| 2004/0239582 A1 | 12/2004 | Seymour |
| 2004/0243147 A1 | 12/2004 | Lipow |
| 2004/0243151 A1 | 12/2004 | Demmy et al. |
| 2004/0243163 A1 | 12/2004 | Casiano et al. |
| 2004/0247415 A1 | 12/2004 | Mangone |
| 2004/0249366 A1 | 12/2004 | Kunz |
| 2004/0254455 A1 | 12/2004 | Iddan |
| 2004/0254566 A1 | 12/2004 | Plicchi et al. |
| 2004/0254590 A1 | 12/2004 | Hoffman et al. |
| 2004/0260315 A1 | 12/2004 | Dell et al. |
| 2004/0267310 A1 | 12/2004 | Racenet et al. |
| 2005/0010158 A1 | 1/2005 | Brugger et al. |
| 2005/0010213 A1 | 1/2005 | Stad et al. |
| 2005/0021078 A1 | 1/2005 | Vleugels et al. |
| 2005/0032511 A1 | 2/2005 | Malone et al. |
| 2005/0033352 A1 | 2/2005 | Zepf et al. |
| 2005/0051163 A1 | 3/2005 | Deem et al. |
| 2005/0054946 A1 | 3/2005 | Krzyzanowski |
| 2005/0057225 A1 | 3/2005 | Marquet |
| 2005/0058890 A1 | 3/2005 | Brazell et al. |
| 2005/0059997 A1 | 3/2005 | Bauman et al. |
| 2005/0070929 A1 | 3/2005 | Dalessandro et al. |
| 2005/0075561 A1 | 4/2005 | Golden |
| 2005/0080342 A1 | 4/2005 | Gilreath et al. |
| 2005/0085693 A1 | 4/2005 | Belson et al. |
| 2005/0090817 A1 | 4/2005 | Phan |
| 2005/0096683 A1 | 5/2005 | Ellins et al. |
| 2005/0116673 A1 | 6/2005 | Carl et al. |
| 2005/0120836 A1 | 6/2005 | Anderson |
| 2005/0124855 A1 | 6/2005 | Jaffe et al. |
| 2005/0125897 A1 | 6/2005 | Wyslucha et al. |
| 2005/0129735 A1 | 6/2005 | Cook et al. |
| 2005/0130682 A1 | 6/2005 | Takara et al. |
| 2005/0131173 A1 | 6/2005 | McDaniel et al. |
| 2005/0131211 A1 | 6/2005 | Bayley et al. |
| 2005/0131390 A1 | 6/2005 | Heinrich et al. |
| 2005/0131436 A1 | 6/2005 | Johnston et al. |
| 2005/0131457 A1 | 6/2005 | Douglas et al. |
| 2005/0137454 A1 | 6/2005 | Saadat et al. |
| 2005/0137455 A1 | 6/2005 | Ewers et al. |
| 2005/0139636 A1 | 6/2005 | Schwemberger et al. |
| 2005/0143759 A1 | 6/2005 | Kelly |
| 2005/0143769 A1 | 6/2005 | White et al. |
| 2005/0145671 A1 | 7/2005 | Viola |
| 2005/0150928 A1 | 7/2005 | Kameyama et al. |
| 2005/0154258 A1 | 7/2005 | Tartaglia et al. |
| 2005/0154406 A1 | 7/2005 | Bombard et al. |
| 2005/0159778 A1 | 7/2005 | Heinrich et al. |
| 2005/0165419 A1 | 7/2005 | Sauer et al. |
| 2005/0169974 A1 | 8/2005 | Tenerz et al. |
| 2005/0171522 A1 | 8/2005 | Christopherson |
| 2005/0177176 A1 | 8/2005 | Gerbi et al. |
| 2005/0177181 A1 | 8/2005 | Kagan et al. |
| 2005/0177249 A1 | 8/2005 | Kladakis et al. |
| 2005/0182298 A1 | 8/2005 | Ikeda et al. |
| 2005/0182443 A1 | 8/2005 | Jonn et al. |
| 2005/0184121 A1 | 8/2005 | Heinrich |
| 2005/0186240 A1 | 8/2005 | Ringeisen et al. |
| 2005/0187545 A1 | 8/2005 | Hooven et al. |
| 2005/0191936 A1 | 9/2005 | Marine et al. |
| 2005/0203550 A1 | 9/2005 | Laufer et al. |
| 2005/0209614 A1 | 9/2005 | Fenter et al. |
| 2005/0216055 A1 | 9/2005 | Scirica et al. |
| 2005/0222587 A1 | 10/2005 | Jinno et al. |
| 2005/0222611 A1 | 10/2005 | Weitkamp |
| 2005/0222616 A1 | 10/2005 | Rethy et al. |
| 2005/0222665 A1 | 10/2005 | Aranyi |
| 2005/0228224 A1 | 10/2005 | Okada et al. |
| 2005/0228446 A1 | 10/2005 | Mooradian et al. |
| 2005/0230453 A1 | 10/2005 | Viola |
| 2005/0240178 A1 | 10/2005 | Morley et al. |
| 2005/0242950 A1 | 11/2005 | Lindsay et al. |
| 2005/0245965 A1 | 11/2005 | Orban, III et al. |
| 2005/0246881 A1 | 11/2005 | Kelly et al. |
| 2005/0251063 A1 | 11/2005 | Basude |
| 2005/0256452 A1 | 11/2005 | DeMarchi et al. |
| 2005/0256546 A1 | 11/2005 | Vaisnys et al. |
| 2005/0258963 A1 | 11/2005 | Rodriguez et al. |
| 2005/0261676 A1 | 11/2005 | Hall et al. |
| 2005/0263563 A1 | 12/2005 | Racenet et al. |

(56) References Cited

U.S. PATENT DOCUMENTS

| | | |
|---|---|---|
| 2005/0267455 A1 | 12/2005 | Eggers et al. |
| 2005/0274034 A1 | 12/2005 | Hayashida et al. |
| 2005/0283188 A1 | 12/2005 | Loshakove et al. |
| 2005/0283226 A1 | 12/2005 | Haverkost |
| 2006/0008787 A1 | 1/2006 | Hayman et al. |
| 2006/0015009 A1 | 1/2006 | Jaffe et al. |
| 2006/0020167 A1 | 1/2006 | Sitzmann |
| 2006/0020258 A1 | 1/2006 | Strauss et al. |
| 2006/0020336 A1 | 1/2006 | Liddicoat |
| 2006/0025812 A1 | 2/2006 | Shelton |
| 2006/0041188 A1 | 2/2006 | Dirusso et al. |
| 2006/0047275 A1 | 3/2006 | Goble |
| 2006/0049229 A1 | 3/2006 | Milliman et al. |
| 2006/0052824 A1 | 3/2006 | Ransick et al. |
| 2006/0052825 A1 | 3/2006 | Ransick et al. |
| 2006/0064086 A1 | 3/2006 | Odom |
| 2006/0079735 A1 | 4/2006 | Martone et al. |
| 2006/0079874 A1 | 4/2006 | Faller et al. |
| 2006/0079879 A1 | 4/2006 | Faller et al. |
| 2006/0086032 A1 | 4/2006 | Valencic et al. |
| 2006/0087746 A1 | 4/2006 | Lipow |
| 2006/0089535 A1 | 4/2006 | Raz et al. |
| 2006/0097699 A1 | 5/2006 | Kamenoff |
| 2006/0100643 A1 | 5/2006 | Laufer et al. |
| 2006/0100649 A1 | 5/2006 | Hart |
| 2006/0106369 A1 | 5/2006 | Desai et al. |
| 2006/0111711 A1 | 5/2006 | Goble |
| 2006/0111723 A1 | 5/2006 | Chapolini et al. |
| 2006/0116634 A1 | 6/2006 | Shachar |
| 2006/0142772 A1 | 6/2006 | Ralph et al. |
| 2006/0144898 A1 | 7/2006 | Bilotti et al. |
| 2006/0154546 A1 | 7/2006 | Murphy et al. |
| 2006/0161050 A1 | 7/2006 | Butler et al. |
| 2006/0161185 A1 | 7/2006 | Saadat et al. |
| 2006/0167471 A1 | 7/2006 | Phillips |
| 2006/0173290 A1 | 8/2006 | Lavallee et al. |
| 2006/0173470 A1 | 8/2006 | Oray et al. |
| 2006/0176031 A1 | 8/2006 | Forman et al. |
| 2006/0176242 A1 | 8/2006 | Jaramaz et al. |
| 2006/0178556 A1 | 8/2006 | Hasser et al. |
| 2006/0180633 A1 | 8/2006 | Emmons |
| 2006/0180634 A1 | 8/2006 | Shelton et al. |
| 2006/0185682 A1 | 8/2006 | Marczyk |
| 2006/0199999 A1 | 9/2006 | Ikeda et al. |
| 2006/0201989 A1 | 9/2006 | Ojeda |
| 2006/0206100 A1 | 9/2006 | Eskridge et al. |
| 2006/0217729 A1 | 9/2006 | Eskridge et al. |
| 2006/0226957 A1 | 10/2006 | Miller et al. |
| 2006/0235368 A1 | 10/2006 | Oz |
| 2006/0241666 A1 | 10/2006 | Briggs et al. |
| 2006/0244460 A1 | 11/2006 | Weaver |
| 2006/0247584 A1 | 11/2006 | Sheetz et al. |
| 2006/0252981 A1 | 11/2006 | Matsuda et al. |
| 2006/0252990 A1 | 11/2006 | Kubach |
| 2006/0252993 A1 | 11/2006 | Freed et al. |
| 2006/0258904 A1 | 11/2006 | Stefanchik et al. |
| 2006/0259073 A1 | 11/2006 | Miyamoto et al. |
| 2006/0261763 A1 | 11/2006 | Iott et al. |
| 2006/0263444 A1 | 11/2006 | Ming et al. |
| 2006/0264831 A1 | 11/2006 | Skwarek et al. |
| 2006/0264929 A1 | 11/2006 | Goble et al. |
| 2006/0271042 A1 | 11/2006 | Latterell et al. |
| 2006/0271102 A1 | 11/2006 | Bosshard et al. |
| 2006/0282064 A1 | 12/2006 | Shimizu et al. |
| 2006/0284730 A1 | 12/2006 | Schmid et al. |
| 2006/0287576 A1 | 12/2006 | Tsuji et al. |
| 2006/0289602 A1 | 12/2006 | Wales et al. |
| 2006/0291981 A1 | 12/2006 | Viola et al. |
| 2007/0005045 A1 | 1/2007 | Mintz et al. |
| 2007/0009570 A1 | 1/2007 | Kim et al. |
| 2007/0010702 A1 | 1/2007 | Wang et al. |
| 2007/0010838 A1 | 1/2007 | Shelton et al. |
| 2007/0016235 A1 | 1/2007 | Tanaka et al. |
| 2007/0018958 A1 | 1/2007 | Tavakoli et al. |
| 2007/0026039 A1 | 2/2007 | Drumheller et al. |
| 2007/0026040 A1 | 2/2007 | Crawley et al. |
| 2007/0027468 A1 | 2/2007 | Wales et al. |
| 2007/0027551 A1 | 2/2007 | Farnsworth et al. |
| 2007/0043387 A1 | 2/2007 | Vargas et al. |
| 2007/0049951 A1 | 3/2007 | Menn |
| 2007/0049966 A1 | 3/2007 | Bonadio et al. |
| 2007/0051375 A1 | 3/2007 | Milliman |
| 2007/0055228 A1 | 3/2007 | Berg et al. |
| 2007/0073341 A1 | 3/2007 | Smith et al. |
| 2007/0073389 A1 | 3/2007 | Bolduc et al. |
| 2007/0078328 A1 | 4/2007 | Ozaki et al. |
| 2007/0078484 A1 | 4/2007 | Talarico et al. |
| 2007/0084897 A1 | 4/2007 | Shelton et al. |
| 2007/0088376 A1 | 4/2007 | Zacharias |
| 2007/0090788 A1 | 4/2007 | Hansford et al. |
| 2007/0093869 A1 | 4/2007 | Bloom et al. |
| 2007/0102472 A1 | 5/2007 | Shelton |
| 2007/0103437 A1 | 5/2007 | Rosenberg |
| 2007/0106113 A1 | 5/2007 | Ravo |
| 2007/0106317 A1 | 5/2007 | Shelton et al. |
| 2007/0118115 A1 | 5/2007 | Artale et al. |
| 2007/0134251 A1 | 6/2007 | Ashkenazi et al. |
| 2007/0135686 A1 | 6/2007 | Pruitt et al. |
| 2007/0135803 A1 | 6/2007 | Belson |
| 2007/0152612 A1 | 7/2007 | Chen et al. |
| 2007/0152829 A1 | 7/2007 | Lindsay et al. |
| 2007/0155010 A1 | 7/2007 | Farnsworth et al. |
| 2007/0170225 A1 | 7/2007 | Shelton et al. |
| 2007/0173687 A1 | 7/2007 | Shima et al. |
| 2007/0173813 A1 | 7/2007 | Odom |
| 2007/0173872 A1 | 7/2007 | Neuenfeldt |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0179477 A1 | 8/2007 | Danger |
| 2007/0185545 A1 | 8/2007 | Duke |
| 2007/0187857 A1 | 8/2007 | Riley et al. |
| 2007/0190110 A1 | 8/2007 | Pameijer et al. |
| 2007/0191868 A1 | 8/2007 | Theroux et al. |
| 2007/0191915 A1 | 8/2007 | Strother et al. |
| 2007/0194079 A1 | 8/2007 | Hueil et al. |
| 2007/0194082 A1 | 8/2007 | Morgan et al. |
| 2007/0197954 A1 | 8/2007 | Keenan |
| 2007/0198039 A1 | 8/2007 | Jones et al. |
| 2007/0203510 A1 | 8/2007 | Bettuchi |
| 2007/0207010 A1 | 9/2007 | Caspi |
| 2007/0208359 A1 | 9/2007 | Hoffman |
| 2007/0208375 A1 | 9/2007 | Nishizawa et al. |
| 2007/0213750 A1 | 9/2007 | Weadock |
| 2007/0225562 A1 | 9/2007 | Spivey et al. |
| 2007/0233163 A1 | 10/2007 | Bombard et al. |
| 2007/0243227 A1 | 10/2007 | Gertner |
| 2007/0244471 A1 | 10/2007 | Malackowski |
| 2007/0244496 A1 | 10/2007 | Hellenkamp |
| 2007/0246505 A1 | 10/2007 | Pace-Floridia et al. |
| 2007/0260132 A1 | 11/2007 | Sterling |
| 2007/0262592 A1 | 11/2007 | Hwang et al. |
| 2007/0270660 A1 | 11/2007 | Caylor et al. |
| 2007/0275035 A1 | 11/2007 | Herman et al. |
| 2007/0276409 A1 | 11/2007 | Ortiz et al. |
| 2007/0279011 A1 | 12/2007 | Jones et al. |
| 2007/0286892 A1 | 12/2007 | Herzberg et al. |
| 2007/0290027 A1 | 12/2007 | Maatta et al. |
| 2007/0296286 A1 | 12/2007 | Avenell |
| 2008/0003196 A1 | 1/2008 | Jonn et al. |
| 2008/0015598 A1 | 1/2008 | Prommersberger |
| 2008/0021486 A1 | 1/2008 | Oyola et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0030170 A1 | 2/2008 | Dacquay et al. |
| 2008/0039746 A1 | 2/2008 | Hissong et al. |
| 2008/0042861 A1 | 2/2008 | Dacquay et al. |
| 2008/0051833 A1 | 2/2008 | Gramuglia et al. |
| 2008/0064920 A1 | 3/2008 | Bakos et al. |
| 2008/0064921 A1 | 3/2008 | Larkin et al. |
| 2008/0065153 A1 | 3/2008 | Allard et al. |
| 2008/0069736 A1 | 3/2008 | Mingerink et al. |

(56) References Cited

U.S. PATENT DOCUMENTS

| | | |
|---|---|---|
| 2008/0071328 A1 | 3/2008 | Haubrich et al. |
| 2008/0077158 A1 | 3/2008 | Haider et al. |
| 2008/0078802 A1 | 4/2008 | Hess et al. |
| 2008/0081948 A1 | 4/2008 | Weisenburgh et al. |
| 2008/0082114 A1 | 4/2008 | McKenna et al. |
| 2008/0082125 A1 | 4/2008 | Murray et al. |
| 2008/0082126 A1 | 4/2008 | Murray et al. |
| 2008/0083807 A1 | 4/2008 | Beardsley et al. |
| 2008/0083811 A1 | 4/2008 | Marczyk |
| 2008/0085296 A1 | 4/2008 | Powell et al. |
| 2008/0086078 A1 | 4/2008 | Powell et al. |
| 2008/0091072 A1 | 4/2008 | Omori et al. |
| 2008/0108443 A1 | 5/2008 | Jinno et al. |
| 2008/0114250 A1 | 5/2008 | Urbano et al. |
| 2008/0125634 A1 | 5/2008 | Ryan et al. |
| 2008/0125749 A1 | 5/2008 | Olson |
| 2008/0128469 A1 | 6/2008 | Dalessandro et al. |
| 2008/0129253 A1 | 6/2008 | Shiue et al. |
| 2008/0135600 A1 | 6/2008 | Hiranuma et al. |
| 2008/0140115 A1 | 6/2008 | Stopek |
| 2008/0140159 A1 | 6/2008 | Bornhoft et al. |
| 2008/0149682 A1 | 6/2008 | Uhm |
| 2008/0154299 A1 | 6/2008 | Livneh |
| 2008/0154335 A1 | 6/2008 | Thrope et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0177392 A1 | 7/2008 | Williams et al. |
| 2008/0190989 A1 | 8/2008 | Crews et al. |
| 2008/0196253 A1 | 8/2008 | Ezra et al. |
| 2008/0196419 A1 | 8/2008 | Dube |
| 2008/0197167 A1 | 8/2008 | Viola et al. |
| 2008/0200755 A1 | 8/2008 | Bakos |
| 2008/0200762 A1 | 8/2008 | Stokes et al. |
| 2008/0200835 A1 | 8/2008 | Monson et al. |
| 2008/0200911 A1 | 8/2008 | Long |
| 2008/0200933 A1 | 8/2008 | Bakos et al. |
| 2008/0200934 A1 | 8/2008 | Fox |
| 2008/0206186 A1 | 8/2008 | Butler et al. |
| 2008/0208058 A1 | 8/2008 | Sabata et al. |
| 2008/0234709 A1 | 9/2008 | Houser |
| 2008/0234866 A1 | 9/2008 | Kishi et al. |
| 2008/0242939 A1 | 10/2008 | Johnston |
| 2008/0243088 A1 | 10/2008 | Evans |
| 2008/0249536 A1 | 10/2008 | Stahler et al. |
| 2008/0249608 A1 | 10/2008 | Dave |
| 2008/0255413 A1 | 10/2008 | Zemlok et al. |
| 2008/0255420 A1 | 10/2008 | Lee et al. |
| 2008/0255663 A1 | 10/2008 | Akpek et al. |
| 2008/0262654 A1* | 10/2008 | Omori ............... A61B 34/72 901/30 |
| 2008/0269596 A1 | 10/2008 | Revie et al. |
| 2008/0281171 A1 | 11/2008 | Fennell et al. |
| 2008/0281332 A1 | 11/2008 | Taylor |
| 2008/0287944 A1 | 11/2008 | Pearson et al. |
| 2008/0293910 A1 | 11/2008 | Kapiamba et al. |
| 2008/0294179 A1 | 11/2008 | Balbierz et al. |
| 2008/0296346 A1 | 12/2008 | Shelton, IV et al. |
| 2008/0297287 A1 | 12/2008 | Shachar et al. |
| 2008/0298784 A1 | 12/2008 | Kastner |
| 2008/0308602 A1 | 12/2008 | Timm et al. |
| 2008/0308603 A1 | 12/2008 | Shelton et al. |
| 2008/0312686 A1 | 12/2008 | Ellingwood |
| 2008/0312687 A1 | 12/2008 | Blier |
| 2008/0315829 A1 | 12/2008 | Jones et al. |
| 2009/0001121 A1 | 1/2009 | Hess et al. |
| 2009/0001130 A1 | 1/2009 | Hess et al. |
| 2009/0004455 A1 | 1/2009 | Gravagna et al. |
| 2009/0005809 A1 | 1/2009 | Hess et al. |
| 2009/0012534 A1 | 1/2009 | Madhani et al. |
| 2009/0015195 A1 | 1/2009 | Loth-Krausser |
| 2009/0020958 A1 | 1/2009 | Soul |
| 2009/0048583 A1 | 2/2009 | Williams et al. |
| 2009/0048589 A1 | 2/2009 | Takashino et al. |
| 2009/0076506 A1 | 3/2009 | Baker |
| 2009/0078736 A1 | 3/2009 | Van Lue |
| 2009/0081313 A1 | 3/2009 | Aghion et al. |
| 2009/0088659 A1 | 4/2009 | Graham et al. |
| 2009/0090763 A1 | 4/2009 | Zemlok et al. |
| 2009/0099579 A1 | 4/2009 | Nentwick et al. |
| 2009/0099876 A1 | 4/2009 | Whitman |
| 2009/0110533 A1 | 4/2009 | Jinno |
| 2009/0112234 A1 | 4/2009 | Crainich et al. |
| 2009/0118762 A1 | 5/2009 | Crainch et al. |
| 2009/0119011 A1 | 5/2009 | Kondo et al. |
| 2009/0131819 A1 | 5/2009 | Ritchie et al. |
| 2009/0132400 A1 | 5/2009 | Conway |
| 2009/0135280 A1 | 5/2009 | Johnston et al. |
| 2009/0143855 A1 | 6/2009 | Weber et al. |
| 2009/0149871 A9 | 6/2009 | Kagan et al. |
| 2009/0171147 A1 | 7/2009 | Lee et al. |
| 2009/0177218 A1 | 7/2009 | Young et al. |
| 2009/0177226 A1 | 7/2009 | Reinprecht et al. |
| 2009/0181290 A1 | 7/2009 | Baldwin et al. |
| 2009/0188964 A1 | 7/2009 | Orlov |
| 2009/0192534 A1 | 7/2009 | Ortiz et al. |
| 2009/0198272 A1 | 8/2009 | Kerver et al. |
| 2009/0204108 A1 | 8/2009 | Steffen |
| 2009/0204109 A1 | 8/2009 | Grove et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0209990 A1* | 8/2009 | Yates ............... A61B 90/98 227/176.1 |
| 2009/0221993 A1 | 9/2009 | Sohi et al. |
| 2009/0227834 A1 | 9/2009 | Nakamoto et al. |
| 2009/0234273 A1 | 9/2009 | Intoccia et al. |
| 2009/0242610 A1 | 10/2009 | Shelton, IV et al. |
| 2009/0246873 A1 | 10/2009 | Yamamoto et al. |
| 2009/0247368 A1 | 10/2009 | Chiang |
| 2009/0247901 A1 | 10/2009 | Zimmer |
| 2009/0248100 A1 | 10/2009 | Vaisnys et al. |
| 2009/0253959 A1 | 10/2009 | Yoshie et al. |
| 2009/0255974 A1 | 10/2009 | Viola |
| 2009/0261141 A1 | 10/2009 | Stratton et al. |
| 2009/0262078 A1 | 10/2009 | Pizzi |
| 2009/0270895 A1 | 10/2009 | Churchill et al. |
| 2009/0273353 A1 | 11/2009 | Kroh et al. |
| 2009/0277288 A1 | 11/2009 | Doepker et al. |
| 2009/0278406 A1 | 11/2009 | Hoffman |
| 2009/0290016 A1 | 11/2009 | Suda |
| 2009/0292283 A1 | 11/2009 | Odom |
| 2009/0306639 A1 | 12/2009 | Nevo et al. |
| 2009/0308907 A1 | 12/2009 | Nalagatla et al. |
| 2009/0318557 A1 | 12/2009 | Stockel |
| 2009/0325859 A1 | 12/2009 | Ameer et al. |
| 2010/0005035 A1 | 1/2010 | Carpenter et al. |
| 2010/0012703 A1 | 1/2010 | Calabrese et al. |
| 2010/0015104 A1 | 1/2010 | Fraser et al. |
| 2010/0016853 A1 | 1/2010 | Burbank |
| 2010/0016888 A1 | 1/2010 | Calabrese et al. |
| 2010/0017715 A1 | 1/2010 | Balassanian |
| 2010/0023024 A1 | 1/2010 | Zeiner et al. |
| 2010/0030233 A1 | 2/2010 | Whitman et al. |
| 2010/0030239 A1 | 2/2010 | Viola et al. |
| 2010/0032179 A1 | 2/2010 | Hanspers et al. |
| 2010/0036370 A1 | 2/2010 | Mirel et al. |
| 2010/0051668 A1 | 3/2010 | Milliman et al. |
| 2010/0057118 A1 | 3/2010 | Dietz et al. |
| 2010/0065604 A1 | 3/2010 | Weng |
| 2010/0069833 A1 | 3/2010 | Wenderow et al. |
| 2010/0069942 A1 | 3/2010 | Shelton, IV |
| 2010/0076483 A1 | 3/2010 | Imuta |
| 2010/0076489 A1 | 3/2010 | Stopek et al. |
| 2010/0081883 A1 | 4/2010 | Murray et al. |
| 2010/0094340 A1 | 4/2010 | Stopek et al. |
| 2010/0094400 A1 | 4/2010 | Bolduc et al. |
| 2010/0100123 A1 | 4/2010 | Bennett |

(56) References Cited

U.S. PATENT DOCUMENTS

| | | |
|---|---|---|
| 2010/0100124 A1 | 4/2010 | Calabrese et al. |
| 2010/0116519 A1 | 5/2010 | Gareis |
| 2010/0122339 A1 | 5/2010 | Boccacci |
| 2010/0133317 A1 | 6/2010 | Shelton, IV et al. |
| 2010/0137990 A1 | 6/2010 | Apatsidis et al. |
| 2010/0138659 A1 | 6/2010 | Carmichael et al. |
| 2010/0145146 A1 | 6/2010 | Melder |
| 2010/0147921 A1 | 6/2010 | Olson |
| 2010/0147922 A1 | 6/2010 | Olson |
| 2010/0159435 A1 | 6/2010 | Mueller et al. |
| 2010/0179022 A1 | 7/2010 | Shirokoshi |
| 2010/0180711 A1 | 7/2010 | Kilibarda et al. |
| 2010/0191262 A1 | 7/2010 | Harris et al. |
| 2010/0191292 A1 | 7/2010 | Demeo et al. |
| 2010/0193566 A1 | 8/2010 | Scheib et al. |
| 2010/0204717 A1 | 8/2010 | Knodel |
| 2010/0204721 A1 | 8/2010 | Young et al. |
| 2010/0217281 A1 | 8/2010 | Matsuoka et al. |
| 2010/0222901 A1 | 9/2010 | Swayze et al. |
| 2010/0228250 A1 | 9/2010 | Brogna |
| 2010/0234687 A1 | 9/2010 | Azarbarzin et al. |
| 2010/0241137 A1 | 9/2010 | Doyle et al. |
| 2010/0245102 A1 | 9/2010 | Yokoi |
| 2010/0249497 A1 | 9/2010 | Peine et al. |
| 2010/0249947 A1 | 9/2010 | Lesh et al. |
| 2010/0256675 A1 | 10/2010 | Romans |
| 2010/0258327 A1 | 10/2010 | Esenwein et al. |
| 2010/0267662 A1 | 10/2010 | Fielder et al. |
| 2010/0274160 A1 | 10/2010 | Yachi et al. |
| 2010/0291184 A1 | 11/2010 | Clark et al. |
| 2010/0292540 A1 | 11/2010 | Hess et al. |
| 2010/0298636 A1 | 11/2010 | Castro et al. |
| 2010/0301097 A1 | 12/2010 | Scirica et al. |
| 2010/0310623 A1 | 12/2010 | Laurencin et al. |
| 2010/0312261 A1 | 12/2010 | Suzuki et al. |
| 2010/0318085 A1 | 12/2010 | Austin et al. |
| 2010/0331856 A1 | 12/2010 | Carlson et al. |
| 2011/0006101 A1 | 1/2011 | Hall et al. |
| 2011/0009694 A1 | 1/2011 | Schultz et al. |
| 2011/0011916 A1 | 1/2011 | Levine |
| 2011/0016960 A1 | 1/2011 | Debrailly |
| 2011/0021871 A1 | 1/2011 | Berkelaar |
| 2011/0022032 A1 | 1/2011 | Zemlok et al. |
| 2011/0024477 A1 | 2/2011 | Hall |
| 2011/0024478 A1 | 2/2011 | Shelton, IV |
| 2011/0025311 A1 | 2/2011 | Chauvin et al. |
| 2011/0028991 A1 | 2/2011 | Ikeda et al. |
| 2011/0029270 A1 | 2/2011 | Mueglitz |
| 2011/0036891 A1 | 2/2011 | Zemlok et al. |
| 2011/0046667 A1 | 2/2011 | Culligan et al. |
| 2011/0052660 A1 | 3/2011 | Yang et al. |
| 2011/0056717 A1 | 3/2011 | Herisse |
| 2011/0060363 A1 | 3/2011 | Hess et al. |
| 2011/0066156 A1 | 3/2011 | McGahan et al. |
| 2011/0082538 A1 | 4/2011 | Dahlgren et al. |
| 2011/0087276 A1 | 4/2011 | Bedi et al. |
| 2011/0088921 A1 | 4/2011 | Forgues et al. |
| 2011/0091515 A1 | 4/2011 | Zilberman et al. |
| 2011/0095064 A1 | 4/2011 | Taylor et al. |
| 2011/0095067 A1 | 4/2011 | Ohdaira |
| 2011/0101069 A1 | 5/2011 | Bombard et al. |
| 2011/0101794 A1 | 5/2011 | Schroeder et al. |
| 2011/0112517 A1 | 5/2011 | Peine et al. |
| 2011/0112530 A1 | 5/2011 | Keller |
| 2011/0114697 A1 | 5/2011 | Baxter, III et al. |
| 2011/0118708 A1 | 5/2011 | Burbank et al. |
| 2011/0125149 A1 | 5/2011 | El-Galley et al. |
| 2011/0125176 A1 | 5/2011 | Yates et al. |
| 2011/0127945 A1 | 6/2011 | Yoneda |
| 2011/0129706 A1 | 6/2011 | Takahashi et al. |
| 2011/0144764 A1 | 6/2011 | Bagga et al. |
| 2011/0147433 A1 | 6/2011 | Shelton, IV et al. |
| 2011/0160725 A1 | 6/2011 | Kabaya et al. |
| 2011/0163146 A1 | 7/2011 | Ortiz et al. |
| 2011/0172495 A1 | 7/2011 | Armstrong |
| 2011/0174861 A1 | 7/2011 | Shelton, IV et al. |
| 2011/0192882 A1 | 8/2011 | Hess et al. |
| 2011/0199225 A1 | 8/2011 | Touchberry et al. |
| 2011/0218400 A1 | 9/2011 | Ma et al. |
| 2011/0218550 A1 | 9/2011 | Ma |
| 2011/0220381 A1 | 9/2011 | Friese et al. |
| 2011/0225105 A1 | 9/2011 | Scholer et al. |
| 2011/0230713 A1 | 9/2011 | Kleemann et al. |
| 2011/0235168 A1 | 9/2011 | Sander |
| 2011/0238044 A1 | 9/2011 | Main et al. |
| 2011/0241597 A1 | 10/2011 | Zhu et al. |
| 2011/0251606 A1 | 10/2011 | Kerr |
| 2011/0256266 A1 | 10/2011 | Orme et al. |
| 2011/0271186 A1 | 11/2011 | Owens |
| 2011/0275901 A1 | 11/2011 | Shelton, IV |
| 2011/0276083 A1 | 11/2011 | Shelton, IV et al. |
| 2011/0278343 A1 | 11/2011 | Knodel et al. |
| 2011/0279268 A1 | 11/2011 | Konishi et al. |
| 2011/0285507 A1 | 11/2011 | Nelson |
| 2011/0290856 A1 | 12/2011 | Shelton, IV et al. |
| 2011/0290858 A1 | 12/2011 | Whitman et al. |
| 2011/0292258 A1 | 12/2011 | Adler et al. |
| 2011/0293690 A1 | 12/2011 | Griffin et al. |
| 2011/0295295 A1 | 12/2011 | Shelton, IV et al. |
| 2011/0313894 A1 | 12/2011 | Dye et al. |
| 2011/0315413 A1 | 12/2011 | Fisher et al. |
| 2012/0004636 A1 | 1/2012 | Lo |
| 2012/0007442 A1 | 1/2012 | Rhodes et al. |
| 2012/0008880 A1 | 1/2012 | Toth |
| 2012/0016239 A1 | 1/2012 | Barthe et al. |
| 2012/0016413 A1 | 1/2012 | Timm et al. |
| 2012/0016467 A1 | 1/2012 | Chen et al. |
| 2012/0029272 A1 | 2/2012 | Shelton, IV et al. |
| 2012/0033360 A1 | 2/2012 | Hsu |
| 2012/0059286 A1 | 3/2012 | Hastings et al. |
| 2012/0064483 A1 | 3/2012 | Lint et al. |
| 2012/0074200 A1 | 3/2012 | Schmid et al. |
| 2012/0078243 A1 | 3/2012 | Worrell et al. |
| 2012/0078244 A1 | 3/2012 | Worrell et al. |
| 2012/0080336 A1 | 4/2012 | Shelton, IV et al. |
| 2012/0080344 A1 | 4/2012 | Shelton, IV |
| 2012/0080478 A1 | 4/2012 | Morgan et al. |
| 2012/0080498 A1 | 4/2012 | Shelton, IV et al. |
| 2012/0086276 A1 | 4/2012 | Sawyers |
| 2012/0095458 A1 | 4/2012 | Cybulski et al. |
| 2012/0109186 A1 | 5/2012 | Parrott et al. |
| 2012/0116261 A1 | 5/2012 | Mumaw et al. |
| 2012/0116262 A1 | 5/2012 | Houser et al. |
| 2012/0116265 A1 | 5/2012 | Houser et al. |
| 2012/0116266 A1 | 5/2012 | Houser et al. |
| 2012/0116381 A1 | 5/2012 | Houser et al. |
| 2012/0118595 A1 | 5/2012 | Pellenc |
| 2012/0123463 A1 | 5/2012 | Jacobs |
| 2012/0125792 A1 | 5/2012 | Cassivi |
| 2012/0130217 A1 | 5/2012 | Kauphusman et al. |
| 2012/0132286 A1 | 5/2012 | Lim et al. |
| 2012/0171539 A1 | 7/2012 | Rejman et al. |
| 2012/0175398 A1 | 7/2012 | Sandborn et al. |
| 2012/0190964 A1 | 7/2012 | Hyde et al. |
| 2012/0197272 A1 | 8/2012 | Oray et al. |
| 2012/0211542 A1 | 8/2012 | Racenet |
| 2012/0220990 A1 | 8/2012 | Mckenzie et al. |
| 2012/0234895 A1 | 9/2012 | O'Connor et al. |
| 2012/0234897 A1 | 9/2012 | Shelton, IV et al. |
| 2012/0239068 A1 | 9/2012 | Morris et al. |
| 2012/0248169 A1 | 10/2012 | Widenhouse et al. |
| 2012/0251861 A1 | 10/2012 | Liang et al. |
| 2012/0253328 A1 | 10/2012 | Cunningham et al. |
| 2012/0271327 A1 | 10/2012 | West et al. |
| 2012/0283707 A1 | 11/2012 | Giordano et al. |
| 2012/0289811 A1 | 11/2012 | Viola et al. |
| 2012/0289979 A1 | 11/2012 | Eskaros et al. |
| 2012/0292367 A1 | 11/2012 | Morgan et al. |
| 2012/0296342 A1 | 11/2012 | Haglund Wendelschafer |
| 2012/0298722 A1 | 11/2012 | Hess et al. |
| 2012/0301498 A1 | 11/2012 | Altreuter et al. |
| 2012/0316424 A1 | 12/2012 | Stopek |
| 2012/0330329 A1 | 12/2012 | Harris et al. |
| 2013/0006227 A1 | 1/2013 | Takashino |

(56) References Cited

U.S. PATENT DOCUMENTS

| | | |
|---|---|---|
| 2013/0008937 A1 | 1/2013 | Viola |
| 2013/0012983 A1 | 1/2013 | Kleyman |
| 2013/0018400 A1 | 1/2013 | Milton et al. |
| 2013/0020375 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0023910 A1 | 1/2013 | Solomon et al. |
| 2013/0026208 A1 | 1/2013 | Shelton, IV et al. |
| 2013/0026210 A1 | 1/2013 | Shelton, IV et al. |
| 2013/0030462 A1 | 1/2013 | Keating et al. |
| 2013/0041292 A1 | 2/2013 | Cunningham |
| 2013/0057162 A1 | 3/2013 | Pollischansky |
| 2013/0068816 A1 | 3/2013 | Mandakolathur Vasudevan et al. |
| 2013/0075447 A1 | 3/2013 | Weisenburgh, II et al. |
| 2013/0087597 A1 | 4/2013 | Shelton, IV et al. |
| 2013/0090534 A1 | 4/2013 | Burns et al. |
| 2013/0096568 A1 | 4/2013 | Justis |
| 2013/0098970 A1 | 4/2013 | Racenet et al. |
| 2013/0106352 A1 | 5/2013 | Nagamine |
| 2013/0112729 A1 | 5/2013 | Beardsley et al. |
| 2013/0116669 A1 | 5/2013 | Shelton, IV et al. |
| 2013/0123816 A1 | 5/2013 | Hodgkinson et al. |
| 2013/0126202 A1 | 5/2013 | Oomori et al. |
| 2013/0131476 A1 | 5/2013 | Siu et al. |
| 2013/0131651 A1 | 5/2013 | Strobl et al. |
| 2013/0136969 A1 | 5/2013 | Yasui et al. |
| 2013/0153641 A1 | 6/2013 | Shelton, IV et al. |
| 2013/0158390 A1 | 6/2013 | Tan et al. |
| 2013/0162198 A1 | 6/2013 | Yokota et al. |
| 2013/0169217 A1 | 7/2013 | Watanabe et al. |
| 2013/0172713 A1 | 7/2013 | Kirschenman |
| 2013/0172878 A1 | 7/2013 | Smith |
| 2013/0175317 A1 | 7/2013 | Yates et al. |
| 2013/0183769 A1 | 7/2013 | Tajima |
| 2013/0211244 A1 | 8/2013 | Nathaniel |
| 2013/0214025 A1 | 8/2013 | Zemlok et al. |
| 2013/0215449 A1 | 8/2013 | Yamasaki |
| 2013/0231681 A1 | 9/2013 | Robinson et al. |
| 2013/0233906 A1 | 9/2013 | Hess et al. |
| 2013/0238021 A1 | 9/2013 | Gross et al. |
| 2013/0248578 A1 | 9/2013 | Arteaga Gonzalez |
| 2013/0253480 A1 | 9/2013 | Kimball et al. |
| 2013/0256373 A1 | 10/2013 | Schmid et al. |
| 2013/0256380 A1 | 10/2013 | Schmid et al. |
| 2013/0267978 A1 | 10/2013 | Trissel |
| 2013/0270322 A1 | 10/2013 | Scheib et al. |
| 2013/0277410 A1 | 10/2013 | Fernandez et al. |
| 2013/0284792 A1 | 10/2013 | Ma |
| 2013/0293353 A1 | 11/2013 | McPherson et al. |
| 2013/0303845 A1 | 11/2013 | Skula et al. |
| 2013/0306704 A1 | 11/2013 | Balbierz et al. |
| 2013/0327552 A1 | 12/2013 | Lovelass et al. |
| 2013/0333910 A1 | 12/2013 | Tanimoto et al. |
| 2013/0334280 A1 | 12/2013 | Krehel et al. |
| 2013/0334283 A1 | 12/2013 | Swayze et al. |
| 2013/0334285 A1 | 12/2013 | Swayze et al. |
| 2013/0341374 A1 | 12/2013 | Shelton, IV et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005702 A1 | 1/2014 | Timm et al. |
| 2014/0005718 A1 | 1/2014 | Shelton, IV et al. |
| 2014/0008289 A1 | 1/2014 | Williams et al. |
| 2014/0014704 A1 | 1/2014 | Onukuri et al. |
| 2014/0014705 A1 | 1/2014 | Baxter, III |
| 2014/0014707 A1 | 1/2014 | Onukuri et al. |
| 2014/0018832 A1 | 1/2014 | Shelton, IV |
| 2014/0022283 A1 | 1/2014 | Chan et al. |
| 2014/0039549 A1 | 2/2014 | Belsky et al. |
| 2014/0041191 A1 | 2/2014 | Knodel |
| 2014/0048580 A1 | 2/2014 | Merchant et al. |
| 2014/0081176 A1 | 3/2014 | Hassan |
| 2014/0094681 A1 | 4/2014 | Valentine et al. |
| 2014/0100558 A1 | 4/2014 | Schmitz et al. |
| 2014/0107697 A1 | 4/2014 | Patani et al. |
| 2014/0115229 A1 | 4/2014 | Kothamasu et al. |
| 2014/0131418 A1 | 5/2014 | Kostrzewski |
| 2014/0135832 A1 | 5/2014 | Park et al. |
| 2014/0151433 A1 | 6/2014 | Shelton, IV et al. |
| 2014/0155916 A1 | 6/2014 | Hodgkinson et al. |
| 2014/0158747 A1 | 6/2014 | Measamer et al. |
| 2014/0166723 A1 | 6/2014 | Beardsley et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0175147 A1 | 6/2014 | Manoux et al. |
| 2014/0175150 A1 | 6/2014 | Shelton, IV et al. |
| 2014/0175152 A1 | 6/2014 | Hess et al. |
| 2014/0181710 A1 | 6/2014 | Baalu et al. |
| 2014/0183244 A1 | 7/2014 | Duque et al. |
| 2014/0188091 A1 | 7/2014 | Vidal et al. |
| 2014/0188159 A1 | 7/2014 | Steege |
| 2014/0207124 A1 | 7/2014 | Aldridge et al. |
| 2014/0209658 A1 | 7/2014 | Skalla et al. |
| 2014/0224857 A1 | 8/2014 | Schmid |
| 2014/0228632 A1 | 8/2014 | Sholev et al. |
| 2014/0228867 A1 | 8/2014 | Thomas et al. |
| 2014/0239047 A1 | 8/2014 | Hodgkinson et al. |
| 2014/0243865 A1 | 8/2014 | Swayze et al. |
| 2014/0246475 A1 | 9/2014 | Hall et al. |
| 2014/0248167 A1 | 9/2014 | Sugimoto et al. |
| 2014/0249557 A1 | 9/2014 | Koch et al. |
| 2014/0249573 A1 | 9/2014 | Arav |
| 2014/0262408 A1 | 9/2014 | Woodard |
| 2014/0263541 A1 | 9/2014 | Leimbach et al. |
| 2014/0263552 A1 | 9/2014 | Hall et al. |
| 2014/0263558 A1 | 9/2014 | Hausen et al. |
| 2014/0276730 A1 | 9/2014 | Boudreaux et al. |
| 2014/0284371 A1 | 9/2014 | Morgan et al. |
| 2014/0288460 A1 | 9/2014 | Ouyang et al. |
| 2014/0291379 A1 | 10/2014 | Schellin et al. |
| 2014/0291383 A1 | 10/2014 | Spivey et al. |
| 2014/0299648 A1 | 10/2014 | Shelton, IV et al. |
| 2014/0303645 A1 | 10/2014 | Morgan et al. |
| 2014/0303660 A1 | 10/2014 | Boyden et al. |
| 2014/0330161 A1 | 11/2014 | Swayze et al. |
| 2014/0330298 A1 | 11/2014 | Arshonsky et al. |
| 2014/0330579 A1 | 11/2014 | Cashman et al. |
| 2014/0358163 A1 | 12/2014 | Farin et al. |
| 2014/0367445 A1 | 12/2014 | Ingmanson et al. |
| 2014/0374130 A1 | 12/2014 | Nakamura et al. |
| 2014/0378950 A1 | 12/2014 | Chiu |
| 2015/0001272 A1 | 1/2015 | Sniffin et al. |
| 2015/0002089 A1 | 1/2015 | Rejman et al. |
| 2015/0008248 A1 | 1/2015 | Giordano et al. |
| 2015/0025549 A1 | 1/2015 | Kilroy et al. |
| 2015/0025571 A1 | 1/2015 | Suzuki et al. |
| 2015/0039010 A1 | 2/2015 | Beardsley et al. |
| 2015/0053737 A1 | 2/2015 | Leimbach et al. |
| 2015/0053743 A1 | 2/2015 | Yates et al. |
| 2015/0053746 A1 | 2/2015 | Shelton, IV et al. |
| 2015/0053748 A1 | 2/2015 | Yates et al. |
| 2015/0060518 A1 | 3/2015 | Shelton, IV et al. |
| 2015/0060519 A1 | 3/2015 | Shelton, IV et al. |
| 2015/0060520 A1 | 3/2015 | Shelton, IV et al. |
| 2015/0060521 A1 | 3/2015 | Weisenburgh, II et al. |
| 2015/0066000 A1 | 3/2015 | An et al. |
| 2015/0076208 A1 | 3/2015 | Shelton, IV |
| 2015/0076209 A1 | 3/2015 | Shelton, IV et al. |
| 2015/0076210 A1 | 3/2015 | Shelton, IV et al. |
| 2015/0076211 A1 | 3/2015 | Irka et al. |
| 2015/0076212 A1 | 3/2015 | Shelton, IV |
| 2015/0082624 A1 | 3/2015 | Craig et al. |
| 2015/0083781 A1 | 3/2015 | Giordano et al. |
| 2015/0083782 A1 | 3/2015 | Scheib et al. |
| 2015/0087952 A1 | 3/2015 | Albert et al. |
| 2015/0088127 A1 | 3/2015 | Craig et al. |
| 2015/0088547 A1 | 3/2015 | Balram et al. |
| 2015/0090760 A1 | 4/2015 | Giordano et al. |
| 2015/0090762 A1 | 4/2015 | Giordano et al. |
| 2015/0127021 A1 | 5/2015 | Harris et al. |
| 2015/0134077 A1 | 5/2015 | Shelton, IV et al. |
| 2015/0150620 A1 | 6/2015 | Miyamoto et al. |

(56) References Cited

U.S. PATENT DOCUMENTS

| | | |
|---|---|---|
| 2015/0173749 A1 | 6/2015 | Shelton, IV et al. |
| 2015/0173756 A1 | 6/2015 | Baxter, III et al. |
| 2015/0173789 A1 | 6/2015 | Baxter, III et al. |
| 2015/0196295 A1 | 7/2015 | Shelton, IV et al. |
| 2015/0196296 A1 | 7/2015 | Swayze et al. |
| 2015/0196299 A1 | 7/2015 | Swayze et al. |
| 2015/0201918 A1 | 7/2015 | Kumar et al. |
| 2015/0201932 A1 | 7/2015 | Swayze et al. |
| 2015/0201936 A1 | 7/2015 | Swayze et al. |
| 2015/0201937 A1 | 7/2015 | Swayze et al. |
| 2015/0201938 A1 | 7/2015 | Swayze et al. |
| 2015/0201939 A1 | 7/2015 | Swayze et al. |
| 2015/0201940 A1 | 7/2015 | Swayze et al. |
| 2015/0201941 A1 | 7/2015 | Swayze et al. |
| 2015/0209045 A1 | 7/2015 | Hodgkinson et al. |
| 2015/0222212 A1 | 8/2015 | Iwata |
| 2015/0223868 A1 | 8/2015 | Brandt et al. |
| 2015/0230697 A1 | 8/2015 | Phee et al. |
| 2015/0230794 A1 | 8/2015 | Wellman et al. |
| 2015/0231409 A1 | 8/2015 | Racenet et al. |
| 2015/0238118 A1 | 8/2015 | Legassey et al. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0297200 A1 | 10/2015 | Fitzsimmons et al. |
| 2015/0297222 A1 | 10/2015 | Huitema et al. |
| 2015/0297223 A1 | 10/2015 | Huitema et al. |
| 2015/0297225 A1 | 10/2015 | Huitema et al. |
| 2015/0297228 A1 | 10/2015 | Huitema et al. |
| 2015/0297233 A1 | 10/2015 | Huitema et al. |
| 2015/0297824 A1 | 10/2015 | Cabiri et al. |
| 2015/0303417 A1 | 10/2015 | Koeder et al. |
| 2015/0313594 A1 | 11/2015 | Shelton, IV et al. |
| 2015/0324317 A1 | 11/2015 | Collins et al. |
| 2015/0352699 A1 | 12/2015 | Sakai et al. |
| 2015/0366585 A1 | 12/2015 | Lemay et al. |
| 2015/0367497 A1 | 12/2015 | Ito et al. |
| 2015/0372265 A1 | 12/2015 | Morisaku et al. |
| 2015/0374372 A1 | 12/2015 | Zergiebel et al. |
| 2015/0374378 A1 | 12/2015 | Giordano et al. |
| 2016/0000431 A1 | 1/2016 | Giordano et al. |
| 2016/0000437 A1 | 1/2016 | Giordano et al. |
| 2016/0000452 A1 | 1/2016 | Yates et al. |
| 2016/0000453 A1 | 1/2016 | Yates et al. |
| 2016/0029998 A1 | 2/2016 | Brister et al. |
| 2016/0030042 A1 | 2/2016 | Heinrich et al. |
| 2016/0030043 A1 | 2/2016 | Fanelli et al. |
| 2016/0051316 A1 | 2/2016 | Boudreaux |
| 2016/0066913 A1 | 3/2016 | Swayze et al. |
| 2016/0069449 A1 | 3/2016 | Kanai et al. |
| 2016/0074035 A1 | 3/2016 | Whitman et al. |
| 2016/0074040 A1 | 3/2016 | Widenhouse et al. |
| 2016/0082161 A1 | 3/2016 | Zilberman et al. |
| 2016/0120545 A1 | 5/2016 | Shelton, IV et al. |
| 2016/0135835 A1 | 5/2016 | Onuma |
| 2016/0135895 A1 | 5/2016 | Faasse et al. |
| 2016/0139666 A1 | 5/2016 | Rubin et al. |
| 2016/0183939 A1 | 6/2016 | Shelton, IV et al. |
| 2016/0183943 A1 | 6/2016 | Shelton, IV |
| 2016/0183944 A1 | 6/2016 | Swensgard et al. |
| 2016/0192960 A1 | 7/2016 | Bueno et al. |
| 2016/0199063 A1 | 7/2016 | Mandakolathur Vasudevan et al. |
| 2016/0199956 A1 | 7/2016 | Shelton, IV et al. |
| 2016/0235494 A1 | 8/2016 | Shelton, IV et al. |
| 2016/0242783 A1 | 8/2016 | Shelton, IV et al. |
| 2016/0242855 A1 | 8/2016 | Fichtinger et al. |
| 2016/0249910 A1 | 9/2016 | Shelton, IV et al. |
| 2016/0249922 A1 | 9/2016 | Morgan et al. |
| 2016/0256159 A1 | 9/2016 | Pinjala et al. |
| 2016/0256184 A1* | 9/2016 | Shelton, IV ......... A61B 17/068 |
| 2016/0256221 A1 | 9/2016 | Smith |
| 2016/0256229 A1 | 9/2016 | Morgan et al. |
| 2016/0262745 A1 | 9/2016 | Morgan et al. |
| 2016/0262921 A1 | 9/2016 | Balbierz et al. |
| 2016/0270781 A1 | 9/2016 | Scirica |
| 2016/0287265 A1 | 10/2016 | Macdonald et al. |
| 2016/0287279 A1 | 10/2016 | Bovay et al. |
| 2016/0302820 A1 | 10/2016 | Hibner et al. |
| 2016/0310143 A1 | 10/2016 | Bettuchi |
| 2016/0314716 A1 | 10/2016 | Grubbs |
| 2016/0314717 A1 | 10/2016 | Grubbs |
| 2016/0345972 A1 | 12/2016 | Beardsley et al. |
| 2016/0367122 A1 | 12/2016 | Ichimura et al. |
| 2016/0374716 A1 | 12/2016 | Kessler |
| 2017/0000553 A1 | 1/2017 | Wiener et al. |
| 2017/0007234 A1 | 1/2017 | Chin et al. |
| 2017/0007244 A1 | 1/2017 | Shelton, IV et al. |
| 2017/0007245 A1 | 1/2017 | Shelton, IV et al. |
| 2017/0007250 A1 | 1/2017 | Shelton, IV et al. |
| 2017/0007347 A1 | 1/2017 | Jaworek et al. |
| 2017/0014125 A1 | 1/2017 | Shelton, IV et al. |
| 2017/0027572 A1 | 2/2017 | Nalagatla et al. |
| 2017/0049448 A1 | 2/2017 | Widenhouse et al. |
| 2017/0055819 A1 | 3/2017 | Hansen et al. |
| 2017/0056002 A1 | 3/2017 | Nalagatla et al. |
| 2017/0056005 A1 | 3/2017 | Shelton, IV et al. |
| 2017/0066054 A1 | 3/2017 | Birky |
| 2017/0079642 A1 | 3/2017 | Overmyer et al. |
| 2017/0086829 A1 | 3/2017 | Vendely et al. |
| 2017/0086830 A1 | 3/2017 | Yates et al. |
| 2017/0086831 A1 | 3/2017 | Shelton, IV et al. |
| 2017/0086842 A1 | 3/2017 | Shelton, IV et al. |
| 2017/0086930 A1 | 3/2017 | Thompson et al. |
| 2017/0095922 A1 | 4/2017 | Licht et al. |
| 2017/0105733 A1 | 4/2017 | Scheib et al. |
| 2017/0106302 A1 | 4/2017 | Cummings et al. |
| 2017/0135711 A1 | 5/2017 | Overmyer et al. |
| 2017/0135717 A1 | 5/2017 | Boudreaux et al. |
| 2017/0135747 A1 | 5/2017 | Broderick et al. |
| 2017/0172382 A1 | 6/2017 | Nir et al. |
| 2017/0172549 A1 | 6/2017 | Smaby et al. |
| 2017/0172662 A1 | 6/2017 | Panescu et al. |
| 2017/0182195 A1 | 6/2017 | Wagner |
| 2017/0182211 A1 | 6/2017 | Raxworthy et al. |
| 2017/0196558 A1 | 7/2017 | Morgan et al. |
| 2017/0196649 A1 | 7/2017 | Yates et al. |
| 2017/0202571 A1 | 7/2017 | Shelton, IV et al. |
| 2017/0202607 A1 | 7/2017 | Shelton, IV et al. |
| 2017/0202770 A1 | 7/2017 | Friedrich et al. |
| 2017/0209145 A1 | 7/2017 | Swayze et al. |
| 2017/0224332 A1 | 8/2017 | Hunter et al. |
| 2017/0224334 A1 | 8/2017 | Worthington et al. |
| 2017/0224339 A1 | 8/2017 | Huang et al. |
| 2017/0231627 A1 | 8/2017 | Shelton, IV et al. |
| 2017/0231628 A1 | 8/2017 | Shelton, IV et al. |
| 2017/0231629 A1 | 8/2017 | Stopek et al. |
| 2017/0238962 A1 | 8/2017 | Hansen et al. |
| 2017/0242455 A1 | 8/2017 | Dickens |
| 2017/0245949 A1 | 8/2017 | Randle |
| 2017/0249431 A1 | 8/2017 | Shelton, IV et al. |
| 2017/0255799 A1 | 9/2017 | Zhao et al. |
| 2017/0262110 A1 | 9/2017 | Polishchuk et al. |
| 2017/0265774 A1 | 9/2017 | Johnson et al. |
| 2017/0281171 A1 | 10/2017 | Shelton, IV et al. |
| 2017/0281173 A1 | 10/2017 | Shelton, IV et al. |
| 2017/0281186 A1 | 10/2017 | Shelton, IV et al. |
| 2017/0281189 A1 | 10/2017 | Nalagatla et al. |
| 2017/0290585 A1 | 10/2017 | Shelton, IV et al. |
| 2017/0296169 A1 | 10/2017 | Yates et al. |
| 2017/0296173 A1 | 10/2017 | Shelton, IV et al. |
| 2017/0296185 A1 | 10/2017 | Swensgard et al. |
| 2017/0296213 A1 | 10/2017 | Swensgard et al. |
| 2017/0312041 A1 | 11/2017 | Giordano et al. |
| 2017/0312042 A1 | 11/2017 | Giordano et al. |
| 2017/0319047 A1 | 11/2017 | Poulsen et al. |
| 2017/0319201 A1 | 11/2017 | Morgan et al. |
| 2017/0333034 A1 | 11/2017 | Morgan et al. |
| 2017/0333035 A1 | 11/2017 | Morgan et al. |
| 2017/0348010 A1 | 12/2017 | Chiang |
| 2017/0348043 A1 | 12/2017 | Wang et al. |
| 2017/0354413 A1 | 12/2017 | Chen et al. |
| 2017/0358052 A1 | 12/2017 | Yuan |
| 2017/0360441 A1 | 12/2017 | Sgroi |

(56) References Cited

U.S. PATENT DOCUMENTS

| | | |
|---|---|---|
| 2018/0000545 A1 | 1/2018 | Giordano et al. |
| 2018/0008356 A1 | 1/2018 | Giordano et al. |
| 2018/0028185 A1 | 2/2018 | Shelton, IV et al. |
| 2018/0042611 A1 | 2/2018 | Swayze et al. |
| 2018/0049794 A1 | 2/2018 | Swayze et al. |
| 2018/0051780 A1 | 2/2018 | Shelton, IV et al. |
| 2018/0055501 A1 | 3/2018 | Zemlok et al. |
| 2018/0055513 A1 | 3/2018 | Shelton, IV et al. |
| 2018/0064440 A1 | 3/2018 | Shelton, IV et al. |
| 2018/0064442 A1 | 3/2018 | Shelton, IV et al. |
| 2018/0064443 A1 | 3/2018 | Shelton, IV et al. |
| 2018/0070942 A1 | 3/2018 | Shelton, IV et al. |
| 2018/0085116 A1 | 3/2018 | Yates et al. |
| 2018/0085117 A1 | 3/2018 | Shelton, IV et al. |
| 2018/0085120 A1 | 3/2018 | Viola |
| 2018/0092710 A1 | 4/2018 | Bosisio et al. |
| 2018/0110522 A1 | 4/2018 | Shelton, IV et al. |
| 2018/0110523 A1 | 4/2018 | Shelton, IV |
| 2018/0114591 A1 | 4/2018 | Pribanic et al. |
| 2018/0116658 A1 | 5/2018 | Aronhalt, IV et al. |
| 2018/0116662 A1 | 5/2018 | Shelton, IV et al. |
| 2018/0125481 A1 | 5/2018 | Yates et al. |
| 2018/0125487 A1 | 5/2018 | Beardsley |
| 2018/0125488 A1 | 5/2018 | Morgan et al. |
| 2018/0125590 A1 | 5/2018 | Giordano et al. |
| 2018/0125594 A1 | 5/2018 | Beardsley |
| 2018/0126504 A1 | 5/2018 | Shelton, IV et al. |
| 2018/0132845 A1 | 5/2018 | Schmid et al. |
| 2018/0132849 A1 | 5/2018 | Miller et al. |
| 2018/0132850 A1 | 5/2018 | Leimbach et al. |
| 2018/0132926 A1 | 5/2018 | Asher et al. |
| 2018/0132952 A1 | 5/2018 | Spivey et al. |
| 2018/0133521 A1 | 5/2018 | Frushour et al. |
| 2018/0140299 A1 | 5/2018 | Weaner et al. |
| 2018/0146960 A1 | 5/2018 | Shelton, IV et al. |
| 2018/0153542 A1 | 6/2018 | Shelton, IV et al. |
| 2018/0153634 A1 | 6/2018 | Zemlok et al. |
| 2018/0161034 A1 | 6/2018 | Scheib et al. |
| 2018/0168572 A1 | 6/2018 | Burbank |
| 2018/0168574 A1 | 6/2018 | Robinson et al. |
| 2018/0168575 A1 | 6/2018 | Simms et al. |
| 2018/0168577 A1 | 6/2018 | Aronhalt et al. |
| 2018/0168578 A1 | 6/2018 | Aronhalt et al. |
| 2018/0168579 A1 | 6/2018 | Aronhalt et al. |
| 2018/0168584 A1 | 6/2018 | Harris et al. |
| 2018/0168590 A1 | 6/2018 | Overmyer et al. |
| 2018/0168592 A1 | 6/2018 | Overmyer et al. |
| 2018/0168597 A1 | 6/2018 | Fanelli et al. |
| 2018/0168598 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168610 A1 | 6/2018 | Shelton, IV et al. |
| 2018/0168614 A1 | 6/2018 | Shelton, IV et al. |
| 2018/0168615 A1 | 6/2018 | Shelton, IV et al. |
| 2018/0168618 A1 | 6/2018 | Scott et al. |
| 2018/0168619 A1 | 6/2018 | Scott et al. |
| 2018/0168623 A1 | 6/2018 | Simms et al. |
| 2018/0168625 A1 | 6/2018 | Posada et al. |
| 2018/0168633 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168649 A1 | 6/2018 | Shelton, IV et al. |
| 2018/0168650 A1 | 6/2018 | Shelton, IV et al. |
| 2018/0168754 A1 | 6/2018 | Overmyer |
| 2018/0228490 A1 | 8/2018 | Richard et al. |
| 2018/0235609 A1 | 8/2018 | Harris et al. |
| 2018/0236181 A1 | 8/2018 | Marlin et al. |
| 2018/0242970 A1 | 8/2018 | Mozdzierz |
| 2018/0250001 A1 | 9/2018 | Aronhalt et al. |
| 2018/0271520 A1 | 9/2018 | Shelton, IV et al. |
| 2018/0271604 A1 | 9/2018 | Grout et al. |
| 2018/0273597 A1 | 9/2018 | Stimson |
| 2018/0289369 A1 | 10/2018 | Shelton, IV et al. |
| 2018/0289371 A1 | 10/2018 | Wang et al. |
| 2018/0296211 A1 | 10/2018 | Timm et al. |
| 2018/0296216 A1 | 10/2018 | Shelton, IV et al. |
| 2018/0296290 A1 | 10/2018 | Namiki et al. |
| 2018/0317905 A1 | 11/2018 | Olson et al. |
| 2018/0333155 A1 | 11/2018 | Hall et al. |
| 2018/0333169 A1 | 11/2018 | Leimbach et al. |
| 2018/0344319 A1 | 12/2018 | Shelton, IV et al. |
| 2018/0353176 A1 | 12/2018 | Shelton, IV et al. |
| 2018/0353177 A1 | 12/2018 | Shelton, IV et al. |
| 2018/0353178 A1 | 12/2018 | Shelton, IV et al. |
| 2018/0353179 A1 | 12/2018 | Shelton, IV et al. |
| 2018/0360445 A1 | 12/2018 | Shelton, IV et al. |
| 2018/0360446 A1 | 12/2018 | Shelton, IV et al. |
| 2018/0360456 A1 | 12/2018 | Shelton, IV et al. |
| 2018/0360471 A1 | 12/2018 | Parfett et al. |
| 2018/0360472 A1 | 12/2018 | Harris et al. |
| 2018/0360473 A1 | 12/2018 | Shelton, IV et al. |
| 2018/0368066 A1 | 12/2018 | Howell et al. |
| 2018/0368833 A1 | 12/2018 | Shelton, IV et al. |
| 2018/0368838 A1 | 12/2018 | Shelton, IV et al. |
| 2018/0368839 A1 | 12/2018 | Shelton, IV et al. |
| 2018/0368843 A1 | 12/2018 | Shelton, IV et al. |
| 2018/0368844 A1 | 12/2018 | Bakos et al. |
| 2018/0368845 A1 | 12/2018 | Bakos et al. |
| 2018/0368846 A1 | 12/2018 | Shelton, IV et al. |
| 2018/0372806 A1 | 12/2018 | Laughery et al. |
| 2019/0000457 A1 | 1/2019 | Shelton, IV et al. |
| 2019/0000459 A1 | 1/2019 | Shelton, IV et al. |
| 2019/0000461 A1 | 1/2019 | Shelton, IV et al. |
| 2019/0000462 A1 | 1/2019 | Shelton, IV et al. |
| 2019/0000466 A1 | 1/2019 | Shelton, IV et al. |
| 2019/0000467 A1 | 1/2019 | Shelton, IV et al. |
| 2019/0000469 A1 | 1/2019 | Shelton, IV et al. |
| 2019/0000470 A1 | 1/2019 | Yates et al. |
| 2019/0000471 A1 | 1/2019 | Shelton, IV et al. |
| 2019/0000472 A1 | 1/2019 | Shelton, IV et al. |
| 2019/0000474 A1 | 1/2019 | Shelton, IV et al. |
| 2019/0000475 A1 | 1/2019 | Shelton, IV et al. |
| 2019/0000476 A1 | 1/2019 | Shelton, IV et al. |
| 2019/0000477 A1 | 1/2019 | Shelton, IV et al. |
| 2019/0000478 A1 | 1/2019 | Messerly et al. |
| 2019/0000481 A1 | 1/2019 | Harris et al. |
| 2019/0000525 A1 | 1/2019 | Messerly et al. |
| 2019/0000531 A1 | 1/2019 | Messerly et al. |
| 2019/0008515 A1 | 1/2019 | Beardsley et al. |
| 2019/0015102 A1 | 1/2019 | Baber et al. |
| 2019/0015165 A1 | 1/2019 | Giordano et al. |
| 2019/0021733 A1 | 1/2019 | Burbank |
| 2019/0029682 A1 | 1/2019 | Huitema et al. |
| 2019/0029701 A1 | 1/2019 | Shelton, IV et al. |
| 2019/0033955 A1 | 1/2019 | Leimbach et al. |
| 2019/0038279 A1 | 2/2019 | Shelton, IV et al. |
| 2019/0038281 A1 | 2/2019 | Shelton, IV et al. |
| 2019/0038282 A1 | 2/2019 | Shelton, IV et al. |
| 2019/0038283 A1 | 2/2019 | Shelton, IV et al. |
| 2019/0038285 A1 | 2/2019 | Mozdzierz |
| 2019/0076143 A1 | 3/2019 | Smith |
| 2019/0090871 A1 | 3/2019 | Shelton, IV et al. |
| 2019/0091183 A1 | 3/2019 | Tomat et al. |
| 2019/0099179 A1 | 4/2019 | Leimbach et al. |
| 2019/0099181 A1 | 4/2019 | Shelton, IV et al. |
| 2019/0099229 A1 | 4/2019 | Spivey et al. |
| 2019/0104919 A1 | 4/2019 | Shelton, IV et al. |
| 2019/0105035 A1 | 4/2019 | Shelton, IV et al. |
| 2019/0105036 A1 | 4/2019 | Morgan et al. |
| 2019/0105037 A1 | 4/2019 | Morgan et al. |
| 2019/0105038 A1 | 4/2019 | Schmid et al. |
| 2019/0105039 A1 | 4/2019 | Morgan et al. |
| 2019/0105043 A1 | 4/2019 | Jaworek et al. |
| 2019/0105044 A1 | 4/2019 | Shelton, IV et al. |
| 2019/0110779 A1 | 4/2019 | Gardner et al. |
| 2019/0110791 A1 | 4/2019 | Shelton, IV et al. |
| 2019/0110792 A1 | 4/2019 | Shelton, IV et al. |
| 2019/0117216 A1 | 4/2019 | Overmyer et al. |
| 2019/0117222 A1 | 4/2019 | Shelton, IV et al. |
| 2019/0117224 A1 | 4/2019 | Setser et al. |
| 2019/0125320 A1 | 5/2019 | Shelton, IV et al. |
| 2019/0125321 A1 | 5/2019 | Shelton, IV et al. |
| 2019/0125324 A1 | 5/2019 | Scheib et al. |
| 2019/0125335 A1 | 5/2019 | Shelton, IV et al. |

(56) References Cited

U.S. PATENT DOCUMENTS

| | | |
|---|---|---|
| 2019/0125336 A1 | 5/2019 | Deck et al. |
| 2019/0125338 A1 | 5/2019 | Shelton, IV et al. |
| 2019/0125342 A1 | 5/2019 | Beardsley et al. |
| 2019/0125343 A1 | 5/2019 | Wise et al. |
| 2019/0125348 A1 | 5/2019 | Shelton, IV et al. |
| 2019/0125352 A1 | 5/2019 | Shelton, IV et al. |
| 2019/0125353 A1 | 5/2019 | Shelton, IV et al. |
| 2019/0125354 A1 | 5/2019 | Deck et al. |
| 2019/0125355 A1 | 5/2019 | Shelton, IV et al. |
| 2019/0125356 A1 | 5/2019 | Shelton, IV et al. |
| 2019/0125357 A1 | 5/2019 | Shelton, IV et al. |
| 2019/0125358 A1 | 5/2019 | Shelton, IV et al. |
| 2019/0125359 A1 | 5/2019 | Shelton, IV et al. |
| 2019/0125360 A1 | 5/2019 | Shelton, IV et al. |
| 2019/0125361 A1 | 5/2019 | Shelton, IV et al. |
| 2019/0125377 A1 | 5/2019 | Shelton, IV |
| 2019/0125378 A1 | 5/2019 | Shelton, IV et al. |
| 2019/0125379 A1 | 5/2019 | Shelton, IV et al. |
| 2019/0125380 A1 | 5/2019 | Hunter et al. |
| 2019/0125384 A1 | 5/2019 | Scheib et al. |
| 2019/0125387 A1 | 5/2019 | Parihar et al. |
| 2019/0125388 A1 | 5/2019 | Shelton, IV et al. |
| 2019/0125430 A1 | 5/2019 | Shelton, IV et al. |
| 2019/0125431 A1 | 5/2019 | Shelton, IV et al. |
| 2019/0125432 A1 | 5/2019 | Shelton, IV et al. |
| 2019/0125454 A1 | 5/2019 | Stokes et al. |
| 2019/0125455 A1 | 5/2019 | Shelton, IV et al. |
| 2019/0125456 A1 | 5/2019 | Shelton, IV et al. |
| 2019/0125457 A1 | 5/2019 | Parihar et al. |
| 2019/0125458 A1 | 5/2019 | Shelton, IV et al. |
| 2019/0125459 A1 | 5/2019 | Shelton, IV et al. |
| 2019/0125476 A1 | 5/2019 | Shelton, IV et al. |
| 2019/0133422 A1 | 5/2019 | Nakamura |
| 2019/0138770 A1 | 5/2019 | Compaijen et al. |
| 2019/0142421 A1 | 5/2019 | Shelton, IV |
| 2019/0150925 A1 | 5/2019 | Marczyk et al. |
| 2019/0151029 A1 | 5/2019 | Robinson |
| 2019/0159778 A1 | 5/2019 | Shelton, IV et al. |
| 2019/0175847 A1 | 6/2019 | Pocreva, III et al. |
| 2019/0183491 A1 | 6/2019 | Shelton, IV et al. |
| 2019/0183496 A1 | 6/2019 | Shelton, IV et al. |
| 2019/0183498 A1 | 6/2019 | Shelton, IV et al. |
| 2019/0183499 A1 | 6/2019 | Shelton, IV et al. |
| 2019/0183501 A1 | 6/2019 | Shelton, IV et al. |
| 2019/0183502 A1 | 6/2019 | Shelton, IV et al. |
| 2019/0183594 A1 | 6/2019 | Shelton, IV et al. |
| 2019/0192138 A1 | 6/2019 | Shelton, IV et al. |
| 2019/0192141 A1 | 6/2019 | Shelton, IV et al. |
| 2019/0192144 A1 | 6/2019 | Parfett et al. |
| 2019/0192146 A1 | 6/2019 | Widenhouse et al. |
| 2019/0192147 A1 | 6/2019 | Shelton, IV et al. |
| 2019/0192148 A1 | 6/2019 | Shelton, IV et al. |
| 2019/0192149 A1 | 6/2019 | Shelton, IV et al. |
| 2019/0192150 A1 | 6/2019 | Widenhouse et al. |
| 2019/0192151 A1 | 6/2019 | Shelton, IV et al. |
| 2019/0192152 A1 | 6/2019 | Morgan et al. |
| 2019/0192153 A1 | 6/2019 | Shelton, IV et al. |
| 2019/0192154 A1 | 6/2019 | Shelton, IV et al. |
| 2019/0192155 A1 | 6/2019 | Shelton, IV et al. |
| 2019/0192156 A1 | 6/2019 | Simms et al. |
| 2019/0192157 A1 | 6/2019 | Scott et al. |
| 2019/0192158 A1 | 6/2019 | Scott et al. |
| 2019/0192159 A1 | 6/2019 | Simms et al. |
| 2019/0192227 A1 | 6/2019 | Shelton, IV et al. |
| 2019/0192235 A1 | 6/2019 | Harris et al. |
| 2019/0192236 A1 | 6/2019 | Shelton, IV et al. |
| 2019/0200844 A1 | 7/2019 | Shelton, IV et al. |
| 2019/0200863 A1 | 7/2019 | Shelton, IV et al. |
| 2019/0200905 A1 | 7/2019 | Shelton, IV et al. |
| 2019/0200906 A1 | 7/2019 | Shelton, IV et al. |
| 2019/0200977 A1 | 7/2019 | Shelton, IV et al. |
| 2019/0200981 A1 | 7/2019 | Harris et al. |
| 2019/0200998 A1 | 7/2019 | Shelton, IV et al. |
| 2019/0201023 A1 | 7/2019 | Shelton, IV et al. |
| 2019/0201024 A1 | 7/2019 | Shelton, IV et al. |
| 2019/0201025 A1 | 7/2019 | Shelton, IV et al. |
| 2019/0201026 A1 | 7/2019 | Shelton, IV et al. |
| 2019/0201027 A1 | 7/2019 | Shelton, IV et al. |
| 2019/0201028 A1 | 7/2019 | Shelton, IV et al. |
| 2019/0201029 A1 | 7/2019 | Shelton, IV et al. |
| 2019/0201030 A1 | 7/2019 | Shelton, IV et al. |
| 2019/0201033 A1 | 7/2019 | Yates et al. |
| 2019/0201034 A1 | 7/2019 | Shelton, IV et al. |
| 2019/0201045 A1 | 7/2019 | Yates et al. |
| 2019/0201046 A1 | 7/2019 | Shelton, IV et al. |
| 2019/0201047 A1 | 7/2019 | Yates et al. |
| 2019/0201104 A1 | 7/2019 | Shelton, IV et al. |
| 2019/0201112 A1 | 7/2019 | Wiener et al. |
| 2019/0201113 A1 | 7/2019 | Shelton, IV et al. |
| 2019/0201114 A1 | 7/2019 | Shelton, IV et al. |
| 2019/0201115 A1 | 7/2019 | Shelton, IV et al. |
| 2019/0201116 A1 | 7/2019 | Shelton, IV et al. |
| 2019/0201118 A1 | 7/2019 | Shelton, IV et al. |
| 2019/0201120 A1 | 7/2019 | Shelton, IV et al. |
| 2019/0201135 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201138 A1 | 7/2019 | Yates et al. |
| 2019/0201139 A1 | 7/2019 | Shelton, IV et al. |
| 2019/0201140 A1 | 7/2019 | Yates et al. |
| 2019/0201141 A1 | 7/2019 | Shelton, IV et al. |
| 2019/0201142 A1 | 7/2019 | Shelton, IV et al. |
| 2019/0201145 A1 | 7/2019 | Shelton, IV et al. |
| 2019/0201594 A1 | 7/2019 | Shelton, IV et al. |
| 2019/0205001 A1 | 7/2019 | Messerly et al. |
| 2019/0205566 A1 | 7/2019 | Shelton, IV et al. |
| 2019/0205567 A1 | 7/2019 | Shelton, IV et al. |
| 2019/0206003 A1 | 7/2019 | Harris et al. |
| 2019/0206004 A1 | 7/2019 | Shelton, IV et al. |
| 2019/0206050 A1 | 7/2019 | Yates et al. |
| 2019/0206551 A1 | 7/2019 | Yates et al. |
| 2019/0206555 A1 | 7/2019 | Morgan et al. |
| 2019/0206561 A1 | 7/2019 | Shelton, IV et al. |
| 2019/0206562 A1 | 7/2019 | Shelton, IV et al. |
| 2019/0206563 A1 | 7/2019 | Shelton, IV et al. |
| 2019/0206564 A1 | 7/2019 | Shelton, IV et al. |
| 2019/0206565 A1 | 7/2019 | Shelton, IV |
| 2019/0206569 A1 | 7/2019 | Shelton, IV et al. |
| 2019/0208641 A1 | 7/2019 | Yates et al. |
| 2019/0209164 A1 | 7/2019 | Timm et al. |
| 2019/0209165 A1 | 7/2019 | Timm et al. |
| 2019/0209171 A1 | 7/2019 | Shelton, IV et al. |
| 2019/0209172 A1 | 7/2019 | Shelton, IV et al. |
| 2019/0209247 A1 | 7/2019 | Giordano et al. |
| 2019/0209248 A1 | 7/2019 | Giordano et al. |
| 2019/0209249 A1 | 7/2019 | Giordano et al. |
| 2019/0209250 A1 | 7/2019 | Giordano et al. |
| 2019/0216558 A1 | 7/2019 | Giordano et al. |
| 2019/0223865 A1 | 7/2019 | Shelton, IV et al. |
| 2019/0261983 A1 | 8/2019 | Granger et al. |
| 2019/0261984 A1 | 8/2019 | Nelson et al. |
| 2019/0261987 A1 | 8/2019 | Viola et al. |
| 2019/0261991 A1 | 8/2019 | Beckman et al. |
| 2019/0269400 A1 | 9/2019 | Mandakolathur Vasudevan et al. |
| 2019/0269402 A1 | 9/2019 | Murray et al. |
| 2019/0269407 A1 | 9/2019 | Swensgard et al. |
| 2019/0269428 A1 | 9/2019 | Allen et al. |
| 2019/0274677 A1 | 9/2019 | Shelton, IV |
| 2019/0274678 A1 | 9/2019 | Shelton, IV |
| 2019/0274679 A1 | 9/2019 | Shelton, IV |
| 2019/0274680 A1 | 9/2019 | Shelton, IV |
| 2019/0274685 A1 | 9/2019 | Olson et al. |
| 2019/0282233 A1 | 9/2019 | Burbank et al. |
| 2019/0290263 A1 | 9/2019 | Morgan et al. |
| 2019/0290264 A1 | 9/2019 | Morgan et al. |
| 2019/0290265 A1 | 9/2019 | Shelton, IV et al. |
| 2019/0290266 A1 | 9/2019 | Scheib et al. |
| 2019/0290267 A1 | 9/2019 | Baxter, III et al. |
| 2019/0290274 A1 | 9/2019 | Shelton, IV |
| 2019/0290281 A1 | 9/2019 | Aronhalt et al. |
| 2019/0290297 A1 | 9/2019 | Haider et al. |
| 2019/0298340 A1 | 10/2019 | Shelton, IV et al. |
| 2019/0298341 A1 | 10/2019 | Shelton, IV et al. |
| 2019/0298342 A1 | 10/2019 | Shelton, IV et al. |

(56) References Cited

U.S. PATENT DOCUMENTS

| | | |
|---|---|---|
| 2019/0298343 A1 | 10/2019 | Shelton, IV et al. |
| 2019/0298346 A1 | 10/2019 | Shelton, IV et al. |
| 2019/0298347 A1 | 10/2019 | Shelton, IV et al. |
| 2019/0298348 A1 | 10/2019 | Harris et al. |
| 2019/0298350 A1 | 10/2019 | Shelton, IV et al. |
| 2019/0298352 A1 | 10/2019 | Shelton, IV et al. |
| 2019/0298353 A1 | 10/2019 | Shelton, IV et al. |
| 2019/0298354 A1 | 10/2019 | Shelton, IV et al. |
| 2019/0298355 A1 | 10/2019 | Shelton, IV et al. |
| 2019/0298356 A1 | 10/2019 | Shelton, IV et al. |
| 2019/0298357 A1 | 10/2019 | Shelton, IV et al. |
| 2019/0298360 A1 | 10/2019 | Shelton, IV et al. |
| 2019/0298361 A1 | 10/2019 | Shelton, IV et al. |
| 2019/0298362 A1 | 10/2019 | Shelton, IV et al. |
| 2019/0307452 A1 | 10/2019 | Shelton, IV et al. |
| 2019/0307453 A1 | 10/2019 | Shelton, IV et al. |
| 2019/0307454 A1 | 10/2019 | Shelton, IV et al. |
| 2019/0307455 A1 | 10/2019 | Shelton, IV et al. |
| 2019/0307456 A1 | 10/2019 | Shelton, IV et al. |
| 2019/0307476 A1 | 10/2019 | Shelton, IV et al. |
| 2019/0307477 A1 | 10/2019 | Shelton, IV et al. |
| 2019/0307478 A1 | 10/2019 | Shelton, IV et al. |
| 2019/0307479 A1 | 10/2019 | Shelton, IV et al. |
| 2019/0314016 A1 | 10/2019 | Huitema et al. |
| 2019/0314017 A1 | 10/2019 | Huitema et al. |
| 2019/0314018 A1 | 10/2019 | Huitema et al. |
| 2019/0321039 A1 | 10/2019 | Harris et al. |
| 2019/0321040 A1 | 10/2019 | Shelton, IV |
| 2019/0321041 A1 | 10/2019 | Shelton, IV |
| 2019/0321062 A1 | 10/2019 | Williams |
| 2019/0328386 A1 | 10/2019 | Harris et al. |
| 2019/0328387 A1 | 10/2019 | Overmyer et al. |
| 2019/0328390 A1 | 10/2019 | Harris et al. |
| 2019/0336128 A1 | 11/2019 | Harris et al. |
| 2019/0343514 A1 | 11/2019 | Shelton, IV et al. |
| 2019/0343515 A1 | 11/2019 | Morgan et al. |
| 2019/0343518 A1 | 11/2019 | Shelton, IV |
| 2019/0343525 A1 | 11/2019 | Shelton, IV et al. |
| 2019/0350581 A1 | 11/2019 | Baxter, III et al. |
| 2019/0350582 A1 | 11/2019 | Shelton, IV et al. |
| 2019/0357909 A1 | 11/2019 | Huitema et al. |
| 2019/0365384 A1 | 12/2019 | Baxter, III et al. |
| 2019/0374224 A1 | 12/2019 | Huitema et al. |
| 2020/0000461 A1 | 1/2020 | Yates et al. |
| 2020/0000468 A1 | 1/2020 | Shelton, IV et al. |
| 2020/0000469 A1 | 1/2020 | Shelton, IV et al. |
| 2020/0000471 A1 | 1/2020 | Shelton, IV et al. |
| 2020/0000531 A1 | 1/2020 | Giordano et al. |
| 2020/0008800 A1 | 1/2020 | Shelton, IV et al. |
| 2020/0008802 A1 | 1/2020 | Aronhalt et al. |
| 2020/0008809 A1 | 1/2020 | Shelton, IV et al. |
| 2020/0015819 A1 | 1/2020 | Shelton, IV et al. |
| 2020/0015915 A1 | 1/2020 | Swayze et al. |
| 2020/0022702 A1 | 1/2020 | Shelton, IV et al. |
| 2020/0029964 A1 | 1/2020 | Overmyer et al. |
| 2020/0030050 A1 | 1/2020 | Shelton, IV et al. |
| 2020/0038016 A1 | 2/2020 | Shelton, IV et al. |
| 2020/0038018 A1 | 2/2020 | Shelton, IV et al. |
| 2020/0038020 A1 | 2/2020 | Yates et al. |
| 2020/0046348 A1 | 2/2020 | Shelton, IV et al. |
| 2020/0046893 A1 | 2/2020 | Shelton, IV et al. |
| 2020/0054320 A1 | 2/2020 | Harris et al. |
| 2020/0054321 A1 | 2/2020 | Harris et al. |
| 2020/0054322 A1 | 2/2020 | Harris et al. |
| 2020/0054323 A1 | 2/2020 | Harris et al. |
| 2020/0054324 A1 | 2/2020 | Shelton, IV et al. |
| 2020/0054325 A1 | 2/2020 | Harris et al. |
| 2020/0054326 A1 | 2/2020 | Harris et al. |
| 2020/0054330 A1 | 2/2020 | Harris et al. |
| 2020/0054332 A1 | 2/2020 | Shelton, IV et al. |
| 2020/0054333 A1 | 2/2020 | Shelton, IV et al. |
| 2020/0054334 A1 | 2/2020 | Shelton, IV et al. |
| 2020/0054355 A1 | 2/2020 | Laurent et al. |
| 2020/0060523 A1 | 2/2020 | Matsuda et al. |
| 2020/0060680 A1 | 2/2020 | Shelton, IV et al. |
| 2020/0060681 A1 | 2/2020 | Shelton, IV et al. |
| 2020/0060713 A1 | 2/2020 | Leimbach et al. |
| 2020/0077994 A1 | 3/2020 | Shelton, IV et al. |
| 2020/0078015 A1 | 3/2020 | Miller et al. |
| 2020/0078016 A1 | 3/2020 | Swayze et al. |
| 2020/0085427 A1 | 3/2020 | Giordano et al. |
| 2020/0085431 A1 | 3/2020 | Swayze et al. |
| 2020/0085435 A1 | 3/2020 | Shelton, IV et al. |
| 2020/0085436 A1 | 3/2020 | Beckman et al. |
| 2020/0085518 A1 | 3/2020 | Giordano et al. |
| 2020/0093484 A1 | 3/2020 | Shelton, IV et al. |
| 2020/0093485 A1 | 3/2020 | Shelton, IV et al. |
| 2020/0093487 A1 | 3/2020 | Baber et al. |
| 2020/0093488 A1 | 3/2020 | Baber et al. |
| 2020/0093506 A1 | 3/2020 | Leimbach et al. |
| 2020/0093550 A1 | 3/2020 | Spivey et al. |
| 2020/0100699 A1 | 4/2020 | Shelton, IV et al. |
| 2020/0100783 A1 | 4/2020 | Yates et al. |
| 2020/0100787 A1 | 4/2020 | Shelton, IV et al. |
| 2020/0107829 A1 | 4/2020 | Shelton, IV et al. |
| 2020/0138434 A1 | 5/2020 | Miller et al. |
| 2020/0138435 A1 | 5/2020 | Shelton, IV et al. |
| 2020/0138436 A1 | 5/2020 | Yates et al. |
| 2020/0138437 A1 | 5/2020 | Vendely et al. |
| 2020/0138534 A1 | 5/2020 | Garcia Kilroy et al. |
| 2020/0146676 A1 | 5/2020 | Yates et al. |
| 2020/0146678 A1 | 5/2020 | Leimbach et al. |
| 2020/0146741 A1 | 5/2020 | Long et al. |
| 2020/0155151 A1 | 5/2020 | Overmyer et al. |
| 2020/0155155 A1 | 5/2020 | Shelton, IV et al. |
| 2020/0178958 A1 | 6/2020 | Overmyer et al. |
| 2020/0178960 A1 | 6/2020 | Overmyer et al. |
| 2020/0187943 A1 | 6/2020 | Shelton, IV et al. |
| 2020/0197027 A1 | 6/2020 | Hershberger et al. |
| 2020/0205811 A1 | 7/2020 | Posey et al. |
| 2020/0214706 A1 | 7/2020 | Vendely et al. |
| 2020/0214731 A1 | 7/2020 | Shelton, IV et al. |
| 2020/0222047 A1 | 7/2020 | Shelton, IV et al. |
| 2020/0229812 A1 | 7/2020 | Parihar et al. |
| 2020/0229814 A1 | 7/2020 | Amariglio et al. |
| 2020/0229816 A1 | 7/2020 | Bakos et al. |
| 2020/0237371 A1 | 7/2020 | Huitema et al. |
| 2020/0246001 A1 | 8/2020 | Ming et al. |
| 2020/0253605 A1 | 8/2020 | Swayze et al. |
| 2020/0261075 A1 | 8/2020 | Boudreaux et al. |
| 2020/0261076 A1 | 8/2020 | Boudreaux et al. |
| 2020/0261077 A1 | 8/2020 | Shelton, IV et al. |
| 2020/0261078 A1 | 8/2020 | Bakos et al. |
| 2020/0261080 A1 | 8/2020 | Bakos et al. |
| 2020/0261081 A1 | 8/2020 | Boudreaux et al. |
| 2020/0261082 A1 | 8/2020 | Boudreaux et al. |
| 2020/0261083 A1 | 8/2020 | Bakos et al. |
| 2020/0261084 A1 | 8/2020 | Bakos et al. |
| 2020/0261085 A1 | 8/2020 | Boudreaux et al. |
| 2020/0261086 A1 | 8/2020 | Zeiner et al. |
| 2020/0261087 A1 | 8/2020 | Timm et al. |
| 2020/0261088 A1 | 8/2020 | Harris et al. |
| 2020/0261089 A1 | 8/2020 | Shelton, IV et al. |
| 2020/0261106 A1 | 8/2020 | Hess et al. |
| 2020/0268377 A1 | 8/2020 | Schmid et al. |
| 2020/0268394 A1 | 8/2020 | Parfett et al. |
| 2020/0275926 A1 | 9/2020 | Shelton, IV et al. |
| 2020/0275927 A1 | 9/2020 | Shelton, IV et al. |
| 2020/0275928 A1 | 9/2020 | Shelton, IV et al. |
| 2020/0275930 A1 | 9/2020 | Harris et al. |
| 2020/0280219 A1 | 9/2020 | Laughery et al. |
| 2020/0281585 A1 | 9/2020 | Timm et al. |
| 2020/0281587 A1 | 9/2020 | Schmid et al. |
| 2020/0281590 A1 | 9/2020 | Shelton, IV et al. |
| 2020/0289112 A1 | 9/2020 | Whitfield et al. |
| 2020/0297340 A1 | 9/2020 | Hess et al. |
| 2020/0297341 A1 | 9/2020 | Yates et al. |
| 2020/0297346 A1 | 9/2020 | Shelton, IV et al. |
| 2020/0297438 A1 | 9/2020 | Shelton, IV et al. |
| 2020/0305862 A1 | 10/2020 | Yates et al. |
| 2020/0305863 A1 | 10/2020 | Yates et al. |
| 2020/0305864 A1 | 10/2020 | Yates et al. |
| 2020/0305865 A1 | 10/2020 | Shelton, IV |
| 2020/0305868 A1 | 10/2020 | Shelton, IV |

(56) References Cited

U.S. PATENT DOCUMENTS

| | | |
|---|---|---|
| 2020/0305869 A1 | 10/2020 | Shelton, IV |
| 2020/0305870 A1 | 10/2020 | Shelton, IV |
| 2020/0305871 A1 | 10/2020 | Shelton, IV et al. |
| 2020/0305872 A1 | 10/2020 | Weidner et al. |
| 2020/0305874 A1 | 10/2020 | Huitema et al. |
| 2020/0315612 A1 | 10/2020 | Shelton, IV et al. |
| 2020/0315616 A1 | 10/2020 | Yates et al. |
| 2020/0315625 A1 | 10/2020 | Hall et al. |
| 2020/0315983 A1 | 10/2020 | Widenhouse et al. |
| 2020/0323526 A1 | 10/2020 | Huang et al. |
| 2020/0330092 A1 | 10/2020 | Shelton, IV et al. |
| 2020/0330093 A1 | 10/2020 | Shelton, IV et al. |
| 2020/0330094 A1 | 10/2020 | Baxter, III et al. |
| 2020/0330096 A1 | 10/2020 | Shelton, IV et al. |
| 2020/0330181 A1 | 10/2020 | Junger et al. |
| 2020/0337693 A1 | 10/2020 | Shelton, IV et al. |
| 2020/0337702 A1 | 10/2020 | Shelton, IV et al. |
| 2020/0337703 A1 | 10/2020 | Shelton, IV et al. |
| 2020/0337791 A1 | 10/2020 | Shelton, IV et al. |
| 2020/0345346 A1 | 11/2020 | Shelton, IV et al. |
| 2020/0345349 A1 | 11/2020 | Kimball et al. |
| 2020/0345352 A1 | 11/2020 | Shelton, IV et al. |
| 2020/0345353 A1 | 11/2020 | Leimbach et al. |
| 2020/0345354 A1 | 11/2020 | Leimbach et al. |
| 2020/0345355 A1 | 11/2020 | Baxter, III et al. |
| 2020/0345356 A1 | 11/2020 | Leimbach et al. |
| 2020/0345357 A1 | 11/2020 | Leimbach et al. |
| 2020/0345358 A1 | 11/2020 | Jenkins |
| 2020/0345359 A1 | 11/2020 | Baxter, III et al. |
| 2020/0345360 A1 | 11/2020 | Leimbach et al. |
| 2020/0345446 A1 | 11/2020 | Kimball et al. |
| 2020/0352562 A1 | 11/2020 | Timm et al. |
| 2020/0367885 A1 | 11/2020 | Yates et al. |
| 2020/0367886 A1 | 11/2020 | Shelton, IV et al. |
| 2020/0375585 A1 | 12/2020 | Swayze et al. |
| 2020/0375592 A1 | 12/2020 | Hall et al. |
| 2020/0375593 A1 | 12/2020 | Hunter et al. |
| 2020/0375597 A1 | 12/2020 | Shelton, IV et al. |
| 2020/0390444 A1 | 12/2020 | Harris et al. |
| 2020/0397433 A1 | 12/2020 | Lytle, IV et al. |
| 2020/0397434 A1 | 12/2020 | Overmyer et al. |
| 2020/0405290 A1 | 12/2020 | Shelton, IV et al. |
| 2020/0405291 A1 | 12/2020 | Shelton, IV et al. |
| 2020/0405292 A1 | 12/2020 | Shelton, IV et al. |
| 2020/0405293 A1 | 12/2020 | Shelton, IV et al. |
| 2020/0405294 A1 | 12/2020 | Shelton, IV |
| 2020/0405295 A1 | 12/2020 | Shelton, IV et al. |
| 2020/0405296 A1 | 12/2020 | Shelton, IV et al. |
| 2020/0405297 A1 | 12/2020 | Shelton, IV et al. |
| 2020/0405301 A1 | 12/2020 | Shelton, IV et al. |
| 2020/0405302 A1 | 12/2020 | Shelton, IV et al. |
| 2020/0405303 A1 | 12/2020 | Shelton, IV |
| 2020/0405305 A1 | 12/2020 | Shelton, IV et al. |
| 2020/0405306 A1 | 12/2020 | Shelton, IV et al. |
| 2020/0405307 A1 | 12/2020 | Shelton, IV et al. |
| 2020/0405308 A1 | 12/2020 | Shelton, IV |
| 2020/0405309 A1 | 12/2020 | Shelton, IV et al. |
| 2020/0405311 A1 | 12/2020 | Shelton, IV et al. |
| 2020/0405312 A1 | 12/2020 | Shelton, IV et al. |
| 2020/0405313 A1 | 12/2020 | Shelton, IV |
| 2020/0405316 A1 | 12/2020 | Shelton, IV et al. |
| 2020/0405341 A1 | 12/2020 | Hess et al. |
| 2020/0405409 A1 | 12/2020 | Shelton, IV et al. |
| 2020/0405410 A1 | 12/2020 | Shelton, IV |
| 2020/0405416 A1 | 12/2020 | Shelton, IV et al. |
| 2020/0405422 A1 | 12/2020 | Shelton, IV et al. |
| 2020/0405436 A1 | 12/2020 | Shelton, IV et al. |
| 2020/0405437 A1 | 12/2020 | Shelton, IV et al. |
| 2020/0405438 A1 | 12/2020 | Shelton, IV et al. |
| 2020/0405439 A1 | 12/2020 | Shelton, IV et al. |
| 2020/0405440 A1 | 12/2020 | Shelton, IV et al. |
| 2020/0405441 A1 | 12/2020 | Shelton, IV et al. |
| 2020/0410177 A1 | 12/2020 | Shelton, IV |
| 2020/0410180 A1 | 12/2020 | Shelton, IV et al. |
| 2021/0000466 A1 | 1/2021 | Leimbach et al. |
| 2021/0000467 A1 | 1/2021 | Shelton, IV et al. |
| 2021/0000470 A1 | 1/2021 | Leimbach et al. |
| 2021/0015480 A1 | 1/2021 | Shelton, IV et al. |
| 2021/0022741 A1 | 1/2021 | Baxter, III et al. |
| 2021/0030416 A1 | 2/2021 | Shelton, IV et al. |
| 2021/0045742 A1 | 2/2021 | Shelton, IV et al. |
| 2021/0052271 A1 | 2/2021 | Harris et al. |
| 2021/0059661 A1 | 3/2021 | Schmid et al. |
| 2021/0059662 A1 | 3/2021 | Shelton, IV |
| 2021/0059664 A1 | 3/2021 | Hensel et al. |
| 2021/0059666 A1 | 3/2021 | Schmid et al. |
| 2021/0059669 A1 | 3/2021 | Yates et al. |
| 2021/0059670 A1 | 3/2021 | Overmyer et al. |
| 2021/0059671 A1 | 3/2021 | Shelton, IV et al. |
| 2021/0059672 A1 | 3/2021 | Giordano et al. |
| 2021/0059673 A1 | 3/2021 | Shelton, IV et al. |
| 2021/0068817 A1 | 3/2021 | Shelton, IV et al. |
| 2021/0068818 A1 | 3/2021 | Overmyer et al. |
| 2021/0068820 A1 | 3/2021 | Parihar et al. |
| 2021/0068829 A1 | 3/2021 | Miller et al. |
| 2021/0068830 A1 | 3/2021 | Baber et al. |
| 2021/0068831 A1 | 3/2021 | Baber et al. |
| 2021/0068832 A1 | 3/2021 | Yates et al. |
| 2021/0068835 A1 | 3/2021 | Shelton, IV et al. |
| 2021/0077092 A1 | 3/2021 | Parihar et al. |
| 2021/0077099 A1 | 3/2021 | Shelton, IV et al. |
| 2021/0077100 A1 | 3/2021 | Shelton, IV et al. |
| 2021/0077109 A1 | 3/2021 | Harris et al. |
| 2021/0085313 A1 | 3/2021 | Morgan et al. |
| 2021/0085314 A1 | 3/2021 | Schmid et al. |
| 2021/0085315 A1 | 3/2021 | Aronhalt et al. |
| 2021/0085316 A1 | 3/2021 | Harris et al. |
| 2021/0085317 A1 | 3/2021 | Miller et al. |
| 2021/0085318 A1 | 3/2021 | Swayze et al. |
| 2021/0085319 A1 | 3/2021 | Swayze et al. |
| 2021/0085320 A1 | 3/2021 | Leimbach et al. |
| 2021/0085321 A1 | 3/2021 | Shelton, IV et al. |
| 2021/0085325 A1 | 3/2021 | Shelton, IV et al. |
| 2021/0085326 A1 | 3/2021 | Vendely et al. |
| 2021/0093321 A1 | 4/2021 | Auld et al. |
| 2021/0093323 A1 | 4/2021 | Scirica et al. |
| 2021/0100541 A1 | 4/2021 | Shelton, IV et al. |
| 2021/0100550 A1 | 4/2021 | Shelton, IV et al. |
| 2021/0100982 A1 | 4/2021 | Laby et al. |
| 2021/0106333 A1 | 4/2021 | Shelton, IV et al. |
| 2021/0107031 A1 | 4/2021 | Bales, Jr. et al. |
| 2021/0121175 A1 | 4/2021 | Yates et al. |
| 2021/0128146 A1 | 5/2021 | Shelton, IV et al. |
| 2021/0137522 A1 | 5/2021 | Shelton, IV et al. |
| 2021/0186490 A1 | 6/2021 | Shelton, IV et al. |
| 2021/0186492 A1 | 6/2021 | Shelton, IV et al. |
| 2021/0186493 A1 | 6/2021 | Shelton, IV et al. |
| 2021/0186494 A1 | 6/2021 | Shelton, IV et al. |
| 2021/0186495 A1 | 6/2021 | Shelton, IV et al. |
| 2021/0186497 A1 | 6/2021 | Shelton, IV et al. |
| 2021/0186498 A1 | 6/2021 | Boudreaux et al. |
| 2021/0186499 A1 | 6/2021 | Shelton, IV et al. |
| 2021/0186500 A1 | 6/2021 | Shelton, IV et al. |
| 2021/0186501 A1 | 6/2021 | Shelton, IV et al. |
| 2021/0186502 A1 | 6/2021 | Shelton, IV et al. |
| 2021/0186503 A1 | 6/2021 | Shelton, IV et al. |
| 2021/0186504 A1 | 6/2021 | Shelton, IV et al. |
| 2021/0186505 A1 | 6/2021 | Shelton, IV et al. |
| 2021/0186506 A1 | 6/2021 | Shelton, IV et al. |
| 2021/0186507 A1 | 6/2021 | Shelton, IV et al. |
| 2021/0212691 A1 | 7/2021 | Smith et al. |
| 2021/0212776 A1 | 7/2021 | Schmitt et al. |
| 2021/0219976 A1 | 7/2021 | DiNardo et al. |
| 2021/0228209 A1 | 7/2021 | Shelton, IV et al. |
| 2021/0236117 A1 | 8/2021 | Morgan et al. |
| 2021/0236124 A1 | 8/2021 | Shelton, IV et al. |
| 2021/0244406 A1 | 8/2021 | Kerr et al. |
| 2021/0244407 A1 | 8/2021 | Shelton, IV et al. |
| 2021/0244410 A1 | 8/2021 | Swayze et al. |
| 2021/0244412 A1 | 8/2021 | Vendely et al. |
| 2021/0259681 A1 | 8/2021 | Shelton, IV et al. |
| 2021/0259687 A1 | 8/2021 | Gonzalez et al. |
| 2021/0259986 A1 | 8/2021 | Widenhouse et al. |
| 2021/0259987 A1 | 8/2021 | Widenhouse et al. |

(56) References Cited

U.S. PATENT DOCUMENTS

| | | |
|---|---|---|
| 2021/0267589 A1 | 9/2021 | Swayze et al. |
| 2021/0267592 A1 | 9/2021 | Baxter, III et al. |
| 2021/0267594 A1 | 9/2021 | Morgan et al. |
| 2021/0267595 A1 | 9/2021 | Posada et al. |
| 2021/0267596 A1 | 9/2021 | Fanelli et al. |
| 2021/0275053 A1 | 9/2021 | Shelton, IV et al. |
| 2021/0275172 A1 | 9/2021 | Harris et al. |
| 2021/0275173 A1 | 9/2021 | Shelton, IV et al. |
| 2021/0275176 A1 | 9/2021 | Beckman et al. |
| 2021/0282767 A1 | 9/2021 | Shelton, IV et al. |
| 2021/0282769 A1 | 9/2021 | Baxter, III et al. |
| 2021/0282774 A1 | 9/2021 | Shelton, IV et al. |
| 2021/0282776 A1 | 9/2021 | Overmyer et al. |
| 2021/0290226 A1 | 9/2021 | Mandakolathur Vasudevan et al. |
| 2021/0290231 A1 | 9/2021 | Baxter, III et al. |
| 2021/0290232 A1 | 9/2021 | Harris et al. |
| 2021/0290233 A1 | 9/2021 | Shelton, IV et al. |
| 2021/0290236 A1 | 9/2021 | Moore et al. |
| 2021/0298745 A1 | 9/2021 | Leimbach et al. |
| 2021/0298746 A1 | 9/2021 | Leimbach et al. |
| 2021/0307748 A1 | 10/2021 | Harris et al. |
| 2021/0307754 A1 | 10/2021 | Shelton, IV et al. |
| 2021/0315566 A1 | 10/2021 | Yates et al. |
| 2021/0315570 A1 | 10/2021 | Shelton, IV |
| 2021/0315571 A1 | 10/2021 | Swayze et al. |
| 2021/0315573 A1 | 10/2021 | Shelton, IV et al. |
| 2021/0315574 A1 | 10/2021 | Shelton, IV et al. |
| 2021/0315576 A1 | 10/2021 | Shelton, IV et al. |
| 2021/0315577 A1 | 10/2021 | Shelton, IV et al. |
| 2021/0322009 A1 | 10/2021 | Huang et al. |
| 2021/0330321 A1 | 10/2021 | Leimbach et al. |
| 2021/0338233 A1 | 11/2021 | Shelton, IV et al. |
| 2021/0338234 A1 | 11/2021 | Shelton, IV et al. |
| 2021/0369273 A1 | 12/2021 | Yates et al. |
| 2021/0378669 A1 | 12/2021 | Shelton, IV et al. |
| 2021/0393260 A1 | 12/2021 | Shelton, IV et al. |
| 2021/0393261 A1 | 12/2021 | Harris et al. |
| 2021/0393262 A1 | 12/2021 | Shelton, IV et al. |
| 2021/0393268 A1 | 12/2021 | Shelton, IV et al. |
| 2021/0393366 A1 | 12/2021 | Shelton, IV et al. |
| 2022/0000478 A1 | 1/2022 | Shelton, IV et al. |
| 2022/0031313 A1 | 2/2022 | Bakos et al. |
| 2022/0031314 A1 | 2/2022 | Bakos et al. |
| 2022/0031315 A1 | 2/2022 | Bakos et al. |
| 2022/0031319 A1 | 2/2022 | Witte et al. |
| 2022/0031320 A1 | 2/2022 | Hall et al. |
| 2022/0031322 A1 | 2/2022 | Parks |
| 2022/0031323 A1 | 2/2022 | Witte |
| 2022/0031324 A1 | 2/2022 | Hall et al. |
| 2022/0031345 A1 | 2/2022 | Witte |
| 2022/0031346 A1 | 2/2022 | Parks |
| 2022/0031350 A1 | 2/2022 | Witte |
| 2022/0031351 A1 | 2/2022 | Moubarak et al. |
| 2022/0061836 A1 | 3/2022 | Parihar et al. |
| 2022/0061843 A1 | 3/2022 | Vendely et al. |
| 2022/0061845 A1 | 3/2022 | Shelton, IV et al. |
| 2022/0061862 A1 | 3/2022 | Shelton, IV et al. |

FOREIGN PATENT DOCUMENTS

| | | |
|---|---|---|
| AU | 2012268848 A1 | 1/2013 |
| AU | 2011218702 B2 | 6/2013 |
| AU | 2012200178 B2 | 7/2013 |
| BR | 112013007744 A2 | 6/2016 |
| BR | 112013027777 A2 | 1/2017 |
| CA | 1015829 A | 8/1977 |
| CA | 1125615 A | 6/1982 |
| CA | 2520413 A1 | 3/2007 |
| CA | 2725181 A1 | 11/2007 |
| CA | 2851239 A1 | 11/2007 |
| CA | 2664874 A1 | 11/2009 |
| CA | 2813230 A1 | 4/2012 |
| CA | 2940510 A1 | 8/2015 |
| CA | 2698728 C | 8/2016 |
| CN | 1163558 A | 10/1997 |
| CN | 2488482 Y | 5/2002 |
| CN | 1634601 A | 7/2005 |
| CN | 2716900 Y | 8/2005 |
| CN | 2738962 Y | 11/2005 |
| CN | 1777406 A | 5/2006 |
| CN | 2785249 Y | 5/2006 |
| CN | 2796654 Y | 7/2006 |
| CN | 2868212 Y | 2/2007 |
| CN | 200942099 Y | 9/2007 |
| CN | 200984209 Y | 12/2007 |
| CN | 200991269 Y | 12/2007 |
| CN | 201001747 Y | 1/2008 |
| CN | 101143105 A | 3/2008 |
| CN | 201029899 Y | 3/2008 |
| CN | 101188900 A | 5/2008 |
| CN | 101203085 A | 6/2008 |
| CN | 101273908 A | 10/2008 |
| CN | 101378791 A | 3/2009 |
| CN | 101507635 A | 8/2009 |
| CN | 101522120 A | 9/2009 |
| CN | 101669833 A | 3/2010 |
| CN | 101716090 A | 6/2010 |
| CN | 101721236 A | 6/2010 |
| CN | 101756727 A | 6/2010 |
| CN | 101828940 A | 9/2010 |
| CN | 101856250 A | 10/2010 |
| CN | 101873834 A | 10/2010 |
| CN | 201719298 U | 1/2011 |
| CN | 102038532 A | 5/2011 |
| CN | 201879759 U | 6/2011 |
| CN | 201949071 U | 8/2011 |
| CN | 102217961 A | 10/2011 |
| CN | 102217963 A | 10/2011 |
| CN | 102243850 A | 11/2011 |
| CN | 102247182 A | 11/2011 |
| CN | 102247183 A | 11/2011 |
| CN | 101779977 B | 12/2011 |
| CN | 102309352 A | 1/2012 |
| CN | 101912284 B | 7/2012 |
| CN | 102125450 B | 7/2012 |
| CN | 202313537 U | 7/2012 |
| CN | 202397539 U | 8/2012 |
| CN | 202426586 U | 9/2012 |
| CN | 102743201 A | 10/2012 |
| CN | 202489990 U | 10/2012 |
| CN | 102228387 B | 11/2012 |
| CN | 102835977 A | 12/2012 |
| CN | 202568350 U | 12/2012 |
| CN | 103037781 A | 4/2013 |
| CN | 103083053 A | 5/2013 |
| CN | 103391037 A | 11/2013 |
| CN | 203328751 U | 12/2013 |
| CN | 103505264 A | 1/2014 |
| CN | 103584893 A | 2/2014 |
| CN | 103635150 A | 3/2014 |
| CN | 103690212 A | 4/2014 |
| CN | 203564285 U | 4/2014 |
| CN | 203564287 U | 4/2014 |
| CN | 203597997 U | 5/2014 |
| CN | 103829981 A | 6/2014 |
| CN | 103829983 A | 6/2014 |
| CN | 103860221 A | 6/2014 |
| CN | 103908313 A | 7/2014 |
| CN | 203693685 U | 7/2014 |
| CN | 203736251 U | 7/2014 |
| CN | 103981635 A | 8/2014 |
| CN | 104027145 A | 9/2014 |
| CN | 203815517 U | 9/2014 |
| CN | 102783741 B | 10/2014 |
| CN | 102973300 B | 10/2014 |
| CN | 204092074 U | 1/2015 |
| CN | 104337556 A | 2/2015 |
| CN | 204158440 U | 2/2015 |
| CN | 204158441 U | 2/2015 |
| CN | 102469995 B | 3/2015 |
| CN | 104422849 A | 3/2015 |
| CN | 104586463 A | 5/2015 |
| CN | 204520822 U | 8/2015 |
| CN | 204636451 U | 9/2015 |

(56) References Cited

FOREIGN PATENT DOCUMENTS

| | | |
|---|---|---|
| CN | 103860225 B | 3/2016 |
| CN | 103750872 B | 5/2016 |
| CN | 105919642 A | 9/2016 |
| CN | 103648410 B | 10/2016 |
| CN | 105997173 A | 10/2016 |
| CN | 106344091 A | 1/2017 |
| CN | 104349800 B | 11/2017 |
| CN | 107635483 A | 1/2018 |
| CN | 208625784 U | 3/2019 |
| DE | 273689 C | 5/1914 |
| DE | 1775926 A | 1/1972 |
| DE | 3036217 A1 | 4/1982 |
| DE | 3210466 A1 | 9/1983 |
| DE | 3709067 A1 | 9/1988 |
| DE | 19534043 A1 | 3/1997 |
| DE | 19851291 A1 | 1/2000 |
| DE | 19924311 A1 | 11/2000 |
| DE | 20016423 U1 | 2/2001 |
| DE | 20112837 U1 | 10/2001 |
| DE | 20121753 U1 | 4/2003 |
| DE | 202004012389 U1 | 9/2004 |
| DE | 10314072 A1 | 10/2004 |
| DE | 102004014011 A1 | 10/2005 |
| DE | 102004041871 A1 | 3/2006 |
| DE | 102004063606 A1 | 7/2006 |
| DE | 202007003114 U1 | 6/2007 |
| DE | 102010013150 A1 | 9/2011 |
| DE | 102012213322 A1 | 1/2014 |
| DE | 102013101158 A1 | 8/2014 |
| EM | 002220467-0008 | 4/2013 |
| EP | 0000756 A1 | 2/1979 |
| EP | 0122046 A1 | 10/1984 |
| EP | 0129442 B1 | 11/1987 |
| EP | 0255631 A1 | 2/1988 |
| EP | 0169044 B1 | 6/1991 |
| EP | 0541950 A1 | 5/1993 |
| EP | 0548998 A1 | 6/1993 |
| EP | 0594148 A1 | 4/1994 |
| EP | 0646357 A1 | 4/1995 |
| EP | 0505036 B1 | 5/1995 |
| EP | 0669104 A1 | 8/1995 |
| EP | 0705571 A1 | 4/1996 |
| EP | 0528478 B1 | 5/1996 |
| EP | 0770355 A1 | 5/1997 |
| EP | 0625335 B1 | 11/1997 |
| EP | 0879742 A1 | 11/1998 |
| EP | 0650701 B1 | 3/1999 |
| EP | 0923907 A1 | 6/1999 |
| EP | 0484677 B2 | 7/2000 |
| EP | 1034747 A1 | 9/2000 |
| EP | 1034748 A1 | 9/2000 |
| EP | 0726632 B1 | 10/2000 |
| EP | 1053719 A1 | 11/2000 |
| EP | 1055399 A1 | 11/2000 |
| EP | 1055400 A1 | 11/2000 |
| EP | 1064882 A1 | 1/2001 |
| EP | 1080694 A1 | 3/2001 |
| EP | 1090592 A1 | 4/2001 |
| EP | 1095627 A1 | 5/2001 |
| EP | 0806914 B1 | 9/2001 |
| EP | 1234587 A1 | 8/2002 |
| EP | 1284120 A1 | 2/2003 |
| EP | 0717967 B1 | 5/2003 |
| EP | 0869742 B1 | 5/2003 |
| EP | 1374788 A1 | 1/2004 |
| EP | 1407719 A2 | 4/2004 |
| EP | 0996378 B1 | 6/2004 |
| EP | 1558161 A1 | 8/2005 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 1330989 B1 | 12/2005 |
| EP | 1632191 A2 | 3/2006 |
| EP | 1082944 B1 | 5/2006 |
| EP | 1253866 B1 | 7/2006 |
| EP | 1723914 A1 | 11/2006 |
| EP | 1285633 B1 | 12/2006 |
| EP | 1011494 B1 | 1/2007 |
| EP | 1767163 A1 | 3/2007 |
| EP | 1837041 A1 | 9/2007 |
| EP | 0922435 B1 | 10/2007 |
| EP | 1599146 B1 | 10/2007 |
| EP | 1330201 B1 | 6/2008 |
| EP | 2039302 A2 | 3/2009 |
| EP | 1719461 B1 | 6/2009 |
| EP | 2116196 A2 | 11/2009 |
| EP | 1769754 B1 | 6/2010 |
| EP | 1627605 B1 | 12/2010 |
| EP | 2316345 A1 | 5/2011 |
| EP | 1962711 B1 | 2/2012 |
| EP | 2486862 A2 | 8/2012 |
| EP | 2486868 A2 | 8/2012 |
| EP | 2517638 A1 | 10/2012 |
| EP | 2606812 A1 | 6/2013 |
| EP | 2649948 A1 | 10/2013 |
| EP | 2649949 A1 | 10/2013 |
| EP | 2668910 A2 | 12/2013 |
| EP | 2687164 A2 | 1/2014 |
| EP | 2713902 A1 | 4/2014 |
| EP | 2743042 A2 | 6/2014 |
| EP | 2764827 A2 | 8/2014 |
| EP | 2777524 A2 | 9/2014 |
| EP | 2789299 A1 | 10/2014 |
| EP | 2842500 A1 | 3/2015 |
| EP | 2853220 A1 | 4/2015 |
| EP | 2878274 A1 | 6/2015 |
| EP | 2298220 B1 | 6/2016 |
| EP | 2510891 B1 | 6/2016 |
| EP | 3031404 A1 | 6/2016 |
| EP | 3047806 A1 | 7/2016 |
| EP | 3078334 A1 | 10/2016 |
| EP | 2364651 B1 | 11/2016 |
| EP | 2747235 B1 | 11/2016 |
| EP | 3095399 A2 | 11/2016 |
| EP | 3120781 A2 | 1/2017 |
| EP | 3135225 A2 | 3/2017 |
| EP | 2789299 B1 | 5/2017 |
| EP | 3225190 A2 | 10/2017 |
| EP | 3326548 A1 | 5/2018 |
| EP | 3363378 A1 | 8/2018 |
| EP | 3409216 A1 | 12/2018 |
| EP | 3476334 A1 | 5/2019 |
| EP | 3275378 B1 | 7/2019 |
| ES | 1070456 U | 9/2009 |
| FR | 459743 A | 11/1913 |
| FR | 999646 A | 2/1952 |
| FR | 1112936 A | 3/1956 |
| FR | 2598905 A1 | 11/1987 |
| FR | 2689749 B1 | 7/1994 |
| FR | 2765794 A1 | 1/1999 |
| FR | 2815842 A1 | 5/2002 |
| GB | 939929 A | 10/1963 |
| GB | 1210522 A | 10/1970 |
| GB | 1217159 A | 12/1970 |
| GB | 1339394 A | 12/1973 |
| GB | 2024012 A | 1/1980 |
| GB | 2109241 A | 6/1983 |
| GB | 2090534 B | 6/1984 |
| GB | 2272159 A | 5/1994 |
| GB | 2336214 A | 10/1999 |
| GB | 2509523 A | 7/2014 |
| GR | 930100110 A | 11/1993 |
| JP | S4711908 Y1 | 5/1972 |
| JP | S5033988 U | 4/1975 |
| JP | S5367286 A | 6/1978 |
| JP | S56112235 A | 9/1981 |
| JP | S60113007 A | 6/1985 |
| JP | S62170011 U | 10/1987 |
| JP | S63270040 A | 11/1988 |
| JP | S63318824 A | 12/1988 |
| JP | H0129503 B2 | 6/1989 |
| JP | H02106189 A | 4/1990 |
| JP | H0378514 U | 8/1991 |

(56) References Cited

FOREIGN PATENT DOCUMENTS

| | | |
|---|---|---|
| JP | H0385009 U | 8/1991 |
| JP | H04215747 A | 8/1992 |
| JP | H04131860 U | 12/1992 |
| JP | H0584252 A | 4/1993 |
| JP | H05123325 A | 5/1993 |
| JP | H05226945 A | 9/1993 |
| JP | H0630945 A | 2/1994 |
| JP | H06237937 A | 8/1994 |
| JP | H06304176 A | 11/1994 |
| JP | H06327684 A | 11/1994 |
| JP | H079622 U | 2/1995 |
| JP | H07124166 A | 5/1995 |
| JP | H07163573 A | 6/1995 |
| JP | H07255735 A | 10/1995 |
| JP | H07285089 A | 10/1995 |
| JP | H0833642 A | 2/1996 |
| JP | H08164141 A | 6/1996 |
| JP | H08182684 A | 7/1996 |
| JP | H08507708 A | 8/1996 |
| JP | H08229050 A | 9/1996 |
| JP | H08289895 A | 11/1996 |
| JP | H09-323068 A | 12/1997 |
| JP | H10118090 A | 5/1998 |
| JP | H10-200699 A | 7/1998 |
| JP | H10296660 A | 11/1998 |
| JP | 2000014632 A | 1/2000 |
| JP | 2000033071 A | 2/2000 |
| JP | 2000112002 A | 4/2000 |
| JP | 2000166932 A | 6/2000 |
| JP | 2000171730 A | 6/2000 |
| JP | 2000210299 A | 8/2000 |
| JP | 2000271141 A | 10/2000 |
| JP | 2000287987 A | 10/2000 |
| JP | 2000325303 A | 11/2000 |
| JP | 2001-69758 A | 3/2001 |
| JP | 2001087272 A | 4/2001 |
| JP | 2001208655 A | 8/2001 |
| JP | 2001514541 A | 9/2001 |
| JP | 2001276091 A | 10/2001 |
| JP | 2002051974 A | 2/2002 |
| JP | 2002054903 A | 2/2002 |
| JP | 2002085415 A | 3/2002 |
| JP | 2002143078 A | 5/2002 |
| JP | 2002153481 A | 5/2002 |
| JP | 2002528161 A | 9/2002 |
| JP | 2002314298 A | 10/2002 |
| JP | 2003135473 A | 5/2003 |
| JP | 2003521301 A | 7/2003 |
| JP | 3442423 B2 | 9/2003 |
| JP | 2003300416 A | 10/2003 |
| JP | 2004147701 A | 5/2004 |
| JP | 2004162035 A | 6/2004 |
| JP | 2004229976 A | 8/2004 |
| JP | 2005013573 A | 1/2005 |
| JP | 2005080702 A | 3/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005137423 A | 6/2005 |
| JP | 2005187954 A | 7/2005 |
| JP | 2005211455 A | 8/2005 |
| JP | 2005328882 A | 12/2005 |
| JP | 2005335432 A | 12/2005 |
| JP | 2005342267 A | 12/2005 |
| JP | 3791856 B2 | 6/2006 |
| JP | 2006187649 A | 7/2006 |
| JP | 2006218228 A | 8/2006 |
| JP | 2006281405 A | 10/2006 |
| JP | 2006291180 A | 10/2006 |
| JP | 2006346445 A | 12/2006 |
| JP | 2007-97252 A | 4/2007 |
| JP | 2007289715 A | 11/2007 |
| JP | 2007304057 A | 11/2007 |
| JP | 2007306710 A | 11/2007 |
| JP | D1322057 | 2/2008 |
| JP | 2008154804 A | 7/2008 |
| JP | 2008220032 A | 9/2008 |
| JP | 2009507526 A | 2/2009 |
| JP | 2009189838 A | 8/2009 |
| JP | 2009189846 A | 8/2009 |
| JP | 2009207260 A | 9/2009 |
| JP | 2009226028 A | 10/2009 |
| JP | 2009538684 A | 11/2009 |
| JP | 2009539420 A | 11/2009 |
| JP | D1383743 | 2/2010 |
| JP | 2010065594 A | 3/2010 |
| JP | 2010069307 A | 4/2010 |
| JP | 2010069310 A | 4/2010 |
| JP | 2010098844 A | 4/2010 |
| JP | 2010214128 A | 9/2010 |
| JP | 2011072574 A | 4/2011 |
| JP | 4722849 B2 | 7/2011 |
| JP | 4728996 B2 | 7/2011 |
| JP | 2011524199 A | 9/2011 |
| JP | 2011200665 A | 10/2011 |
| JP | D1432094 | 12/2011 |
| JP | 2012115542 A | 6/2012 |
| JP | 2012143283 A | 8/2012 |
| JP | 5154710 B1 | 2/2013 |
| JP | 2013099551 A | 5/2013 |
| JP | 2013126430 A | 6/2013 |
| JP | D1481426 | 9/2013 |
| JP | 2013541982 A | 11/2013 |
| JP | 2013541983 A | 11/2013 |
| JP | 2013541997 A | 11/2013 |
| JP | D1492363 | 2/2014 |
| JP | 2014121599 A | 7/2014 |
| JP | 2014171879 A | 9/2014 |
| JP | 1517663 S | 2/2015 |
| JP | 2015512725 A | 4/2015 |
| JP | 2015513956 A | 5/2015 |
| JP | 2015513958 A | 5/2015 |
| JP | 2015514471 A | 5/2015 |
| JP | 2015516838 A | 6/2015 |
| JP | 2015521524 A | 7/2015 |
| JP | 2015521525 A | 7/2015 |
| JP | 2016007800 A | 1/2016 |
| JP | 2016508792 A | 3/2016 |
| JP | 2016512057 A | 4/2016 |
| JP | 2016530949 A | 10/2016 |
| JP | 2017513563 A | 6/2017 |
| JP | 1601498 S | 4/2018 |
| JP | 2019513530 A | 5/2019 |
| KR | 20100110134 A | 10/2010 |
| KR | 20110003229 A | 1/2011 |
| KR | 300631507 | 3/2012 |
| KR | 300747646 | 6/2014 |
| KR | 20180053811 A | 5/2018 |
| RU | 1814161 C | 5/1993 |
| RU | 2008830 C1 | 3/1994 |
| RU | 2052979 C1 | 1/1996 |
| RU | 2066128 C1 | 9/1996 |
| RU | 2069981 C1 | 12/1996 |
| RU | 2098025 C1 | 12/1997 |
| RU | 2104671 C1 | 2/1998 |
| RU | 2110965 C1 | 5/1998 |
| RU | 2141279 C1 | 11/1999 |
| RU | 2144791 C1 | 1/2000 |
| RU | 2161450 C1 | 1/2001 |
| RU | 2181566 C2 | 4/2002 |
| RU | 2187249 C2 | 8/2002 |
| RU | 32984 U1 | 10/2003 |
| RU | 2225170 C2 | 3/2004 |
| RU | 42750 U1 | 12/2004 |
| RU | 61114 U1 | 2/2007 |
| RU | 61122 U1 | 2/2007 |
| RU | 2430692 C2 | 10/2011 |
| SU | 189517 A | 1/1967 |
| SU | 297156 A | 5/1971 |
| SU | 328636 A | 9/1972 |
| SU | 511939 A1 | 4/1976 |
| SU | 674747 A1 | 7/1979 |

(56) References Cited

FOREIGN PATENT DOCUMENTS

| | | |
|---|---|---|
| SU | 728848 A1 | 4/1980 |
| SU | 1009439 A | 4/1983 |
| SU | 1042742 A1 | 9/1983 |
| SU | 1271497 A1 | 11/1986 |
| SU | 1333319 A2 | 8/1987 |
| SU | 1377052 A1 | 2/1988 |
| SU | 1377053 A1 | 2/1988 |
| SU | 1443874 A1 | 12/1988 |
| SU | 1509051 A1 | 9/1989 |
| SU | 1561964 A1 | 5/1990 |
| SU | 1708312 A1 | 1/1992 |
| SU | 1722476 A1 | 3/1992 |
| SU | 1752361 A1 | 8/1992 |
| SU | 1814161 A1 | 5/1993 |
| WO | WO-9308754 A1 | 5/1993 |
| WO | WO-9315648 A1 | 8/1993 |
| WO | WO-9420030 A1 | 9/1994 |
| WO | WO-9517855 A1 | 7/1995 |
| WO | WO-9520360 A1 | 8/1995 |
| WO | WO-9623448 A1 | 8/1996 |
| WO | WO-9635464 A1 | 11/1996 |
| WO | WO-9639086 A1 | 12/1996 |
| WO | WO-9639088 A1 | 12/1996 |
| WO | WO-9724073 A1 | 7/1997 |
| WO | WO-9734533 A1 | 9/1997 |
| WO | WO-9827870 A1 | 7/1998 |
| WO | WO-9903407 A1 | 1/1999 |
| WO | WO-9903409 A1 | 1/1999 |
| WO | WO-9948430 A1 | 9/1999 |
| WO | WO-0024322 A1 | 5/2000 |
| WO | WO-0024330 A1 | 5/2000 |
| WO | WO-0053112 A2 | 9/2000 |
| WO | WO-0024448 A2 | 10/2000 |
| WO | WO-0057796 A1 | 10/2000 |
| WO | WO-0105702 A1 | 1/2001 |
| WO | WO-0154594 A1 | 8/2001 |
| WO | WO-0158371 A1 | 8/2001 |
| WO | WO-0162164 A2 | 8/2001 |
| WO | WO-0162169 A2 | 8/2001 |
| WO | WO-0191646 A1 | 12/2001 |
| WO | WO-0219932 A1 | 3/2002 |
| WO | WO-0226143 A1 | 4/2002 |
| WO | WO-0236028 A1 | 5/2002 |
| WO | WO-02065933 A2 | 8/2002 |
| WO | WO-03055402 A1 | 7/2003 |
| WO | WO-03094747 A1 | 11/2003 |
| WO | WO-03079909 A3 | 3/2004 |
| WO | WO-2004019803 A1 | 3/2004 |
| WO | WO-2004032783 A1 | 4/2004 |
| WO | WO-2004047626 A1 | 6/2004 |
| WO | WO-2004047653 A2 | 6/2004 |
| WO | WO-2004056277 A1 | 7/2004 |
| WO | WO-2004078050 A2 | 9/2004 |
| WO | WO-2004078051 A2 | 9/2004 |
| WO | WO-2004096015 A2 | 11/2004 |
| WO | WO-2006044581 A2 | 4/2006 |
| WO | WO-2006051252 A1 | 5/2006 |
| WO | WO-2006059067 A1 | 6/2006 |
| WO | WO-2006073581 A1 | 7/2006 |
| WO | WO-2006085389 A1 | 8/2006 |
| WO | WO-2007015971 A2 | 2/2007 |
| WO | WO-2007074430 A1 | 7/2007 |
| WO | WO-2007129121 A1 | 11/2007 |
| WO | WO-2007137304 A2 | 11/2007 |
| WO | WO-2007142625 A2 | 12/2007 |
| WO | WO-2008021969 A2 | 2/2008 |
| WO | WO-2008061566 A1 | 5/2008 |
| WO | WO-2008089404 A2 | 7/2008 |
| WO | WO-2009005969 A2 | 1/2009 |
| WO | WO-2009067649 A2 | 5/2009 |
| WO | WO-2009091497 A2 | 7/2009 |
| WO | WO-2010126129 A1 | 11/2010 |
| WO | WO-2010134913 A1 | 11/2010 |
| WO | WO-2011008672 A2 | 1/2011 |
| WO | WO-2011044343 A2 | 4/2011 |
| WO | WO-2012006306 A2 | 1/2012 |
| WO | WO-2012013577 A1 | 2/2012 |
| WO | WO-2012044606 A2 | 4/2012 |
| WO | WO-2012061725 A1 | 5/2012 |
| WO | WO-2012072133 A1 | 6/2012 |
| WO | WO-2012166503 A1 | 12/2012 |
| WO | WO-2013087092 A1 | 6/2013 |
| WO | WO-2013151888 A1 | 10/2013 |
| WO | WO-2014004209 A2 | 1/2014 |
| WO | WO-2014113438 A1 | 7/2014 |
| WO | WO-2014175894 A1 | 10/2014 |
| WO | WO-2015032797 A1 | 3/2015 |
| WO | WO-2015076780 A1 | 5/2015 |
| WO | WO-2015137040 A1 | 9/2015 |
| WO | WO-2015138760 A1 | 9/2015 |
| WO | WO-2015187107 A1 | 12/2015 |
| WO | WO-2016100682 A1 | 6/2016 |
| WO | WO-2016107448 A1 | 7/2016 |
| WO | WO-2019036490 A1 | 2/2019 |

OTHER PUBLICATIONS

ASTM procedure D2240-05, "Standard Test Method for Rubber Property-Durometer Hardness," (Published Apr. 2010).

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

Disclosed Anonymously, "Motor-Driven Surgical Stapler Improvements," Research Disclosure Database No. 526041, Published: Feb. 2008.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).

Datasheet for Panasonic TK Relays Ultra Low Profile 2 A Polarized Relay, Copyright Matsushita Electric Works, Ltd. (Known of at least as early as Aug. 17, 2010), 5 pages.

Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).

Miyata et al., "Biomolecule-Sensitive Hydrogels," Advanced Drug Delivery Reviews, 54 (2002) pp. 79-98.

Jeong et al., "Thermosensitive Sol-Gel Reversible Hydrogels," Advanced Drug Delivery Reviews, 54 (2002) pp. 37-51.

Covidien Brochure, "Endo GIA™ Ultra Universal Stapler," (2010), 2 pages.

Qiu et al., "Environment-Sensitive Hydrogels for Drug Delivery," Advanced Drug Delivery Reviews, 53 (2001) pp. 321-339.

Hoffman, "Hydrogels for Biomedical Applications," Advanced Drug Delivery Reviews, 43 (2002) pp. 3-12.

Hoffman, "Hydrogels for Biomedical Applications," Advanced Drug Delivery Reviews, 54 (2002) pp. 3-12.

Peppas, "Physiologically Responsive Hydrogels," Journal of Bioactive and Compatible Polymers, vol. 6 (Jul. 1991) pp. 241-246.

Peppas, Editor "Hydrogels in Medicine and Pharmacy," vol. I, Fundamentals, CRC Press, 1986.

Young, "Microcellular foams via phase separation," Journal of Vacuum Science & Technology A 4(3), (May/Jun. 1986).

Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.

http://ninpgan.net/publications/51-100/89.pdf; 2004, Ning Pan, on Uniqueness of Fibrous Materials, Design & Nature II. Eds: Colins, M. and Brebbia, C. WIT Press, Boston, 493-504.

(56) References Cited

OTHER PUBLICATIONS

Solorio et al., "Gelatin Microspheres Crosslinked with Genipin for Local Delivery of Growth Factors," J. Tissue Eng. Regen. Med. (2010), 4(7): pp. 514-523.
Covidien iDrive™ Ultra in Service Reference Card, "iDrive™ Ultra Powered Stapling Device," (4 pages).
Covidien iDrive™ Ultra Powered Stapling System ibrochure, "The Power of iDrive™ Ultra Powered Stapling System and Tri-Staple™ Technology," (23 pages).
Covidien "iDrive™ Ultra Powered Stapling System, A Guide for Surgeons," (6 pages).
Covidien "iDrive™ Ultra Powered Stapling System, Cleaning and Sterilization Guide," (2 pages).
Covidien Brochure "iDrive™ Ultra Powered Stapling System," (6 pages).
Covidien Brochure, "Endo GIA™ Reloads with Tri-Staple™ Technology," (2010), 1 page.
Covidien Brochure, "Endo GIA™ Reloads with Tri-Staple™ Technology and Endo GIA™ Ultra Universal Staplers," (2010), 2 pages.
Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
Pitt et al., "Attachment of Hyaluronan to Metallic Surfaces," J. Biomed. Mater. Res. 68A: pp. 95-106, 2004.
Indian Standard: Automotive Vehicles—Brakes and Braking Systems (IS 11852-1:2001), Mar. 1, 2001.
Patrick J. Sweeney: "RFID for Dummies", Mar. 11, 2010, pp. 365-365, XP055150775, ISBN: 978-1-11-805447-5, Retrieved from the Internet: URL: books.google.de/books?isbn=1118054474 [retrieved on Nov. 4, 2014]—book not attached.
Allegro MicroSystems, LLC, Automotive Full Bridge MOSFET Driver, A3941-DS, Rev. 5, 21 pages, http://www.allegromicro.com/~/media/Files/Datasheets/A3941-Datasheet.ashx?la=en.
Data Sheet of LM4F230H5QR, 2007.
Seils et al., Covidien Summary: Clinical Study "UCONN Biodynamics: Final Report on Results," (2 pages).
Byrne et al., "Molecular Imprinting Within Hydrogels," Advanced Drug Delivery Reviews, 54 (2002) pp. 149-161.
Fast, Versatile Blackfin Processors Handle Advanced RFID Reader Applications; Analog Dialogue: vol. 40—Sep. 2006; http://www.analog.com/library/analogDialogue/archives/40-09/rfid.pdf; Wayback Machine to Feb. 15, 2012.
Chen et al., "Elastomeric Biomaterials for Tissue Engineering," Progress in Polymer Science 38 (2013), pp. 584-671.
Matsuda, "Thermodynamics of Formation of Porous Polymeric Membrane from Solutions," Polymer Journal, vol. 23, No. 5, pp. 435-444 (1991).
Covidien Brochure, "Endo GIA™ Black Reload with Tri-Staple™ Technology," (2012), 2 pages.
Biomedical Coatings, Fort Wayne Metals, Research Products Corporation, obtained online at www.fwmetals.com on Jun. 21, 2010 (1 page).
The Sodem Aseptic Battery Transfer Kit, Sodem Systems, 2000, 3 pages.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20., pp. 1744-1748.
Serial Communication Protocol; Michael Lemmon Feb. 1, 2009; http://www3.nd.edu/~lemmon/courses/ee224/web-manual/web-manual/lab12/node2.html; Wayback Machine to Apr. 29, 2012.
Lyon et al. "The Relationship Between Current Load and Temperature for Quasi-Steady State and Transient Conditions," SPIE—International Society for Optical Engineering. Proceedings, vol. 4020, (pp. 62-70), Mar. 30, 2000.
Anonymous: "Sense & Control Application Note Current Sensing Using Linear Hall Sensors," Feb. 3, 2009, pp. 1-18. Retrieved from the Internet: URL: http://www.infineon.com/dgdl/Current_Sensing_Rev.1.1.pdf?fileId=db3a304332d040720132d939503e5f17 [retrieved on Oct. 18, 2016].
Mouser Electronics, "LM317M 3-Terminal Adjustable Regulator with Overcurrent/Overtemperature Self Protection", Mar. 31, 2014 (Mar. 31, 2014), XP0555246104, Retrieved from the Internet: URL: http://www.mouser.com/ds/2/405/lm317m-440423.pdf, pp. 1-8.
Mouser Electronics, "LM317 3-Terminal Adjustable Regulator with Overcurrent/Overtemperature Self Protection", Sep. 30, 2016 (Sep. 30, 2016), XP0555246104, Retrieved from the Internet: URL: http://www.mouser.com/ds/2/405/lm317m-440423.pdf, pp. 1-9.
Cuper et al., "The Use of Near-Infrared Light for Safe and Effective Visualization of Subsurface Blood Vessels to Facilitate Blood Withdrawal in Children," Medical Engineering & Physics, vol. 35, No. 4, pp. 433-440 (2013).
Yan et al, Comparison of the effects of Mg—6Zn and Ti—3Al-2.5V alloys on TGF-β/TNF-α/VEGF/b-FGF in the healing of the intestinal track in vivo, Biomed. Mater. 9 (2014), 11 pages.
Pellicer et al. "On the biodegradability, mechanical behavior, and cytocompatibility of amorphous Mg72Zn23Ca5 and crystalline Mg70Zn23Ca5Pd2 alloys as temporary implant materials," J Biomed Mater Res Part A ,2013:101A:502-517.
Anonymous, Analog Devices Wiki, Chapter 11: The Current Mirror, Aug. 20, 2017, 22 pages. https://wiki.analog.com/university/courses/electronics/text/chapter-11?rev=1503222341.
Yan et al., "Comparison of the effects of Mg—6Zn and titanium on intestinal tract in vivo," J Mater Sci: Mater Med (2013), 11 pages.
Brar et al., "Investigation of the mechanical and degradation properties of Mg—Sr and Mg—Zn—Sr alloys for use as potential biodegradable implant materials," J. Mech. Behavior of Biomed. Mater. 7 (2012) pp. 87-95.
Texas Instruments: "Current Recirculation and Decay Modes," Application Report SLVA321—Mar. 2009; Retrieved from the Internet: URL:http://www.ti.com/lit/an/slva321/slva321 [retrieved on Apr. 25, 2017], 7 pages.
Qiu Li Loh et al.: "Three-Dimensional Scaffolds for Tissue Engineering Applications: Role of Porosity and Pore Size", Tissue Engineering Part B-Reviews, vol. 19, No. 6, Dec. 1, 2013, pp. 485-502.
Gao et al., "Mechanical Signature Enhancement of Response Vibrations in the Time Lag Domain," Fifth International Congress on Sound and Vibration, Dec. 15-18, 1997, pp. 1-8.
Trendafilova et al., "Vibration-based Methods for Structural and Machinery Fault Diagnosis Based on Nonlinear Dynamics Tools," In: Fault Diagnosis in Robotic and Industrial Systems, IConcept Press LTD, 2012, pp. 1-29.
Youtube.com; video by Fibran (retrieved from URL https://www.youtube.com/watch?v=vN2Qjt51gFQ); (Year: 2018).
Foot and Ankle: Core Knowledge in Orthopaedics; by DiGiovanni MD, Elsevier; (p. 27, left column, heading "Materials for Soft Orthoses", 7th bullet point); (Year: 2007).
Lee, Youbok, "Antenna Circuit Design for RFID Applications," 2003, pp. 1-50, DS00710C, Microchip Technology Inc., Available: http://ww1.microchip.com/downloads/en/AppNotes/00710c.pdf.
Kawamura, Atsuo, et al. "Wireless Transmission of Power and Information Through One High-Frequency Resonant AC Link Inverter for Robot Manipulator Applications," Journal, May/Jun. 1996, pp. 503-508, vol. 32, No. 3, IEEE Transactions on Industry Applications.
Honda HS1332AT and ATD Model Info, powerequipment.honda.com [online], published on or before Mar. 22, 2016, [retrieved on May 31, 2019], retrieved from the Internet [URL: https://powerequipment.honda.com/snowblowers/models/hss1332at-hss1332atd] {Year: 2016).
Slow Safety Sign, shutterstock.com [online], published on or before May 9, 2017, [retrieved on May 31, 2019], retrieved from the https://www.shutterstock.com/image-victor/slow-safety-sign-twodimensional-turtle-symbolizing- . . . see PDF in file for full URL] (Year: 2017).
Warning Sign Beveled Buttons, by Peter, flarestock.com [online], published on or before Jan. 1, 2017, [retrieved on Jun. 4, 2019], retrieved from the Internet [URL: https://www.flarestock.com/stock-images/warning-sign-beveled-buttons/70257] (Year: 2017).

(56) References Cited

OTHER PUBLICATIONS

Arrow Sign Icon Next Button, by Blan-k, shutterstock.com [online], published on or before Aug. 6, 2014, [retrieved on Jun. 4, 2019], retrieved from the Internet [URL:https://www.shutterstock.com/de/image-vector/arrow-sign-icon-next-button-navigation-207700303?irgwc=1&utm . . . see PDF in file for full URL] (Year: 2014).

Elite Icons, by smart/icons, iconfinder.com [online], published on Aug. 18, 2016, [retrieved on Jun. 4, 2019], retrieved from the Internet [URL: https://www.iconfinder.com/iconsets/elite] (Year: 2016).

Tutorial overview of inductively coupled RFID Systems, UPM, May 2003, pp. 1-7, UPM Rafsec,<http://cdn.mobiusconsulting.com/papers/rfidsvstems.pdf>.

Schroeter, John, "Demystifying UHF Gen 2 RFID, HF RFID," Online Article, Jun. 2, 2008, pp. 1-3, <https://www.edn.com/design/industrial-control/4019123/Demystifying-UHF-Gen-2-RFID-HF-RFID>.

Adeeb, et al., "An Inductive Link-Based Wireless Power Transfer System for Biomedical Applicatons," Research Article, Nov. 14, 2011, pp. 1-12, vol. 2012, Article ID 879294, Hindawi Publishing Corporation.

Pushing Pixels (GIF), published on dribble.com, 2013.

Sodium stearate C18H35NaO2, Chemspider Search and Share Chemistry, Royal Society of Chemistry, pp. 1-3, 2015, http://www.chemspider.com/Chemical-Structure.12639.html, accessed May 23, 2016.

NF Monographs: Sodium Stearate, U.S. Pharmacopeia, http://www.pharmacopeia.cn/v29240/usp29nf24s0_m77360.html, accessed May 23, 2016.

Fischer, Martin H, "Colloid-Chemical Studies on Soaps", The Chemical Engineer, pp. 184-193, Aug. 1919.

V.K. Ahluwalia and Madhuri Goyal, A Textbook of Organic Chemistry, Section 19.11.3, p. 356, 2000.

A.V. Kasture and S.G. Wadodkar, Pharmaceutical Chemistry-II: Second Year Diploma in Pharmacy, Nirali Prakashan, p. 339, 2007.

Forum discussion regarding "Speed is Faster", published on Oct. 1, 2014 and retrieved on Nov. 8, 2019 from URL https://english.stackexchange.com/questions/199018/how-is-that-correct-speed-is-faster-or-prices-are-cheaper (Year: 2014).

"Understanding the Requirements of ISO/IEC 14443 for Type B Proximity Contactless Identification Cards," retrieved from https://www.digchip.com/application-notes/22/15746.php on Mar. 2, 2020, pp. 1-28 (Nov. 2005).

Jauchem, J.R., "Effects of low-level radio-frequency (3 kHz to 300 GHz) enery on human cardiovascular, reproductive, immune, and other systems: A review of the recent literatured," Int. J. Hyg. Environ. Health 211 (2008) 1-29.

Sandvik, "Welding Handbook," https://www.meting.rs/wp-content/uploads/2018/05/welding-handbook.pdf, retrieved on Jun. 22, 2020. pp. 5-6.

Ludois, Daniel C., "Capacitive Power Transfer for Rotor Field Current in Synchronous Machines," IEEE Transactions on Power Electronics, Institute of Electrical and Electronics Engineers, USA, vol. 27, No. 11, Nov. 1, 2012, pp. 4638-4645.

Rotary Systems: Sealed Slip Ring Categories, Rotary Systems, May 22, 2017, retrieved from the internet: http://web.archive.org/we/20170522174710/http:/rotarysystems.com: 80/slip-rings/sealed/, retrieved on Aug. 12, 2020, pp. 1-2.

IEEE Std 802.3-2012 (Revision of IEEE Std 802.3-2008, published Dec. 28, 2012.

"ATM-MPLS Network Interworking Version 2.0, af-aic-0178.001" ATM Standard, The ATM Forum Technical Committee, published Aug. 2003.

Yang et al.; "4D printing reconfigurable, deployable and mechanically tunable metamaterials," Material Horizions, vol. 6, pp. 1244-1250 (2019).

"Council Directive 93/42/EEC of Jun. 14, 1993 Concerning Medical Devices," Official Journal of the European Communities, L&C. Ligislation and Competition, S, No. L 169, Jun. 14, 1993, pp. 1-43.

\* cited by examiner

MECHANISMS FOR MOTOR CONTROL ADJUSTMENTS OF A MOTORIZED SURGICAL INSTRUMENT

CROSS-REFERENCE TO RELATED APPLICATION

This application is a non-provisional application claiming priority under 35 U.S.C. § 119(e) to U.S. Provisional Patent Application Ser. No. 62/868,457, entitled SURGICAL SYSTEMS WITH MULTIPLE RFID TAGS, filed on Jun. 28, 2019, the entire disclosure of which is hereby incorporated by reference herein.

BACKGROUND

The present invention relates to surgical instruments and, in various embodiments, to surgical cutting and stapling instruments and staple cartridges therefor that are designed to cut and staple tissue. In various embodiments, RFID technology can be used to identify the components of a surgical instrument, such as staple cartridges, for example. Examples of surgical systems which use RFID technology can be found in the disclosures of U.S. Pat. No. 7,959,050, entitled ELECTRICALLY SELF-POWERED SURGICAL INSTRUMENT WITH MANUAL RELEASE, which issued on Jun. 14, 2011, and U.S. Patent Application No. 2015/0053743, entitled ERROR DETECTION ARRANGEMENTS FOR SURGICAL INSTRUMENT ASSEMBLIES, which published on Feb. 26, 2015, and both of which are incorporated by reference herein in their entireties.

SUMMARY

In various embodiments, a surgical instrument is disclosed including an end effector, a shaft, and a housing. The end effector includes an anvil, a staple cartridge including staples deployable toward the anvil and through tissue grasped between the anvil and the staple cartridge, a cutting member configured to cut the tissue, and a first radio-frequency identification (RFID) tag configured to store end effector information. The shaft includes a distal portion selectively transitionable with the end effector between a first attached configuration and a first detached configuration, a first RFID scanner near the distal portion, a proximal portion, and a second RFID tag configured to store shaft information. The first RFID scanner is configured to detect the first RFID tag in the first attached configuration. The housing is selectively transitionable with the proximal portion of the shaft between a second attached configuration and a second detached configuration. The housing includes a second RFID scanner configured to detect the second RFID tag in the second attached configuration, a motor configured to apply a load to the end effector to staple and cut the tissue, and a control circuit. The control circuit is configured to receive input from the first RFID scanner indicative of the end effector information, receive input from the second RFID scanner indicative of the shaft information, and adjust at least one parameter of operation of the motor based on the end effector information and the shaft information In various embodiments, a surgical instrument is disclosed including an end effector and a housing assembly. The end effector includes an anvil, a staple cartridge including staples deployable toward the anvil and through tissue grasped between the anvil and the staple cartridge, a cutting member configured to cut the tissue, and a first RFID tag configured to store end effector information. The housing assembly includes a shaft selectively transitionable with the end effector between an attached configuration and an detached configuration, an RFID scanner configured to detect the RFID tag in the attached configuration, a motor configured to apply a load to the end effector to staple and cut the tissue, and a control circuit configured. The control circuit is configured to receive input from the RFID scanner indicative of the end effector information and adjust at least one parameter of operation of the motor based on the end effector information.

In various embodiments, a surgical instrument includes an end effector, a shaft, and a housing. The end effector includes a stapling head assembly, an anvil movable a closure distance relative to the stapling head assembly to transition the end effector from an open configuration to a closed configuration, and a first RFID tag configured to store end effector information. Tissue is grasped between the anvil and the stapling head assembly in the closed configuration. The shaft includes a distal portion selectively transitionable with the end effector between a first attached configuration and a first detached configuration, a first RFID scanner near the distal portion, a proximal portion, and a second RFID tag configured to store shaft information. The first RFID scanner is configured to detect the first RFID tag in the first attached configuration. The housing is selectively transitionable with the proximal portion of the shaft between a second attached configuration and a second detached configuration. The housing includes a second RFID scanner configured to detect the second RFID tag in the second attached configuration, a motor configured to generate a closure motion to cause the anvil to move the closure distance, and a control circuit. The control circuit is configured to receive input from the first RFID scanner indicative of the end effector information, receive input from the second RFID scanner indicative of the shaft information, and adjust at least one parameter of operation of the motor based on the end effector information and the shaft information.

BRIEF DESCRIPTION OF THE DRAWINGS

The features of various aspects are set forth with particularity in the appended claims. The various aspects, however, both as to organization and methods of operation, together with further objects and advantages thereof, may best be understood by reference to the following description, taken in conjunction with the accompanying drawings as follows.

Figure 42:
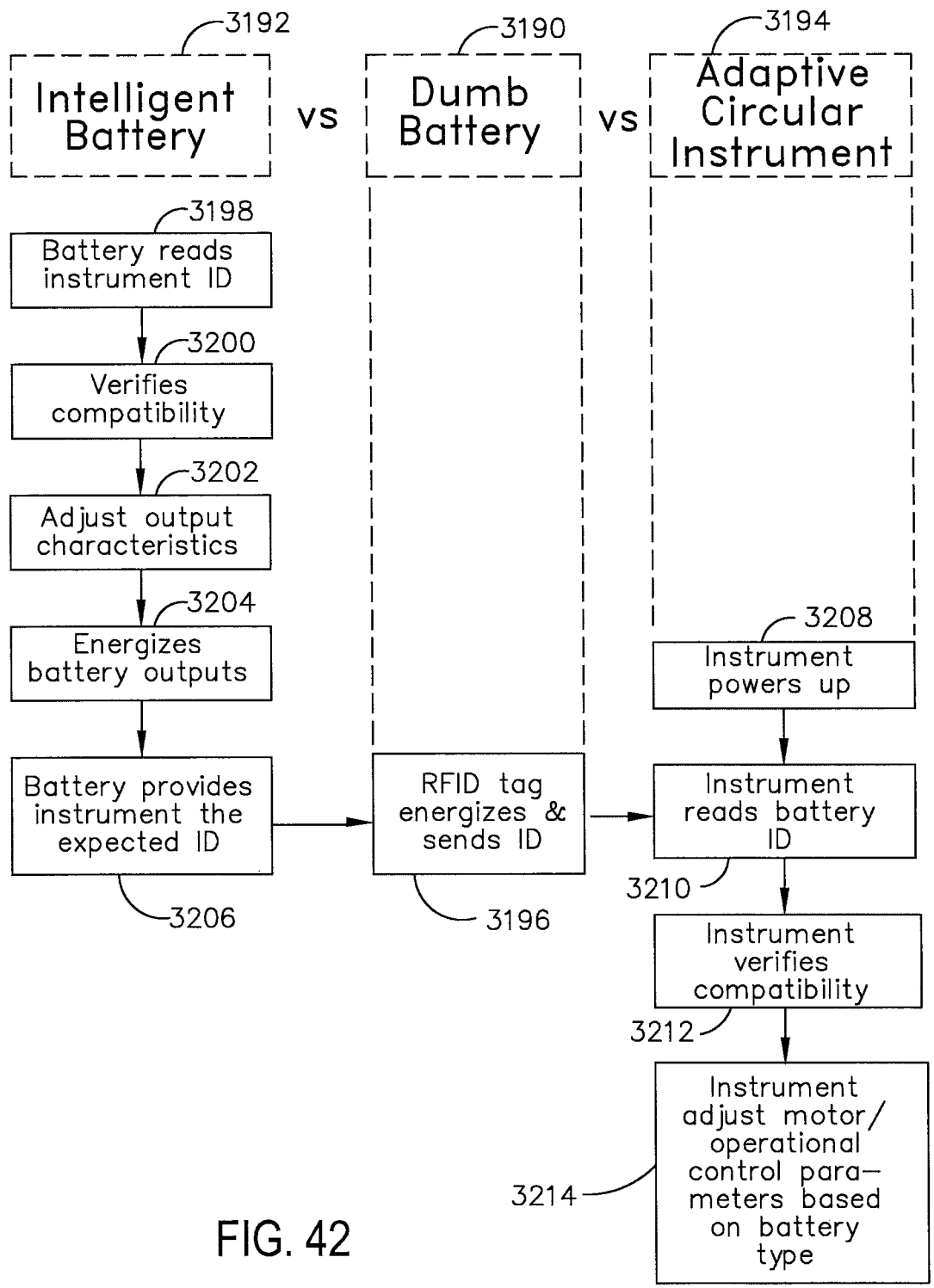

FIG. 42 illustrates various operational differences between a dumb battery, an intelligent battery and an adaptive surgical instrument, in accordance with at least one aspect of the present disclosure.

Figure 43:
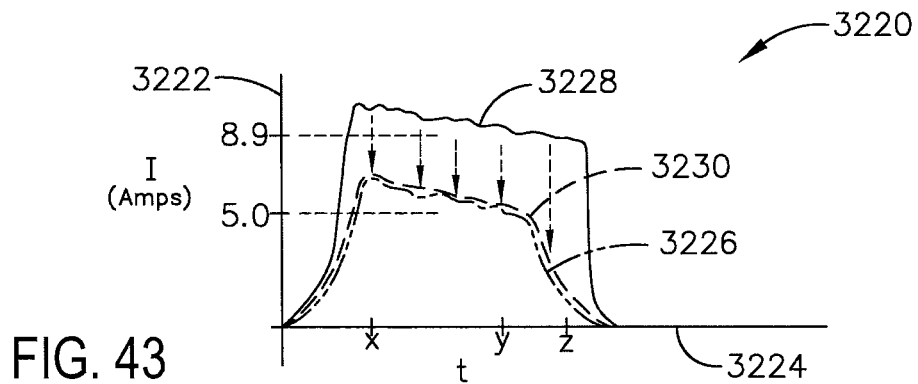

FIG. 43 illustrates a graph which shows the output current capabilities of different battery packs when utilized with the adaptive surgical instrument of FIG. 42, in accordance with at least one aspect of the present disclosure.

Figure 44:
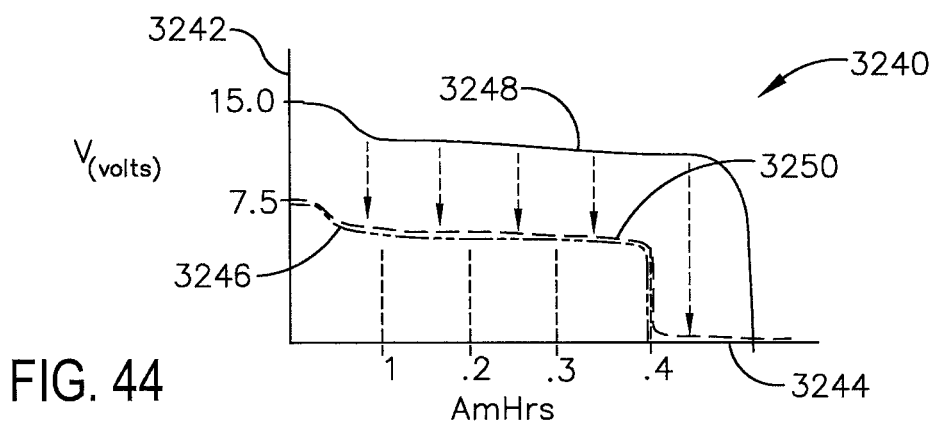

FIG. 44 illustrates a graph which shows the output voltage capabilities of different battery packs when utilized with the adaptive surgical instrument of FIG. 42, in accordance with at least one aspect of the present disclosure.

Figure 45:
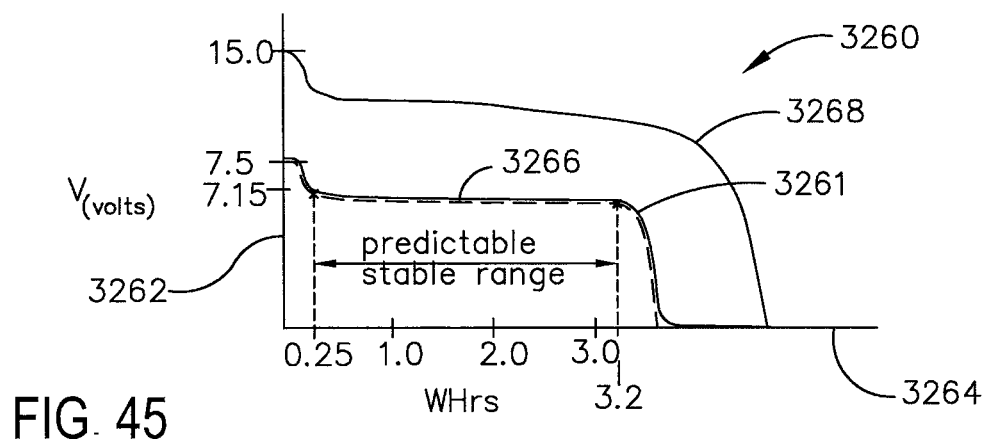

FIG. 45 illustrates a graph which shows the output voltage capabilities of different battery packs when utilized with the adaptive surgical instrument of FIG. 42, in accordance with at least one aspect of the present disclosure.

Figure 46:
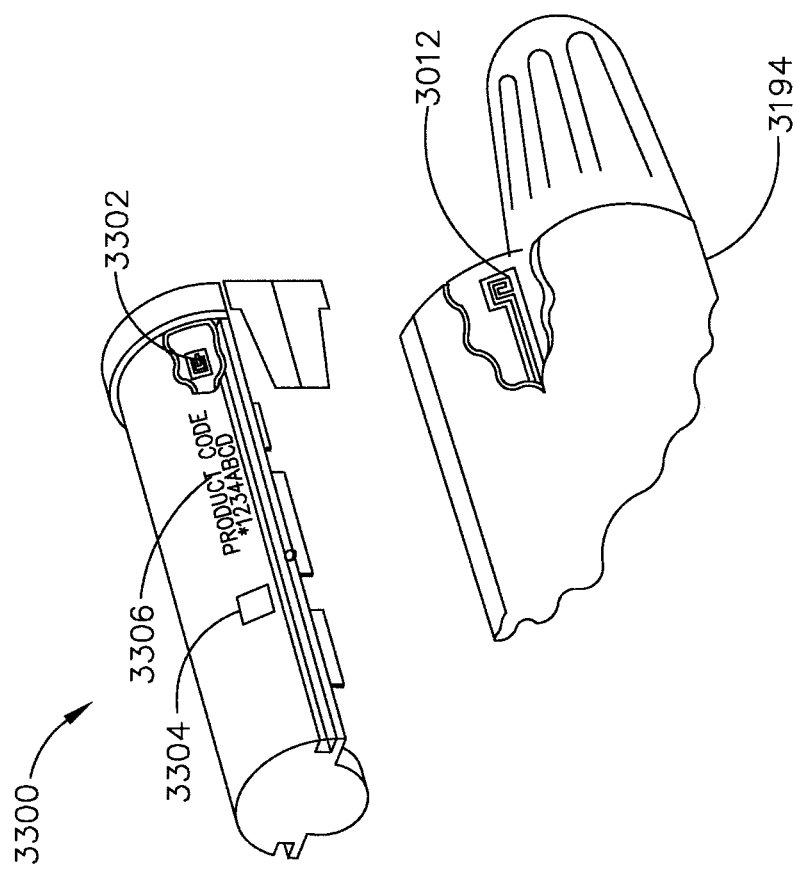

FIG. 46 illustrates a battery for use with the adaptive surgical instrument of FIG. 42, in accordance with at least aspect of the present disclosure.

Figure 47:
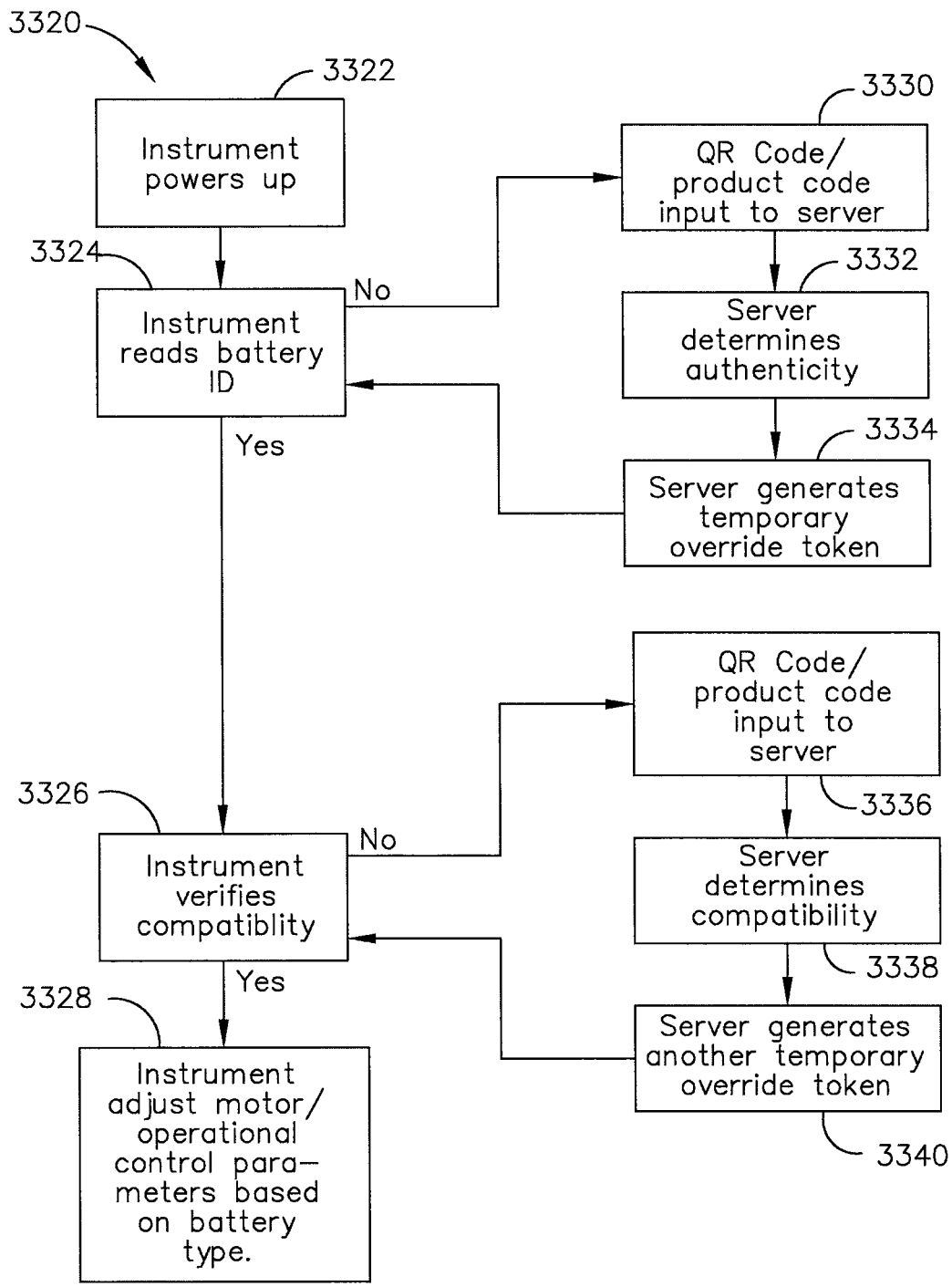

FIG. 47 illustrates a logic flow diagram of a process depicting a control program or a logic configuration for operating the adaptive surgical instrument of FIG. 42, in accordance with at least one aspect of the present disclosure.

Figure 48:
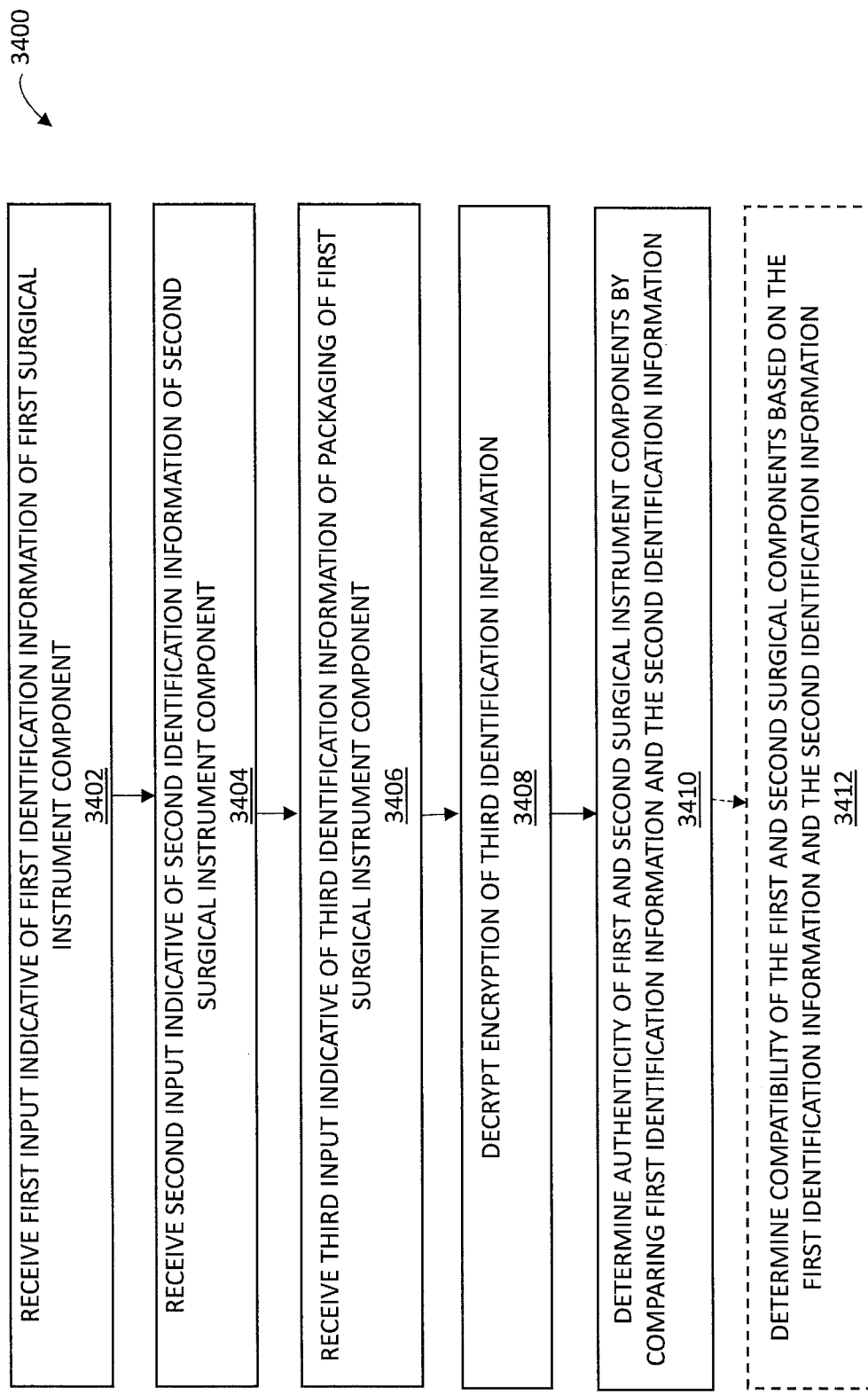

FIG. 48 illustrates a logic flow diagram of a process depicting a control program or a logic configuration for verifying authenticity and/or compatibility of surgical instruments components of a surgical instrument, in accordance with at least one aspect of the present disclosure.

DESCRIPTION

Applicant of the present application owns the following U.S. Patent Applications that were filed on Jun. 30, 2019 and which are each herein incorporated by reference in their respective entireties:

U.S. patent application Ser. No. 16/458,104, entitled METHOD FOR AUTHENTICATING THE COMPATIBILITY OF A STAPLE CARTRIDGE WITH A SURGICAL INSTRUMENT, now U.S. Pat. No. 11,229,437;

U.S. patent application Ser. No. 16/458,108, entitled SURGICAL INSTRUMENT SYSTEM COMPRISING AN RFID SYSTEM, now U.S. Patent Application Publication No. 2020/0405436;

U.S. patent application Ser. No. 16/458,114, entitled SURGICAL INSTRUMENT COMPRISING AN ALIGNED RFID SENSOR, now U.S. Pat. No. 11,350,938;

now U.S. patent application Ser. No. 16/458,105, entitled SURGICAL STAPLING SYSTEM HAVING AN INFORMATION DECRYPTION PROTOCOL, now U.S. Patent Application Publication No. 2020/0405302;

U.S. patent application Ser. No. 16/458,110, entitled SURGICAL STAPLING SYSTEM HAVING AN INFORMATION ENCRYPTION PROTOCOL, now U.S. Pat. No. 11,259,803;

U.S. patent application Ser. No. 16/458,120, entitled SURGICAL STAPLING SYSTEM HAVING A LOCKOUT MECHANISM FOR AN INCOMPATIBLE CARTRIDGE, now U.S. Pat. No. 11,298,127;

U.S. patent application Ser. No. 16/458,125, entitled SURGICAL STAPLING SYSTEM HAVING A FRANGIBLE RFID TAG, now U.S. Pat. No. 11,246,678; and U.S. patent application Ser. No. 16/458,103, entitled PACKAGING FOR A REPLACEABLE COMPONENT OF A SURGICAL STAPLING SYSTEM, now U.S. Patent Application Publication No. 2020/0405296.

Applicant of the present application owns the following U.S. Patent Applications that were filed on Jun. 30, 2019 and which are each herein incorporated by reference in their respective entireties:

U.S. patent application Ser. No. 16/458,107, entitled METHOD OF USING MULTIPLE RFID CHIPS WITH A SURGICAL ASSEMBLY, now U.S. Patent Application Publication No. 2020/0405311;

U.S. patent application Ser. No. 16/458, 109, entitled MECHANISMS FOR PROPER ANVIL ATTACHMENT SURGICAL STAPLING HEAD ASSEMBLY, now U.S. Patent Application Publication No. 2020/0405312;

U.S. patent application Ser. No. 16/458,115, entitled SURGICAL INSTRUMENT WITH BATTERY COMPATIBILITY VERIFICATION FUNCTIONALITY, now U.S. Patent Application Publication No. 2020/0405313;

U.S. patent application Ser. No. 16/458,117, entitled SURGICAL SYSTEM WITH RFID TAGS FOR UPDATING MOTOR ASSEMBLY PARAMETERS, now U.S. Patent Application Publication No. 2020/0405439;

U.S. patent application Ser. No. 16/458,121, entitled SURGICAL SYSTEMS WITH MULTIPLE RFID TAGS, now U.S. Patent Application Publication No. 2020/0405440;

U.S. patent application Ser. No. 16/458,122, entitled RFID IDENTIFICATION SYSTEMS FOR SURGICAL INSTRUMENTS, now U.S. Patent Application Publication No. 2020/0410177;

U.S. patent application Ser. No. 16/458,106, entitled RFID IDENTIFICATION SYSTEMS FOR SURGICAL INSTRUMENTS, now U.S. Patent Application Publication No. 2020/0405316;

U.S. patent application Ser. No. 16/458,112, entitled SURGICAL RFID ASSEMBLIES FOR DISPLAY AND COMMUNICATION, now U.S. Patent Application Publication No. 2020/0405409;

U.S. patent application Ser. No. 16/458,116, entitled SURGICAL RFID ASSEMBLIES FOR COMPATIBILITY DETECTION, now U.S. Patent Application Publication No. 2020/0410180; and U.S. patent application Ser. No. 16/458,118, entitled SURGICAL RFID ASSEMBLIES FOR INSTRUMENT OPERATIONAL SETTING CONTROL, now U.S. Patent Application Publication No. 2020/0405410.

Applicant of the present application owns the following U.S. Patent Applications that were filed on May 1, 2018 and which are each herein incorporated by reference in their respective entireties:

U.S. Provisional Patent Application Ser. No. 62/665,129, entitled SURGICAL SUTURING SYSTEMS;

U.S. Provisional Patent Application Ser. No. 62/665,139, entitled SURGICAL INSTRUMENTS COMPRISING CONTROL SYSTEMS;

U.S. Provisional Patent Application Ser. No. 62/665,177, entitled SURGICAL INSTRUMENTS COMPRISING HANDLE ARRANGEMENTS;

U.S. Provisional Patent Application Ser. No. 62/665,128, entitled MODULAR SURGICAL INSTRUMENTS;

U.S. Provisional Patent Application Ser. No. 62/665,192, entitled SURGICAL DISSECTORS; AND U.S. Provisional Patent Application Ser. No. 62/665,134, entitled SURGICAL CLIP APPLIER.

Applicant of the present application owns the following U.S. Patent Applications that were filed on Aug. 24, 2018 which are each herein incorporated by reference in their respective entireties:

- U.S. patent application Ser. No. 16/112,129, entitled SURGICAL SUTURING INSTRUMENT CONFIGURED TO MANIPULATE TISSUE USING MECHANICAL AND ELECTRICAL POWER;
- U.S. patent application Ser. No. 16/112,155, entitled SURGICAL SUTURING INSTRUMENT COMPRISING A CAPTURE WIDTH WHICH IS LARGER THAN TROCAR DIAMETER;
- U.S. patent application Ser. No. 16/112,168, entitled SURGICAL SUTURING INSTRUMENT COMPRISING A NON-CIRCULAR NEEDLE;
- U.S. patent application Ser. No. 16/112,180, entitled ELECTRICAL POWER OUTPUT CONTROL BASED ON MECHANICAL FORCES;
- U.S. patent application Ser. No. 16/112,193, entitled REACTIVE ALGORITHM FOR SURGICAL SYSTEM;
- U.S. patent application Ser. No. 16/112,099, entitled SURGICAL INSTRUMENT COMPRISING AN ADAPTIVE ELECTRICAL SYSTEM;
- U.S. patent application Ser. No. 16/112,112, entitled CONTROL SYSTEM ARRANGEMENTS FOR A MODULAR SURGICAL INSTRUMENT;
- U.S. patent application Ser. No. 16/112,119, entitled ADAPTIVE CONTROL PROGRAMS FOR A SURGICAL SYSTEM COMPRISING MORE THAN ONE TYPE OF CARTRIDGE;
- U.S. patent application Ser. No. 16/112,097, entitled SURGICAL INSTRUMENT SYSTEMS COMPRISING BATTERY ARRANGEMENTS;
- U.S. patent application Ser. No. 16/112,109, entitled SURGICAL INSTRUMENT SYSTEMS COMPRISING HANDLE ARRANGEMENTS;
- U.S. patent application Ser. No. 16/112,114, entitled SURGICAL INSTRUMENT SYSTEMS COMPRISING FEEDBACK MECHANISMS;
- U.S. patent application Ser. No. 16/112,117, entitled SURGICAL INSTRUMENT SYSTEMS COMPRISING LOCKOUT MECHANISMS;
- U.S. patent application Ser. No. 16/112,095, entitled SURGICAL INSTRUMENTS COMPRISING A LOCKABLE END EFFECTOR SOCKET;
- U.S. patent application Ser. No. 16/112,121, entitled SURGICAL INSTRUMENTS COMPRISING A SHIFTING MECHANISM;
- U.S. patent application Ser. No. 16/112,151, entitled SURGICAL INSTRUMENTS COMPRISING A SYSTEM FOR ARTICULATION AND ROTATION COMPENSATION;
- U.S. patent application Ser. No. 16/112,154, entitled SURGICAL INSTRUMENTS COMPRISING A BIASED SHIFTING MECHANISM;
- U.S. patent application Ser. No. 16/112,226, entitled SURGICAL INSTRUMENTS COMPRISING AN ARTICULATION DRIVE THAT PROVIDES FOR HIGH ARTICULATION ANGLES;
- U.S. patent application Ser. No. 16/112,062, entitled SURGICAL DISSECTORS AND MANUFACTURING TECHNIQUES;
- U.S. patent application Ser. No. 16/112,098, entitled SURGICAL DISSECTORS CONFIGURED TO APPLY MECHANICAL AND ELECTRICAL ENERGY;
- U.S. patent application Ser. No. 16/112,237, entitled SURGICAL CLIP APPLIER CONFIGURED TO STORE CLIPS IN A STORED STATE;
- U.S. patent application Ser. No. 16/112,245, entitled SURGICAL CLIP APPLIER COMPRISING AN EMPTY CLIP CARTRIDGE LOCKOUT;
- U.S. patent application Ser. No. 16/112,249, entitled SURGICAL CLIP APPLIER COMPRISING AN AUTOMATIC CLIP FEEDING SYSTEM;
- U.S. patent application Ser. No. 16/112,253, entitled SURGICAL CLIP APPLIER COMPRISING ADAPTIVE FIRING CONTROL; and
- U.S. patent application Ser. No. 16/112,257, entitled SURGICAL CLIP APPLIER COMPRISING ADAPTIVE CONTROL IN RESPONSE TO A STRAIN GAUGE CIRCUIT.

Applicant of the present application owns the following U.S. Patent Applications that were filed on Oct. 26, 2018 which are each herein incorporated by reference in their respective entireties:

- U.S. patent application Ser. No. 16/172,130, entitled CLIP APPLIER COMPRISING INTERCHANGEABLE CLIP RELOADS;
- U.S. patent application Ser. No. 16/172,066, entitled CLIP APPLIER COMPRISING A MOVABLE CLIP MAGAZINE;
- U.S. patent application Ser. No. 16/172,078, entitled CLIP APPLIER COMPRISING A ROTATABLE CLIP MAGAZINE;
- U.S. patent application Ser. No. 16/172,087, entitled CLIP APPLIER COMPRISING CLIP ADVANCING SYSTEMS;
- U.S. patent application Ser. No. 16/172,094, entitled CLIP APPLIER COMPRISING A CLIP CRIMPING SYSTEM;
- U.S. patent application Ser. No. 16/172,128, entitled CLIP APPLIER COMPRISING A RECIPROCATING CLIP ADVANCING MEMBER;
- U.S. patent application Ser. No. 16/172,168, entitled CLIP APPLIER COMPRISING A MOTOR CONTROLLER;
- U.S. patent application Ser. No. 16/172,164, entitled SURGICAL SYSTEM COMPRISING A SURGICAL TOOL AND A SURGICAL HUB; and
- U.S. patent application Ser. No. 16/172,303, entitled METHOD FOR OPERATING A POWERED ARTICULATING MULTI-CLIP APPLIER.

Applicant of the present application owns the following U.S. Patent Applications, filed on Dec. 4, 2018, the disclosure of each of which is herein incorporated by reference in its entirety:

- U.S. patent application Ser. No. 16/209,385, titled METHOD OF HUB COMMUNICATION, PROCESSING, STORAGE AND DISPLAY;
- U.S. patent application Ser. No. 16/209,395, titled METHOD OF HUB COMMUNICATION;
- U.S. patent application Ser. No. 16/209,403, titled METHOD OF CLOUD BASED DATA ANALYTICS FOR USE WITH THE HUB;

U.S. patent application Ser. No. 16/209,407, titled METHOD OF ROBOTIC HUB COMMUNICATION, DETECTION, AND CONTROL;

U.S. patent application Ser. No. 16/209,416, titled METHOD OF HUB COMMUNICATION, PROCESSING, DISPLAY, AND CLOUD ANALYTICS;

U.S. patent application Ser. No. 16/209,423, titled METHOD OF COMPRESSING TISSUE WITHIN A STAPLING DEVICE AND SIMULTANEOUSLY DISPLAYING THE LOCATION OF THE TISSUE WITHIN THE JAWS;

U.S. patent application Ser. No. 16/209,427, titled METHOD OF USING REINFORCED FLEXIBLE CIRCUITS WITH MULTIPLE SENSORS TO OPTIMIZE PERFORMANCE OF RADIO FREQUENCY DEVICES;

U.S. patent application Ser. No. 16/209,433, titled METHOD OF SENSING PARTICULATE FROM SMOKE EVACUATED FROM A PATIENT, ADJUSTING THE PUMP SPEED BASED ON THE SENSED INFORMATION, AND COMMUNICATING THE FUNCTIONAL PARAMETERS OF THE SYSTEM TO THE HUB;

U.S. patent application Ser. No. 16/209,447, titled METHOD FOR SMOKE EVACUATION FOR SURGICAL HUB;

U.S. patent application Ser. No. 16/209,453, titled METHOD FOR CONTROLLING SMART ENERGY DEVICES;

U.S. patent application Ser. No. 16/209,458, titled METHOD FOR SMART ENERGY DEVICE INFRASTRUCTURE;

U.S. patent application Ser. No. 16/209,465, titled METHOD FOR ADAPTIVE CONTROL SCHEMES FOR SURGICAL NETWORK CONTROL AND INTERACTION;

U.S. patent application Ser. No. 16/209,478, titled METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE;

U.S. patent application Ser. No. 16/209,490, titled METHOD FOR FACILITY DATA COLLECTION AND INTERPRETATION; and U.S. patent application Ser. No. 16/209,491, titled METHOD FOR CIRCULAR STAPLER CONTROL ALGORITHM ADJUSTMENT BASED ON SITUATIONAL AWARENESS.

Before explaining various aspects of surgical devices and systems in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Various surgical systems and instruments (e.g. surgical stapling instrument, surgical clip applier, surgical suturing instrument) are described in connection with the present disclosure. The surgical systems and/or instruments comprise a radio-frequency identification (RFID) system that includes one or more RFID scanners and one or more RFID tags, as will be discussed in greater detail below. Examples of surgical systems which use RFID technology are disclosed in U.S. Pat. No. 7,959,050 and U.S. Patent Application No. 2015/0053743, both of which are incorporated by reference herein in their entireties.

Radio-frequency identification (RFID) is used in a variety of industries to track and identify objects. RFID relies on radio waves to transfer digitally-stored information from a RFID tag to a RFID reader or receiver configured to receive the information. RFID technology uses RFID tags, sometimes referred to as chips, which contain electronically-stored information, and RFID readers, which serve to identify and communicate with the RFID tags. There are two different types of RFID systems—active RFID systems and passive RFID systems. Active RFID systems include RFID tags that comprise an on-board power source to broadcast their signals. Active RFID tags can include a battery within the RFID tag which allows the active RFID tag to function independently from the RFID reader. As such, RFID tags in an active RFID system do not need to wait to receive a signal from a RFID reader before sending out information. Instead, the active RFID tags are free to continuously send out a signal, or beacon. Many commercially available active RFID systems often operate at one of two main frequency ranges—433 MHz and 915 MHz, but any suitable frequency range can be used. Typically, a RFID tag must be within a specific distance or frequency range in order to be identified by its corresponding RFID reader.

Passive RFID systems include RFID tags which do not comprise an on-board power source but instead receive the energy needed to operate from an RFID reader. Contrary to active RFID tags, RFID tags in a passive RFID system do not actively send out a signal before receiving a prompt. Instead, passive RFID tags wait to receive information from a RFID reader before sending out a signal. Many commercially-available passive RFID systems often operate within three frequency ranges—Low Frequency ("LF"), High Frequency ("HF") & Near-Field Communication ("NFC"), and Ultra High Frequency ("UHF"). The LF bandwidth is 125-134 KHz and includes a longer wavelength with a short read range of approximately one to ten centimeters. The HF and NFC bandwidth is 13.56 MHz and includes a medium wavelength with a typical read range of one centimeter to one meter. The UHF bandwidth is 865-960 MHz and includes a short, high-energy wavelength of one meter which translates into a long read range. The above being said, any suitable frequency can be used.

A variety of RFID systems comprising differently-sized RFID tags exist. However, some are better suited for use in technology areas that require the tracking of very small objects. For example, Hitachi Chemical Co. Ltd. is a leading manufacturer in the RFID technology field. The Ultra Small size UHF RFID tag manufactured by Hitachi Chemical Co. Ltd. is typically no larger than 1.0 to 13 mm and enables communication between a RFID tag and a RFID reader at distances of several centimeters or more. Due to its compact nature, the Hitachi RFID tag is suitable for very small products which need to be identified. Each Hitachi RFID tag comprises an antenna, an IC chip connected to the antenna, and a sealing material that seals the IC chip and the antenna. Because the Hitachi RFID tag incorporates an antenna and an IC chip in a single unit, the Hitachi RFID tag is convenient enough to easily affix to any small object using an adhesive or tape, for example.

The Hitachi RFID tag comprises a square stainless steel plate and a metal antenna. The antenna comprises a LC resonant circuit or any other suitable circuit and is electrically connected to the plate. After the plate and the antenna are connected to one another, the antenna and plate are sealed together in a single unit with a sealing material. The sealing material is primarily composed of epoxy, carbon, and silica to enhance the heat resistance capabilities of the Hitachi RFID tag. That is, the heat resistance of the RFID tag substantially depends on the heat resistance capabilities of the sealing material. The sealing material has a high heat resistance withstanding temperatures of up to 250 to 300° C. for shorter time periods, such as a few seconds, and is resistant to heat for longer periods of time up to 150° C. Accordingly, the Hitachi RFID tag has a higher heat resistance than conventional RFID tags and can still operate normally even at high temperatures. Additional information regarding the Hitachi RFID tag can be found in U.S. Pat. No. 9,171,244, which is incorporated by reference herein in its entirety.

Figure 1:
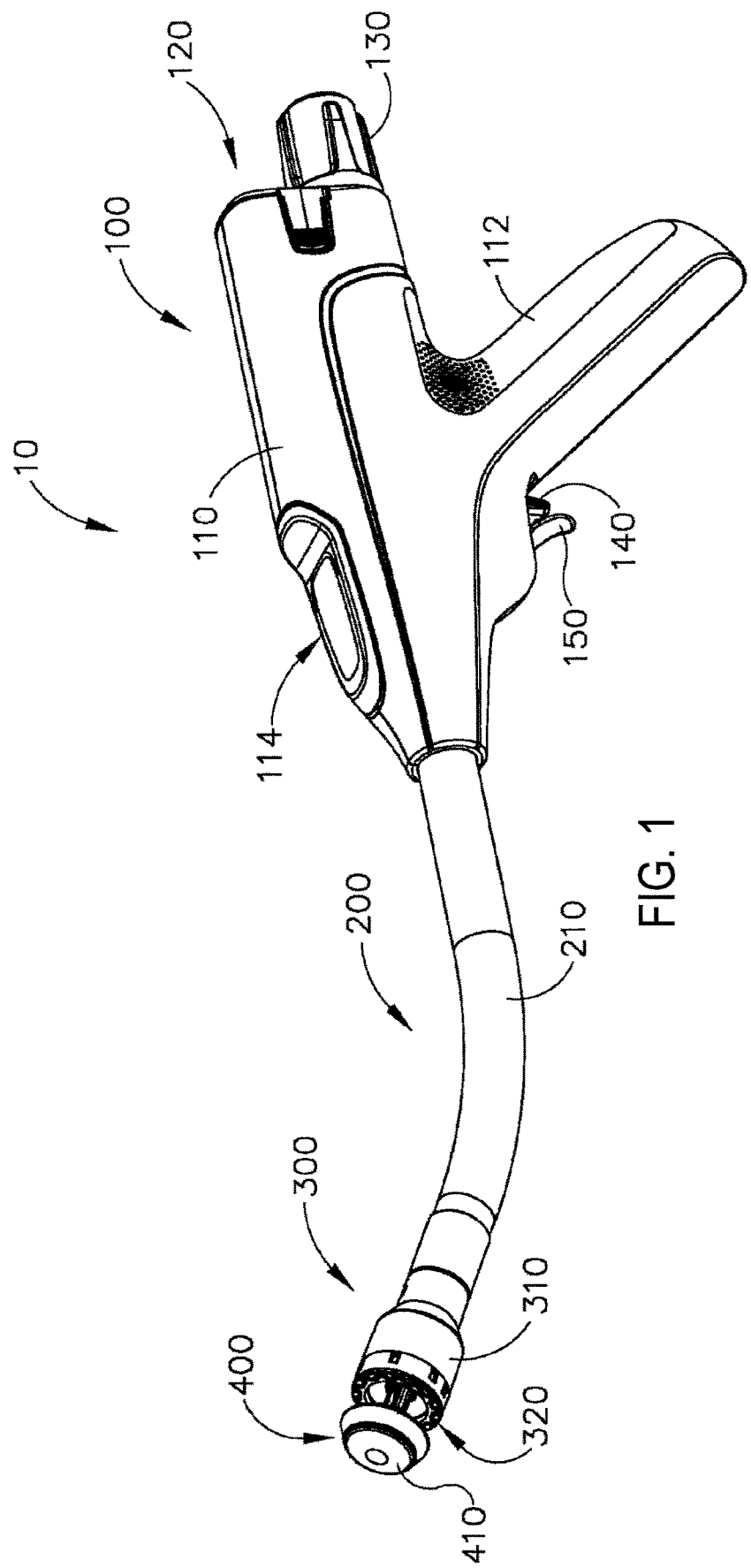
FIG. 1 depicts a perspective view of an exemplary circular stapler, in accordance with at least one aspect of the present disclosure.
Figure 2:
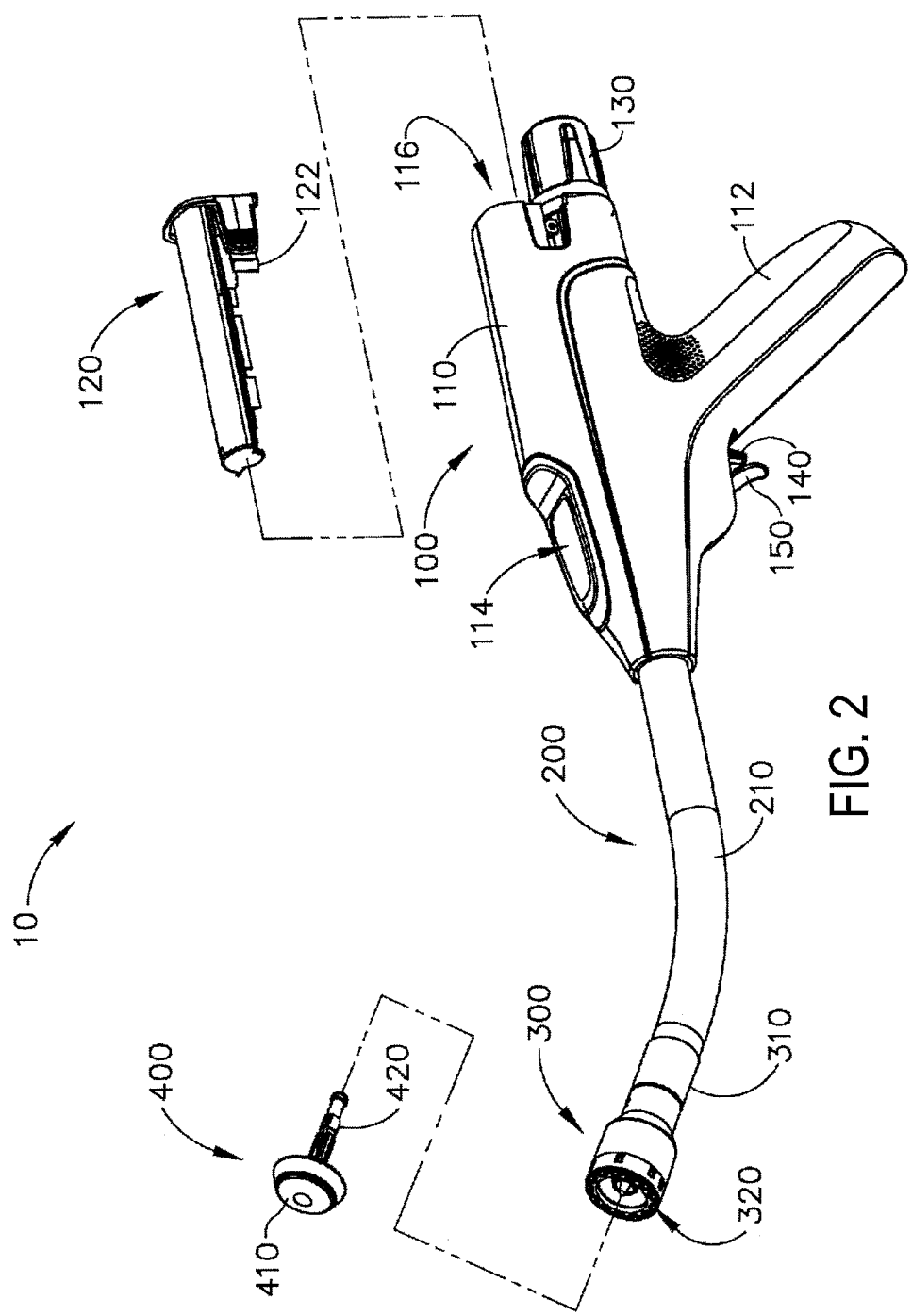
FIG. 2 depicts a perspective view of the circular stapler of FIG. 1, with a battery pack removed from a housing assembly and an anvil removed from a stapling head assembly, in accordance with at least one aspect of the present disclosure.

FIGS. 1-2 depict an example surgical circular stapling instrument 10 that can be adapted to include an RFID system and a control system thereof, in accordance with at least one aspect of the present disclosure. The stapling instrument 10 may be used to provide an end-to-end anastomosis between two sections of an anatomical lumen such as a portion of a patient's digestive tract. Instrument 10 of this example comprises a housing assembly 100, a shaft assembly 200, a stapling head assembly 300, and an anvil 400. Housing assembly 100 comprises a casing 110 defining an obliquely oriented pistol grip 112. Although the housing assembly 100 is depicted in the form of a handle, this is not limiting. In various instances, the housing assembly 100 can be a component of a robotic system, for example.

Housing assembly 100 further includes a window 114 that permits viewing of a movable indicator needle. In some versions, a series of hash marks, colored regions, and/or other fixed indicators are positioned adjacent to window 114 in order to provide a visual context for indicator needle, thereby facilitating operator evaluation of the position of needle within window 114. The movement of the indicator needle corresponds to a closing motion of the anvil 400 relative to the stapling head assembly 300. The hash marks, colored regions, and/or other fixed indicators can define an optimal anvil closure zone for firing the instrument 10. Accordingly, when the indicator needle is in the optimal anvil closure zone, the user may fire the instrument 10. Various suitable alternative features and configurations for housing assembly 100 will be apparent to those of ordinary skill in the art in view of the teachings herein.

Instrument 10 of the present example further includes a power source which can be in the form of a battery pack 120. Battery pack 120 is operable to provide electrical power to a motor 160 (FIG. 15) in pistol grip 112. In various aspects, battery pack 120 is removable from housing assembly 100. In particular, as shown in FIGS. 1-2, battery pack 120 may be inserted into a socket 116 defined by casing 110. Once battery pack 120 is fully inserted in socket 116, latches 122 of battery pack 120 may resiliently engage interior features of casing 110 to provide a snap fit. To remove battery pack 120, the operator may press latches 122 inwardly to disengage latches 122 from the interior features of casing 110 then pull battery pack 120 proximally from socket 116. It should be understood that battery pack 120 and housing assembly 100 may have complementary electrical contacts, pins and sockets, and/or other features that provide paths for electrical communication from battery pack 120 to electrically powered components in housing assembly 100 when battery pack 120 is inserted in socket 116. It should also be understood that, in some versions, battery pack 120 is unitarily incorporated within housing assembly 100 such that battery back 120 cannot be removed from housing assembly 100.

Shaft assembly 200 extends distally from housing assembly 100 and includes a preformed bend. In some versions, the preformed bend is configured to facilitate positioning of stapling head assembly 300 within a patient's colon. Various suitable bend angles or radii that may be used will be apparent to those of ordinary skill in the art in view of the teachings herein. In some other versions, shaft assembly 200 is straight, such that shaft assembly 200 lacks a preformed bend. Various exemplary components that may be incorporated into shaft assembly 200 will be described in greater detail below.

Stapling head assembly 300 is located at the distal end of shaft assembly 200. As shown in FIGS. 1-2, anvil 400 is configured to removably couple with shaft assembly 200, adjacent to stapling head assembly 300. Anvil 400 and stapling head assembly 300 are configured to cooperate to manipulate tissue in three ways, including clamping the tissue, cutting the tissue, and stapling the tissue. A knob 130 at the proximal end of housing assembly 100 is rotatable relative to casing 110 to provide precise clamping of the tissue between anvil 400 and stapling head assembly 300. When a safety trigger 140 of housing assembly 100 is pivoted away from a firing trigger 150 of housing assembly 100, firing trigger 150 may be actuated to thereby provide cutting and stapling of the tissue.

In the following discussion of anvil 400, the terms "distal" and "proximal" and variations thereof will be used with reference to the orientation of anvil 400 when anvil 400 is coupled with shaft assembly 200 of instrument 10. Thus, proximal features of anvil 400 will be closer to the operator of instrument 10; while distal features of anvil 400 will be further from the operator of instrument 10.

Figure 4:
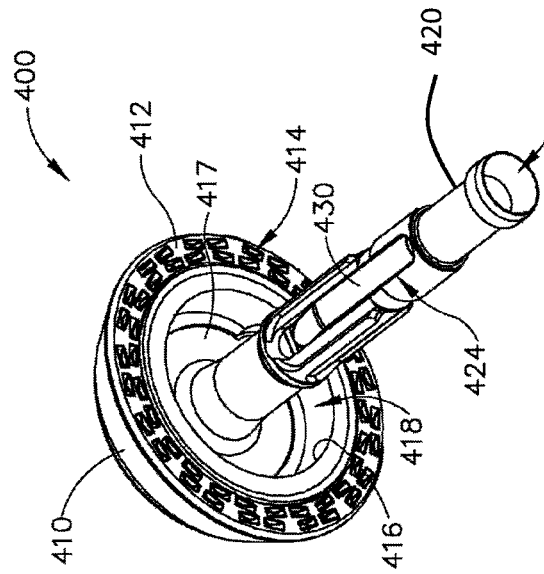
FIG. 4 depicts another perspective view of the anvil of FIG. 3, in accordance with at least one aspect of the present disclosure.

Referring to FIG. 4, anvil 400 of the present example comprises a head 410 and a shank 420. Head 410 includes a proximal surface 412 that defines a plurality of staple forming pockets 414. Staple forming pockets 414 are arranged in two concentric annular arrays. In some other versions, staple forming pockets 414 are arranged in three or more concentric annular arrays. Staple forming pockets 414 are configured to deform staples as the staples are driven into staple forming pockets 414. For instance, each staple forming pocket 414 may deform a generally "U" shaped staple into a "B" shape as is known in the art. As best seen in FIG. 4, proximal surface 412 terminates at an inner edge 416, which defines an outer boundary of an annular recess 418 surrounding shank 420.

Shank 420 defines a bore 422 and includes a pair of pivoting latch members 430 positioned in bore 422. Latch members 430 are positioned within bore 422 such that their distal ends are positioned at the proximal ends of lateral openings 424, which are formed through the sidewall of shank 420.

Lateral openings 424 thus provide clearance for the distal ends 434 of the latch members 430 to deflect radially outwardly from the longitudinal axis defined by shank 420. However, latch members 430 are configured to resiliently bias their distal ends radially inwardly toward the longitudinal axis defined by shank 420. Latch members 430 thus act as retaining clips. This allows anvil 400 to be removably secured to a trocar 330 of stapling head assembly 300. It should be understood, however, that latch members 430 are merely optional. Anvil 400 may be removably secured to a trocar 330 using any other suitable components, features, or techniques.

In addition to or in lieu of the foregoing, anvil 400 may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or U.S. Pat. No. 8,910,847, the disclosures of which are incorporated by reference herein. Still other suitable configurations will be apparent to one of ordinary skill in the art in view of the teachings herein.

Figure 3:
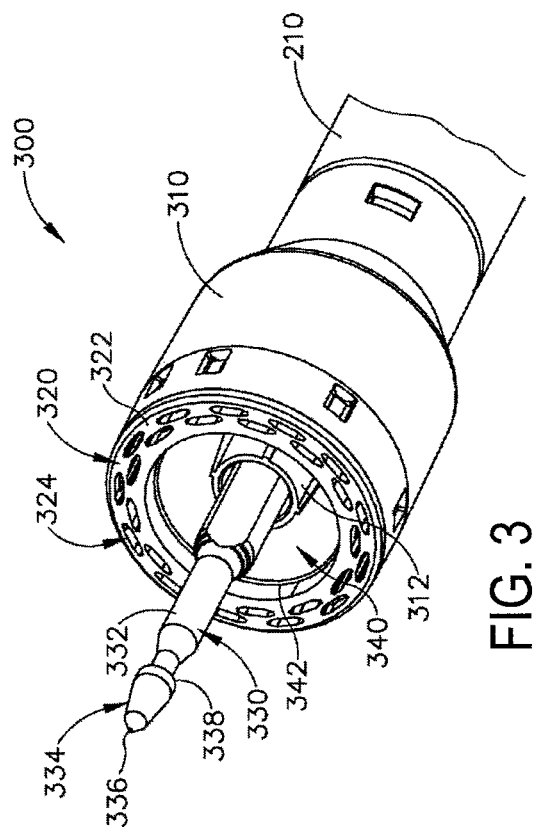
FIG. 3 depicts a perspective view of the stapling head assembly of the circular stapler of FIG. 1, in accordance with at least one aspect of the present disclosure.

Referring to FIG. 3, stapling head assembly 300 of the present example is coupled to a distal end of shaft assembly 200 and comprises a tubular casing 310 housing a slidable staple driver member. A cylindrical inner core member 312 extends distally within tubular casing 310. Tubular casing 310 is fixedly secured to an outer sheath 210 of shaft assembly 200, such that tubular casing 310 serves as a mechanical ground for stapling head assembly 300.

Trocar 330 is positioned coaxially within inner core member 312 of tubular casing 310. Trocar 330 is operable to translate distally and proximally relative to tubular casing 310 in response to rotation of knob 130 relative to casing 110 of housing assembly 100. Trocar 330 comprises a shaft 332 and a head 334. Head 334 includes a pointed tip 336 and an inwardly extending proximal surface 338. Shaft 332 thus provides a reduced outer diameter just proximal to head 334, with surface 338 providing a transition between that reduced outer diameter of shaft 332 and the outer diameter of head 334. While tip 336 is pointed in the present example, tip 336 is not sharp. Tip 336 will thus not easily cause trauma to tissue due to inadvertent contact with tissue. Head 334 and the distal portion of shaft 332 are configured for insertion in bore 422 of anvil 420. Anvil 400 is thus secured to trocar 330 through a snap fit due to latch members 430.

Figure 5:
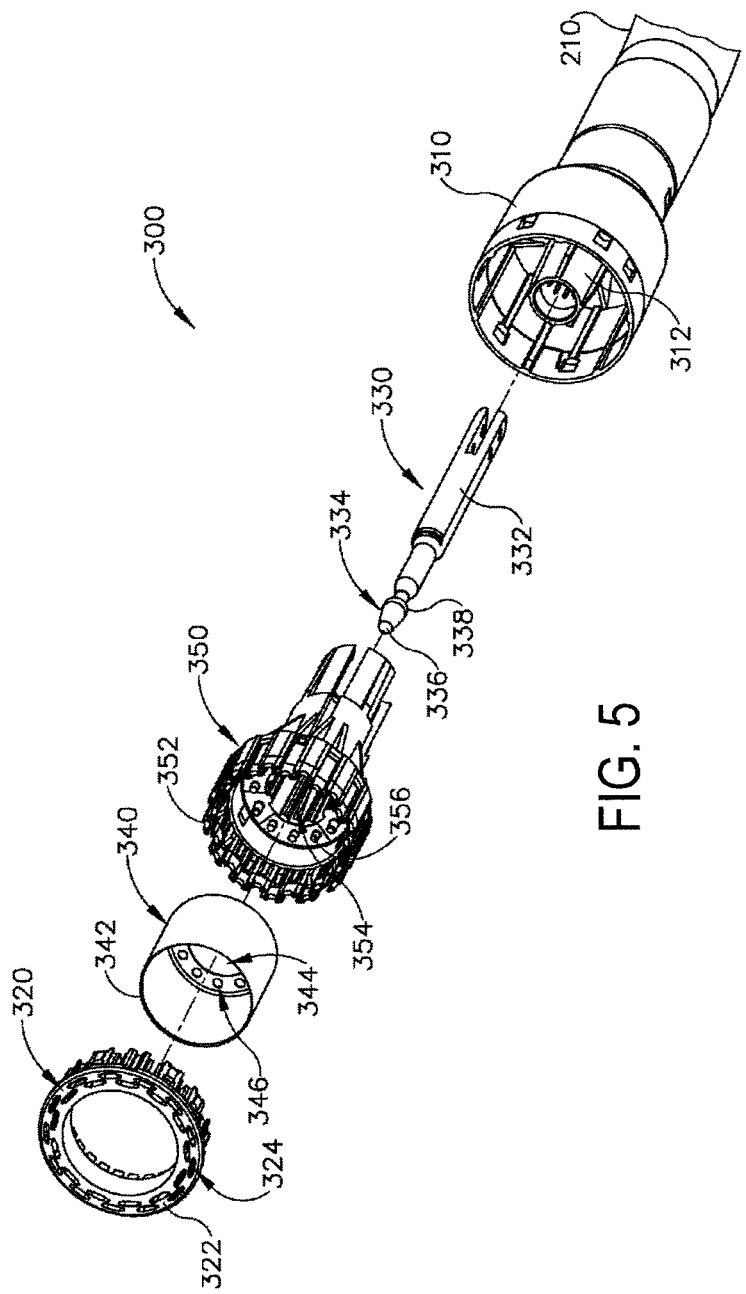
FIG. 5 depicts an exploded perspective view of the stapling head assembly of FIG. 3, in accordance with at least one aspect of the present disclosure.

As illustrated in FIG. 5, Staple driver member 350 is operable to actuate longitudinally within tubular casing 310 in response to activation of a motor 160. Staple driver member 350 includes two distally presented concentric annular arrays of staple drivers 352. Staple drivers 352 are arranged to correspond with the arrangement of staple forming pockets 414 described above. Thus, each staple driver 352 is configured to drive a corresponding staple into a corresponding staple forming pocket 414 when stapling head assembly 300 is actuated. It should be understood that the arrangement of staple drivers 352 may be modified just like the arrangement of staple forming pockets 414 as described above. Staple driver member 350 also defines a bore 354 that is configured to coaxially receive core member 312 of tubular casing 310. An annular array of studs 356 project distally from a distally presented surface surrounding bore 354.

A cylindrical knife member 340 is coaxially positioned within staple driver member 350. Knife member 340 includes a distally presented, sharp circular cutting edge 342. Knife member 340 is sized such that knife member 340 defines an outer diameter that is smaller than the diameter defined by the inner annular array of staple drivers 352. Knife member 340 also defines an opening that is configured to coaxially receive core member 312 of tubular casing 310. An annular array of openings 346 formed in knife member 340 is configured to complement the annular array of studs 356 of staple driver member 350, such that knife member 340 is fixedly secured to staple driver member 350 via studs 356 and openings 346. Other suitable structural relationships between knife member 340 and stapler driver member 350 will be apparent to those of ordinary skill in the art in view of the teachings herein.

A deck member 320 is fixedly secured to tubular casing 310. Deck member 320 includes a distally presented deck surface 322 defining two concentric annular arrays of staple openings 324. Staple openings 324 are arranged to correspond with the arrangement of staple drivers 352 and staple forming pockets 414 described above. Thus, each staple opening 324 is configured to provide a path for a corresponding staple driver 352 to drive a corresponding staple through deck member 320 and into a corresponding staple forming pocket 414 when stapling head assembly 300 is actuated. It should be understood that the arrangement of staple openings 322 may be modified just like the arrangement of staple forming pockets 414 as described above. It should also be understood that various structures and techniques may be used to contain staples within stapling head assembly 300 before stapling head assembly 300 is actuated. Such structures and techniques that are used to contain staples within stapling head assembly 300 may prevent the staples from inadvertently falling out through staple openings 324 before stapling head assembly 300 is actuated. Various suitable forms that such structures and techniques may take will be apparent to those of ordinary skill in the art in view of the teachings herein.

Figure 6:
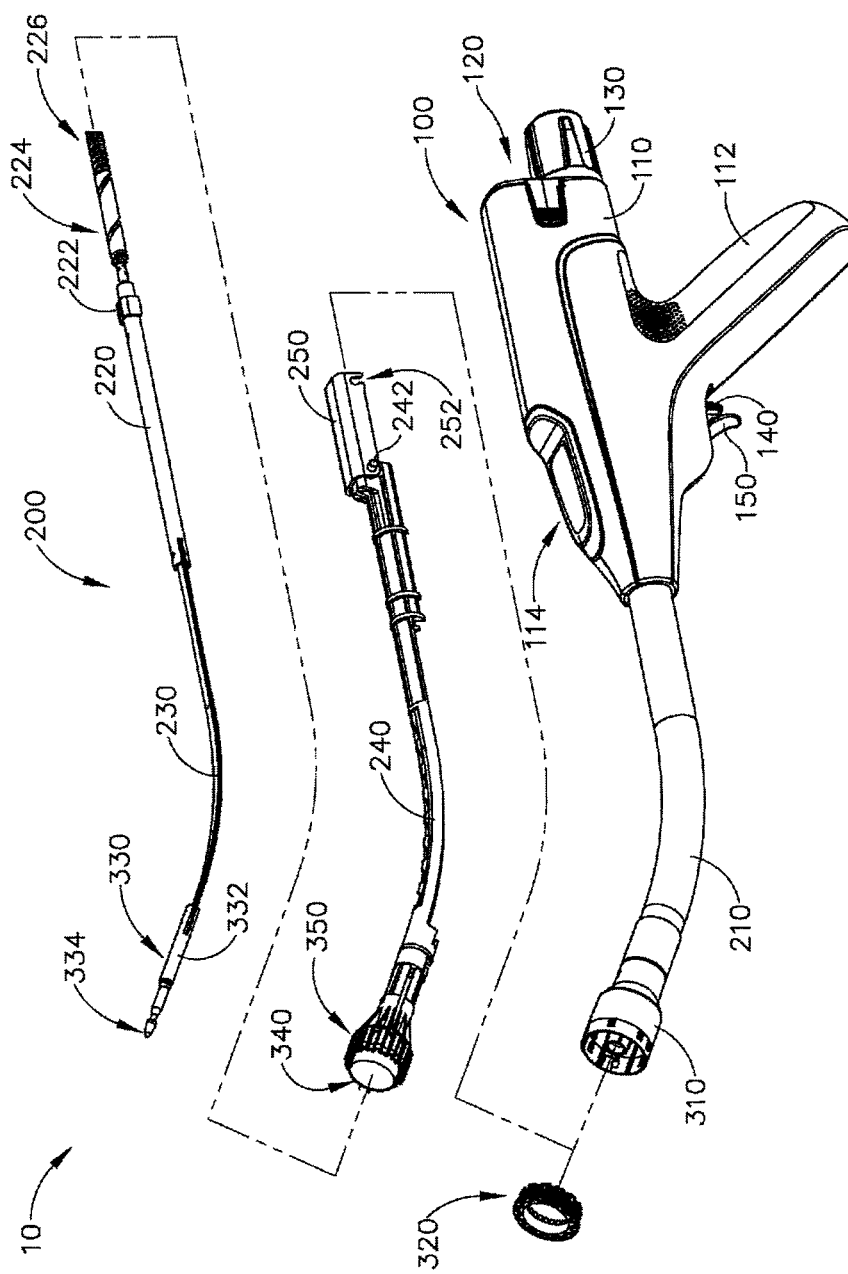
FIG. 6 depicts an exploded perspective view of the circular stapler of FIG. 1, with portions of the shaft assembly shown separately from each other, in accordance with at least one aspect of the present disclosure.
Figure 7:
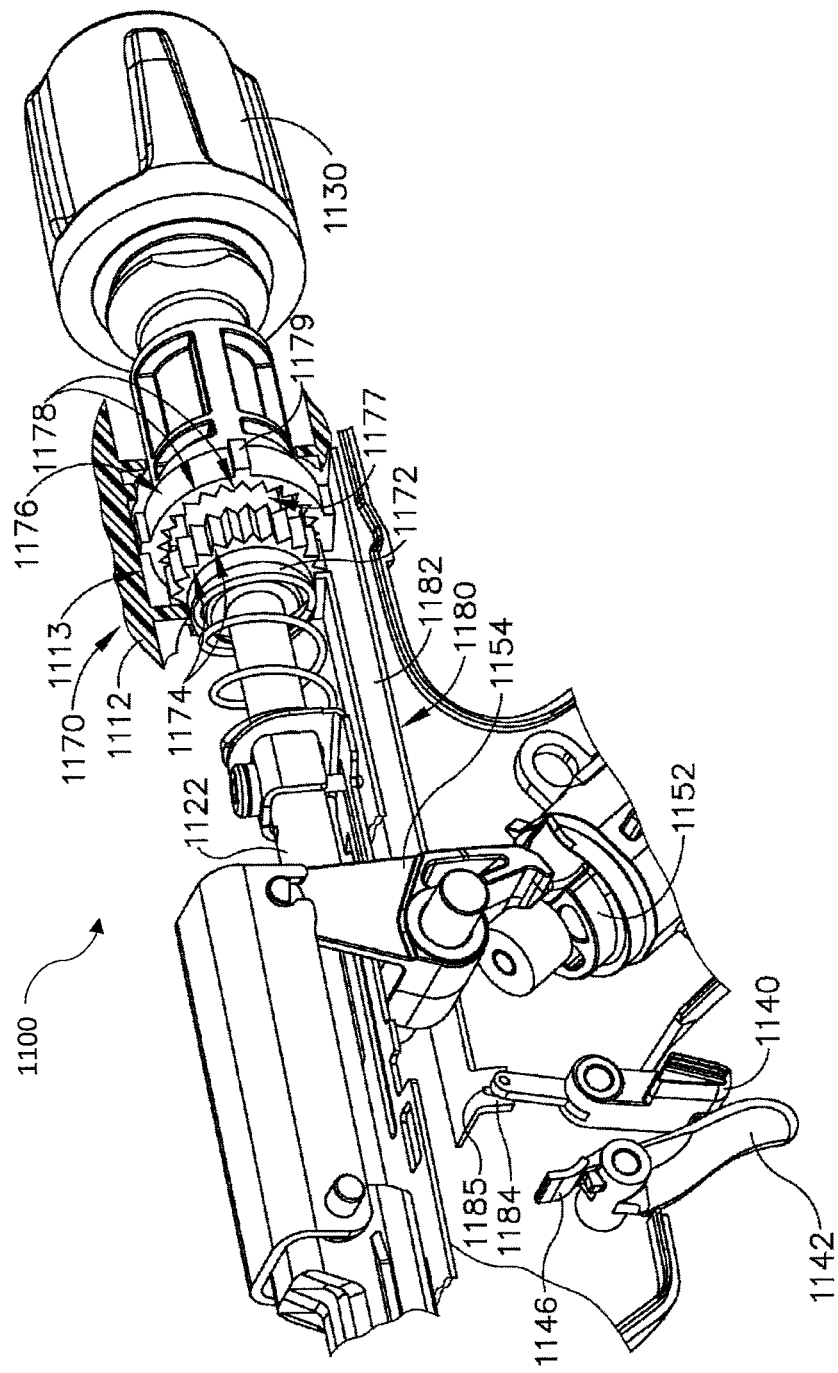
FIG. 7 depicts a detailed perspective view of an anvil actuation assembly of the housing assembly of FIG. 6, in accordance with at least one aspect of the present disclosure.

As best seen in FIG. 6, deck member 320 defines an inner diameter that is just slightly larger than the outer diameter defined by knife member 340. Deck member 320 is thus configured to allow knife member 340 to translate distally to a point where cutting edge 342 is distal to deck surface 322.

In addition to or in lieu of the foregoing, stapling head assembly 300 may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or U.S. Pat. No. 8,910,847, the entire disclosures of which are incorporated by reference herein. Still other suitable configurations will be apparent to one of ordinary skill in the art in view of the teachings herein.

FIG. 6 shows various components of shaft assembly 200, which couples components of stapling head assembly 300 with components of housing assembly 100. In particular, and as noted above, shaft assembly 200 includes an outer sheath 210 that extends between housing assembly 100 and tubular casing 310. In the present example, outer sheath 210 is rigid and includes a preformed curved section as noted above.

Shaft assembly 200 further includes a trocar actuation rod 220 and a trocar actuation band assembly 230. The distal end of trocar actuation band assembly 230 is fixedly secured to the proximal end of trocar shaft 332. The proximal end of trocar actuation band assembly 230 is fixedly secured to the distal end of trocar actuation rod 220. It should therefore be understood that trocar 330 will translate longitudinally relative to outer sheath 210 in response to translation of trocar actuation band assembly 230 and trocar actuation rod 220 relative to outer sheath 210. Trocar actuation band assembly 230 is configured to flex such that trocar actuation band assembly 230 may follow along the preformed curve in shaft assembly 200 as trocar actuation band assembly 230 is translated longitudinally relative to outer sheath 210. However, trocar actuation band assembly 230 has sufficient column strength and tensile strength to transfer distal and proximal forces from trocar actuation rod 220 to trocar shaft 332. Trocar actuation rod 220 is rigid. A clip 222 is fixedly secured to trocar actuation rod 220 and is configured to cooperate with complementary features within housing assembly 100 to prevent trocar actuation rod 220 from rotating within housing assembly 100 while still permitting trocar actuation rod 220 to translate longitudinally within housing assembly 100. Trocar actuation rod 220 further includes a coarse helical threading 224 and a fine helical threading 226.

Shaft assembly 200 further includes a stapling head assembly driver 240 that is slidably received within outer sheath 210. The distal end of stapling head assembly driver 240 is fixedly secured to the proximal end of staple driver member 350. The proximal end of stapling head assembly driver 240 is secured to a drive bracket 250 via a pin 242. It should therefore be understood that staple driver member 350 will translate longitudinally relative to outer sheath 210 in response to translation of stapling head assembly driver 240 and drive bracket 250 relative to outer sheath 210. Stapling head assembly driver 240 is configured to flex such that stapling head assembly driver 240 may follow along the preformed curve in shaft assembly 200 as stapling head assembly driver 240 is translated longitudinally relative to outer sheath 210. However, stapling head assembly driver 240 has sufficient column strength to transfer distal forces from drive bracket 250 to staple driver member 350.

It should be understood that shaft assembly 200 may further include one or more spacer elements within outer sheath 210. Such spacer elements may be configured to support trocar actuation band assembly 230 and/or stapling head assembly driver 240 as trocar actuation band assembly 230 and/or stapling head assembly driver 240 translate through outer sheath 210. For instance, such spacer elements may prevent trocar actuation band assembly 230 and/or stapling head assembly driver 240 from buckling as trocar actuation band assembly 230 and/or stapling head assembly driver 240 translate through outer sheath 210. Various suitable forms that such spacer elements may take will be apparent to those of ordinary skill in the art in view of the teachings herein.

In addition to or in lieu of the foregoing, shaft assembly 200 may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or U.S. Pat. No. 8,910,847, the disclosures of which are incorporated by reference herein in their entireties. Still other suitable configurations will be apparent to one of ordinary skill in the art in view of the teachings herein.

Additional operational details of the surgical instrument 10, and other instruments suitable for use with the present disclosure, are also described in United States Patent Publication No. 20160374665, titled SURGICAL STAPLER WITH ELECTROMECHANICAL LOCKOUT, filed Jun. 26, 2015, which is hereby incorporated by reference herein in its entirety.

Figure 8:
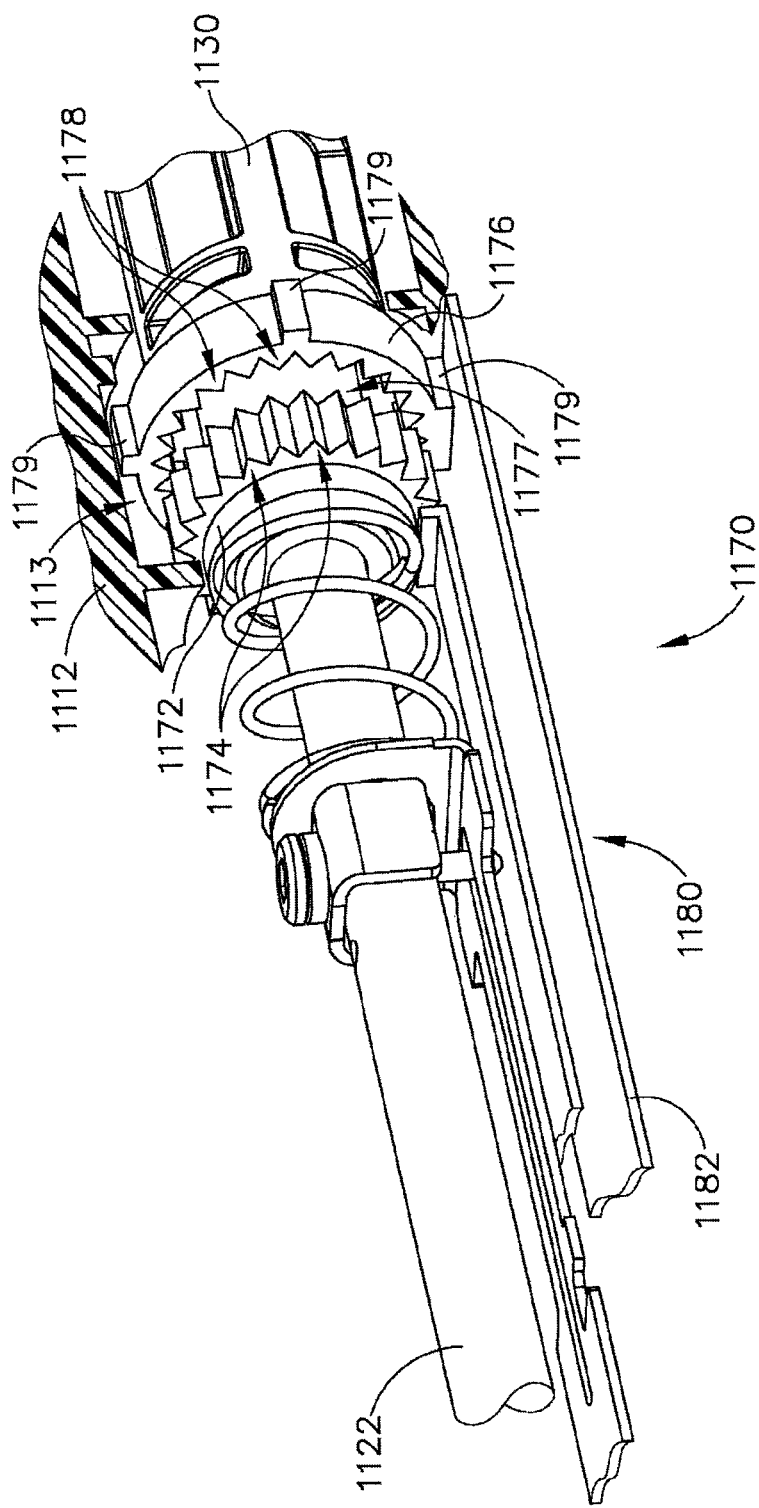
FIG. 8 depicts a detailed perspective view of an anvil lockout assembly of the anvil actuation assembly of FIG. 7, with the anvil lockout assembly in an unlocked position, in accordance with at least one aspect of the present disclosure.
Figure 12:
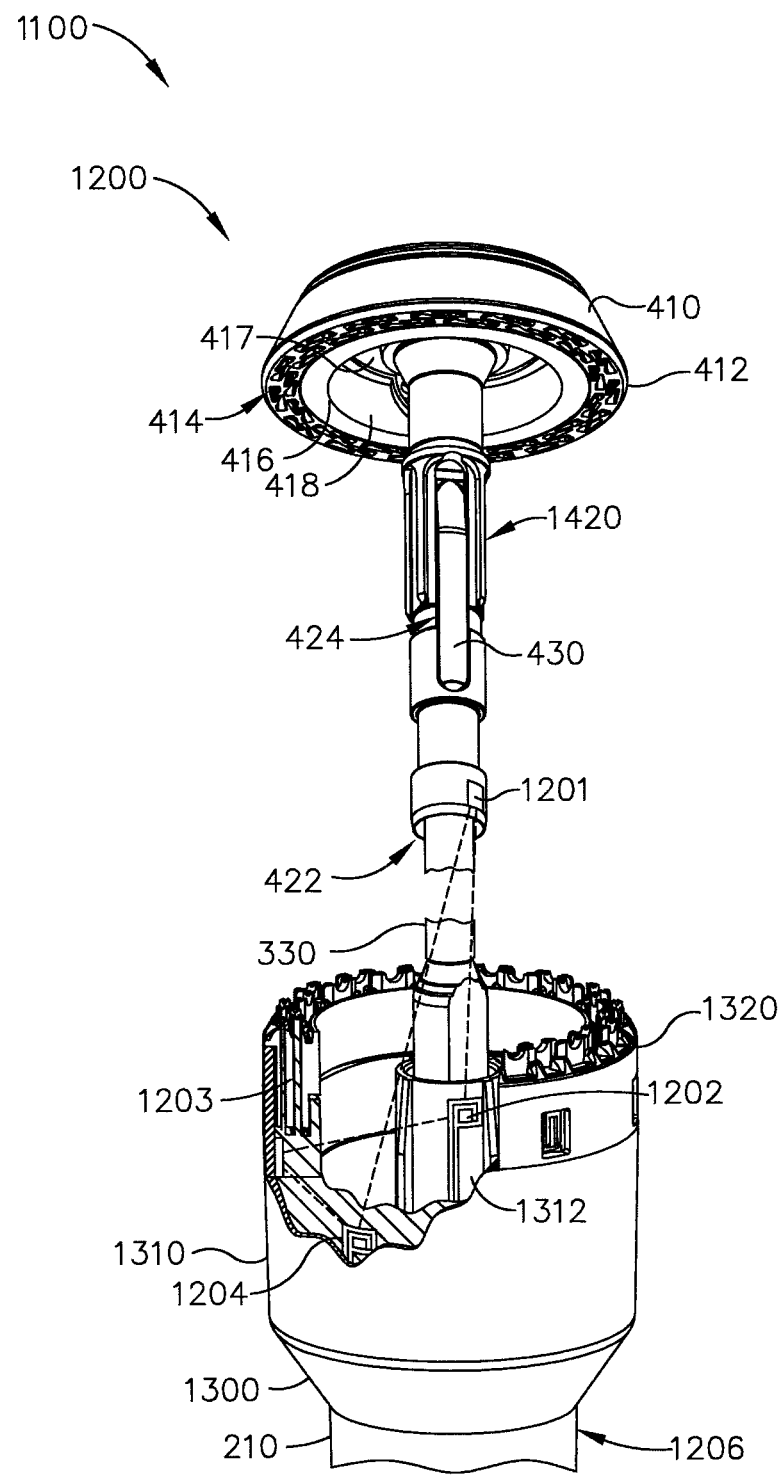
FIG. 12 depicts stapling head assembly and an anvil being coupled to a trocar of the stapling head assembly, in accordance with at least one aspect of the present disclosure.

Instrument 1100 is similar in many respects to instrument 10. For example, like instrument 10, instrument 1100 is a surgical instrument configured to grasp, staple, and/or cut tissue. Also, like instrument 10, instrument 1100 includes a shaft assembly 1206 (FIG. 12), a stapling head assembly 1300 (FIG. 12), and an anvil 1200 (FIG. 12). In addition, Instrument 1100 includes a lockout assembly such as, for example, an anvil lockout assembly 1170. Anvil lockout assembly 1170 is generally configured to prevent further adjustment of the longitudinal position of the anvil once safety trigger 1140 is actuated. Such a feature may be desirable because lockout of the anvil may prevent an operator from improperly changing the gap distance d once a suitable gap distance d is reached. Anvil lockout assembly 1170 comprises an inner lockout member 1172, an outer lockout member 1176, and an actuation member 1180. As is best seen in FIG. 8, inner lockout member 1172 is disposed about a portion of a portion of knob 1130 and is fixedly secured thereto. Inner lockout member 1172 of the present example includes a plurality of triangular teeth 1174 extending radially outwardly from inner lockout member 1172. Teeth 1174 are configured to engage with corresponding teeth 1184 of outer lockout member 1176 to prevent rotation of knob 1130, thereby preventing translation of trocar actuation rod 1122.

Various lockout out assemblies that are suitable for use with the present disclosure are described in U.S. Pat. No. 7,143,923, entitled SURGICAL STAPLING INSTRUMENT HAVING A FIRING LOCKOUT FOR AN UNCLOSED ANVIL, which issued on Dec. 5, 2006; U.S. Pat. No. 7,044,352, SURGICAL STAPLING INSTRUMENT HAVING A SINGLE LOCKOUT MECHANISM FOR PREVENTION OF FIRING, which issued on May 16, 2006; U.S. Pat. No. 7,000,818, SURGICAL STAPLING INSTRUMENT HAVING SEPARATE DISTINCT CLOSING AND FIRING SYSTEMS, which issued on Feb. 21, 2006; U.S. Pat. No. 6,988,649, SURGICAL STAPLING INSTRUMENT HAVING A SPENT CARTRIDGE LOCKOUT, which issued on Jan. 24, 2006; and U.S. Pat. No. 6,978,921, SURGICAL STAPLING INSTRUMENT INCORPORATING AN E-BEAM FIRING MECHANISM, which issued on Dec. 27, 2005, which are incorporated by reference herein in their entireties.

Outer lockout member 1176 has a generally cylindrical shape and defines an opening 1177 that is sized to receive inner lockout member 1172. The inner diameter of outer lockout member 1176 defines a plurality of teeth 1178, which correspond to teeth 1147 of inner lockout member 1172. Teeth 1178 are configured to engage teeth 1174 of inner lockout member 1172 to prevent further adjustment of the longitudinal position of anvil 1200, by preventing further rotation of knob 1130. Outer lockout member 1176 further includes a plurality of protrusions 1179 protruding radially outwardly from the outer diameter of outer lockout member 1176. Protrusions 1179 are disposed in corresponding channels 1113 within casing 1112 to rotationally fix outer lockout member 1176 in position while still permitting at least some translation.

Although inner and outer lockout members 1172, 1176 of the present example are shown as including teeth 1174, 1178, it should be understood that in other examples any other suitable surfacing treatment or geometry may be used. For instance, in some examples lockout members 1172, 1176 include corresponding knurled surfaces, bumps, splines, ridges, detent features, or any other suitable surface treatment or geometry that may be configured to correspondingly engage to prevent relative rotational movement between lockout members 1172, 1176.

Actuation member 1180 comprises an elongate body 1182 extending from outer lockout member 1176 to safety trigger 1140. In particular, body 1182 includes a trigger bracket 1184 that is configured to couple with safety trigger 1140. Trigger bracket 1184 includes a channel 1185 that permits bracket 1184 to be pivotably coupled to safety trigger 1140. Similarly, the proximal end of body 1182 is configured to couple with at least one protrusion 1179 of outer lockout member 1176. Accordingly, movement of safety trigger 1140 is transferred to outer lockout member 1176 via actuation member 1180. In other words, outer lockout member 1176 translates longitudinally in response to pivoting of safety trigger 1140. Outer lockout member 1176 is generally responsive to safety trigger 1140 to selectively lock actuation of the anvil 1200.

Figure 9:
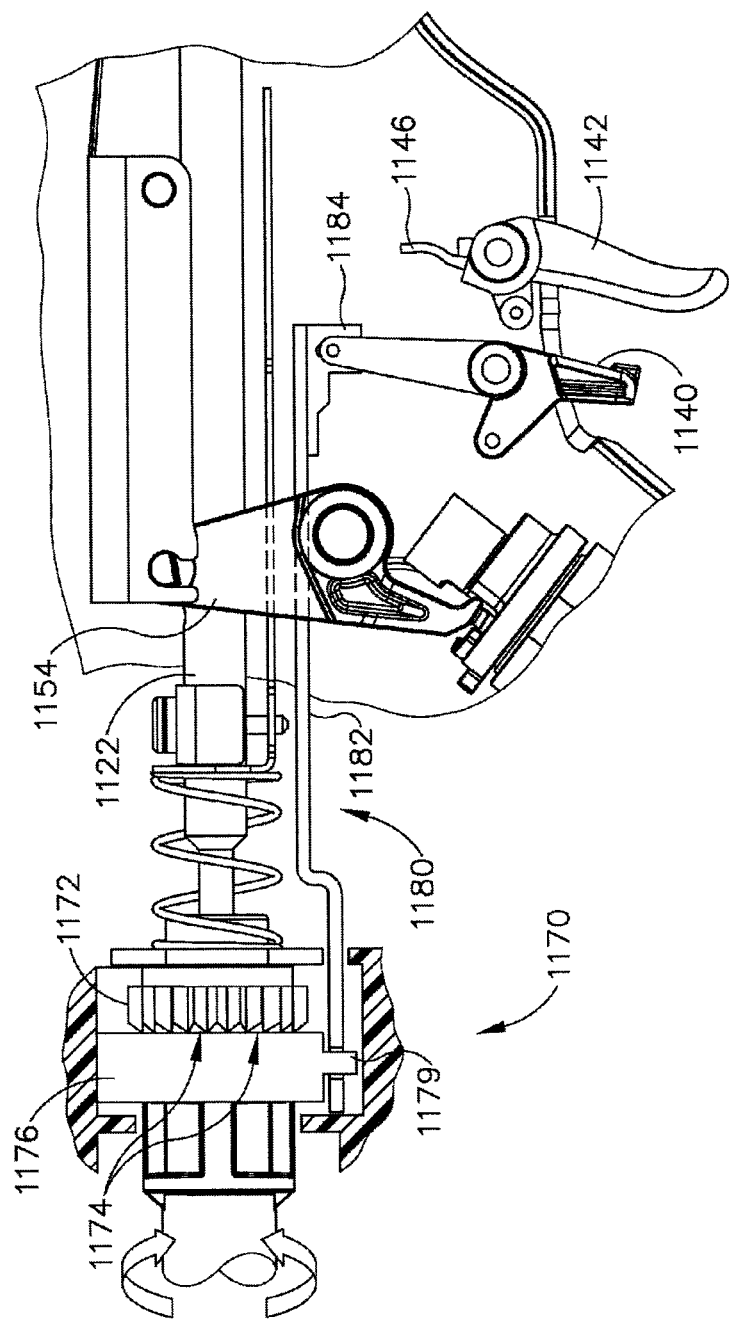
FIG. 9 depicts a detailed side elevational view of the anvil actuation assembly of FIG. 7, with the anvil lockout assembly of FIG. 8 in the unlocked position, in accordance with at least one aspect of the present disclosure.
Figure 10:
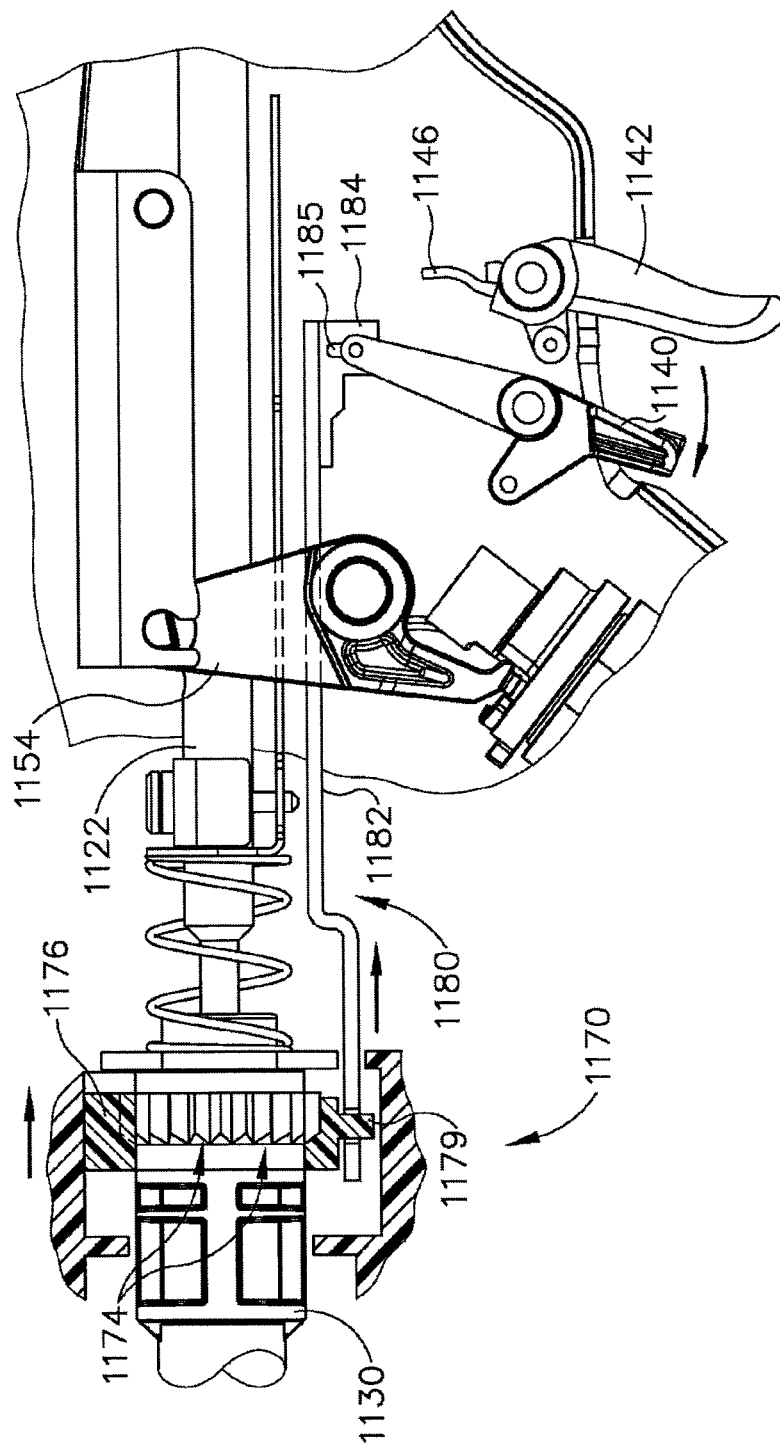
FIG. 10 depicts another detailed side elevational view of the anvil actuation assembly of FIG. 7, with the anvil lockout assembly of FIG. 8 in a locked position, in accordance with at least one aspect of the present disclosure.
Figure 11:
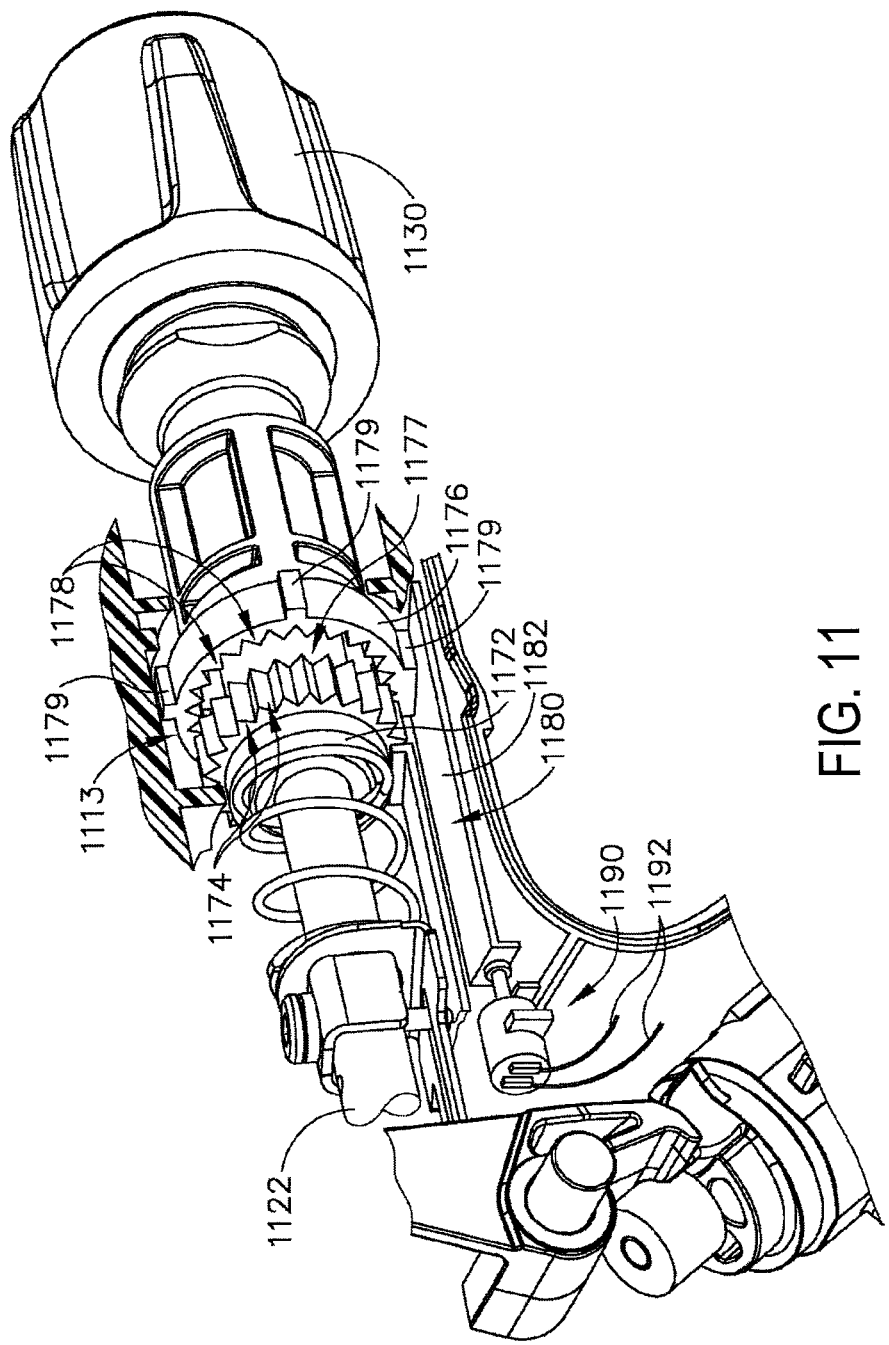
FIG. 11 depicts a detailed perspective view of an alternative configuration of the anvil lockout assembly of FIG. 8, in accordance with at least one aspect of the present disclosure.

FIGS. 9-11 show an exemplary sequence of operation of anvil lockout assembly 1170. As can be seen in FIG. 9, anvil lockout assembly 1170 initially begins in an unlocked state. In such a state, outer lockout member 1176 is positioned proximally away from inner lockout member 1172 such that inner lockout member 1172 is freely rotatable relative to outer lockout member 1176. It should be understood that when inner lockout member 1172 is freely rotatable, knob 1130 is similarly freely rotatable such that the longitudinal position of the anvil may be adjusted via trocar actuation rod 1122.

Once the operator has rotated knob 1130 to adjust the longitudinal position of the anvil to achieve an appropriate gap distance d, it may be desirable to prevent further adjustment of the longitudinal position of the anvil. FIG. 10 shows anvil lockout assembly 1170 in a locked state. To advance anvil lockout assembly 1170 to the locked state, the operator may pivot safety trigger 1140 proximally. Proximal movement of safety trigger 1140 causes safety trigger 1140 to drive actuation member 1180 distally.

Distal movement of actuation member 1180 results in corresponding movement of outer lockout member 1176. As outer lockout member 1176 is moved distally, teeth 1178 of outer lockout member 1176 will begin to engage teeth 1174 of inner lockout member 1176. Once teeth 1178 of outer lockout member 1176 fully engage with teeth 1174 of inner lockout member 1176, outer lockout member 1176 will prevent relative rotational movement of inner lockout member 1172 via protrusions 1179 and casing 1112. Because inner lockout member 1172 is fixedly secured to knob 1130, rotational movement of knob 1130 will also be prevented. With knob 1130 locked in position, further adjustment of the longitudinal position of the anvil will be prevented. With further adjustment of the longitudinal position of the anvil prevented, the operator may then actuate firing trigger 1142 to initiate the stapling sequence.

Figure 15:
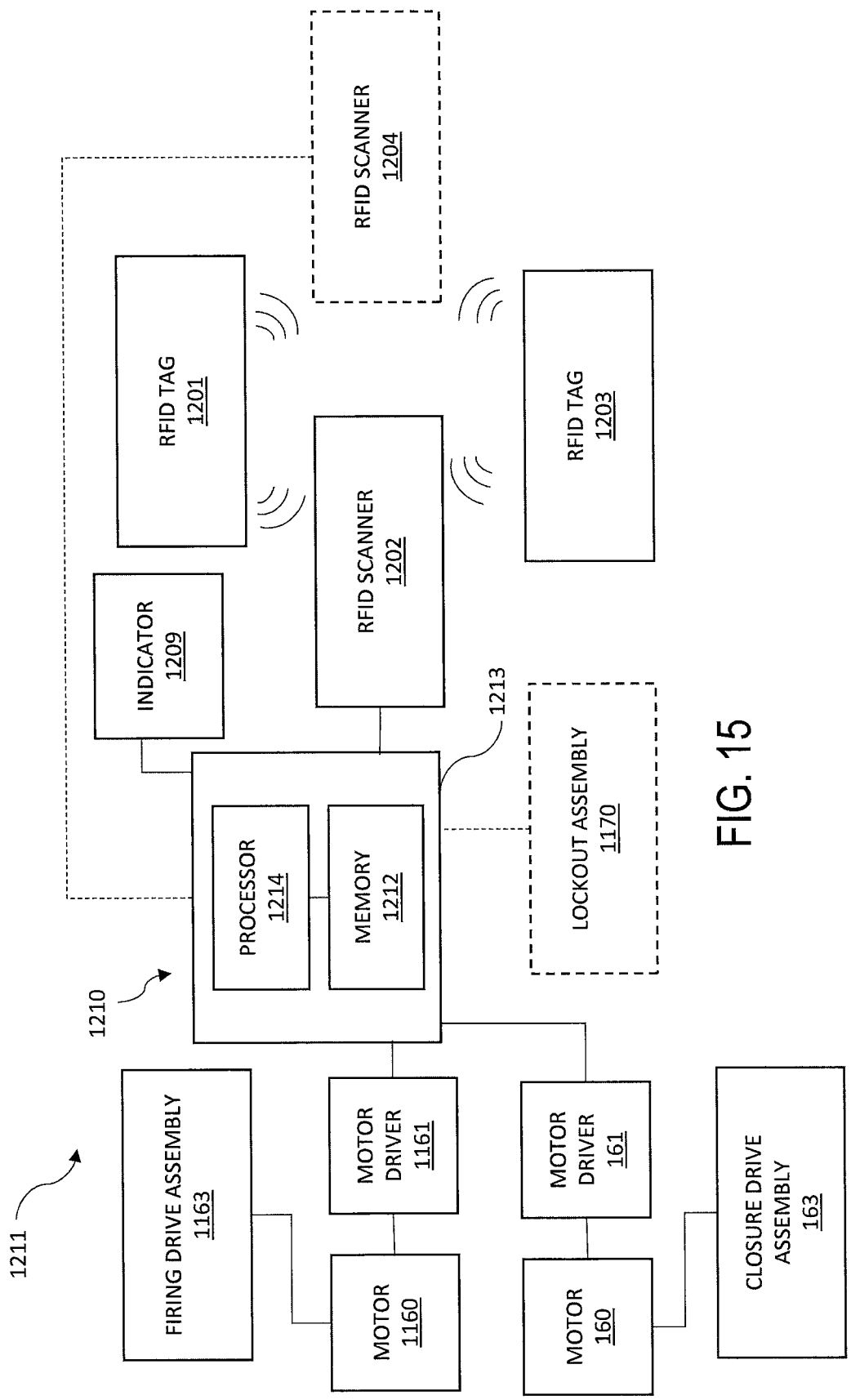
FIG. 15 depicts a control system of a surgical stapling instrument, in accordance with at least one aspect of the present disclosure.

In some examples, it may be desirable to drive outer lockout member 1176 using an actuation mechanism 1190 such as a solenoid. As illustrated in FIG. 11, actuation mechanism 1190 is aligned with the longitudinal axis of actuation member 1180 and is fixedly secured to actuation member 1180. To accommodate actuation mechanism 1190, actuation member 1180 may be shortened or otherwise modified to intersect with actuation mechanism 1190. Actuation mechanism 1190 includes a plurality of wires 1192 that may connect to a circuit board, switch, and/or sensor. In various examples, the wires 1192 are connected to the control circuit 1210 (FIG. 15). In various examples, the actuation mechanism 1190 may be actuated using safety trigger 1140 using a similar configuration as safety trigger 1040 of instrument 100. For instance, actuation of safety trigger 1140 may complete a circuit that activates actuation mechanism 1190, thereby driving lockout member 1176 longitudinally into engagement with lockout member 1172.

In operation, actuation mechanism 1190 generally provides the same function as safety trigger 1140, except actuation mechanism 1190 removes the necessity for actuation member 1180 to extend the entire distance to safety trigger 1140. Although actuation mechanism 1190 is shown and described herein as comprising a solenoid, it should be understood that any other suitable actuator may be used as will be apparent to those of ordinary skill in the art in view of the teachings herein.

Figure 13:
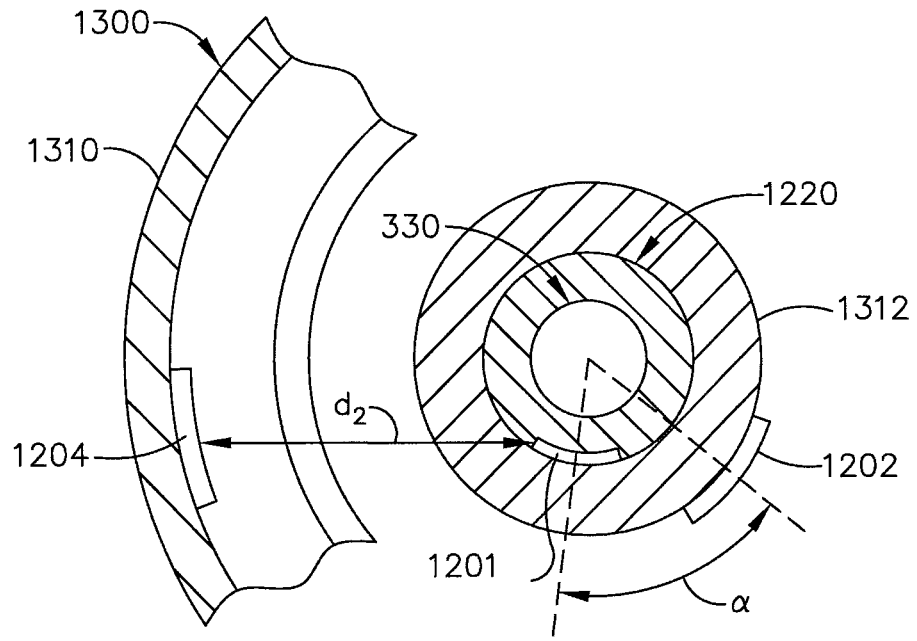
FIG. 13 depicts a partial transverse cross-sectional view of an anvil in an improper seating orientation with a stapling head assembly, in accordance with at least one aspect of the present disclosure.
Figure 14:
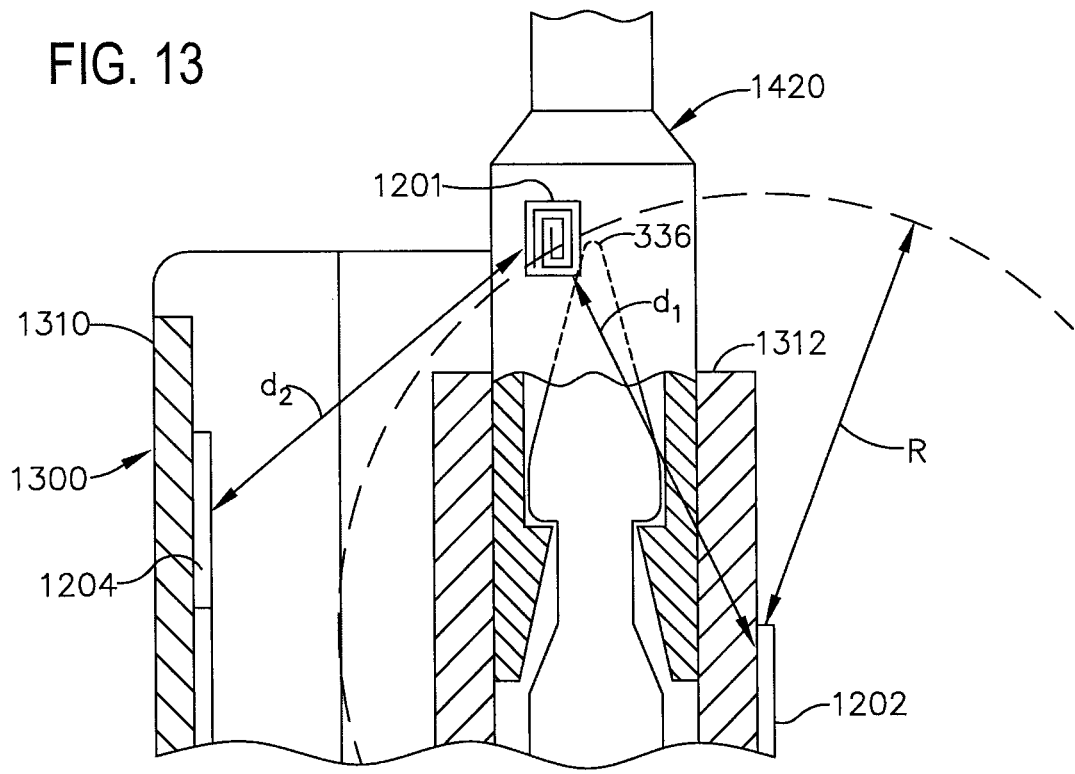
FIG. 14 depicts a partial longitudinal cross-sectional view of an anvil in an improper seating orientation with a stapling head assembly, in accordance with at least one aspect of the present disclosure.

Referring primarily to FIGS. 12-14, a distinct issue with circular staplers is that their anvils are detachable from their stapling head assemblies, and must be separately introduced to a surgical site in different manners and from different access points. Accordingly, unlike other stapling instruments, circular staplers are at risk of anvil-staple head assembly mismatching and/or anvil-staple cartridge mismatching. Further, to be properly assembled or coupled an anvil and a stapling head assembly must be properly oriented with respect to each other at a specific orientation at the surgical site. Improper orientation of an anvil and a corresponding stapling head assembly, as illustrated in FIG. 13, can lead to a misalignment between the staple forming pockets 414 (FIG. 12) of the anvil and staple openings 324 (FIG. 3) of a staple cartridge 1320, which may lead to improper staple formation. In addition, the improper orientation of an anvil and a corresponding stapling head assembly can lead to improper seating of the anvil with respect to the stapling head assembly. An improperly seated, or partially seated, anvil may become unseated, or separated from the stapling head assembly, due to externally applied loads from the tissue captured between the anvil and the stapling head assembly during closure.

To address the issues above, the surgical instrument 1100 includes an anvil 1200 equipped with a radio-frequency identification (RFID) tag 1201 recognizable or detectable by an RFID scanner 1202 on a stapling head assembly 1300 of the surgical instrument 1100. Likewise, the staple cartridge 1320 includes an RFID tag 1203 also recognizable or detectable by the RFID scanner 1202. The RFID tag 1201 stores information about the anvil 1200, and the RFID tag 1203 stores information about the staple cartridge 1320. As described below, the information can be checked and compared for authentication and/or compatibility.

The identification mechanisms described herein can either be active systems or passive systems. In various embodiments, a combination of active and passive identification systems are used. Passive systems can include, for example, a barcode, a quick response (QR) code, and/or a radio frequency identification (RFID) tag. Passive systems do not comprise an internal power source, and the passive systems described herein require a reader and/or scanner to send a first signal, such as an interrogation signal, for example.

Passive radio frequency identification (RFID) systems communicate information by using radio frequencies. Such passive RFID systems comprise an RFID scanner and an RFID tag with no internal power source. The RFID tag is powered by electromagnetic energy transmitted from the RFID scanner. Each RFID tag comprises a chip, such as a microchip, for example, that stores information about the replaceable component and/or a surgical instrument with which the replaceable component is compatible. While the chip may only contain an identification number, in various instances, the chip can store additional information such as, for example, the manufacturing data, shipping data, and/or maintenance history. Each RFID tag comprises a radio antenna that allows the RFID tag to communicate with the RFID scanner. The radio antenna extends the range in which the RFID tag can receive signals from the RFID scanner and transmit response signals back to the RFID scanner. In a passive RFID system, the RFID scanner, which also comprises its own antenna, transmits radio signals that activate RFID tags that are positioned within a predetermined range. The RFID scanner is configured to receive the response signals that are "bounced back" from RFID tags, allowing the RFID scanner is to capture the identification information representative of the replaceable component. In various instances, the one or more response signals comprise the same signal as the interrogation signal. In various instances, the one or more response signals comprise a modified signal from the interrogation signal. In various instances, the RFID scanner is also able to write, or encode, information directly onto the RFID tag. In any event, the RFID scanner is able to pass information about the replaceable component to a controller, such as the control system of a surgical instrument and/or a remote surgical system or hub. The RFID scanner is configured to read multiple RFID tags at once, as the RFID tags are activated by radio signals. Additionally, in certain instances, the RFID scanner is able to update, or rewrite, information stored on an RFID tag in signal range with the RFID scanner. The updates can, for example, be transmitted to the RFID scanner from a surgical hub, or any suitable server. Various surgical hubs are described in described in U.S. patent application Ser. No. 16/209,395, titled METHOD OF HUB COMMUNICATION, and filed Dec. 4, 2018, which is hereby incorporated by reference in its entirety.

Active radio frequency identification (RFID) systems also comprise an RFID tag and an RFID scanner. However, the RFID tag in an active RFID system comprises an internal power source. Active RFID systems utilize battery-powered RFID tags that are configured to continuously broadcast their own signal. One type of active RFID tag is commonly referred to as a "beacon." Such beacon RFID tags do not wait to receive a first signal from an RFID scanner. Instead, the beacon RFID tag continuously transmits its stored information. For example, the beacon can send out its information at an interval of every 3-5 seconds. Another type of active RFID tag comprises a transponder. In such systems, the RFID scanner transmits a signal first. The RFID transponder tag then sends a signal back to the RFID scanner with the relevant information. Such RFID transponder tag systems are efficient, as they conserve battery life when, for example, the RFID tag is out of range of the RFID scanner. In various instances, the active RFID tag comprises an on-board sensor to track an environmental parameter. For example, the on-board sensor can track moisture levels, temperature, and/or other data that might be relevant.

In operation the anvil 1200 is coupled or attached to the stapling head assembly 1300, as illustrated in FIG. 12. When the RFID tag 1201 is at or below an attachment threshold distance, defined by the radius (R) of a perimeter extending around the RFID scanner 1202, the RFID scanner 1202 is able to detect or recognize the RFID tag 1201. The attachment distance is the distance between the RFID tag 1201 and the RFID scanner 1203 while the anvil 1200 is coupled or attached to stapling head assembly 1300.

Further to the above, the RFID tag 1303 is positioned under the deck member 320 of the stapling head assembly 1300, and can be detected as well by the RFID scanner 1202. As described in greater detail below, signal strength between the RFID scanner 1202 and one or both of the RFID tags 1201, 1203 can be used to determine whether the anvil 1200 is properly oriented and/or fully seated with respect to the stapling head assembly 1300.

Referring to FIG. 12, the anvil 1200 is similar in many respects to the anvil 400. For example, like the anvil 400, the anvil 1200 includes the head 410, the staple forming pockets 414, and a shank 1420. In the example of FIG. 12, the RFID tag 1201 is supported by the shank 1420, on an outer surface thereof, near the bore 422. In at least one example, a recess or pocket is defined in the shank 1420, and the RFID tag 1201 is positioned in the recess or pocket. The RFID tag 1201 can be held in place in the recess, or pocket, using any suitable technique such as, for example, friction fitting or biocompatible adhesive.

As described above in greater detail, the anvil 1200 is coupled or assembled with the stapling head assembly 1300 by advancing the anvil 1200 toward the trocar 330 such that the trocar 330 is received through the bore 422, as illustrated in FIG. 12. Proximal surface 338 of the head 334 of the trocar 330 and latch shelves 436 of the shank 1420 have complementary positions and configurations such that latch shelves 436 engage proximal surface 338 when shank 1420 of anvil 1200 is fully seated on trocar 330 of the stapling head assembly 1300, as illustrated in FIG. 14. Anvil 1200 is thus secured to trocar 330 through a snap fit due to latch members 430. In the example illustrated in FIG. 14, the RFID tag 1201 is at a first longitudinal position that is distal, or slightly distal, to a second longitudinal position of the pointed tip 226 of the head 334 of the trocar 330.

In at least one example, the RFID tag 1201 is positioned on the shank 1420 at a first longitudinal position that corresponds, or substantially corresponds, to a second longitudinal position of the tip 336 of the head 334 of the trocar 330 when the anvil 1200 is properly oriented and fully seated with respect to the stapling head assembly 1300. In other words, the tip 336 of the head 334 of the trocar 330, when it is received in the shank 1420 at its final seating position, is transversely aligned, or at least substantially aligned, with the RFID tag 1201. In at least one example, the RFID tag 1201 is positioned on the shank 1420 at a position distal to the bore 422 and proximal to the lateral openings 424 and/or proximal to the latch members 430 (FIGS. 3-4).

Referring to FIG. 12, the RFID scanner 1202 is located on an outer surface of a cylindrical inner core member 1312 that extends distally within a tubular casing 1310 of the stapling head assembly 1300. Tubular casing 1310 is fixedly secured to an outer sheath 210 of shaft assembly 1206, such that tubular casing 1310 serves as a mechanical ground for stapling head assembly 1300. The RFID scanner 1202 is supported by the inner core member 1312, on an outer surface thereof, near its distal end. In at least one example, a recess or pocket is defined in the inner core member 1312, and the RFID scanner 1202 is positioned in the recess or pocket. The RFID scanner 1202 can be held in place in the recess, or pocket, using any suitable technique such as, for example, friction fitting or biocompatible adhesive. Alternatively, the RFID scanner 1202 can be positioned on an inner surface of the cylindrical inner core member 1312. In the example of FIG. 12, the RFID scanner 1202 is located at a distal portion of the inner core member 1312 below the deck member 320 of the staple cartridge 1320. In various example, the RFID tag 1201 and the RFID tag 1203 are insulated from the shank 1420 and the inner core member 1312, respectively, using any suitable insulative material.

In various examples, RFID tag 1201 and the RFID tag 1203 are recognizable or detectable by the RFID scanner 1202 in a closed configuration of the instrument 1100 where tissue is captured between the anvil 1200 and stapling head assembly 1300.

FIG. 15 illustrates a logic diagram of a control system 1211 of a surgical instrument or tool in accordance with one or more aspects of the present disclosure. The control system 1211 includes a control circuit 1210 that can be integrated with the RFID scanner 1202 or can be coupled to, but positioned separately from, the RFID scanner 1202 in the housing assembly 100, for example. The control circuit 1210 can be configured to receive input from the RFID scanner 1202 indicative of the information about the staple cartridge 1320 stored in the RFID tag 1203 and/or information about the anvil 1200 stored in the RFID tag 1201.

In various examples, the RFID tag 1203 stores identification information of the staple cartridge 1320 and the RFID tag 1201 stores identification information of the anvil 1200. In such examples, the control circuit 1210 receives input from the RFID scanner 1202 indicative of the identification information of the staple cartridge 1320 and verifies the identity of the staple cartridge 1320 based on the input. Further, the control circuit 1210 receives input from RFID scanner 1202 indicative of the identification information of the anvil 1200 and verifies the identity of the anvil 1200 based on the input.

In at least one example, the control circuit 1210 includes a microcontroller 1213 that has a processor 1214 and a storage medium such as, for example, a memory 1212. The memory 1212 stores program instructions for performing various processes such as, for example, identity verification. The program instructions, when executed by the processor 1214, cause the processor 1214 to verify the identity of the staple cartridge 1320 and the identity of the anvil 1200 by comparing the identification information received from the RFID tags 1201, 1203 to identification information stored in the memory 1212 in the form of an identity database or table, for example.

In at least one example, the control circuit 1210 can be configured to check compatibility of the anvil 1200 with staple cartridge 1320 of the stapling head assembly 1300 based on input from the RFID scanner 1202. The processor 1214 can, for example, check the identity information of the anvil 1200 and the staple cartridge 1320 against a compatibility database or table stored in memory 1212.

In various examples, the memory 1212 comprises a local memory of the instrument 1100. In other examples, identity databases or tables and/or compatibility databases or tables can be downloaded from a remote server. In various aspects, the instrument 1100 may transmit the information received from RFID tags 1201, 1203 to a remote server that stores the databases or tables for performing the identity and/or compatibility checks remotely.

Figure 16:
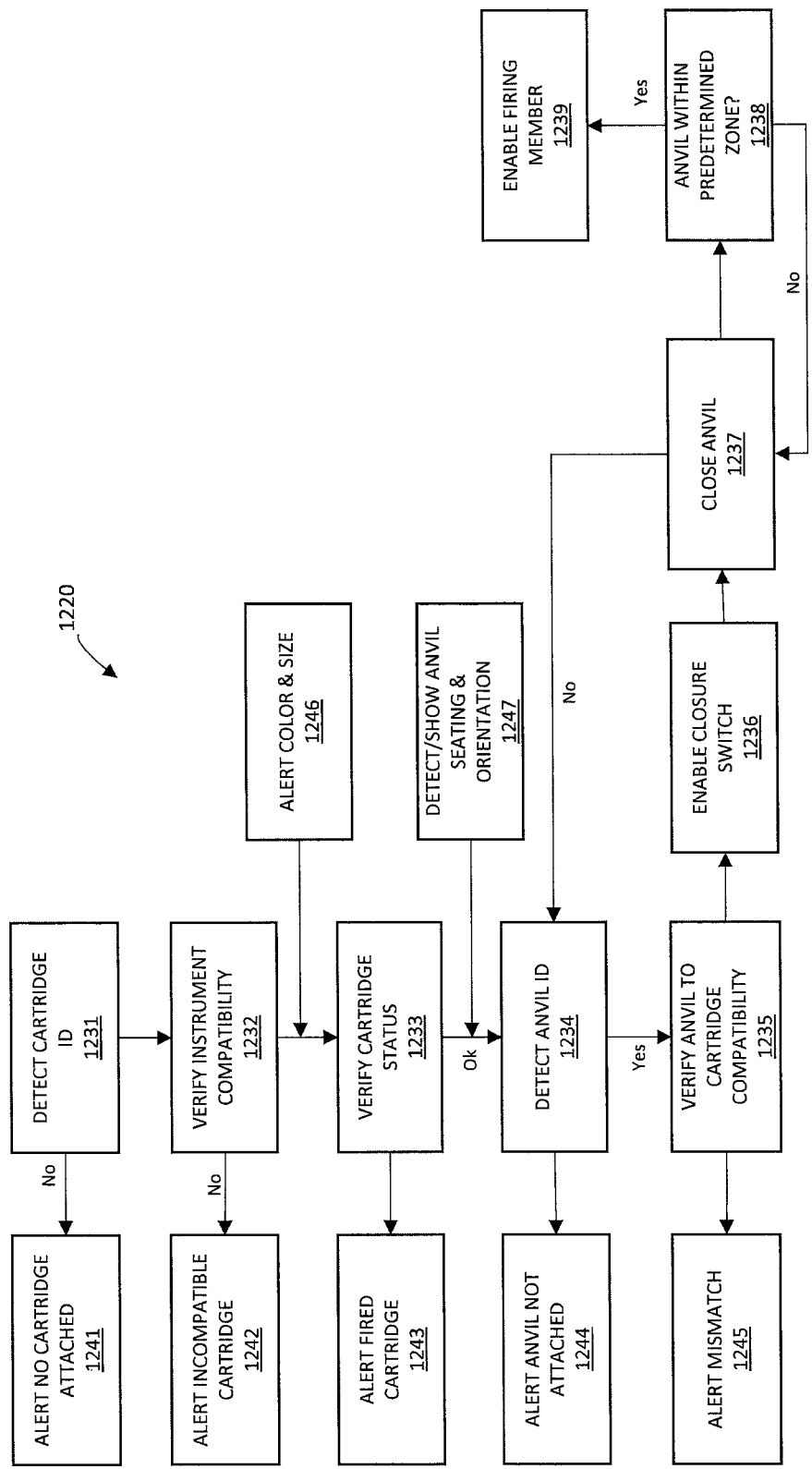
FIG. 16 depicts a logic flow diagram of a process depicting a control program or a logic configuration for operating a surgical stapling instrument, in accordance with at least one aspect of the present disclosure.

FIG. 16 is a logic flow diagram of a process 1220 depicting a control program or a logic configuration for operating a surgical stapling instrument such as, for example, the instrument 1100. In at least one example, the process 1220 is executed by a control circuit 1210 (FIG. 15) that includes a processor 1214 and a memory 1212 storing a set of computer-executable instructions that, when executed by the processor 1214, cause the processor 1214 to perform of the process 1220. In certain examples, a set of computer-executable instructions, stored in the memory 1212 may cause the processor 1214 to perform discrete portions of the process 1220. Although the process 1220 is described as being executed by a control circuit 1210, this is merely for brevity, and it should be understood that the process 1220 and other processes described herein, or portions thereof, can be executed by circuitry that can include a variety of hardware and/or software components and may be located in or associated with various suitable systems such as, for example, combinational logic circuits or sequential logic circuits.

As illustrated in FIG. 16, the process 1220 includes detecting 1231 identification information of the staple cartridge 1320. In at least one example, the control circuit 1210 receives input from the RFID scanner 1202 indicative of the identification information of the staple cartridge 1320 stored in the RFID tag 1203. If authentication of the staple cartridge ID is not successful, or staple cartridge ID is not detected, the control circuit 1210 causes an indicator 1209 to alert 1241 that the staple cartridge 1320 is not attached and/or that the staple cartridge authentication failed.

In various instances, the indicator 1209 may comprise one or more visual feedback systems such as display screens, backlights, and/or LEDs, for example. In certain instances, the indicator 1209 may comprise one or more audio feedback systems such as speakers and/or buzzers, for example. In certain instances, the indicator 1209 may comprise one or more haptic feedback systems, for example. In certain instances, the indicator 1209 may comprise combinations of visual, audio, and/or haptic feedback systems, for example.

The process 1220 further includes verifying 1232 compatibility of the staple cartridge 1320 and the instrument 1100. In at least one example, the control circuit 1210 checks the identification information of the staple cartridge 1320 against staple cartridge-instrument compatibility database or table, which can be stored in the memory 1212, for example. If compatibility is verified 1232, the control circuit 1210 causes the indicator 1209 to alert 1242 that the staple cartridge 1320 is compatible with the instrument 1100. At this stage, the control circuit 1210 may also cause the indicator 1209 to alert 1246 the user regarding color and/or size of the attached staple cartridge 1320.

The process 1220 further includes verifying 1233 a cartridge firing status. Staple cartridges are generally disposed of after filing. To ensure that a previously fired staple cartridge is not accidently re-used without staples, the RFID tag 1201 of a staple cartridge 1320 that has been previously fired stores a previously-fired status. In at least one example, the control circuit 1210 causes the RFID scanner 1202 to change the firing status of a staple cartridge 1320 from an unfired status to a previously fired status after completion of a firing sequence. Further, if the control circuit 1210 received input from the RFID scanner 1202 indicating that an attached staple cartridge 1320 has been previously fired, the control circuit 1210 may cause the indicator 1209 to alert 1243 the user of the same.

The process 1220 further includes detecting 1234 identification information of the anvil 1200. In at least one example, the control circuit 1210 receives input from the RFID scanner 1202 indicative of the identification information of the anvil 1200 stored in the RFID tag 1201. If authentication of the anvil ID is not successful, or if no anvil ID is received, the control circuit 1210 may cause an indicator 1209 to alert 1244 that the anvil is not attached and/or that the anvil authentication failed.

Referring still to FIG. 16, if a proper anvil identification is detected 1234, the process 1220 further checks 1235 compatibility of the anvil 1200 and the staple cartridge 13020. If the anvil 1200 and the staple cartridge 13020 are incompatible, the process 1220 alerts 1245 a user regarding the mismatch. If, however, the anvil 1200 and the staple cartridge 13020 are compatible, the control circuit 1210 permits 1236 closure drive assembly 136 (FIG. 15) to proceed 1237 with anvil closure. During anvil closure, the control circuit 1210 continues to monitor the RFID scanner 1202 to ensure that the anvil 1200 remains attached or coupled to the stapling head assembly 1300 throughout the closure process. If during closure the RFID scanner 1202 loses the signal from the RFID tag 1201, the control circuit 1210 causes the closure drive assembly 136 to pause the closure, and alert 1244 the user that the anvil 1200 is not attached, or at least not detected. Otherwise, the anvil closure continues until a closed configuration between the anvil 1200 and the stapling head assembly 1300 is achieved 1238 by reaching 1238 a predetermined zone or threshold.

At, or beyond, the predetermined zone or threshold, the control circuit 1210 permits 1239 the firing drive assembly 1136 to begin a firing sequence to staple and cut tissue captured between the anvil 1200 and the staple cartridge 1320 in the closed configuration.

The process 1220 further includes assessing or detecting 1247 anvil orientation and/or seating with respect to the stapling head assembly 1300. As illustrated in FIG. 12, the shank 1420 of anvil 1200 is fully seated on trocar 330 of the stapling head assembly 1300 when latch shelves 436 engage proximal surface 338. At this point, the RFID tag 1201 reaches or crosses the attachment threshold distance and, as such, is detected by the RFID scanner 1202. The detection of the RFID tag 1201 by the RFID scanner 1202 indicates full seating of the anvil 1200 with respect to the stapling head assembly 1300. In at least one example, receiving an input from the RFID scanner 1202 indicative of detection of the RFID tag 1201 causes the control circuit 1210 to determine that the anvil 1200 is fully seated with respect to the stapling head assembly 1300.

Referring to FIGS. 12 and 15, in various examples, an RFID scanner 1204 is employed in addition to the RFID scanner 1202 to detect the RFID tag 1201 and/or the RFID tag 1203. The RFID scanner 1204 can be positioned within the stapling head assembly 1300. In the example illustrated in FIG. 12, the RFID scanner 1204 is supported by the tubular casing 1310. The control circuit 1210 can be configured to receive input from the RFID scanner 1204 in addition to the input from the RFID scanner 1202. In at least one example, the RFID scanner 1204 is configured to detect the RFID tag 1203 while the RFID scanner 1202 can be configured to detect the RFID tag 1201.

With regard to anvil orientation, the control circuit 1210 is configured to determine whether an attached anvil 1200 is properly oriented with respect to the stapling head assembly 1300 by using the RFID scanner 1202 and/or the RFID scanner 1204 to detect and measure strength of the signal transmitted by the RFID tag 1201. In a proper orientation of the anvil 1200, the RFID scanner 1202 detects the signal from the RFID tag 1201 and measures a unique first signal strength that corresponds to the distance d1 between the RFID tag 1201 and the RFID scanner 1202. Likewise, the RFID scanner 1204 detects the signal from the RFID tag 1201 and measures a unique second signal strength that corresponds to the distance d2 between the RFID tag 1201 and the RFID scanner 1204. The control circuit 1210 can be configured to assess proper orientation of the anvil 1200 based on the first signal strength and/or the second signal strength.

FIG. 13 depicts an improper orientation of the anvil 1200 where the shank 1420 is at an angle α away from proper orientation with the stapling head assembly 1300. The misalignment between the anvil 1200 and the stapling head assembly 1300 causes the distances d1, d2 to be different from their values at proper orientation, which causes the first signal strength and second signal strength to be different from their values at a proper orientation. In the example of FIG. 13, the misalignment between the anvil 1200 and the stapling head assembly 1300 increases the value of the distance d1 and decreases the value of the distance d2. As such, the misalignment at FIG. 13 decreases the first signal strength and increases the second signal strength from their values at a proper orientation.

Accordingly, by monitoring the strength of the signal transmitted by the RFID tag 1201, the control circuit 1210 is able to assess whether the anvil 1200 is properly oriented with respect to the 1300. In various instances, the memory 1212 stores a database or table of signal strength values, or ranges, that represent a proper orientation of the anvil 1200. In such instances, the control circuit 1210 may check the signal strength values collected by the RFID scanner 1202 and/or RFID scanner 1204 against the values, or ranges, in the database, or table, to assess whether the anvil 1200 is properly oriented.

In various examples, proper orientation of an anvil 1200 with respect to the stapling head assembly 1300 is examined by the control circuit 1210 after determining that the anvil 1200 is fully seated, as described above. In other examples, proper orientation of an anvil 1200 with respect to the stapling head assembly 1300 is examined by the control circuit 1210 at a closed, or at least partially closed, configuration of the instrument 1100. In certain examples, proper orientation of an anvil 1200 with respect to the stapling head assembly 1300 is continuously examined by the control circuit 1210 following the detection of the RFID tag 1201 by the RFID scanner 1202 and/or RFID scanner 1204.

Figure 17:
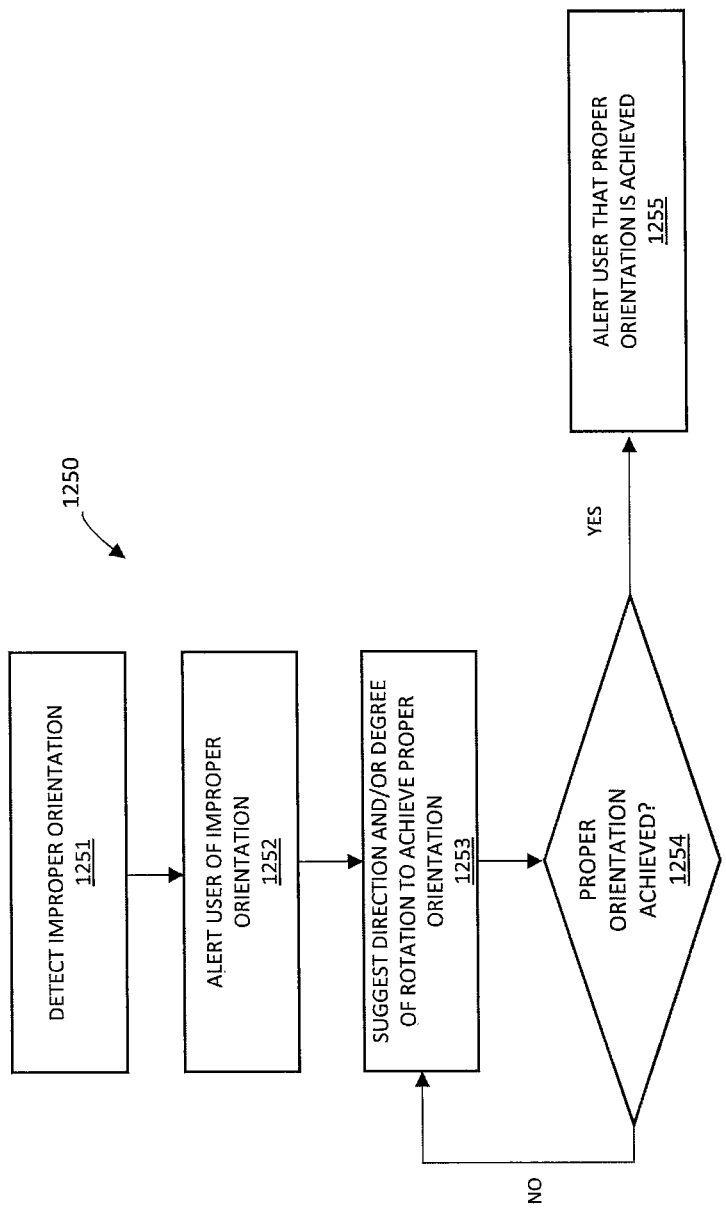
FIG. 17 depicts a logic flow diagram of a process depicting a control program or a logic configuration for properly orienting an anvil with respect to stapling head assembly of a surgical stapling instrument, in accordance with at least one aspect of the present disclosure.

FIG. 17 depicts a logic flow diagram of a process 1250 depicting a control program or a logic configuration for properly orienting an anvil with respect to stapling head assembly of a surgical stapling instrument. In at least one example, the process 1250 is executed by a control circuit 1210 (FIG. 15) that includes a processor 1214 and a memory 1212 storing a set of computer-executable instructions that, when executed by the processor 1214, cause the processor 1214 to perform of the process 1250. In certain examples, a set of computer-executable instructions, stored in the memory 1212 may cause the processor 1214 to perform discrete portions of the process 1250. Although the process 1250 is described as being executed by a control circuit 1210, this is merely for brevity, and it should be understood that the process 1250 and other processes described herein, or portions thereof, can be executed by circuitry that can include a variety of hardware and/or software components and may be located in or associated with various suitable systems such as, for example, combinational logic circuits or sequential logic circuits.

Referring to FIGS. 15 and 17, the control circuit 1210 is configured to detect 1251 an improper orientation of the anvil 1200 with respect to the stapling head assembly 1300, as described above. Further, the control circuit 1210 may employ the indicator 1209 to alert 1252 a user regarding the improper orientation. In addition, the control circuit 1210 may suggest 1253 through the indicator 1209 a direction and/or degree of rotation of the anvil 1200 to achieve a proper orientation. The control circuit 1210 may continue to check 1254 whether proper orientation is achieved based on input from the RFID scanner 1201 and/or RFID scanner 1204. When proper orientation is detected by the control circuit 1210, the control circuit 1210 may further cause the indicator 1209 to alert 1255 the user that the anvil 1200 now properly aligned with the stapling head assembly 1300.

As described above in greater detail, the instrument 1100 includes an anvil lockout assembly 1170. The anvil lockout assembly 1170 is generally configured to prevent further adjustment of the longitudinal position of the anvil once safety trigger 1140 is actuated. In various examples, the anvil lockout assembly 1170 includes an outer lockout member 1176 that is generally responsive to a safety trigger 1140 to selectively lock actuation of the anvil 1200. In other examples, the control circuit 1210 is configured to drive outer lockout member 1176 using an actuation mechanism 1190 such as a solenoid. In either event, the anvil lockout assembly 1170 is configured to transition between an unlocked state and a locked state, wherein: (i) in the unlocked state, the lockout assembly 1170 is configured to permit translation of the anvil 1200, and (ii) in the locked state, the lockout assembly 1170 is configured to prevent translation of the anvil 1200. In various examples, the control circuit 1210 employs the indicator 1209 to alert a user that it is safe to transition the lockout assembly 1170 to the unlocked state based on input from the RFID scanner 1202 and/or the RFID scanner 1204 indicative of detecting the RFID tag 1201. In other examples, the control circuit 1210 employs the actuation mechanism 1190 to transition the lockout assembly 1170 to the unlocked state based on input from the RFID scanner 1202 and/or the RFID scanner 1204 indicative of detecting the RFID tag 1201.

Further to the above, in certain examples, the control circuit 1210 detects detachment of the anvil 1200 from the stapling head assembly 1300 based on a loss of the input from the RFID scanner 1202 and/or the RFID scanner 1204, or an input from the RFID scanner 1202 and/or the RFID scanner 1204 indicative of a loss of the signal transmitted by RFID tag 1201. In response, the control circuit 1210 may cause the indicator 1209 to alert a user of the detachment of the anvil 1200 and, optionally, provide instructions regarding reattachment of the anvil 1200 to the stapling head assembly 1300. Additionally, or alternatively, the control circuit 1210 may cause the actuation mechanism 1190 to transition the lockout assembly 1170 to the locked state until reattachment of the anvil 1200 is detected by the control circuit 1210 based on input from RFID scanner 1202 and/or the RFID scanner 1204 indicative of redetection of the signal from the RFID tag 1201, for example.

Referring to FIG. 15, motors 160, 1160 are coupled to motor drivers 161 and 1161, respectively, which are configured to control the operation of the motors 160 and 1160 including the flow of electrical energy from a power source (e.g. battery pack 120) to the motors 160 and 1160. In various examples, the processor 1214 is coupled to the motors 160, 1160 through the motor drivers 1160, 1161. In various forms, the motor 160 and/or the motor 1160 may be a brushed direct current (DC) motor with a gearbox and mechanical links to effect a tissue treatment by a surgical end effector. In one aspect, motor drivers 1160, 1161 may be in the form of an A3941 available from Allegro Microsystems, Inc. Other motor drivers may be readily substituted for use with the control system 11211.

In various forms, the motors 160, 1160 may be a brushed DC driving motor having a maximum rotational speed of approximately 25,000 RPM. In other arrangements, the motors 160, 1160 may include a brushless motor, a cordless motor, a synchronous motor, a stepper motor, or any other suitable electric motor. The motor driver 161, 1161 may comprise an H-bridge driver comprising field-effect transistors (FETs), for example. The motors 160, 1160 can be powered by a power source. The power source may comprise a battery which may include a number of battery cells connected in series that can be used as the power source to power the surgical instrument or tool. In certain circumstances, the battery cells of the power source may be replaceable and/or rechargeable. In at least one example, the battery cells can be lithium-ion batteries which can be couplable to and separable from the power source.

In various aspects, a motor driver in accordance with the present disclosure may be a full-bridge controller for use with external N-channel power metal-oxide semiconductor field-effect transistors (MOSFETs) specifically designed for inductive loads, such as brush DC motors. The motor driver may comprise a unique charge pump regulator that provides full (>10 V) gate drive for battery voltages down to 7 V and allows the A3941 to operate with a reduced gate drive, down to 5.5 V. A bootstrap capacitor may be employed to provide the above battery supply voltage required for N-channel MOSFETs. An internal charge pump for the high-side drive allows DC (100% duty cycle) operation. The full bridge can be driven in fast or slow decay modes using diode or synchronous rectification. In the slow decay mode, current recirculation can be through the high-side or the low-side FETs. The power FETs are protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 480 comprising an absolute positioning system.

In various aspects, one or more of the motors of the present disclosure can include a rotatable shaft that operably interfaces with a gear assembly that is mounted in meshing engagement with a set, or rack, of drive teeth on a displacement member of a firing drive assembly 1163 or a closure drive assembly 163, for example. A sensor element may be operably coupled to a gear assembly such that a single revolution of the position sensor element corresponds to some linear longitudinal translation of the displacement member. An arrangement of gearing and sensors can be connected to the linear actuator, via a rack and pinion arrangement, or a rotary actuator, via a spur gear or other connection. A power source supplies power to the absolute positioning system and an output indicator may display the output of the absolute positioning system. The displacement member represents the longitudinally movable drive member comprising a rack of drive teeth formed thereon for meshing engagement with a corresponding drive gear of the gear reducer assembly. The displacement member represents the longitudinally movable a closure member, firing member, firing bar, I-beam, or combinations thereof.

In certain examples, as illustrated in FIG. 15, transition of the anvil 1200 to a closed configuration with the stapling head assembly 1300 is driven by the motor 1160. In such examples, the control circuit 1210 permits the motor 1160 to drive closure of the anvil 1200 if proper orientation, full seating, and/or proper identity of the anvil 1200 is detected by the control circuit 1210 based on input from the RFID scanner 1202 and/or RFID scanner 1204, as described above. Accordingly, a detected failure at establishing one or more of proper orientation, full seating, and/or proper identity of the anvil 1200 causes the control circuit 1210 to prevent the motor 1160 from starting and/or completing closure of the anvil 1200.

In certain examples, the control circuit 1210 permits the motor 160 to drive staple firing and advancement of the cylindrical knife member 340 if staple cartridge-anvil compatibility is confirmed based on the information stored in the RFID tags 1201, 1203 as reported by RFID scanners 1202, 1204. Conversely, the control circuit 1210 is configured to prevent the motor 160 from driving staple firing and advancement of the cylindrical knife member 340 if the staple cartridge-anvil compatibility cannot be established based on the information stored in the RFID tags 1201, 1203 as reported by RFID scanners 1202, 1204.

In various examples, antennas of one or more of the RFID tags 1201, 1203 and the RFID scanners 1202, 1204 may be supplemented with booster antennas that are engaged upon connection. In various examples, the antennas of active RFID tags on the surgical instrument 1100 such as, for example, the RFID tag 1201 and RFID tag 1203 can be cut during normal operation of the surgical instrument 1100 in planned manner. The lost signals from such RFID tags can signify completion of a surgical task.

In various aspects, an RFID tag can be positioned along the pathway of the cylindrical knife member 340. The RFID tag may transmit a signal through its antenna to the RFID scanner 1202, for example. When the antenna is severed by the knife member 340, the signal is lost. The signal loss can confirm advancement of the knife member 340.

In one example, the RFID tag is positioned on a breakable washer of the anvil 1200. In such example, the breakable washer is broken by the knife member 340 toward the end of a full distal range of motion of the knife member 340. The knife member 340 cuts the antenna of the RFID tag while breaking the breakable washer. When the antenna is severed, the signal transmitted from the RFID tag to the RFID scanner 1202, for example, is lost. The RFID scanner 1202 can be coupled to the control circuit 1210, and can report the signal loss to the control circuit 1210. The signal loss is interpreted by the control circuit 1210 to indicate completion of a firing sequence of the surgical instrument 1100.

In various aspects, as described above greater detail, a surgical instrument such as, for example, the instrument 1100 includes an anvil 1200 movable toward a stapling head assembly 1300 to capture tissue therebetween in a closed configuration. The tissue is then stapled and cut in a firing sequence of the surgical instrument 1100. The instrument 1100 further includes an RFID tag such as, for example, the RFID tag 1201 and an RFID scanner such as, for example, the RFID scanner 1202 that is configured to read and/or write to the RFID tag 1201. The RFID tag 1201 and the RFID scanner 1202 define an RFID system that can be employed by a control circuit 1210 to determine a characteristic of the tissue based on the RF signal backscatter from the tissue.

The positions of the RFID tag 1201 and the RFID scanner 1202 with respect to the tissue grasped between the anvil 1200 and the stapling head assembly 1300 can be selected for optimal measurements of the RF signal backscatter. In at least one example, the RFID tag 1201 and the RFID scanner 1202 can be positioned on opposite sides of the tissue.

The RF signal from the backscatter data can be gathered and correlated with known tissue characteristics to permit tissue analysis. In various aspects, the spectral characteristics of the backscatter data can be analyzed to determine various characteristics of the tissue. In at least one example, the backscatter data is employed to identify boundary features within the tissue. In at least one example, the backscatter data can be used to assess thickness of the tissue grasped between the anvil 1200 and the stapling head assembly 1300.

Figure 18:
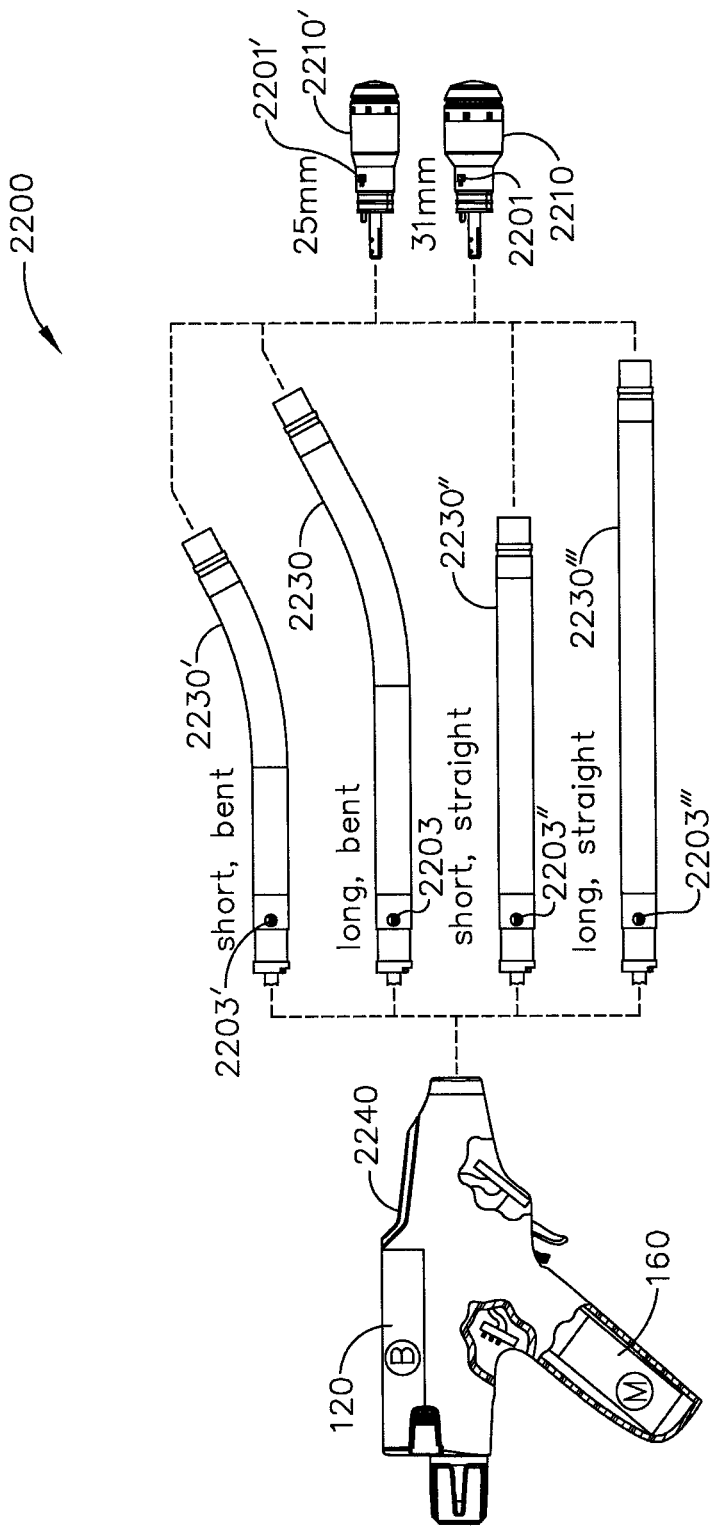
FIG. 18 depicts a surgical instrument that can be selectively assembled from any one of a number of different end effectors, any one of a number of different shafts, and a housing assembly, in accordance with at least one aspect of the present disclosure.

FIG. 18 depicts a surgical instrument 2200 that can be selectively assembled from any one of a number of different end effectors such as, for example, end effectors 2210, 2210', any one of a number of different shafts such as, for example, shafts 2230, 2230', 2230", 2230'", and a housing assembly 2240. Components of the surgical instrument 2200 are selected based on various factors including surgical procedure type, tissue type, and/or patient anatomy.

In various instances, the end effectors of the surgical instrument 2200 are circular stapler end effectors of different sizes. In the example of FIG. 18, 25 mm and 31 mm circular stapler end effectors are depicted. However this is not limiting, other suitable end effectors can be readily utilized with the surgical instrument 2200. In the example illustrated in FIG. 18, the shafts 2230, 2230', 2230", 2230'" comprise profiles that are different in length and/or curvature. However this is not limiting, shafts with other suitable shaft profiles can be readily used with the surgical instrument 2200.

Further to the above, the shafts 2230, 2230', 2230", 2230'" comprise RFID tags 2203, 2203', 2203", 2203'", respectively, which store shaft information, as described in greater detail below. In addition, the end effectors 2210, 2210' comprise RFID tags 2201, 2201', respectively, which store end-effector information, as described in greater detail below.

Figure 19:
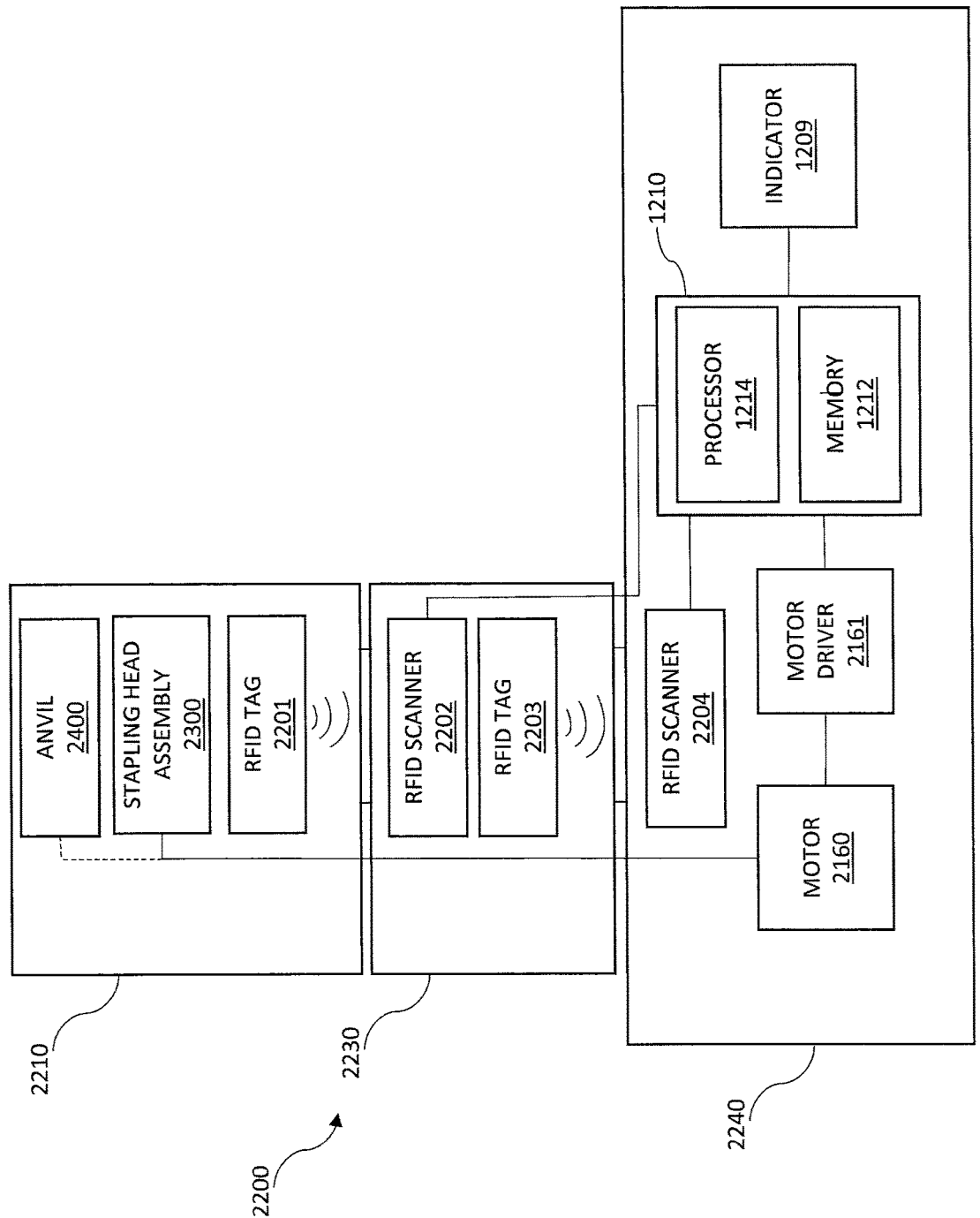
FIG. 19 depicts a schematic diagram of an assembled surgical instrument, in accordance with at least one aspect of the present disclosure.

FIG. 19 depicts a schematic diagram an example surgical instrument 2200 assembled from the end effector 2210, the shaft 2230, and a housing assembly 2240. Various components and/or connections between components of the end effector 2210, the shaft 2230, and a housing assembly 2240 are removed for clarity. The surgical instrument 2200 is similar in many respects to the surgical instruments 100, 1100. For example, the end effector 2210 has a stapling head assembly 2300 that is similar in many respect to the stapling head assemblies 300, 1300, and an anvil 2400 that is similar in many respects to the anvils 400, 1200.

In operation, as described above in greater detail with respect to the surgical instruments 100, 1100, the anvil 2400 is coupled to the stapling head assembly 2300. The anvil 2400 is then retracted from a starting position toward the stapling head assembly 2300 a closure stroke or distance "d" to transition the stapling head assembly 2300 from an open configuration to a closed configuration. Tissue is grasped between the anvil 2400 and the stapling head assembly 2300 in the closed configuration. Further, the stapling head assembly 2300 includes a staple cartridge that houses staples that are deployed from the staple cartridge toward the anvil 2400 in the closed configuration. The staples are deployed through the grasped tissue and are formed by Staple forming pockets 414 of the anvil 2400. In addition, a knife member 340 is translated distally to a point where cutting edge 342 is distal to a deck surface 322 of the stapling head assembly 2300 to cut the tissue.

In addition to or in lieu of the foregoing, stapling head assembly 2300 and anvil 2400 may be further constructed and operated in accordance with at least some of the teachings of U.S. Pat. Nos. 5,205,459; 5,271,544; 5,275,322; 5,285,945; 5,292,053; 5,333,773; 5,350,104; 5,533,661; and/or U.S. Pat. No. 8,910,847, the entire disclosures of which are incorporated by reference herein. Still other suitable configurations will be apparent to one of ordinary skill in the art in view of the teachings herein.

Referring still to FIG. 19, the housing assembly 2240 includes one or more motors 2160 and one or more motor drivers 2161, which are similar in many respects to motors 160,1160 and motor drivers 161, 1161. In various examples, the control circuit 1210 is configured to control a motor driver 2161 to cause a motor 2160 to move the anvil 2400 a closure stroke or distance "d" toward the stapling head assembly 2300 to transition the end effector 2210 from the open configuration to the closed configuration. The control circuit 1210 is further configured to control a motor driver 2161 to cause a motor 2160 to apply a load onto the end effector 2210 in a firing motion to deploy the staples into tissue grasped by the end effector 1210 in the closed configuration, and cut the grasped tissue by advancing the knife member 340 distally through the tissue. In at least one example, the knife member 340 is advanced toward a breakable washer of the anvil 2400. In such example, the breakable washer is broken by the knife member 340 toward the end of a full distal range of motion of the knife member 340.

Figure 20:
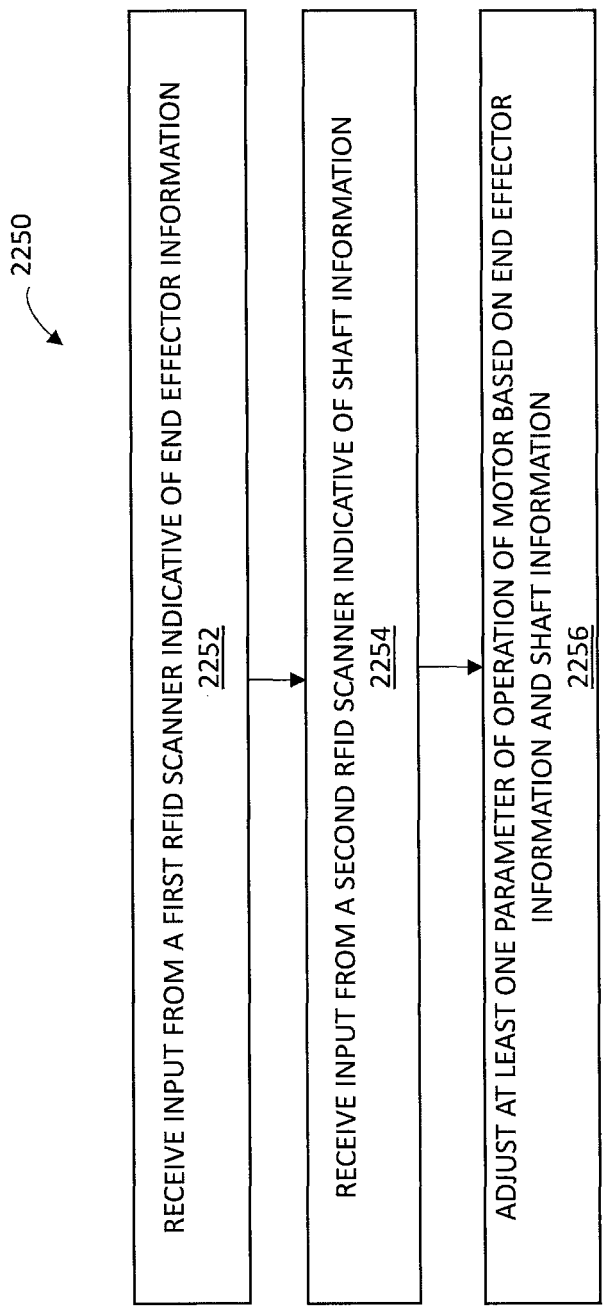
FIG. 20 depicts a logic flow diagram of a process depicting a control program or a logic configuration for adjusting at least one operational parameter of a motor of the surgical instrument of FIG. 19.

To properly staple and cut tissue by a surgical instrument 2200, operational parameters of the motor(s) 2160 need to be adjusted to yield closure distances and/or firing loads that are suitable for a selected end effector 2210 and/or shaft 2230 of the surgical instrument 2200. Longer and/or curved shafts, for example, require different closure distances than shorter ones. Likewise, larger staple cartridges generally require higher firing loads than smaller ones. To address this matter, the end effectors of a surgical instrument 2200 are equipped with RFID tags 2201 that store end-effector information, and are detectable by RFID scanners 2202. Additionally, in certain instances, the shafts of the surgical instrument 2200 are also equipped with RFID tags 2203 that store shaft information, and are detectable by RFID scanners 2204. As illustrated in FIG. 20, in accordance with a process 2250, the control circuit 1210 can be configured to receive 2252 input from an RFID scanner 2202 indicative of the end-effector information, receive 2254 input from an RFID scanner 2204 indicative of the shaft information, and adjust 2256 at least one parameter of operation of the motor(s) 2160 to yield closure distances and/or firing loads that are based on the end-effector information and the shaft information.

In at least one example, the process 2250 is executed by a control circuit 1210 (FIG. 15) that includes a processor 1214 and a memory 1212 storing a set of computer-executable instructions that, when executed by the processor 1214, cause the processor 1214 to perform of the process 2250. In certain examples, a set of computer-executable instructions, stored in the memory 1212 may cause the processor 1214 to perform discrete portions of the process 2250. Although the process 2250 is described as being executed by a control circuit 1210, this is merely for brevity, and it should be understood that the process 2250 and other processes described herein, or portions thereof, can be executed by circuitry that can include a variety of hardware and/or software components and may be located in or associated with various suitable systems such as, for example, combinational logic circuits or sequential logic circuits.

In the example illustrated in FIG. 19, the RFID tag 2201 and corresponding RFID scanner 2202 are arranged such that the RFID tag 2201 is within the detection range of the RFID scanner 2202 when the end effector 2210 is an assembled configuration with the shaft 2230. Also, the RFID tag 2203 and corresponding RFID scanner 2204 are arranged such that the RFID tag 2203 is within the detection range of the RFID scanner 2204 when the shaft 2230 is an assembled configuration with housing assembly 2240. Accordingly, the RFID scanner 2202 is positioned at the distal portion of the shaft 2230 while the RFID tag 2203 is positioned at the proximal portion of the shaft 2230. In at least one example, one or both of the RFID tag 2201 and the RFID scanner 2202 are positioned at an interface between the end effector 2210 and the shaft 2230. Additionally, or alternatively, one or both of the RFID tag 2203 and the RFID scanner 2204 are positioned at an interface between the shaft 2230 and housing assembly 2240.

Further to the above, end-effector information stored in the RFID tag 2201 can be read by the RFID scanner 2202 in the assembled configuration, and can be communicated to the control circuit 1210. Also, shaft information stored in the RFID tag 2203 can be read by the RFID the scanner 2204, and can be communicated to the control circuit 1210. In various aspects, the end effector-information can include identification information, manufacturer information, staple cartridge size, type, and/or color, anvil type, and/or one more suitable adjustment values for default closure distances and/or firing loads. Likewise, the shaft information can include identification information, manufacturer information, shaft profiles, and/or one more suitable adjustment values for default closure distances and/or firing loads.

Figure 21:
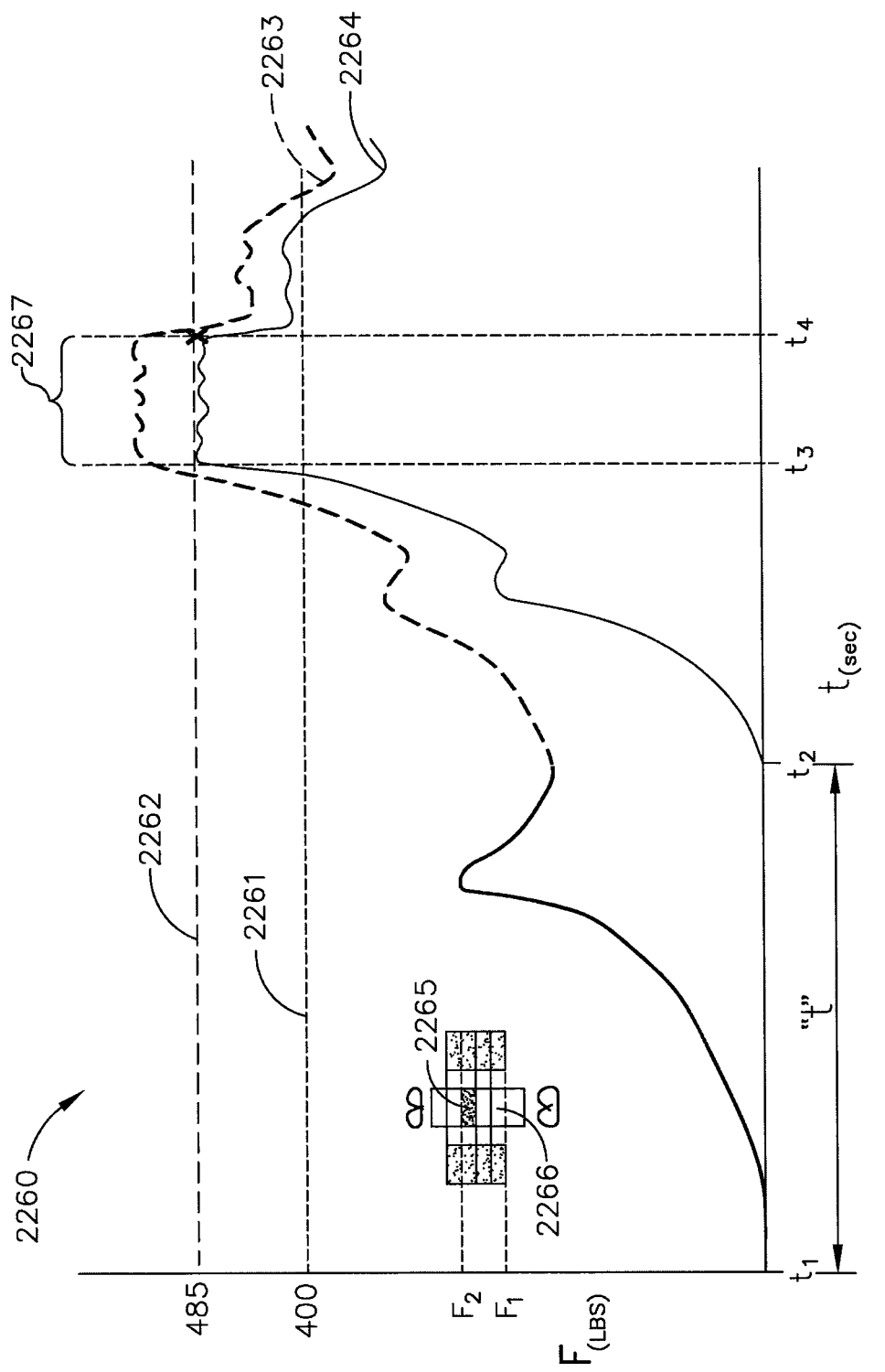
FIG. 21 depicts a graph illustrating firing loads of the surgical instrument of FIG. 19 in accordance with two different firing algorithms.

Referring to FIG. 21, a graph 2260 represents a relationship between firing Load (lbs) on the Y-axis and firing time (sec) on the X-axis. Graph 21 depicts a default, unadjusted, firing algorithm 2263 and an adjusted firing algorithm 2263. The graph 2260 further depicts a default maximum firing load threshold 2261 (e.g. 400 lbs) and a final maximum firing load threshold 2262 (e.g. 485 lbs) for a firing load applied by a motor 2160 to the end effector 2210 of the surgical instrument 2200. The default maximum firing load threshold 2261 is adjusted to the final maximum firing load threshold 2262 based on end-effector information of the end effector 2210 that is stored in the RFID tag 2201 and read by the RFID scanner 2202 of the surgical instrument 2200. In the example of FIG. 21, the end-effector information represents a staple cartridge that comprises a larger size (e.g. 31 mm) than a default staple cartridge (e.g. 25 mm). The default staple cartridge size (e.g. 25 mm) is associated with the default firing algorithm 2263 and default maximum firing load threshold 2261. Meanwhile, the larger staple cartridge size (e.g. 31 mm) is associated with the final firing algorithm 2264 and final maximum firing load threshold 2262.

The end-effector information stored in the RFID tag 2201 can include the staple cartridge size and/or a firing load adjustment value (e.g. 85 lbs) based on the cartridge size. In the event of the staple cartridge size, the control circuit 1210 can use a database or a lookup table of staple cartridge sizes and corresponding firing load adjustment values to look up a suitable firing load adjustment values.

Further, input from the RFID scanner 2201 indicative of the end-effector information causes the control circuit 1210 to adjust the default maximum firing load threshold 2261 (e.g. 400) to the final maximum firing load threshold 2262 (e.g. 485 lbs), and maintain a firing algorithm 2264 below the final maximum firing load threshold 2262, as illustrated in FIG. 20.

In the example of FIG. 21, the control circuit 1210 adjusts or introduces a minimum wait-time "t" before causing the motor 2160 to apply the firing algorithm 2263 to the end effector 2210. In various instances, the minimum wait-time "t" is a time period between completion of a closure sequence of an end effector of the surgical instrument 2200, where tissue is grasped by the end effector in a closed configuration, and commencement of a firing sequence of the end effector, where the grasped tissue is stapled and cut. The minimum wait time "t" permits tissue creep where the grasped tissue adjusts to a lower average pressure thereby reducing the maximum firing load necessary to complete the firing sequence of the end effector 2210 to a value at or below the final maximum firing load threshold 2262. In the default firing algorithm 2263, without the minimum wait-time "t", the firing algorithm 2263 must be interrupted 2267 for a time period from time t3 to time t4 to prevent the firing load from exceeding the final maximum firing load threshold 2262. By comparison, the firing algorithm 2264 is continued through the time period between t3 and t4, as illustrated in FIG. 21

Referring still to FIG. 21, another factor that can influence the minimum wait time "t" is the user-selected form height of the staples deployed from the stapling head assembly 2300. The control circuit 1210 can prompt a user through the indicator 1209 to select a desired form height of the staples. In at least one example, the control circuit 1210 can present the user with a number of form height options to choose from. Additionally, or alternatively, the control circuit 1210 can recommend an optimal form height based on the tissue being treated by the surgical instrument 2200. In any event, the user-selected form height can cause the control circuit 1210 to further adjust the minimum wait time "t". In at least one example, the memory 1212 stores, in a database or a lookup table, form heights and corresponding wait-time adjustments. The control circuit 1210 can adjust the minimum wait time "t" by identifying a wait-time adjustment associated with a user-selected form height, and then adjusting the minimum wait time "t" in accordance with the identified wait-time adjustment.

Generally, a more formed staple is associated with a greater firing load, and requires a greater minimum wait time "t" than a lesser formed staple. In the example of FIG. 21, the user-selected form height 2265 is associated with a firing load "F2", and is greater than a minimum form height 2266 associated with a minimum firing load "F1". The minimum firing loads "F1" and "F2" represent firing loads at which staple legs begin to buckle. Accordingly, the wait time "t" of the example of FIG. 21 is a result of the greater (31 mm) than the default (25 mm) staple cartridge size, and the selected form height 2265.

Figure 22:
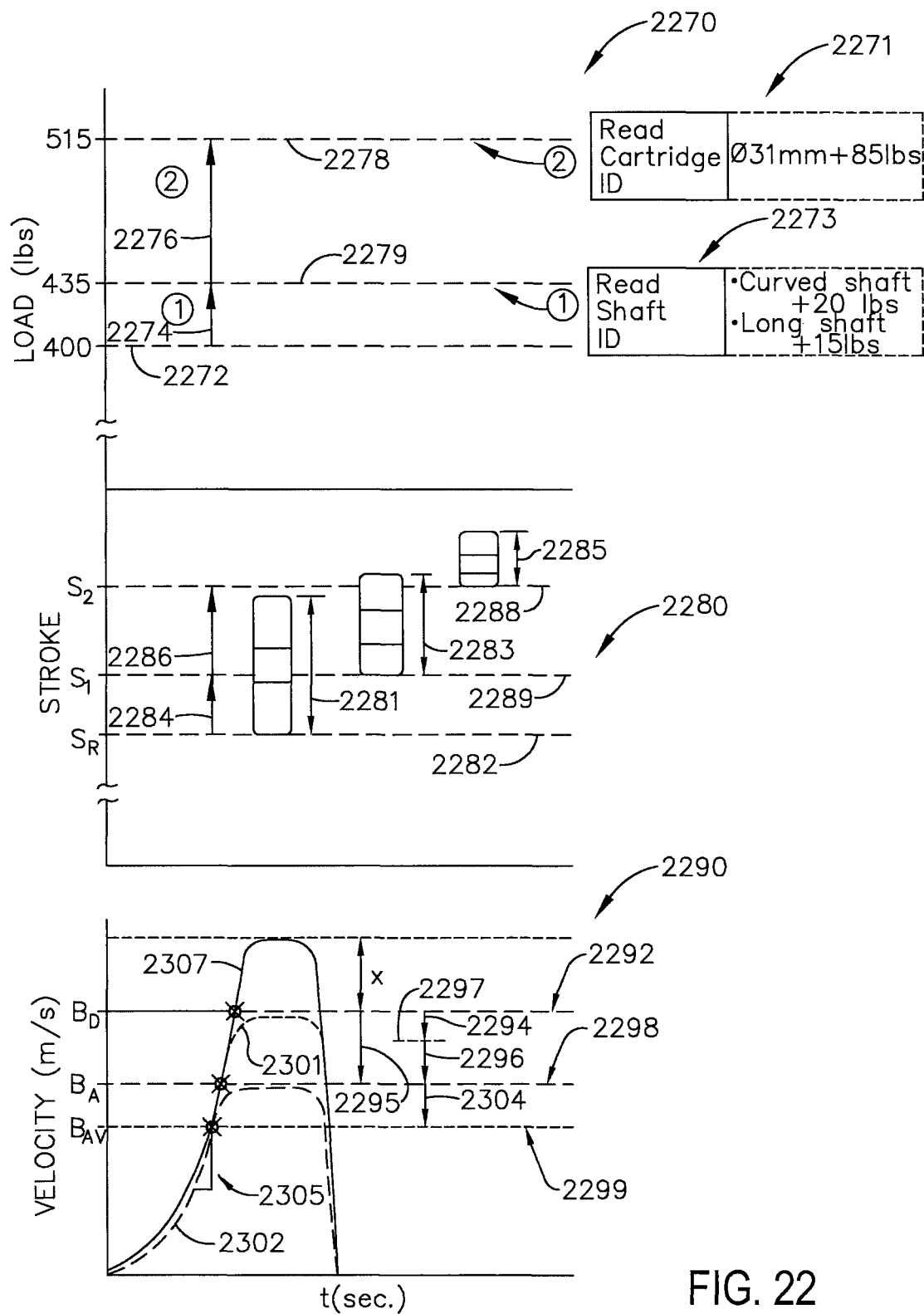
FIG. 22 depicts graphs illustrating adjustments of various closure and firing thresholds of the surgical instrument of FIG. 19.

Referring to FIG. 22, Graph 2270 illustrates adjustments made to a default maximum firing load threshold 2272 (e.g. 400 lbs) of the surgical instrument 2200. The adjustments are based on end-effector information 2271 and shaft information 2273 received by a control circuit 1210 from RFID scanners 2202, 2204, as described above in greater detail. The shaft information 2273 identifies a long curved shaft 2230, and provides a corresponding first adjustment value 2274 (e.g. 35 lbs) to the default maximum firing load threshold 2272. Similarly, the end-effector information 2271 identifies an end effector 2210 with staple cartridge comprising a size of 31 mm, and provides a corresponding second adjustment value 2276 (e.g. 85 lbs) to the default maximum firing load threshold 2272. Adding the adjustment values 2274, 2276 to the default maximum firing load threshold 2272 yields a final maximum firing load threshold 2278. As described above, the adjustment values 2274, 2276 can be part of the end-effector information 2271 and the shaft information 2273, respectively, or can be determined by the control circuit 1210 from a database or lookup table stored in the memory 1212, for example, based on the identification information of the end effector 2210 and the shaft 2230.

In at least one example, a surgical instrument 2200 can be assembled from a curved long shaft 2230 and an end effector 2210' comprising a default staple cartridge size (e.g. 25 mm). In such examples, the end effector information yields a zero adjustment value, and the shaft information yields the first adjustment value 2274 that modifies the default maximum firing load threshold 2272 to a final maximum firing load threshold 2279, as illustrated in Graph 2270. In other examples, the surgical instrument 2200 can be assembled from various combinations of end effectors and shafts that yield different adjustment values for modifying the default maximum firing load threshold 2272.

Referring to FIG. 22, Graph 2280 illustrates adjustments made to a default minimum closure stroke or distance 2282 of the surgical instrument 2200. A minimum closure stroke or distance a surgical instrument 2200 is a minimum permissible or recommended closure stroke or distance that bring an end effector of the surgical instrument 2200 such as, for example, the end effector 2210 to a closed configuration suitable for deploying staples into tissue grasped between an anvil and a staple cartridge of the end effector. The adjustments to the default minimum closure stroke or distance 2282 are based on end-effector information 2271 and shaft information 2273 received by a control circuit 1210 from RFID scanners 2202, 2204, as described above in greater detail.

The shaft information 2273 identifies a long curved shaft 2230, and provides a corresponding first adjustment value 2284 to the default minimum closure stroke or distance 2282. The added length and curvature of the shaft 2230, in comparison to a default shaft, yields a longer minimum closure stroke or distance 2289 than the default minimum closure stroke or distance 2282. Similarly, the end-effector information 2271 identifies an end effector 2210 with a staple cartridge comprising a size of 31 mm, and provides a corresponding second adjustment value 2286 to the default minimum closure stroke or distance 2282. Adding the adjustment values 2284, 2286 to the default minimum closure stroke or distance 2282 yields a final default minimum closure stroke or distance 2288. As described above, the adjustment values 2284, 2286 can be part of the end-effector information 2271 and the shaft information 2273, respectively, or can be determined by the control circuit 1210 from a database or lookup table stored in the memory 1212, for example, based on identification information of the end effector 2210 and the shaft 2230.

In at least one example, a surgical instrument 2200 can be assembled from a curved long shaft 2230 and an end effector 2210' comprising a default staple cartridge size (e.g. 25 mm). In such examples, the end effector information yields a zero adjustment value and the shaft information yields the first adjustment value 2284, which modify the default minimum closure stroke or distance 2282 to a final minimum closure stroke or distance 2289, as illustrated in Graph 2280. In other examples, the surgical instrument 2200 can be assembled from various combinations of end effectors and shafts that yield different adjustment values for modifying the default minimum closure stroke or distance 2282.

Further to the above, the end-effector information 2271 and the shaft information 2273 can cause the control circuit 1210 to adjust a default closure range 2281 of user-selectable closure strokes or distances of the surgical instrument 2200. A closure range of a surgical instrument 2200 is a range of permissible or recommended closure strokes or distances that bring an end effector of the surgical instrument 2200 such as, for example, the end effector 2210 to a closed configuration suitable for deploying staples into tissue grasped between an anvil and a staple cartridge of the end effector. In at least one example, the closure range of a surgical instrument 2200 can be in the form of a visual guide presented to a user by the indicator 1209.

In various examples, the closure range of a surgical instrument 2200 is defined by the control circuit 1210 based on the end-effector information and/or the shaft information received from the RFID scanners 2203, 2204. Graph 2280 depicts, for example, a default closure range 2281, an adjusted closure range 2283, and an adjusted closure range 2285. The adjusted closure range 2283 is defined by the control circuit 1210 in response to the shaft information transmitted from the RFID scanner 2204. The adjusted closure range 2285 is defined by the control circuit 1210 in response to end-effector information transmitted from the RFID scanner 2202 and shaft information transmitted from the RFID scanner 2204. In other words, the adjusted closure range 2285 is defined by the cumulative impact of the end-effector information and the shaft information.

In various aspects, the transmitted shaft information can include the adjusted closure range 2283. Alternatively, the transmitted shaft information can includes upper and lower adjustment values of the default closure range 2281. Alternatively, the transmitted shaft information can include shaft identification information. In at least one example, the control circuit 1210 can determine an adjusted closure range 2283 from a database or lookup table stored in the memory 1212, for example, based on the shaft identification information.

In various aspects, the transmitted end-effector information can include an adjusted closure range. Alternatively, the transmitted end-effector information can includes upper and lower adjustment values of the default closure range 2281. Alternatively, the transmitted end-effector information can include end-effector identification information. In at least one example, the control circuit 1210 can determine an adjusted closure range from a database or lookup table stored in the memory 1212, for example, based the end-effector identification information.

In at least one example, the control circuit 1210 can determine an adjusted closure range 2285 from a database or lookup table stored in the memory 1212, for example, based on shaft identification information and end-effector identification information. In at least one example, the control circuit 1210 can determine an adjusted closure range 2285 from the cumulative impact of upper and lower adjustment values of the default closure range 2281, which are provided by the end-effector information and shaft information.

Referring still to FIG. 22, Graph 2290 illustrates firing velocity (m/s) on the Y-axis verses time (seconds) on the X-axis. In example of Graph 2290, the firing velocity represents the velocity of a longitudinally movable firing member coupled to a motor 2160 (FIG. 19) of the surgical instrument 2200, and configured to effect deployment of staples from the stapling head assembly 2300 toward the anvil 2400, and advancement of the knife member 340, as described above in greater detail. In other examples, the firing velocity can be a rotation velocity of the motor 2160.

Graph 2290 illustrates adjustments made to a default maximum threshold 2292 of the firing velocity of the surgical instrument 2200, which are based on end-effector information and shaft information received by a control circuit 1210 from RFID scanners 2202, 2204, as described above in greater detail. The shaft information identifies a long curved shaft 2230, and provides a corresponding first adjustment value 2294 to the default maximum threshold 2292. Similarly, the end-effector information identifies an end effector 2210 with a staple cartridge comprising a size of 31 mm, and provides a corresponding second adjustment value 2296 to the default maximum threshold 2292.

In the example of Graph 2290, the adjustment values 2294, 2296 are combined 2295 to reduce the default maximum threshold 2292 to a final maximum threshold 2298 of the firing velocity of the surgical instrument 2200. The adjustment values 2294, 2296 can be part of the end-effector information and the shaft information, respectively, or can be determined by the control circuit 1210 from a database or lookup table stored in the memory 1212, for example, based on identification information of the end effector 2210 and the shaft 2230.

In at least one example, a surgical instrument 2200 can be assembled from a curved long shaft 2230 and an end effector 2210' comprising a default staple cartridge size (e.g. 25 mm). In such examples, the end effector information yields a zero adjustment value and the shaft information yields the adjustment value 2294, which modify the default maximum threshold 2282 to a final maximum threshold 2297, as illustrated in Graph 2290. In other examples, the surgical instrument 2200 can be assembled from various combinations of end effectors and shafts that yield different adjustment values for modifying the default maximum threshold 2292 of the firing velocity.

Further to the above, Graph 2290 depicts three firing velocity curves 2307, 2301, 2302 that represent three different firing algorithms. The firing velocity curve 2307 represents a first firing algorithm that failed to comply with the default maximum threshold 2292 of the firing velocity due to failure to account for inertia of the firing member. The firing velocity curve 2301 represents a second firing algorithm that failed to comply with a statically adjusted maximum threshold 2298 due to failure to account for inertia of the firing member. The firing velocity curve 2302 represents a third firing algorithm that dynamically modified a statically adjusted final maximum threshold 2298 by an adjustment value 2304 to achieve a dynamically and statically adjusted final maximum threshold 2299. The adjustment value 2304 is based on a slope 2305 of the velocity curve 2302.

Figure 23:
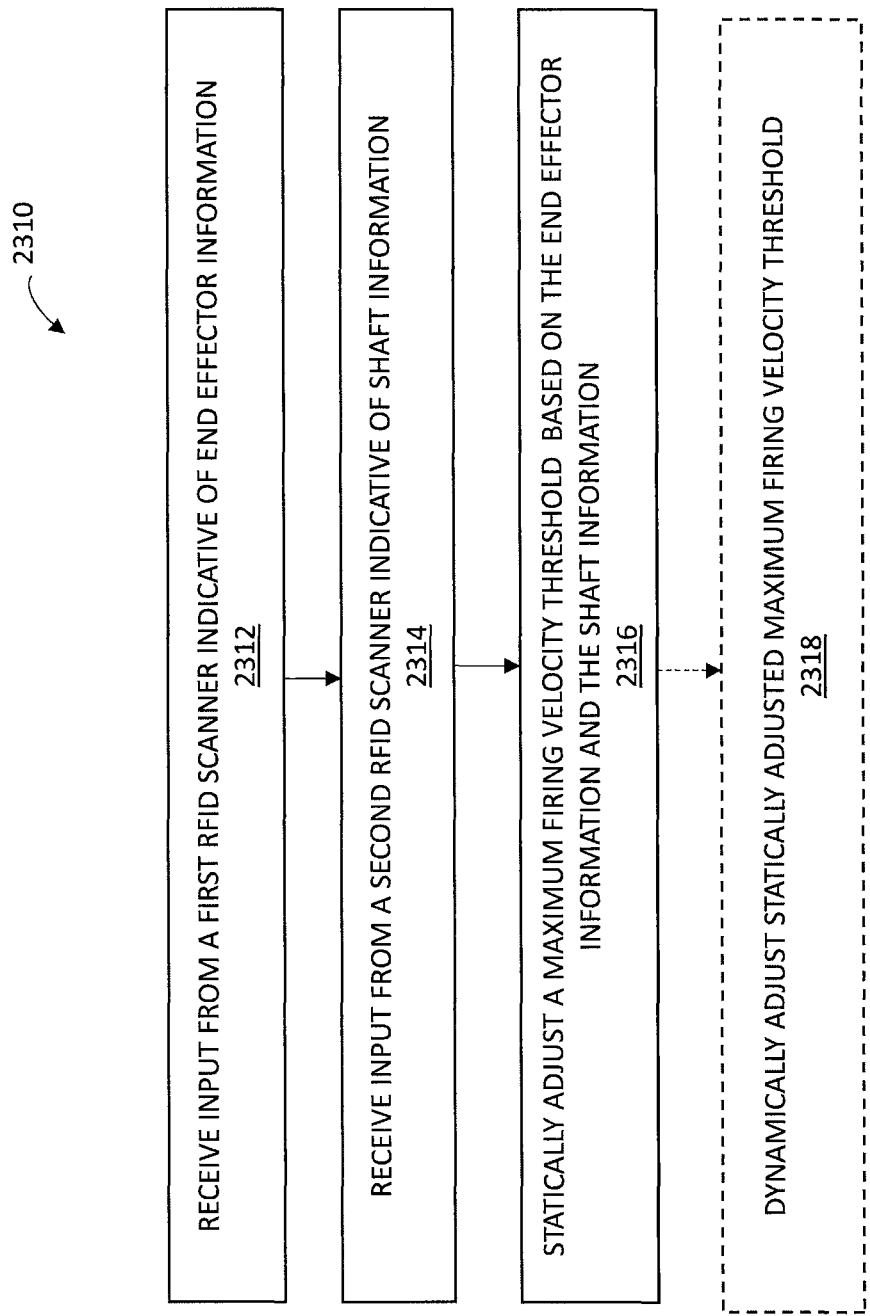
FIG. 23 depicts a logic flow diagram of a process depicting a control program or a logic configuration for operating a surgical stapling instrument, in accordance with at least one aspect of the present disclosure.

In at least one example, as illustrated in FIG. 23, a process 2310 depicting a control program or a logic configuration for operating the surgical instrument 2200, in accordance with at least one aspect of the present disclosure. In at least one example, the process 2310 is executed by a control circuit 1210 (FIG. 15) that includes a processor 1214 and a memory 1212 storing a set of computer-executable instructions that, when executed by the processor 1214, cause the processor 1214 to perform of the process 2310. In certain examples, a set of computer-executable instructions, stored in the memory 1212 may cause the processor 1214 to perform discrete portions of the process 2310. Although the process 2310 is described as being executed by a control circuit 1210, this is merely for brevity, and it should be understood that the process 2310 and other processes described herein, or portions thereof, can be executed by circuitry that can include a variety of hardware and/or software components and may be located in or associated with various suitable systems such as, for example, combinational logic circuits or sequential logic circuits.

Further to the above, the process 2310 comprises receiving 2312 input from the RFID scanner 2202 indicative of the end-effector information, receiving 2314 input from the RFID scanner 2204 indicative of the shaft information, and statically adjusting 2316 a default maximum threshold 2292 of the firing velocity of the surgical instrument 2200 to a final maximum threshold 2298 based on the end-effector information and the shaft information. Additionally, in certain instances, the process 2310 further comprises dynamically adjusting 2318 the final maximum threshold 2298 of the firing velocity to a new final maximum threshold 2299 based on the slope 2305 of the firing velocity curve 2302 to account for the firing member inertia, as illustrated in the example of Graph 2290.

Figure 24:
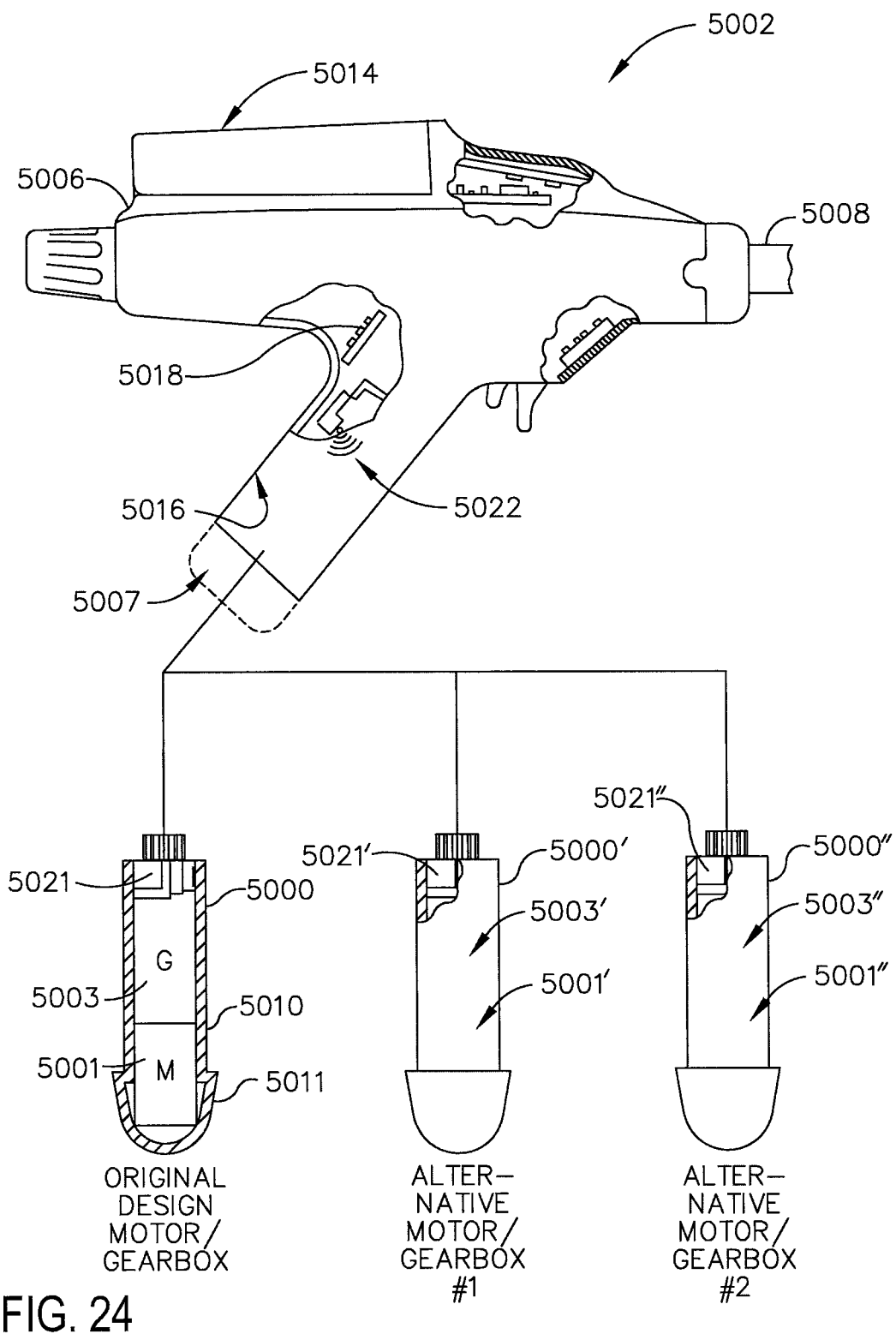
FIG. 24 depicts a partial elevational view of a surgical instrument and three motor assemblies for use with the surgical instrument, in accordance with at least one aspect of the present disclosure.

Referring primarily to FIG. 24, three motor assemblies 5000, 5000', 5000" are interchangeably usable with a surgical instrument 5002. The motor assemblies 5000, 5000', 5000" include motors 5001, 5001', 5001" and gearboxes 5003, 5003', 5003", respectively. The motors 5001, 5001', 5001", even with similar design parameters, have differing outputs based on winding techniques, wire quality, internal component quality, and/or magnetic densities. Further, the gearboxes 5003, 5003', 5003" associated with the motors 5001, 5001', 5001" also have variable losses and efficiencies based on their materials, lubrications, tolerance stack-up, and manufacturing methodologies. The implication of these variations is that motor assemblies such as, for example, the motor assemblies 5000, 5000', 5000" are likely to have dramatically different efficiencies and outputs for the same applied voltage and current, even if they are produced by a single supplier. In various aspects, the surgical instrument 5002 addresses these variations by employing an RFID system 5004 (FIG. 27) that is configured for detection and communication with a motor assembly 5000, for example, in order to retrieve information associated with the motor assembly 5000 that can aid the surgical instrument 5002 in addressing motor-assembly variations. In various aspects, the detection of a motor assembly such as, for example, the motor assembly 5000 is achieved only when the surgical instrument 5002 is in an assembled configuration with the motor assembly 5000, as described in greater detail below.

Figure 26:
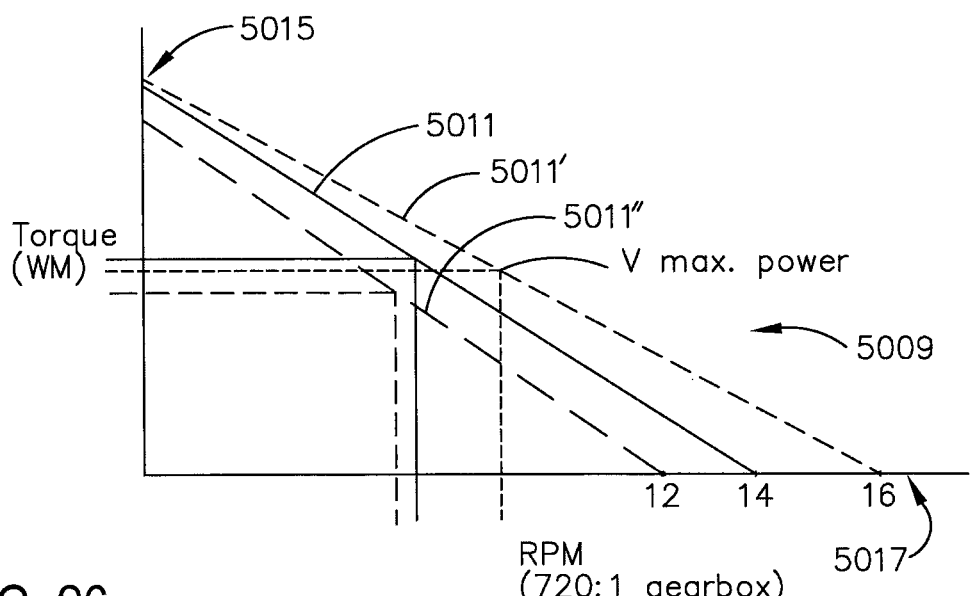
FIG. 26 is graph depicting a relationship between motor torque on the Y-axis and motor speed on the X-axis for three different motors, in accordance with at least one aspect of the present disclosure.

FIG. 26 is a graph 5009 with three lines 5011, 5011', 5011" that represent the relationship between motor torque (NM) on the Y-axis and motor speed (RPM) on the X-axis for the motors 5001, 5001', 5001", respectively. The lines 5011, 5011', 5011" demonstrate variations that exist among interchangeable motors. The lines 5011, 5011', 5011" intersect the Y-axis at different points that represent the motor-stall torques 5015, and intersect the X-axis at different points that represent the no-load speeds 5017. The graph 5009 also shows the motors' speeds at maximum suitable power. In various aspects, as described below in greater detail, information extracted from the relationships represented by the lines 5011, 5011', 5011" can used by a control circuit 1210 to adjust one or more operational parameters of a motor, select an a control algorithm, and/or adjust a default control algorithm to ensure delivery of predictable outputs from the motor assemblies 5000, 5000', 5000".

Referring still to FIG. 24, the surgical instrument 5002 includes a housing assembly 5006 that has a motor-assembly compartment 5007 configured to interchangeably receive, and be releasably coupled with, motor assemblies such as, for example the motor assemblies 5000, 5000', 5000". For brevity, the following description of the interaction between the surgical instrument 5002 and a motor assembly will focus on the motor assembly 5000. Nonetheless the following description is equally applicable to other suitable motor assemblies such as, for example, the motor assemblies 5000'. Although the housing assembly 5006 is depicted in the form of a handle, this is not limiting. In various instances, the housing assembly 100 can be a component of a robotic system, for example.

The surgical instrument 5002 is similar in many respects to other surgical instruments described elsewhere herein such as, for example, the surgical instruments 100, 1100. For example, the surgical instrument 5002 includes a shaft 5008 extending distally from the housing assembly 5006, and an end effector 5019 extending distally from the shaft 5008. Various end effectors suitable for use with the surgical instrument 5002 such as, for example, a circular stapler end effector that includes an anvil 400 and a stapling head assembly 300, are described elsewhere in the present disclosure and/or other disclosures incorporated by reference in the present disclosure.

The motor assembly 5000 is movable relative to the housing assembly 5006 between an assembled configuration and an unassembled configuration with the housing assembly 500. Various suitable electrical connectors can be employed to connect a power source 5014 in the housing assembly 5006 to the motor assembly 5000 to power to the motor 5001 in the assembled configuration. Also, various suitable mechanical connectors can be employed to operably transmit a motion, generated by the motor 5001, from the gearbox 5003 to the end effector to treat tissue grasped by the end effector.

U.S. Pat. No. 9,504,520, titled SURGICAL INSTRUMENT WITH MODULAR MOTOR, and issued Nov. 29, 2016, which is hereby incorporated by reference herein in its entirety, describes several mechanical and electrical connectors that are suitable for use with the surgical instrument 5002 and the motor assembly 5000. In at least one example, a motor assembly 5000 comprises a body 5010, a base 5011, and a pair of pogo pins, for example, that are configured to deliver electrical power to the motor 5001 housed within body 5010. Pogo pins can engage a plurality of wires in the housing assembly 5006, which are coupled to an electrical power source 5014. In various aspects, the motor assembly 5000 is secured or retained within, or at least partially within, the motor-assembly compartment 5007 of the housing assembly 5006 by latching members, clamps, clips, screw-down members, etc. When motor assembly 5000 is inserted into the motor-assembly compartment 5007, the mechanical and electrical connectors of the motor assembly 5000 are coupled to corresponding structures within the housing assembly 5006 through an electro-mechanical interface 5023 (FIG. 27) to form the assembled configuration.

Figure 27:
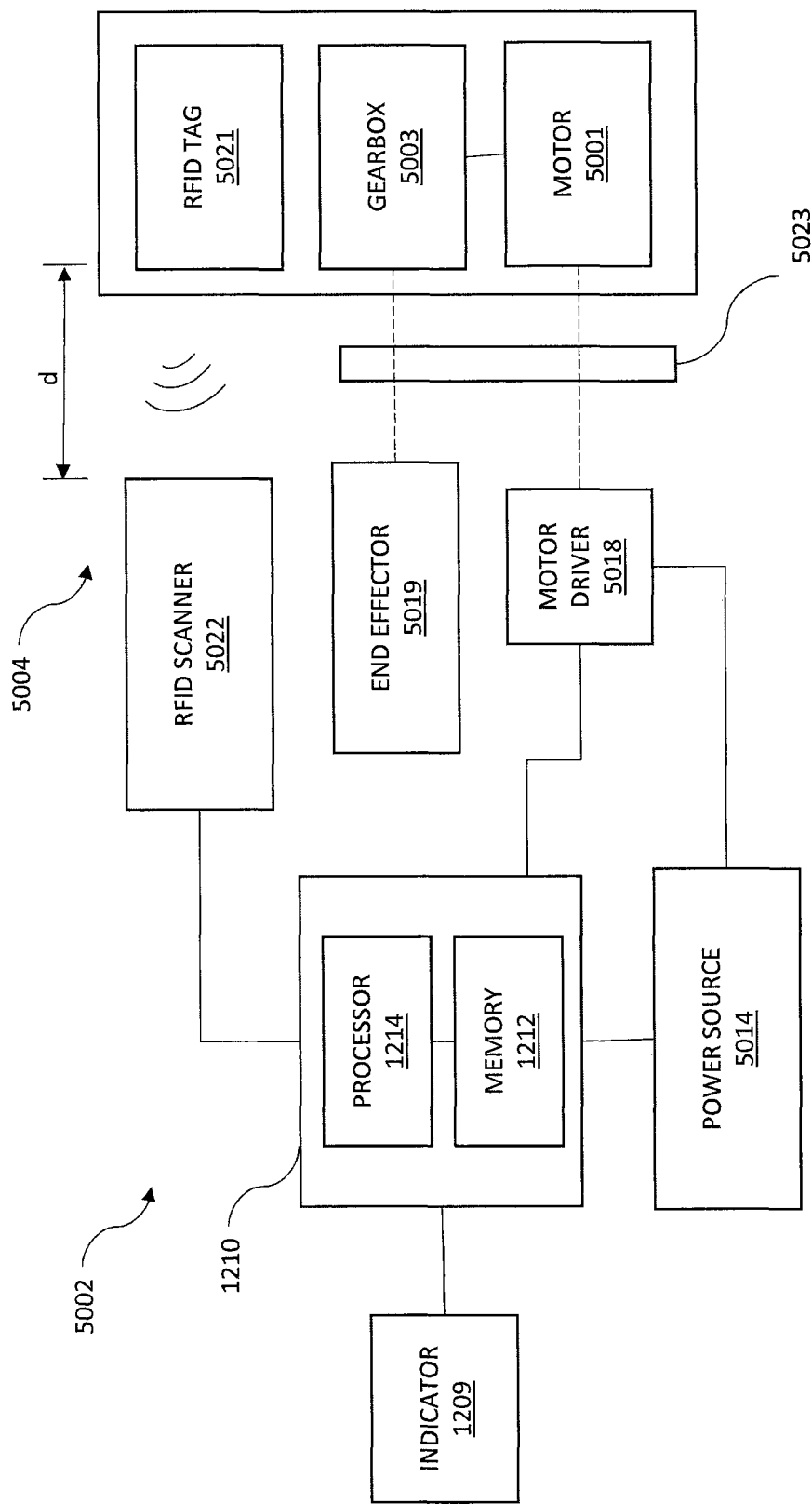
FIG. 27 depicts a control system of the surgical instrument of FIG. 24, in accordance with at least one aspect of the present disclosure.

Referring to FIG. 27, the RFID system 5004 includes an RFID scanner 5022 and RFID tag 5021 detectable by the RFID scanner in the assembled configuration. In various aspects, the RFID scanner 5022 is configured to read and/or write to the RFID tag 5021 in the assembled configuration. In the example illustrated in FIG. 27, the RFID scanner 5022 comprises a detection range defined by a distance "d". The RFID tag 5021 is at or within the detection range defined by the distance "d" when the motor assembly 5000 is in an assembled configuration with the housing assembly 5006.

Referring still to FIG. 27, the RFID scanner 5022 is coupled to a control circuit 1210 that includes a microcontroller comprising a processor 1214 and a storage medium such as, for example, the memory 1212, as described elsewhere herein in greater detail. The RFID tag 5021 stores information indicative of the motor assembly 5000, which is read by the RFID scanner 5022 while the motor assembly 5000 is retained by the motor-assembly compartment 5007 in the assembled configuration.

In at least one example, the control circuit 1210 receives an input from the RFID scanner 5022 indicative of the motor-assembly information, and adjusts one or more parameters of operation of the motor 5001 based on the motor-assembly information. The control circuit 1210 can employ a motor driver 5018 to perform the parameter adjustments. In the example illustrated in FIG. 27, the motor driver 5018 is positioned within the housing assembly 5006, and interfaces with the motor 5001 in the assembled configuration through the electro-mechanical interface 5023. In other examples, the motor driver 5018 is a part of the motor assembly 5000, and is configured to interface with the control circuit 1210 through the electro-mechanical interface 5023.

Figure 28:
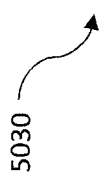
FIG. 28 depicts a table or database of various control algorithms of the surgical instrument of FIG. 25, in accordance with at least one aspect of the present disclosure.

Referring to FIG. 28, the processor 1214 of the control circuit 1210 can be configured to select a control algorithm of the surgical instrument 5002 based on the motor-assembly information retrieved from the RFID tag 5021 by the RFID scanner 5022. The control algorithms can be stored in the memory 1214, for example, in the form of a database or a look-up table 5030. Alternatively, or additionally, the motor-assembly information of a motor assembly can include a control algorithm recommended for use with the motor assembly.

In various examples, the motor-assembly information of a motor assembly 5000, for example, comprises one or more of identification information, manufacturer information, and specific tolerances of the motor 5001 and/or the gearbox 5003, for example. The motor-assembly information can include model numbers, lot numbers, manufacturing dates, and/or any other relevant information.

In the example illustrated in FIG. 28, each row represents a control algorithm associated with a motor assembly, which can be selected by the processor 1214 based on the retrieved motor-assembly information. The values in the outer left column are based on input from the RFID scanner 5022 indicative of the motor-assembly information of motor assemblies $MA_1$-$MA_n$. In at least one example, the values in the outer left column can be motor-assembly identification or model numbers. The middle columns include values of motor velocity, inertia/dynamic breaking, stroke length, current limits/force limits that are associated with each of the motor assemblies $MA_1$-$MA_n$. The values in the outer right column represent suitable voltage and discharge values of a power source 5014 configured to power motor assemblies $MA_1$-$MA_n$ when coupled to the surgical instrument 5002.

Referring still to FIG. 5, in various aspects, the control circuit 1210 is configured to employ the RFID system 5004 to retrieve motor-assembly information that identify a motor assembly coupled to the surgical instrument 5002. The control circuit 1210 then determines, from the look-up table 5030 suitable voltage and discharge values for the power source 5014 based on the retrieved motor-assembly information.

In various aspects, the control circuit 1210 employs a formula or calibration factor to adjust the operational parameters of a motor assembly 5000, for example. The formula or calibration factor can be stored by the RFID tag 5021, and received by the control circuit 1210 through input from the RFID scanner 5022. Alternatively, the formula or calibration factor can be retrieved from a storage medium such as, for example, the memory 1212 based on identification information of the memory assembly associated with such formula or calibration factor.

Figure 25:
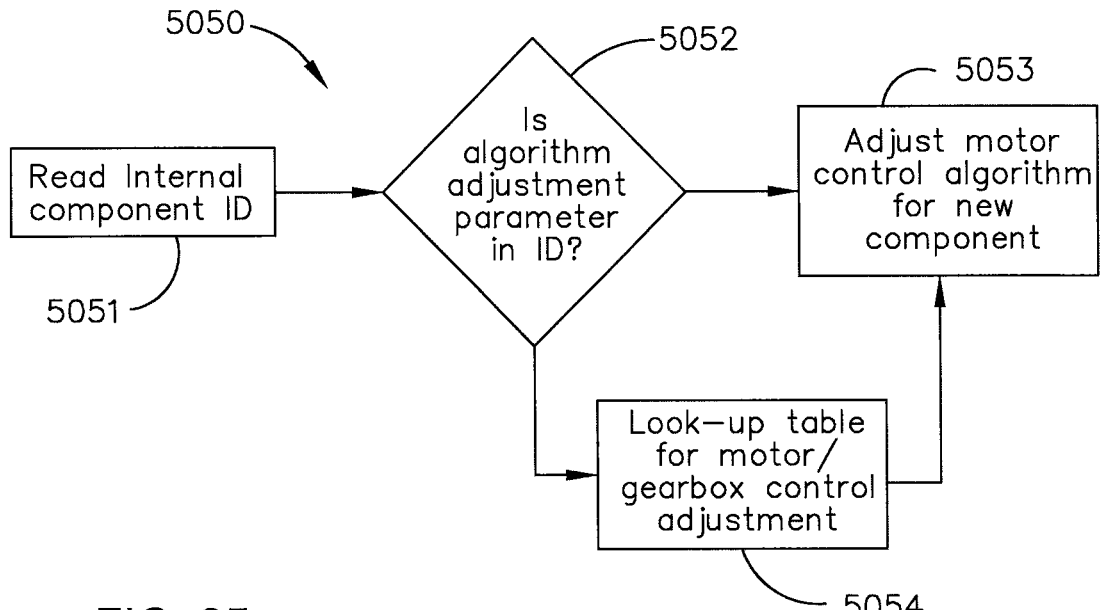
FIG. 25 depicts a logic flow diagram of a process depicting a control program or a logic configuration for adjusting operational parameters of a motor of the surgical instrument of FIG. 24, in accordance with at least one aspect of the present disclosure.

Referring to FIG. 25, a logic flow diagram of a process 5050 depicts a control program or a logic configuration for adjusting operational parameters of a motor 5001, for example, of the surgical instrument 5002. In at least one example, the process 5050 is executed by a control circuit 1210 (FIG. 27) that includes a processor 1214 and a memory 1212 storing a set of computer-executable instructions that, when executed by the processor 1214, cause the processor 1214 to perform of the process 5050. In certain examples, a set of computer-executable instructions, stored in the memory 1212 may cause the processor 1214 to perform discrete portions of the process 5050. Although the process 5050 is described as being executed by a control circuit 1210, this is merely for brevity, and it should be understood that the process 5050 and other processes described herein, or portions thereof, can be executed by circuitry that can include a variety of hardware and/or software components and may be located in or associated with various suitable systems such as, for example, combinational logic circuits or sequential logic circuits.

In various aspects, the process 5050 includes reading 5051 an internal component identification information from an RFID tag 5021 by an RFID scanner 5022, for example. In at least one example, the internal component is a motor assembly 5000, a motor 5001, a gearbox 5003, or a power source 5014. The process 5050 further determines 5052 whether an algorithm adjustment parameter is included with the internal component identification information. If so, the process 5050 adjusts 5053 a control algorithm associated with the internal component in accordance with the received algorithm adjustment parameter. If an algorithm adjustment parameter is included, the process 5050 uses 5054 the internal component identification information to retrieve an algorithm adjustment parameter, or select a suitable control algorithm, for the internal component based on a database or look-up table of internal component identification information and corresponding algorithm adjustment parameters, or control algorithms.

Many surgical instruments utilize a battery to provide the electrical power required to operate a surgical instrument. Such batteries can include, for example, a primary cell/non-rechargeable battery such as an alkaline battery or a lithium battery, or a secondary cell/rechargeable battery such as a nickel metal hydride battery or a lithium ion battery. The different types of batteries can have different materials, chemistries, sizes, electrical characteristics (e.g., nominal voltages, discharge rates, etc.), discharge efficiencies, and costs. The type of battery utilized in a given surgical instrument is typically selected based on a variety of factors such as, among other things, disposable vs. rechargeable, size, output characteristics and cost.

As battery technology continues to advance, different battery chemistries having different capacities, output characteristics, etc. continue to evolve. It is now conceivable that throughout the useful life of a given surgical instrument, different battery packs which have differing capabilities and are made by different manufacturers may be utilized at different times with the given surgical instrument. For such instances, in order to optimize the performance of the surgical instrument, it is desirable for the given surgical instrument to be able to differentiate between the different batteries.

It is also now conceivable that throughout the useful life of a given battery, the given battery may be utilized to power different surgical instruments at different times, where the power requirements of the different surgical instruments can vary. Therefore, in order to match the capability of the battery with the power requirement of a given surgical instrument, it is desirable for the battery to be able to differentiate between the different surgical instruments and to be able to adjust the electrical characteristics of the battery as needed.

Figure 29:
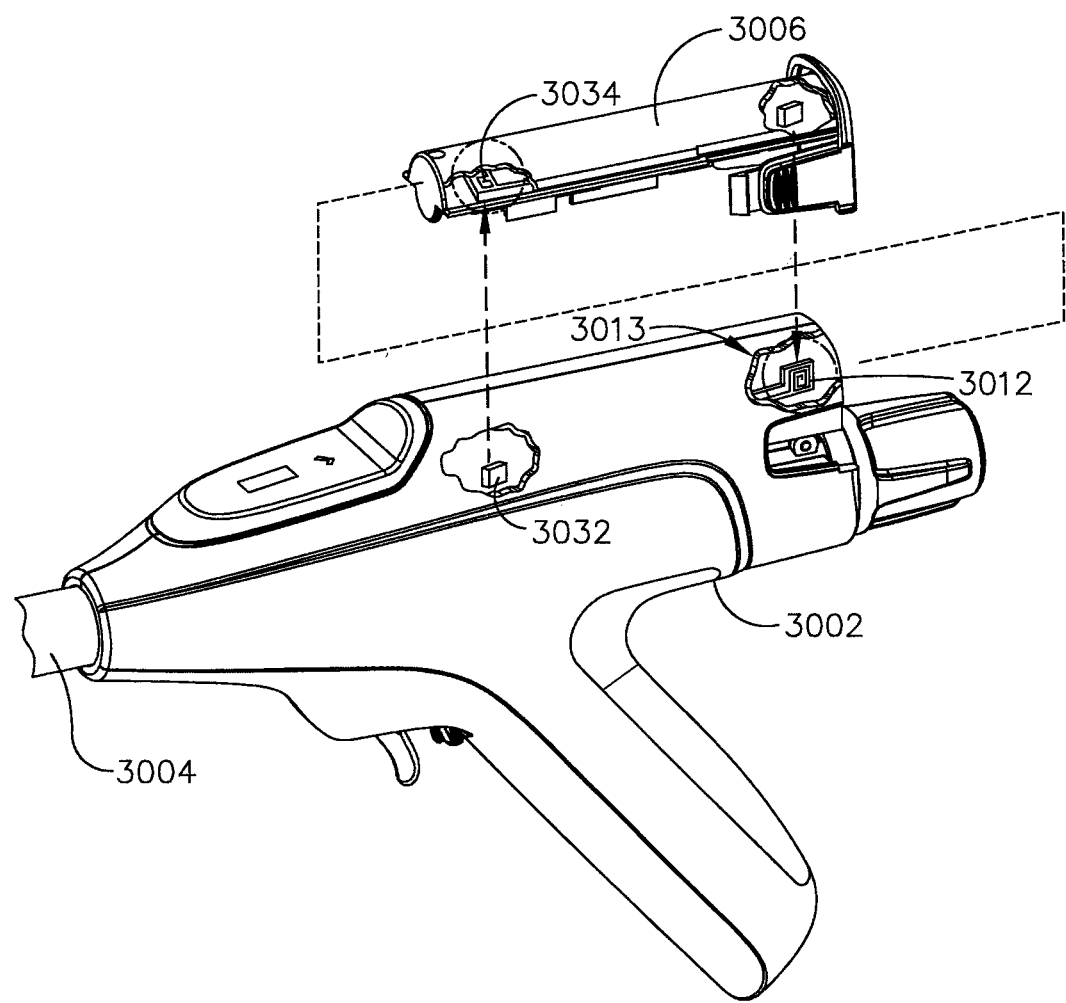
FIG. 29 illustrates a partial perspective view of a surgical instrument, in accordance with at least one aspect of the present disclosure.

FIG. 29 illustrates a partial perspective view of a surgical instrument 3000, in accordance with at least one aspect of the present disclosure. The surgical instrument 3000 is similar to the surgical circular stapling instrument 10 described hereinabove and includes a housing assembly 3002, a shaft assembly 3004, a stapling head assembly (not shown) and an anvil (not shown), where the housing assembly 3002 is similar or identical to the housing assembly 100, the shaft assembly 3004 is similar or identical to the shaft assembly 200, the stapling head assembly (not shown) is similar or identical to the stapling head assembly 300 and the anvil (not shown) is similar or identical to the anvil 400. As shown in FIG. 29, the surgical instrument 3000 is also configured to receive a battery 3006. In some aspects, the surgical instrument 3000 further includes the battery 3006. Although not shown for purposes of clarity in FIG. 29, the surgical instrument also includes an electric motor 3008 (See FIG. 30) which is similar or identical to the motor 160. The electric motor 3008 is couplable with the battery 3006, and is configured to move the anvil toward the staple head assembly to grasp tissue between the anvil and the staple head assembly, and to fire staples of the stapling head assembly into the grasped tissue. Although the surgical instrument 3000 is shown as a circular stapler, it will be appreciated that according to other aspects, the surgical instrument 3000 may be a linear stapler or other powered surgical instrument. In various aspects the adaptive surgical instrument 3194 is similar in many respects to the surgical instrument 2200, and can be assembled from one or more of the interchangeable components of the surgical instrument 2200 illustrated in FIG. 18.

The battery 3006 may be any suitable type of battery, and may include any suitable number of cells. For example, according to various aspects, the battery 3006 may include a lithium battery such as a lithium manganese oxide (Li—MnO$_2$) or CR123 battery, a lithium ion battery such as a 15270 battery, an alkaline battery such as a manganese oxide (MnO$_2$) battery, a nickel metal hydride battery, etc. In at least one aspect, the battery 3006 is in the form of a battery pack which includes a plurality of cells. For purposes of brevity, the battery 3006 will be referred to hereinafter as the battery pack 3006. The battery pack 3006 is similar to the battery pack 120 but is different in that the battery pack 3006 includes a radio-frequency identification (RFID) tag 3010 positioned within the battery pack 3006. The RFID tag 3010 stores information related to the battery pack 3006 and such information may include, for example, a battery identification number, the manufacturer/brand of batteries in the battery pack 3006, the chemistry/type of batteries (lithium, lithium-ion, etc.) in the battery pack 3006, whether the type of batteries in the battery pack 3006 are chargeable or non-rechargeable, the capacity of the battery pack 3006, the nominal voltage of the batteries in the battery pack 3006, the current draw characteristics of the batteries in the battery pack 3006, other output characteristics of the battery pack 3006, etc. The RFID tag 3010 is very compact in size (e.g., 13 mm square or less), thereby allowing for the RFID tag 3010 to be incorporated into the battery pack 3006 without unduly increasing the overall size of the battery pack 3006. According to various aspects, the RFID tag 3010 may be similar to the miniaturized RFID tag described in U.S. Pat. No. 9,171,244.

The surgical instrument 3000 is different from the surgical circular stapling instrument 10 in that the surgical instrument 3000 further includes an RFID scanner 3012. The RFID scanner 3012 is positioned within the housing assembly 3002 and is configured to read the information stored at the RFID tag 3010, where the stored information is related to the battery pack 3006. The RFID scanner 3012 is also configured to communicate data indicative of the read information to a control circuit 3014 (See FIG. 30) of the surgical instrument 3000 for processing. The RFID tag 3010 and the RFID scanner 3012 cooperate to collectively allow for the surgical instrument 3000 to be able to identify the battery pack 3006, and determine whether the battery pack 3006 is suitable for use with the surgical instrument 3000.

As illustrated in FIG. 29, the RFID scanner 3012 is positioned at a battery interface 3013 of the housing assembly 3002. The RFID tag 3010 is configured to be detected by the RFID scanner 3012 in an assembled, or at least partially assembled, configuration of the battery 3006 with the housing assembly 3002. This approach eliminates the need for a separate scanning step by tethering the detection of the RFID tag 3010 by the RFID scanner 3012 to the assembly of the battery 3006 to the housing assembly 3002. It also ensures that the detected battery 3006 is the one ultimately assembled with the housing assembly 3002. In various aspects, the detection range of an RFID scanner 3012 is limited such that it is only able to detect a corresponding RFID tag 3010 in an assembled, or at least partially assembled, configuration of the battery 3006 with the housing assembly 3002.

Similarly, the RFID tag 3032 is positioned at the battery interface 3013 of the housing assembly 3002. The RFID tag 3032 is configured to be detected by the RFID scanner 3034 in an assembled, or at least partially assembled, configuration of the battery 3006 with the housing assembly 3002. In various aspects, the detection range of an RFID scanner 3034 is limited such that it is only able to detect a corresponding RFID tag 3032 in an assembled, or at least partially assembled, configuration of the battery 3006 with the housing assembly 3002.

In various aspects, as illustrated in FIG. 29, the RFID scanner 3034 and the RFID tag 3010 are configured to be aligned with the RFID tag 3032 and the RFID scanner 3012, respectively, in the assembled configuration. The alignment, once achieved, brings the RFID tag 3010 within the detection range of the RFID scanner 3012, and the RFID tag 3032 within the detection range of the RFID scanner 3034.

Figure 30:
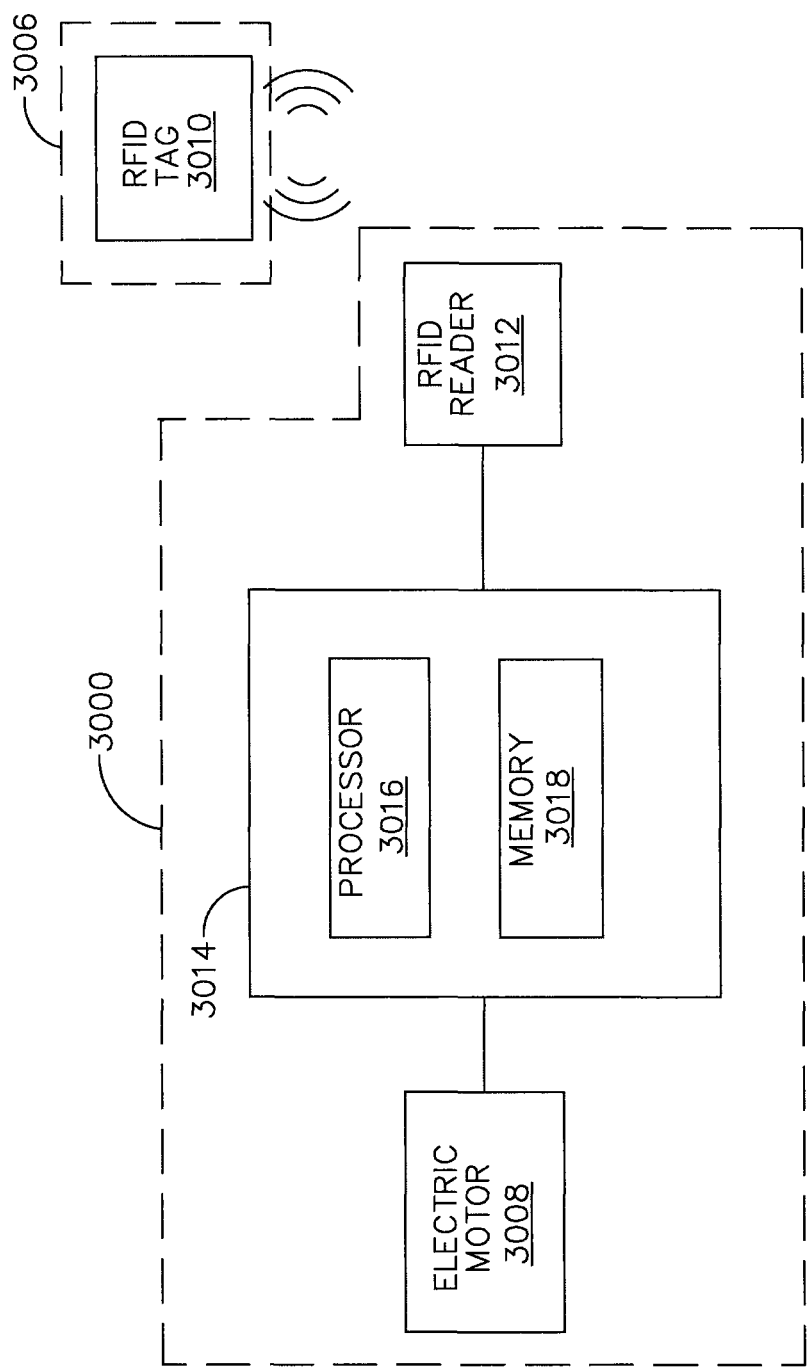
FIG. 30 illustrates a control circuit of the surgical instrument of FIG. 29, in accordance with at least one aspect of the present disclosure.

FIG. 30 illustrates a control circuit 3014 of the surgical instrument 3000, in accordance with at least one aspect of the present disclosure. The control circuit 3014 is communicably connected to the RFID scanner 3012 and is similar to the control circuit 1210 in that the control circuit 3014 includes a processor 3016 and a storage medium such as, for example, a memory 3018. The memory 3018 stores program instructions for performing various processes such as, for example, determining whether the battery pack 3006 is compatible for use with the surgical instrument 3000 (e.g., battery compatibility verification). The program instructions, when executed by the processor 3016, cause the processor 3016 to verify the compatibility of the battery pack 3006 with the surgical instrument 3000 by comparing the information received from the RFID tag 3010 to information stored in the memory 3018. The information stored at the memory 3018 may be in the form of, for example, a compatibility database or a lookup table which includes information regarding identification information for batteries which can be utilized with the surgical instrument 3000, output characteristics of batteries which can be utilized with the surgical instrument 3000, etc. According to various aspects, the control circuit 3014 is communicably connected to other processors and/or memories of the surgical instrument 3000 and/or a surgical hub system, and the described functionality of the control circuit 3014 can be realized with the other processors and/or memories of the surgical instrument 3000 and/or the surgical hub system. The surgical hub system is described in U.S. patent application Ser. No. 16/209,395, titled METHOD OF HUB COMMUNICATION, and filed Dec. 4, 2018, the entire content of which is hereby incorporated by reference herein.

Figure 31:
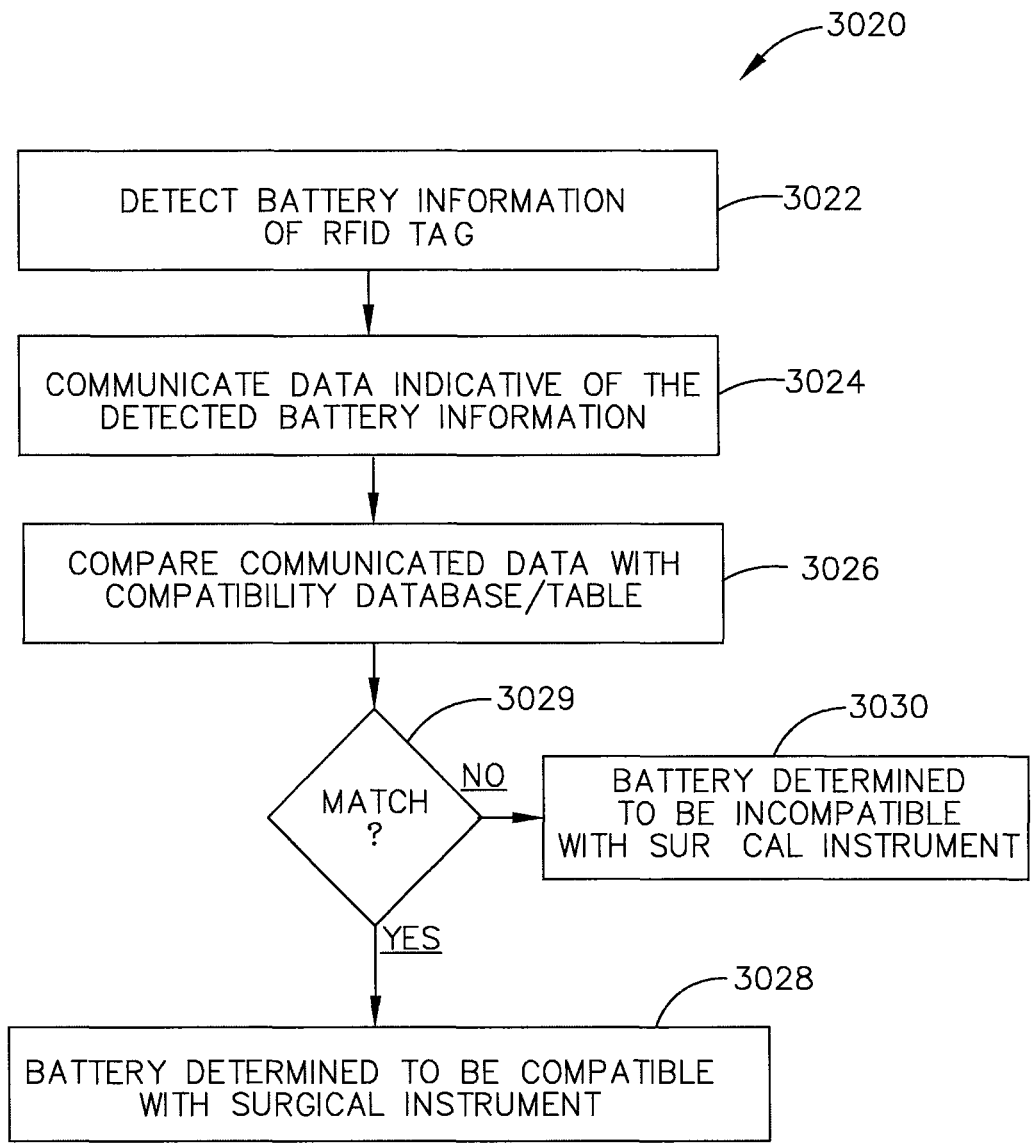
FIG. 31 illustrates a logic flow diagram of a process depicting a control program or a logic configuration for operating the surgical instrument of FIG. 29, in accordance with at least one aspect of the present disclosure.

FIG. 31 illustrates a logic flow diagram of a process 3020 depicting a control program or a logic configuration for operating the surgical instrument 3000, in accordance with at least one aspect of the present disclosure. In at least one example, the process 3020 is executed by the control circuit 3014. In certain examples, a set of computer-executable instructions, stored in the memory 3018 of the control circuit 3014, may cause the processor 3016 of the control circuit 3014 to perform discrete operations of the process 3020. Although the process 3020 is being described in the context of being executed by the control circuit 3014, it will be understood that the process 3020 and other processes described herein, or portions thereof, can be executed by circuitry that can include a variety of hardware and/or software components and may be located in or associated with various suitable systems such as, for example, combinational logic circuits or sequential logic circuits.

As illustrated in FIG. 31, the process 3020 includes detecting 3022 battery information of the RFID tag 3010 via the RFID scanner 3012. In various aspects, the RFID scanner 3012 can perform the detection whenever the battery pack 3006 is brought in close proximity to the surgical instrument 3000. In other instances, the RFID scanner 3012 performs the detection after the battery pack 3006 is inserted into the housing assembly 3002 of the surgical instrument 3000. The RFID scanner 3012 thereafter communicates 3024 data which is indicative of the detected battery information of the RFID tag 3010 to the control circuit 3014. The communication of the data may be realized by wired communication or by wireless communication. The processor 3016 of the control circuit 3014 thereafter checks/compares 3026 the communicated data against a battery/surgical instrument compatibility database or lookup table which may be stored in the memory 3018 of the control circuit 3014. If the check/comparison 3026 results in a match 3029, the processor 3016 determines 3028 the battery pack 3006 is compatible for use with the surgical instrument 3000, and a user of the surgical instrument 3000 may be alerted to the compatibility by a visual or audible indicator such as, for example, a light emitting diode or a speaker. However, if the check/comparison 3026 does not result in a match 3029, the processor 3016 determines 3030 the battery pack 3006 is incompatible for use with the surgical instrument 3000, and a user of the surgical instrument 3000 may be alerted to the incompatibility by a visual or audible indicator such as, for example, a light emitting diode or a speaker. Additionally, in at least one aspect, when the processor 3016 determines that the battery pack 3006 is incompatible with the surgical instrument 3000, the processor 3016 may communicate a signal or instruction which operates to cause one or more functionalities of the surgical instrument 3000 to be electrically locked out (e.g., by preventing power being applied to the electric motor 3008 of the surgical instrument 3000). Although the process 3020 was described in the context of a given battery pack 3006, it will be appreciated that the above-described process 3020 may be repeated any number of times for any number of different battery packs.

Returning to FIG. 29, in at least one aspect, the surgical instrument 3000 further includes an RFID tag 3032 positioned within the housing assembly 3002, and the battery pack 3006 further includes an RFID scanner 3034 positioned within the battery pack 3006. The RFID tag 3032 is similar to the RFID tag 3010, and stores information related to the surgical instrument 3000. Such information may include, for example, a surgical instrument identification number, the manufacturer/brand of the surgical instrument, the type of surgical instrument (circular stapler, linear stapler, grasper, etc.), type of motor in the surgical device (brushed, brushless), performance capabilities of the surgical instrument, control algorithms residing at the surgical instrument, etc. The RFID scanner 3034 is similar to the RFID scanner 3012, and is configured to read the information stored at the RFID tag 3032, where the stored information is related to the surgical instrument 3000, and communicate data which is indicative of the read information to a control circuit 3040 (See FIG. 32) of the battery pack 3006 for processing. The RFID tag 3032 and the RFID scanner 3034 collectively allow for the battery pack 3006 to be able to identify the surgical instrument 3000, and verify that the surgical instrument 3000 is suitable for use with the battery pack 3006.

Figure 32:
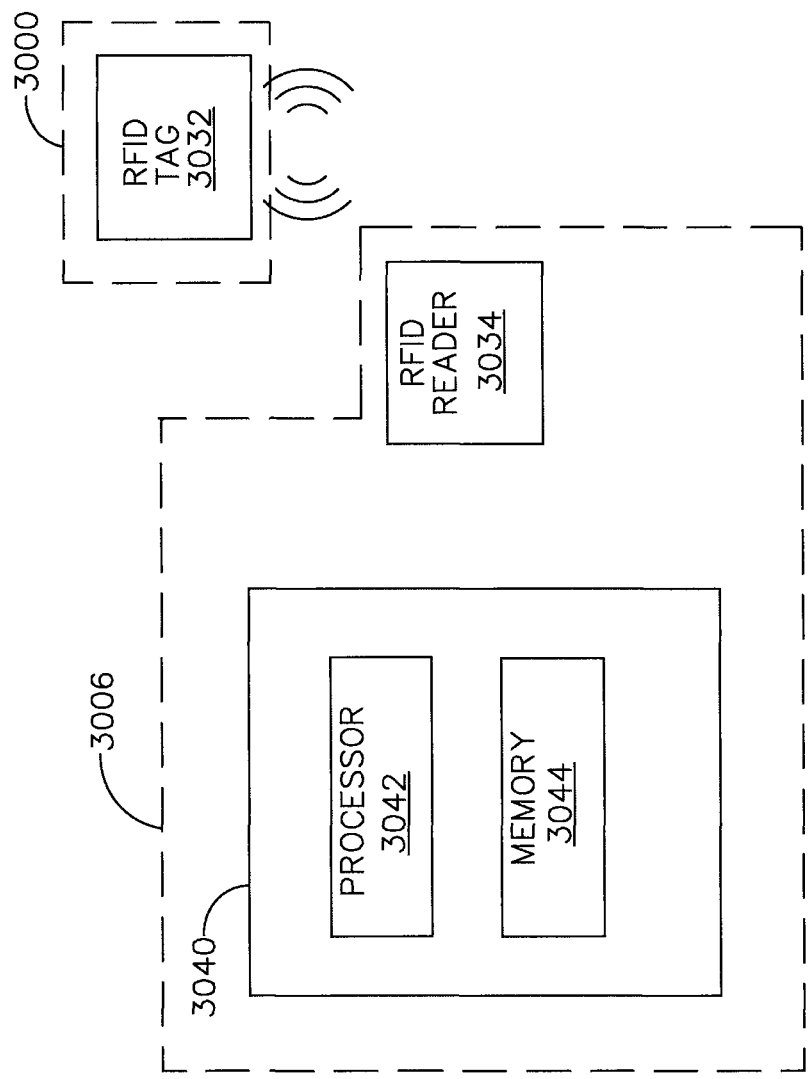
FIG. 32 illustrates a control circuit of the battery pack, in accordance with at least one aspect of the present disclosure.

FIG. 32 illustrates a control circuit 3040 of the battery pack 3006, in accordance with at least one aspect of the present disclosure. The control circuit 3040 is communicably connected to the RFID scanner 3034 and is similar to the control circuit 3014 in that the control circuit 3040 includes a processor 3042 and a storage medium such as, for example, a memory 3044. The memory 3044 stores program instructions for performing various processes such as, for example, determining whether the surgical instrument 3000 is compatible for use with the battery pack 3006 (e.g., surgical instrument compatibility verification). The program instructions, when executed by the processor 3042, cause the processor 3044 to verify the compatibility of the surgical instrument 3000 with the battery pack 3006 by comparing the information received from the RFID tag 3032 to information stored in the memory 3044. The information stored at the memory 3044 may be in the form of, for example, a compatibility database or a lookup table which includes information regarding identification information for various surgical instruments, power requirements of the various surgical instruments, performance parameters of the various surgical instruments, etc. The process executed by the control circuit 3040 to verify the compatibility of the surgical instrument 3000 with the battery pack 3006 is analogous to the process 3020 utilized by the control circuit 3014 to verify the compatibility of the battery pack 3006 with the surgical instrument 3000. For example, when the processor 3042 determines that the surgical instrument 3000 is incompatible with the battery pack 3006, the processor 3042 may communicate a signal or instruction which operates to electrically lockout the battery pack 3006 and prevent the battery pack 3006 from providing power to the surgical instrument 3000.

In view of the above-described aspects, it will be appreciated that a number of different batteries can be compatible with the surgical instrument 3000. Stated differently, the surgical instrument 3000 can be compatible with a number of different batteries. When the surgical instrument 3000 includes the RFID scanner 3012 and the RFID tag 3032, and various batteries include a RFID tag and a RFID scanner with functionality similar or identical to those of the RFID tag 3010 and the RFID scanner 3034, the surgical instrument 3000 can identify a plurality of different batteries and determine the compatibility of each of those batteries with the surgical instrument 3000. Similarly, when the battery pack 3006 includes the RFID tag 3010 and the RFID scanner 3034, and various surgical instruments include a RFID tag and a RFID scanner with functionality similar or identical to those of the RFID tag 3032 and the RFID scanner 3032, the battery pack 3006 can identify a plurality of different surgical instruments and determine the compatibility of each of those surgical instruments with the battery pack 3006.

Figure 33:
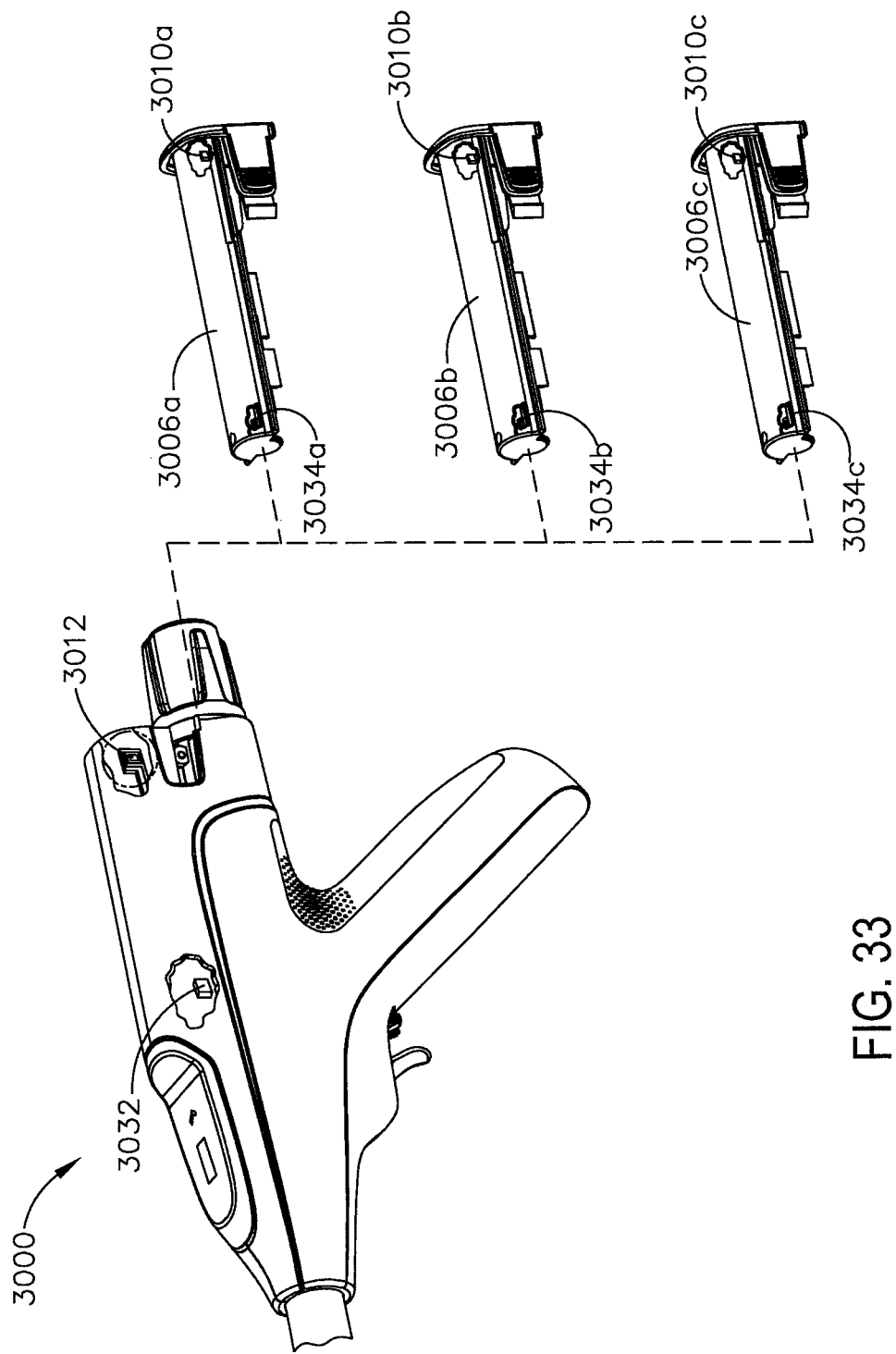
FIG. 33 illustrates the compatibility of the surgical instrument of FIG. 29 with a plurality of different battery packs, in accordance with at least one aspect of the present disclosure.

FIG. 33 illustrates the compatibility of the surgical instrument 3000 with a plurality of different battery packs 3006a, 3006b, 3006c, in accordance with at least one aspect of the present disclosure. The battery pack 3006a includes a RFID tag 3010a and a RFID scanner 3034a positioned therein, the battery pack 3006b includes a RFID tag 3010b and a RFID scanner 3034b positioned therein, and the battery pack 3006c includes a RFID tag 3010c and a RFID scanner 3034c positioned therein. According to various aspects, the battery pack 3006a includes a CR123/lithium battery, the battery pack 3006b includes a 15270/lithium ion battery, and the battery pack 3006c includes a battery other than a lithium battery or a lithium ion battery. When any one of the battery packs 3006a, 3006b, 3006c is in proximity to or is received by the surgical instrument 3000, as described above, the respective RFID tag/RFID scanner pairs allow for (1) the surgical instrument 3000 to be able to identify the applicable battery pack 3006a, 3006b, 3006c, and determine whether the applicable battery pack 3006a, 3006b, 3006c is compatible with/suitable for use with the surgical instrument 3000 and (2) any of the battery packs 3006a, 3006b, 3006c to be able to identify the surgical instrument 3000 and determine whether the surgical instrument 3000 is compatible with/suitable for use with the applicable battery pack 3006a, 3006b, 3006c.

Figure 34:
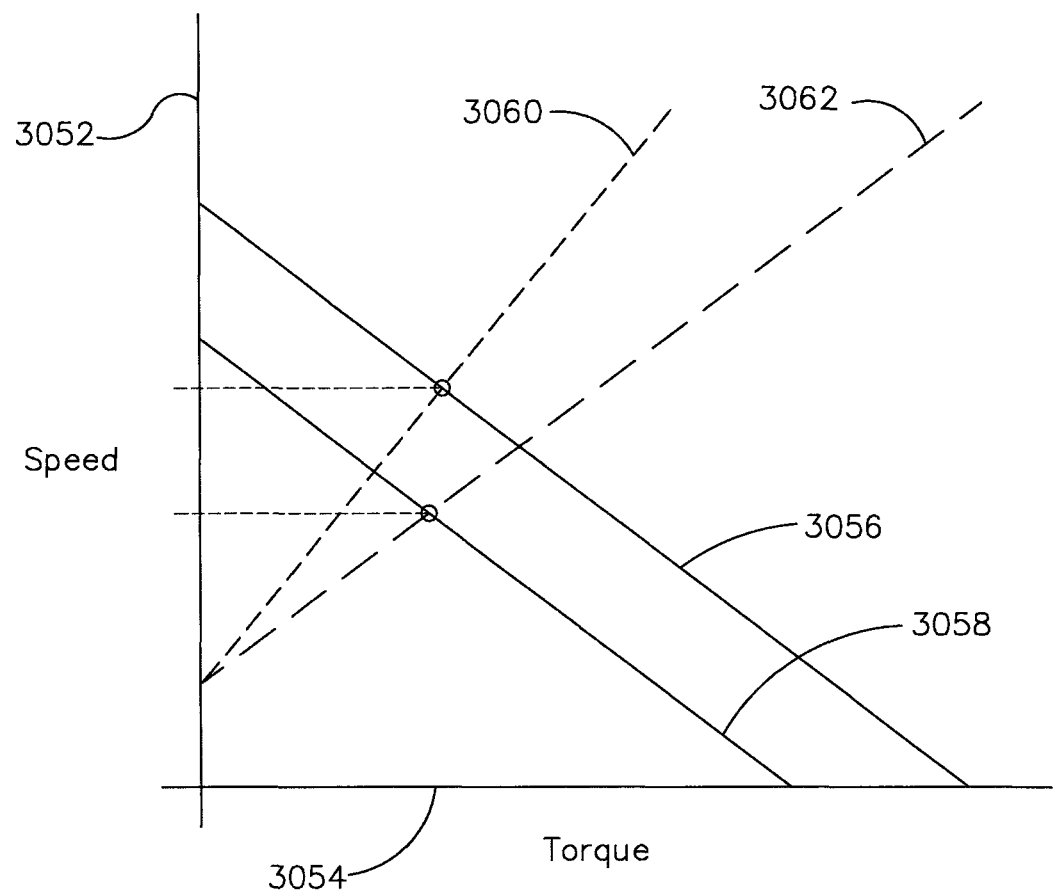
FIG. 34 illustrates a graph which shows various motor torque/speed/current relationships for the surgical instrument of FIG. 29 when powered by different battery packs, in accordance with at least one aspect of the present disclosure.

Different batteries can have different chemistries, different capacities, different output characteristics, different operational abilities, etc., and different surgical instruments can have different power requirements. FIG. 34 illustrates a graph 3050 which shows various motor torque/speed/current relationships for the surgical instrument 3000 when powered by different battery packs, in accordance with at least one aspect of the present disclosure. For the graph 3050, units of speed (or current) are shown along the vertical axis 3052 and units of torque are shown along the horizontal axis 3054. The solid line 3056 represents the torque-speed relationship for a lithium ion/15270 battery, where the left end of the solid line 3056 represents the no load speed and the right end of the solid line 3056 represents the stall torque. The solid line 3058 represents the torque-speed relationship for a lithium/CR-123 battery, where the left end of the solid line 3058 represents the no load speed and the right end of the solid line 3058 represents the stall torque. In general, the torque is inversely proportional to the speed of an output shaft of the electric motor 3008 of the surgical instrument 3000. In other words, the greater the speed—the lower the torque (or the greater the torque, the lower the speed).

The dashed line 3060 represents the current drawn from a lithium ion/15270 battery, where the left end of the dashed line 3060 represents the no load current and the right end of the dashed line 3060 represents the stall current. The dashed line 3062 represents the current drawn from a lithium/CR-123 battery, where the left end of the dashed line 3062 represents the no load current and the right end of the dashed line 3062 represents the stall current. For both batteries, the no-load current is greater than zero because it takes a certain amount of current to overcome the internal friction of the electric motor 3008. In general, when an external load is applied, the current drawn from the respective batteries increases to produce the torque required to match it (the torque is proportional to the applied current), and the speed of the electric motor 3008 is reduced. As the external bad is further increased, the speed of the electric motor 3008 is further reduced, eventually reaching stall. In view of the above, it will be appreciated that the motor torque/speed/current relationships can vary appreciably based on the specific battery pack utilized to power the surgical instrument 3000.

Figure 35:
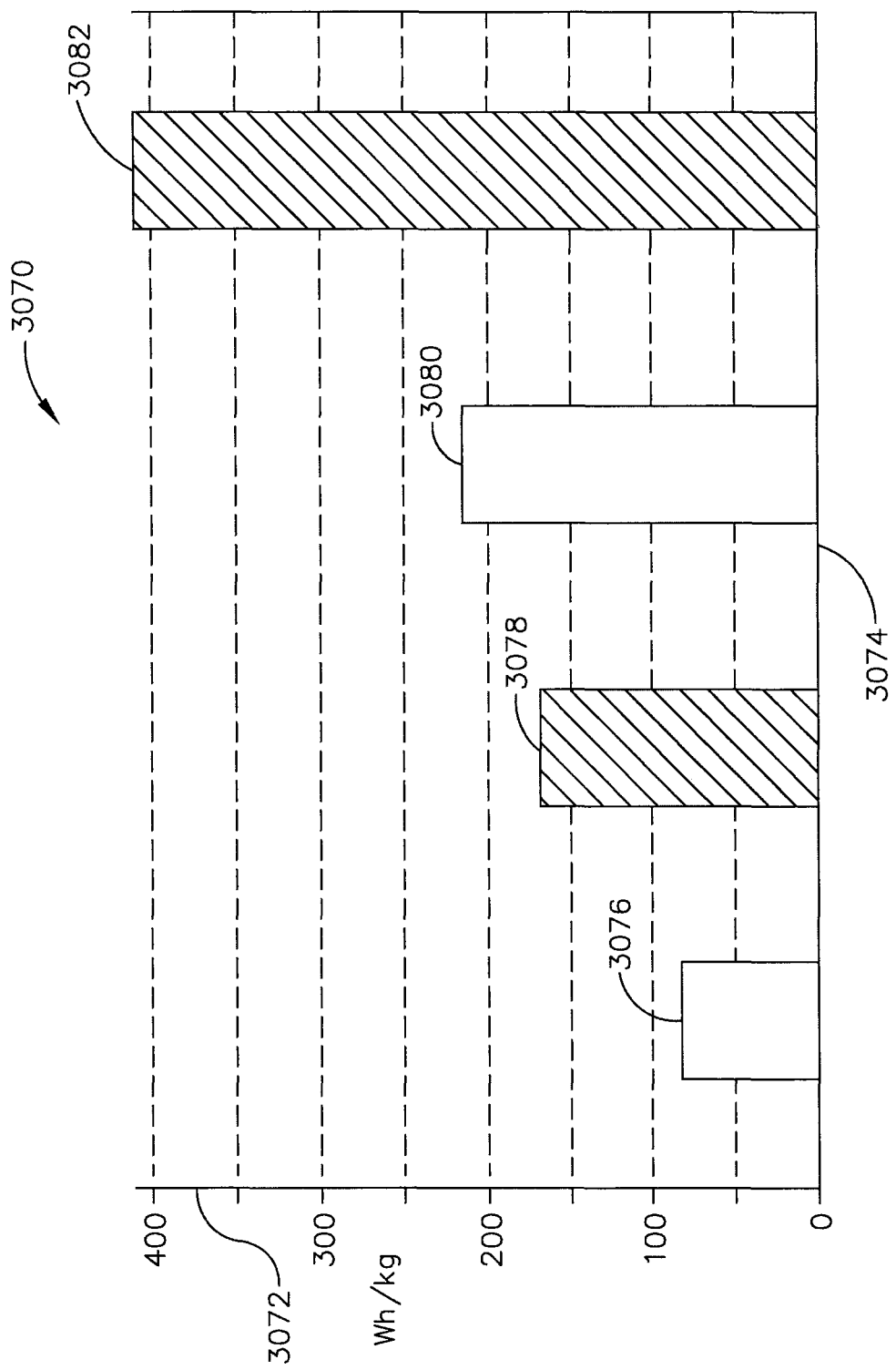
FIG. 35 illustrates a bar graph which shows various energy densities for different battery packs which can be utilized with the surgical instrument of FIG. 29, in accordance with at least one aspect of the present disclosure.
Figure 36:
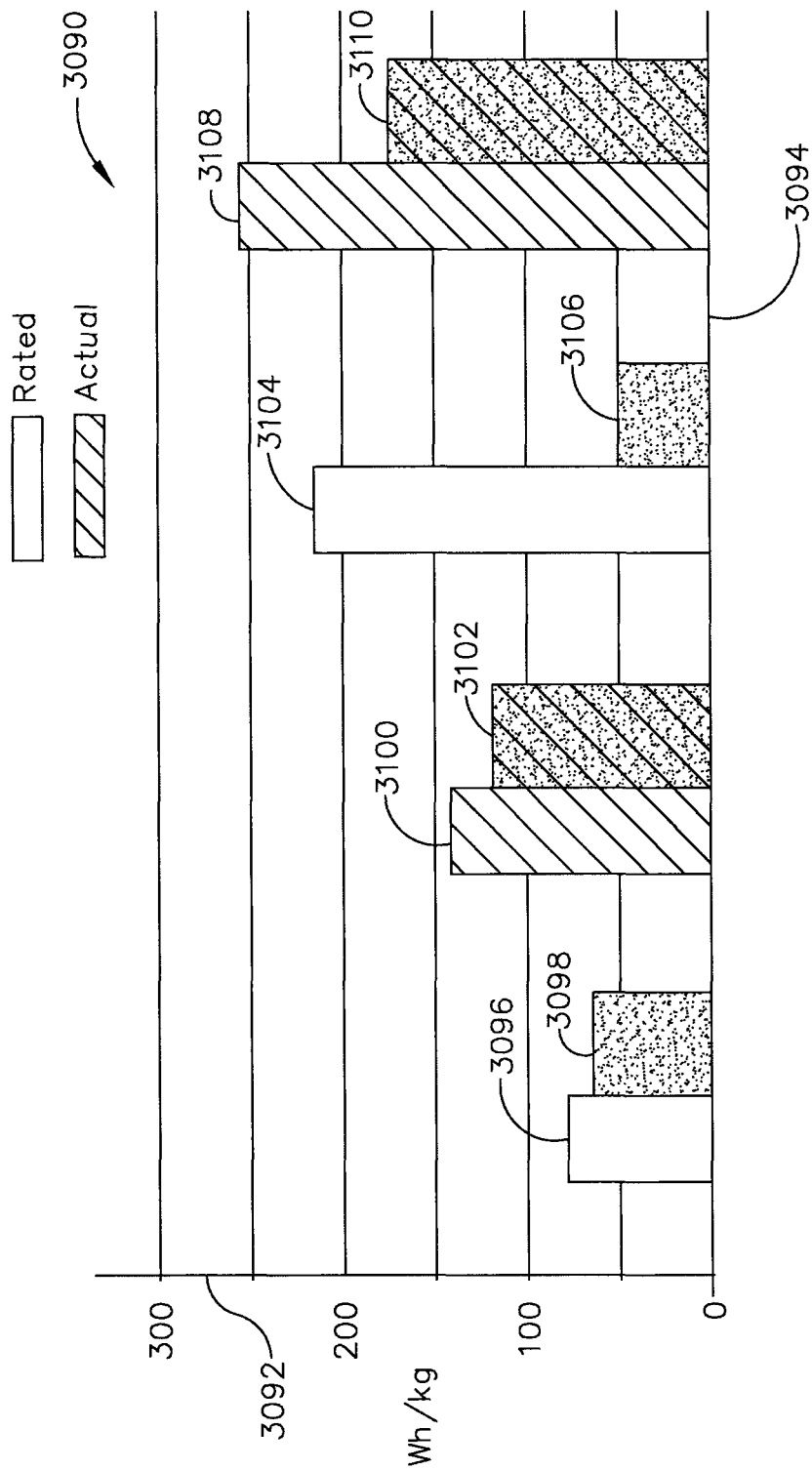
FIG. 36 illustrates a bar graph which shows comparisons of actual energy densities vs. rated energy densities for different battery packs which can be utilized with the surgical instrument of FIG. 29, in accordance with at least one aspect of the present disclosure.

FIG. 35 illustrates a bar graph 3070 which shows various energy densities for different battery packs which can be utilized with the surgical instrument 3000, in accordance with at least one aspect of the present disclosure. The respective energy densities are representative of the amounts of energy stored in the different battery packs per unit mass. For the graph 3070, watt-hours per kilogram of mass (Wh/Kg) are shown along the vertical axis 3072 and the different battery packs are shown along the horizontal axis 3074. The bar 3076 representative of the energy density of a nickel metal hydride rechargeable battery is shown as being approximately 80 Wh/Kg, the bar 3078 representative of the energy density of a lithium ion rechargeable battery is shown as being approximately 160 Wh/Kg, the bar 3080 representative of the energy density of an alkaline manganese oxide ($MnO_2$) battery is shown as being approximately 205 Wh/Kg, and the bar 3082 representative of the energy density of a primary/disposable lithium battery is shown as being approximately 400 Wh/Kg. In view of the above, it will be appreciated that the energy densities of the various battery packs which can be utilized with the surgical instrument 3000 can vary appreciably, FIG. 36 illustrates a bar graph 3090 which shows comparisons of actual energy densities vs. rated energy densities for different battery packs which can be utilized with the surgical instrument 3000, in accordance with at least one aspect of the present disclosure. For the graph 3090, watt-hours per kilogram of mass (Wh/Kg) are shown along the vertical axis 3092 and the different battery packs are shown along the horizontal axis 3094. For each different type of battery, the actual energy density is less than the rated energy density. In some instances such as for a nickel metal hydride rechargeable battery or a lithium ion rechargeable battery, the actual energy density is only approximately 15%-20% less than the rated energy density. For a primary/disposable lithium battery, the actual energy density is approximately 30% less than the rated energy density. For the alkaline manganese oxide ($MnO_2$) battery, the actual energy density is approximately 75% less than the rated energy density. More specifically, for a nickel metal hydride rechargeable battery, the bar 3096 representative of the rated energy density is shown as being approximately 75 Wh/Kg and the bar 3098 representative of the actual energy density is shown as being approximately 60 Wh/Kg. For a primary/disposable lithium ion battery, the bar 3100 representative of the rated energy density is shown as being approximately 140 Wh/Kg and the bar 3102 representative of the actual energy density is shown as being approximately 120 Wh/Kg. For the alkaline manganese oxide ($MnO_2$) battery, the bar 3104 representative of the rated energy density is shown as being approximately 210 Wh/Kg and the bar 3106 representative of the actual energy density is shown as being approximately 50 Wh/Kg. For the primary/disposable lithium battery, the bar 3108 representative of the rated energy density is shown as being approximately 250 Wh/Kg and the bar 3110 representative of the actual energy density is shown as being approximately 170 Wh/Kg. In view of the above, it will be appreciated that the calculated/rated energy density of a given battery which can be utilized with the surgical instrument 3000 can vary appreciably.

Figure 37:
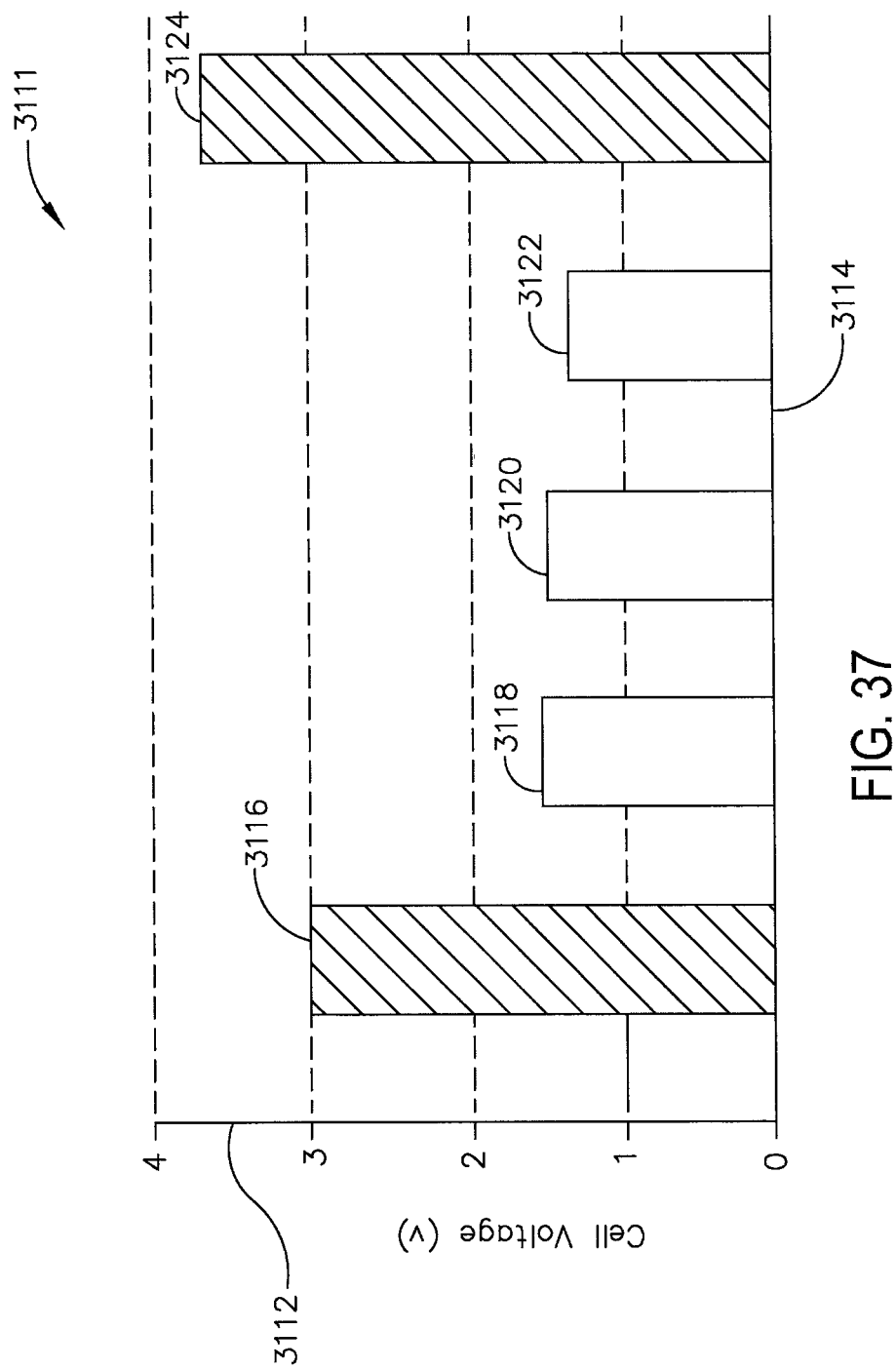
FIG. 37 illustrates a bar graph which shows nominal voltages of different battery packs which can be utilized with the surgical instrument of FIG. 29, in accordance with at least one aspect of the present disclosure.

FIG. 37 illustrates a bar graph 3111 which shows nominal voltages of different battery packs which can be utilized with the surgical instrument 3000, in accordance with at least one aspect of the present disclosure. For the graph 3111, units of cell voltage (V) are shown along the vertical axis 3112 and the different battery packs are shown along the horizontal axis 3114. For a primary/disposable lithium battery, the bar 3116 representative of the nominal cell voltage is shown as being approximately 3.0 volts. For a silver oxide battery, the bar 3118 representative of the nominal cell voltage is shown as being approximately 1.6 volts. For an alkaline manganese oxide ($MnO_2$) battery, the bar 3120 representative of the nominal cell voltage is shown as being approximately 1.5 volts. For a nickel metal hydride rechargeable battery, the bar 3122 representative of the nominal cell voltage is shown as being approximately 1.3 volts. For a lithium ion rechargeable battery, the bar 3124 representative of the nominal cell voltage is shown as being approximately 3.8 volts. In view of the above, it will be appreciated that the nominal voltages of different battery cells which can be utilized with the surgical instrument 3000 can vary appreciably.

Different brands of batteries, which can be made by different companies, can have different capacities (e.g., Ampere-Hours) for a given discharge rate (e.g., current/hour). For example, different brands of CR-123A/CR17335 batteries can have different capacities for given discharge rates. Different capacities for given discharge rates for different brands of CR-123A/CR17335 batteries are set forth in Table B1 below, where the respective discharge currents will discharge the respective batteries in one hour.

TABLE B1

Figure 38:
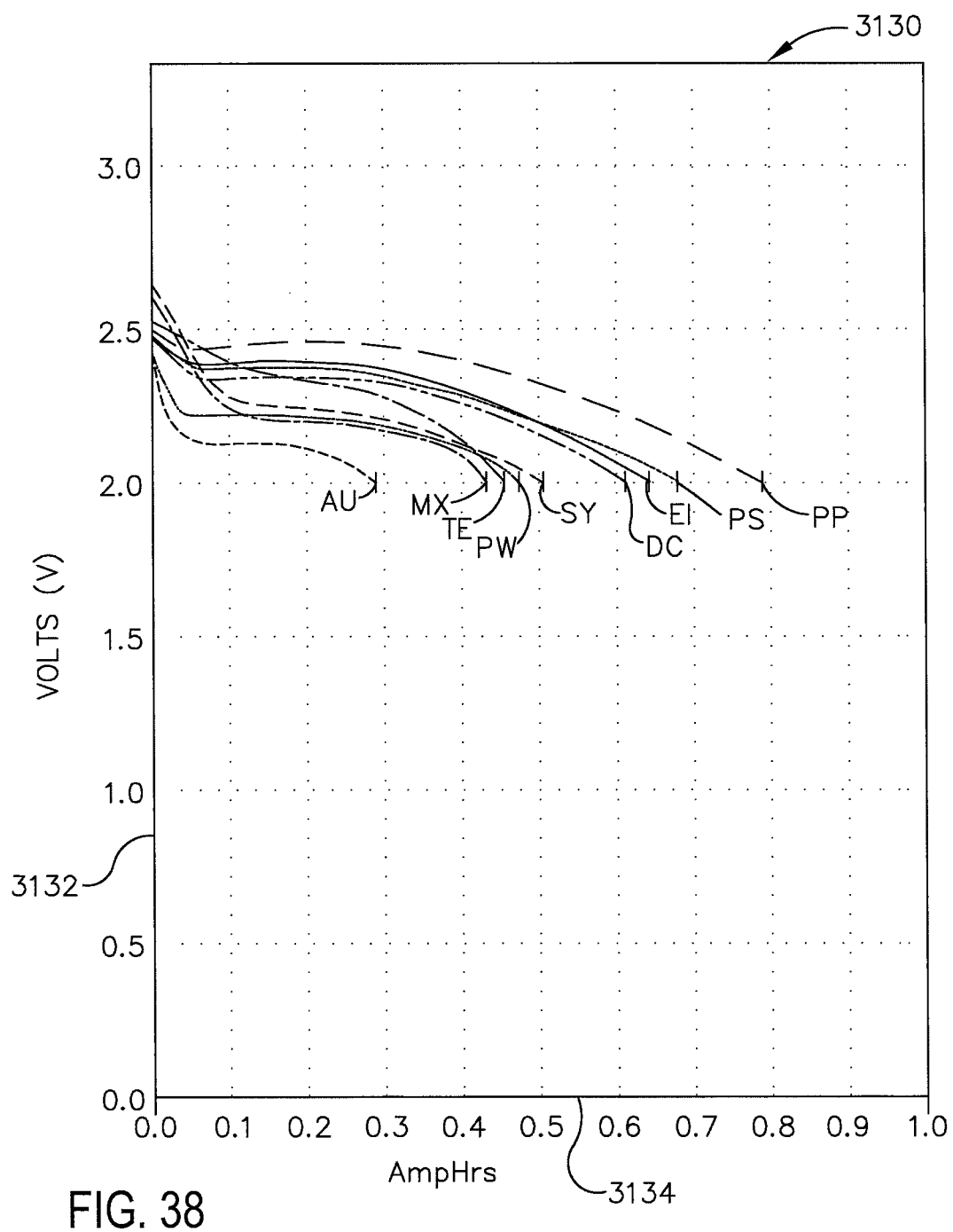
FIG. 38 illustrates a graph which shows discharge curves of different battery packs which can be utilized with the surgical instrument of FIG. 29, in accordance with at least one aspect of the present disclosure.

| Brand Name | Code Used in FIG. 38 | Amp-Hrs @ 100 mA Discharge Current | Amp-Hrs @ 700 mA Discharge Current | Amp-Hrs @ 1500 mA Discharge Current | Amp-Hrs @ 2200 mA Discharge Current |
|---|---|---|---|---|---|
| Autec | AU | 0.616 | 0.688 | 0.439 | 0.625 |
| Duracell | DC | | 1.234 | 0.632 | 0.730 |
| Energizer | EI | | 1.210 | 0.655 | 0.700 |
| Maxell | MX | | 1.100 | 0.466 | 0.543 |
| Panasonic | PS | | 1.260 | 0.692 | 0.692 |
| Powerizer | PW | | 0.880 | 0.499 | 0.502 |
| PowPower | PP | | 1.040 | 0.801 | 0.817 |
| Sanyo | SY | | 1.080 | 0.487 | 0.557 |
| Tenergy | TE | | 0.900 | 0.488 | 0.626 |

As shown in Table B1, the capacity of a battery can vary based on the discharge current. For example, for the Autec battery, the capacity is shown in Table B1 as being 0.616 Amp-Hrs at a 100 mA discharge current, 0.688 Amp-Hrs at a 700 mA discharge current, 0.439 Amp-Hrs at a 1500 mA discharge current and 0.625 AmpHrs at a 2200 mA discharge current. As also shown in Table B1, at a discharge current of 700MA, the capacities of the different brands of CR-123A/CR17335 batteries can vary from a low of 0.688 Amp-Hrs for the Autec battery to a high of 1.260 Amp-Hrs for the Panasonic battery. At a discharge current of 1500 mA, the capacities of the different brands of CR-123A/CR17335 batteries can vary from a low of 0.439 Amp-Hrs for the Autec brand to a high of 0.801 Amp-Hrs for the PowPower brand. At a discharge current of 2200 mA, the capacities of the different brands of CR-123A/CR17335 batteries can vary from a low of 0.543 Amp-Hrs for the Maxell brand to a high of 0.817 Amp-Hrs for the PowPower brand. In view of the above, it will be appreciated that the capacities of different batteries which can be utilized with the surgical instrument 3000 can vary appreciably based on both the manufacturer/brand of the battery and the discharge current of the battery.

FIG. 38 illustrates a graph 3130 which shows discharge curves of different CR123A/CR17335 batteries which can be utilized with the surgical instrument 3000, in accordance with at least one aspect of the present disclosure. For the graph 3130, units of voltage (Volts) are shown along the vertical axis 3132, units of energy charge in Ampere-Hours (Amp-Hrs) are shown along the horizontal axis 3134, and the respective discharge curves are labeled with the two-letter codes listed in Table B1 (e.g., AU, DC, EI, MX, PS, PW, PP, SY, TE) for the different brands of batteries. The respective discharge curves correspond to the different brands of CR-123A/CR17335 batteries listed in Table B1 above, and are based on a discharge current of 1500 mA. As shown in FIG. 38, each brand of CR-123A/CR17335 battery can have its own characteristic nominal voltage and its own characteristic discharge curve. Stated differently, each brand of CR-123A/CR17335 battery can provide different voltages for different amounts of time. For example, the Autec battery (Au) is shown as having provided 0.3 Amp-Hrs of energy charge before its voltage drops to 2.0 volts whereas the PowPower battery (PP) is shown as having provided approximately 0.8 Amp-Hrs of energy charge before its voltage drops to 2.0 volts. In view of the above, it will be appreciated that the energy charge provided by different batteries which can be utilized with the surgical instrument 3000 can vary appreciably.

Figure 39:
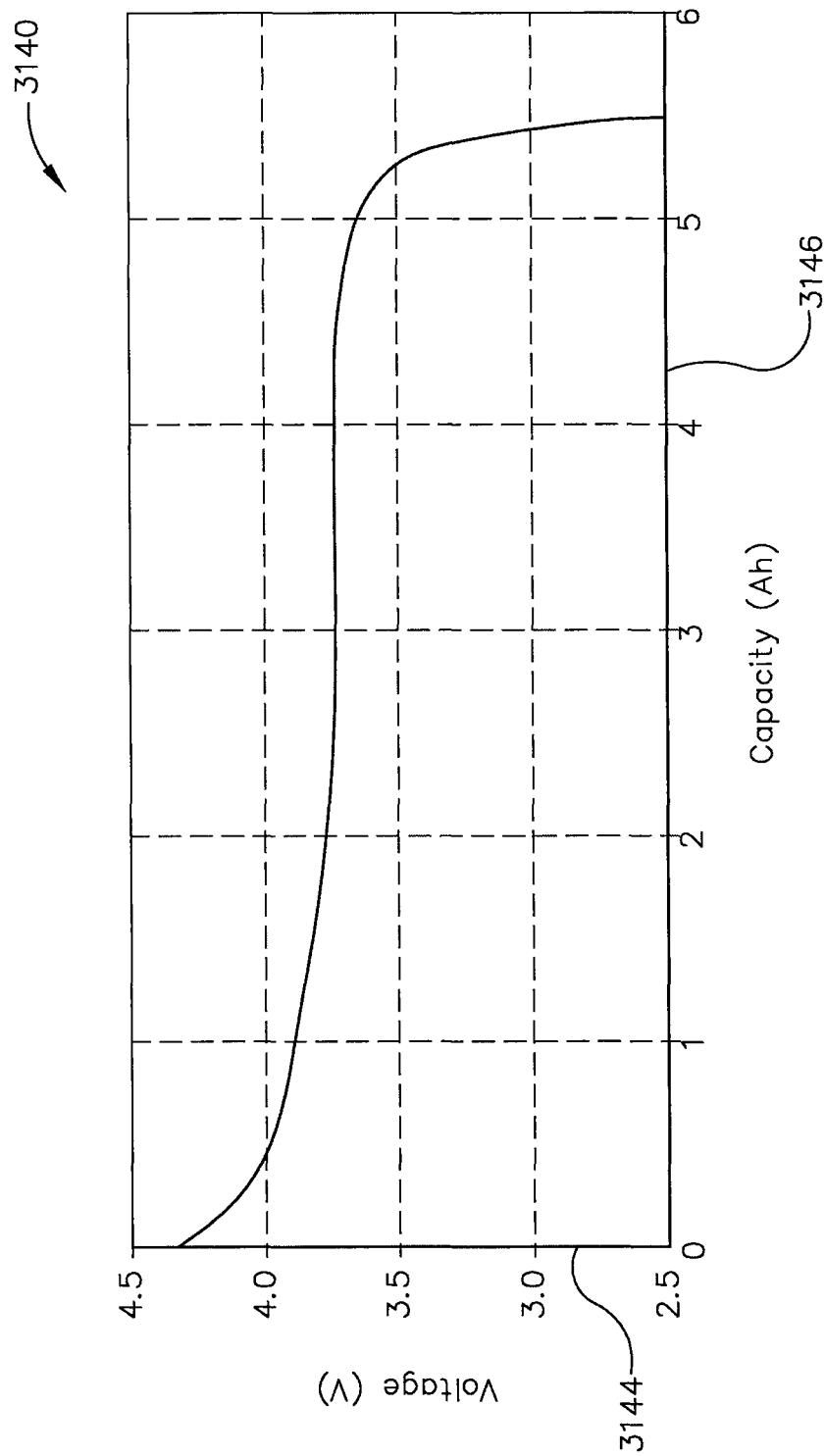
FIG. 39 illustrates a graph which shows a discharge curve for a lithium-Ion battery which can be utilized with the surgical instrument of FIG. 29, in accordance with at least one aspect of the present disclosure.

FIG. 39 illustrates a graph 3140 which shows a discharge curve 3142 for a lithium-ion battery which can be utilized with the surgical instrument 3000, in accordance with at least one aspect of the present disclosure. For the graph 3140, units of voltage (Volts) are shown along the vertical axis 3144 and units of capacity (Ah) are shown along the horizontal axis 3146. As shown in FIG. 39, the nominal voltage of the lithium-ion battery is approximately 4.3 volts, the lithium-ion battery provides a voltage of at least approximately 3.75 volts until the lithium-ion battery has discharged approximately 5.0 Ah of capacity, then the voltage provided by the lithium-ion battery drops significantly thereafter until the lithium-ion battery has fully discharged approximately 5.5 Ah of its capacity.

Figure 40:
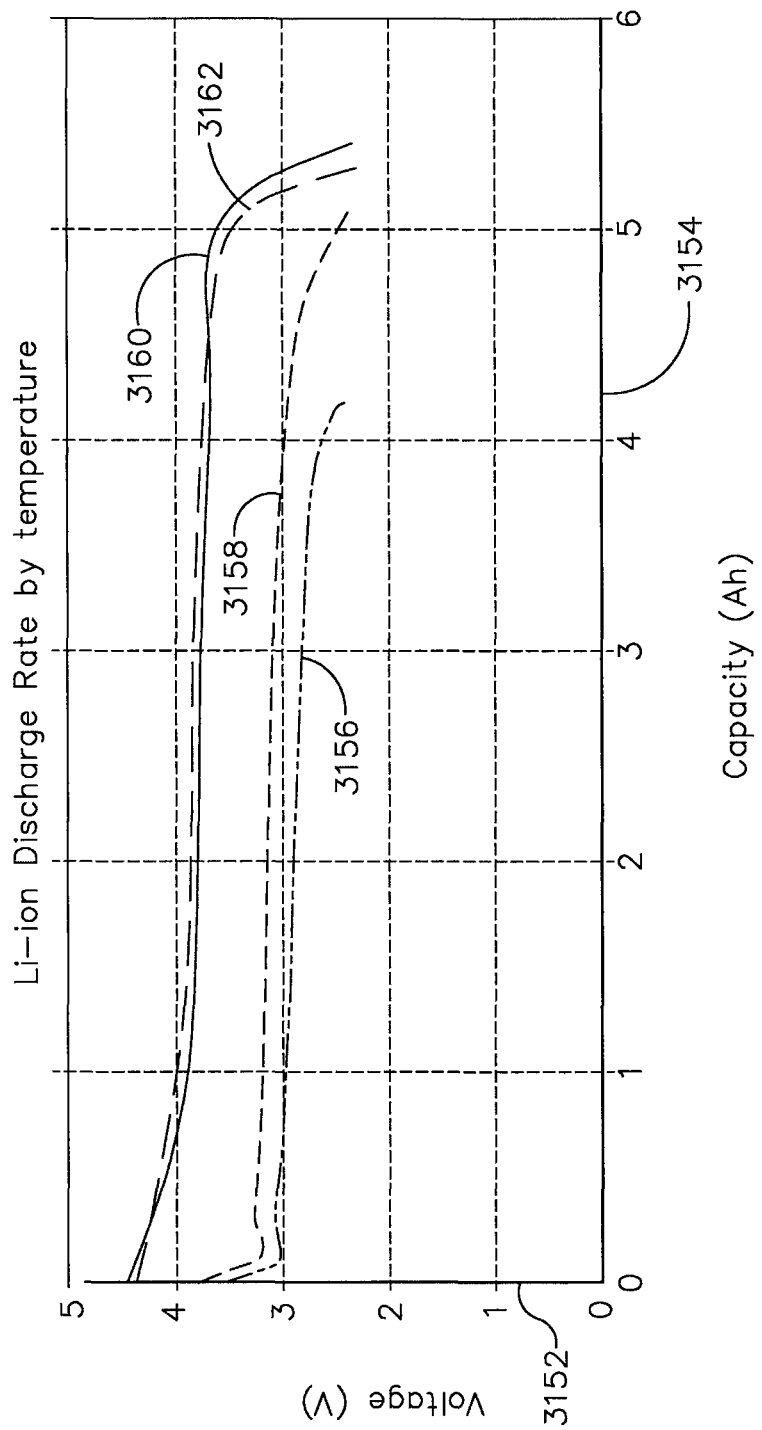
FIG. 40 illustrates a graph which shows different discharge curves for different temperatures of a lithium-ion battery which can be utilized with the surgical instrument of FIG. 29, in accordance with at least one aspect of the present disclosure.

The discharge rate of a given battery can vary by temperature, sometimes dramatically. FIG. 40 illustrates a graph 3150 which shows different discharge curves for different temperatures of a lithium-ion battery which can be utilized with the surgical instrument 3000, in accordance with at least one aspect of the present disclosure. For the graph 3150, units of voltage (Volts) are shown along the vertical axis 3152, units of capacity (Ah) are shown along the horizontal axis 3154, and the discharge current is 1100 mA which is equivalent to a C/5 rate for the lithium-ion battery. A C-rate is a measure of the rate at which a battery is discharged relative to its maximum capacity. As shown in FIG. 40, for the discharge curve 3156, which represents the discharge curve for the lithium-ion battery at −40° C., the lithium-ion battery provides a voltage of at least 3.0 volts until the lithium-ion battery has discharged approximately 2.0 Ah of capacity, then provides a voltage slightly below 3.0 volts until the lithium-ion battery has discharged approximately 3.5 Ah of capacity, then the voltage provided by the lithium-ion battery begins to drop significantly thereafter. For the discharge curve 3158, which represents the discharge curve for the lithium-ion battery at −30° C., the lithium-ion battery provides a voltage of at least 3.0 volts until the lithium-ion battery has discharged approximately 4.1 Ah of capacity, then the voltage provided by the lithium-ion battery begins to drop significantly thereafter. For the discharge curve 3160, which represents the discharge curve for the lithium-ion battery at 20° C., the lithium-ion battery provides a voltage of at least 3.8 volts until the lithium-ion battery has discharged approximately 4.8 Ah of capacity, then the voltage provided by the lithium-ion battery begins to drop significantly thereafter. For the discharge curve 3162, which represents the discharge curve for the lithium-ion battery at 60° C., the lithium-ion battery provides a voltage of at least 3.80 volts until the lithium-ion battery has discharged approximately 4.5 Ah of capacity, then the voltage provided by the lithium-ion battery begins to drop significantly thereafter. In view of the above, it will be appreciated that the discharge rate of a given lithium-ion battery does not vary linearly by temperature, and temperatures which are too cold or too hot can negatively affect the performance of the lithium-ion battery.

Figure 41:
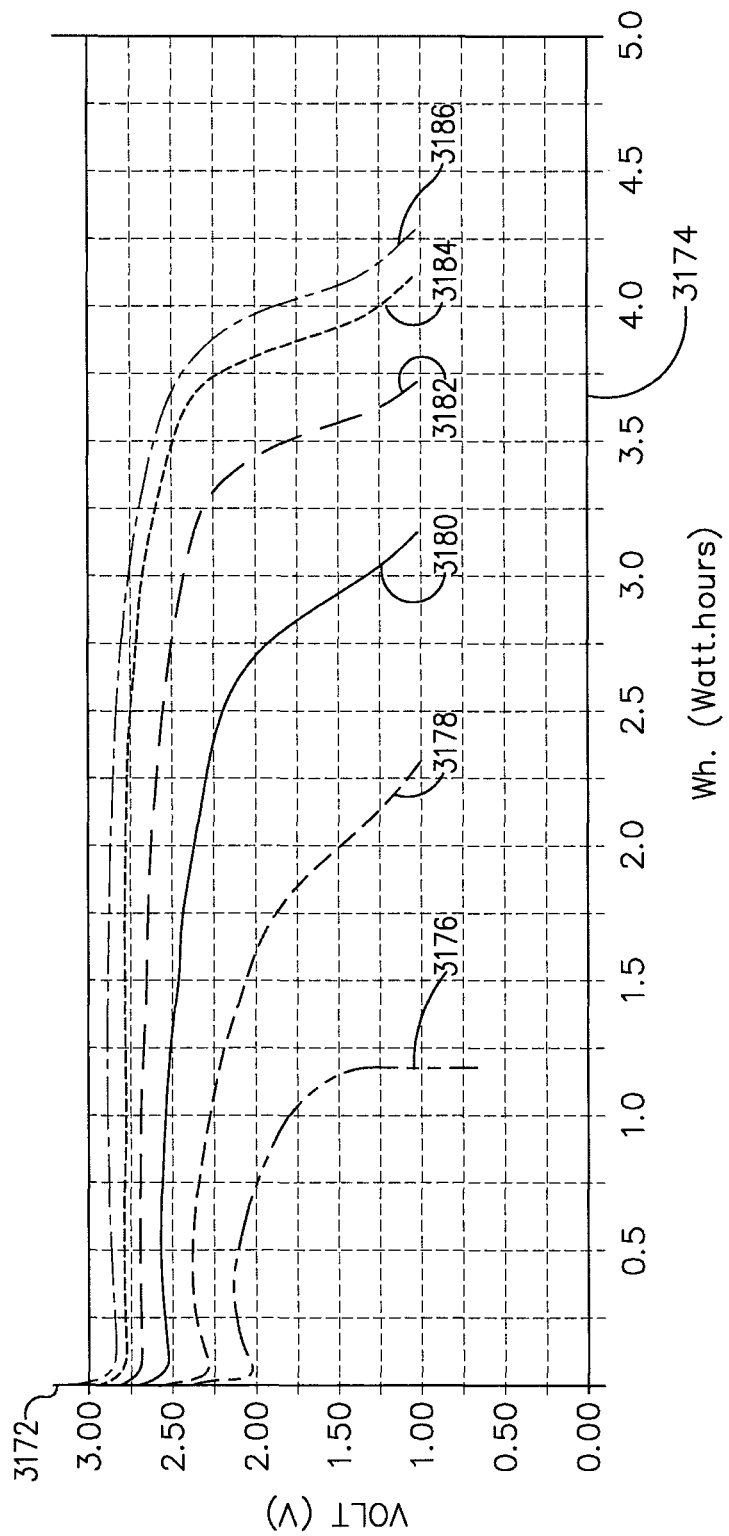
FIG. 41 illustrates a graph which shows different discharge curves for different discharge rates of a CR123 battery which can be utilized with the surgical instrument of FIG. 29, in accordance with at least one aspect of the present disclosure.

The energy capacity of a given battery can vary based on the rate the battery is discharged. FIG. 41 illustrates a graph 3170 which shows different discharge curves for different discharge rates of a CR123 battery which can be utilized with the surgical instrument 3000, in accordance with at least one aspect of the present disclosure. For the graph 3170, units of voltage (Volts) are shown along the vertical axis 3172, units of power in Watt-Hours (Wh) are shown along the horizontal axis 3174, and the CR123 battery is a Panasonic Lithium Power battery. As shown by the discharge curve 3176, for a discharge current of 3.0 amperes, the energy capacity of the battery is approximately 1.2 Wh. As shown by the discharge curve 3178, for a discharge current of 2.0 amperes, the energy capacity of the battery is approximately 2.3 Wh. As shown by the discharge curve 3180, for a discharge current of 1.0 amperes, the energy capacity of the battery is approximately 3.2 Wh. As shown by the discharge curve 3182, for a discharge current of 0.5 amperes, the energy capacity of the battery is approximately 3.7 Wh. As shown by the discharge curve 3184, for a discharge current of 0.2 amperes, the energy capacity of the battery is approximately 4.1 Wh. As shown by the discharge curve 3186, for a discharge current of 0.1 amperes, the energy capacity of the battery is approximately 4.25 Wh. In view of the above, it will be appreciated that, in general, the lower the discharge current, the greater the energy capacity of the CR123 battery. Stated differently, in general, the higher the discharge current, the lower the energy capacity of the CR123 battery.

FIG. 42 illustrates various operational differences between a dumb battery 3190, an intelligent battery 3192 and an adaptive surgical instrument 3194, in accordance with at least one aspect of the present disclosure. In various aspects, the battery pack 3006 can be configured as the dumb battery 3190. For the dumb battery 3190, an RFID tag of the dumb battery 3190 is energized 3196 when the dumb battery 31900 is brought into proximity with or received by a surgical instrument (e.g., the surgical instrument 3000), and the dumb battery 3190 then communicates battery identification information to an RFID scanner of the surgical instrument. The surgical instrument may then utilize the battery identification information as described above to verify the compatibility of the dumb battery 3190 with the surgical instrument.

In various aspects, the battery pack 3006 can be configured as the intelligent battery 3192. The intelligent battery 3192 is configured to read 3198 identification information of a surgical instrument, determine/verify 3200 whether the identified surgical instrument is compatible for use with the intelligent battery 3192, adjust 3202 the output characteristics of the intelligent battery 3192 as needed for proper performance of the identified surgical instrument, energize 3204 the outputs of the intelligent battery 3192, then provide 3206 the identified surgical instrument with expected battery identification information so that the identified surgical instrument recognizes it is being powered by a known compatible battery. In this way, newer more intelligent batteries that are not necessarily identified in compatibility databases/lookup tables of the identified surgical instrument can nonetheless be permitted to provide power to the identified surgical instrument. As described in more detail hereinafter, the intelligent battery 3192 can mimic the performance of a known compatible battery.

In various aspects, the surgical instrument 3000 can be configured as the adaptive surgical instrument 3194. For the adaptive surgical instrument 3194, the adaptive surgical instrument 3194 powers up 3208, reads 3210 the battery identification information provided by a battery such as, for example, the intelligent battery 3192 or the dumb battery 3190 when the battery is brought in proximity to or is received by the adaptive surgical instrument 3194, determines/verifies 3212 whether the identified battery is compatible for use with the adaptive surgical instrument 3194, then adjusts 3214 the operation (e.g., motor operation, operational control parameters, etc.) of the adaptive surgical instrument 3194 based on the received battery identification information. For example, in various aspects, the operation of the adaptive surgical instrument 3194 can vary depending on whether the identified battery is rechargeable or non-rechargeable, the chemistry of the identified battery (e.g., nickel metal hydride, lithium ion, alkaline manganese oxide, lithium, etc.) and/or the output capabilities of the identified battery. In this way, the adaptive surgical instrument 3194 can utilize a much wider variety of different batteries than otherwise possible.

For a given battery pack, the relationship between the voltage potential of the battery pack and the current drawn from the battery pack is given by the equation $V=IR$, where V is the voltage of the battery pack, I is the current drawn from the battery pack and R is the resistance of the load connected to the battery pack. Because different battery packs can have different voltage potentials and different internal resistances, the current to be drawn from the battery pack can vary from battery pack to battery pack when powering a given surgical instrument. Voltage and current values for two different battery packs, one which includes four CR123A batteries and one which includes four 15270 batteries, are shown in Table B2 below for various resistances.

TABLE B2

| Battery | Resistance | Voltage | Current |
| --- | --- | --- | --- |
| CR123A | 1.5 ohms | 7.5 volts | 5.0 amperes |
| 15270 | 1.68 ohms | 15.0 volts | 8.9 amperes |

FIG. 43 illustrates a graph 3220 which shows the output current capabilities of different battery packs when utilized with the adaptive surgical instrument 3194, in accordance with at least one aspect of the present disclosure. For the graph 3220, units of current I (amperes) are shown along the vertical axis 3222 and units of time are shown along the horizontal axis 3224. As shown in FIG. 43, the current output 3226 from a standard CR-123 battery pack (e.g., 4 batteries) can average approximately 5.0 amperes between the times X and Y, and the current output 3228 from a standard 15270 battery can average approximately 8.9 amperes between the times X and Z. By utilizing the above-described RFID capability, the adaptive surgical instrument 3194 can cause the current drawn from the standard 15270 battery pack to mimic 3230 the current which would be drawn from the standard CR-123 battery pack. In various aspects, the adaptive surgical instrument 3194 can achieve this by adapting a speed control algorithm of the adaptive surgical instrument 3194 to lower the speed of the electric motor 3008, by increasing the resistance which is seen by the 15270 battery pack, by using a voltage divider, etc. to cause the 15270 battery pack to adjust its current output to effectively mimic the current output of the standard CR-123 battery pack. For example, according to various aspects, a processor of a control circuit of the adaptive surgical instrument 3194 can communicate an instruction which operates to adapt a speed control algorithm of the adaptive surgical instrument 3194 or by using a voltage divider, for example. As the surgical instrument 3000 may be configured as the adaptive surgical instrument 3194, the control circuit of the adaptive surgical instrument 3194 may be similar or identical to the control circuit 1210 and/or the control circuit 3014. For instances where the 15270 battery pack is an intelligent battery pack (e.g., the intelligent battery 3192), the adaptive surgical instrument 3194 can communicate instructions to the intelligent battery pack to operate as a CR-123 battery pack would.

FIG. 44 illustrates a graph 3240 which shows the output voltage capabilities of different battery packs when utilized with the adaptive surgical instrument 3194, in accordance with at least one aspect of the present disclosure. For the graph 3240, units of voltage (Volts) are shown along the vertical axis 3242 and units of capacity in Ampere-Hours (AmHrs) are shown along the horizontal axis 3244. As shown in FIG. 44, the voltage output 3246 from a standard CR-123 battery pack discharging at a rate of 1.25 amperes per hour can average approximately 7.0 volts during the time the standard CR-123 battery pack has discharged from approximately 0.05 AmHrs to approximately 0.4 AmHrs, and the voltage output 3248 from a standard 15270 battery pack can average approximately 14.0 volts during the time the standard 15270 battery pack has discharged from approximately 0.08 AmHrs to approximately 0.5 AmHrs. By utilizing the above-described RFID capability, the adaptive surgical instrument 3194 can cause the voltage provided by the standard 15270 battery pack to mimic 3250 the voltage provided by the standard CR-123 battery pack. In various aspects, the adaptive surgical instrument 3194 can achieve this by adapting a speed control algorithm of the adaptive surgical instrument 3194 to lower the speed of the electric motor 3008, by increasing the resistance which is seen by the 15270 battery pack, etc. to cause the 15270 battery pack to adjust its voltage output to effectively mimic the voltage output of the standard CR-123 battery pack. For instances where the 15270 battery pack is an intelligent battery pack (e.g., the intelligent battery 3192), the adaptive surgical instrument 3194 can communicate instructions to the intelligent battery pack to operate as a CR-123 battery pack would. In at least one example, a voltage divider could be employed to adjust the voltage output of the battery pack.

FIG. 45 illustrates a graph 3260 which shows the output voltage capabilities of different battery packs when utilized with the adaptive surgical instrument 3194, in accordance with at least one aspect of the present disclosure. For the graph 3260, units of voltage (Volts) are shown along the vertical axis 3262 and units of power in Watt-Hours (Whrs) are shown along the horizontal axis 3264. The graph 3260 is similar to the graph 3240, but is different in that units of power are shown along the horizontal axis 3264. As shown in FIG. 45, the voltage output 3266 from a standard CR-123 battery pack can average approximately 7.15 volts during the time the standard CR-123 battery pack has provided approximately 0.25 watt-hours of power to the time the standard CR-123 battery pack has provided approximately 3.2 watt-hours of power. During this time period, the voltage provided by the standard CR-123 battery pack is both predictable and stable. Therefore, when the above-described RFID capability is utilized by the adaptive surgical instrument 3194 to cause the voltage 3268 provided by the standard 15270 battery pack to mimic 3261 the voltage provided by the standard CR-123 battery pack. It follows that the "adjusted" voltage provided by the standard CR-123 battery pack is also both predictable and stable during the above-described time period.

The dimensional size of many surgical instruments continues to get smaller and smaller. Despite the reduced size, many of the surgical instruments have to accommodate increasing loads, higher performance requirements, and higher over stress conditions. For surgical instruments which include radio-frequency identification (RFID) technology such as radio-frequency identification tags and/or radio-frequency identification scanners, in order to meet the reduced size requirements, the profile of the RFID tags and/or RFID scanners and the associated electronics are continually getting smaller and lower. These smaller systems may not have the memory overhead, processing power, or capacities (range, power, etc.) necessary to accomplish all of the tasks a user would like from the identification systems of the surgical instruments. Therefore, in order to provide additional capabilities like encryption, authentication of multiple components, compatibility verification of multiple components, reprocessing tracking, etc., in various aspects, it can be desirable to utilize encryption/decryption keys which are external to the surgical instrument, and printed or secondary stored data locations to help expand the capabilities and capacities of these smaller less capable systems.

Returning to FIG. 42, it will be appreciated that the above-described functionality of the adaptive surgical instrument 3194 is dependent upon the RFID tag 3010 of the battery pack 3006 being able to communicate the battery identification information to the adaptive surgical instrument 3194 and the RFID scanner 3012 of the adaptive surgical instrument 3194 being able to read the battery identification information provided by the RFID tag 3010 of the battery pack 3006. In certain instances, the adaptive surgical instrument 3194 is unable to determine the compatibility of the battery pack 3006. For example, in instances where the RFID tag 3010 of the battery pack 3006 has experienced a failure (e.g., a failure in an integrated circuit chip of the RFID tag 3010, a failure in the electrical connection between the integrated circuit chip and the antenna of the RFID tag 3010, etc.) such that the RFID tag 3010 fails to communicate the battery identification information, the adaptive surgical instrument 3194 is unable to determine the compatibility of the battery pack 3006. Similarly, in instances where the RFID scanner 3012 of the adaptive surgical instrument 3194 has experienced a failure (e.g., a failure of a wire in the circuitry of the RFID scanner 3012, a failure in a communication board of the RFID scanner 3012, etc.) such that the adaptive surgical instrument 3194 is not able to capture, process and/or communicate the battery identification information provided by the battery pack 3006, the adaptive surgical instrument 3194 is unable to determine the compatibility of the battery pack 3006. For such instances, it is desirable to have secondary/alternative ways of determining the compatibility of a given battery pack with a given adaptive surgical instrument.

FIG. 46 illustrates a battery 3300 for use with the adaptive surgical instrument 3194 of FIG. 42, in accordance with at least aspect of the present disclosure. The battery 3300 may be any suitable type of battery, and may include any suitable number of cells. For brevity, the battery 3300 will be referred to hereinafter as the battery pack 3300. The battery pack 3300 is similar to the battery pack 3006 in that the battery pack 3300 includes a radio-frequency identification (RFID) tag 3302, but is different in that the battery pack 3300 also includes a quick response (QR) code 3304 and/or a product code 3306 positioned on an external surface of the battery pack 3300. The RFID tag 3302 may be similar or identical to the RFID tag 3010.

The QR code 3304 is a machine-readable optical label which contains information about the battery pack 3300. Such information can include, for example, a battery identification number, the manufacturer/brand of batteries in the battery pack 3300, the chemistry/type of batteries (lithium, lithium-ion, etc.) in the battery pack 3300, whether the type of batteries in the battery pack 3300 are chargeable or non-rechargeable, the capacity of the battery pack 3300, the nominal voltage of the batteries in the battery pack 3300, the current draw characteristics of the batteries in the battery pack 3300, other output characteristics of the battery pack 3300, etc. In various aspects, a smartphone, tablet, etc. equipped with a camera and a QR code scanner application can be utilized to read the QR code 3304 from the battery pack 3300.

The product code 3306 may include any sequence of numbers, letters, symbols, etc. which uniquely identify the battery pack 3300. In some aspects, the product code 3306 may be utilized to assist the adaptive surgical instrument 3194 in determining whether the battery pack 3300 is compatible for use with the adaptive surgical instrument 3194.

FIG. 47 illustrates a logic flow diagram of a process 3320 depicting a control program or a logic configuration for operating the adaptive surgical instrument 3194, in accordance with at least one aspect of the present disclosure. In at least one example, the process 3320 is executed by a control circuit 1210 (FIG. 15) that includes a processor 1214 and a memory 1212 storing a set of computer-executable instructions that, when executed by the processor 1214, cause the processor 1214 to perform of the process 3320. In certain examples, a set of computer-executable instructions, stored in the memory 1212 may cause the processor 1214 to perform discrete portions of the process 3320. Although the process 3320 is described as being executed by a control circuit 1210, this is merely for brevity, and it should be understood that the process 3320 and other processes described herein, or portions thereof, can be executed by circuitry that can include a variety of hardware and/or software components and may be located in or associated with various suitable systems such as, for example, combinational logic circuits or sequential logic circuits.

The process 3320 includes ways/methods for determining whether a given battery pack such as, for example, the battery pack 3300, is compatible for use with the adaptive surgical instrument 3194. For brevity, the process 3320 will be described in the context of its applicability with the battery pack 3300. The alternative ways/methods may be utilized in instances where (1) the battery pack 3300 is unable to communicate the battery identification information to the adaptive surgical instrument 3194 and/or the RFID scanner 3012 of the adaptive surgical instrument 3194 is unable to read battery identification information provided by the RFID tag 3302 of the battery pack 3300 and (2) the adaptive surgical instrument 3194 is unable to determine/verify the compatibility of the battery pack 3300 with the adaptive surgical instrument 3194.

As shown in FIG. 47, the adaptive surgical instrument 3194 powers up 3322, then tries to read 3324 the battery identification information provided by the battery pack 3300, when the battery pack 3300 is brought in proximity to or is received by the adaptive surgical instrument 3194. In instances where the adaptive surgical instrument 3194 is able to read 3324 the battery identification information, a control circuit of the adaptive surgical instrument 3194 (e.g., the control circuit 3014 and/or another control circuit of the adaptive surgical instrument 3194) determines/verifies 3326 whether the identified battery is compatible for use with the adaptive surgical instrument 3194, then adjusts 3328 the operation (e.g., motor operation, operational control parameters, etc.) of the adaptive surgical instrument 3194 based on the received battery identification information, as described elsewhere herein in greater detail. For example, in various aspects, the operation of the adaptive surgical instrument 3194 can vary depending on whether the identified battery is rechargeable or non-rechargeable, the chemistry of the identified battery (e.g., nickel metal hydride, lithium ion, alkaline manganese oxide, lithium, etc.) and/or the output capabilities of the identified battery. In this way, the adaptive surgical instrument 3194 can utilize a much wider variety of different batteries than otherwise possible. In at least one aspect, in addition to storing information in the form of a compatibility database or a lookup table, the memory 3018 of the control circuit 3014 may also store information in the form of an authentication database.

However, in instances where the adaptive surgical instrument 3194 is unable to read 3324 the battery identification information (e.g., due to failures in either the RFID tag 3302 of the battery pack 3300 and/or failures of the RFID scanner 3012 of the adaptive surgical instrument 3194), an indication such as, for example, a visual indication or an audible indication, can be provided through the indicator 1209 (FIG. 19) which notifies a user of the failure of the adaptive surgical instrument 3194 to read 3324 the battery identification information. The user or another party may then cause the QR code 3304 and/or the product code 3306 of the battery pack 3300 to be input 3330 to a server. In at least one aspect, the smartphone, tablet, etc. utilized to capture the QR code 3304 may communicate the QR code 3304 to the server through a wired or wireless connection. The communication of the QR code 3304 to the server may be an encrypted communication, just as the communications between the battery pack 3300 and adaptive surgical instrument 3194 may be. The server may be any suitable server such as, for example, a server of a surgical hub system. An example of a surgical hub system is described in U.S. patent application Ser. No. 16/209,395, titled METHOD OF HUB COMMUNICATION, and filed Dec. 4, 2018, the entire content of which is hereby incorporated by reference herein.

The server is configured to compare the battery identification information provided by the QR code 3304 and/or the product code 3306 to a database/table to determine 3332 the authenticity of the battery pack 3300 identified by the QR code 3304 and/or product code 3306. For instances where the server determines that the battery pack 3300 identified by the QR code 3304 and/or product code 3306 is authenticated, the server can generate 3334 a temporary override token which is communicated through a wired or wireless connection to the adaptive surgical instrument 3194, where a control circuit of the adaptive surgical instrument 3194 (e.g., the control circuit 3014 and/or another control circuit of the adaptive surgical instrument 3194) utilizes the temporary override token as a substitute for the unread battery identification information. The communication of the temporary override token to the adaptive surgical instrument 3194 may be an encrypted communication. The temporary override token effectively acts to override the lockout of the operation of the adaptive surgical instrument 3194 which can occur when the battery pack 3300 is not authenticated by the adaptive surgical instrument 3194. In at least one aspect, the lockout operation is initiated and/or carried out by the control circuit 3014. For instances where the battery pack 3300 identified by the QR code 3304 and/or product code 3306 is not authenticated, an indication such as, for example, a visual indication or an audible indication, can be provided through the indicator 1209, which notifies a user of the failure to authenticate the battery pack 3300.

With the temporary override token in place, the adaptive surgical instrument 3194 may then determine/verify 3326 whether the identified battery pack 3300 is compatible for use with the adaptive surgical instrument 3194 as described above. However, if for any reason the adaptive surgical instrument 3194 is unable to verify that the identified battery pack 3300 is compatible with the adaptive surgical instrument 3194, an indication such as, for example, a visual indication or an audible indication, can be provided which notifies a user of the failure of the adaptive surgical instrument 3194 to verify the compatibility of the battery pack 3300 with the adaptive surgical instrument 3194. In such instances, the user or another party may then cause the QR code 3304 and/or the product code 3306 of the battery pack 3300 to be input 3336 to the server. The server is further configured to compare the battery identification information provided by the QR code 3304 and/or the product code 3306 to a database/table to determine 3338 whether the battery pack 3300 identified by the QR code 3304 and/or product code 3306 is compatible for use with the adaptive surgical instrument 3194. For instances where the server determines that the battery pack 3300 identified by the QR code 3304 and/or product code 3306 is compatible with the adaptive surgical instrument 3194, the server can generate 3340 another temporary override token which is communicated to the adaptive surgical instrument 3194, where a control circuit of the adaptive surgical instrument 3194 (e.g., the control circuit 3014 and/or another control circuit of the adaptive surgical instrument 3194) utilizes the temporary override token as a substitute for the unverified compatibility determination. The communication of another temporary override token to the adaptive surgical instrument 3194 may be an encrypted communication. The other temporary override token effectively acts to override the lockout of the operation of the adaptive surgical instrument 3194 which can occur when the compatibility of the battery pack 3300 is not verified by the adaptive surgical instrument 3194. The adaptive surgical instrument 3194 may thereafter adjust 3328 the operation (e.g., motor operation, operational control parameters, etc.) of the adaptive surgical instrument 3194 as described above.

Although the description of the process 3320 of FIG. 47 was limited to (1) determining authenticity of the battery pack 3300 and (2) determining/verifying compatibility of the battery pack 3300 and the adaptive surgical instrument 3194, the basic logic of the process 3320 may also be utilized to determine the compatibility of any number of components and/or sub-systems which can be utilized with the adaptive surgical instrument 3194. For example, by providing a given staple cartridge and a given anvil with the above-described RFID capability, the adaptive surgical instrument 3194 can receive staple cartridge identification information from the RFID tag of the given staple cartridge and anvil identification information from the RFID tag of the given anvil. In at least one aspect, the shaft assembly of the adaptive surgical instrument 3194 is configured to receive the anvil, and the adaptive surgical instrument 3194 is configured to receive the staple cartridge. In instances where the staple cartridge identification information and the anvil identification information are encrypted, a control circuit of the adaptive surgical instrument 3194 (e.g., the control circuit 3014 and/or another control circuit of the adaptive surgical instrument 3194) can utilize a universal private key to decrypt the received staple cartridge identification information and the received anvil identification information, then determine/verify the compatibility of the given staple cartridge with the given anvil, as well as the compatibility of the given staple cartridge and the given anvil with the adaptive surgical instrument 3194. In instances where it is determined that the staple cartridge is not compatible with the anvil, the server and/or another system may provide an indication of the source of the incompatibility issue and provide details regarding how to correct the incompatibility issue through the indicator 1209, for example.

Additionally, the basic logic of the process 3320, and QR codes, product codes and one or more servers as described above, can be utilized to determine authenticity/compatibility of any number of components and/or sub-systems when the adaptive surgical instrument 3194 is unable to receive/read the applicable identification information. For example, in addition to determining the authenticity of the battery pack 3300 and the compatibility of the battery pack 3300 with the adaptive surgical instrument 3194 when the adaptive surgical instrument 3194 is unable to receive/read the applicable identification information (e.g., due to a failure of the RFID tags and/or RFID scanners), the same basic process of utilizing the QR codes, product codes and one or more servers can be utilized to determine the authenticity of anvils and staple cartridges, as well as the compatibility of a given anvil with a given cartridge, as well as the compatibility of the given anvil and the given cartridge with the adaptive surgical instrument 3194. In instances where the server determines that the staple cartridge is not compatible with the anvil, the server and/or another system may provide an indication of the source of the incompatibility issue and provide details regarding how to correct the incompatibility issue.

Additionally, as many components and sub-systems which can be utilized with the adaptive surgical instrument 3194 come in a packaging, if applicable QR codes and/or product codes are included on the packaging, the basic logic of the process 3320, and QR codes, product codes and one or more servers as described above, can be utilized to determine authenticity/compatibility of any number of components and/or sub-systems which are presumed to be in the packaging.

FIG. 48 illustrates a logic flow diagram of a process 3400 depicting a control program or a logic configuration for verifying authenticity and/or compatibility of surgical instruments components of a surgical instrument such as, for example, the surgical instruments 2200, 3194. In at least one example, the process 3400 is executed by a control circuit 1210 (FIG. 15) that includes a processor 1214 and a memory 1212 storing a set of computer-executable instructions that, when executed by the processor 1214, cause the processor 1214 to perform of the process 3400. In certain examples, a set of computer-executable instructions, stored in the memory 1212 may cause the processor 1214 to perform discrete portions of the process 3400. Although the process 3320 is described as being executed by a control circuit 1210, this is merely for brevity, and it should be understood that the process 3400 and other processes described herein, or portions thereof, can be executed by circuitry that can include a variety of hardware and/or software components and may be located in or associated with various suitable systems such as, for example, combinational logic circuits or sequential logic circuits.

In various examples, the control circuit 1210, for example, can employ the process 3400 to verify authenticity and/or compatibility of a surgical instrument and a battery pack releasably couplable to the surgical instrument between an assembled configuration and an unassembled configuration. In other examples, the control circuit 1210, for example, can employ the process 3400 verifies authenticity and/or compatibility of an anvil and a staple cartridge of a surgical instrument.

As illustrated in FIG. 48, the process 3400 includes receiving 3402 a first input indicative of a first identification information of a first surgical instrument component of a surgical instrument such as, for example, the surgical instrument 2200 (FIG. 19). The first identification information can be stored in a first RFID tag of the first surgical instrument component. The process 3400 includes receiving 3404 a second input indicative of a second identification information of a second surgical instrument component of the surgical instrument. The second identification information can be stored in a second RFID tag of the second surgical instrument component. As illustrated in FIG. 19, for example, control circuit 1210 can be coupled to one or more RFID scanner configured to read the stored identification information.

The process 3400 further includes receiving 3406 a third input indicative of a third identification information of a packaging of the first surgical instrument component of the surgical instrument. In a first example, the packaging comprises an RFID tag that stores the third identification information. In a second example, the packaging comprises a CR code that comprises the third identification information. In a third example, the packaging comprises a product number that comprises the third identification information. The third identification information is an encrypted conglomeration of the first identification information and the second identification information, and can be retrieved by the control circuit 1210 via an RFID scanner in the first example, or any suitable smartphone, tablet, etc. equipped with a camera in the second and third examples.

In various instances, the process 3400 further includes decrypting 3408 the encryption of the third identification information, and determining 3410 authenticity of the first and second surgical instrument components by comparing the first identification information and the second identification information to the decrypted third identification information. In certain instances, the memory 1212 may store a decryption key that can be utilized by the processor 1214 to decrypt the encryption of the third identification information.

Furthermore, in certain examples, the process 3400 may include determining 3412 compatibility of the first and second surgical components based on the first identification information and the second identification information. In at least one example, the memory 1212 stores a compatibility database or lookup table that can be utilized by the processor 1214 to assess compatibility of the first and second surgical instrument components. In certain examples, the first identification information identify the surgical instrument itself, and can be stored in the memory 1212 of the control circuit 1210 where it can be retrieved by the processor 1214. In certain examples, the second surgical instrument component is a battery pack such as, for example, the battery pack 120. In at least one example, the first surgical instrument component is an anvil such as, for example, the anvil 2400, while the second surgical instrument component is a staple cartridge such as, for example, the staple cartridge of the stapling head assembly 2300. Other examples of first and second surgical instrument components suitable for use with the process 3400 are contemplated by the present disclosure.

Various aspects of the subject matter described herein are set out in the following examples.

EXAMPLE SET 1

Example 1—A surgical instrument comprising a housing, a shaft assembly extending distally from the housing, a stapling head assembly located at a distal end of the shaft assembly, an anvil couplable with the stapling head assembly, and an anvil adjustment assembly. The stapling head assembly comprises a distal surface. The stapling head assembly is operable to drive an annular array of staples through the distal surface. The stapling head assembly comprises a radio-frequency identification (RFID) scanner. The anvil is translatable relative to the stapling head assembly toward a closed configuration. The anvil comprises an RFID tag. The anvil adjustment assembly comprises a translating member. The translating member is operable to translate relative to the housing along a longitudinal axis to thereby adjust a longitudinal position of the anvil relative to the distal surface of the stapling head assembly. The RFID tag is detectable by the RFID scanner at or below an attachment threshold distance.

Example 2—The surgical instrument of Example 1, wherein the RFID tag is adapted to store information about the anvil.

Example 3—The surgical instrument of Examples 1 or 2, wherein the anvil comprises a head and a shank extending from the head. The shank supports the RFID tag.

Example 4—The surgical instrument of Example 3, wherein the shank comprises a recess sized to receive the RFID tag.

Example 5—The surgical instrument of Examples 3 or 4, wherein the RFID tag is insulated from the shank.

Example 6—The surgical instrument of any one of Examples 1-5, wherein the RFID tag is detectable by the RFID scanner in the closed configuration.

Example 7—The surgical instrument of any one of Examples 1-6, wherein the stapling head assembly comprises an inner core member. The inner core member supports the RFID scanner.

Example 8—The surgical instrument of any one of Examples 1-7, further comprising a control circuit configured to detect a proper seating orientation of the anvil with respect to the stapling head assembly based on input from the RFID scanner.

Example 9—The surgical instrument of any one of Examples 1-8, further comprising a control circuit configured to check compatibility of the anvil with a staple cartridge of the stapling head assembly based on input from the RFID scanner indicative of information about the anvil.

Example 10—The surgical instrument of any one of Examples 1-9, further comprising a control circuit configured to detect the closed configuration based on input from the RFID scanner.

Example 11—The surgical instrument of Example 10, further comprising an indicator coupled to the control circuit. The control circuit is configured to cause the indicator to issue an alert indicative of the closed configuration.

Example 12—The surgical instrument of any one of Examples 1-11, further comprising a lockout assembly. The lockout assembly is configured to transition between a first state and a second state. In the first state, the lockout assembly is configured to permit translation of the translating member. In the second state, the lockout assembly is configured to prevent translation of the translating member.

Example 13—The surgical instrument of Example 12, further comprising a control circuit configured to select between the first state and the second state based on input from the RFID scanner.

Example 14—The surgical instrument of any one of Examples 1-13, further comprising a control circuit configured to detect detachment of the anvil from the stapling head assembly based on loss of a signal between the RFID scanner and the RFID tag.

Example 15—A surgical instrument comprising a shaft assembly, a stapling head assembly located at a distal end of the shaft assembly, and an anvil couplable with the stapling head assembly. The stapling head assembly comprises a staple cartridge and an RFID scanner. The staple cartridge comprises a cartridge deck. The stapling head assembly is operable to drive staples from the staple cartridge through the cartridge deck. The staple cartridge comprises a first RFID tag. The first RFID tag is adapted to store information about the staple cartridge. The RFID scanner is configured to detect the first RFID tag of the staple cartridge retained the stapling head assembly. The anvil is translatable relative to the stapling head assembly toward a closed configuration. The anvil comprises a second RFID tag. The second RFID tag is adapted to store information about the anvil. The RFID scanner is configured to detect the second RFID tag in the closed configuration.

Example 16—The surgical instrument of Example 15, further comprising a control circuit coupled to the RFID scanner. The control circuit is configured to determine compatibility between the anvil and the staple cartridge based on the information stored in the first RFID tag and the information stored in the second RFID tag.

Example 17—The surgical instrument of Examples 15 or 16, further comprising a control circuit coupled to the RFID scanner. The control circuit is configured to determine a firing status of the staple cartridge based on the information stored in the first RFID tag.

Example 18—The surgical instrument of any one of Examples 15-17, further comprising a control circuit configured to detect a proper seating orientation of the anvil with respect to the stapling head assembly based on signals transmitted to the RFID scanner from the first RFID tag and the second RFID tag.

Example 19—A surgical instrument comprising a housing, a shaft assembly extending distally from the housing, a stapling head assembly located at a distal end of the shaft assembly, an anvil couplable with the stapling head assembly, and an RFID system. The stapling head assembly comprises a distal surface. The stapling head assembly is operable to drive an annular array of staples through the distal surface. The anvil is translatable relative to the stapling head assembly toward a closed configuration to capture tissue therebetween. The RFID system comprises an RFID scanner and an RFID tag adapted to store information about the anvil. The RFID tag is configured to transmit an RF signal indicative of the information to the RFID scanner in the closed configuration. The surgical instrument further comprises a control circuit coupled to the RFID scanner. The control circuit is configured to determine a characteristic of the tissue based on RF signal backscatter from the tissue.

Example 20—The surgical instrument of Example 19, wherein the characteristic is tissue thickness.

EXAMPLE SET 2

Example 1—A surgical instrument comprising an end effector, a shaft, and a housing. The end effector comprises an anvil, a staple cartridge including staples deployable toward the anvil and through tissue grasped between the anvil and the staple cartridge, a cutting member configured to cut the tissue, and a first radio-frequency identification (RFID) tag configured to store end effector information. The shaft comprises a distal portion selectively transitionable with the end effector between a first attached configuration and a first detached configuration, a first RFID scanner near the distal portion, a proximal portion, and a second RFID tag configured to store shaft information. The first RFID scanner is configured to detect the first RFID tag in the first attached configuration. The housing is selectively transitionable with the proximal portion of the shaft between a second attached configuration and a second detached configuration. The housing comprises a second RFID scanner configured to detect the second RFID tag in the second attached configuration, a motor configured to apply a load to the end effector to staple and cut the tissue, and a control circuit. The control circuit is configured to receive input from the first RFID scanner indicative of the end effector information, receive input from the second RFID scanner indicative of the shaft information, and adjust at least one parameter of operation of the motor based on the end effector information and the shaft information.

Example 2—The surgical instrument of Example 1, wherein the end effector information is indicative of a staple cartridge size. The shaft information is indicative of a shaft profile.

Example 3—The surgical instrument of Example 2, wherein the control circuit is configured to determine a final maximum load threshold of the load applied by the motor to the end effector based on the staple cartridge size and the shaft profile.

Example 4—The surgical instrument of Example 3, wherein the control circuit is configured to determine the final maximum load threshold by adjusting a default maximum load threshold by a first adjustment value based on the staple cartridge size and a second adjustment value based on the shaft profile.

Example 5—The surgical instrument of any one of Examples 2-4, wherein the control circuit is configured to delay an activation of the motor a predetermined time period based on the staple cartridge size.

Example 6—The surgical instrument of any one of Examples 1-5, wherein the control circuit is configured to receive input from a user and adjust the at least one parameter of operation of the motor based on at least two of the user input, the end effector information, and the shaft information.

Example 7—The surgical instrument of Example 6, wherein the input from the user comprises a user-selected form height.

Example 8—A surgical instrument comprising an end effector and a housing assembly. The end effector comprises an anvil, a staple cartridge including staples deployable toward the anvil and through tissue grasped between the anvil and the staple cartridge, a cutting member configured to cut the tissue, and a first RFID tag configured to store end effector information. The housing assembly comprises a shaft selectively transitionable with the end effector between an attached configuration and an detached configuration, an RFID scanner configured to detect the RFID tag in the attached configuration, a motor configured to apply a load to the end effector to staple and cut the tissue, and a control circuit. The control circuit is configured to receive input from the RFID scanner indicative of the end effector information and adjust at least one parameter of operation of the motor based on the end effector information.

Example 9—The surgical instrument of Example 8, wherein the end effector information is indicative of a staple cartridge size.

Example 10—The surgical instrument of Example 9, wherein the control circuit is configured to determine a final maximum load threshold of the load applied by the motor to the end effector based on the staple cartridge size.

Example 11—The surgical instrument of Example 10, wherein the control circuit is configured to determine the final maximum load threshold by adjusting a default maximum load threshold by an adjustment value based on the staple cartridge size.

Example 12—The surgical instrument of any one of Examples 9-11, wherein the control circuit is configured to delay an activation of the motor a predetermined time period based on the staple cartridge size.

Example 13—The surgical instrument of any one of Examples 8-12, wherein the control circuit is configured to receive input from a user and adjust the at least one parameter of operation of the motor based on the user input and the end effector information.

Example 14—The surgical instrument of Example 13, wherein the input from the user comprises a user-selected form height.

Example 15—A surgical instrument comprising an end effector, a shaft, and a housing. The end effector comprises a stapling head assembly, an anvil movable a closure distance relative to the stapling head assembly to transition the end effector from an open configuration to a closed configuration, and a first RFID tag configured to store end effector information. Tissue is grasped between the anvil and the stapling head assembly in the closed configuration. The shaft, comprises a distal portion selectively transitionable with the end effector between a first attached configuration and a first detached configuration, a first RFID scanner near the distal portion, a proximal portion, and a second RFID tag configured to store shaft information. The first RFID scanner is configured to detect the first RFID tag in the first attached configuration. The housing is selectively transitionable with the proximal portion of the shaft between a second attached configuration and a second detached configuration. The housing comprises a second RFID scanner configured to detect the second RFID tag in the second attached configuration, a motor configured to generate a closure motion to cause the anvil to move the closure distance, and a control circuit. The control circuit is configured to receive input from the first RFID scanner indicative of the end effector information, receive input from the second RFID scanner indicative of the shaft information, and adjust at least one parameter of operation of the motor based on the end effector information and the shaft information.

Example 16—The surgical instrument of Example 15, wherein the end effector information is indicative of a staple cartridge size. The shaft information is indicative of a shaft profile.

Example 17—The surgical instrument of Example 16, wherein the control circuit is configured to determine a final minimum threshold of the closure distance based on the staple cartridge size and the shaft profile.

Example 18—The surgical instrument of Example 17, wherein the control circuit is configured to determine the final minimum threshold of the closure distance by adjusting a default minimum threshold of the closure distance by a first adjustment value based on the staple cartridge size and a second adjustment value based on the shaft profile.

Example 19—The surgical instrument of Example 15, wherein the control circuit is configured to adjust a user-selectable closure-distance range of the anvil based on the end effector information and the shaft information.

EXAMPLE SET 3

Example 1—A surgical instrument comprising a housing assembly including a battery interface configured to releasably retain a battery, a radio-frequency identification scanner positioned at the battery interface, and a control circuit. The radio-frequency identification scanner is configured to receive information from the battery. The control circuit is configured to determine a compatibility of the battery with the surgical instrument based on the information received from the battery.

Example 2—The surgical instrument of Example 1, wherein the housing assembly is configured to receive the battery in an assembled configuration.

Example 3—The surgical instrument of Example 2, wherein the radio-frequency identification scanner is further configured to receive the information from a radio-frequency identification tag of the battery in the assembled configuration.

Example 4—The surgical instrument of Example 2, further comprising the battery. The battery comprises a radio-frequency identification tag in a detection range of the radio-frequency identification scanner in the assembled configuration.

Example 5—The surgical instrument of Example 4, wherein the radio-frequency identification tag stores at least one of the following: a battery identification number, a manufacturer of the battery, a chemistry of the battery, whether the battery is rechargeable, a capacity of the battery, a nominal voltage of the battery, a current draw characteristic of the battery, and an output characteristic of the battery.

Example 6—The surgical instrument of any one of Examples 1-5, wherein the control circuit comprises a processor electrically connected to the radio-frequency identification scanner and a memory electrically connected to the processor.

Example 7—The surgical instrument of Example 6, wherein the memory stores at least one of the following: a compatibility database and a lookup table.

Example 8—The surgical instrument of any one of Examples 1-7, further comprising an electric motor positioned within the housing assembly. The control circuit is further configured to electronically lockout operation of the electric motor.

Example 9—A surgical instrument comprising a housing assembly including a battery interface, a radio-frequency identification tag positioned at the battery interface, an electric motor positioned within the housing assembly, a battery electrically couplable to the electric motor, and a control circuit. The battery comprises a radio-frequency identification scanner. The radio-frequency identification scanner is configured to receive information from the radio-frequency identification tag of the surgical instrument in an assembled configuration with the housing assembly. The control circuit is configured to determine a compatibility of the surgical instrument with the battery based on the information received from the radio-frequency identification tag.

Example 10—The surgical instrument of Example 9, wherein the radio-frequency identification tag stores at least one of the following: a surgical instrument identification number, a manufacturer of the surgical instrument, a type of the surgical instrument, a type of the electric motor, a performance capability of the surgical instrument, and a control algorithm residing at the surgical instrument.

Example 11—The surgical instrument of Examples 9 or 10, wherein the control circuit comprises a processor electrically connected to the radio-frequency identification scanner and a memory electrically connected to the processor.

Example 12—The surgical instrument of Example 11, wherein the memory stores at least one of the following: a compatibility database and a lookup table.

Example 13—The surgical instrument of any one of Examples 9-12, wherein the surgical instrument further comprises a second radio-frequency identification tag positioned within the battery a second radio-frequency identification scanner positioned at the battery interface, and a second control circuit. The second radio-frequency identification scanner is configured to receive information from the second radio-frequency identification tag in the assembled configuration. The second control circuit configured to determine a compatibility of the battery with the surgical instrument based on the information received from the second radio-frequency identification tag.

Example 14—A surgical instrument comprising a housing assembly, a radio-frequency identification scanner positioned within the housing assembly, and a control circuit. The housing assembly is configured to receive a first battery and a second battery after the first battery has been removed from the housing assembly. Output characteristics of the second battery are different from output characteristics of the first battery. The control circuit is configured to adjust operation of the surgical instrument to cause the second battery to mimic the output characteristics of the first battery.

Example 15—The surgical instrument of Example 14, wherein at least one of the output characteristics of the first battery comprises a voltage of the first battery.

Example 16—The surgical instrument of Examples 14 or 15, wherein at least one of the output characteristics of the first battery comprises a current drawn from the first battery.

Example 17—The surgical instrument of at least one of Examples 14-16, wherein at least one of the output characteristics of the first battery comprises an output capacity of the first battery.

Example 18—The surgical instrument of at least one of Examples 14-17, wherein at least one of the output characteristics of the first battery comprises power provided by the first battery.

Example 19—The surgical instrument of at least one of Examples 14-18, wherein the radio-frequency identification scanner is configured to receive first information from the first battery and second information from the second battery.

Example 20—The surgical instrument of at least one of Examples 14-19, wherein the control circuit comprises a processor electrically connected to the radio-frequency identification scanner and a memory electrically connected to the processor.

EXAMPLE SET 4

Example 1—A surgical instrument comprising an end effector operable to treat tissue, a shaft extending proximally from the end effector, and a housing assembly extending proximally from the shaft. The housing assembly comprises a radio-frequency identification (RFID) scanner and a motor-assembly compartment comprising a motor assembly interchangeably retained by the motor-assembly compartment in an assembled configuration. The motor assembly is movable relative to the motor-assembly compartment between the assembled configuration and an unassembled configuration. The motor assembly comprises a motor configured to drive the end effector to treat the tissue and an RFID tag detectable by the RFID scanner in the assembled configuration. The RFID tag stores motor-assembly information.

Example 2—The surgical instrument of Example 1, further comprising a control circuit configured to receive an input from the RFID scanner in the assembled configuration, the input being indicative of the motor-assembly information.

Example 3—The surgical instrument of Example 2, wherein the control circuit is further configured to adjust at least one parameter of operation of the motor based on the motor-assembly information.

Example 4—The surgical instrument of Examples 2 or 3, wherein the control circuit is further configured to select a control algorithm of the surgical instrument based on the motor-assembly information.

Example 5—The surgical instrument of Example 4, wherein the control circuit is further configured to select the control algorithm from control algorithms each associated with a different motor-assembly information.

Example 6—The surgical instrument of any one of Examples 2-5, wherein the control circuit is further configured to determine a motor setting based on the motor-assembly information.

Example 7—The surgical instrument of any one of Examples 1-6, wherein the motor assembly comprises a gearbox operably coupled to the motor.

Example 8—The surgical instrument of Example 7, wherein the motor-assembly information comprises gearbox information and motor information.

Example 9—The surgical instrument of any one of Examples 1-8, further comprising a power source coupled to the motor assembly in the assembled configuration.

Example 10—The surgical instrument of Example 9, wherein the power source is configured to generate a power output to cause the motor to drive the end effector to treat the tissue.

Example 11—The surgical instrument of Example 10, wherein the control circuit is further configured to determine a value of the power output based on the motor-assembly information.

Example 12—A surgical instrument comprising an end effector operable to treat tissue, a shaft extending proximally from the end effector, and a housing assembly extending proximally from the shaft. The housing assembly comprising a radio-frequency identification (RFID) scanner and a motor-assembly compartment comprising a motor assembly interchangeably retained by the motor-assembly compartment in an assembled configuration. The motor assembly is movable relative to the motor-assembly compartment between the assembled configuration and an unassembled configuration. The motor assembly comprises a motor configured to drive the end effector to treat the tissue and an RFID tag positioned at or within a detection range of the RFID scanner in the assembled configuration. The RFID tag stores motor-assembly information.

Example 13—The surgical instrument of Example 12, further comprising a control circuit configured to receive an input from the RFID scanner in the assembled configuration, the input being indicative of the motor-assembly information.

Example 14—The surgical instrument of Example 13, wherein the control circuit is further configured to adjust at least one parameter of operation of the motor based on the motor-assembly information.

Example 15—The surgical instrument of Examples 13 or 14, wherein the control circuit is further configured to select a control algorithm of the surgical instrument based on the motor-assembly information.

Example 16—The surgical instrument of Example 15, wherein the control circuit is further configured to select the control algorithm from control algorithms each associated with a different motor-assembly information.

Example 17—The surgical instrument of any one of Examples 13-16, wherein the control circuit is further configured to determine a motor setting based on the motor-assembly information.

EXAMPLE SET 5

Example 1—A surgical instrument comprising a housing assembly, a shaft assembly coupled to the housing assembly, at least one radio-frequency identification scanner configured to receive information from radio-frequency identification tags which correspond to components which are couplable to the surgical instrument, and a control circuit. The control circuit is configured to determine, for each component, authenticity of the component based on the information received from the radio-frequency identification tags.

Example 2—The surgical instrument of Example 1, wherein the information comprises a first identification information of a first component of the components and a second identification information of a second component of the components. The at least one radio-frequency identification scanner is configured to receive a third identification information from a radio-frequency identification tag of a packaging of the first component, and wherein the third identification information is encrypted.

Example 3—The surgical instrument of Example 2, wherein the control circuit is configured to decrypt the third identification information and determine authenticity of the first component and the second component by comparing the first identification information and the second identification information to the decrypted third identification information.

Example 4—The surgical instrument of Examples 3 or 4, wherein the control circuit employs a private key to decrypt the third identification information.

Example 5—The surgical instrument of any one of Examples 1-4, wherein the components comprise a battery, an anvil, and a staple cartridge.

Example 6—The surgical instrument of Example 5, wherein the housing assembly is configured to receive the battery.

Example 7—The surgical instrument of Examples 5 or 6, wherein the surgical instrument is configured to receive the staple cartridge.

Example 8—The surgical instrument of any one of Examples 1-7, wherein the control circuit comprises a processor electrically connected to the at least one radio-frequency identification scanner and a memory electrically connected to the processor.

Example 9—The surgical instrument of Example 8, wherein the memory stores at least one of the following: an authentication database, a compatibility database, and a lookup table.

Example 10—The surgical instrument of any one of Examples 1-9, wherein the control circuit is further configured to electronically lockout operation of the surgical instrument based on a determination of a lack of authenticity for any one of the components.

Example 11—The surgical instrument of Example 10, wherein the control circuit is further configured to override the lockout of the surgical instrument based on a temporary override token received from a server.

Example 12—The surgical instrument of Example 11, wherein the temporary override token is based on at least one of the following: a quick response code associated with any one of the components and a product code associated with any one of the components.

Example 13—The surgical instrument of any one of Examples 1-12, wherein the control circuit is further configured to determine, for each component, whether the component is compatible with the surgical instrument based on the information received from the radio-frequency identification tags.

Example 14—The surgical instrument of any one of Examples 1-13, wherein the control circuit is further configured to determine whether one of the components is compatible with another one of the components based on the information received from the radio-frequency identification tags.

Example 15—The surgical instrument of Example 1, wherein the control circuit is further configured to override a lockout of the surgical instrument based on a temporary override token received from a server.

Example 16—A surgical assembly comprising a surgical instrument comprising a first identification information, a battery pack couplable to the surgical instrument, and a control circuit. The battery pack is configured to transmit energy to the surgical instrument in an assembled configuration with the surgical instrument. The battery pack comprises a battery RFID tag storing a second identification information. The control circuit is configured to receive input indicative of an encrypted third identification information stored in an RFID tag of a packaging of the surgical instrument, decrypt the third identification information, and determine authenticity of the surgical instrument and the battery pack by comparing the first identification information and the second identification information to the decrypted third identification information.

Example 17—The surgical assembly of Example 16, wherein the control circuit is further configured to determine compatibility of the battery pack with the surgical instrument based on the first identification information and the second identification information.

Example 18—The surgical assembly of Examples 16 or 17, wherein the control circuit comprises a processor and a memory electrically connected to the processor. The memory stores at least one of the following: a compatibility database and a lookup table.

Example 19—A surgical assembly comprising a surgical instrument component and a surgical instrument. The surgical instrument component comprises an RFID tag storing a first identification information of the surgical instrument component. The surgical instrument component is releasably couplable to the surgical instrument between an assembled configuration and an unassembled configuration. The surgical instrument comprises an RFID scanner configured to read the first identification information and a control circuit coupled to the RFID scanner. The control circuit is configured to detect incompatibility of the surgical instrument component with the surgical instrument based on the first identification information, retrieve a second identification information of the surgical instrument component, retrieve a temporary override token based on the second identification information, and employ the temporary override token to bypass the incompatibility detection.

Example 20—The surgical assembly of Example 19, wherein the second identification information is a serial number of the surgical instrument component.

Example 21—The surgical assembly of Examples 19 or 20, wherein a QR code comprises the second identification information.

While several forms have been illustrated and described, it is not the intention of the applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor comprising one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

In various aspects, a microcontroller of control circuit in accordance with the present disclosure may be any single-core or multicore processor such as those known under the trade name ARM Cortex by Texas Instruments. In one aspect, the main microcontroller 461 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the housing portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A surgical instrument, comprising:
    an end effector, comprising:
        an anvil;
        a staple cartridge including staples deployable toward the anvil and through tissue grasped between the anvil and the staple cartridge;
        a cutting member configured to cut the tissue; and
        a first radio-frequency identification (RFID) tag configured to store end effector information;
    a shaft, comprising:
        a distal portion selectively transitionable with the end effector between a first attached configuration and a first detached configuration;
        a first RFID scanner near the distal portion, wherein the first RFID scanner is configured to detect the first RFID tag in the first attached configuration;
        a proximal portion; and
        a second RFID tag configured to store operational shaft information; and
    a housing selectively transitionable with the proximal portion of the shaft between a second attached configuration and a second detached configuration, wherein the housing comprises:
        a second RFID scanner configured to detect the second RFID tag in the second attached configuration;
        a motor configured to apply a load to the end effector to staple and cut the tissue; and
        a control circuit configured to:
            receive input from the first RFID scanner indicative of the end effector information;
            receive input from the second RFID scanner indicative of the operational shaft information; and
            adjust at least one parameter of operation of the motor based on the end effector information and the operational shaft information, wherein the at least one parameter of operation of the motor adjusts closure distances and/or firing loads.

2. The surgical instrument of claim 1, wherein the end effector information is indicative of a staple cartridge size, and wherein the operational shaft information is indicative of a shaft profile.

3. The surgical instrument of claim 2, wherein the control circuit is configured to determine a final maximum load threshold of the load applied by the motor to the end effector based on the staple cartridge size and the shaft profile.

4. The surgical instrument of claim 3, wherein the control circuit is configured to determine the final maximum load threshold by adjusting a default maximum load threshold by a first adjustment value based on the staple cartridge size and a second adjustment value based on the shaft profile.

5. The surgical instrument of claim 2, wherein the control circuit is configured to delay an activation of the motor a predetermined time period based on the staple cartridge size.

6. The surgical instrument of claim 1, wherein the control circuit is configured to:
receive input from a user; and
adjust the at least one parameter of operation of the motor based on at least two of the user input, the end effector information, and the operational shaft information.

7. The surgical instrument of claim 6, wherein the input from the user comprises a user-selected form height.

8. A surgical instrument, comprising:
an end effector, comprising:
an anvil;
a staple cartridge including staples deployable toward the anvil and through tissue grasped between the anvil and the staple cartridge;
a cutting member configured to cut the tissue; and
a first RFID tag configured to store end effector information;
a housing assembly, comprising:
a shaft selectively transitionable with the end effector between an attached configuration and a detached configuration;
an RFID scanner configured to detect the first RFID tag in the attached configuration;
a motor configured to apply a load to the end effector to staple and cut the tissue; and
a control circuit configured to:
receive input from the RFID scanner indicative of the end effector information; and
adjust at least one parameter of operation of the motor based on the end effector information, wherein the at least one parameter of operation of the motor adjusts closure distances and/or firing loads that are based on the RFID scanner indicative of the end effector information, and wherein the end effector information is indicative of a staple cartridge size.

9. The surgical instrument of claim 8, wherein the control circuit is configured to determine a final maximum load threshold of the load applied by the motor to the end effector based on the staple cartridge size.

10. The surgical instrument of claim 9, wherein the control circuit is configured to determine the final maximum load threshold by adjusting a default maximum load threshold by an adjustment value based on the staple cartridge size.

11. The surgical instrument of claim 8, wherein the control circuit is configured to delay an activation of the motor a predetermined time period based on the staple cartridge size.

12. The surgical instrument of claim 8, wherein the control circuit is configured to:
receive input from a user; and
adjust the at least one parameter of operation of the motor based on the user input and the end effector information.

13. The surgical instrument of claim 12, wherein the input from the user comprises a user-selected form height.

14. A surgical instrument, comprising:
an end effector, comprising:
a stapling head assembly;
an anvil movable a closure distance relative to the stapling head assembly to transition the end effector from an open configuration to a closed configuration, wherein tissue is grasped between the anvil and the stapling head assembly in the closed configuration; and
a first RFID tag configured to store end effector information;
a shaft, comprising:
a distal portion selectively transitionable with the end effector between a first attached configuration and a first detached configuration;
a first RFID scanner near the distal portion, wherein the first RFID scanner is configured to detect the first RFID tag in the first attached configuration;
a proximal portion; and
a second RFID tag configured to store operational shaft information; and
a housing selectively transitionable with the proximal portion of the shaft between a second attached configuration and a second detached configuration, wherein the housing comprises:
a second RFID scanner configured to detect the second RFID tag in the second attached configuration;
a motor configured to generate a closure motion to cause the anvil to move the closure distance; and
a control circuit configured to:
receive input from the first RFID scanner indicative of the end effector information;
receive input from the second RFID scanner indicative of the operational shaft information; and
adjust at least one parameter of operation of the motor based on the end effector information and the operational shaft information, wherein the at least one parameter of operation of the motor adjusts closure distances and/or firing loads.

15. The surgical instrument of claim 14, wherein the end effector information is indicative of a staple cartridge size, and wherein the operational shaft information is indicative of a shaft profile.

16. The surgical instrument of claim 15, wherein the control circuit is configured to determine a final minimum threshold of the closure distance based on the staple cartridge size and the shaft profile.

17. The surgical instrument of claim 16, wherein the control circuit is configured to determine the final minimum threshold of the closure distance by adjusting a default minimum threshold of the closure distance by a first adjustment value based on the staple cartridge size and a second adjustment value based on the shaft profile.

18. The surgical instrument of claim 14, wherein the control circuit is configured to adjust a user-selectable closure-distance range of the anvil based on the end effector information and the operational shaft information.

19. The surgical instrument of claim 8, further comprising a second RFID tag configured to store operational shaft information, wherein the control circuit is further configured to adjust the at least one parameter of operation of the motor based on the operational shaft information, and wherein the at least one parameter of operation of the motor further adjusts closure distances and/or firing loads based on the operational shaft information.

* * * * *